US012746283B2

(12) United States Patent
Wallace

(10) Patent No.: US 12,746,283 B2
(45) Date of Patent: Sep. 29, 2026

(54) DENGUE VACCINE UNIT DOSE AND ADMINISTRATION THEREOF

(71) Applicant: Takeda Vaccines, Inc., Cambridge, MA (US)

(72) Inventor: Derek Wallace, Brookline, MA (US)

(73) Assignee: Takeda Vaccines, Inc., Cambridge, MA (US)

( * ) Notice: Subject to any disclaimer, the term of this patent is extended or adjusted under 35 U.S.C. 154(b) by 0 days.

(21) Appl. No.: 18/149,742

(22) Filed: Jan. 4, 2023

(65) Prior Publication Data

US 2023/0355748 A1 Nov. 9, 2023

Related U.S. Application Data

(63) Continuation of application No. 16/561,953, filed on Sep. 5, 2019, now Pat. No. 11,590,221.

(30) Foreign Application Priority Data

| | | |
|---|---|---|
| Sep. 5, 2018 | (EP) | 18192701 |
| Sep. 5, 2018 | (EP) | 18192711 |
| Sep. 5, 2018 | (EP) | 18192717 |
| Sep. 5, 2018 | (EP) | 18192776 |
| Sep. 5, 2018 | (EP) | 18192787 |
| Sep. 5, 2018 | (EP) | 18192793 |
| Sep. 5, 2018 | (EP) | 18192800 |
| Sep. 5, 2018 | (EP) | 18192814 |
| Jan. 29, 2019 | (EP) | 19154334 |
| Mar. 7, 2019 | (EP) | 19161184 |

(51) Int. Cl.

| | |
|---|---|
| ***A61K 39/295*** | (2006.01) |
| ***A61K 35/76*** | (2015.01) |
| *A61K 39/00* | (2006.01) |
| *A61P 31/14* | (2006.01) |

(52) U.S. Cl.
CPC ............ *A61K 39/295* (2013.01); *A61K 35/76* (2013.01); *A61K 2039/545* (2013.01); *A61P 31/14* (2018.01)

(58) Field of Classification Search
None
See application file for complete search history.

(56) References Cited

U.S. PATENT DOCUMENTS

| | | | |
|---|---|---|---|
| 4,810,092 | A | 3/1989 | Auth |
| 5,021,347 | A | 6/1991 | Yasui et al. |
| 5,229,293 | A | 7/1993 | Matsuura et al. |
| 5,494,671 | A | 2/1996 | Lai et al. |
| 5,514,375 | A | 5/1996 | Paoletti et al. |
| 6,165,477 | A | 12/2000 | Ivy et al. |
| 6,184,024 | B1 | 2/2001 | Lai et al. |
| 6,254,873 | B1 | 7/2001 | Putnak |
| 6,660,273 | B2 | 12/2003 | Pletnev et al. |
| 7,094,411 | B2 | 8/2006 | Kinney et al. |
| 7,641,907 | B2 | 1/2010 | Kinney |
| 8,673,316 | B2 | 3/2014 | Kinney et al. |
| 9,783,579 | B2 | 10/2017 | Stinchcomb |
| 10,857,222 | B2 | 12/2020 | Noriega et al. |
| 11,007,261 | B2 | 5/2021 | Wallace et al. |
| 11,464,815 | B2 | 10/2022 | Wallace |
| 11,590,221 | B2 | 2/2023 | Wallace |
| 2006/0062803 | A1 | 3/2006 | Kinney et al. |
| 2007/0026016 | A1 | 2/2007 | Pasteur |
| 2010/0215692 | A1 | 8/2010 | Quentin-Millet |
| 2010/0303860 | A1 | 12/2010 | Stinchcomb et al. |
| 2011/0150771 | A1 | 6/2011 | Kinney et al. |
| 2011/0311579 | A1 | 12/2011 | Mason et al. |
| 2014/0302088 | A1 | 10/2014 | Stinchcomb et al. |
| 2015/0150961 | A1 | 6/2015 | Stinchcomb et al. |
| 2015/0265695 | A1 | 9/2015 | Yao et al. |
| 2017/0049874 | A1 | 2/2017 | Livengood et al. |
| 2017/0304426 | A1 | 10/2017 | Tornieporth et al. |
| 2019/0381163 | A1 | 12/2019 | Wallace et al. |
| 2020/0061151 | A1 | 2/2020 | Stinchcomb et al. |
| 2020/0069751 | A1 | 3/2020 | Wallace |
| 2023/0149538 | A1 | 5/2023 | Wallace |
| 2023/0233628 | A1 | 7/2023 | Wallace |
| 2023/0355748 | A1 | 11/2023 | Wallace |
| 2024/0150729 | A1* | 5/2024 | Chadha .................... C12N 7/00 |

FOREIGN PATENT DOCUMENTS

| | | | |
|---|---|---|---|
| CN | 10123809 | A | 8/2008 |
| CN | 101238144 | A | 8/2008 |
| CN | 101238209 | A | 8/2008 |

(Continued)

OTHER PUBLICATIONS

Press Release: "Takeda Completes Enrollment of More Than 20,000 Children and Adolescents in Global Phase 3 Trial of Dengue Vaccine Candidate" Apr. 5, 2017—DEN-301, 4 pages.

Press Release: "Takeda's Pipeline Has Potential to Contribute Signi?cantly to Revenue Growth Over Next Decade," Dec. 9, 2020, 4 pages.

Puerta-Guardo et al., "Dengue Virus NS1 Disrupts the Endothelial Glycocalyx, Leading to Hyperpermeability," PloS Pathog, Jul. 14, 2016, vol. 12, No. 7, pp. 1-29.

Rinderknecht et al., "Immunogenicity and Safety of an Inactivated Hepatitis A Vaccine When Coadministered With Mea-sles-mumps-rubella and Varicella Vaccines in Children Less Than 2 Years of Age," Pediatric Infectious Disease Journal, Oct. 1, 2011, vol. 30, No. 10, pp. e179-e185.

(Continued)

*Primary Examiner* — Benjamin P Blumel
(74) *Attorney, Agent, or Firm* — Honigman LLP

(57) ABSTRACT

The invention relates to a single unit dose of a dengue vaccine composition and methods and uses for preventing dengue disease and methods for stimulating an immune response to all four dengue virus serotypes in a subject or subject population. The unit dose of a dengue vaccine composition includes constructs of each dengue serotype, such as TDV-1, TDV-2, TDV-3 and TDV-4, at various concentrations in order to improve protection from dengue infection.

21 Claims, 13 Drawing Sheets

Specification includes a Sequence Listing.

(56) References Cited

FOREIGN PATENT DOCUMENTS

| | | | |
|---|---|---|---|
| CN | 1012385144 | A | 8/2008 |
| CN | 101560520 | A | 10/2009 |
| CN | 101657463 | A | 2/2010 |
| CN | 102711817 | A | 10/2012 |
| CN | 104736568 | A1 | 6/2015 |
| DE | 29810020 | U1 | 6/2008 |
| EP | 1159968 | A1 | 12/2001 |
| EP | 2353609 | A1 | 8/2011 |
| EP | 15306101.5 | | 7/2015 |
| EP | 3620174 | A1 | 3/2020 |
| EP | 3892737 | A1 | 10/2021 |
| JP | H05276941 | A | 10/1993 |
| JP | 2003-523189 | A | 8/2003 |
| JP | 2016-513970 | A | 5/2016 |
| KR | 10- 2008-0018271 | A | 2/2008 |
| TW | 200740458 | A | 11/2007 |
| TW | 1726312 | B | 3/2014 |
| WO | 1990001946 | A1 | 3/1990 |
| WO | 1992003545 | A1 | 3/1992 |
| WO | 1993006214 | A1 | 4/1993 |
| WO | 1996040933 | A1 | 12/1996 |
| WO | 1998037911 | A1 | 9/1998 |
| WO | 1999063095 | A1 | 12/1999 |
| WO | 0139802 | A1 | 6/2001 |
| WO | 2001060847 | A2 | 8/2001 |
| WO | 2001060847 | A3 | 4/2002 |
| WO | 2002072036 | A2 | 9/2002 |
| WO | 2002072036 | A3 | 5/2003 |
| WO | 2003101397 | A2 | 12/2003 |
| WO | 2006134443 | A1 | 12/2006 |
| WO | 2009048658 | A9 | 6/2009 |
| WO | 2009139725 | A1 | 11/2009 |
| WO | 2010003670 | A1 | 1/2010 |
| WO | 2010141386 | A1 | 12/2010 |
| WO | 2011038473 | A1 | 4/2011 |
| WO | 2012177970 | A1 | 12/2012 |
| WO | 2013063248 | A1 | 5/2013 |
| WO | 2013188315 | A1 | 12/2013 |
| WO | 2014016360 | A1 | 1/2014 |
| WO | 2014016362 | A1 | 1/2014 |
| WO | 2014074912 | A1 | 5/2014 |
| WO | 2014093182 | A1 | 6/2014 |
| WO | 2014150939 | A2 | 9/2014 |
| WO | 2016034629 | A1 | 3/2016 |
| WO | 2017005652 | A1 | 1/2017 |
| WO | 2017005654 | A1 | 1/2017 |
| WO | 2017041156 | A1 | 3/2017 |
| WO | 2017179017 | A1 | 10/2017 |
| WO | 2018027075 | A1 | 2/2018 |
| WO | 2018052375 | A1 | 3/2018 |
| WO | 2019077622 | A1 | 4/2019 |

OTHER PUBLICATIONS

Roehrig et al., "Guidelines for Plaque-Reduction Neutralization Testing of Human Antibodies to Dengue Viruses," Viral Immunology, Jun. 1, 2008, vol. 21, No. 2, pp. 123-132.
Rupp et al., "Safety and immunogenicity of different doses and schedules of a live attenuated tetravalent dengue vaccine (TDV) in healthy adults: A Phase 1b randomized study," Vaccine, Nov. 1, 2015, vol. 33, No. 46, pp. 6351-6359.
Saez-Llorens et al., "Immunogenicity and safety of one versus two doses of tetravalent dengue vaccine in healthy chil-dren aged 2-17 years in Asia and Latin America: 18-month interim data from a phase 2, randomised, placebo-controlled study," Lancet Infect Dis, Nov. 6, 2017, vol. 18, pp. 162-170.
Schilling et al., "Coadministration of a 9-Valent Human Papillomavirus Vaccine With Meningococcal and Tdap Vaccines," Pediatrics, Sep. 1, 2015, vol. 136, No. 3, pp. e563-e572.
Sela, Michael, "The Choice of Carrier." In Synthetic Vaccines vol. I, R. Amon, (ed) CRC Press Inc., Boca Raton, FL. Chapter 6, 1987, pp. 83-92.
Sirivichayakul et al., "Safety and immunogenicity of a Tetravalent Dengue Vaccine Candidate in Healthy Children and Adults in Dengue-Endemic Regions: A Randomized, Placebo-Controlled Phase 2 Study," Journal of Infectious Diseases, Dec. 23, 2015, vol. 213, No. 10, pp. 1562-1572.
Sridhar et al., "Effect of Dengue Serostatus on Dengue Vaccine Safety and Efficacy," New England Journal of Medicine, Jul. 26, 2018, vol. 379, No. 4, pp. 327-340.
Stanaway et al., "The global burden of dengue: an analysis from the Global Burden of Disease Study 2013," Lancet Infect Dis., Jun. 16, 2016, vol. 16, No. 6, pp. 712-723.
Stocks et al: "Signal Peptidase Cleavage at the Flavivirus C-prM Junction: Dependence on the Viral NS2B-3 Protease for Efficient Processing Requires Determinants in C, the Signal Peptide, and prM," Journal Of Virology, LNKDPUBMED: 9499070, Mar. 1998, Mar. 1998 (Mar. 1998), vol. 72, No. 3, pp. 2141-2149.
Timiryasova et al., "Optimization and Validation of a Plaque Reduction Neutralization Test for the Detection of Neutraliz-ing Antibodies to Four Serotypes of Dengue Virus Used in Support of Dengue Vaccine Development," American Journal Of Tropical Medicine & Hygiene, May 1, 2013, vol. 88, No. 5, pp. 962-970.
Trent Dennis W. et al., "Partial Nucleotide Sequence of St. Louis Encephalitis Virus RNA: Structural Proteins, NS1, ns2a, and ns2b," Virology, 1987, vol. 156, pp. 293-304.
Trent Dennis W. et al., "Recombinant dengue virus vaccines." In: Dengue and Dengue Hemorrhagic Fever. D.J. Gubler and G. Kuno (eds.). CAB International, New York, NY Chapter 18, 1997, pp. 379-403.
Tsai et al "Japanese Encephalitis Vaccines," In Vaccines, (3rd edition) Plotkin and Orenstein (eds), W.B. Saunders Company, Philadelphia, PA. Chapter 27, 1999, pp. 672-710.
Update: "Surveillance for Weste Nile Virus in Overwintering Mosquitoes—New York, 2000," Morb. Mortal. Wkly. Rep., Mar. 10, 2000, vol. 49, No. 09, pp. 178-179.
Update: "West Nile Virus Activity—Northeastern United States, 2000," Morb. Mortal. Wkly. Rep., Sep. 15, 2000, vol. 49, No. 36, pp. 820-822.
Vesikari et al., "Safety and Immunogenicity of a Booster Dose of the 1O-Valent Pneumococcal Nontypeable Haemophilus influenza Protein D Conjugate Vaccine Coadministered With Measles-Mumps-Rubella-Varicella Vaccine in Children Aged 12to 16 Months," Pediatric Infectious Disease Journal, Jun. 1, 2010, vol. 29, No. 6, pp. e47-e56.
Villar et al., "Safety and immunogenicity of a recombinant tetravalent dengue vaccine in 9-16 year olds: a randomized, controlled, phase II trial in Latin America," Pediatr Infect Dis J, Oct. 2013, vol. 32, No. 10, pp. 1102-1109.
Wang et al., "Immune Response to Neonatal Genetic Immunization," Virology, 1997, vol. 228, pp. 278-284.
Wichmann et al., "Live-attenuated tetravalent dengue vaccines: The needs and challenges of post-licensure evaluation of vaccine safety and effectiveness," Vaccine, Oct. 1, 2017, vol. 35, No. 42, pp. 5535-5542.
Wilder-Smith et al., "Age specific differences in efficacy and safety for the CYD-tetravalent dengue vaccine," Expert Re-view of Vaccines, Apr. 2, 2016, vol. 15, No. 4, pp. 437-441.
World Health Organization, "Dengue vaccine research: Immunization, Vaccines and Biologicals" www.who.int/immunization/research/development/dengue_vaccines/en/, Sep. 12, 2018, 3 pages.
World Health Organization, "Guidelines for plaque reduction neutralization testing of human antibodies to dengue viruses," Immunization, Vaccines and Biologicals, Sep. 21, 2007 pp. 1-36, Retrieved from the internet [retrieved on Oct. 29, 2018].
World Health Organization, "Table 3: Recommendations for Interrupted or Delayed Routine Immunization—Sum-mary of WHO position papers," Aug. 2018, 10 pages.
World Health Organization, Dengue Vaccine Research, website page at www.who.int/immunuzation/research/development/dengue_vaccines/en, last updated Dec. 5, 2017, 3 pages.
World Health Organization, Recommendations for all immunization programmes, Aug. 1, 2018, Retrieved from the Internet, 10 pages.
World Health Organization, Updated Questions and Answers related to the dengue vaccine Dengvaxia and its use, website page at

(56) References Cited

OTHER PUBLICATIONS www.who.int/immunization/diseases/dengue/q_and_a_dengue_vaccine_dengvaxia_use/en/published Dec. 22, 2017, 7 pages.
Butrapet, S. et al., "Chimeric Dengue Type 2/Type 1 Viruses Induce Immune Responses in Cynomolgus Monkeys," Southeast Asian J. Trap. Med. Public Health, Sep. 2002, vol. 33, No. 3, pp. 589-599.
Zhang et al., "Passive Protection of Mice, Goats, and Monkeys Against Japanese Encephalitis With Monoclonal Antibodies," 1989, J. Med. Virol., vol. 29, pp. 133-138.
Villar, L. et al., "Efficacy of a Tetravalent Dengue Vaccine in Children in Latin America," New England Journal of Medicine, Jan. 8, 2015, vol. 372, No. 2, pp. 113-123.
Aberle, J. et al., "A DNA Immunization Model Study with Constructs Expressing the Tick-Borne Encephalitis Virus Envelope Protein E in Different Physical Forms," Journal of Immunology, 1999, vol. 163, pp. 6756-6761.
Allison, S. et al., "Synthesis and Secretion of Recombinant Tick-Borne Encephalitis Virus Protein E in Soluble and Particulate Form," Journal of Virology, Sep. 1995, vol. 69, No. 9, pp. 5816-5820.
Alvarez, R. et al., "A Phase I Study of Recombinant Adenovirus Vector-Mediated Delivery of an Anti-erbB-2 Single-Chain (sFv) Antibody Gene for Previously Treated Ovarian and Extraovarian Cancer Patients," Mary Ann Liebert, Inc., Human Gene Therapy, Jan. 20, 1997, vol. 8, pp. 229-242.
Anderson, J. et al., "Isolation of West Nile Virus from Mosquitoes, Crows, and a Cooper's Hawk in Connecticut", Ovid: Anderson: Science, vol. Dec. 17, 1999, vol. 286(5448), pp. 2331-2333.
Arroyo, J. et al., Molecular Basis for Attenuation of Neurovirulence of a Yellow Fever Virus/Japanese Encephalitis Virus Chimera Vaccine (ChimeriVax-JE), Journal of Virology, Jan. 2001, vol. 75, No. 2, pp. 934-942.
Asnis, D. et al., "The West Nile Virus Outbreak of 1999 in New York: The Flushing Hospital Experience," Clinical Infectious Diseases, 2000, vol. 30, pp. 413-418.
Azevedo, V. et al., "Main features of DNA-based immunization vectors," Brazilian Journal of Medical and Biological Research 1999, vol. 32, No. 2, pp. 147-153.
Bhamarapravati, N. et al., "Immunization with a live attenuated dengue-2-virus candidate vaccine (?16681-PDK 53 : clinical, immunological and biological responses in adult volunteers," Bulletin of the World Health Organization, 1987, vol. 65, No. 2, pp. 189-195.
Bhamarapravati, N. et al., "Live attenuated tetravalent dengue vaccine," Cab International, Wallingford, OX, UK, 1997, Dengue and Dengue Hamorrhagic Fever, D.J. Gubler and G. Kuno (ed), Chapter 17, pp. 367-377.
Bhamarapravati, N. et al., "Live attenuated tetravalent dengue vaccine," Vaccine, 2000, vol. 18, pp. 44-47.
Bhatt, T. et al., "Growth characteristics of the chimeric Japanese encephalitis virus vaccine candidate, chimeriVax-je (Yf/Je SA14-14-2), in culex tritaeniorhynchus, aedes albopictus, and aedes aegypti mosquitoes," Am. J. Trop. Med. Hyg., 2000, vol. 62, No. 4, pp. 480-484.
Blok, J. et al., "Comparison of a Dengue-2 Virus and Its Candidate Vaccine Derivative: Sequence Relationships with the Flaviviruses and Other Viruses," Virology, 1992, vol. 187, pp. 573-590.
Bray, M. et al., "Construction of intertypic chimeric dengue viruses by substitution of structural protein genes," Proc. Nat. Acad. Sci. USA, Medical Sciences, Nov. 1991, vol. 88, pp. 10342-10346.
Bray, M. et al., "Mice Immunized with Recombinant Vaccinia Virus Expressing Dengue 4 Virus Structural Proteins with or without Nonstructural Protein NS1 are Protected against Fatal Dengue Virus Encephalitis," Journal of Virology, Jun. 1989, vol. 63, No. 6, pp. 2853-2856.
Bray, M. et al., "Monkeys Immunized with Intertypic Chimeric Dengue Viruses Are Protected against Wild-Type Virus Challenge," Journal of Virology, Jun. 1996, vol. 70, No. 6, pp. 4162-4166.
Butrapet, S. et al., "Attenuation markers of a candidate dengue type 2 vaccine virus, strain 16681 (PDK-53), are defined by mutations in the 5' noncoding region and nonstructural proteins 1 and 3," J. Virol., Apr. 2000, vol. 74, No. 7, pp. 3111-3119.
Kelly, E. et al., "Evolution of attenuating mutations in dengue-2 strain S16803 PDK50 vaccine and comparison of growth kinetics with parent virus," Virus Genes, 2011, vol. 43, pp. 18-26.
Khin, M. et al., "Infection, Dissemination, Transmission, and Biological Attributes of Dengue-2 PDK53 Candidate Vaccine Virus after Oral Infection in Aedes Aegypti," Am. J. Trop. Med. Hyg., 1994, vol. 51, No. 6, pp. 864-869.
Kimura-Kuroda, J. et al., "Topographical Analysis of Antigenic Determinants on Envelope Glycoprotein V3 (E) of Japanese Encephalitis Virus, Using Monoclonal Antibodies" Journal of Virology, Jan. 1983, vol. 45, No. 1, pp. 124-132.
Kimura-Kuroda, J. et al., "Antigenic Comparison of Envelope Protein E between Japanese Encephalitis Virus and Some Other Flaviviruses Using Monoclonal Antibodies," J. Gen. Virol., 1986, vol. 67, pp. 2663-1672.
Kinney, R. et al. "Construction of Infectious cDNA Clones for Dengue 2 Virus: Strain 16681 and Its Attenuated Vaccine Derivative, Strain PDK-531" Virology, 1997, vol. 230, No. 2, pp. 300-308.
Kinney, R. et al., "Development of New Vaccines against Dengue Fever and Japanese Encephalitis," Intervirology, 2001, vol. 44, pp. 176-197.
Klinman, D. et al., "CpG motifs as immune adjuvants," Vaccine, 1999, vol. 17, pp. 19-25.
Kochel, T. et al., "Inoculation of plasmids expressing the dengue-2 envelope gene elicit neutralizing antibodies in mice," Vaccine. 1997, vol. 15, No. 5, pp. 547-552.
Köhler, G. et al., "Continuous cultures of fused cells secreting antibody of predefined specificity," Nature, Aug. 7, 1975, vol. 256, pp. 495-497.
Konishi, E. et al., "Avipox virus-vectored Japanese encephalitis virus vaccines: use as vaccine candidates in combination with purified subunit immunogens," Vaccine, 1994, vol. 12, No. 7, pp. 633-638.
Konishi, E. et al., "Comparison of Protective Immunity Elicited by Recombinant Vaccinia Viruses That Synthesize E or NS1 of Japanese Encephalitis Virus," Virology, 1991, vol. 185, pp. 401-410.
Konishi, E. et al., "Generation and Characterization of a Mammalian Cell Line Continuously Expressing Japanese Encephalitis Virus Subviral Particles," Journal of Virology, Mar. 2001, vol. 75, No. 5, pp. 2204-2212.
Konishi, E. et al., "Induction of Protective Immunity against Japanese Encephalitis in Mice by Immunization with a Plasmid Encoding Japanese Encephalitis Virus Premembrane and Envelope Genes," Journal of Virology, Jun. 1998, vol. 72, No. 6, pp. 4925-4930.
Konishi, E. et al., "Mice Immunized with a Subviral Particle Containing the Japanese Encephalitis Virus prM/M and E Proteins Are Protected from Lethal JEV Infection," Virology, 1992, vol. 188, pp. 714-720.
Kozak, M. "Circumstances and Mechanisms of Inhibition of Translation by Secondary Structure in Eucaryotic mRNAs," Molecular and Cellular Biology, Nov. 1989, vol. 9, No. 11, pp. 5134-5142.
Kuno, G. et al., "Phylogeny of the Genus Flavivirus," Journal of Virology, Jan. 1998, vol. 72, No. 1, pp. 73-83.
Laemmli, U., "Cleavage of Structural Proteins during the Assembly of the Head of Bacteriophage T4," Nature, Aug. 15, 1970, vol. 227, pp. 680-685.
Lai, C. et al., "Evaluation of molecular strategies to develop a live dengue vaccine," Clinical and Diagnostic Virology, 1998, vol. 10, pp. 173-179.
Lai, C. et al., "Immunization of Monkeys with Baculovirus Recombinant-expressed Dengue Envelope and NS1 Glycoproteins Induces Partial Resistance to Challenge with Homotypic Dengue Virus," Vaccines 90: Modern approaches to New Vaccines including Prevention of AIDS, Cold Spring Harbor, NY,1990, pp. 119-124.
Liljeström, P. et al., "In Vitro Mutagenesis of a Full-Length eDNA Clone of Semliki Forest Virus: the Small 6,000-Molecular-Weight Membrane Protein Modulates Virus Release," Journal of Virology, Aug. 1991, vol. 65, No. 8, pp. 4107-4113.
Lin, Y. et al., "DNA Immunization with Japanese Encephalitis Virus Nonstructural Protein NS1 Elicits Protective Immunity in Mice," Journal of Virology, Jan. 1998, vol. 72, No. 1, pp. 191-200.

(56) References Cited

OTHER PUBLICATIONS

Mackow, E. et al., "The Nucleotide Sequence of Dengue Type 4 Virus: Analysis of Genes Coding for Nonstructural Proteins," Virology, 1987, vol. 159, pp. 217-228.
Mandl, C. et al., "Complete Genomic Sequence of Powassan Virus: Evaluation of Genetic Elements in Tick-Borne versus Mosquito-Borne Flaviviruses," Virology, 1993, vol. 194, pp. 173-184.
Martin, D. et al., "Standardization of Immunoglobulin M Capture Enzyme-Linked Immunosorbent Assays for Routine Diagnosis of Arboviral Infections," Journal of Clinical Microbiology, May 2000, vol. 38, No. 5, pp. 1823-1826.
Mason, P. et al., "Japanese Encephalitis Virus-Vaccinia Recombinants Produce Particulate Forms of the Structural Membrane Proteins and Induce High Levels of Protection against Lethal JEV infection," Virology, 1991, vol. 180, pp. 294-305.
Mason, P. et al., "Sequence of the Dengue-1 Virus Genome in the Region Encoding the Three Structural Proteins and the Major Nonstructural Protein NS1," Virology, 1987, vol. 161, pp. 262-267.
Men, R. et al., "Dengue Type 4 Virus Mutants Containing Deletions in the 3' Noncoding Region of the RNA Genome: Analysis of Growth Restriction in Cell Culture and Altered Viremia Pattern and Immunogenicity in Rhesus Monkeys," Journal of Virology, Jun. 1996, vol. 70, No. 6, pp. 3930-3937.
Midgley, C.M., et al., Men, R. et al., "Dengue Type 4 Virus Mutants Containing Deletions in the 3' Noncoding Region of the RNA Genome: Analysis of Growth Restriction in Cell Culture and Altered Viremia Pattern and Immunogenicity in Rhesus Monkeys," Journal of Virology, Jun. 1996, vol. 70, No. 6, pp. 3930-3937. Structural analysis of a dengue cross-reactive antibody complexed with envelope domain III reveals the molecular basis of cross-reactivity. J Immunol. May 15, 2012; 188(10): 4971-4979.
Mir, L. et al., "High-efficiency gene transfer into skeletal muscle mediated by electric pulses," Applied Biological Sciences, Proc. Natl. Acad. Sci. USA, Apr. 1999, vol. 96, pp. 4262-4267.
Monath, T. et al., "Recombinant, chimeric live, attenuated vaccine (ChimeriVax) incorporating the envelope genes of Japanese encephalitis (SA14-14-2) virus and the capsid and nonstructural genes of yellow fever (17D) virus is safe, immunogenic and protective in non-human primates," Vaccine, 1999, vol. 17pp. 1869-1882.
NCT02993757 "Immunogenicity and Safety of a Tetravalent Dengue Vaccine Administered Concomitantly or Sequentially With Gardasil," ClinicalTrials.gov, Apr. 5, 2018, Retrieved from the Internet Oct. 25, 2018, 10 pages.
NCT03525119 "Immunogenicity and Safety of Tetravalent Dengue Vaccine (TDV) Co-administered With an Hepatitis A Virus Vaccine," ClinicalTrials.gov, May 15, 2018, Retrieved from the Internet Oct. 26, 2018, 12 pages.
Nitayaphan, S. et al., "Nucleotide Sequence of the Virulent SA-14 Strain of Japanese Encephalitis Virus and Its Attenuated Vaccine Derivative, SA-14-14-2," Virology, 1990, vol. 177, pp. 541-552.
Nowak, T. et al., "Analysis of the Terminal 4 Sequences of West Nile Virus Structural Proteins and of the in Vitro Translation of these Proteins Allow the Proposal of a Complete Scheme of the Proteolytic Cleavages Involved in Their Synthesis," Virology, Academic Press. Orlando, Apr. 1, 1989, vol. 169, No. 2, pp. 365-376.
Osatomi, K. et al., "Complete Nucleotide Sequence of Dengue Type 3 Virus Genome RNA," Virology, 1990, vol. 176, pp. 643-647.
Osorio, J. et al "Efficacy of a Tetravalent Chimeric Dengue Vaccine (DENVax) in Cynomolgus Macaques," Am. J. Trop. Med. Hyg., 2011, vol. 84, No. 6, pp. 978-987.
Osorio, J. et al., "Development of DENVax: A chimeric dengue-2 PDK-53-based tetravalent vaccine for protection against dengue fever," Vaccine, Jul. 11, 2011, vol. 29, No. 42, pp. 7251-7260.
Phillpotts, R. et al., "Immunisation with DNA polynucleotides protects mice against lethal challenge with St. Louis encephalitis virus." Arch Virol., 1996, vol. 141, pp. 743-749.
Pletnev, A. et al., "Chimeric Tick-Borne Encephalitis and Dengue Type 4 Viruses: Effects of Mutations on Neurovirulence in Mice." J. Virol., Aug. 1993, vol. 67, No. 8, pp. 4956-4963.
Pletnev, A. et al., "Construction and characterization of chimeric tick-borne encephalitis/ dengue type 4 viruses." Proc. Nat. Acad. Sci. USA, Medical Sciences, Nov. 1992, vol. 89: pp. 10532-10536.
Press Release: "Takeda's Dengue Vaccine Candidate Meets Primary Endpoint in Pivotal Phase 3 Efficacy Trial," Jan. 29, 2019, 4 pages.
Puri, B. et al., "Molecular analysis of dengue virus attenuation after serial passage in primary in dog kidney cells." J. Gen Virol., 1997, vol. 78, pp. 2287-2291.
Putnak, et al., "Comparative Evaluation of Three Assays for Measurement of Dengue Virus Neutralizing Antibodies," The American Journal of Tropical Medicine and Hygiene, 2008, vol. 79, No. 1, pp. 115-122.
Rice, C. et al., "Nucleotide Sequence of Yellow Fever Virus: Implications for Flavivirus Gene Expression and Evolution," Science, 1985, vol. 229, pp. 726-733.
Rice, C. et al., "Transcription of Infectious Yellow Fever RNA From Full-Length eDNA Templates Produced by In Vitro Ligation," The New Biologist, Dec. 1989, vol. 1, No. 3, pp. 285-296.
Roehrig, J. et al., "Identification of Epitopes on the E Glycoprotein of Saint Louis Encephalitis Virus Using Monoclonal Antibodies." Virology, 1983, vol. 128, pp. 118-126.
Roehrig, J. et al., "Synthetic Peptides Derived from the Deduced Amino Acid Sequence of the E-Glycoprotein of Murray Valley Encephalitis Virus Elicit Antiviral Antibody," Virology, 1989, vol. 171, pp. 49-60.
Sabchareon, A. et al., "Safety and Immunogenicity of Tetravalent Live-Attenuated Dengue Vaccines in Thai Adult Volunteers: Role of Serotype Concentration, Ratio, and Multiple Doses," Am. J. Trop. Med. Hyg., 2002, vol. 66, No. 3, pp. 264-272.
Sabchareon, et al., "Protective efficacy of the recombinant, live-attenuated, CYD tetravalent dengue vaccine in Thai schoolchildren: a randomised, controlled phase 2b trial," The Lancet, Nov. 3, 2012, vol. 380, pp. 1559-1567.
Saez-Llorens et al., "Safety and immunogenicity of one versus two doses of Takeda's tetravalent dengue vaccine in chil-dren in Asia and Latin America: interim results from a phase 2, randomized, placebo-controlled study," Lancet Infectious Disease, Elsevier Ltd, US, Mar. 30, 2017, vol. 17, No. 6, pp. 615-625.
*AK Steel Corporation* v. *Sollac and Ugine*; United States Court of Appeals for the Federal Circuit; http://laws.lp.findlaw.com/fed/031074.html (Sep. 24, 2003), 8 pages.
Anonymous, "Guidelines for plaque reduction neutralization testing of human antibodies to dengue viruses," Sep. 21, 2007 (Sep. 21, 2007), p. 1-36,; Retrieved from the Internet:; URL:http://apps.who.int/iris/bitstream/handle/10665/69687/who_ivb_07.07_eng.pdf;jsessionid=E54172674C933124415AFC5BB972E6B9?sequence=1; XP055519586.
Arnon Ruth "Synthetic Vaccines vol. I" CRC Press, Inc. Boca Raton, Florida pp. 83-92.
Beatty et al., "Dengue virus NS1 triggers endothelial permeability and vascular leak that is prevented by NS1 vaccination," Sci. Transl. Med. Sep. 9, 2015, vol. 7, No. 304, pp. 1-13.
Benjamin, Sarah, "Optimization and analysis of live attenuated denvax-4 constructs," Masters Thesis: Colorado State University, Summer 2013, 97 pages.
Bhatt et al., "The global distribution and burden of dengue," Nature, Apr. 25, 2013, vol. 496 (7446), pp. 504-507.
Biswal et al., "Efficacy of a Tetravalent Dengue Vaccine in Healthy Children Aged 4-16 years: a randomised, placebo-controlled, phase 3 trial," Lancet, Mar. 17, 2020, vol. 395, pp. 1423-1433.
Biswal et al., "Efficacy of a Tetravalent Dengue Vaccine in Healthy Children and Adolescents," New England Journal of Medicine, Nov. 21, 2019, vol. 381, No. 21, pp. 2009-2019.
Biswal Presentation "Takeda Tetravalent Dengue Vaccine (TDV) Candidate: An Update (DEN-204)," Asia Dengue Summit, Jan. 13, 2016, 17 pages.
Brewoo et al., "Immunogenicity and efficacy of chimeric dengue vaccine (DENVax) formulations in interferon-deficient AG129 mice," Vaccine, Feb. 1, 2012, vol. 30, No. 8, pp. 1513-1520.
Capeding et al., "Clinical efficacy and safety of a novel tetravalent dengue vaccine in healthy children in Asia: a phase 3, randomised, observer-masked, placebo-controlled trial," Lancet, 2014, vol. 384, pp. 1358-1365.

(56) References Cited

OTHER PUBLICATIONS

Chu et al., "CD8+ T-cell Responses in Flavivirus-Naïve Individuals Following Immunization with a Live-Attenuated Tetrava-lent Dengue Vaccine Candidate" Major Article, JID, Nov. 15, 2015, vol. 212, pp. 1618-1628.
Crevat et al., "First Experience of Concomitant Vaccination Against Dengue and MMR in Toddlers," Pediatric Infectious Disease Journal, Aug. 1, 2015, vol. 34, No. 8, pp. 884-892.
Database UniProt Accession No. D2KQW7 Database UniProt SubName: Full=Polyprotein (ECO:0000313 EMBL: ADA00411.1); XP002731516, retrieved from EBI accession No. UNIPROT:D2KQW7, http://ibis/exam/dbfetch.jsp?id=UNIPROT:D2KQW7 Feb. 9, 2010, 2 pages.
Database UniProt Accession No. P29991 "RecName: Full=Genome polyprotein; Contains: RecName: Full=Capsid protein C; AltName: Full=Core protein; Contains: RecName: Full=prM; Contains," XP002731514, retrieved from EBI accession No. UNIPROT: P29991; Apr. 1, 1993 http://ibis/exam/dbfetch.jsp?id=UNIPROT%3AP29991 .6 pages.
Database UniProt Accession No. Q9WLZ7, XP-002731515, http://ibis/exam/dbfetch.jsp?id=UNIPROT%3AQ9WLZ7, 2 pages.
DeLaBarrera et al., "Comparative Evaluation of Three Assays for Measurement of Dengue Virus Neutralizing Antibodies," Dengue Virus NS1 Disrupts the Endothelial Glycocalyx, Leading to Hyperpermeability, Jul. 1, 2008, vol. 79, No. 1, pp. 115-122.
Dubey et al., "Immunogenicity and safety of a tetravalent dengue vaccine in healthy adults in India: A randomized, observer-blind, placebo-controlled phase II trial," Human Vaccines and Immunotherapeutics, Aug. 20, 2015, vol. 12, No. 2, pp. 512-518.
Endy, "Dengue Human Infection Model Performance Parameters," Journal Infectious Diseases, 2014, vol. 209 (Suppl. 2), pp. S56-S60.
European Search Report dated Feb. 12, 2019 for corresponding EP application 18192701.3, 22 pages.
European Search Report dated May 3, 2019 for corresponding EP application 19161184.7, 16 pages.
European Search Report dated Nov. 13, 2018 for corresponding EP application 18192701.3, 20 pages.
European Search Report dated Nov. 13, 2018 for corresponding EP application 18192711.2, 16 pages.
European Search Report dated Nov. 13, 2018 for corresponding EP application 18192717.9, 16 pages.
European Search Report dated Nov. 13, 2018 for corresponding EP application 18192787.2, 18 pages.
European Search Report dated Nov. 13, 2018 for corresponding EP application 18192793.0, 16 pages.
European Search Report dated Nov. 13, 2018 for corresponding EP application 18192800.3, 18 pages.
European Search Report dated Nov. 13, 2018 for corresponding EP application 18192814.4, 16 pages.
European Search Report dated Nov. 29, 2018 for corresponding EP application 18192776.5, 17 pages.
Gentry et al., "Identification of distinct antigenic determinants on dengue-2 virus using monoclonal antibodies," May 1982, Am. J. Trop. Med. Hyg., vol. 31, No. 3, Pt. 1, pp. 548-555.
Glasner et al., "Dengue virus NS1 cytokine-independent vascular leak is dependent on endothelial glycocalyx components," PloS Pathog., Nov. 9, 2017, vol. 13, No. 11, pp. 1-22.
Hadinegoro et al., "Efficacy and Long-Term Safety of a Dengue Vaccine in Regions of Endemic Disease," New England Journal of Medicine, Sep. 24, 2015, vol. 373, No. 13, p. 1195-1206.
Henchal et al., "Epitopic Analysis of Antigenic Determinants on the Surface of Dengue-2 Virions Using Monoclonal Antibod-ies," Am. J. Trop. Med. Hyg., 1985, vol. 34, No. 1, pp. 162-169.
Jackson et al., "A phase 1 study of safety and immunogenicity following intradermal administration of a tetravalent dengue vaccine candidate," Vaccine, May 19, 2018, vol. 36, pp. 3976-3983.
King et al., "Simultaneous administration of childhood vaccines: An important public health policy that is safe and effica-cious," Pediatric Infectious Disease Jour, Lippincott Williams & Wilkins, US, Jan. 1, 1994, vol. 13, No. 5, pp. 394-407.
Lanciotti R. et al., "Origin of the West Nile Virus Responsible for an Outbreak of Encephalitis in the Northeastern United States," Science, Dec. 17, 1999, vol. 286, pp. 2333-2337.
Lorenzato Presentation "Update of Takeda's dengue candidate vaccine development programme (DEN-204)," Brazilian Tropical Medicine Congress (Medtrop) Sep. 5, 2018, 29 pages.
López et al., "Immunogenicity and Safety of Yellow Fever Vaccine (Stamaril) When Administered Concomitantly With a Tet-ravalent Dengue Vaccine Candidate in Healthy Toddlers at 12-13 Months of Age in Colombia and Peru :A Randomized Trial," Pediatric Infectious Disease Journal, Oct. 1, 2016, vol. 35, No. 10, pp. 1140-1147.
López-Medina et al., ""Effcacy of a Dengue Vaccine Candidate (TAK-003) in Healthy Children and Adolescents 2 Years after Vaccination,"" The Journal of Infectious Diseases, 2021, pp. 1-12.
Mcintosh Presentation "Takeda vacuna contra el dengue," ALAPE Sep. 5-8, 2018, Luque Asunción, Paraguay, 27 pages.
Melo et al., "Immunogenicity and Safety of a Booster Injection of DTap-IPV//Hib (Pentaxim) Administered Concomitantly With Tetravalent Dengue Vaccine in Healthy Toddlers 15-18 Months of Age in Mexico : A Randomized Trial," Pediatric Infec-tious Disease Journal, Jun. 1, 2017, vol. 36, No. 6, pp. 602-608.
Mullard, "Sanofi's dengue vaccine rounds final corner," Nature Reviews Drug Discovery, Nov. 2014, vol. 13, pp. 801-802.
NCT02425098 "Safety and Immunogenicity With Two Different Serotype 2 Potencies of Takeda's Tetravalent Dengue Vac-cine Candidate (TDV) in Adults in Singapore," Clinical Trials.gov, Jul. 16, 2019—DEN 205, Retrieved from internet Jul. 4, 2019, 12 pages.
Novello et al., "Update: West Nile Virus Activity—Northeastern United States, 2000," http://www.cdc.gov/mmwr/preview/mmwrhtml/mm4936a4.htm MMWR Weekly Sep. 15, 2000 / vol. 49, No. 36, pp. 820-822.
Osatomi et al., "Nucleotide Sequence of Dengue Type 3 Virus Genomic RNA Encoding Viral Structural Proteins," Virus Genes, Oct. 1988, vol. 2, No. 1, pp. 99-108. Abstract Only.
Osorio et al., "A recombinant, chimeric tetravalent dengue vaccine candidate based on a dengue virus serotype 2 back-bone," Expert Review Of Vaccines, Apr. 2, 2016, vol. 15, No. 4, pp. 497-508.
Osorio et al., "Safety and immunogenicity of a recombinant live attenuated tetravalent dengue vaccine (DENVax) in fla-vivirus-naive healthy adults in Colombia: a randomised, placebo-controlled, phase 1 study," Lancet Infectious Diseases, Sep. 1, 2014, vol. 14, No. 9, pp. 830-838.
Pinheiro-Michelsen et al., "Anti-dengue Vaccines: From Development to Clinical Trials," Frontiers in Immunology, Jun. 18, 2020, vol. 11, Art. 1252, pp. 1-18.
Press Release: "Potential Impact of Takeda's Dengue Vaccine Candidate Reinforced by Long-Term Safety and Efficacy Results," May 22, 2021, 5 pages.
Press Release: "Takeda Begins Regulatory Submissions for Dengue Vaccine Candidate in EU and Dengue-Endemic Countries," Mar. 25, 2021, 4 pages.
Sato, Y. et al., "Immunostimulatory DNA Sequences Necessary for Effective Intradermal Gene Immunization," Science, Jul. 19, 1996, vol. 273, No. 5273, pp. 352-354.
Seeger, C. et al., "The cloned genome of ground squirrel hepatitis virus is infectious in the animal," Proc. Nat. Acad. Sci. USA, Medical Sciences, Sep. 1984, vol. 81, pp. 5849-5852.
Smithburn, K. et al., "A Neurotropic Virus Isolated From The Blood Of a Native Of Uganda," Am. J. Trop. Med. Hyg., 1940, vol. 20, pp. 471-492.
Sumiyoshi, H. et al., "Complete Nucleotide Sequence of Japanese Encephalitis Virus Genome RNA," Virology, 1987, vol. 161, pp. 497-510.
Takeda Vaccines, Anonymous, "Immunogenicity and Safety of Tetravalent Dengue Vaccine (TDV) Co-administered With an Hepatitis A Virus Vaccine", May 15, 2018, pp. 1-12.
Tardei, G. et al., "Evaluation of Immunoglobulin M (IgM) and IgG Enzyme Immunoassays in Serologic Diagnosis of West Nile Virus Infection," J. Clin. Microbiol. Jun. 2000, vol. 38, No. 6, pp. 2232-2239.
Troyer, J. et al., "A Live Attenuated Recombinant Dengue-4 Virus Vaccine Candidate With Restricted Capacity For Dissemination In

(56) References Cited

OTHER PUBLICATIONS

Mosquitoes And Lack Of Transmission From Vaccinees To Mosquitoes," Am. J. Trop. Med. Hyg., 2001, vol. 65, No. 5, pp. 414-419.
Tsai, T. et al., "Japanese Encephalitis Vaccines," In Vaccines, (2nd edition), Plotkin and Mortimer (eds.), W.B. Saunders Co., Philadelphia, PA. Chapter 24, 1994, pp. 671-713.
Van Der Most, R. et al., "Chimeric yellow fever/dengue virus as a candidate dengue vaccine: quantification of the dengue virus-specific CD8 T-cell response," Journal of Virology, Sep. 1, 2000 2(Sep. 1, 2000), vol. 74. No. 17, pp. 8094-8101.
Vaughn, D. et al., "Testing of dengue 2 live-attenuated vaccine (strain 16681 PDK 53) in ten American volunteers," Vaccine 1996, vol. 14 No. 4, pp. 329-336.
Venugopal, K. et al., "Immunity to St. Louis encephalitis virus by sequential immunization with recombinant vaccinia and baculovirus derived PrM/E proteins," Vaccine, 1995, vol. 13, No. 11, pp. 1000-1005.
Wallace, D. et al., Presentation: "Takeda's dengue vaccine candidate in children: one or two doses?", Abstract 5th Pan American Dengue Research Network Meeting,age Apr. 20-23, 2016, DEN-204, p. 86.
Wallace, D., Presentation: "Persistence of neutralizing antibodies one year after two doses of a candidate recombinant tetra-valent dengue vaccine in subjects aged from 1.5 to 45 years," ASTMH 64th Annual Meeting, Oct. 27, 2015, DEN-203, 2 pages.
Wolff, J. et al., "Long-term persistence of plasmid DNA and foreign gene expression in mouse muscle," Hum. Mol. Genet., 1992, vol. 1, No. 6, pp. 363-369.
Xie, X. et al., "Membrane Topology and Function of Dengue Virus NS2A Protein," Journal of Virology, Apr. 2013, vol. 87, No. 8, pp. 4609-4622.
Yamshchikov, V. et al., "Processing of the Intracellular Form of the West Nile Virus Capsid Protein by the Viral NS2B-NS3 Protease: an In Vitro Study," Journal of Virology, LNKDPUBMED:8057458, Sep. 1994, vol. 68, No. 9, pp. 5765-5771.
Yang, X. et al., "A p300/CBP-associated factor that competes with the adenoviral oncoprotein E1A," Nature, Jul. 25, 1996, vol. 382.
Yoksan, S. et al., "Dengue Virus Vaccine Development: Study on Biological Markers of Uncloned Dengue 1-4 Viruses Serially Passaged in Primary Kidney Cells," Arbovirus Research in Australia—Proceedings 4th Symposium, T. D. St. George, B.H. Kay, and J. Blok (eds.), CSIRO/QIMR, Brisbane 1986, pp. 35-38.
Zhang, Y. et al., "Immunization of Mice with Dengue Structural Proteins and Nonstructural Protein NS1 Expressed by Baculovirus Recombinant Induces Resistance to Dengue Virus Encephalitis," J. Viro., Aug. 1988, vol. 62, No. 8, pp. 3027-3031.
Zhao, B. et al., "Cloning Full-Length Dengue Type 4 Viral DNA Sequences: Analysis of Genes Coding for Structural Proteins," Virology, 1986, vol. 155, pp. 77-88.
Zhao, B. et al., "Expression of Dengue Virus Structural Proteins and Nonstructural Protein NS1 by a Recombinant Vaccinia Virus," Journal of Virology, Dec. 1987, vol. 61, No. 12, pp. 4019-4022.
Brito, Luis A., et al., "Vaccine adjuvant formulations: A pharmaceutical perspective," Seminars in Immunology, vol. 25, No. 2, pp. 130-145, Jan. 2, 2013.
Ginley, D.M., "The development of a performance test procedure and measurement technique in a batch system NBS IR 85-3030." National Institute of Standards and Technology (NIST), Jul. 1985, pp. 1-152, retrieved from the Internet Dec. 31, 1985.
Jianrong Tang; "Current status of research and development of new dengue vaccines"; Foreign Medical Sciences (Section of Biological Products for Prophylaxis, Diagnosis and Therapy), vol. 04; Aug. 10, 2002; Full text.
Pengfei Li & Shuo Shen; "Advances in Research of Dengue Virus Vaccines"; Progress in Microbiology and Immunology, vol. 06; Dec. 20, 2012; Full text.
CN Office Action + English translation for CN application 2023072602931350 dated Jul. 26, 2023.
US Office Action for U.S. Appl. No. 17/229,109, dated Sep. 7, 2023.
US Office Action for U.S. Appl. No. 17/478,537, dated Sep. 13, 2023.
Butrapet, S. et al., "Determining genetic stabilities of chimeric dengue vaccine candidates based on dengue 2 PDK-53 virus by sequencing and quantitative TaqMAMA," Journal of Virological Methods, 2005, vol. 131, No. 1, pp. 1-9.
Cahour, A. et al., "Growth-Restricted Dengue Virus Mutants Containing Deletions in the 5' Noncoding Region of the RNA Genome," Virology, 1995, vol. 207, pp. 68-76.
Calvert, A. et al., "Non-structural proteins of dengue 2 virus offer limited protection to interferon-deficient mice after dengue 2 virus challenge,", Journal of General Virology, vol. 87, 2006, pp. 339-346.
Caufour, A. et al., "Construction, characterization and immunogenicity of recombinant yellow fever 17D-dengue type 2 viruses," Virus Research, 2001, vol. 79, pp. 1-14.
Chambers, T. et al., "Flavivirus Genome Organization, Expression, and Replication," Annu. Rev. Microbiol. 1990, vol. 44, pp. 649-688.
Chambers, T. et al., "Yellow Fever Virus/Dengue-2 Virus and Yellow Fever Virus/Dengue-4 Virus Chimeras: Biological Characterization, Immunogenicity, and Protection against Dengue Encephalitis in the Mouse Model," Journal of Virology, Mar. 2003. Vol. 77, No. 6, pp. 3655-3668.
Chambers, T. et al., "Yellow Fever/Japanese Encephalitis Chimeric Viruses: Construction and Biological Properties," Journal of Virology, Apr. 1999, vol. 73, No. 4, pp. 3095-3101.
Chang, G. et al., "A Single Intramuscular Injection of Recombinant Plasmid DNA Induces Protective Immunity and Prevents Japanese Encephalitis in Mice," Journal of Virology, May 2000, vol. 74, No. 9, pp. 4244-4252.
Chen, W. et al., "Construction of Intertypic Chimeric Dengue Viruses Exhibiting Type 3 Antigenicity and Neurovirulence for Mice," Journal of Virology, Aug. 1995, vol. 69, No. 8, pp. 5186-5190.
Chokephaibulkit K., "Combination Vaccines," Chot Mai Het Thang Phaet, Journal Of The Medical Association of Thai, Medical Association of Thailand, Aug. 1, 2002, vol. 85, No. Suppl. 2, pp. S694-S699.
Clarke, D. et al., "Techniques for Hemagglutination and Hemagglutination-Inhibition with Arthropod-Borne Viruses," The Rockefeller Foundation Virus Laboratories, New York, N.Y., Am. J. Trop. Med. Hyg., 1958, p. 561-573.
Cooper, J. et al., " Update: Surveillance for West Nile Virus in Overwintering Mosquitoes—New York, 2000," 3 pages.
Davis, B. et al., "West Nile Virus Recombinant DNA Vaccine Protects Mouse and Horse from Virus Challenge and Expresses In Vitro a Noninfectious Recombinant Antigen That Can Be Used in Enzyme-Linked Immunosorbent Assays," Journal of Virology, May 2001, vol. 75, No. 9, pp. 4040-4047.
Deubel, V. et al., "Nucleotide Sequence and Deduced Amino Acid Sequence of the Nonstructural Proteins of Dengue Type 2 Virus, Jamaica Genotype: Comparative Analysis of the Full-Length Genome" Virology, 1988, vol. 165, pp. 234-244.
Deubel, V. et al., "Nucleotide Sequence and Deduced Amino Acid Sequence of the Structural Proteins of Dengue Type 2 Virus, Jamaica Genotype," Virology, 1986, vol. 155, pp. 365-377.
Dharakul, T. et al., "Dengue Virus-Specific Memory T Cell Responses in Human Volunteers Receiving a Live Attenuated Dengue Virus Type 2 Candidate Vaccine," JID Jul. 1994, vol. 170, pp. 27-33.
Dmitriev, I. et al., "Immunization with recombinant vaccinia viruses expressing structural and part of the nonstructural region of tick-borne encephalitis virus eDNA protect mice against lethal encephalitis," Journal of Biotechnology, 1996, vol. 44, pp. 97-103.
Duarte Dos Santos, C. et al., "Complete nucleotide sequence of yellow fever virus vaccine strains 17DD and 17D-213," Virus Research 1995, vol. 35, pp. 35-41.
Durbin, A. et al., "Attenuation and Immunogenicity in Humans of a Live Dengue Virus Type-4 Vaccine Candidate with a 30 Nucleotide Deletion in its 3'-Untranslated Region," Am. J. Trop. Med. Hyg. 2001, vol. 65(5), pp. 405-413.
Falgout, B. et al., "Immunization of Mice with Recombinant Vaccinia Virus Expressing Authentic Dengue Virus Nonstructural Protein NS1 Protects against Lethal Dengue Virus Encephalitis," Journal of Virology, Sep. 1990, vol. 64, No. 9, pp. 4356-4363.

(56) References Cited

OTHER PUBLICATIONS

Falgout, B. et al., "Proper Processing of Dengue Virus Nonstructural Glycoprotein NS1 Requires the N-Terminal Hydrophobic Signal Sequence and the Downstream Nonstructural Protein NS2a," Journal of Virology, May 1989, vol. 63, No. 5, pp. 1852-1860.
Garmendia, A. et al., "Recovery and Identification of West Nile Virus from a Hawk in Winter," Journal of Clinical Microbiology, Aug. 2000, vol. 38, No. 8, pp. 3110-3111.
George et al., "Safety and immunogenicity of a Live Attenuated Tetravalent Dengue Vaccine Candidate in Flavivirus-Naïve Adults: A Randomized, Double-Blinded Phase 1 Clinical Trial," Journal of Infectious Diseases, Mar. 19, 2015, vol. 212, No. 7, pp. 1032-1041.
Gruenberg, A. et al., "Partial Nucleotide Sequence and Deduced Amino Acid Sequence of the Structural Proteins of Dengue Virus Type 2, New Guinea C and PUO-218 Strains" J. gen. Virol., 1988, vol. 69, pp. 1391-1398.
Guirakhoo, F. et al., "Construction, Safety, and Immunogenicity in Nonhuman Primates of a Chimeric Yellow Fever-Dengue Virus Tetravalent Vaccine" Journal of Virology, Aug. 2001, vol. 75, No. 16, pp. 7290-7304.
Guirakhoo, F. et al., "Immunogenicity, Genetic Stability, and Protective Efficacy of a Recombinant, Chimeric Yellow Fever-Japanese Encephalitis Virus (ChimeriVax-JE) as a Live, Attenuated Vaccine Candidate against Japanese Encephalitis," Virology, 1999, vol. 257, pp. 363-372.
Guirakhoo, F. et al., "Recombinant Chimeric Yellow Fever-Dengue Type 2 Virus Is Immunogenic and Protective in Nonhuman Primates" Journal of Virology, The American Society for Microbiology, Jun. 1, 2000, vol. 74, No. 12, pp. 5477-5485.
Guirakhoo, F. et al., "Viremia and Immunogenicity in Nonhuman Primates of a Tetravalent Yellow Fever-Dengue Chimeric Vaccine: Genetic Reconstructions, Dose Adjustment, and Antibody Responses against Wild-type Dengue Virus Isolates" Virology, 2002, vol. 298, pp. 146-159.
Hahn, Y. et al., "Nucleotide Sequence of Dengue 2 RNA and Comparison of the Encoded Proteins with Those of Other Flaviviruses," Virology, 1988, vol. 162, pp. 167-180.
Halstead, S. et al., Observations related to the pathogenesis of dengue hemorrhagic fever. II. Antigenic and Biologic Properties of Dengue Viruses and their Association with disease in the host; Yale Journal of Biology and Medicine, Apr. 1970, vol. 42, pp. 276-292.
Hashimoto, H. et al., "Molecular Cloning and Complete Nucleotide Sequence of the Genome of Japanese Encephalitis Virus Beijing-1 Strain," Virus Genes, 1988, vol. 1, No. 3, pp. 305-317.
Heinz, F. et al., "Flaviviruses" Immunochemistry of viruses II, The basis for serodiagnosis and vaccines, (edited by von Regenmortel and Neurath), Elsevier Science Publishers B.V., Chapter 14, 1990 pp. 289-305.
Henchal E. et al., "Dengue Virus-Specific and Flavivirus Group Determinants Identified with Monoclonal Antibodies by Indirect Immunofluorescence," Flavivirus-Specific and Group Determinants, Am. J. Trop Med. Hyg., 1982, vol. 31, No. 4, pp. 830-836.
Hennessy, S. et al., "Effectiv ness of live-attenuated Japanese encephalitis vaccine (SA14-14-2): a case-control study" The Lancet, vol. 347, Jun. 8, 1996, pp. 1583-1586.
Ho, T. et al., "DNA vaccination induces a long-term antibody response and protective immunity against pseudorabies virus in mice" Archives of Virology, 1998, vol. 143, pp. 115-125.
Hsiang-Chi, L. et al., "Dengue Type 4 Live-Attenuated Vaccine Viruses Passaged in Vero Cells Affect Genetic Stability and Dengue-Induced Hemorrhaging in Mice," PLOS One, Oct. 28, 2011 (Oct. 28, 2011), vol. 6, No. 10, p. e25800.
Huang, C. et al., "Chimeric Dengue 2 PDK-53/West Nile NY99 Viruses Retain the Phenotypic Attenuation Markers of the Candidate PDK-53 Vaccine Virus and Protect Mice against Lethal Challenge with West Nile Virus" Journal of Virology, vol. 79, No. 12, Jun. 2005, pp. 7300-7310.
Huang, C. et al., "Chimeric Dengue Type 2 (Vaccine Strain PDK-53)/Dengue Type 1 Virus as a Potential Candidate Dengue Type 1 Virus Vaccine" Journal Of Virology, Apr. 2000, vol. 74, No. 7, pp. 3020-3028.
Huang, C. et al., "Concomitant administration of live attenuated Japanese encephalitis chimeric virus vaccine (JE-CV) and measles, mumps, rubella (MMR) vaccine: Randomized study in toddlers in Taiwan," Vaccine, Sep. 1, 2014, vol. 32, No. 41, pp. 5363-5369.
Huang, C. et al., "Dengue 2 PDK-53 virus as a chimeric carrier for tetravalent dengue vaccine development," J. Virology, Nov. 2003, vol. 77, No. 21, pp. 11436-11447.
Huang, C. et al., "Genetic and Phenotypic Characterization of Manufacturing Seeds for a Tetravalent Dengue Vaccine (DENVax)," PLOS Neglected Dis, May 2013, vol. 7, No. 5, e2243, 11 pages.
Hubálek, Z. et al., "West Nile Fever—a Reemerging Mosquito-Borne Viral Disease in Europe" Emerging Infectious Diseases, Sep.-Oct. 1999, vol. 5, No. 5, pp. 643-650.
Hunt, A. et al., "Relationships of Bunyamwera Group Viruses by Neutralization" Am. J. Trop. Med. Hyg. 1979, vol. 28, No. 4, pp. 740-749.
Jia, X. et al., "Genetic analysis of West Nile New York 1999 encephalitis virus" The Lancet, Dec. 4, 1999, vol. 354, pp. 1971-1972.
Jirakanjanakit, N. et al., "Dynamics of Susceptibility and Transmissibility of The Live Attenuated, Candidate Vaccines Dengue-1 PDK-13, Dengue-3 PGMK30F3, and Dengue-4 PDK-48 after Oral Infection in Aedes Aegypti," Am. J. Trop. Med. Hyg. 1999, vol. 61, No. 4, pp. 672-676.
Johnson, A. et al., "Detection of Anti-Arboviral Immunoglobulin G by Using a Monoclonal Antibody-Based Capture Enzyme-Linked Immunosorbent Assay," Journal of Clinical Microbiology, May 2000, vol. 38, No. 5, pp. 1827-1831.
Johnson, B. et al., "Growth Characteristics of ChimeriVax-DEN2 Vaccine Virus in Aedes Aegypti and Aedes Albopictus Mosquitoes," Am. J. Trop Med. Hyg., 2002, vol. 67, No. 3, pp. 260-265.
JP 19920043682 Feb. 28, 1992 "Non-infective structure particle prepn., useful as vaccine—by infecting preliminarily flavivirus infected cell with cDNA integrated recombinant vaccinia virus, and then sepg. non-infective structure particles contg. E-protein of flavivirus" XP-00211903; Abtract Only.; (Cited as JP H05276941A).
Kanesa-Thasan, N. et al., "Safety and immunogenicity of attenuated dengue virus vaccines (Aventis Pasteur) in human volunteers," Vaccine, 2001 vol. 19 pp. 3179-3188.
Kawano, H et al., "Genetic Determinants of Dengue Type 4 Virus Neurovirulence for Mice," Journal of Virology, Nov. 1993, vol. 67, No. 11, pp. 6567-6575.
CN Office Action + English translation for CN application 202110718703.8 dated Sep. 2023.
Glasner, D.R., et al., Magnitude and functionality of NS1-specific antibody response elicited by Takeda's Tetravalent Dengue Vaccine Candidate, Poster No. 1618 presented at the American Society of Tropical Medicine & Hygiene Conference on Oct. 28 to Nov. 1, 2018.
Abstract, There will be epidemics . . . , American Society of Tropical Medicine & Hygiene 67th Annual Meeting, Abstract Book, vol. 99, No. 4, Oct. 2018.
CYD51 results summary, Title of the study: "Evaluation of the Immune Response to Different Schedules of a Tetravalent Dengue Vaccine Administered With or Without Yellow Fever Vaccine in US Adults", Sponsor: Sanofi Pasteur, Jul. 22, 2020.
Thisyakorn et al., "Dengue vaccine: a key for prevention," Expert Review of Vaccines, 2020, vol. 19, No. 6, pp. 499-506.
Vidor, E., "The Nature and Consequences of Intra- and Inter-Vaccine Interference", J. Comp. Path. 2007, vol. 137, S62-S66.
Silva, Juliana Romualdo Nascimento et al., "Mutual interference on the immune response to yellow fever vaccine and combined vaccine against measles, mumps and rubella", Vaccine 29 (2011) 6327-6334.
History of Changes for Study: NCT 03342898 Immunogenicity and Safety of Tetravalent Dengue Vaccine (TDV) Administered with a Yellow Fever Vaccine in Adults; ClinicalTrials.gov archive.

(56) References Cited

OTHER PUBLICATIONS

Sridhar, S., et al. "Effect of Dengue Serostatus on Dengue Vaccine Safety and Efficacy," The New England Journal of Medicine, pp. 1-14, Jun. 13, 2018.
EU Clinical Trials Register, Clinical trial results: "Immunogenicity and Safety of Yellow Fever Vaccine (Stamaril®) Administered Concomitantly with Tetravalent Dengue Vaccine in Healthy Toddlers at 12-13 Months of Age in Colombia and Peru" Clinical trial results 2014-001714-26 version 1, EU CTR publication date: Feb. 8, 2016.
Kirstein, et al. "Immunogenicity of the CYD tetravalent dengue vaccine using an accelerated schedule: randomised phase II study in US adults" BMC Infectious Diseases (2018) 18:475.
Lang, Jean et al, "Q&A Session Oct. 6, 2011—I International Symposium on Dengue, FMUSP, Sao Paulo" Rev. Inst. Med. Trop. Sao Paulo 54(Suppl. 18):S28-S30, Oct. 2012.
Sage Working Group on Yellow Fever Vaccine: Interference between YF vaccine and other vaccines, Jan. 11, 2012; BNSDOCID: XP_55222731A_I_.
Anderson, Kathryn B. et al, "Interference and Facilitation between Dengue Serotypes in a Tetravalent Live Dengue Virus Vaccine Candidate" JID 2011:204 (Aug. 1) 442-450.
Nasveld, Peter E., et al, "Concomitant or sequential administration of live attenuated Japanese encephalitis chimeric virus vaccine and yellow fever 17D vaccine" Human Vaccines 6:11, 906-914; Nov. 2010; © 2010 Landes Bioscience.
Fujita, Nobuya et al, "Research on Dengue in Tissue Culture" Kobe J. Med. Sci. 15, 163-180, Dec. 1969.
Guy, Bruno et al, "Preclinical and clinical development of YFV 17D-based chimeric vaccines against dengue, West Nile and Japanese encephalitis viruses" Vaccine 28 (2010) 632-649.
ClinicalTrials.gov archive, History of Changes for Study: NCT01436396 "Study of Yellow Fever Vaccine Administrated With Tetravalent Dengue Vaccine in Healthy Toddlers" Apr. 9, 2020.
ClinicalTrials.gov archive, History of Changes for Study: NCT01488890 "Immune Response to Different Schedules of a Tetravalent Dengue Vaccine Given With or Without Yellow Fever Vaccine" Apr. 9, 2020.
MMWR Morbidity and Mortality Weekly Report "Yellow Fever Vaccine Recommendations of the Advisory Committee on Immunization Practices (ACIP)" Jul. 30, 2010 / vol. 59 / No. RR-7.
Clinical Study Report; Title of study: "Immunogenicity and Safety of Yellow Fever Vaccine (Stamaril®) Administered Concomitantly with Tetravalent Dengue Vaccine in Healthy Toddlers at 12-13 Months of Age in Colombia and Peru" Sponsor: Sanofi Pasteur; According to template: QSD-001970 Version N° 7.0 (Nov. 26, 2019).
FDA Advisory No. 2017-318 mailed Dec. 4, 2017.
Sanofi Pasteur, Dengvaxia package insert, 2023.
Press Release; "Sanofi Updates Information on Dengue Vaccine," Nov. 29, 2017.
Wilder-Smith, Annelies. "Four-year safety follow-up of the tetravalent dengue vaccine CYD-TDV." Clinical microbiology and infection : the official publication of the European Society of Clinical Microbiology and Infectious Diseases 24 7 (2018): 680-681.
Hans L. Bock et al "Does the Concurrent Administration of an Inactivated Hepatitis A Vaccine Influence the Immune Response to Other Travellers Vaccines?" JtravelMed 2000; 7:74-78.
Takahiro Kiyomusa et al. "Pediatric travelers" vaccine, Japanese Journal of Pediatrics, 2016, vol. 69, No. 5, p. 900-906.
Laris-González, Almudena et al. "Safety of Administering Live Vaccines during Pregnancy: A Systematic Review and Meta-Analysis of Pregnancy Outcomes." Vaccines 8 (2020): n. pag.
Sridhar, Saranya et al. "Effect of Dengue Serostatus on Dengue Vaccine Safety and Efficacy." The New England Journal of Medicine 379 (2018): 327-340.
Rinderknecht, Stephen et al. "Immunogenicity and Safety of an Inactivated Hepatitis A Vaccine When Coadministered With Measles-mumps-rubella and Varicella Vaccines in Children Less Than 2 Years of Age." The Pediatric Infectious Disease Journal 30 (2011): e179-e185.
Keelapang, Poonsook et al. "Generation and preclinical evaluation of a DENV-1/2 prM+E chimeric live attenuated vaccine candidate with enhanced prM cleavage." Vaccine 31 44 (2013): 5134-40.
Ishikawa, Tomohiro et al "Special Feature: What Happens Next? Vaccinations in Japan—Topics on vaccines expected to be introduced in the future" Department of Microbiology, Dokkyo Medical University School of Medicine, Biken Endowed Department of Dengue Vaccine Development, Faculty of Tropical Medicine, Mahidol University, The Journal of Pediatric Practice, 2016, vol. 79, No. 4, p. 547-552.
Wagstaff, Antona J. et al. "Inactivated Hepatitis A Vaccine (HM175 Strain)." Clinical Immunotherapeutics 6 (1996): 68-88.
Whitehead, Stephen S. and Kanta Subbarao. "Which Dengue Vaccine Approach Is the Most Promising, and Should We Be Concerned about Enhanced Disease after Vaccination? The Risks of Incomplete Immunity to Dengue Virus Revealed by Vaccination." Cold Spring Harbor perspectives in biology 10 6 (2018): n. pag.
Halstead, Scott B.. "Which Dengue Vaccine Approach Is the Most Promising, and Should We Be Concerned about Enhanced Disease after Vaccination? There Is Only One True Winner." Cold Spring Harbor perspectives in biology 10 6 (2018): n. pag.
Katzelnick, Leah C. and Eva Harris. "Immune correlates of protection for dengue: State of the art and research agenda." Vaccine 35 36 (2017): 4659-4669.
Goubau, Patrick et al. "Effect of virus strain and antigen dose on immunogenicity and reactogenicity of an inactivated hepatitis A vaccine." Vaccine 10 Suppl 1 (1992): S114-8.
Aggarwal, A., & Garg, N. (2018). Newer Vaccines against Mosquito-borne Diseases. The Indian Journal of Pediatrics, 85, 117-123.
Van Hoecke, C et al. "Concomitant vaccination against hepatitis A and typhoid fever." Journal of travel medicine 5 3 (1998): 116-20.
Kaltenböck, Astrid et al. "Safety and immunogenicity of concomitant vaccination with the cell-culture based Japanese Encephalitis vaccine IC51 and the hepatitis A vaccine HAVRIX1440 in healthy subjects: A single-blind, randomized, controlled Phase 3 study." Vaccine 27 33 (2009): 4483-9.
Noronha, Alinea S et al. "Systematic review of human papillomavirus vaccine coadministration." Vaccine 32 23 (2014): 2670-4.
Konishi, Eiji. "Issues Related to Recent Dengue Vaccine Development." Tropical Medicine and Health 39 (2011): 63-71.
Thomas, Stephen J. and In-Kyu Yoon. "A review of Dengvaxia®: development to deployment." Human Vaccines & Immunotherapeutics 15 (2019): 2295-2314.
Sage Working Group Background Paper on Yellow Fever Vaccine, Mar. 19, 2013.
Coronel, D. et al. (Nov. 22, 2019) LB-5345-CYD-TDV Dengue vaccine: Alternative vaccination schedules with reduced No. of doses in healthy individuals aged 9 to 50 years in Latin America and Asia-Pacific regions [Poster Presentation]. ASTMH 68th Annual Meeting, National Harbor, MD, United States.
De Silva, A. M. and Harris, E. (2018) Which Dengue Vaccine Approach Is the Most Promising, and Should We Be Concerned about Enhanced Disease after Vaccination? The Path to a Dengue Vaccine: Learning from Human Natural Dengue Infection Studies and Vaccine Trials. Cold Spring Harbor Perspectives In Biology, 10, 1-11.
European Medicines Agency (Oct. 13, 2022) Assessment Report Qdenga. (ema.europa.eu).
European Medicines Agency (Oct. 14, 2022) New vaccine to protect people in the EU and worldwide against dengue [Press Release].
European Medicines Agency (Apr. 12, 2022) Dengvaxia EPAR Product Information (https://www.ema.europa.eu/en/medicines/human/EPAR/dengvaxia).
European Medicines Agency (Oct. 18, 2018) Assessment Report Dengvaxia.
Guy, B. et al. (2009) Evaluation of interferences between Dengue vaccine serotypes in a monkey model. American Journal of Tropical Medicine and Hygiene, 80(2) 302-311.
Guy, B. et al. (Jul. 13, 2011) From research to phase III: Preclinical, industrial and clinical development of the Sanofi Pasteur tetravalent dengue vaccine. Vaccine, 29, 7229-7241.

(56) References Cited

OTHER PUBLICATIONS

Halstead, S. B. (Nov. 3, 2012) Dengue vaccine development: a 75% solution. Lancet, 380, 1535-1536.
Li, L. et al. (2019, June 6) Potent neutralizing antibodies elicited by dengue vaccine in rhesus macaque target diverse epitopes. PLoS Pathog, 15(6), 1-29.
Ong, E. Z. et al. (Nov. 14, 2025) Dengue virus infection reprograms baseline innate immune gene expression. Med, 6(11), 100841.
Petri, E. et al. (Sep. 7, 2024) Early onset of protection of the TAK-003 dengue vaccine: Data from the DEN-301 clinical trial. Vaccine, 42, 126309.
Qiao, M. et al. (2011) Priming Effect of Dengue and Yellow Fever Vaccination on the Immunogenicity, Infectivity, and Safety of a Tretravalent Dengue Vaccine in Humans. American Journal of Tropical Medicine and Hygiene, 85(4) 724-731.
Rabaa, M. A. et al. (Sep. 5, 2017) Genetic epidemiology of dengue viruses in phase III trials of the CYD tetravalent dengue vaccine and implications for efficacy. eLife, 6, 1-22.
Rothman, A. L. (2011, August) Immunity to dengue virus: a tale of original antigenic sin and tropical cytokine storms. Immunology, 11, 532-543.
Takeda Pharmaceutical Company Limited (Nov. 7, 2017) Takeda's dengue vaccine candidate associated with reduced incidence of dengue in children and adolescents; New 18-month interim phase 2 data published in The Lancet Infectious Diseases [Press Release].
Takeda Pharmaceutical Company Limited (Nov. 6, 2019) Takeda's dengue vaccine candidate demonstrates protection in children ages four to 16 years, regardless of previous dengue exposure [Press Release].
Takeda Pharmaceutical Company Limited (Jun. 9, 2022) Takeda's dengue vaccine candidate provides continued protection against dengue fever through 4.5 years in pivotal clinical trial [Press Release].
Takeda Pharmaceutical Company Limited (Nov. 5, 2019) Takeda unveils new dengue vaccine manufacturing plant in Germany [Press Release].
Takeda Pharmaceutical Company Limited (Oct. 6, 2023) Summary of Product Characteristics Qdenga (Indonesia) https://registrasiobat.pom.go.id/daftar-produk/assesment-report/DKI2264500244A1.
Thomas, S. J. and Rothman, A. L. (Jun. 27, 2015) Trials and tribulations on the path to developing a dengue vaccine. Vaccine, 33, D24-D31.
Tricou, V. et al. (Mar. 8, 2023) Immunogenicity and safety of concomitant and sequential administration of yellow fever YF-17D vaccine and tetravalent dengue vaccine candidate TAK-003: a phase 3 randomized, controlled study. PLOS Neglected Tropical Diseases, 17(3), 1-18.
Vigne, C. et al. (Jul. 11, 2017) Integrated immunogencity analysis of a tetravalent dengue vaccine up to 4 y after vaccination. Human Vaccines & Immunotherapeutics, 13:9, 2004-2016.
Wahala, M. P. B. and De Silva, A. M. (Nov. 25, 2011) The human antibody response to dengue virus infection. Viruses, 3, 2374-2395.
Wilder-Smith, A. (Nov. 29, 2019) Dengue vaccine development: status and future. Bundesgesundheitsbl (2020), 63, 40-44.
Wilder-Smith, A. (Oct. 2019) The first licensed dengue vaccine: can it be used in travelers? Current Opinion in Infectious Diseases, 32(5), 394-400.
World Health Organization (Oct. 1-5, 2006) Report of the Scientific Working GroupGeneva, Switzerland. https://www.who.int/publications/i/item/tdr-swg-08.

* cited by examiner

| | Month 0 | Month 3.0 | Month 14.5 | Month 15.9 | Month 18.0 |
|---|---|---|---|---|---|
| Placebo - Seronegative | n=1,832 | n=1,817 | n=1,744 | n=94 | n=7 |
| Placebo - Seropositive | n=4,852 | n=4,805 | n=4,607 | n=218 | n=6 |
| TDV - Seronegative | n=3,714 | n=3,690 | n=3,615 | n=157 | n=10 |
| TDV - Seropositive | n=9,661 | n=9,591 | n=9,391 | n=417 | n=10 |

| | Month 0 | Month 3.0 | Month 14.5 | Month 15.9 | Month 18.0 |
|---|---|---|---|---|---|
| Placebo - Seronegative | n=1,832 | n=1,827 | n=1,776 | n=94 | n=7 |
| Placebo - Seropositive | n=4,852 | n=4,823 | n=4,700 | n=220 | n=6 |
| TDV - Seronegative | n=3,714 | n=3,693 | n=3,635 | n=157 | n=10 |
| TDV - Seropositive | n=9,661 | n=9,599 | n=9,435 | n=417 | n=10 |

DENGUE VACCINE UNIT DOSE AND ADMINISTRATION THEREOF

CROSS REFERENCE TO RELATED APPLICATIONS

This application is a continuation application of U.S. application Ser. No. 16/561,953 filed on Sep. 5, 2019, which claims priority to EP 19161184.7, filed, Mar. 7, 2019, EP 19154334.7, filed Jan. 29, 2019, EP 18192701.3, filed Sep. 5, 2018, EP 18192776.5, filed Sep. 5, 2018, EP 18192787.2, filed Sep. 5, 2018, EP 18192793.0, filed Sep. 5, 2018, EP 18192800.3, filed Sep. 5, 2018, EP 18192711.2, filed Sep. 5, 2018, EP 18192717.9, filed Sep. 5, 2018, and EP 18192814.4, filed Sep. 5, 2018. The entire contents of the aforementioned applications are incorporated herein by reference in their entireties.

SEQUENCE LISTING

This application incorporates by reference in its entirety, the Sequence Listing XLM entitled "T08269US2C1_updated_18Oct.xml" (127 KB), which was created on Oct. 18, 2022.

FIELD OF THE INVENTION

The present invention relates to a safe and effective method of inoculation against dengue disease and a corresponding safe and effective dengue vaccine. In particular the present invention relates to a safe and effective method of inoculation against dengue disease irrespective of serostatus and a corresponding safe and effective dengue vaccine. The present invention relates also to unit doses of a dengue vaccine composition and methods for administering a unit dose of a dengue vaccine composition to a subject or a subject population in a broad age group. The present invention is also related to particular concomitant administration regimes, wherein the unit does/vaccine composition is administered concomitantly with one or more of: a yellow fever (YF) vaccine, a hepatitis A vaccine, a human papillomavirus (HPV) vaccine, a combined measles, mumps and rubella (MMR) vaccine, a combined tetanus, diphtheria, and pertussis (whooping cough) (Tdap) vaccine, and/or a combined vaccine for diphtheria, tetanus, pertussis, poliomyelitis and *Haemophilus influenzae* type b (DTap/IPV/Hib), or any combination of the concomitant administration regimes mentioned above. The unit dose according to this invention provides immune responses against all serotypes of dengue virus, i.e. DENV-1, DENV-2, DENV-3 and DENV-4.

BACKGROUND OF THE INVENTION

Vaccines for protection against viral infections have been effectively used to reduce the incidence of human disease. One of the most successful technologies for viral vaccines is to immunize animals or humans with a weakened or attenuated virus strain (a "live attenuated virus"). Due to limited replication after immunization, the attenuated virus strain does not cause disease. However, the limited viral replication is sufficient to express the full repertoire of viral antigens and can generate potent and long-lasting immune responses to the virus. Thus, upon subsequent exposure to a pathogenic virus strain, the immunized individual is protected from the disease. These live attenuated viral vaccines are among the most successful vaccines used in public health.

Dengue disease is a mosquito-borne disease caused by infection with a dengue virus. Dengue virus infections can lead to debilitating and painful symptoms, including a sudden high fever, headaches, joint and muscle pain, nausea, vomiting and skin rashes. To date, four serotypes of dengue virus have been identified: dengue-I (DENV-1), dengue-2 (DENV-2), dengue-3 (DENV-3) and dengue-4 (DENV-4). Dengue virus serotypes 1-4 can also cause dengue hemorrhagic fever (DHF) and dengue shock syndrome (DSS). In the most severe cases, DHF and DSS can be life threatening. Dengue viruses cause 50-100 million cases of debilitating dengue fever, 500,000 cases of DHF/DSS, and more than 20,000 deaths each year, a large portion of which are children. All four dengue virus serotypes are endemic throughout the tropical regions of the world and constitute the most significant mosquito-borne viral threat to humans there. Dengue viruses are transmitted to humans primarily by *Aedes aegypti* mosquitoes, but also by *Aedes albopictus* mosquitoes. Infection with one dengue virus serotype results in life-long protection from re-infection by that serotype, but does not prevent secondary infection by one of the other three dengue virus serotypes. In fact, previous infection with one dengue virus serotype may lead to an increased risk of severe disease (DHF/DSS) upon secondary infection with a different serotype.

To date, only one vaccine, a tetravalent dengue vaccine based on a yellow fever backbone, CYD-TDV (Dengvaxia®, Sanofi Pasteur, Lyon, France), has been licensed in several countries based on the clinical demonstration of an overall vaccine efficacy (VE) against virologically-confirmed dengue (VCD) of 56-61% in children in Asia and Latin America (Capeding M R et al. Clinical efficacy and safety of a novel tetravalent dengue vaccine in healthy children in Asia: a phase 3, randomised, observer-masked, placebo-controlled trial. Lancet 2014, 384:1358-65; Villar L A et al. Safety and immunogenicity of a recombinant tetravalent dengue vaccine in 9-16 year olds: a randomized, controlled, phase II trial in Latin America. Pediatr Infect Dis J 2013, 32:1102-9). However, clinical trials have shown that Dengvaxia® can enhance, rather than reduce, the risk of severe disease due to dengue infection in individuals who had not been previously infected by a dengue virus (seronegative populations). Therefore, Dengvaxia® is only recommended for use in individuals who had been previously infected with at least one dengue virus serotype (seropositive populations). More specifically, according to the European Medicine Agencys European Public Assessment report (EPAR) for the product, Dengvaxia® is only for use in people from 9 to 45 years of age who have been infected with dengue virus before and who live in areas where this infection is endemic. Endemic areas are areas where the disease occurs regularly throughout the year. See also Sridhar S et al. Effect of Dengue Serostatus on Dengue Vaccine Safety and Efficacy. N Engl J Med 2018, 379:327-40; and World Health Organization. Dengue vaccine: WHO position paper—September 2018. Wkly. Epidemiol. Rec. 2018, 93:457-476. S. R. Hadinegoro et al. report in the New England Journal of Medicine, Vol. 373, page 1195, in "Efficacy and Long-Term Safety of a Dengue Vaccine in Regions of Endemic Disease" a pooled risk of hospitalization for virologically-confirmed dengue disease among those under the age of 9 years of 1.58 indicating an increased risk for the vaccinated group with respect to severe dengue. This leaves a substantial unmet need for an effective vaccine with a good safety profile in both dengue-naïve and seropositive individuals, including those dengue-naïve populations living in endemic areas, younger individuals who may not have developed any seropositive response to dengue or been exposed to dengue, and travelers and individuals from non-endemic regions. There is also a need for outbreak control or travel vaccination, offering a reduction in the risk of dengue after only one dose.

One further disadvantage of the only currently approved dengue vaccine, Dengvaxia®, is that it must only be given to people who have had a positive test result showing a previous infection with dengue virus (EPAR), i.e. individuals with known serostatus for dengue. Thus, individuals with unknown serostatus for dengue cannot be vaccinated with Dengvaxia®.

There is hence a need for a dengue vaccine and corresponding method of inoculation that stimulates an immune response to all dengue serotypes, preferably a balanced immune response to all serotypes, and protects against dengue disease of any severity (including DSS, DHF), both in seronegative and seropositive populations, which is safe for a larger group of ages, in particular also for subjects of 9 years and younger. The development of a safe and effective vaccine capable of protecting all populations, including both seronegative and seropositive populations, and in particular children and young adults and elderly subjects in endemic settings and for the purpose of traveling, represents an important approach to the prevention and control of this global disease.

There is thus a medical need for a dengue vaccine and corresponding method of inoculation which, as well as being safe and efficacious irrespective of serostatus and in a broad age group. There is a need for a dengue vaccine and corresponding method of inoculation that avoids costly and time consuming serostatus tests or seroprevalence considerations. There is a need for a dengue vaccine and corresponding method of inoculation that can be used in an outbreak situation. Furthermore there is a medical need for a dengue vaccine which as well as being safe and effective can also be administered to individuals with unknown dengue serostatus, children under 9 years and seronegative individuals.

There is also a need for a vaccine that is administered in fewer doses than the current Dengvaxia® dosing schedule of 3 doses, 6 months apart, such as a vaccine that can be administered in only two doses or one dose to be efficacious.

The above objects are commensurate with the research priorities provided by the WHO in the Dengue Vaccine: WHO position paper—September 2018 (Wkly. Epidemiol. Rec. 2018, 93:457-476).

Yellow fever (YF) is an acute viral hemorrhagic disease transmitted by infected mosquitoes of the *Aedes aegypti* specie. Symptoms of yellow fever take 3 to 6 days to develop and include fever, headache, jaundice, muscle pain, nausea, vomiting and fatigue. A small proportion of patients (about 15% of people) who contract the virus develop a severe disease that can lead to bleeding, shock, organ failure, and sometimes death. The virus is endemic in tropical areas of Africa and Central and South America.

Dengue fever and yellow fever (YF) viruses belong to the same family of flaviviridae and share antigenic determinants, which may result in cross-reacting antibodies. They are both transmitted between humans by mosquitoes (primarily *Aedes aegypti*), and are both endemic in tropical areas of Africa and Latin America with a high public health impact.

Today there exists a yellow fever vaccine (YF-17D vaccine) which is based on a live, attenuated viral strain, and is the only commercially available YF vaccine administered as a single subcutaneous injection. The YF-17D vaccine is highly effective (approaching 100%) and generally safe with the exception of very rare cases of vaccine-associated neurotropic and viscerotropic disease. Vaccination against YF is also required for travelers to certain countries in accordance with the International Health Regulations, and is also recommended by the WHO for all subjects travelling to areas where there is evidence of persistent or periodic YF virus transmission. A YF-17D vaccine is available under the product name YF-VAX® from Sanofi.

A yellow fever vaccine is recommended for people from nine months of age and older who are living in or traveling to endemic areas, persons travelling to or through countries requiring. A single dose of yellow fever vaccine administered subcutaneously is usually sufficient to confer sustained lifelong protective immunity against yellow fever. However, for people who remain at risk, a booster dose is recommended every 10 years.

Hence, there is a need for a safe and effective method of simultaneously preventing dengue disease and yellow fever.

Hepatitis A is a liver disease caused by the hepatitis A virus (HAV). The virus is primarily spread when an uninfected (and unvaccinated) person ingests food or water that is contaminated with the feces of an infected person. The disease is closely associated with unsafe water or food, inadequate sanitation and poor personal hygiene. The virus can also be transmitted through close physical contact with an infectious person. Unlike hepatitis B and C, hepatitis A infection does not cause chronic liver disease and is rarely fatal, but it can cause debilitating symptoms and fulminant hepatitis (acute liver failure), which is often fatal. Hepatitis A occurs sporadically and in epidemics worldwide, with a tendency for cyclic recurrences.

The hepatitis A virus is one of the most frequent causes of foodborne infection. Epidemics related to contaminated food or water can erupt explosively, such as the epidemic in Shanghai in 1988 that affected about 300,000 people. Hepatitis A viruses persist in the environment and can withstand food-production processes routinely used to inactivate and/or control bacterial pathogens. The disease can lead to significant economic and social consequences in communities. It can take weeks or months for people recovering from the illness to return to work, school, or daily life. The impact on food establishments identified with the virus, and local productivity in general, can be substantial. In developing countries with poor sanitary conditions and hygienic practices, most children (90%) have been infected with the hepatitis A virus before the age of 10 years.

The number of people traveling internationally has grown substantially in recent decades. According to the United Nations World Tourism Organization (UNWTO), over 1.1 billion tourists travelled abroad in 2014. The risk of becoming ill during international travel depends on many factors, such as the region of the world visited, the length of the trip, and the diversity of planned activities. Vaccine recommendations are a prominent part of health preparations before international travel. Vaccination against hepatitis A virus is commonly recommended for travelers to at-risk areas around the world including Asia, Africa, and Latin America.

For routine hepatitis A vaccination, a two-dose schedule is recommended, particularly in travelers at substantial risk of contracting hepatitis A and in immunocompromised individuals. However, in healthy individuals, comparable effectiveness has been achieved with a single dose. The vaccination schedule for children/adolescents (12 months through 18 years of age) as well as for adults (≥19 years of age)

consists of a primary dose administered intramuscularly, and a further booster dose administered intramuscularly 6 to 18 months later.

Available hepatitis A vaccines include HAVRIX® and VAQTA®.

Hence, there is a need for a safe and effective method of simultaneously preventing dengue disease and hepatitis A.

Human papillomavirus (HPV) is a common virus that is passed from one person to another through direct skin-to-skin contact during sexual activity. Most sexually active people will be infected with HPV at some time in their lives and the infection is most common in people in their late teens and early 20s. There are about 40 types of HPV that can infect the genital areas of men and women. While most HPV types cause no symptoms and are cleared by the body's immune system, some HPV types are persistent and can cause cervical cancer in women and other less common cancers—like cancers of the anus, penis, vagina, vulva and oropharynx or warts in the genital areas of men and women, called genital warts.

HPV vaccination prevents HPV-associated cervical cancers as well as HPV-associated cancers of the anus, vulva, vagina, and oropharynx. The vaccination can also prevent HPV-associated genital warts. HPV vaccination is recommended in particular for 11 and 12 year-old girls. It is also recommended for girls and women age 13 through 26 years of age who have not yet been vaccinated or completed the vaccine series. HPV vaccine can also be given to girls beginning at age 9 years. The CDC recommends 11 to 12 year olds girls get two doses of HPV vaccine to protect against cancers caused by HPV. More recently, vaccination of boys in the same age ranges has also been recommended.

The routine HPV vaccination schedule for adolescents who start the vaccination series before the 15th birthday includes two doses of a HPV vaccine. The two doses are usually separated by 6 to 12 months. The minimum interval between doses is five calendar months. A three dose schedule is recommended for subjects who start the series on or after the 15th birthday and for subjects with certain immunocompromising conditions (such as cancer, HIV infection, or taking immunosuppressive drugs). The second dose is usually given 1 to 2 months after the first dose and the third dose 6 months after the first dose. The minimum interval between the first and second doses of vaccine is usually 4 weeks. The minimum interval between the second and third doses of vaccine is usually 12 weeks. The minimum interval between the first and third doses is usually 5 calendar months. If the vaccination series is interrupted, the series does not need to be restarted.

Available HPV vaccines include Gardasil® 9, which is a recombinant 9-valent HPV (9vHPV) vaccine for preventing HPV serotypes 6, 11, 16, 18, 31, 33, 45, 52, and 58. The HPV vaccine does not include any live or inactivated HPV, but the Li proteins of the respective HPV serotypes.

Hence, there is a need for a safe and effective method of simultaneously preventing dengue disease and HPV-associated cancers or genital warts.

Measles is a highly contagious infectious disease caused by the measles virus, a single-stranded, negative-sense, enveloped (non-segmented) RNA virus of the genus *Morbillivirus* within the family Paramyxoviridae. Complications occur in about 30% of cases and may include diarrhea, blindness, inflammation of the brain, and pneumonia, among others. Encephalitis occurs in approximately one of every 2000 reported cases; survivors often have permanent brain damage and mental retardation. Death, predominantly from respiratory and neurological causes, occurs in one of every 3000 reported measles cases. The risk of death is greater for infants and adults than for children and adolescents. Contracting measles during pregnancy increases fetal risk. Most commonly, this risk involves premature labor and moderately increases rates of spontaneous abortion and of low birth weight. Subacute sclerosing panencephalitis, a slow virus infection of the central nervous system, is associated with measles virus. Measles is an airborne disease which spreads easily through the coughs and sneezes of infected people and may also be spread through contact with saliva or nasal secretions.

Mumps is an acute disease of children and young adults, caused by the mumps virus, a single-stranded, negative-sense RNA virus of the genus *Rubulavirus* within the family Paramyxoviridae. Mumps virus produces no symptoms in about one-third of infected people. In those with a clinical response, glandular and nerve tissue are most often affected and the most common symptoms include fever and swelling of the parotid glands. Complications may include meningitis (15%), pancreatitis (4%), inflammation of the heart, or permanent deafness. Frequent viruria and abnormal renal function suggest that mumps virus may infect the kidneys. Mumps is highly contagious and spreads rapidly among people living closely together by respiratory droplets or direct contact with an infected person.

Rubella (German measles) is an infection caused by the rubella virus, a single-stranded, positive-sense RNA virus of the genus *Rubivirus* within the family Togaviridae. The virus usually results in a mild illness, accompanied by few constitutional symptoms, and occurs most commonly in childhood. If the infection occurs in a woman in early pregnancy however, the virus may cross the placenta to reach the fetus, in which the infection can induce birth defects. These defects may be serious and permanent and include congenital heart disease, cataract formation, deafness and mental retardation. Rubella is usually spread through the air via coughs of people who are infected.

Combined vaccine for measles, mumps and rubella (MMR) is used widely for the immunization of children in certain regions of the world, because of its advantages over the individual vaccines. Combined vaccine provokes an adequate immune response in children simultaneously for the three infections.

MMR vaccines are indicated for simultaneous vaccination against measles, mumps, and rubella in individuals 12 months of age or older. Individuals first vaccinated at 12 months of age or older should be revaccinated prior to elementary school entry. Revaccination is intended to seroconvert those who do not respond to the first dose. The Advisory Committee on Immunization Practices (ACIP) recommends administration of the first dose at 12 to 15 months of age and administration of the second dose at 4 to 6 years of age.

Hence, there is a need for a safe and effective method of simultaneously preventing dengue disease and measles, mumps and rubella.

Tetanus is caused by an infection with the bacterium *Clostridium tetani* which is commonly found in soil, saliva, dust, and manure. The bacteria generally enter the body through a break in the skin such as a cut or puncture wound by a contaminated object. The bacteria produce toxins that interfere with muscle contractions, resulting in the typical signs of muscle spasms. It affects the brain and nervous system and causes extremely painful muscle spasms, usually all over the body. Spasms of the jaw can make it impossible to open the mouth, a condition called "lockjaw." Tetanus kills one out of ten people infected with the disease.

Diphtheria is an infection caused by the bacterium *Corynebacterium diphtheriae* which primarily infects the throat and upper airways, and produces a toxin affecting other organs. Diphtheria has an acute onset and the main characteristics are sore throat, low fever and swollen glands in the neck. The toxin may, in severe cases, cause myocarditis or peripheral neuropathy. The diphtheria toxin causes a membrane of dead tissue to build up over the throat and tonsils, making breathing and swallowing difficult. Diphtheria is a very contagious infection and the bacteria usually spread between people by direct contact or through the air, but it may also be spread by contaminated objects.

Pertussis, or whooping cough, caused by the bacterium *Bordetella pertussis* is an airborne disease that results in an extremely contagious respiratory infection that can lead to severe breathing problems, especially in infants. Pertussis first appears like an ordinary cold, but then causes intense, uncontrollable coughing spells which can cause difficulty breathing, vomiting, and disturbed sleep. A person may cough so hard that they vomit, break ribs, or become very tired from the effort. Children less than one year old may have little or no cough and instead have periods where they do not breathe. A high-pitched "whoop" noise is heard when the person tries to take a breath after coughing. Complications include pneumonia or death. Pertussis can affect people of all ages, but can be very serious and even deadly, for babies less than a year old.

Tdap is a combination vaccine that protects against the three potentially life-threatening bacterial diseases tetanus, diphtheria, and pertussis (whooping cough). Tdap stands for tetanus and diphtheria toxoids with acellular pertussis. Tdap is an inactive vaccine produced by using dead bacteria. It is recommended that vaccination against tetanus, diphtheria and pertussis carried out in infancy (in children of less than 7 years of age) is done by using a particular diphtheria toxoid, tetanus toxoid and acellular pertussis absorbed vaccine, such as INFANRIX® from GlaxoSmithKline. A further booster Tdap vaccine is recommended for children of greater than 10 years to ensure that immunity against tetanus, diphtheria and pertussis is maintained into adulthood. A booster Tdap vaccine based on combined tetanus toxoid, reduced diphtheria toxoid and acellular pertussis (adsorbed) is available under the brand name BOOSTRIX® from GlaxoSmithKline. Tdap vaccination is administered intramuscularly as a single dose.

Hence, there is a need for a safe and effective method of simultaneously preventing dengue disease and tetanus, diphtheria, and pertussis.

In addition to diphtheria, tetanus and pertussis, poliomyelitis, often called polio or infantile paralysis, is a highly infectious viral disease caused by the poliovirus. It invades the nervous system, and can cause total paralysis in a matter of hours. The virus is transmitted by person-to-person spread mainly through the fecal-oral route or, less frequently, by a common vehicle (for example, contaminated water or food) and multiplies in the intestine. Initial symptoms are fever, fatigue, headache, vomiting, stiffness of the neck and pain in the limbs. 1 in 200 infections leads to irreversible paralysis (usually in the legs). Among those paralyzed, 5% to 10% die when their breathing muscles become immobilized. Polio mainly affects children under 5 years of age. There is no cure for polio, it can only be prevented.

*Haemophilus influenzae* type b (Hib) is a bacteria responsible for severe pneumonia, meningitis and other invasive diseases almost exclusively in children aged less than 5 years. It is transmitted through the respiratory tract from infected to susceptible individuals. Hib also causes potentially severe inflammatory infections of the face, mouth, blood, epiglottis, joints, heart, bones, peritoneum, and trachea. Although this problem occurs worldwide the burden of Hib disease was considerably higher in resource-poor countries, prior to the introduction of the vaccine into their national immunization programs. In 2000, Hib was estimated to have caused two to three million cases of serious disease, notably pneumonia and meningitis, and 386,000 deaths in young children. Hib disease is observed in all parts of the world but is difficult to confirm because it requires prompt laboratory investigation in patients that have not received prior antibiotic treatment.

Commercially available combined DTaP/IPV/Hib vaccines include Pentacel®, which is based on combined diphtheria toxoid, tetanus toxoid, acellular pertussis (adsorbed), and inactivated poliovirus in combination with a Hib conjugate vaccine.

Hence, there is a need for a safe and effective method of simultaneously preventing dengue disease and diphtheria, tetanus, pertussis, poliomyelitis and diseases caused by *Haemophilus influenzae* type b.

Furthermore, it has been reported that elderly subjects infected with dengue virus often present atypically, wherein fever may be the only symptom and are less likely to present with typical symptoms and signs of dengue fever which may be defined as fever plus at least one of the following symptoms: bone pain, myalgia, arthralgia, retro-orbital pain, headache and maculopapular rash (Lee et al. (2013) Am. J. Emerg. Med. 31(5): 783-787). Yet, elderly adults are at increased risk of developing severe dengue and DHF/DSS compared to younger subjects (Liu et al. (2008) Am. J. Infect. Dis. 4(1): 10-17; Lin et al. (2012) Emerg. Infect. Dis. 18(10): 2003-1009; Rowe et al. (2014) PloS Negl. Trop. Dis. 8(4)). Several reasons which may contribute to severe disease in the elderly have been discussed, such as impaired physiological and immune functions, an increased probability of acquiring secondary dengue and an increased prevalence of chronic diseases and other comorbidities in the elderly, i.e. above 60 (see the discussion in Lin et al. (2017) Expert Review of Anti-infective Therapy 15(8): 729-735).

OBJECTS AND SUMMARY

It is an object of the present invention to provide a safe and effective vaccine and corresponding method of inoculation against all serotypes of dengue virus for dengue-endemic and dengue non-endemic populations and for a broad range of ages, in particular for subjects between 2 months and 60 years of age, and independent of previous exposure to dengue virus and corresponding seropositive or seronegative status before vaccination.

It is an object of the present invention to minimize the risk of DHF and DSS caused by infection with DENV-1, DENV-2, DENV-3 or DENV-4, in particular following vaccination in children of young age and individuals of any age who have never been previously exposed to dengue, or who are seronegative to dengue before vaccination.

It is an object of the invention to provide a vaccine and corresponding method of inoculating for controlling a dengue outbreak situation.

It is an object of the invention to provide a vaccine and corresponding method of inoculating which is useful in settings less familiar with clinical management of dengue or in those with fewer resources.

It is an object of the invention to provide a vaccine and corresponding method of inoculating which avoids testing for individual serostatus before individual inoculation or analysis of seroprevalence rates in areas to be mass vaccinated.

It is an object of the invention to provide a vaccine and corresponding method of inoculating which reduces and/or avoids the risk for later antibody dependent enhancement.

It is an object of the invention to provide a vaccine and corresponding method which reduces and/or avoids dengue NS1 toxicosis.

It is an object of the invention to provide a vaccine and corresponding method of inoculating which induces cross reactive multitypic antibody and/or cell mediated immunity.

It is one object of the present invention to provide a safe and effective protection against dengue disease and yellow fever.

It is another object of the present invention to provide a safe and effective protection against dengue disease and hepatitis A.

It is a further object of the present invention to provide a safe and effective protection against dengue disease and HPV-associated cancers or genital warts.

It is a certain object of the present invention to provide a safe and effective protection against dengue disease and measles, mumps and rubella.

It is another object of the present invention to provide safe and effective protection against dengue disease and tetanus, diphtheria, and pertussis.

It is another object of the present invention to provide a safe and effective protection against dengue disease and diphtheria, tetanus, pertussis, poliomyelitis and diseases caused by *Haemophilus influenzae* type b.

It is another object of the present invention to provide safe and effective protection against any combination of the above mentioned diseases.

It is another object of the present invention to provide a vaccine which stimulates a balanced immune response to all four dengue serotypes in a subject, in particular in an elderly subject (i.e. more than 60 years of age).

The present invention is therefore directed in part to a dengue vaccine for a method of mass vaccination without individual testing for serostatus or prior evaluation of seroprevalence rates. This mass vaccination includes endemic regions including outbreak situations as well as in non-endemic regions for travelers.

The present invention is therefore directed to a tetravalent dengue virus composition including four live attenuated dengue virus strains representing serotype 1, serotype 2, serotype 3 and serotype 4, wherein preferably the tetravalent dengue virus composition includes a chimeric dengue serotype 2/1 strain and a dengue serotype 2 strain and a chimeric dengue serotype 2/3 strain and a chimeric dengue serotype 2/4 strain, wherein preferably the dengue serotype 2 strain is derived from the wild type virus strain DEN-2 16681 (represented by SEQ ID NO 11) and differs in at least three nucleotides from the wild type as follows:

a) 5-noncoding region (NCR)-57 (nt-57 C-to-T)

b) NS1-53 Gly-to-Asp (nt-2579 G-to-A)

c) NS3-250 Glu-to-Val (nt-5270 A-to-T); and the three chimeric dengue strains being derived from the serotype 2 strain by replacing the structural proteins prM and E from serotype 2 strain with the corresponding structural proteins from the other dengue serotypes, resulting in the following chimeric dengue strains:

a DENV-2/1 chimera, a DENV-2/3 chimera and a DENV-2/4 chimera.

The present invention is in particular directed to a composition or lyophilized unit dose which upon reconstitution with 0.5 mL of a pharmaceutically acceptable diluent comprises:

(i) a dengue serotype 1 in a concentration of at least 3.3 log 10 pfu/0.5 ml, (ii) a dengue serotype 2, in a concentration of at least 2.7 log 10 pfu/0.5 ml, (iii) a dengue serotype 3, in a concentration of at least 4.0 log 10 pfu/0.5 ml, and (iv) a dengue serotype 4, in a concentration of at least 4.5 log 10 pfu/0.5 ml.

The present invention is also in particular directed to such a composition or unit dose which upon reconstitution with a pharmaceutically acceptable diluent (i), (ii), (iii), and (iv) provide a total concentration of pfu/0.5 mL and based on said total concentration the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 8%, or preferably at least 10%, or at least 12%, or at least 14%, or at least 16%, or at least 18%.

The present invention is also in particular directed to such method and use wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 2%, the concentration of (iv) in pfu/0.5 mL is at least 50%, the concentration of (i) in pfu/0.5 mL is at least 1%, and the concentration of (iii) in pfu/0.5 mL is at least 6%.

The present invention is therefore directed to a method including and corresponding use of a tetravalent dengue virus composition including four live attenuated dengue virus strains representing serotype 1, serotype 2, serotype 3 and serotype 4, the method being directed to inoculating a subject against virologically confirmable dengue disease, wherein in particular the tetravalent dengue virus composition includes a chimeric dengue serotype 2/1 strain and a dengue serotype 2 strain and a chimeric dengue serotype 2/3 strain and a chimeric dengue serotype 2/4 strain, wherein in particular the dengue serotype 2 strain is derived from the wild type virus strain DEN-2 16681 (represented by SEQ ID NO 11) and differs in at least three nucleotides from the wild type as follows:

d) 5-noncoding region (NCR)-57 (nt-57 C-to-T)

e) NS1-53 Gly-to-Asp (nt-2579 G-to-A)

f) NS3-250 Glu-to-Val (nt-5270 A-to-T); and the three chimeric dengue strains being derived from the serotype 2 strain by replacing the structural proteins prM and E from serotype 2 strain with the corresponding structural proteins from the other dengue serotypes, resulting in the following chimeric dengue strains:

a DENV-2/1 chimera, a DENV-2/3 chimera and a DENV-2/4 chimera.

The present invention is in particular directed to such method and use wherein the unit dose is lyophilized and upon reconstitution with 0.5 mL of a pharmaceutically acceptable diluent comprises:

(i) a dengue serotype 1 in a concentration of at least 3.3 log 10 pfu/0.5 ml, (ii) a dengue serotype 2, in a concentration of at least 2.7 log 10 pfu/0.5 ml, (iii) a dengue serotype 3, in a concentration of at least 4.0 log 10 pfu/0.5 ml, and (iv) a dengue serotype 4, in a concentration of at least 4.5 log 10 pfu/0.5 ml.

The present invention is also in particular directed to such method and use wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 8%, or at least 10%, or at least 12%, or at least 14%, or at least 16%, or at least 18%, and wherein the subject is preferably 2 to 17 years of age or 4 to 16 years of age.

The present invention is also in particular directed to such method and use wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 2%, the concentration of (iv) in pfu/0.5 mL is at least 50%, the concentration of (i) in pfu/0.5 mL is at least 1%, and the concentration of (iii) in pfu/0.5 mL is at least 6%, wherein the subject is 18 to 60 years of age.

The present invention is therefore directed to a method and corresponding use, the method comprising a primary vaccination with only two administrations of the unit dose comprising the steps of:

(A) administering a first unit dose of the tetravalent dengue virus composition to the subject, and (B) administering a second unit does of the tetravalent dengue virus composition to the subject within 3 months of administration of the first unit dose, wherein preferably the method and use do not include a step of determination whether there was a previous dengue infection in the subject before administration of the unit dose or wherein the serostatus of the subject is unknown before administration of the unit dose or wherein the method and use do not include a step of determination of a previous dengue infection in the subjects preferably at any time before, during or after the steps of administration or wherein the serostatus of the subject is unknown preferably at any time before, during or after the steps of administration.

According to one embodiment such a method and use do not include the active surveillance with respect to febrile illness of the subject after the administration of the first- and second-unit dose. During active surveillance any subject with febrile illness (defined as fever ≥38° C. on any 2 of 3 consecutive days) will be asked to return to the site for dengue fever evaluation by the Investigator. Subjects/guardians will be contacted at least weekly to ensure robust identification of febrile illness by reminding subjects/guardians of their obligation to return to the site in case of febrile illness. This contact will be implemented through appropriate methods that may differ in each trial site (eg, phone calls, text messaging, home visits, school-based surveillance).

According to one embodiment such a method and use do not include vaccine immunogenicity analysis including GMTs for dengue neutralizing antibodies.

According to one embodiment such a method and use do not include a reactogenicity analysis. Such a reactogenicity analysis relates to solicited local AEs (injection site pain, injection site erythema, and injection site swelling) and solicited systemic AEs (child <6 years: fever, irritability/fussiness, drowsiness and loss of appetite; child ≥6 years: asthenia, fever, headache, malaise and myalgia) which will e.g. be assessed for 7 days and 14 days, respectively, following each vaccination (vaccination day included) via collection of diary cards.

The method according to the invention does not require the testing of the serostatus before vaccination and thus allows immediate treatment and outbreak control. According to certain embodiments the invention is directed to a method and use wherein the subject is exposed to a dengue outbreak. In certain such embodiments the outbreak is due to a dengue serotype 2, and/or due to a serotype 1.

According to certain embodiments the method of inoculation against the virologically confirmable dengue disease is due to a dengue serotype 2, and/or due to a dengue serotype 1.

According to one embodiment the method comprises a primary vaccination consisting of the steps of:

(A) selecting a subject for administration of the unit doses of the tetravalent dengue virus composition in need for protection against dengue infection without determination of a previous dengue infection, and (B) administering a first unit dose of the tetravalent dengue virus composition to the subject, and (C) administering a second unit dose of the tetravalent dengue virus composition to the subject within 3 months of administration of the first unit dose.

Therefore the method of inoculating is finalized without determination of a previous dengue infection. The method further optionally comprises at least 1 years after the administration of the second unit dose a booster dose of the unit dose.

According to one embodiment the method and use is directed to a method of inoculating a subject against virologically confirmable dengue disease with a tetravalent dengue virus composition including four live attenuated dengue virus strains representing serotype 1, serotype 2, serotype 3 and serotype 4, the dengue serotype 2 strain being derived from the wild type virus strain DEN-2 16681 (represented by SEQ ID NO 11) and differing in at least three nucleotides from the wild type as follows:

a) 5-noncoding region (NCR)-57 (nt-57 C-to-T)

b) NS1-53 Gly-to-Asp (nt-2579 G-to-A)

c) NS3-250 Glu-to-Val (nt-5270 A-to-T); and the three chimeric dengue strains being derived from the serotype 2 strain by replacing the structural proteins prM and E from serotype 2 strain with the corresponding structural proteins from the other dengue serotypes, resulting in the following chimeric dengue strains:

a DENV-2/1 chimera, a DENV-2/3 chimera and a DENV-2/4 chimera, the method comprises a primary vaccination consisting of the steps of:

(A) selecting a subject for administration of the unit doses of the tetravalent dengue virus composition in need for protection against dengue infection without determination whether there was a previous dengue infection, and (B) administering a first unit dose of the tetravalent dengue virus composition to the subject, and (C) administering a second unit dose of the tetravalent dengue virus composition to the subject within 3 months of administration of the first unit dose.

Therefore the method of inoculating is finalized without determination of a previous dengue infection. The method further optionally comprises at least 1 years after the administration of the second unit dose a booster dose of the unit dose.

According to the invention the method and use is applicable to subjects of all kinds of ages. The present invention is in particular directed to such a method and use wherein the subject is under 9 years of age, or 4 to 5 years of age, or 6 to 11 years of age, or 12 to 16 years, or 6 to 16 years of age, or 4 to 16 years of age, or 2 to 17 years of age, or 9 years of age, or over 9 years of age, or 9 to 17 years of age, or 18 to 60 years of age, or 18 to 45 years of age, or 46 to 60 years of age, or over 60 years of age.

In particular the present invention is directed to such use wherein the method is safe.

In particular the present invention is directed to such use wherein the method provides a combined vaccine efficacy against virologically-confirmed dengue with hospitalization against all four serotypes with a 2-sided 95% confidence interval, wherein the lower bound is more than 65%, when measured against placebo in a subject population of at least 5,000 healthy 4 to 16 year old subjects irrespective of serostatus at baseline from first administration of the administration schedule until 12 to 18 months after the last administration of the administration schedule.

In particular the present invention is directed to such use wherein the method is effective.

In particular the present invention is directed to such use wherein the method provides a combined vaccine efficacy against all four serotypes, in preventing virologically confirmable dengue disease with a 2-sided 95% confidence interval, wherein the lower bound is more than 60%, when measured against placebo in a subject population of at least 5,000 healthy subjects irrespective of serostatus at baseline and 14 to 16 years of age, from the first administration of the administration schedule until 18 months after the last administration of the administration schedule.

The present invention is also directed in part to a reconstituted dengue vaccine composition for use in a method of preventing virologically confirmable dengue disease in a subject comprising consecutively administering at least a first and a second unit dose of the dengue vaccine composition to the subject, wherein said first and second unit dose are administered subcutaneously within 3 months and at least 4 weeks apart, optionally at about day 1 and at about day 90, wherein the dengue vaccine composition is a tetravalent dengue virus composition including four dengue virus strains representing dengue serotype 1, dengue serotype 2, dengue serotype 3 and dengue serotype 4, optionally wherein the dengue virus strains are live, attenuated, and wherein upon reconstitution with 0.5 mL of a pharmaceutically acceptable diluent (i) dengue serotype 1 has a concentration of at least 3.3 log 10 pfu/0.5 mL and optionally to 5.0 log 10 pfu/0.5 mL, (ii) dengue serotype 2 has a concentration of at least 2.7 log 10 pfu/0.5 mL and optionally to 4.9 log 10 pfu/0.5 mL, (iii) dengue serotype 3 has a concentration of at least 4.0 log 10 pfu/0.5 mL and optionally to 5.7 log 10 pfu/0.5 mL, and (iv) dengue serotype 4 has a concentration of at least 4.5 log 10 pfu/0.5 mL and optionally to 6.2 log 10 pfu/0.5 mL.

The present invention is therefore directed in part to a dengue vaccine composition for use in a method of preventing virologically confirmable dengue disease (VCD) in a subject comprising consecutively administering at least a first and a second unit dose of the dengue vaccine composition to the subject, wherein said first and second unit dose are administered subcutaneously within 3 months and at least 4 weeks apart, optionally at about day 1 and at about day 90, and wherein the dengue vaccine composition is a tetravalent dengue virus composition including four live, attenuated dengue virus strains representing dengue serotype 1, dengue serotype 2, dengue serotype 3 and dengue serotype 4, wherein the attenuated dengue virus strains comprise chimeric dengue viruses and preferably at least one non-chimeric dengue virus, and wherein the dengue serotype 1 and the dengue serotype 2 are present each in a concentration based on the total concentration in pfu/0.5 mL which is within 5%-points of each other and/or are together less than about 10% of the total concentration in pfu/0.5 mL, in particular wherein the dengue serotype 3 is at least about 10% of the total concentration in pfu/0.5 mL and in particular wherein the dengue serotype 4 is at least about 70% of the total concentration in pfu/0.5 mL.

The present invention is therefore directed in part to a unit dose of a dengue vaccine composition and use thereof, the unit dose comprising:

a tetravalent dengue virus composition including four live attenuated dengue serotypes (e.g. virus strains):

(i) a dengue serotype 1 (e.g. chimeric dengue serotype 2/1 strain), (ii) a dengue serotype 2 (e.g. dengue serotype 2 strain), (iii) a dengue serotype 3 (e.g. chimeric dengue serotype 2/3 strain), (iv) a dengue serotype 4 (e.g. chimeric dengue serotype 2/4 strain), and one or more pharmaceutically acceptable excipients thereof.

The present invention is further directed in part to a unit dose of a dengue vaccine composition and use thereof, the unit dose comprising:

a tetravalent virus composition including four live attenuated dengue virus strains:

(i) a dengue serotype 1 (e.g. chimeric dengue serotype 2/1 strain) in a concentration of at least 3.3 log 10 pfu/0.5 ml, (ii) a dengue serotype 2 (e.g. dengue serotype 2 strain) in a concentration of at least 2.7 log 10 pfu/0.5 ml, (iii) a dengue serotype 3 (e.g. chimeric dengue serotype 2/3 strain) in a concentration of at least 4.0 log 10 pfu/0.5 ml, and (iv) a dengue serotype 4 (e.g. chimeric dengue serotype 2/4 strain) in a concentration of at least 4.5 log 10 pfu/0.5 ml, and one or more pharmaceutically acceptable excipients.

The present invention is further directed in part to a unit dose of a dengue vaccine composition and use thereof, the unit dose comprising:

a tetravalent virus composition including four live attenuated dengue virus strains, wherein the unit dose is lyophilized and upon reconstitution with 0.5 mL of a pharmaceutically acceptable diluent comprises:

(i) a dengue serotype 1 (e.g. chimeric dengue serotype 2/1 strain) in a concentration of at least 3.3 log 10 pfu/0.5 ml, (ii) a dengue serotype 2 (e.g. dengue serotype 2 strain) in a concentration of at least 2.7 log 10 pfu/0.5 ml, (iii) a dengue serotype 3 (e.g. chimeric dengue serotype 2/3 strain) in a concentration of at least 4.0 log 10 pfu/0.5 ml, and (iv) a dengue serotype 4 (e.g. chimeric dengue serotype 2/4 strain) in a concentration of at least 4.5 log 10 pfu/0.5 ml.

The present invention is further directed in part to a unit dose of a dengue vaccine composition and use thereof, wherein said unit dose is lyophilized and obtained by lyophilizing 0.5 mL of a solution comprising:

a tetravalent virus composition including four live attenuated dengue virus strains:

(i) a dengue serotype 1 (e.g. chimeric dengue serotype 2/1 strain) in a concentration of at least 3.3 log 10 pfu/0.5 ml, (ii) a dengue serotype 2 (e.g. dengue serotype 2 strain) in a concentration of at least 2.7 log 10 pfu/0.5 ml, (iii) a dengue serotype 3 (e.g. chimeric dengue serotype 2/3 strain) in a concentration of at least 4.0 log 10 pfu/0.5 ml, and (iv) a dengue serotype 4 (e.g. chimeric dengue serotype 2/4 strain) in a concentration of at least 4.5 log 10 pfu/0.5 ml, and one or more pharmaceutically acceptable excipients.

The present invention is in particular directed to such unit dose or composition wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 8%, or at least 10%, or at least 12%, or at least 14%, or at least 16%, or at least 18%, in particular wherein the concentration of (iii) in pfu/0.5 mL is at least 10%.

The present invention is in particular directed to such unit dose or composition, wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 2%, the concentration of (iv) in pfu/0.5 mL is at least 50%, the concentration of (i) in pfu/0.5 mL is at least 1%, and the concentration of (iii) in pfu/0.5 mL is at least 6%.

The present invention is further directed in part to a kit for preparing a reconstituted unit dose and use thereof, the kit comprising the following components:

a) a lyophilized unit dose of the present invention as described herein, and b) a pharmaceutically acceptable diluent for reconstitution.

The present invention is further directed in part to a container, such as a vial, comprising one to ten unit doses of the present invention as described herein.

The present invention is further directed to a method of preventing dengue disease in a subject comprising administering to the subject a reconstituted unit dose of a dengue vaccine composition as described herein, for example by subcutaneous injection.

The present invention is further directed to the use of the reconstituted unit dose of a dengue vaccine composition as described herein for the manufacture of a medicament for preventing dengue disease in a subject, for example by subcutaneous injection.

The present invention is further directed to the reconstituted unit dose of a dengue vaccine composition as described herein for use in a method of preventing dengue disease in a subject, for example by subcutaneous injection.

The present invention is further directed to a method of preventing dengue disease in a subject population, comprising administering to the subject population a reconstituted unit dose of a vaccine composition as described herein, wherein the subject population is seronegative to all dengue serotypes. In said method the geometric mean neutralizing antibody titers (GMTs) when tested in at least 40, or at least 50, or at least 60 subjects at day 180 or day 365 after at least a first administration of said unit dose, and optionally a second administration of said unit dose 90 days after said first administration, may provide a ratio of not more than 50, or not more than 40, or nor more than 30, or not more than 20 for the GMT of dengue serotype 2 to the GMT of dengue serotype 4 (GMT DENV-2:GMT DENV-4), and optionally a ratio of not more than 20 for the GMT of dengue serotype 2 to the GMT of dengue serotype 1 (GMT DENV-2:GMT DENV-1), and optionally a ratio of not more than 20 for the GMT of dengue serotype 2 to the GMT of dengue serotype 3 (GMT DENV-2:GMT DENV-3).

The present invention is further directed to a method of preventing dengue disease in a subject, comprising administering to the subject a reconstituted unit dose of a vaccine composition as described herein, wherein the subject is seronegative to all dengue serotypes. In said method the neutralizing antibody titers when tested in the subject at day 180 or day 365 after at least a first administration of said unit dose, and optionally a second administration of said unit dose 90 days after said first administration, may provide a ratio of not more than 50, or not more than 40, or nor more than 30, or not more than 20 for the neutralizing antibody titer of dengue serotype 2 to the neutralizing antibody titer of dengue serotype 4, and optionally a ratio of not more than 20 for the neutralizing antibody titer of dengue serotype 2 to the neutralizing antibody titer of dengue serotype 1, and optionally a ratio of not more than 20 for the neutralizing antibody titer of dengue serotype 2 to the neutralizing antibody titer of dengue serotype 3.

In one preferred embodiment, the methods of preventing dengue disease of the present invention are not associated with an increased likelihood of solicited systemic adverse events, such as in children under 9 or seronegative individuals.

The present invention is therefore directed in part to a method of preventing dengue disease as well as yellow fever.

The present invention is therefore directed in part to a method of preventing dengue disease as well as hepatitis A.

The present invention is therefore directed in part to a method of preventing dengue disease as well as HPV-associated cancers or genital warts.

The present invention is therefore directed in part to a method of preventing dengue disease as well as measles, mumps and rubella.

The present invention is therefore directed in part to a method of preventing dengue disease as well as tetanus, diphtheria, and pertussis.

The present invention is therefore directed in part to a method of preventing dengue disease as well as diphtheria, tetanus, pertussis, poliomyelitis and diseases caused by *Haemophilus influenzae* type b.

The present invention is therefore also directed in part to a method of prevention any combination of the above mentioned diseases.

The present invention is further directed in part to the use of the reconstituted unit dose of a dengue vaccine composition/tetravalent dengue virus composition as described herein for the manufacture of a medicament for preventing dengue disease in a subject, for example by subcutaneous injection.

The present invention is further directed in part to the reconstituted unit dose of a dengue vaccine composition/tetravalent dengue virus composition as described herein for use in a method of preventing dengue disease in a subject, as described herein.

Definitions

In describing the present invention, the following terms are to be used as indicated below. As used herein, the singular forms "a," "an," and "the" include plural references unless the context clearly indicates otherwise.

As used herein, the terms "unit dose of a dengue vaccine composition", "unit dose" and "unit dose of the invention as described herein" refer to the amount of a dengue vaccine which is administered to a subject in a single dose. In one embodiment, one unit dose is present in a vial and this unit dose is administered to a subject, e.g. optionally after reconstitution. In one embodiment, more than one unit dose of the dengue vaccine composition may be present in a vial so that with the content of one vial more than one subject can be vaccinated.

A "lyophilized unit dose" or "unit dose in lyophilized form" refers to the unit dose that is obtained by subjecting a given volume of the liquid dengue vaccine composition, such as 0.5 mL, to lyophilization.

Thus, the aqueous formulations of the dengue vaccine composition being produced by combining the pharmaceutically acceptable excipients and the dengue virus composition comprising the four dengue virus strains, preferably TDV-1 to TDV-4, is subjected to lyophilization to obtain the lyophilized unit dose.

A "reconstituted unit dose" or "unit dose in reconstituted form" is obtained from the lyophilized dose by reconstitution with a pharmaceutically acceptable diluent. The diluent does not contain dengue virus. The reconstituted unit dose is a liquid which can be administered to a subject, for example by injection, such as subcutaneous injection.

As used herein, the term "upon reconstitution with 0.5 mL" is not limiting the reconstitution to be performed using 0.5 mL of the diluent, but refers to the concentration of the dengue viruses that will be present in the reconstituted unit dose when 0.5 mL diluent are used for reconstitution. While using a different volume for reconstitution (e.g. 0.8 mL) will result in a different concentration of dengue viruses in the reconstituted unit dose, the administration of the total volume of the unit dose (e.g. 0.8 mL) will result in the same total amount of dengue virus being administered.

As used herein, a "concentration of at least X log 10 pfu/0.5 mL" refers to the concentration of a dengue serotype in 0.5 mL, but is not limiting the unit dose to be 0.5 mL. If the unit dose has a volume different than 0.5 mL, or is lyophilized from a volume different than 0.5 mL, or is reconstituted with a volume different than 0.5 mL, said concentration will differ from the "concentration of at least X log 10 pfu/0.5 mL". However, if the unit dose has a volume of 0.5 mL, or is lyophilized from a volume of 0.5 mL, or is reconstituted with a volume of 0.5 mL, said concentration will be the "concentration of at least X log 10 pfu/0.5 mL". Thus, while the concentration may differ, the total amount of virus in the unit dose remains the same.

As used herein, the term "dengue serotype" refers to a species of dengue virus which is defined by its cell surface antigens and therefore can be distinguished by serological methods known in the art. At present, four serotypes of dengue virus are known, i.e. dengue serotype 1 (DENV-1), dengue serotype 2 (DENV-2), dengue serotype 3 (DENV-3) and dengue serotype 4 (DENV-4).

As used herein, the term "tetravalent dengue virus composition" refers to a dengue virus composition comprising four different immunogenic components from the four different dengue serotypes DENV-1, DENV-2, DENV-3 and DENV-4, preferably comprising four different live, attenuated dengue viruses, each representing one dengue serotype, and which aims to stimulate immune responses to all four dengue serotypes.

As used herein, the term "live attenuated dengue virus" refers to a viable dengue virus which is mutated to provide reduced virulence. The live attenuated dengue virus can be a dengue virus in which all components are derived from the same dengue serotype or it can be a chimeric dengue virus having parts from two or more dengue serotypes.

A "virus strain" and in particular a "dengue virus strain" is a genetic subtype of a virus, in particular of a dengue virus, which is characterized by a specific nucleic acid sequence. A dengue serotype may comprise different strains with different nucleic acid sequences which have the same cell surface antigens. A dengue virus strain can be a dengue virus in which all components are derived from the same dengue serotype or it can be a chimeric dengue virus having parts from two or more dengue serotypes.

As used herein, "TDV-2" refers to a molecularly characterized and cloned dengue serotype 2 strain derived from the live attenuated DEN-2 PDK-53 virus strain. The PDK-53 strain is described for example in Bhamarapravati et al. (1987) Bulletin of the World Health Organization 65(2): 189-195. In one embodiment, the TDV-2 strain served as a backbone for the chimeric TDV-1, TDV-3 and TDV-4 strains into which parts from the TDV-1, TDV-3 and TDV-4 strains were introduced.

A "non-chimeric dengue virus" or "non-chimeric dengue serotype strain" or "non-chimeric dengue strain" comprises only parts from one dengue serotype. In particular, a non-chimeric dengue virus does not include parts from a different flavivirus such as yellow fever virus, Zika virus, West Nile virus, Japanese encephalitis virus, St. Louis encephalitis virus, tick-borne encephalitis virus. TDV-2 is an example of a non-chimeric dengue virus.

A "chimeric dengue virus" or "chimeric dengue serotype strain" or "chimeric dengue strain" comprises parts from at least two different dengue serotypes. As used herein, the chimeric dengue virus does not include parts from a different flavivirus such as yellow fever virus, Zika virus, West Nile virus, Japanese encephalitis virus, St. Louis encephalitis virus, tick-borne encephalitis virus. In particular, the chimeric dengue virus described herein does not include parts from the yellow fever virus. As used herein, a "chimeric dengue serotype 2/1 strain" or "DENV-2/1 chimera" or "TDV-1" refers to a dengue virus chimeric construct which comprises parts from both DENV-2 and DENV-1. In particular, in the chimeric dengue serotype 2/1 strain the prM and E proteins from DENV-1 replace the prM and E proteins from DENV-2 as detailed below. As used herein, a "chimeric dengue serotype 2/3 strain" or "DENV-2/3 chimera" or "TDV-3" refers to a dengue virus chimeric construct which comprises parts from both DENV-2 and DENV-3. In particular, in the chimeric dengue serotype 2/3 strain the prM and E proteins from DENV-3 replace the prM and E proteins from DENV-2 as detailed below. As used herein, a "chimeric dengue serotype 2/4 strain" or "DENV-2/4 chimera" or "TDV-4" refers to a dengue virus chimeric construct which comprises parts from both DENV-2 and DENV-4. In particular, in the chimeric dengue serotype 2/4 strain the prM and E proteins from DENV-4 replace the prM and E proteins from DENV-2 as detailed below.

As used herein, "TDV" refers to a tetravalent live attenuated dengue vaccine that comprises a mixture of the four live attenuated dengue virus strains TDV-1, TDV-2, TDV-3 and TDV-4 expressing surface antigens from the four dengue serotypes DENV-1, DENV-2, DENV-3 and DENV-4, respectively. In one embodiment (e.g. also in the examples), TDV-1 has the nucleotide sequence according to SEQ ID No. 1 and/or the amino acid sequence according to SEQ ID No. 2. In one embodiment, TDV-2 has the nucleotide sequence according to SEQ ID No. 3 and/or the amino acid sequence according to SEQ ID No. 4. In one embodiment, TDV-3 has the nucleotide sequence according to SEQ ID No. 5 and/or the amino acid sequence according to SEQ ID No. 6. In one embodiment, TDV-4 has the nucleotide sequence according to SEQ ID No. 7 and/or the amino acid sequence according to SEQ ID No. 8.

As used herein, the term "dengue disease" refers to the disease which is caused by infection with dengue virus. Symptoms of dengue disease include sudden high fever, headaches, joint and muscle pain, nausea, vomiting and skin rashes. The term dengue disease also includes the more severe forms of dengue hemorrhagic fever (DHF) and dengue shock syndrome (DSS). Symptoms of DHF include increased vascular permeability, hypovolemia and abnormal blood clotting mechanisms. Subjects with DHF may present with severe manifestations of plasma leakage and hemorrhage. When a subject with DHF experiences shock he or she will be categorized as having DSS. Symptoms of DSS include bleeding that may appear as tiny spots of blood on the skin and larger patches of blood under the skin. Prolonged shock is the main factor associated with complications including massive gastrointestinal hemorrhage that can lead to death. As used herein, DHF cases are defined as VCD cases meeting WHO 1997 DHF criteria. In the context of preventing dengue disease in elderly subjects, the term "preventing dengue disease" preferably includes preventing DHF and/or DSS. In the context of preventing dengue disease in elderly subjects, the term "preventing dengue disease" preferably includes preventing severe end-organ manifestations of dengue such as hepatomegaly and acute renal failure.

As used herein, "preventing dengue disease" refers to preventing a subject from developing one or more symptoms of dengue disease because of an infection with a dengue virus. In particular, preventing dengue disease is achieved by vaccinating or inoculating a subject with a dengue vaccine composition, such as the reconstituted unit dose described herein. As used herein, the term "prophylactically treating dengue disease" is equivalent to "preventing dengue disease". In a particular embodiment, preventing dengue disease includes preventing DHS and/or DSS.

As used herein, the terms "virologically-confirmed dengue disease", "VCD case", or "VCD fever" refer to febrile illness or illness clinically suspected to be dengue disease with a positive serotype-specific reverse transcriptase polymerase chain reaction (RT-PCR). The term "virologically confirmable dengue" disease refers to a subject having febrile illness or illness clinically suspected to be dengue disease, wherein testing the subject, e.g. using RT-PCR, would confirm the presence of at least one dengue serotype. Severe forms of VCD fever will be identified as follows: Dengue Hemorrhagic Fever (DHF) was defined according to the WHO 1997 criteria. Severe dengue was defined through an assessment of an independent Dengue Case Adjudication Committee which will assess all hospitalized VCD cases (severe/non-severe) based on criteria redefined in a charter. All non-hospitalized cases are considered non-severe.

As used herein, the term "febrile illness" is defined as temperature ≥38° C. on any 2 of 3 consecutive days.

As used herein, the terms "virologically-confirmed dengue disease with hospitalization", is considered to be a surrogate for severe dengue and the "incidence of virologically-confirmed dengue disease with hospitalization" is used as a safety parameter. As used herein, the "relative risk with respect to virologically-confirmed dengue disease with hospitalization" means the number of events of virologically confirmed dengue disease with hospitalization divided by the number of subjects treated with the unit dose as disclosed herein over the number of events of virologically confirmed dengue disease with hospitalization divided by the number of subjects treated with placebo. If the "relative risk with respect to virologically-confirmed dengue disease with hospitalization" is 1 or lower the vaccine provides for the same or less risk for virologically-confirmed dengue disease with hospitalization as placebo and is considered "safe". In this context the risk of virologically-confirmed dengue disease with hospitalization may be also 0.9 or less, 0.8 or less, 0.7 or less, 0.6 or less, 0.5 or less, 0.4 or less, 0.3 or less, 0.2 or less, or 0.1 or less, in particular when determined from 30 days after a second administration until 12 months after a second administration, in particular when determined in age groups selected from the age group of 4 to 16 year old subjects, the age group of 4 to under 9 year old subjects, the age group of 2 to under 9 year old subjects, the age group of 4 to 5 year old subjects, the age group of 6 to 11 year old subjects, and the age group of 12 to 16 year old subjects.

As used herein, alternatively a vaccine is considered "safe" when the vaccine efficacy (VE) with respect to virologically-confirmed dengue disease with hospitalization is 0% or higher. This means that the vaccine provides for the same likelihood or less for virologically-confirmed dengue disease with hospitalization as placebo. In particular considered "safe" is the combined vaccine efficacy against virologically-confirmed dengue with hospitalization against all four serotypes with a 2-sided 95% confidence interval, wherein the lower bound is more than 25%, in particular when measured against placebo in a subject population of at least 1,500 or at least 2,000 healthy subjects (in particular when measured in age groups selected in particular from the age group of 4 to 16 year old subjects, the age group of 4 to under 9 year old subjects, the age group of 2 to under 9 year old subjects, the age group of 4 to 5 year old subjects, the age group of 6 to 11 year old subjects, and the age group of 12 to 16 year old subjects) being seronegative against all serotypes at baseline or being seropositive against at least one serotype at baseline, in particular when said unit dose or said placebo is administered at least twice within less than 6 months, such as within 3 months, about from first administration or from 30 days after the second or last administration of the administration schedule until at least 12 months, until 12 to 18 months, until 12 months, or until 18 months after the second or last administration of the administration schedule. In particular, the lower bound may be more than 30%, more than 40%, more than 50%, more than 60%, more than 65%, more than 66%, more than 67%, more than 68% more than 70%, or more than 75%. In particular, the 2-sided 95% confidence interval of the combined vaccine efficacy against virologically-confirmed dengue with hospitalization against all four serotypes when comparing seropositive and seronegative subjects provides for lower bounds of the 2-sided confidence interval which are within 10% points or within 15% points or within 20% points. In a particular embodiment "safe" means providing a combined vaccine efficacy against virologically-confirmed dengue with hospitalization against all four serotypes with a 2-sided 95% confidence interval, wherein the lower bound is more than 65%, when measured against placebo in a subject population of at least 5,000 healthy 4 to 16 year old subjects irrespective of serostatus at baseline from first administration of the administration schedule until 12 to 18 months after the last administration of the administration schedule.

If one of the criteria as defined above for the term "safe" is fulfilled, the vaccine is considered safe within the meaning of this invention. In this context, safe in particular refers to a vaccine that is safe for all subjects irrespective of their serostatus at baseline. This means that the vaccine can be administered without the need to determine the occurrence of a previous dengue infection in the subject before administration. Preferably, the vaccine is safe as defined above with respect to all age groups starting from 4 years of age and preferably irrespective of the serostatus, in particular from 4 years of age to 60 years of age, or 4 years of age to 16 years of age. Relevant subgroups in this context are under 9 years of age, from 2 years of age to under 9 years of age, from 4 years of age to under 9 years of age, 4 to 5 years of age, 6 to 11 years of age and 12 to 16 years of age or any age group within 4 to 16 years of age. For further definitions of VE against virologically-confirmed dengue disease with hospitalization reference is made to the disclosure below with respect to certain methods of treatment.

As used herein, "vaccine efficacy" or "VE" measure the proportionate reduction in cases among vaccinated persons. Vaccine efficacy (VE) is measured by calculating the risk of disease among vaccinated and unvaccinated persons and determining the percentage reduction in risk of disease among vaccinated persons relative to unvaccinated persons. The greater the percentage reduction of illness in the vaccinated group, the greater the vaccine efficacy. For example, a VE of 90% indicates a 90% reduction in disease occurrence among the vaccinated group, or a 90% reduction from the number of cases you would expect if they have not been vaccinated. The vaccine efficiency is calculated by the formula: 100*(1−HR), wherein HR is the Hazard Ratio which is defined as the Hazard rate of vaccine ($\lambda v$) divided by the Hazard rate of placebo ($\lambda c$), i.e. $HR=\lambda v/\lambda c$. $\lambda v$ denote the hazard rate for the subjects vaccinated with a tetravalent dengue vaccine composition as disclosed herein and $\lambda c$ denote the hazard rate for unvaccinated subjects, i.e. subjects receiving placebo. The hazard rate ratio HR is estimated from a Cox proportional hazard model with study vaccine as a factor, adjusted for age, and stratified by region. As used herein the term "combined vaccine efficacy against all four serotypes" is defined as the vaccine efficacy in relation to the risk of dengue disease irrespective of the serotype being responsible for the virologically-confirmed dengue disease and the subject baseline serostatus. A vaccine is considered "effective" in case the combined vaccine efficacy is above 30%. In this context the combined vaccine efficacy may be also 40% or more, 50% or more, 60% or more, 70% or more, 72% or more, or 80% or more, in particular when determined from 30 days after a second administration until 12 months after a second administration or 18 months after a second vaccination, in particular when determined in age groups selected from the age group of 4 to 16 year old subjects, the age group of 4 to under 9 year old subjects, the age group of 2 to under 9 year old subjects, the age group of 4 to 5 year old subjects, the age group of 6 to 11 year old subjects, and the age group of 12 to 16 year old subjects. In this context, effective in particular refers to a vaccine that is effective for all subjects irrespective of their serostatus at baseline. Preferably, the vaccine is effective with respect to all age groups starting from 4 years of age and preferably irrespective of the serostatus, in particular from 4 years of age to 60 years of age or from 4 years of age to 16 years of age and irrespective of the serostatus. Relevant subgroups in this context are under 9 years of age, from 2 years of age to under 9 years of age, from 4 years of age to under 9 years of age, 4 to 5 years of age, 6 to 11 years of age and 12 to 16 years of age or any age group within 4 to 16 years of age. In certain embodiments "effective" means providing a combined vaccine efficacy against all four serotypes, in preventing virologically confirmable dengue disease with a 2-sided 95% confidence interval, wherein the lower bound is more than 60%, when measured against placebo in a subject population of at least 5,000 healthy subjects irrespective of serostatus at baseline and 4 to 16 years of age, from the first administration of the administration schedule until 18 months after the last administration of the administration schedule. Further specific efficacies can be defined. As used herein, "combined vaccine efficacy against all four serotypes in seronegative subjects" refers to the efficacy measured in subjects which are seronegative at baseline. As used herein, "vaccine efficacy against a specific serotype, e.g. serotype 1" refers to the efficacy in relation to a specific serotype being responsible for the virologically-confirmed dengue disease. As used herein, "combined vaccine efficacy against all four serotypes against virologically-confirmed dengue with hospitalization" refers to the efficacy wherein only virologically-confirmed dengue cases with hospitalization are considered. Such vaccine efficacies can be determined with respect to subjects being seronegative or seropositive at baseline and for different age groups.

As used herein, the "relative risk" means the number of events of virologically confirmed dengue disease divided by the number of subjects treated with the unit dose as disclosed herein over the number of events of virologically confirmed dengue disease divided by the number of subjects treated with placebo. As used herein the term"combined relative risk against all four serotypes" is defined as the relative risk in relation to the risk of dengue disease irrespective of the serotype being responsible for the virologically-confirmed dengue disease and the subject baseline serostatus.

As used herein, "vaccinating" or "inoculating" refers to the administration of a vaccine to a subject, with the aim to prevent the subject, from developing one or more symptoms of a disease. As used herein, "vaccinating against dengue disease" or "inoculating against dengue disease" refers to the administration of a dengue vaccine composition to a subject, with the aim to prevent the subject, from developing one or more symptoms of dengue disease. In principle the method comprises a primary vaccination and optionally one or more booster vaccinations. The primary vaccination is defined as the primary administration schedule for administering the composition or unit dose as disclosed herein to establish a protective immune response and e.g. consists of two administrations e.g. within three months. Whenever an administration is mentioned within this disclosure such administration refers to the primary vaccination unless it is specified as booster vaccination. The booster vaccination refers to an administration or administration schedule which takes place after the primary vaccination e.g. at least 1 year or even 5 or 10 years after the last administration, e.g. the second administration, of the primary vaccination schedule. The booster administration attempts at enhancing or reestablishing the immune response of the primary vaccination.

As used herein, the terms "subject" or "subjects" are limited to human subjects (e.g. infants, children or adults). The terms "elderly subject" or "elderly subjects" refer to subjects with an age of more than 60 years, such as 61 years to 100 years, 61 years to 90 years, 61 years to 80 years, 61 years to 75 years, or 61 years to 70 years.

As used herein, "subject population" refers to a group of subjects. The subject population may refer to least 40 subjects, at least 50 subjects, at least 60 subjects, at least 100 subjects or at least 1000 subjects and is defined by certain parameters. The parameters that may be used to define a subject population include, but are not limited to, the age of the subjects, whether the subjects are from a dengue endemic region or from a dengue non-endemic region and the serostatus of the subjects.

As used herein, "endemic region" refers to a region where a disease or infectious agent is constantly present and/or usually prevalent in a population within this region. As used herein, "non-endemic region" refers to a region from which the disease is absent or in which it is usually not prevalent. Accordingly, a "dengue endemic region" refers to geographic areas in which an infection with dengue virus is constantly maintained at a baseline level. A "dengue non-endemic region" is a geographic area in which an infection with dengue virus is not constantly maintained at a baseline level. Accordingly, subject populations or subjects "from a dengue endemic region" or "from a dengue non-endemic region" refer to subject populations or subjects living in geographic areas as defined above. Whether a geographic area or a subject population is dengue-endemic or not can be determined by different calculatory methods such as the ones described in Bhatt et al. (2013) Nature 496 (7446): 504-507 and supplementary material and in Stanaway et al. (2016) Lancet Infect Dis. 16(6): 712-723 and supplementary material. Overviews of dengue endemic regions and dengue epidemiology are regularly published, for example, by the WHO or CDC. Typical dengue-endemic regions are in Latin America, Southeast Asia and the Pacific islands and dengue endemic countries include, but are not limited to, Australia, Brazil, Bangladesh, Colombia, China, Dominican Republic, Indonesia, India, Mexico, Malaysia, Nicaragua, Nigeria, Pakistan, Panama, Philippines, Puerto Rico, Singapore, Sri Lanka, Thailand and Vietnam. The area's force of infection is measured by seroprevalence surveys provided as seroprevalence rate. Areas with very high force of infection are considered to have a seroprevalence rate of more than 80%. As used herein the term "region" when it concerns seroprevalence rates refers to a geographic area where the seroprevalence rate could be determined or is known, e.g. a village, a town, a city, a region, a county, a state, a province or parts of the foregoing or a whole country.

As used herein, "serostatus" refers to the amount of antibodies a subject has with respect to a certain infectious agent, in particular dengue virus. As used herein, "seronegative" or "seronaïve" means that the subject does not have neutralizing antibodies against any one of dengue serotypes DENV-1, DENV-2, DENV-3 and DENV-4 in the serum. A seronegative or seronaïve subject or subject population is defined by a neutralizing antibody titer of less than 10 for each one of the four dengue serotypes. A subject or subject population having a neutralizing antibody titer of equal to or more than 10 for at least one dengue serotype is defined as being "seropositive" with respect to said dengue serotype. Serostatus at baseline refers to the serostatus before the administration of a dengue vaccine composition as described herein.

As used herein, a "neutralizing antibody titer" refers to the amount of antibodies in the serum of a subject that neutralize the respective dengue serotype. The neutralizing antibody titer against DENV-1, DENV-2, DENV-3 and DENV-4 is determined in a serum sample of the subject using known methods such as the plaque reduction neutralization test (PRNT) as described in the WHO Guidelines (World Health Organization Department of Immunization Vaccines Biologicals (2007) Guidelines for plaque reduction neutralization testing of human antibodies to dengue viruses, WHO/IVB/07.07) or a microneutralization (MNT50) assay as described herein. As used herein, the "ratio of not more than 20 for the neutralizing antibody titer of dengue serotype 2 to the neutralizing antibody titer of dengue serotype 4" means that the neutralizing antibody titer of dengue serotype 2 is divided by the neutralizing antibody titer of dengue serotype 4 and that the ratio obtained hereby is no more than 20. In other words, the neutralizing antibody titer of dengue serotype 2 is not more than 20-times higher than the neutralizing antibody titer of dengue serotype 4 in the subject.

As used herein, the terms "geometric mean neutralizing antibody titer" and "GMT" refer to the geometric mean value of the titer of neutralizing antibodies against the corresponding dengue serotype in the serum of subjects in a subject population. The geometric mean value is calculated by a well-known formula. As used herein, the "ratio of not more than 20 for the GMT of dengue serotype 2 to the GMT of dengue serotype 4" means that the geometric mean neutralizing antibody titer of dengue serotype 2 (GMT DENV-2) is divided by the geometric mean neutralizing antibody titer of dengue serotype 4 (GMT DENV-4) and that the ratio obtained hereby is no more than 20. In other words, the geometric mean neutralizing antibody titer of dengue serotype 2 is not more than 20-times higher than the geometric mean neutralizing antibody titer of dengue serotype 4 in the subject population.

As used herein, an "immune response" refers to a subject's response to the administration of the dengue vaccine. In particular, the immune response includes the formation of neutralizing antibodies to one or more dengue serotypes. It may also include the stimulation of a cell-mediated response or the formation of antibodies to non-structural proteins such as NS1. An immune response is stimulated by the administration of a unit dose of the invention as described herein, if the titer of neutralizing antibodies against at least one dengue virus serotype and preferably against all four dengue virus serotypes is increased after said administration of said unit dose. An immune response is stimulated by the administration of a unit dose of the invention as described herein, if the secretion of interferon gamma by peripheral blood mononuclear cells stimulated with peptides from dengue virus proteins is increased after said administration of said unit dose. An immune response is stimulated by the administration of a unit dose of the invention as described herein, if the titer of antibodies to non-structural proteins such as NS1 is increased after said administration of said unit dose. In a particular embodiment, the administration of a reconstituted unit dose of the present invention as described herein stimulates the formation of neutralizing antibodies to one or more dengue serotypes, a cell-mediated response and the formation of antibodies to non-structural proteins such as NS1.

As used herein, a "balanced immune response" means that the immune response to the four dengue serotypes is sufficient to provide protection against infection by all four dengue serotypes and preferably the immune response to the four dengue serotypes has a similar strength. In particular, the neutralizing antibody titer against the four dengue serotypes at day 180 or day 365 after administration of a first reconstituted unit dose of the invention as described herein is similar, i.e. it differs by less than factor 30, by less than factor 25 or by less than factor 20.

The "total concentration in pfu/0.5 ml" which serves as a base value for the calculation of the percentage concentration for each individual component of a tetravalent dengue vaccine is shown for one exemplary tetravalent vaccine composition comprising dengue serotype 1 in a concentration of 3.60 log 10 pfu/0.5 ml, a dengue serotype 2 concentration of 4.00 log 10 pfu/0.5 ml, a dengue serotype 3 concentration of 4.60 log 10 pfu/0.5 ml and a dengue serotype 4 concentration of 5.11 log 10 pfu/0.5 ml. Primarily, the logarithmic values of the concentrations are converted into numerical values. The results of this conversion are $4\times10^3$ pfu/0.5 ml for serotype 1, $1\times10^4$ pfu/0.5 ml for serotype 2, $4\times10^4$ pfu/0.5 ml for serotype 3 and $1.3\times10^5$ pfu/0.5 ml for serotype 4. The total concentration in pfu/0.5 ml is the sum of the preceding numerical values resulting in $1.84\times10^5$ pfu/0.5 ml.

The "percentage concentration" for each of the serotypes 1, 2, 3 and 4 is obtained by dividing the numerical concentration value (expressed as pfu/0.5 ml) of an individual serotype by the total concentration (expressed in pfu/0.5 ml) and multiplying the result by 100 i.e.: Percentage concentration of serotype 1=($4\times10^3$ pfu/0.5 ml÷$1.84\times10^5$ pfu/0.5 ml)×100=2% Percentage concentration of serotype 2=($1\times10^4$ pfu/0.5 ml÷$1.84\times10^5$ pfu/0.5 ml)×100=5% Percentage concentration of serotype 3=($4\times10^4$ pfu/0.5 ml÷$1.84\times10^5$ pfu/0.5 ml)×100=22% Percentage concentration of serotype 4=($1.3\times10^5$ pfu/0.5 ml÷$1.84\times10^5$ pfu/0.5 ml)×100=71%. The percentage concentrations are rounded to whole numbers.

As used herein the "concomitant" administration of vaccines refers to a combined administration of two or more vaccines. In the context of parts of the invention, the combined administration of two or more vaccines refers to combining the administration schedule of a dengue vaccine, such as the unit dose of the invention, with the administration schedule of a fellow fever vaccine, such as YF-17D, and/or of a hepatitis A vaccine, such as HAVRIX® or VAQTA®, and/or of a HPV vaccine, such as a 9vHPV vaccine, and/or of a combined measles, mumps and rubella (MMR) vaccine, and/or of a combined Tdap vaccine, such as a combined tetanus toxoid, reduced diphtheria toxoid and acellular pertussis (adsorbed) vaccine, such as BOOSTRIX®, and/or of a DTaP/IPV/HIB vaccine, in particular a combined DTaP/IPV/Hib vaccine, such as Pentacel®.

As used herein "simultaneous" administration means an administration of at least two different vaccines, such as a dengue vaccine and a fellow fever vaccine, or a dengue vaccine and a hepatitis A vaccine, or a dengue vaccine and a HPV vaccine, or a dengue vaccine and a MMR vaccine, or a dengue vaccine and a Tdap vaccine, or a dengue vaccine and a DTaP/IPV/Hib vaccine on the same day. The simultaneous administration may be administered by the same medical practitioner, such as during the same medical appointment.

As used herein "sequential" administration means an administration of at least two different vaccines, such as a dengue vaccine and a fellow fever vaccine, or a dengue vaccine and a hepatitis A vaccine, or a dengue vaccine and a HPV vaccine, or a dengue vaccine and a MMR vaccine, or a dengue vaccine and a Tdap vaccine, or a dengue vaccine and a DTaP/IPV/Hib vaccine on subsequent days, such as within 90 days, but in a combined administration schedule including the administration of the dengue vaccine and the fellow fever vaccine.

As used herein "HPV-associated cancers or genital warts" refers to cancers and genital wards caused by an HPV infection, respectively. The HPV serotypes 16, 18, 45, 31, 33, 52, 58, also referred to as "high-risk" HPV serotypes, are the types most common in cervical cancers, wherein the two HPV serotypes 16 and 18 cause about 70% of cervical cancers worldwide. The HPV serotypes 6 and 11, also referred to as "low-risk" HPV serotypes, cause genital warts.

As used herein a "9vHPV vaccine" refers to a 9-valent HPV vaccine that provides protection against the HPV serotypes 6, 11, 16, 18, 31, 33, 45, 52, and 58. In particular, the 9vHPV vaccine is used to prevent cervical, vulvar, vaginal, and anal cancers, precancerous or dysplastic lesions, and genital warts caused by one or more of these HPV serotypes.

As used herein, a "MMR vaccine" refers to a combined vaccine for measles, mumps and rubella. Several MMR vaccine are known in the prior art and include M-M-R® II, Priorix®, Tresivac®, and Trimovax®.

As used herein, a "Tdap vaccine" refers to a combined vaccine for tetanus, diphtheria and pertussis. Tdap vaccines known in the prior art include INFANRIX® (for vaccination of children from 6 weeks to 7 years of age), and BOOSTRIX® from GlaxoSmithKline and Adacel from Sanofi Pasteur (both for use in individuals of 10 years of age or older).

As used herein, "DTaP" refers to diphtheria, tetanus and acellular pertussis.

As used herein, "IPV" refers to inactivated poliovirus.

As used herein, "Hib" refers to *Haemophilus influenzae* type b.

As used herein, a "DTaP/IPV/Hib vaccine" refers to a combined vaccine for diphtheria, tetanus, pertussis, poliomyelitis and *Haemophilus influenzae* type b. A DTaP/IPV/Hib vaccine known in the prior art includes Pentacel® from Sanofi Pasteur.

As used herein, the term "chronic disease or condition" includes those diseases and conditions which persist in an elderly subject for three months or more. In particular, it includes diabetes, hypertension, allergies, previous strokes, ischemic heart disease, chronic renal impairment and chronic obstructive pulmonary disease.

As used herein, the term "impaired immune system" means that at least one function of at least one component of the immune system is weaker than in younger subjects, i.e. in subjects with an age of less than 60 years. These functions include a lower antioxidant response of monocytes against oxidative stress induced by dengue virus and lower T cell responses and cytokine production in response to dengue virus infection.

As used herein, "solicited systemic adverse events" in children under 6 years are defined as fever, irritability/fussiness, drowsiness and loss of appetite that occurred within 14 days after each vaccination, and in children of 6 years or more are defined as fever, headache, asthenia, malaise and myalgia that occurred within 14 days after each vaccination.

As used herein, "solicited local adverse events" are injection site pain, injection site erythema and injection site swelling that occurred within 7 days after each vaccination.

As used herein, "unsolicited adverse events" are any adverse events (AEs) that are not solicited local or systemic AEs, as defined above.

As used herein, a "serious adverse event" or "SAE" is any untoward medical occurrence or effect that at any dose results in death, is life-threatening, requires inpatient hospitalization or prolongation of existing hospitalization, results in persistent or significant disability/incapacity, is a congenital anomaly/birth defect or is medically important due to other reasons than the above mentioned criteria.

The relationship of each AE, including solicited systemic AEs (solicited local AEs are considered as related) to trial vaccine(s) will be assessed using the following categories: As used herein, "IP-Related AE" or "vaccine related AE" means that there is suspicion that there is a relationship between the vaccine and the AE (without determining the extent of probability); there is a reasonable possibility that the vaccine contributed to the AE. As used herein, "Non-IP Related" or "non-vaccine related" means that there is no suspicion that there is a relationship between the vaccine and the AE; there are other more likely causes and administration of the vaccine is not suspected to have contributed to the AE.

As used herein, a subject or subject population being "2 to 17 years of age" refers to a subject or subject population being 2 to 17 years of age on the first day of the administration of the dengue vaccine composition as described herein.

As used herein "%-points" refers to the difference of two %-values in a %-value. For example two values in % which are within 5%-points refers to e.g. one value at 1% and a second value at 6%.

As used herein, the term "determination of the previous dengue infection in the subject before administration" means that a previous dengue infection has to be assessed before vaccination in that there is a laboratory confirmed history of dengue or through an appropriately validated serological test e.g. by the method as disclosed herein such as the MNT50 test described in Example 2 or any serotesting with adequate performance in terms of specificity and cross reactivity based on the locale disease epidemiology.

As used herein % w/v refers to % mg/ml wherein e.g. 150 mg/ml are 15% w/v.

DETAILED DESCRIPTION

Dengue Virus Strains

Figure 1:
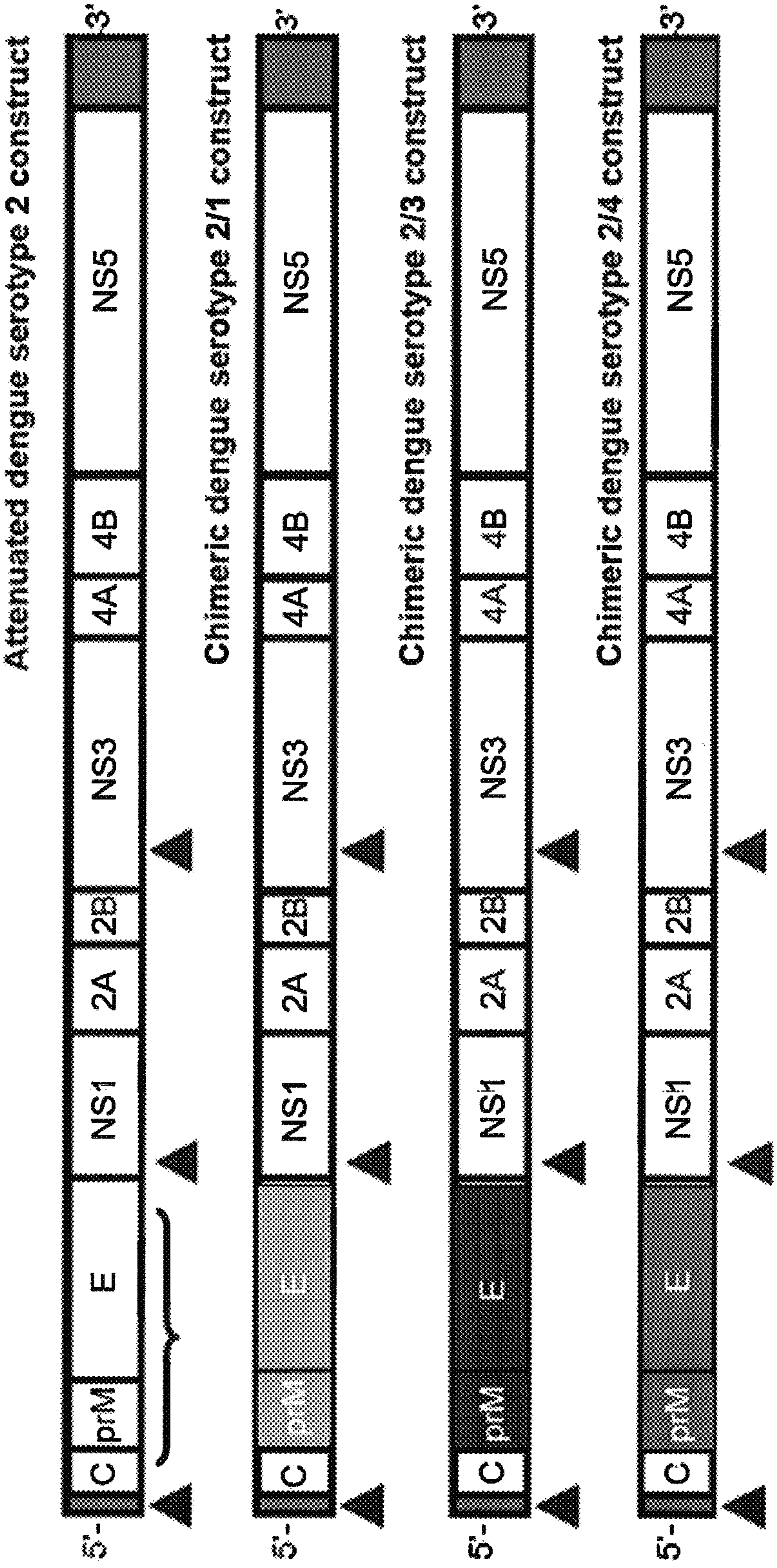
FIG. 1: Genetic structure of the four dengue strains contained in TDV. The solid red triangles indicate the three attenuating mutations present in the 5'NCR, NS1 and NS3 proteins. The TDV-1, TDV-3 and TDV-4 strains are chimeric viruses where the prM and E genes from dengue serotype 1, 3 and 4, respectively, are inserted into the TDV-2 backbone.

The dengue virus is a single stranded, positive sense RNA virus of the family flaviviridae. The taxonomy is outlined in Table 1. The family flaviviridae includes three genera, flavivirus, hepacivirus and pestivirus. The genus flavivirus contains highly pathogenic and potentially hemorrhagic fever viruses, such as yellow fever virus and dengue virus, encephalitic viruses, such as Japanese encephalitis virus, Murray Valley encephalitis virus and West Nile virus, and a number of less pathogenic viruses.

TABLE 1

Dengue Virus Taxonomy of the GMO Parental Strain

| | |
|---|---|
| Family | Flaviviridae |
| Genus | *Flavivirus* |

TABLE 1-continued

| Dengue Virus Taxonomy of the GMO Parental Strain | |
|---|---|
| Species | Dengue virus |
| Strains | Dengue Serotype 2 (Strain 16681), Strain DEN-2 PDK-53 |
| GMO parent | TDV-2 |

The flavivirus genome comprises in 5' to 3' direction (see FIG. 1):

a 5-noncoding region (5'-NCR), a capsid protein (C) encoding region, a pre-membrane protein (prM) encoding region, an envelope protein (E) encoding region, a region encoding nonstructural proteins (NSI, NS2A, NS2B, NS3, NS4A, NS4B, NS5) and a 3' noncoding region (3-NCR).

The viral structural proteins are C, prM and E, and the nonstructural proteins are NSI to NS5. The structural and nonstructural proteins are translated as a single polyprotein and processed by cellular and viral proteases.

The unit dose of the invention as described herein comprises a dengue virus composition that comprises four live attenuated dengue virus strains (tetravalent dengue virus composition) representing dengue serotype 1, dengue serotype 2, dengue serotype 3 and dengue serotype 4. Preferably the composition comprises chimeric dengue viruses and optionally at least one non-chimeric dengue virus, in particular a molecularly characterized and cloned dengue serotype 2 strain derived from the live attenuated DEN-2 PDK-53 virus strain (TDV-2), and three chimeric dengue strains derived from the TDV-2 strain by replacing the structural proteins prM and E from TDV-2 with the corresponding structural proteins from the other dengue serotypes, resulting in the following chimeric dengue strains:

a DENV-2/1 chimera (TDV-1), a DENV-2/3 chimera (TDV-3) and a DENV-2/4 chimera (TDV-4).

The genetically modified tetravalent dengue vaccine TDV is based on a molecularly characterized and cloned dengue-2 virus strain (TDV-2). This attenuated TDV-2 strain was generated by cDNA cloning of the attenuated laboratory-derived DEN-2 PDK-53 virus strain that was originally isolated at Mahidol University, Bangkok, Thailand (Kinney et al. (1997) Virology 230(2): 300-308). DEN-2 PDK-53 was generated by 53 serial passages in primary dog kidney (PDK) cells at 32° C. (Bhamarapravati et al. (1987) Bull. World Health Organ. 65(2): 189-195).

The attenuated DEN-2 PDK-53 strain (the precursor of TDV-2) was derived from the wild type virus strain DEN-2 16681 (SEQ ID NO 11) and differs in nine nucleotides from the wild type as follows (Kinney et al. (1997) Virology 230(2): 300-308):

(i) 5-noncoding region (NCR)-57 (nt-57 C-to-T): major attenuation locus (ii) prM-29 Asp-to-Val (nt-524 A-to-T)

(iii) nt-2055 C-to-T (E gene) silent mutation (iv) NS1-53 Gly-to-Asp (nt-2579 G-to-A): major attenuation locus (v) NS2A-181 Leu-to-Phe (nt-4018 C-to-T)

(vi) NS3-250 Glu-to-Val (nt-5270 A-to-T): major attenuation locus (vii) nt-5547 (NS3 gene) T-to-C silent mutation (viii) NS4A-75 Gly-to-Ala (nt-6599 G-to-C)

*nt-8571 C-to-T (NS5 gene) silent mutation

The three nucleotide changes located in the 5' noncoding region (NCR) (nucleotide 57) (mutation (i)), the NS-1 (amino acid 828 of SEQ ID NO. 4) (mutation (iv)) and NS-3 genes (amino acid 1725 of SEQ ID NO. 4) (mutation (vi)) form the basis for the attenuation phenotype of the DEN-2 PDK-53 strain (Butrapet et al. (2000) J. Virol. 74(7): 3111-3119) (Table 2). These three mutations are referred to herein as the "attenuating mutations" and are comprised in TDV-1, TDV-2, TDV-3 and TDV-4.

TABLE 2

Attenuating mutations in the common genetic backbone of all TDV strains

| Location of Mutation | Nucleotide Change in TDV-2 | Amino Acid Change in TDV-2 |
|---|---|---|
| 5' Noncoding Region (5'NCR) | 57 C to T | Not applicable (silent) |
| Nonstructural Protein 1 (NS1) | 2579 G to A | 828 Gly to Asp |
| Nonstructural Protein 3 (NS3) | 5270 A to T | 1725 Glu to Val |

In one embodiment, TDV-2 comprises in addition to the three attenuating mutations one or more mutations selected from:

a) a mutation in the prM gene at nucleotide 524 from adenine to thymine resulting in an amino acid change at position 143 from aspartic acid to valine, and/or b) a silent mutation in the E gene at nucleotide 2055 from cytosine to thymine, and/or c) a mutation in the NS2A gene at nucleotide 4018 from cytosine to thymine_resulting in an amino acid change at position 1308 from leucine to phenylalanine, and/or d) a silent mutation in the NS3 gene at nucleotide 5547 from thymine_to cytosine, and/or e) a mutation in the NS4A gene at nucleotide 6599 from guanine to cytosine resulting in an amino acid change at position 2168 from glycine to alanine, and/or f) a silent mutation in the prM gene at nucleotide 900 from thymine_to cytosine.

The silent mutation in the NS5 gene at nucleotide 8571 from cytosine to thymine_of DEN-2 PDK-53 is not present in the TDV-2 strain.

In another embodiment, TDV-2 comprises in addition to the three attenuating mutations one or more mutations selected from:

g) a mutation in the prM gene at nucleotide 592 from adenine to guanine resulting in an amino acid change at position 166 from lysine to glutamic acid, and/or h) a mutation in the NS5 gene at nucleotide 8803 from adenine to guanine resulting in an amino acid change at position 2903 from isoleucine to valine.

In another embodiment, TDV-2 comprises in addition to the three attenuating mutations the mutations a) and g), preferably the mutations a), g), c), e) and h), more preferably the mutations a), g), c), e), h) and b), even more preferably the mutations a), g), c), e), h), b) and d), and most preferably the mutations a) to h). The nucleotide positions and amino acids positions of TDV-2 refer to the nucleotide sequence as shown in SEQ ID NO. 3 and amino acid sequence as shown in SEQ ID NO. 4.

The dengue virus structural envelope (E) protein and pre-membrane (prM) protein have been identified as the primary antigens that elicit a neutralizing protective antibody response (Plotkin 2001). For creation of the tetravalent dengue vaccine (TDV), TDV-2 was modified by replacing the nucleic acid sequence encoding the DENV-2 prM and E glycoproteins with the nucleic acid sequence encoding the corresponding wild type prM and E glycoproteins from the DENV-1, DENV-3, and DENV-4 wild type strains DENV-1 16007, DENV-3 16562 or DENV-4 1036 virus, respectively, (see Table 3) using standard molecular genetic engineering methods (Huang et al. (2003) J. Virol. 77(21): 11436-11447).

and m), preferably the mutations l), m), c) and e), even more preferably the mutations l), m), c), e), d) and n), and most preferably the mutations l), m), c), e), d), n), i), j) and k). The nucleotide positions and amino acids positions of TDV-1 refer to the nucleotide sequence as shown in SEQ ID NO. 1 and amino acid sequence as shown in SEQ ID NO. 2.

TABLE 3

Viral origin of prM/E gene regions of the TDV virus strains

| Virus | Strain Origin | Source | Reference | Nucleotide sequence | Amino acid sequence |
|---|---|---|---|---|---|
| DENV-1 | 16007 Thailand, 1964 | DHF/DSS patient | Halstead and Simasthien, 1970 | SEQ ID NO. 9 | SEQ ID NO. 10 |
| DENV-2 | 16681 Thailand, 1964 | DHF/DSS patient | Halstead and Simasthien, 1970 | SEQ ID NO. 11 | SEQ ID NO. 12 |
| DENV-3 | 16562 Philippines, 1964 | DHF patient | Halstead and Simasthien, 1970 | SEQ ID NO. 13 | SEQ ID NO. 14 |
| DENV-4 | 1036 Indonesia, 1976 | DF patient | Gubler et al., 1979 | SEQ ID NO. 15 | SEQ ID NO. 16 |

A diagram of the four TDV strains comprised in the dengue vaccine composition is shown in FIG. 1.

The chimeric dengue strains TDV-1, TDV-3 and TDV-4 express the surface antigens prM and E of the DENV-1, DENV-3 or DENV-4 viruses, as depicted in Table 3 respectively, and retain the genetic alterations responsible for the attenuation of TDV-2. Thus, each of the TDV-1, TDV-3 and TDV-4 strains comprises the attenuating mutations described in Table 2.

In one embodiment, TDV-1 comprises in addition to the three attenuating mutations one or more mutations selected from:

c) a mutation in the NS2A gene at nucleotide 4018 from cytosine to thymine resulting in an amino acid change at position 1308 from leucine to phenylalanine, and/or d) a silent mutation in the NS3 gene at nucleotide 5547 from thymine to cytosine, and/or e) a mutation in the NS4A gene at nucleotide 6599 from guanine to cytosine resulting in an amino acid change at position 2168 from glycine to alanine, and/or i) a silent mutation in the E gene at nucleotide 1575 from thymine to cytosine, and/or j) a silent mutation in the junction site between the prM-E gene and the DEN-2 PDK-53 backbone at nucleotide 453 from adenine to guanine, and/or k) a mutation in the junction site between the prM-E gene and the DEN-2 PDK-53 backbone at nucleotides 2381/2382 from thymine-guanine to cytosine-cytosine resulting in an amino acid change at position 762 from valine to alanine.

In another embodiment, TDV-1 comprises in addition to the three attenuating mutations one or more mutations selected from:

l) a mutation in the NS2A gene at nucleotide 3823 from adenine to cytosine resulting in an amino acid change at position 1243 from isoleucine to leucine, and/or m) a mutation in the NS2B gene at nucleotide 4407 from adenine to thymine resulting in an amino acid change at position 1437 from glutamic acid to aspartic acid, and/or n) a silent mutation in the NS4B gene at nucleotide 7311 from adenine to guanine.

In another embodiment, the TDV-1 strain comprises in addition to the three attenuating mutations the mutations l)

In one embodiment, TDV-3 comprises in addition to the three attenuating mutations one or more mutations selected from:

c) a mutation in the NS2A gene at nucleotide 4012 from cytosine to thymine resulting in an amino acid change at position 1306 from leucine to phenylalanine, and/or d) a silent mutation in the NS3 gene at nucleotide 5541 from thymine to cytosine, and/or e) a mutation in the NS4A gene at nucleotide 6593 from guanine to cytosine resulting in an amino acid change at position 2166 from glycine to alanine, and/or j) a silent mutation in the junction site between the prM-E gene and the DEN-2 PDK-53 backbone at nucleotide 453 from adenine to guanine, and/or k) a mutation in the junction site between the prM-E gene and the DEN-2 PDK-53 backbone at nucleotides 2375/2376 from thymine-guanine to cytosine-cytosine resulting in an amino acid change at position 760 from valine to alanine, and/or o) a silent mutation in the prM gene at nucleotide 552 from cytosine to thymine, and/or p) a mutation in the E gene at nucleotide 1970 from adenine to thymine resulting in an amino acid change at position 625 from histidine to leucine.

In another embodiment, TDV-3 comprises in addition to the three attenuating mutations one or more mutations selected from:

q) a mutation in the E gene at nucleotide 1603 from adenine to thymine resulting in an amino acid change at position 503 from threonine to serine, and/or r) a silent mutation in the NS5 gene at nucleotide 7620 from adenine to guanine.

In another embodiment, TDV-3 comprises in addition to the three attenuating mutations the mutations p) and q), preferably the mutations p), q), c) and e), even more preferably the mutations p), q), c), e), d) and r), and most preferably the mutations p), q), c), e), d), r), j), k) and o). The nucleotide positions and amino acids positions of TDV-3 refer to the nucleotide sequence as shown in SEQ ID NO. 5 and amino acid sequence as shown in SEQ ID NO. 6.

In one embodiment, TDV-4 comprises in addition to the three attenuating mutations one or more mutations selected from:

c) a mutation in the NS2A gene at nucleotide 4018 from cytosine to thymine resulting in an amino acid change at position 1308 from leucine to phenylalanine, and/or d) a silent mutation in the NS3 gene at nucleotide 5547 from thymine to cytosine, and/or e) a mutation in the NS4A gene at nucleotide 6599 from guanine to cytosine resulting in an amino acid change at position 2168 from glycine to alanine, and/or j) a silent mutation in the junction site between the prM-E gene and the DEN-2 PDK-53 backbone at nucleotide 453 from adenine to guanine, and/or k) a mutation in the junction site between the prM-E gene and the DEN-2 PDK-53 backbone at nucleotides 2381/2382 from thymine-guanine to cytosine-cytosine resulting in an amino acid change at position 762 from valine to alanine, and/or s) a mutation in the C gene at nucleotide 396 from adenine to cytosine resulting in an amino acid change at position 100 from arginine to serine, and/or t) a silent mutation in the E gene at nucleotide 1401 from adenine to guanine, and/or u) a mutation in the E gene at nucleotide 2027 from cytosine to thymine resulting in an amino acid change at position 644 from alanine to valine, and/or v) a mutation in the E gene at nucleotide 2275 from adenine to cytosine resulting in an amino acid change at position 727 from methionine to leucine.

In another embodiment, TDV-4 comprises in addition to the three attenuating mutations one or more mutations selected from:

w) a silent mutation in the C gene at nucleotide 225 from adenine to thymine, and/or x) a mutation in the NS2A gene at nucleotide 3674 from adenine to guanine resulting in an amino acid change at position 1193 from aspartic acid to glycine, and/or y) a mutation in the NS2A gene at nucleotide 3773 from adenine to an adenine/guanine mix resulting in an amino acid change at position 1226 from lysine to a lysine/arginine mix, and/or z) a silent mutation in the NS3 gene at nucleotide 5391 from cytosine to thymine, and/or aa) a mutation in the NS4A gene at nucleotide 6437 from cytosine to thymine resulting in an amino acid change at position 2114 from alanine to valine, and/or bb) a silent mutation in the NS4B gene at nucleotide 7026 from thymine to a thymine/cytosine mix, and/or cc) a silent mutation in the NS5 gene at nucleotide 9750 from adenine to cytosine.

In another embodiments, TDV-4 comprises in addition to the three attenuating mutations the mutation s), u) and v), preferably the mutations s), u), v), c), e), x), y) and aa), even more preferably the mutations s), u), v), c), e), x), y), aa) and w), even more preferably the mutations s), u), v), c), e), x), y), aa), w), d), z), bb) and cc), and most preferably the mutations s), u), v), c), e), x), y), aa), w), d), z), bb), cc), j), k) and t). The nucleotide positions and amino acids positions of TDV-4 refer to the nucleotide sequence as shown in SEQ ID NO. 7 and amino acid sequence as shown in SEQ ID NO. 8.

In a preferred embodiment, TDV-1 has the nucleotide sequence of SEQ ID NO. 1, TDV-2 has the nucleotide sequence of SEQ ID NO. 3, TDV-3 has the nucleotide sequence of SEQ ID NO. 5, and/or TDV-4 has the nucleotide sequence of SEQ ID NO. 7. In a further preferred embodiment, TDV-1 has the amino acid sequence of SEQ ID NO. 2, TDV-2 has the amino acid sequence of SEQ ID NO. 4, TDV-3 has the amino acid sequence of SEQ ID NO. 6, and TDV-4 has the amino acid sequence of SEQ ID NO. 8. In a further preferred embodiment, TDV-1 has a nucleotide sequence encoding the amino acid sequence of SEQ ID NO. 2, TDV-2 has a nucleotide sequence encoding the amino acid sequence of SEQ ID NO. 4, TDV-3 has a nucleotide sequence encoding the amino acid sequence of SEQ ID NO. 6, and TDV-4 has a nucleotide sequence encoding the amino acid sequence of SEQ ID NO. 8.

TABLE 4

Sequences of the TDV virus strains

| SEQ ID NO. | dengue virus strain | sequence type |
|---|---|---|
| SEQ ID NO. 1 | TDV-1 | nucleotide sequence |
| SEQ ID NO. 2 | TDV-1 | amino acid sequence |
| SEQ ID NO. 3 | TDV-2 | nucleotide sequence |
| SEQ ID NO. 4 | TDV-2 | amino acid sequence |
| SEQ ID NO. 5 | TDV-3 | nucleotide sequence |
| SEQ ID NO. 6 | TDV-3 | amino acid sequence |
| SEQ ID NO. 7 | TDV-4 | nucleotide sequence |
| SEQ ID NO. 8 | TDV-4 | amino acid sequence |

Thus, in a particularly preferred embodiment, the unit dose of the invention as described herein comprises the live attenuated dengue virus strains TDV-1, TDV-2, TDV-3 and TDV-4, wherein TDV-1, TDV-3 and TDV-4 are based on TDV-2 and comprise the prM and E regions of DENV-1, -3 and -4, respectively. In another particularly preferred embodiment, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

The E protein of DENV-3 has two fewer amino acids than the E protein of DENV-2. Therefore, the nucleotides and encoded amino acid backbone of TDV-2 starting after the E region of DENV-3 at nucleotide 2374 of SEQ ID NO. 5 and amino acid 760 of SEQ ID NO. 6 are 6 nucleotides less and 2 amino acids less than the original TDV-2 nucleotide and amino acid positions, respectively.

Dengue Vaccine Composition

The present invention is in part directed to a unit dose of a dengue vaccine composition as described. The dengue vaccine composition comprises a tetravalent dengue virus composition, also referred to as dengue virus composition, and pharmaceutically acceptable excipients.

Dengue Virus Composition, Virus Concentrations and %-Concentrations

The present invention is in part directed to a unit dose of a dengue vaccine composition, wherein the dengue vaccine composition comprises a tetravalent dengue virus composition including four live attenuated dengue virus strains:

(i) a dengue serotype 1 preferably in a concentration of at least 3.3 log 10 pfu/0.5 mL, (ii) a dengue serotype 2 preferably in a concentration of at least 2.7 log 10 pfu/0.5 mL, (iii) a dengue serotype 3 preferably in a concentration of at least 4.0 log 10 pfu/0.5 mL, and (iv) a dengue serotype 4 preferably strain in a concentration of at least 4.5 log 10 pfu/0.5 mL.

In one embodiment, the dengue vaccine composition comprises a tetravalent dengue virus composition including four live attenuated dengue virus strains:

(i) a dengue serotype 1 preferably in a concentration of at least 3.3 log 10 pfu/0.5 mL to 3.8 log 10 pfu/0.5 mL,
(ii) a dengue serotype 2 preferably in a concentration of at least 2.7 log 10 pfu/0.5 mL,
(iii) a dengue serotype 3 preferably in a concentration of at least 4.0 log 10 pfu/0.5 mL, and
(iv) a dengue serotype 4 preferably strain in a concentration of at least 4.5 log 10 pfu/0.5 ml or 4.6 log 10 pfu/0.5 mL, optionally to 6.2 log 10 pfu/0.5 ml.

The present invention is further in part directed to a unit dose of a dengue vaccine composition, wherein the dengue vaccine composition comprises a tetravalent dengue virus composition including four live attenuated dengue virus strains:

(i) a chimeric dengue serotype 2/1 strain in a concentration of at least 3.3 log 10 pfu/0.5 mL,
(ii) a dengue serotype 2 strain in a concentration of at least 2.7 log 10 pfu/0.5 mL,
(iii) a chimeric dengue serotype 2/3 strain in a concentration of at least 4.0 log 10 pfu/0.5 mL, and
(iv) a chimeric dengue serotype 2/4 strain in a concentration of at least 4.5 log 10 pfu/0.5 mL.

In one embodiment, the dengue vaccine composition comprises a tetravalent dengue virus composition including four live attenuated dengue virus strains:

(i) a chimeric dengue serotype 2/1 strain in a concentration of at least 3.3 log 10 pfu/0.5 mL to 3.8 log 10 pfu/0.5 ml,
(ii) a dengue serotype 2 strain in a concentration of at least 2.7 log 10 pfu/0.5 mL,
(iii) a chimeric dengue serotype 2/3 strain in a concentration of at least 4.0 log 10 pfu/0.5 mL, and
(iv) a chimeric dengue serotype 2/4 strain in a concentration of at least 4.5 log 10 pfu/0.5 mL or at least 4.6 log 10 pfu/0.5 mL to optionally 6.2 log 10 pfu/0.5 ml.

Preferably, the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4.

In one embodiment, the dengue vaccine composition comprises a tetravalent dengue virus composition including four live attenuated dengue virus strains wherein:

(i) the dengue serotype 1 (e.g. chimeric dengue serotype 2/1 strain) has a concentration of 3.3 log 10 pfu/0.5 mL to 5.3 log 10 pfu/0.5 mL,
(ii) the dengue serotype 2 (e.g. dengue serotype 2 strain) has a concentration of 2.7 log 10 pfu/0.5 mL to 5.0 log 10 pfu/0.5 mL,
(iii) the dengue serotype 3 (e.g. chimeric dengue serotype 2/3 strain) has a concentration of 4.0 log 10 pfu/0.5 mL to 6.0 log 10 pfu/0.5 mL, and
(iv) the dengue serotype 4 (e.g. chimeric dengue serotype 2/4 strain) has a concentration of 4.5 log 10 pfu/0.5 mL to 6.5 log 10 pfu/0.5 mL.

In one such embodiment, the dengue vaccine composition comprises a tetravalent dengue virus composition including four live attenuated dengue virus strains wherein:

(i) the dengue serotype 1 (e.g. chimeric dengue serotype 2/1 strain) has a concentration of 3.3 log 10 pfu/0.5 mL to 5.0 log 10 pfu/0.5 mL,
(ii) the dengue serotype 2 (e.g. dengue serotype 2 strain) has a concentration of 2.7 log 10 pfu/0.5 mL to 4.9 log 10 pfu/0.5 mL,
(iii) the dengue serotype 3 (e.g. chimeric dengue serotype 2/3 strain) has a concentration of 4.0 log 10 pfu/0.5 mL to 5.7 log 10 pfu/0.5 mL, and
(iv) the dengue serotype 4 (e.g. chimeric dengue serotype 2/4 strain) has a concentration of 4.5 log 10 pfu/0.5 mL to 6.2 log 10 pfu/0.5 mL.

In a further such embodiment, the dengue vaccine composition comprises a tetravalent dengue virus composition including four live attenuated dengue virus strains wherein:

(i) a dengue serotype 1 (e.g. chimeric dengue serotype 2/1 strain) has a concentration of 3.3 log 10 pfu/dose to 5.0 log 10 pfu/dose,
(ii) a dengue serotype 2 (e.g. dengue serotype 2 strain) has a concentration of 2.7 log 10 pfu/dose to 4.9 log 10 pfu/dose,
(iii) a dengue serotype 3 (e.g. chimeric dengue serotype 2/3 strain) has a concentration of 4.0 log 10 pfu/dose to 5.7 log 10 pfu/dose, and
(iv) a dengue serotype 4 (e.g. chimeric dengue serotype 2/4 strain) has a concentration of 4.5 log 10 pfu/dose to 5.5 log 10 pfu/dose.

In a further such embodiment, the dengue vaccine composition comprises a tetravalent dengue virus composition including four live attenuated dengue virus strains wherein:

(i) a dengue serotype 1 (e.g. chimeric dengue serotype 2/1 strain) has a concentration of 3.3 log 10 pfu/dose to 4.1 log 10 pfu/dose,
(ii) a dengue serotype 2 (e.g. dengue serotype 2 strain) has a concentration of 2.7 log 10 pfu/dose to 3.6 log 10 pfu/dose,
(iii) a dengue serotype 3 (e.g. chimeric dengue serotype 2/3 strain) has a concentration of 4.0 log 10 pfu/dose to 4.7 log 10 pfu/dose, and
(iv) a dengue serotype 4 (e.g. chimeric dengue serotype 2/4 strain) has a concentration of 4.5 log 10 pfu/dose to 5.3 log 10 pfu/dose.

In a further such embodiment, the dengue vaccine composition comprises a tetravalent dengue virus composition including four live attenuated dengue virus strains wherein:

(i) a dengue serotype 1 (e.g. chimeric dengue serotype 2/1 strain) has a concentration of 3.3 log 10 pfu/0.5 mL to 3.6 log 10 pfu/0.5 mL,
(ii) a dengue serotype 2 (e.g. dengue serotype 2 strain) has a concentration of 2.7 log 10 pfu/0.5 mL to 4.0 log 10 pfu/0.5 mL,
(iii) a dengue serotype 3 (e.g. chimeric dengue serotype 2/3 strain) has a concentration of 4.0 log 10 pfu/0.5 mL to 4.6 log 10 pfu/0.5 mL, and
(iv) a dengue serotype 4 (e.g. chimeric dengue serotype 2/4 strain) has a concentration of 4.5 log 10 pfu/0.5 ml or 4.6 log 10 pfu/0.5 mL to 5.1 log 10 pfu/0.5 mL.

In another embodiment, the dengue vaccine composition comprises a tetravalent dengue virus composition including four live attenuated dengue virus strains wherein:

(i) the dengue serotype 1 (e.g. chimeric dengue serotype 2/1 strain) has a concentration of 4.3 log 10 pfu/0.5 mL to 4.4 log 10 pfu/0.5 mL,
(ii) the dengue serotype 2 (e.g. dengue serotype 2 strain) has a concentration of 3.7 log 10 pfu/0.5 mL to 3.8 log 10 pfu/0.5 mL,
(iii) the dengue serotype 3 (e.g. chimeric dengue serotype 2/3 strain) has a concentration of 4.5 log 10 pfu/0.5 mL to 5.0 log 10 pfu/0.5 mL, and
(iv) the dengue serotype 4 (e.g. chimeric dengue serotype 2/4 strain) has a concentration of 5.5 log 10 pfu/0.5 mL to 5.6 log 10 pfu/0.5 mL.

In a particularly preferred embodiment, the dengue vaccine composition comprises a tetravalent dengue virus composition including four live attenuated dengue virus strains wherein:

(i) the dengue serotype 1 (e.g. chimeric dengue serotype 2/1 strain) has a concentration of 4.4 log 10 pfu/0.5 mL,
(ii) the dengue serotype 2 (e.g. dengue serotype 2 strain) has a concentration of 3.8 log 10 pfu/0.5 mL,
(iii) the dengue serotype 3 (e.g. chimeric dengue serotype 2/3 strain) has a concentration of 4.5 log 10 pfu/0.5 mL, and
(iv) the dengue serotype 4 (e.g. chimeric dengue serotype 2/4 strain) has a concentration of 5.6 log 10 pfu/0.5 mL.

In another particularly preferred embodiment, the dengue vaccine composition comprises a tetravalent dengue virus composition including four live attenuated dengue virus strains wherein:

(i) the dengue serotype 1 (e.g. chimeric dengue serotype 2/1 strain) has a concentration of 3.6 log 10 pfu/0.5 mL,
(ii) the dengue serotype 2 (e.g. dengue serotype 2 strain) has a concentration of 4.0 log 10 pfu/0.5 mL,
(iii) the dengue serotype 3 (e.g. chimeric dengue serotype 2/3 strain) has a concentration of 4.6 log 10 pfu/0.5 mL, and
(iv) the dengue serotype 4 (e.g. chimeric dengue serotype 2/4 strain) has a concentration of 5.1 log 10 pfu/0.5 mL.

In another preferred embodiment, the dengue vaccine composition comprises a tetravalent dengue virus composition including four live attenuated dengue virus strains wherein the arithmetic sum of all four serotypes is less than 6.7 log 10 pfu/0.5 mL, preferably less than 5.5 log 10 pfu/0.5 mL. In certain such embodiments, the arithmetic sum of all four serotypes is at least 4.6 log 10 pfu/0.5 mL. In a preferred embodiment, the dengue vaccine composition comprises a tetravalent dengue virus composition including four live attenuated dengue virus strains wherein the arithmetic sum of all four serotypes is in the range of 4.6 log 10 pfu/0.5 mL to 6.7 log 10 pfu/0.5 mL, preferably in the range of 4.6 log 10 pfu/0.5 mL to 5.5 log 10 pfu/0.5 mL.

Preferably, in said embodiments the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

The present invention is in part directed to a unit dose of a dengue vaccine composition, wherein the dengue vaccine composition comprises a tetravalent dengue virus composition including four live attenuated dengue virus strains:

(i) a dengue serotype 1 (e.g. chimeric dengue serotype 2/1 strain) in a concentration of at least 3.3 log 10 pfu/dose,
(ii) a dengue serotype 2 (e.g. dengue serotype 2 strain) in a concentration of at least 2.7 log 10 pfu/dose,
(iii) a dengue serotype 3 (e.g. chimeric dengue serotype 2/3 strain) in a concentration of at least 4.0 log 10 pfu/dose, and
(iv) a dengue serotype 4 (e.g. chimeric dengue serotype 2/4 strain) in a concentration of at least 4.5 log 10 pfu/dose.

In one embodiment, the dengue vaccine composition comprises a tetravalent dengue virus composition including four live attenuated dengue virus strains wherein:

(i) the dengue serotype 1 (e.g. chimeric dengue serotype 2/1 strain) has a concentration of 3.3 log 10 pfu/dose to 5.3 log 10 pfu/dose,
(ii) the dengue serotype 2 (e.g. dengue serotype 2 strain) has a concentration of 2.7 log 10 pfu/dose to 5.0 log 10 pfu/dose,
(iii) the dengue serotype 3 (e.g. chimeric dengue serotype 2/3 strain) has a concentration of 4.0 log 10 pfu/dose to 6.0 log 10 pfu/dose, and
(iv) the dengue serotype 4 (e.g. chimeric dengue serotype 2/4 strain) has a concentration of 4.5 log 10 pfu/dose to 6.5 log 10 pfu/dose.

In one such embodiment, the dengue vaccine composition comprises a tetravalent dengue virus composition including four live attenuated dengue virus strains wherein:

(i) the dengue serotype 1 (e.g. chimeric dengue serotype 2/1 strain) has a concentration of 3.3 log 10 pfu/dose to 5.0 log 10 pfu/dose,
(ii) the dengue serotype 2 (e.g. dengue serotype 2 strain) has a concentration of 2.7 log 10 pfu/dose to 4.9 log 10 pfu/dose,
(iii) the dengue serotype 3 (e.g. chimeric dengue serotype 2/3 strain) has a concentration of 4.0 log 10 pfu/dose to 5.7 log 10 pfu/dose, and
(iv) the dengue serotype 4 (e.g. chimeric dengue serotype 2/4 strain) has a concentration of 4.5 log 10 pfu/dose to 6.2 log 10 pfu/dose.

In a further such embodiment, the dengue vaccine composition comprises a tetravalent dengue virus composition including four live attenuated dengue virus strains wherein:

(i) a dengue serotype 1 (e.g. chimeric dengue serotype 2/1 strain) has a concentration of 3.3 log 10 pfu/dose to 5.0 log 10 pfu/dose,
(ii) a dengue serotype 2 (e.g. dengue serotype 2 strain) has a concentration of 2.7 log 10 pfu/dose to 4.9 log 10 pfu/dose,
(iii) a dengue serotype 3 (e.g. chimeric dengue serotype 2/3 strain) has a concentration of 4.0 log 10 pfu/dose to 5.7 log 10 pfu/dose, and
(iv) a dengue serotype 4 (e.g. chimeric dengue serotype 2/4 strain) has a concentration of 4.5 log 10 pfu/dose to 5.5 log 10 pfu/dose.

In a further such embodiment, the dengue vaccine composition comprises a tetravalent dengue virus composition including four live attenuated dengue virus strains wherein:

(i) a dengue serotype 1 (e.g. chimeric dengue serotype 2/1 strain) has a concentration of 3.3 log 10 pfu/dose to 4.1 log 10 pfu/dose,
(ii) a dengue serotype 2 (e.g. dengue serotype 2 strain) has a concentration of 2.7 log 10 pfu/dose to 3.6 log 10 pfu/dose,
(iii) a dengue serotype 3 (e.g. chimeric dengue serotype 2/3 strain) has a concentration of 4.0 log 10 pfu/dose to 4.7 log 10 pfu/dose, and
(iv) a dengue serotype 4 (e.g. chimeric dengue serotype 2/4 strain) has a concentration of 4.5 log 10 pfu/dose to 5.3 log 10 pfu/dose.

In a further such embodiment, the dengue vaccine composition comprises a tetravalent dengue virus composition including four live attenuated dengue virus strains wherein:

(i) a dengue serotype 1 (e.g. chimeric dengue serotype 2/1 strain) has a concentration of 3.3 log 10 pfu/dose to 3.6 log 10 pfu/dose, (ii) a dengue serotype 2 (e.g. dengue serotype 2 strain) has a concentration of 2.7 log 10 pfu/dose to 4.0 log 10 pfu/dose, (iii) a dengue serotype 3 (e.g. chimeric dengue serotype 2/3 strain) has a concentration of 4.0 log 10 pfu/dose to 4.6 log 10 pfu/dose, and (iv) a dengue serotype 4 (e.g. chimeric dengue serotype 2/4 strain) has a concentration of 4.5 log 10 pfu/dose 4.6 log 10 pfu/dose to 5.1 log 10 pfu/dose.

In another embodiment, the dengue vaccine composition comprises a tetravalent dengue virus composition including four live attenuated dengue virus strains wherein:

(i) the dengue serotype 1 (e.g. chimeric dengue serotype 2/1 strain) has a concentration of 4.3 log 10 pfu/dose to 4.4 log 10 pfu/dose, (ii) the dengue serotype 2 (e.g. dengue serotype 2 strain) has a concentration of 3.7 log 10 pfu/dose to 3.8 log 10 pfu/dose, (iii) the dengue serotype 3 (e.g. chimeric dengue serotype 2/3 strain) has a concentration of 4.5 log 10 pfu/dose to 5.0 log 10 pfu/dose, and (iv) the dengue serotype 4 (e.g. chimeric dengue serotype 2/4 strain) has a concentration of 5.5 log 10 pfu/dose to 5.6 log 10 pfu/dose.

In a particularly preferred embodiment, the dengue vaccine composition comprises a tetravalent dengue virus composition including four live attenuated dengue virus strains wherein:

(i) the dengue serotype 1 (e.g. chimeric dengue serotype 2/1 strain) has a concentration of 4.4 log 10 pfu/dose, (ii) the dengue serotype 2 (e.g. dengue serotype 2 strain) has a concentration of 3.8 log 10 pfu/dose, (iii) the dengue serotype 3 (e.g. chimeric dengue serotype 2/3 strain) has a concentration of 4.5 log 10 pfu/dose, and (iv) the dengue serotype 4 (e.g. chimeric dengue serotype 2/4 strain) has a concentration of 5.6 log 10 pfu/dose.

In another particularly preferred embodiment, the dengue vaccine composition comprises a tetravalent dengue virus composition including four live attenuated dengue virus strains wherein:

(i) the dengue serotype 1 (e.g. chimeric dengue serotype 2/1 strain) has a concentration of 3.6 log 10 pfu/dose, (ii) the dengue serotype 2 (e.g. dengue serotype 2 strain) has a concentration of 4.0 log 10 pfu/dose, (iii) the dengue serotype 3 (e.g. chimeric dengue serotype 2/3 strain) has a concentration of 4.6 log 10 pfu/dose, and (iv) the dengue serotype 4 (e.g. chimeric dengue serotype 2/4 strain) has a concentration of 5.1 log 10 pfu/dose.

In another preferred embodiment, the dengue vaccine composition comprises a tetravalent dengue virus composition including four live attenuated dengue virus strains wherein the arithmetic sum of all four serotypes is less than 6.7 log 10 pfu/dose, preferably less than 5.5 log 10 pfu/dose. In certain such embodiments, the arithmetic sum of all four serotypes is at least 4.6 log 10 pfu/dose. in a preferred embodiment, the dengue vaccine composition comprises a tetravalent dengue virus composition including four live attenuated dengue virus strains wherein the arithmetic sum of all four serotypes is in the range of 4.6 log 10 pfu/dose to 6.7 log 10 pfu/dose, preferably in the range of 4.6 log 10 pfu/dose to 5.5 log 10 pfu/dose.

In one embodiment in the composition (i), (ii), (iii), and (iv) provide a total concentration of pfu/0.5 mL and based on said concentration, the concentration of (iii) at least 10% of the total concentration in pfu/0.5 mL.

In one embodiment in the composition (i), (ii), (iii), and (iv) provide a total concentration of pfu/0.5 mL and based on said total concentration the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 8%, or at least 10%, or at least 12%, or at least 14%, or at least 16%, or at least 18%.

It is preferred that the concentration in the reconstituted unit dose of (iii) in pfu/0.5 mL is at least 10%.

In one embodiment in the composition (i), (ii), (iii), and (iv) provide a total concentration of pfu/0.5 mL and based on said total concentration the concentration of (ii) in pfu/0.5 mL is less than 2%, the concentration of (iv) in pfu/0.5 mL is at least 50%, the concentration of (i) in pfu/0.5 mL is at least 1%, and the concentration of (iii) in pfu/0.5 mL is at least 6%.

Preferably, in said embodiments the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

The concentration of the different dengue viruses is preferably determined by an immuno-focus assay known in the art. For example, the concentration may be determined by an immuno-focus assay wherein serial dilutions of dengue virus are applied to monolayers of adherent cells, such as Vero cells. After a period of time which allows infectious viruses to bind to the cells and to be taken up by the cells, an overlay containing thickening agents, such as agarose or carboxymethylcellulose, is added to prevent diffusion of viruses so that progeny viruses can only infect cells adjacent to the original infected cells. After a period of incubation to allow viral replication, cells are fixed and stained using serotype-specific anti-dengue monoclonal antibodies and a secondary antibody such as an antibody labeled with alkaline phosphatase. The foci are stained by adding a suitable substrate for the enzyme attached to the secondary antibody, such as 5-bromo-4-chloro-3-indolyl-phosphate/nitro blue tetrazolium phosphatase substrate. The number of plaques on the plate corresponds to the plaque forming units of the virus in the solutions applied to the cells. For example, a concentration of 1,000 pfu/μl indicates that 1 μl of the solution applied to the cells contains enough viruses to produce 1,000 plaques in a cell monolayer.

The dengue vaccine composition comprises a tetravalent dengue virus composition including four live attenuated dengue virus strains, wherein a chimeric dengue serotype 2/1 strain, a dengue serotype 2 strain, a chimeric dengue serotype 2/3 strain, and a chimeric dengue serotype 2/4 strain provide a total concentration in pfu/0.5 mL. The term "total concentration in pfu/0.5 mL" or "total concentration in pfu/dose" is the sum of the concentrations of the dengue serotype 1 (e.g. chimeric dengue serotype 2/1 strain), dengue serotype 2 (e.g. the dengue serotype 2 strain), the dengue serotype 3 (e.g. chimeric dengue serotype 2/3 strain) and the dengue serotype 4 (e.g. chimeric dengue serotype 2/4 strain), preferably the sum of the concentrations of TDV-1, TDV-2, TDV-3 and TDV-4, and is defined as 100% of the dengue virus concentration as determined by pfu (plaque forming units) in 0.5 mL or in a dose.

In one embodiment, the dengue vaccine composition comprises a tetravalent dengue virus composition including four live attenuated dengue virus strains, wherein a dengue serotype 1 (e.g. chimeric dengue serotype 2/1 strain), a dengue serotype 2 (e.g. dengue serotype 2 strain), a dengue serotype 3 (e.g. chimeric dengue serotype 2/3 strain), and a dengue serotype 4 (e.g. chimeric dengue serotype 2/4 strain) provide a total concentration in pfu/0.5 mL, wherein based on said total concentration the concentration of a dengue serotype 2 (e.g. dengue serotype 2 strain) measured in pfu/0.5 mL is less than 10% of the total concentration, or less than 8%, or less than 6% of the total concentration, and wherein the concentration of a dengue serotype 4 (e.g. chimeric dengue serotype 2/4 strain) measured in pfu/0.5 mL is at least 50% or at least 60% or at least 65% of the total concentration. In one embodiment, based on said total concentration the concentration of a dengue serotype 2 (e.g. dengue serotype 2 strain) measured in pfu/0.5 mL is 0.3 to 10% or 0.5 to 8% of the total concentration and the concentration of a dengue serotype 4 (e.g. chimeric dengue serotype 2/4 strain) measured in pfu/0.5 mL is 50% to 90% or 60% to 88% of the total concentration. This means that the concentration of the dengue serotype 2 (e.g. dengue serotype 2 strain) is lower than the concentration of the dengue serotype 4 (e.g. chimeric dengue serotype 2/4 strain).

In one such embodiment, the concentration of a dengue serotype 1 (e.g. chimeric dengue serotype 2/1 strain) measured in pfu/0.5 mL is at least 1% of the total concentration, and/or the concentration of a dengue serotype 3 (e.g. chimeric dengue serotype 2/3 strain) measured in pfu/0.5 mL is at least 6% of the total concentration, or at least 7% or 8%, 10%, 12%, 14%, 16% or 18% of the total concentration. In one such embodiment, the concentration of a dengue serotype 2 (e.g. chimeric dengue serotype 2/1 strain) measured in pfu/0.5 mL is 1% to 7% or 2% to 6% or 2.0% to 5.0% of the total concentration, and/or the concentration of a dengue serotype 3 (e.g. chimeric dengue serotype 2/3 strain) measured in pfu/0.5 mL is 6% to 25% or 7% to 25% or 10% to 25% or 18% to 25% of the total concentration. This means that the concentration of the dengue serotype 1 (e.g. chimeric dengue serotype 2/1 strain) is lower than the concentration of the dengue serotype 3 (e.g. chimeric dengue serotype 2/3 strain).

In a preferred embodiment, the concentration of a dengue serotype 2 strain, such as TDV-2, measured in pfu/0.5 mL is less than 10% of the total concentration, preferably less than 6% or less than 2%, the concentration of a dengue serotype 4 (e.g. chimeric dengue serotype 2/4 strain), such as TDV-4, measured in pfu/0.5 mL is at least 50% of the total concentration, preferably at least 65%, the concentration of a dengue serotype 1 (e.g. chimeric dengue serotype 2/1 strain), such as TDV-1, measured in pfu/0.5 mL is at least 1% of the total concentration, preferably between 1% and 7% or 2.0% to 5.0%, and the concentration of a dengue serotype 3 (e.g. chimeric dengue serotype 2/3 strain), such as TDV-3, measured in pfu/0.5 mL is at least 6% of the total concentration, preferably between 6% and 25% or 10% to 25% or 18% to 25%.

In a further preferred embodiment, a dengue virus composition comprising a dengue serotype 1 (e.g. chimeric dengue serotype 2/1 strain), a dengue serotype 2 (e.g. dengue serotype 2 strain), a dengue serotype 1 (e.g. chimeric dengue serotype 2/3 strain), and a dengue serotype 4 (e.g. chimeric dengue serotype 2/4 strain), such as TDV-1, TDV-2, TDV-3 and TDV-4, is provided, wherein the concentration of the dengue serotype 1 (e.g. chimeric dengue serotype 2/1 strain) measured in pfu/0.5 mL is at least 1% of the total concentration, preferably between 1% and 7% or 2.0% and 5.0%, the concentration of the dengue serotype 2 (e.g. dengue serotype 2 strain) measured in pfu/0.5 mL is less than 10% of the total concentration, preferably less than 6% or less than 2% and the concentration of the dengue serotype 3 (e.g. chimeric dengue serotype 2/3 strain) measured in pfu/0.5 mL is at least 6% of the total concentration, preferably between 6% and 25% or 10% to 25% or 18% to 25%. It is particularly preferred that the dengue serotype 4 (e.g. chimeric dengue serotype 2/4 strain) has the highest concentration of all four dengue serotypes.

In a further preferred embodiment, the dengue vaccine composition comprises a tetravalent dengue virus composition including four live attenuated dengue virus strains, wherein the concentration of the dengue serotype 1 (e.g. chimeric dengue serotype 2/1 strain) measured in pfu/0.5 mL is 1% to 7% of the total concentration, the concentration of the dengue serotype 2 (e.g. dengue serotype 2 strain) measured in pfu/0.5 mL is less than 8% of the total concentration, such as in the range of 1% to 8% of the total concentration, the concentration of the dengue serotype 3 (e.g. chimeric dengue serotype 2/3 strain) measured in pfu/0.5 mL is at least 10% of the total concentration, and the concentration of the dengue serotype 4 (e.g. chimeric dengue serotype 2/4 strain) measured in pfu/0.5 mL is at least 65% of the total concentration, such as in the range of 65% to 80%. In certain such embodiments, the arithmetic sum of all four serotypes is in the range of 4.6 log 10 pfu/0.5 mL to 6.7 log 10 pfu/0.5 mL, preferably in the range of 4.6 log 10 pfu/0.5 mL to 5.5 log 10 pfu/0.5 mL.

In a further preferred embodiment the dengue serotype 1 (e.g. chimeric dengue serotype 2/1 strain) such as TDV-1 and the dengue serotype 2 (e.g. dengue serotype 2 strain) such as TDV-2 are present each in a concentration based on the total concentration in pfu/0.5 mL which is within 5%-points of each other and/or are together less than about 10% of the total concentration in pfu/0.5 mL. In certain such embodiments the dengue serotype 3 (e.g. chimeric dengue serotype 2/3 strain) such as TDV-3 is preferably at least about 10% of the total concentration in pfu/0.5 mL and more preferably the dengue serotype 4 (e.g. chimeric dengue serotype 2/4 strain) such as TDV-4 is at least about 70% of the total concentration in pfu/0.5 mL. In certain such embodiments the dengue serotype 4 (e.g. chimeric dengue serotype 2/4 strain) such as TDV-4 represents the highest concentration in the composition of all four serotypes, preferably with at least about 70% of the total concentration in pfu/0.5 mL, dengue serotype 3 (e.g. chimeric dengue serotype 2/3 strain) such as TDV-3 represents the second highest concentration in the composition of all four serotypes, preferably with at least about 10% of the total concentration in pfu/0.5 mL, and dengue serotype 1 (e.g. chimeric dengue serotype 2/1 strain) such as TDV-1 and dengue serotype 2 (e.g. dengue serotype 2 strain) such as TDV-2 each represent lower concentrations than the concentration of serotype 3 (e.g. chimeric dengue serotype 2/3 strain) such as TDV-3, and optionally together represent less than about 10% of the total concentration in pfu/0.5 mL.

Preferably, in said embodiments the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

According to a further embodiment, the chimeric dengue serotype 2/4 strain, preferably TDV-4, has the highest concentration in the dengue vaccine composition, followed by the chimeric dengue serotype 2/3 strain, preferably TDV-3, followed by the chimeric dengue serotype 2/1 strain, preferably TDV-1, followed by the dengue serotype 2 strain, preferably TDV-2. It is particularly preferred that the dengue serotype 2 strain has the lowest concentration of the four strains present in the dengue vaccine composition.

Whenever reference is made to a concentration/0.5 ml, this does not limit the volume of the unit dose described herein to 0.5 ml. 0.5 ml is the reference volume for the determination of the concentrations of the virus strains in the composition in pfu/ml. The volume and/or amount per unit dose is described in the respective chapter.

Pharmaceutically Acceptable Excipients

The present invention is in part directed to a unit dose of a dengue vaccine composition, wherein the dengue vaccine composition comprises one or more pharmaceutically acceptable excipients. In one embodiment, the dengue vaccine composition comprises a non-reducing sugar, a surfactant, a protein and an inorganic salt. Preferably, the non-reducing sugar is trehalose, the surfactant is poloxamer 407, the protein is human serum albumin and the inorganic salt is sodium chloride.

In one embodiment, the unit dose of a dengue vaccine composition comprises the following pharmaceutically acceptable excipients:

- from about 10% w/v to about 20% w/v α,α-trehalose dihydrate or an equimolar amount of other forms of α,α-trehalose,
- from about 0.5% w/v to about 1.5% w/v poloxamer 407,
- from about 0.05% w/v to about 2% w/v human serum albumin, and
- from about 70 mM to 140 mM sodium chloride.

In one embodiment, the unit dose of a dengue vaccine composition comprises the following pharmaceutically acceptable excipients when measured in 0.5 ml:

- from about 10% w/v to about 20% w/v α,α-trehalose or an equimolar amount of other forms of α,α-trehalose,
- from about 0.5% w/v to about 1.5% w/v poloxamer 407,
- from about 0.05% w/v to about 2% w/v human serum albumin, and
- from about 70 mM to 140 mM sodium chloride, and preferably
- has a pH of 7 to 8.5.

In one embodiment, the unit dose of a dengue vaccine composition comprises the following pharmaceutically acceptable excipients when measured in 0.5 ml:

- from about 143 mg/ml to about 185 mg/ml α,α-trehalose dihydrate or an equimolar amount of other forms of α,α-trehalose,
- from about 9.1 mg/ml to about 12.4 mg/ml poloxamer 407,
- from about 0.88% mg/ml to about 1.32 mg/ml human serum albumin, and
- from about 70 mM to 140 mM sodium chloride, and preferably
- has a pH of 7 to 8.5.

In a preferred embodiment, the lyophilized unit dose of the invention as described herein comprises the following pharmaceutically acceptable excipients:

- about 15% w/v α,α-trehalose dihydrate,
- about 1% w/v poloxamer 407,
- about 0.1% w/v human serum albumin, and
- about 100 mM sodium chloride.

In a preferred embodiment, the lyophilized unit dose of the invention as described herein comprises the following pharmaceutically acceptable excipients when measured in 0.5 ml:

- about 15% w/v α,α-trehalose,
- about 1% w/v poloxamer 407,
- about 0.1% w/v human serum albumin, and
- about 100 mM sodium chloride.

In a preferred embodiment, the lyophilized unit dose of the invention as described herein comprises the following pharmaceutically acceptable excipients:

- about 82.9 mg α,α-trehalose dihydrate,
- about 5 mg poloxamer 407,
- about 0.5 mg human serum albumin, and
- about 50 μmoles sodium chloride.

In a preferred embodiment, the reconstituted unit dose of the invention as described herein comprises the following pharmaceutically acceptable excipients:

- about 15% w/v α,α-trehalose dihydrate,
- about 1% w/v poloxamer 407,
- about 0.1% w/v human serum albumin, and
- about 137 mM sodium chloride, and preferably
- has a pH of 7 to 8.5

In a preferred embodiment, the reconstituted unit dose of the invention as described herein comprises the following pharmaceutically acceptable excipients when measured in 0.5 ml:

- about 15% w/v α,α-trehalose,
- about 1% w/v poloxamer 407,
- about 0.1% w/v human serum albumin, and preferably
- about 137 mM sodium chloride and preferably
- has a pH of 7 to 8.5.

In a preferred embodiment, the reconstituted unit dose of the invention as described herein comprises the following pharmaceutically acceptable excipients:

- about 82.9 mg α,α-trehalose dihydrate,
- about 5 mg poloxamer 407,
- about 0.5 mg human serum albumin, and preferably
- about 68.5 μmoles sodium chloride, and preferably
- has a pH of 7 to 8.5.

The human serum albumin may be a native or recombinant human serum albumin (rHSA). The poloxamer 407 may be e.g. Pluronic F127.

In one embodiment, the unit dose further comprises a buffer. The buffer may be phosphate buffered saline (PBS). The buffer may include at least one of sodium chloride (NaCl), monosodium dihydrogen phosphate ($NaH_2PO_4$), disodium hydrogen phosphate ($Na_2HPO_4$), potassium chloride (KCl), and potassium dihydrogen phosphate ($KH_2PO_4$). In a preferred embodiment, the buffer may include disodium hydrogen phosphate ($Na_2HPO_4$), potassium chloride (KCl), and potassium dihydrogen phosphate ($KH_2PO_4$).

The buffer may have a pH in the range of 7.0 to 8.5 at 25° C.

Unit Dose

The present invention is directed in part to a unit dose of a dengue vaccine composition comprising a tetravalent dengue virus composition as described herein and pharmaceutically acceptable excipients as described herein.

The present invention is directed in part to a unit dose of a dengue vaccine composition as described above e.g. of (i) a dengue serotype 1 (e.g. chimeric dengue serotype 2/1 strain) with a concentration of at least 3.3 log 10 pfu/0.5 mL,
(ii) a dengue serotype 2 (e.g. dengue serotype 2 strain) with a concentration of at least 2.7 log 10 pfu/0.5 mL,
(iii) a dengue serotype 3 (e.g. chimeric dengue serotype 2/3 strain) with a concentration of at least 4.0 log 10 pfu/0.5 mL, and
(iv) a dengue serotype 4 (e.g. chimeric dengue serotype 2/4 strain) with a concentration of at least 4.5 log 10 pfu/0.5 mL.

Preferably, the chimeric dengue serotype 2/1 strain is TDV-1, the dengue serotype 2 strain is TDV-2, the chimeric dengue serotype 2/3 strain is TDV-3, and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

In one embodiment, the unit dose is lyophilized. In one such embodiment, the lyophilized unit dose is obtained by subjecting a volume of 0.5 mL of the aqueous dengue vaccine composition produced by combining pharmaceutically acceptable excipients as described herein and the dengue vaccine composition as described herein comprising the four dengue virus strains, in particular TDV-1 to TDV-4, to lyophilization. In a preferred embodiment the residual moisture content as determined by Karl Fischer Determination is equal to or less than 5.0%, preferably equal to or less than 3%.

In another embodiment, the unit dose is reconstituted. The reconstituted unit dose is obtained by subjecting the lyophilized unit dose to reconstitution with a pharmaceutically acceptable diluent, preferably before administration of the dengue vaccine. In one such embodiment, reconstitution will be accomplished by adding a pharmaceutically acceptable diluent, such as water for injection, phosphate buffered saline or an aqueous sodium chloride solution, to the lyophilized unit dose. In one embodiment, an aqueous sodium chloride solution, such as a 37 mM aqueous sodium chloride solution, is added to the lyophilized unit dose for reconstitution. In one such embodiment, the lyophilized unit dose will be reconstituted with 0.3 to 0.8 mL, or 0.4 to 0.7 mL, or 0.5 mL of diluent. In a preferred embodiment, the lyophilized unit dose is reconstituted with 0.3 to 0.8 mL, 0.4 to 0.7 mL or 0.5 mL of 37 mM aqueous sodium chloride solution. In a more preferred embodiment, the lyophilized unit dose is reconstituted with 0.5 mL of 37 mM aqueous sodium chloride solution. The reconstituted unit dose can subsequently be administered subcutaneously.

It is preferred that the unit dose in lyophilized form is the final product after manufacture of the unit dose and the storage form of the unit dose, wherein the unit dose in reconstituted form is prepared before administration of the unit dose to a subject.

The present invention is, moreover, directed in part to a unit dose of a dengue vaccine composition comprising: a tetravalent virus composition including four live attenuated dengue virus strains, wherein the unit dose is lyophilized and upon reconstitution with 0.5 mL of a pharmaceutically acceptable diluent comprises:

(i) a dengue serotype 1, such as a chimeric dengue serotype 2/1 strain, in a concentration of at least 3.3 log 10 pfu/0.5 ml,
(ii) a dengue serotype 2, such as a dengue serotype 2 strain, in a concentration of at least 2.7 log 10 pfu/0.5 ml,
(iii) a dengue serotype 3, such as a chimeric dengue serotype 2/3 strain, in a concentration of at least 4.0 log 10 pfu/0.5 ml, and
(iv) a dengue serotype 4, such as a chimeric dengue serotype 2/4 strain, in a concentration of at least 4.5 log 10 pfu/0.5 ml.

In one embodiment, the reconstituted unit dose has a volume of e.g. 0.5 mL, wherein upon reconstitution with a pharmaceutically acceptable diluent (i), (ii), (iii), and (iv) provide a total concentration of pfu/0.5 mL and based on said concentration, the concentration of (iii) at least 10% of the total concentration in pfu/0.5 mL.

In another embodiment the reconstituted unit dose has a volume of e.g. 0.5 mL, wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 8%, or at least 10%, or at least 12%, or at least 14%, or at least 16%, or at least 18%.

It is preferred that the concentration in the reconstituted unit dose of (iii) in pfu/0.5 mL is at least 10%.

In one embodiment the reconstituted unit dose has a volume of e.g. 0.5 mL, wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 2%, the concentration of (iv) in pfu/0.5 mL is at least 50%, the concentration of (i) in pfu/0.5 mL is at least 1%, and the concentration of (iii) in pfu/0.5 mL is at least 6%.

In one embodiment, the present invention is directed to a lyophilized unit dose of a dengue vaccine composition comprising upon reconstitution with 0.5 mL of a pharmaceutically acceptable diluent a dengue serotype 1 (e.g. chimeric dengue serotype 2/1 strain) with a concentration of at least 3.3 log 10 pfu/0.5 mL, a dengue serotype 2 (e.g. dengue serotype 2 strain) with a concentration of at least 2.7 log 10 pfu/0.5 mL, a dengue serotype 3 (e.g. chimeric dengue serotype 2/3 strain) with a concentration of at least 4.0 log 10 pfu/0.5 mL, and a dengue serotype 4 (e.g. chimeric dengue serotype 2/4 strain) with a concentration of at least 4.5 log 10 pfu/0.5 mL and pharmaceutically acceptable excipients as described herein, wherein the unit dose is preferably formulated in 0.5 mL before lyophilization. Preferably, the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

In one such embodiment, the lyophilized unit dose is obtained by lyophilizing 0.5 mL of a dengue vaccine composition comprising a dengue serotype 1 (e.g. chimeric dengue serotype 2/1 strain) in a concentration of 3.3 log 10 pfu/dose to 5.0 log 10 pfu/0.5 mL, a dengue serotype 2 (e.g. dengue serotype 2 strain) in a concentration of 2.7 log 10 pfu/dose to 4.9 log 10 pfu/0.5 mL, a dengue serotype 3 (e.g. chimeric dengue serotype 2/3 strain) in a concentration of 4.0 log 10 pfu/dose to 5.7 log 10 pfu/0.5 mL, and a dengue serotype 4 (e.g. chimeric dengue serotype 2/4 strain) in a concentration of 4.5 log 10 pfu/dose to 5.5 log 10 pfu/0.5 mL and pharmaceutically acceptable excipients as described herein. Preferably, the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4.

In one such embodiment, the lyophilized unit dose is obtained by lyophilizing 0.5 mL of a dengue vaccine composition comprising a dengue serotype 1 (e.g. chimeric dengue serotype 2/1 strain) in a concentration of 3.3 log 10 pfu/0.5 mL to 3.6 log 10 pfu/0.5 mL, a dengue serotype 2 (e.g. dengue serotype 2 strain) in a concentration of 2.7 log 10 pfu/0.5 mL to 4.0 log 10 pfu/0.5 mL, a dengue serotype 3 (e.g. chimeric dengue serotype 2/3 strain) in a concentration of 4.0 log 10 pfu/0.5 mL to 4.6 log 10 pfu/0.5 mL, and a dengue serotype 4 (e.g. chimeric dengue serotype 2/4 strain) in a concentration of 4.5 log 10 pfu/0.5 mL or 4.6 log 10 pfu/0.5 mL to 5.1 log 10 pfu/0.5 mL and pharmaceutically acceptable excipients as described herein. Preferably, the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4.

In certain embodiments, the lyophilized unit dose refers to 0.5 mL before lyophilization, wherein TDV-2 and TDV-4 are present in certain relative amounts, based on the total concentration of TDV-1, TDV-2, TDV-3 and TDV-4 in pfu/0.5 mL, and the concentration of TDV-2 measured in pfu/0.5 mL is less than 10% or less than 8% or less than 6%, and the concentration of TDV-4 measured in pfu/0.5 mL is at least 50% or at least 65%. In some of these embodiments, the concentration of TDV-1 measured in pfu/0.5 mL is at least 1% and/or the concentration of TDV-3 measured in pfu/0.5 mL is at least 6%, 7%, 8%, 10%, 12%, 14%, 16% or at least 18%.

In certain embodiments, the reconstituted unit dose has a volume of 0.5 mL and TDV-2 and TDV-4 are present in certain relative amounts, based on the total concentration of TDV-1, TDV-2, TDV-3 and TDV-4 in pfu/0.5 mL, and the concentration of TDV-2 measured in pfu/0.5 mL is less than 10% or less than 8% or less than 6%, and the concentration of TDV-4 measured in pfu/0.5 mL is at least 50% or at least 65%. In some of these embodiments, the concentration of TDV-1 measured in pfu/0.5 mL is at least 1% and/or the concentration of TDV-3 measured in pfu/0.5 mL is at least 6%, 7%, 8%, 10%, 12%, 14%, 16% or at least 18%.

In a further preferred embodiment, the reconstituted unit dose has a volume of 0.5 mL and comprises a tetravalent dengue virus composition including four live attenuated dengue virus strains, wherein the concentration of the dengue serotype 1 (e.g. dengue serotype 2/1 strain) measured in pfu/0.5 mL is 1% to 7% of the total concentration, the concentration of the dengue serotype 2 (e.g dengue serotype 2 strain) measured in pfu/0.5 mL is less than 8% of the total concentration, such as in the range of 1% to 8% of the total concentration, the concentration of the dengue serotype 3 (e.g. dengue serotype 2/3 strain) measured in pfu/0.5 mL is at least 10% of the total concentration, and the concentration of the dengue serotype 4 (e.g. dengue serotype 2/4 strain) measured in pfu/0.5 mL is at least 65% of the total concentration, such as in the range of 65% to 80%. In certain such embodiments, the arithmetic sum of all four serotypes is in the range of 4.6 log 10 pfu/0.5 mL to 6.7 log 10 pfu/0.5 mL, preferably in the range of 4.6 log 10 pfu/0.5 mL to 5.5 log 10 pfu/0.5 mL.

In a further preferred embodiment, the reconstituted unit dose has a volume of 0.5 mL and comprises a tetravalent dengue virus composition including four live attenuated dengue virus strains, wherein the dengue serotype 1 (e.g. chimeric dengue serotype 2/1 strain) such as TDV-1 and the dengue serotype 2 (e.g. dengue serotype 2 strain) such as TDV-2 are present each in a concentration based on the total concentration in pfu/0.5 mL which is within 5%-points of each other and/or are together less than about 10% of the total concentration in pfu/0.5 mL. In certain such embodiments the dengue serotype 3 (e.g. chimeric dengue serotype 2/3 strain) such as TDV-3 is preferably at least about 10% of the total concentration in pfu/0.5 mL and more preferably the dengue serotype 4 (e.g. chimeric dengue serotype 2/4 strain) such as TDV-4 is at least about 70% of the total concentration in pfu/0.5 mL. In certain such embodiments the dengue serotype 4 (e.g. chimeric dengue serotype 2/4 strain) such as TDV-4 represents the highest concentration in the composition of all four serotypes, preferably with at least about 70% of the total concentration in pfu/0.5 mL, dengue serotype 3 (e.g. chimeric dengue serotype 2/3 strain) such as TDV-3 represents the second highest concentration in the composition of all four serotypes, preferably with at least about 10% of the total concentration in pfu/0.5 mL, and dengue serotype 1 (e.g. chimeric dengue serotype 2/1 strain) such as TDV-1 and dengue serotype 2 (e.g. dengue serotype 2 strain) such as TDV-2 each represent lower concentrations than the concentration of serotype 3 (e.g. chimeric dengue serotype 2/3 strain) such as TDV-3, and optionally together represent less than about 10% of the total concentration in pfu/0.5 mL.

The lyophilized unit dose reconstituted in 0.5 mL will provide the above concentrations for the four dengue serotypes. While the unit dose of a dengue vaccine composition as described herein refers to the concentrations of the dengue serotypes in 0.5 mL, the lyophilized unit dose can be reconstituted with other volumes of a pharmaceutically acceptable diluent, such as an aqueous sodium chloride solution, without changing the absolute virus amount administered or the ratios of the viruses to one another.

In certain embodiments, the lyophilized unit dose of the invention is prepared from a solution comprising a non-reducing sugar, a surfactant, a protein and an inorganic salt.

In certain embodiments, the lyophilized unit dose of the invention is prepared from a solution comprising trehalose, poloxamer 407, human serum albumin and sodium chloride.

In certain embodiments, the lyophilized unit dose of the invention is prepared from a solution comprising about 10% w/v to about 20% w/v α,α-trehalose dihydrate or an equimolar amount of other forms of α,α-trehalose, from about 0.5% w/v to about 1.5% w/v poloxamer 407, from about 0.05% w/v to about 2% w/v human serum albumin, and about 70 mM to about 120 mM sodium chloride.

In preferred embodiments, the lyophilized unit dose of the invention as described herein is prepared from a solution comprising about 15% w/v α,α-trehalose dihydrate, about 1% w/v poloxamer 407, about 0.1% w/v human serum albumin and about 100 mM sodium chloride.

In one embodiment, the solution from which the lyophilized unit dose is prepared further comprises a buffer. The buffer may be phosphate buffered saline (PBS). The buffer may include at least one of sodium chloride (NaCl), monosodium dihydrogen phosphate ($NaH_2PO_4$), disodium hydrogen phosphate ($Na_2HPO_4$), potassium chloride (KCl), and potassium dihydrogen phosphate ($KH_2PO_4$). In a preferred embodiment, the buffer may include disodium hydrogen phosphate ($Na_2HPO_4$), potassium chloride (KCl), and potassium dihydrogen phosphate ($KH_2PO_4$). The buffer may have a pH in the range of about 7.0 to about 8.5 at 25° C. or a pH of about 6.8 to about 7.6 at 25° C., preferably a pH of about 7.2 at 25° C.

In preferred embodiments, the reconstituted unit dose of the invention as described herein comprising about 15% w/v α,α-trehalose dihydrate, about 1% w/v poloxamer 407, about 0.1% w/v human serum albumin and about 137 mM sodium chloride. The reconstituted unit dose may have a pH of about 7.0 to about 8.5 at 25° C., preferably a pH of about 7.2 at 25° C.

The unit dose of the invention as described herein activates multiple arms of the immune system—neutralizing antibodies, cellular immunity and anti-NS1 antibodies—in both seronegative and seropositive subject populations or in both seronegative and seropositive subjects. Thus, the unit dose of the invention as described herein protects both dengue seronegative and dengue seropositive subject populations or subjects against dengue disease.

In one embodiment, one unit dose is present in a container, preferably a vial, and said unit dose is administered to a subject after reconstitution. In one embodiment, more than one unit dose of the dengue vaccine composition may be present in a container, preferably a vial, so that with the content of one container, preferably a vial, more than one subject can be vaccinated. In one embodiment, the container comprising more than one unit doses of the invention as described herein is used for providing the reconstituted unit dose to be used in the methods of the invention as described herein.

The certain embodiments, the container comprising the unit dose of the invention is part of a kit. Thus, the invention is directed in part to a kit for preparing a reconstituted unit dose comprising a lyophilized unit dose of the present invention as described herein, and a pharmaceutically acceptable diluent for reconstitution.

In certain embodiments, the diluent for reconstitution provided in a container, preferably a vial, or a pre-filled syringe. In some embodiments, the diluent for reconstitution is selected from water for injection, phosphate buffered saline or an aqueous sodium chloride solution. In a preferred embodiment, the diluent for reconstitution is 30 to 40 mM sodium chloride, such as 37 mM sodium chloride.

In certain embodiments, the kit may further comprise a yellow fever vaccine, in particular YF-17D. In some embodiments, the yellow fever vaccine may be in a separate container, such as a vial. In another embodiment, the yellow fever vaccine and the unit dose of the invention may be in the same container. Thus, the invention is directed in part to a combined dengue/yellow fever vaccine, wherein the unit dose of the invention as described herein is combined with a yellow fever vaccine. Such a combined dengue/yellow fever vaccine comprises the unit dose of the invention as described herein and a yellow fever vaccine, in particular YF-17D, in the same formulation. In certain embodiments, the invention is directed to a kit comprising such a combined dengue/yellow fever vaccine and a unit dose of the invention as described herein.

In certain embodiments, the kit may further comprise a hepatitis A vaccine, such as HAVRIX® or VAQTA®. In some embodiments, the hepatitis A vaccine may be in a separate container, such as a vial. In another embodiment, the hepatitis A vaccine and the unit dose of the invention may be in the same container. Thus, the invention is directed in part to a combined dengue/hepatitis A vaccine, wherein the unit dose of the invention as described herein is combined with a hepatitis A vaccine. Such a combined dengue/hepatitis A vaccine comprises the unit dose of the invention as described herein and a hepatitis A vaccine, such as HAVRIX® or VAQTA®, in the same formulation. In certain embodiments, the invention is directed to a kit comprising such a combined dengue/hepatitis A vaccine and a unit dose of the invention as described herein.

In certain embodiments, the kit may further comprise a HPV vaccine, in particular a 9vHPV vaccine, such as GARDASIL® 9. In some embodiments, the HPV vaccine may be in a separate container, such as a vial. In another embodiment, the HPV vaccine and the unit dose of the invention may be in the same container. Thus, the invention is directed in part to a combined dengue/HPV vaccine, wherein the unit dose of the invention as described herein is combined with a HPV vaccine. Such a combined dengue/HPV vaccine comprises the unit dose of the invention as described herein and a HPV vaccine, in particular a 9vHPV vaccine, such as GARDASIL® 9, in the same formulation. In certain embodiments, the invention is directed to a kit comprising such a combined dengue/HPV vaccine and a unit dose of the invention as described herein.

In certain embodiments, the kit may further comprise a MMR vaccine, such as M-M-R® II. In some embodiments, the MMR vaccine may be in a separate container, such as a vial. In another embodiment, the MMR vaccine and the unit dose of the invention may be in the same container. Thus, the invention is directed in part to a combined dengue/MMR vaccine, wherein the unit dose of the invention as described herein is combined with a MMR vaccine. Such a combined dengue/MMR vaccine comprises the unit dose of the invention as described herein and a MMR vaccine, such as M-M-R® II, in the same formulation. In certain embodiments, the invention is directed to a kit comprising such a combined dengue/MMR vaccine and a unit dose of the invention as described herein.

In certain embodiments, the kit may further comprise a Tdap vaccine, in particular a combined tetanus toxoid, reduced diphtheria toxoid and acellular pertussis (adsorbed) vaccine, such as BOOSTRIX®. In some embodiments, the Tdap vaccine may be in a separate container, such as a vial. In another embodiment, the Tdap vaccine and the unit dose of the invention may be in the same container. Thus, the invention is directed in part to a combined dengue/Tdap vaccine, wherein the unit dose of the invention as described herein is combined with a Tdap vaccine. Such a combined dengue/Tdap vaccine comprises the unit dose of the invention as described herein and a Tdap vaccine, in particular a combined tetanus toxoid, reduced diphtheria toxoid and acellular pertussis (adsorbed) vaccine, such as BOOSTRIX®, in the same formulation. In certain embodiments, the invention is directed to a kit comprising such a combined dengue/Tdap vaccine and a unit dose of the invention as described herein.

In certain embodiments, the kit may further comprise a DTaP/IPV/Hib vaccine, in particular a combined DTaP/IPV/

Hib vaccine, such as Pentacel®. In some embodiments, the DTaP/IPV/Hib vaccine may be in a separate container, such as a vial. In another embodiment, the DTaP/IPV/Hib vaccine and the unit dose of the invention may be in the same container. Thus, the invention is directed in part to a combined dengue/DTaP/IPV/Hib vaccine, wherein the unit dose of the invention as described herein is combined with a DTaP/IPV/Hib vaccine. Such a combined dengue/DTaP/IPV/Hib vaccine comprises the unit dose of the invention as described herein and a DTaP/IPV/Hib vaccine, in particular a combined DTaP/IPV/Hib vaccine, such as Pentacel®, in the same formulation. In certain embodiments, the invention is directed to a kit comprising such a combined dengue/DTaP/IPV/Hib vaccine and a unit dose of the invention as described herein.

Yellow Fever Vaccine

YF-VAX®, a yellow fever vaccine from Sanofi, for subcutaneous use, is prepared by culturing the YF-17D strain of yellow fever virus in living avian leukosis virus-free (ALV-free) chicken embryos. The vaccine contains sorbitol and gelatin as a stabilizer and is lyophilized. No preservative is added. YF-VAX is formulated to contain not less than 4.74 $\log_{10}$ pfu per 0.5 mL dose throughout the life of the product.

Hepatitis A Vaccine

HAVRIX®, a hepatitis A vaccine from GlaxoSmithKline, is a sterile suspension of inactivated virus for intramuscular administration. The virus (strain HM175) is propagated in MRC-5 human diploid cells. After removal of the cell culture medium, the cells are lysed to form a suspension. This suspension is purified through ultrafiltration and gel permeation chromatography procedures. Treatment of this lysate with formalin ensures viral inactivation. Viral antigen activity is referenced to a standard using an enzyme linked immunosorbent assay (ELISA), and is therefore expressed in terms of ELISA Units (EL.U.). Each 1-mL dose for adults (≥18 years of age) of vaccine contains 1440 EL.U. of viral antigen, adsorbed on 0.5 mg of aluminum as aluminum hydroxide. Each 0.5-mL dose for children and adolescents (12 months through 18 years of age) of vaccine contains 720 EL.U. of viral antigen, adsorbed onto 0.25 mg of aluminum as aluminum hydroxide. HAVRIX® contains the following excipients: Amino acid supplement (0.3% w/v) in a phosphate-buffered saline solution and polysorbate 20 (0.05 mg/mL). From the manufacturing process, HAVRIX® also contains residual MRC-5 cellular proteins (not more than 5 µg/mL), formalin (not more than 0.1 mg/mL), and neomycin sulfate (not more than 40 ng/mL), an aminoglycoside antibiotic included in the cell growth media. HAVRIX® is formulated without preservatives.

VAQTA®, a hepatitis A vaccine from Merck Sharp & Dohme Corp., is an inactivated whole virus vaccine derived from hepatitis A virus grown in cell culture in human MRC-5 diploid fibroblasts. It contains inactivated virus of a strain, which was originally derived by further serial passage of a proven attenuated strain. The virus is grown, harvested, purified by a combination of physical and high performance liquid chromatographic techniques developed at the Merck Research Laboratories, formalin inactivated, and then adsorbed onto amorphous aluminum hydroxyphosphate sulfate. VAQTA® is a sterile suspension for intramuscular injection. One milliliter of the vaccine contains approximately 50 U of hepatitis A virus antigen, which is purified and formulated without a preservative. Within the limits of current assay variability, the 50 U dose of VAQTA® contains less than 0.1 µg of non-viral protein, less than $4\times10^{-6}$ µg of DNA, less than $10^{-4}$ µg of bovine albumin, and less than 0.8 µg of formaldehyde. Other process chemical residuals are less than 10 parts per billion (ppb), including neomycin. Each 0.5-mL pediatric dose contains 25 U of hepatitis A virus antigen and adsorbed onto approximately 0.225 mg of aluminum provided as amorphous aluminum hydroxyphosphate sulfate, and 35 µg of sodium borate as a pH stabilizer, in 0.9% sodium chloride. Each 1-mL adult dose contains 50 U of hepatitis A virus antigen and adsorbed onto approximately 0.45 mg of aluminum provided as amorphous aluminum hydroxyphosphate sulfate, and 70 µg of sodium borate as a pH stabilizer, in 0.9% sodium chloride.

HPV Vaccine

GARDASIL® 9, a HPV vaccine from Merck, is a non-infectious recombinant 9-valent vaccine prepared from the purified virus-like particles (VLPs) of the major capsid (Li) protein of HPV serotypes 6, 11, 16, 18, 31, 33, 45, 52, and 58. The Li proteins are produced by separate fermentations using recombinant *Saccharomyces cerevisiae* and self-assembled into VLPs. The fermentation process involves growth of *S. cerevisiae* on chemically-defined fermentation media which include vitamins, amino acids, mineral salts, and carbohydrates. The VLPs are released from the yeast cells by cell disruption and purified by a series of chemical and physical methods. The purified VLPs are adsorbed on preformed aluminum-containing adjuvant (amorphous aluminum hydroxyphosphate sulfate or AAHS). The 9-valent HPV VLP vaccine is a sterile liquid suspension that is prepared by combining the adsorbed VLPs of each HPV serotype and additional amounts of the aluminum-containing adjuvant and the final purification buffer. GARDASIL 9 is a sterile suspension for intramuscular administration. Each 0.5-mL dose contains approximately 30 µg of HPV serotype 6 Li protein, 40 µg of HPV serotype 11 Li protein, 60 µg of HPV serotype 16 Li protein, 40 µg of HPV serotype 18 Li protein, 20 µg of HPV serotype 31 Li protein, 20 µg of HPV serotype 33 Li protein, 20 µg of HPV serotype 45 Li protein, 20 µg of HPV serotype 52 Li protein, and 20 µg of HPV serotype 58 Li protein. Each 0.5-mL dose of the vaccine also contains approximately 500 µg of aluminum (provided as AAHS), 9.56 mg of sodium chloride, 0.78 mg of L-histidine, 50 µg of polysorbate 80, 35 µg of sodium borate.

MMR Vaccine

Several MMR vaccines are known in the prior art and include M-M-R® II, Priorix®, Tresivac®, and Trimovax®.

M-M-R® II, a MMR vaccine from Merck Sharp & Dohme Corp, is a live virus vaccine for vaccination against measles, mumps and rubella. M-M-R® II is a sterile lyophilized preparation of (1) ATTENUVAX® (measles virus vaccine live), a more attenuated line of measles virus, derived from Enders' attenuated Edmonston strain and propagated in chick embryo cell culture, (2) MUMPSVAX® (mumps virus vaccine live), the Jeryl Lynn™ (B level) strain of mumps virus propagated in chick embryo cell culture, and (3) MERUVAX® II (rubella virus vaccine live), the Wistar RA 27/3 strain of live attenuated rubella virus propagated in WI-38 human diploid lung fibroblasts. The growth medium for measles and mumps is Medium 199 (a buffered salt solution containing vitamins and amino acids and supplemented with fetal bovine serum) containing SPGA (sucrose, phosphate, glutamate, and recombinant human albumin) as stabilizer and neomycin. The growth medium for rubella is Minimum Essential Medium (MEM) (a buffered salt solution containing vitamins and amino acids and supplemented with fetal bovine serum) containing recombinant human albumin and neomycin. Sorbitol and hydrolyzed gelatin stabilizer are added to the individual virus harvests. The cells, virus pools, and fetal bovine serum are all screened for the absence of adventitious agents. The reconstituted vaccine is for subcutaneous administration. Each 0.5 mL dose contains not less than 1,000 $TCID_{50}$ (tissue culture infectious doses) of measles virus, 12,500 $TCID_{50}$ of mumps virus, and 1,000 $TCID_{50}$ of rubella virus. Each dose of the vaccine is calculated to contain sorbitol (14.5 mg), sodium phosphate, sucrose (1.9 mg), sodium chloride, hydrolyzed gelatin (14.5 mg), recombinant human albumin (50.3 mg), fetal bovine serum (<1 ppm), other buffer and media ingredients and approximately 25 μg of neomycin. The product contains no preservative. The lyophilized vaccine is reconstituted before administration.

Combined Tetanus, Diphtheria, and Pertussis (Tdap) Vaccine

BOOSTRIX®, a combined tetanus toxoid, reduced diphtheria toxoid and acellular pertussis (adsorbed) (Tdap) vaccine, is a non-infectious, sterile vaccine for intramuscular administration. It contains tetanus toxoid, diphtheria toxoid, and pertussis antigens (inactivated pertussis toxin (iPT) and formaldehyde-treated filamentous hemagglutinin (FHA) and pertactin (PRN)). The antigens are the same as those in INFANRIX®, but BOOSTRIX® is formulated with reduced quantities of these antigens.

BOOSTRIX® is supplied as a 0.5 mL suspension for injection. Each 0.5 mL dose of BOOSTRIX® is formulated to contain 5 Limits of flocculation (Lf) of tetanus toxoid, 2.5 Lf of diphtheria toxoid, 8 μg of iPT, 8 μg of formaldehyde treated FHA, and 2.5 μg of PRN (69 kiloDalton outer membrane protein), aluminum hydroxide as adjuvant (not more than 0.39 mg aluminum by assay), 4.5 mg of sodium chloride, 5100 μg of residual formaldehyde, and 5100 μg of polysorbate 80 (Tween 80).

Tetanus toxin is produced by growing *Clostridium tetani* in a modified Latham medium derived from bovine casein. The diphtheria toxin is produced by growing *Corynebacterium diphtheriae* in Fenton medium containing a bovine extract. Both toxins are detoxified with formaldehyde, concentrated by ultrafiltration, and purified by precipitation, dialysis, and sterile filtration. Tetanus and diphtheria toxoid potency is determined by measuring the amount of neutralizing antitoxin in previously immunized guinea pigs.

The acellular pertussis antigens (iPT, FHA, and PRN) are isolated from *Bordetella pertussis* culture grown in modified Stainer-Scholte liquid medium. iPT and FHA are isolated from the fermentation broth, PRN is extracted from the cells by heat treatment and flocculation. The antigens are purified in successive chromatographic and precipitation steps. iPT is detoxified using glutaraldehyde and formaldehyde. FHA and PRN are treated with formaldehyde. Each antigen is individually adsorbed onto aluminum hydroxide. The potency of the acellular pertussis components (inactivated iPT and formaldehyde-treated FHA and PRN) is determined by enzyme-linked immunosorbent assay (ELISA) on sera from previously immunized mice.

Combined Diphtheria, Tetanus, Pertussis, Poliomyelitis and *Haemophilus influenzae* Type b (DTaP/IPV/Hib) Vaccine Pentacel®, a combined DTaP/IPV/Hib vaccine, consists of a diphtheria and tetanus toxoids and acellular pertussis adsorbed and inactivated poliovirus (DTaP-IPV) component and an ActHIB® component combined through reconstitution for intramuscular injection. ActHIB® (*Haemophilus* b Conjugate Vaccine (Tetanus Toxoid Conjugate)), consists of *Haemophilius influenzae* type b capsular polysaccharide (polyribosyl-ribitol-phosphate (PRP)) covalently bound to tetanus toxoid (PRP-T). The DTaP-IPV component is supplied as a sterile liquid used to reconstitute the lyophilized ActHIB® component to form Pentacel®.

Each 0.5 mL dose contains 15 Limits of flocculation (Lf) diphtheria toxoid, 5 Lf tetanus toxoid, acellular pertussis antigens (20 μg detoxified pertussis toxin (PT), 20 μg filamentous hemagglutinin (FHA), 3 μg pertactin (PRN), 5 μg fimbriae types 2 and 3 (FIM)), inactivated polioviruses (40 D-antigen units (DU) Type 1 (Mahoney), 8 DU Type 2 (MEF-1), 32 DU Type 3 (Saukett)) and 10 μg PRP of *Haemophilius influenzae* type b covalently bound to 24 μg of tetanus toxoid (PRP-T).

Other ingredients per 0.5 mL dose include 1.5 mg aluminum phosphate (0.33 mg aluminum) as the adjuvant, polysorbate 80 (approximately 10 ppm by calculation), 42.5 mg sucrose, 55 μg residual formaldehyde, <50 ng residual glutaraldehyde, 550 ng residual bovine serum albumin, 3.3 mg (0.6% v/v) 2-phenoxyethanol (not as a preservative), <4 μg of neomycin and <4 μg polymyxin B sulfate.

*Corynebacterium diphtheriae* is grown in modified Mueller's growth medium. After purification by ammonium sulfate fractionation, the diphtheria toxin is detoxified with formaldehyde and diafiltered.

*Clostridium tetani* is grown in modified Mueller-Miller casamino acid medium without beef heart infusion. Tetanus toxin is detoxified with formaldehyde and purified by ammonium sulfate fractionation and diafiltration. Diphtheria and tetanus toxoids are individually adsorbed onto aluminum phosphate.

The acellular pertussis vaccine antigens are produced from *Bordetella pertussis* cultures grown in Stainer-Scholte medium modified by the addition of casamino acids and dimethyl-beta-cyclodextrin. PT, FHA and PRN are isolated separately from the supernatant culture medium. FIM are extracted and co-purified from the bacterial cells. The pertussis antigens are purified by sequential filtration, salt-precipitation, ultrafiltration and chromatography. PT is detoxified with glutaraldehyde. FHA is treated with formaldehyde and the residual aldehydes are removed by ultrafiltration. The individual antigens are adsorbed separately onto aluminum phosphate.

Poliovirus Type 1, Type 2 and Type 3 are each grown in separate cultures of MRC-5 cells, a line of normal human diploid cells, by the microcarrier method. The cells are grown in CMRL (Connaught Medical Research Laboratories) 1969 medium, supplemented with calf serum. For viral growth, the culture medium is replaced by Medium 199, without calf serum. After clarification and filtration, the viral suspensions are concentrated by ultrafiltration, and purified by liquid chromatography steps. The monovalent viral suspensions are inactivated with formaldehyde. Monovalent concentrates of each inactivated poliovirus are combined to produce a trivalent poliovirus concentrate.

The adsorbed diphtheria, tetanus and acellular pertussis antigens are combined with aluminum phosphate (as adjuvant), 2-phenoxyethanol (not as a preservative) and water for injection, into an intermediate concentrate. The trivalent poliovirus concentrate is added and the DTaP-IPV component is diluted to its final concentration. The DTaP-IPV component does not contain a preservative.

Both diphtheria and tetanus toxoids induce at least 2 neutralizing units per mL in the guinea pig potency test. The potency of the acellular pertussis antigens is evaluated by the antibody response of immunized mice to detoxified PT, FHA, PRN and FIM as measured by enzyme-linked immunosorbent assay (ELISA). The potency of inactivated poliovirus antigens is determined by measuring antibody-mediated neutralization of poliovirus in sera from immunized rats.

PRP, a high molecular weight polymer, is prepared from the *Haemophilus influenzae* type b strain 1482 grown in a semi-synthetic medium. The tetanus toxoid for conjugation to PRP is prepared by ammonium sulfate purification, and formalin inactivation of the toxin from cultures of *Clostridium tetani* (Harvard strain) grown in a modified Mueller and Miller medium. The toxoid is filter sterilized prior to the conjugation process. The ActHIB® component does not contain a preservative. Potency of the ActHIB® component is specified on each lot by limits on the content of PRP polysaccharide and protein per dose and the proportion of polysaccharide and protein that is characterized as high molecular weight conjugate.

Method of Preventing and Uses, Method of Inoculating and Uses

Method of Preventing, Method of Inoculating

The present invention is directed in part to a method of preventing dengue disease (in particular virologically confirmable dengue, VCD) in a subject. Thus, in certain embodiments the invention is directed to a method of preventing dengue disease in a subject, comprising administering to the subject, a unit dose/tetravalent dengue virus composition, in particular a reconstituted unit dose of the invention as described herein.

The present invention is directed in part to a method of preventing dengue hemorrhagic fever (DHF) and dengue shock syndrome (DSS). Thus, in certain embodiments the invention is directed to a method of preventing dengue hemorrhagic fever (DHF) and dengue shock syndrome (DSS), comprising administering to the subject a reconstituted unit dose/tetravalent dengue virus composition of the invention as described herein.

The present invention is therefore directed to a method of inoculating a subject against virologically confirmable dengue disease with a tetravalent dengue virus composition including four live attenuated dengue virus strains representing serotype 1, serotype 2, serotype 3 and serotype 4, wherein in particular the tetravalent dengue virus composition includes a chimeric dengue serotype 2/1 strain and a dengue serotype 2 strain and a chimeric dengue serotype 2/3 strain and a chimeric dengue serotype 2/4 strain, wherein in particular the dengue serotype 2 strain is derived from the wild type virus strain DEN-2 16681 (SEQ ID NO 11) and differs in at least three nucleotides from the wild type as follows:

a) 5-noncoding region (NCR)-57 (nt-57 C-to-T): major attenuation locus
b) NS1-53 Gly-to-Asp (nt-2579 G-to-A): major attenuation locus
c) NS3-250 Glu-to-Val (nt-5270 A-to-T): major attenuation locus; and wherein the three chimeric dengue strains are derived from the serotype 2 strain by replacing the structural proteins prM and E from serotype 2 strain with the corresponding structural proteins from the other dengue serotypes, resulting in the following chimeric dengue strains:

a DENV-2/1 chimera,
a DENV-2/3 chimera and
a DENV-2/4 chimera.

Further information regarding the serotypes of the tetravalent composition can be derived from section "Dengue virus strains" above.

The tetravalent dengue virus composition for such a method may be in the form of a unit dose comprising:

(i) a dengue serotype 1 in a concentration of at least 3.3 log 10 pfu/0.5 ml,
(ii) a dengue serotype 2, in a concentration of at least 2.7 log 10 pfu/0.5 ml,
(iii) a dengue serotype 3, in a concentration of at least 4.0 log 10 pfu/0.5 ml, and
(iv) a dengue serotype 4, in a concentration of at least 4.5 log 10 pfu/0.5 ml.

The present invention is in particular directed to such a method wherein the unit dose is lyophilized and upon reconstitution with 0.5 mL of a pharmaceutically acceptable diluent comprises:

(i) a dengue serotype 1 in a concentration of at least 3.3 log 10 pfu/0.5 ml,
(ii) a dengue serotype 2, in a concentration of at least 2.7 log 10 pfu/0.5 ml,
(iii) a dengue serotype 3, in a concentration of at least 4.0 log 10 pfu/0.5 ml, and
(iv) a dengue serotype 4, in a concentration of at least 4.5 log 10 pfu/0.5 ml.

The present invention is also in particular directed to such a method wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 8%, or at least 10%, or at least 12%, or at least 14%, or at least 16%, or at least 18%, and wherein preferably the subject is 2 to 17 years of age or 4 to 16 years of age.

The present invention is also in particular directed to such a method wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 2%, the concentration of (iv) in pfu/0.5 mL is at least 50%, the concentration of (i) in pfu/0.5 mL is at least 1%, and the concentration of (iii) in pfu/0.5 mL is at least 6%, wherein preferably the subject is 18 to 60 years of age.

Further information regarding the tetravalent composition or the unit dose can be derived from section "Dengue vaccine composition" and "Unit dose" above.

The present invention is therefore directed to a method and corresponding use, the method comprising a primary vaccination with only two administrations of the unit dose comprising the steps of:

(A) administering a first unit dose of the tetravalent dengue virus composition to the subject, and
(B) administering a second unit does of the tetravalent dengue virus composition to the subject within 3 months of administration of the first unit dose.

According to this embodiment the administration of only two doses within 3 months is sufficient to provide effective protection against a subsequent dengue infection.

Such method preferably provides a combined vaccine efficacy against all four serotypes in preventing virologically confirmable dengue disease with a 2-sided 95% confidence interval, wherein the lower bound is more than 60%, when measured against placebo in a subject population of at least 5,000 healthy subjects irrespective of serostatus at baseline and 14 to 16 years of age, from the first administration of the administration schedule until 18 months after the second administration of the administration schedule.

Such method also preferably provides a combined vaccine efficacy against all four serotypes, in preventing virologically confirmable dengue disease with a 2-sided 95% confidence interval, wherein the lower bound is more than 45%, when measured against placebo in a subject population of at least 1,500 or at least 2,000 healthy subjects seronegative against all serotypes at baseline and 14 to 16 years of age, from 30 days after the second administration of the administration schedule until 18 months after the second administration of the administration schedule.

According to certain embodiments the method of inoculation against the virologically confirmable dengue disease is due to a dengue serotype 2, and/or due to a dengue serotype 1. The method has very high efficacy against dengue serotype 2 and dengue serotype 1 and the highest efficacy against dengue serotype 2.

In certain embodiments, the invention is directed to said methods having a vaccine efficacy against serotype 1, in preventing virologically confirmable dengue disease with a 2-sided 95% confidence interval, wherein the lower bound is more than 25%, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the lower bound is more than 30%, is more than 35% is more than 40%, is more than 45%, is more than 50%, or is more than 54%. In certain such embodiments the subject population of at least 1,500 is seronegative against all serotypes at base line and the lower bound is more than 35%. In certain such embodiments the seronegative and seropositive population each provide a vaccine efficacy against serotype 1 with a 2-sided 95% confidence interval, wherein the lower bounds are within 10%-points.

In certain embodiments, the invention is directed to said methods having a vaccine efficacy against serotype 1, in preventing virologically confirmable dengue disease, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the vaccine efficacy is more than 40%, is more than 50%, is more than 60%, or is more than 65%. In certain such embodiments the subject population of at least 1,500 is seronegative against all serotypes at base line. In certain such embodiments the seronegative and seropositive population each provide a vaccine efficacy against serotype 1 which are within 5%-points.

In certain embodiments, the invention is directed to said methods having a vaccine efficacy against serotype 2, in preventing virologically confirmable dengue disease with a 2-sided 95% confidence interval, wherein the lower bound is more than 25%, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the lower bound is more than 50%, is more than 60%, is more than 70%, is more than 80%, or is more than 85%. In certain such embodiments the subject population of at least 1,500, is seronegative against all serotypes. In certain such embodiments the seronegative and seropositive population each provide a vaccine efficacy against serotype 2 with a 2-sided 95% confidence interval, wherein the lower bounds are within 5%-points.

In certain embodiments, the invention is directed to said methods having a vaccine efficacy against serotype 2, in preventing virologically confirmable dengue disease, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the vaccine efficacy is more than 60%, is more than 70%, is more than 80%, or is more than 90%. In certain such embodiments the subject population of at least 1,500 is seronegative against all serotypes at base line. In certain such embodiments the seronegative and seropositive population each provide a vaccine efficacy against serotype 2 which are within 5%-points.

The efficacy of the method is further described in more detail below in this the section.

In certain embodiments the unit dose is reconstituted and administered by subcutaneous injection. According to some of these embodiments, the subcutaneous injection is administered to the arm, preferably to the deltoid region of the arm.

According to one embodiment such a method does not include a step of determination whether there was a previous dengue infection in the subject before administration of the unit dose or wherein the serostatus of the subject is unknown before administration of the unit dose.

According to one embodiment such a method does not include a step of determination of a previous dengue infection in the subjects preferably at any time before, during or after the steps of administration or wherein the serostatus of the subject is unknown preferably at any time before, during or after the steps of administration.

The method according to the invention does not require the testing of the serostatus before vaccination and thus allows immediate treatment and outbreak control. According to certain embodiments the use is for a method wherein the subject is exposed to a dengue outbreak. In certain such embodiments the outbreak is due to a dengue serotype 2, and/or due to a serotype 1.

According to one embodiment such a method the subject is from a region wherein the seroprevalence rate is unknown and/or wherein the seroprevalence rate is below 80%, or below 70%, or below 60%.

According to one embodiment of such a method the subject is seronegative at baseline and is from a region or travels to a region wherein the seroprevalence rate is high with respect to serotype 1 and/or serotype 2 i.e. 80%, or 90% or above.

According this embodiment the vaccine and corresponding method is safe for seronegative and seropositive subjects and thus does not require an analysis of the serostatus or a determination of a previous dengue infection or a high seroprevalence rate in the region. Such a method preferably provides a combined vaccine efficacy against virologically-confirmed dengue with hospitalization against all four serotypes with a 2-sided 95% confidence interval, wherein the lower bound is more than 65%, when measured against placebo in a subject population of at least 5,000 healthy 4 to 16 year old subjects irrespective of serostatus at baseline, preferably in at least 1,500 healthy 4 to 16 year old subjects seronegative at baseline, from first administration of the administration schedule until 12 to 18 months after the second administration of the administration schedule. Preferably, the 2-sided 95% confidence interval of the combined vaccine efficacy against virologically-confirmed dengue with hospitalization against all four serotypes when comparing seropositive and seronegative subjects provides for lower bounds of the 2-sided confidence interval which are within 10% points or within 15% points or within 20% points. The method is preferably safe with respect to serotype 1 and serotype 2 which may therefore be used in outbreak situations due to serotype 1 and/or serotype 2 or even for seronegative subjects (e.g. travelers) or subjects with unknown serostatus in regions with very high seroprevalence rates (>80%) due to serotype 1 and/or serotype 2.

The safety of the method is further described in more detail in the section "method of preventing, method of inoculating".

According to one embodiment such a method does not include the active surveillance with respect to febrile illness of the subject after the administration of the first- and second-unit dose. During active surveillance any subject with febrile illness (defined as fever ≥38° C. on any 2 of 3 consecutive days) will be asked to return to the site for dengue fever evaluation by the Investigator. Subjects/guardians will be contacted at least weekly to ensure robust identification of febrile illness by reminding subjects/guardians of their obligation to return to the site in case of febrile illness. This contact will be implemented through appropriate methods that may differ in each trial site (eg, phone calls, text messaging, home visits, school-based surveillance).

According to one embodiment such a method does not include vaccine immunogenicity analysis including GMTs for dengue neutralizing antibodies.

According to one embodiment such a method does not include a reactogenicity analysis. Such a reactogenicity analysis relates to solicited local AEs (injection site pain, injection site erythema, and injection site swelling) and solicited systemic AEs (child <6 years: fever, irritability/fussiness, drowsiness and loss of appetite; child ≥6 years: asthenia, fever, headache, malaise and myalgia) which will e.g. be assessed for 7 days and 14 days, respectively, following each vaccination (vaccination day included) via collection of diary cards.

According to one embodiment the method does not include an active surveillance, an immunogenicity analysis and a reactogenicity analysis.

According to such embodiments the vaccine and the corresponding method of inoculation are safe and therefore do not require further steps of surveillance or analysis.

In view of the above the method according to one embodiment comprises a primary vaccination consisting of the steps of:

(A) selecting a subject for administration of the unit doses of the tetravalent dengue virus composition in need for protection against dengue infection without determination of a previous dengue infection, and (B) administering a first unit dose of the tetravalent dengue virus composition to the subject, and (C) administering a second unit dose of the tetravalent dengue virus composition to the subject within 3 months of administration of the first unit dose.

Therefore the method of inoculating is finalized without determination of a previous dengue infection. The method further optionally comprises at least 1 years after the administration of the second unit dose a booster dose of the unit dose.

Selecting the subject may include all types of considerations but preferably not the determination of a previous dengue infection. The selection may include consideration of the age, health conditions, and threat of infection. The threat of infection includes consideration of the seroprevalence rate in the region in which the subject normally lives or intends to travel, the serotype specific seroprevalence rate and an outbreak situation or serotype specific outbreak situations. The subject may be selected due to its exposure to serotype 1 and/or serotype 2 or due to the fact it requires protection against a specific dengue serotype, i.e. serotype 1 and/or serotype 2.

According to the invention the method is applicable to subjects of all kinds of ages. According to one embodiment the subject is under 9 years of age, or 4 to 5 years of age, or 6 to 11 years of age or 12 to 16 years, or 6 to 16 years of age or 4 to 16 years of age, or 2 to 17 years of age, or 9 years of age, or over 9 years of age, or 9 to 17 years of age, or 18 to 45 years of age, or 46 to 60 years of age, or over 60 years of age.

In particular the present invention is directed to such a method wherein the method which is safe.

In particular the present invention is directed to such a method providing a combined vaccine efficacy against virologically-confirmed dengue with hospitalization against all four serotypes with a 2-sided 95% confidence interval, wherein the lower bound is more than 65%, when measured against placebo in a subject population of at least 5,000 healthy 4 to 16 year old subjects irrespective of serostatus at baseline from first administration of the administration schedule until 12 to 18 months after the last administration of the administration schedule.

In particular the present invention is directed to such a method wherein the method which is effective.

In particular the present invention is directed to such a method providing a combined vaccine efficacy against all four serotypes, in preventing virologically confirmable dengue disease with a 2-sided 95% confidence interval, wherein the lower bound is more than 60%, when measured against placebo in a subject population of at least 5,000 healthy subjects irrespective of serostatus at baseline and 14 to 16 years of age, from the first administration of the administration schedule until 18 months after the last administration of the administration schedule.

In certain embodiments, the invention is directed to said methods, wherein the subject is seronegative to all dengue serotypes.

The present invention is directed in part to a method of preventing dengue disease (in particular virologically confirmable dengue, VCD) in a subject population. Thus, in certain embodiments the invention is directed to a method of preventing dengue disease in a subject population, comprising administering to the subject population a unit dose, in particular a reconstituted unit dose of the invention as described herein.

The present invention is in part directed to said method for preventing dengue disease (in particular virologically confirmable dengue, VCD) in a subject population comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to said method for preventing dengue disease (in particular virologically confirmable dengue, VCD) in a subject comprising administering to the subject at least a first reconstituted unit dose of the invention as described herein, wherein certain ratios of neutralizing antibody titers at day 180 or 365 after administration of said first unit dose to the subject are achieved. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2: neutralizing antibody titer for GMT DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

The geometric mean neutralizing antibody titers (GMTs) of a subject population or the neutralizing antibody titers of a subject are determined in accordance with the microneutralization test disclosed herein, for example according to the method described in Example 2. Without wishing to be bound to any theory, it is presently understood that a method inducing a more balanced immune response due to the administration of the reconstituted unit dose of the invention as described herein, in terms of less differences between the geometric mean neutralizing antibody titers (GMTs) against the four dengue serotypes or the neutralizing antibody titers against the four dengue serotypes, is beneficial to the subject or subject population to be vaccinated. In particular, it is understood that a much greater response to any one of the four serotypes, such as to DENV-2 in comparison to the other serotypes, is less beneficial.

The present invention is in part directed to said method for preventing dengue disease (in particular virologically confirmable dengue, VCD) in a subject or subject population wherein the method provides a seropositivity rate in a subject population of at least 50 subjects including the administration of two unit doses subcutaneously at day 1 and at day 90, wherein the subjects of the subject population are seronegative to all dengue serotypes at baseline. In certain such embodiments, at least 80% of the subject population are seropositive for all four dengue serotypes at least one month after administration of the first unit dose, such as at day 30, and/or at least 80% of the subject population are seropositive for all four dengue serotypes before or at the time of the administration of the second unit dose, such as at day 90, and/or at least 80%, or at least 85%, or at least 90%, or at least 95% of the subject population are seropositive for all four dengue serotypes after the administration of the second unit dose, such as at day 120, and/or at least 80%, or at least 85%, or at least 90% of the subject population are seropositive for all four dengue serotypes after the administration of the second unit dose, such as at day 270.

The present invention is in part directed to said method for preventing dengue disease (in particular virologically confirmable dengue, VCD) in a subject or subject population wherein the method provides a seropositivity rate in a subject population of at least 100 subjects including administration of two unit doses subcutaneously at day 1 and at day 90, wherein the subjects of the subject population comprises from 20% to 40% subjects who are seronegative to all dengue serotypes and from 60% to 80% subjects who are seropositive to at least one dengue serotype at base line, wherein at day 120 and/or day 270 the seropositivity rate for all four dengue serotypes in the seronegative part of the subject population and the seropositivity rate for all four dengue serotypes in the seropositive part of the subject population do not deviate more than 10%-points and/or wherein at day 120 the seropositivity rate for all four dengue serotypes in the seronegative part of the subject population and the seropositivity rate for all four dengue serotypes in the seropositive part of the subject population do not deviate more than 5%-points.

The present invention is in part directed to a method of preventing virologically confirmable dengue disease in a subject or subject population comprising administering to the subject or subject population a reconstituted unit dose of a tetravalent dengue virus composition including four live, attenuated dengue serotypes, in particular the virus strains as described herein.

The present invention is in part directed to a method of preventing virologically confirmable dengue disease with hospitalization in a subject or subject population comprising administering to the subject or subject population a reconstituted unit dose of a tetravalent dengue virus composition including four live, attenuated dengue serotypes, in particular the virus strains as described herein.

In certain embodiments, the method includes a reconstituted unit dose/tetravalent dengue virus composition of a dengue vaccine composition administered for preventing dengue disease in a subject or a subject population, the reconstituted unit dose comprising: a tetravalent virus composition including four live attenuated dengue virus strains, wherein a unit dose is lyophilized and upon reconstitution with 0.5 mL of a pharmaceutically acceptable diluent the reconstituted unit dose is obtained which comprises:

(i) a dengue serotype 1, such as a chimeric dengue serotype 2/1 strain, in a concentration of at least 3.3 log 10 pfu/0.5 ml, (ii) a dengue serotype 2, such as a dengue serotype 2 strain, in a concentration of at least 2.7 log 10 pfu/0.5 ml, (iii) a dengue serotype 3, such as a chimeric dengue serotype 2/3 strain, in a concentration of at least 4.0 log 10 pfu/0.5 ml, and (vi) a dengue serotype 4, such as a chimeric dengue serotype 2/4 strain, in a concentration of at least 4.5 log 10 pfu/0.5 ml.

It is preferred that the reconstituted unit dose/tetravalent dengue virus composition is used in the method of preventing dengue disease of the present invention, wherein upon reconstitution of the unit dose with a pharmaceutically acceptable diluent (i), (ii), (iii), and (iv) provide a total concentration of pfu/0.5 mL and based on said total concentration the concentration of (ii) in pfu/0.5 mL is less than 2%, the concentration of (iv) in pfu/0.5 mL is at least 50%, the concentration of (i) in pfu/0.5 mL is at least 1%, and the concentration of (iii) in pfu/0.5 mL is at least 6% and wherein the subject or subject population is of 18 to 60 years of age.

In another preferred embodiment, the reconstituted unit dose/tetravalent dengue virus composition is used in the method of preventing dengue disease of the present invention, wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 8% and wherein the subject or subject population is of 2 to 17 years of age.

In certain embodiments, the invention is directed to said methods, wherein said unit dose comprises a tetravalent dengue virus composition including four live attenuated dengue serotypes, in particular the virus strains described herein wherein the serotypes have certain concentrations as described herein with respect to the virus composition and unit dose such as:

(i) a dengue serotype 1 (e.g. chimeric dengue serotype 2/1 strain) has a concentration of 3.3 log 10 pfu/dose to 5.0 log 10 pfu/dose, or 3.3 log 10 pfu/0.5 mL to 5.0 log 10 pfu/0.5 mL (ii) a dengue serotype 2 (e.g. dengue serotype 2 strain) has a concentration of 2.7 log 10 pfu/dose to 4.9 log 10 pfu/0.5 dose, or 2.7 log 10 pfu/0.5 ml to 4.9 log 10 pfu/0.5 ml (iii) a dengue serotype 3 (e.g. chimeric dengue serotype 2/3 strain) has a concentration of 4.0 log 10 pfu/dose to 5.7 log 10 pfu/0.5 dose, or 4.0 log 10 pfu/0.5 mL to 5.7 log 10 pfu/0.5 mL and (iv) a dengue serotype 4 (e.g. chimeric dengue serotype 2/4 strain) has a concentration of 4.5 log 10 pfu/dose to 5.5 log 10 pfu/0.5 dose, or 4.5 log 10 pfu/0.5 mL to 5.5 log 10 pfu/0.5 mL.

In preferred such embodiments, the subject or subject population is of 2 to 17 years of age, such as 4 to 16 years of age, and preferably less than 9 years of age. In other preferred embodiments, the subject or subject population is 4-5 years of age, 6-11 years of age or 12-16 years of age.

In certain embodiments, the invention is directed to said methods, wherein said unit dose upon reconstitution with 0.5 mL of a pharmaceutically acceptable diluent has a concentration of 3.3 log 10 pfu/0.5 mL to 3.6 log 10 pfu/0.5 mL for dengue serotype 1 (e.g. chimeric dengue serotype 2/1 strain), has a concentration of 2.7 log 10 pfu/0.5 mL to 4.0 log 10 pfu/0.5 mL for dengue serotype 2 (e.g. dengue serotype 2 strain), has a concentration of 4.0 log 10 pfu/0.5 mL to 4.6 log 10 pfu/0.5 mL for dengue serotype 3 (e.g. chimeric dengue serotype 2/3 strain) and has a concentration of 4.5 log 10 pfu/0.5 mL or 4.6 log 10 pfu/0.5 mL to 5.1 log 10 pfu/0.5 mL for dengue serotype 4 (e.g. chimeric dengue serotype 2/4 strain). In preferred such embodiments, the subject or subject population is of 2 to 17 years of age, such as 4 to 16 years of age, and preferably less than 9 years of age. In other preferred embodiments, the subject or subject population is 4-5 years of age, 6-11 years of age or 12-16 years of age.

In certain embodiments, the invention is directed to said methods, wherein the concentration of the dengue serotype 1 (e.g. chimeric dengue serotype 2/1 strain) measured in pfu/0.5 mL is 1% to 7% of the total concentration, the concentration of the dengue serotype 2 (e.g. dengue serotype 2 strain) measured in pfu/0.5 mL is less than 8% of the total concentration, such as in the range of 1% to 8% of the total concentration, the concentration of the dengue serotype 3 (e.g. chimeric dengue serotype 2/3 strain) measured in pfu/0.5 mL is at least 10% of the total concentration, and the concentration of the dengue serotype 4 (e.g. chimeric dengue serotype 2/4 strain) measured in pfu/0.5 mL is at least 65% of the total concentration, such as in the range of 65% to 80%. In certain such embodiments, the arithmetic sum of all four serotypes is in the range of 4.6 log 10 pfu/0.5 mL to 6.7 log 10 pfu/0.5 mL, preferably in the range of 4.6 log 10 pfu/0.5 mL to 5.5 log 10 pfu/0.5 mL Preferably, in said embodiments the subject or subject population is of 2 to 17 years of age, such as 4 to 16 years of age, and even more preferably less than 9 years of age. In other preferred embodiments, the subject or subject population is 4-5 years of age, 6-11 years of age or 12-16 years of age.

In a further preferred embodiment, the invention is directed to said methods, wherein the dengue serotype 1 (e.g. chimeric dengue serotype 2/1 strain) such as TDV-1 and the dengue serotype 2 (e.g. dengue serotype 2 strain) such as TDV-2 are present each in a concentration based on the total concentration in pfu/0.5 mL which is within 5%-points of each other and/or are together less than about 10% of the total concentration in pfu/0.5 mL. In certain such embodiments the dengue serotype 3 (e.g. chimeric dengue serotype 2/3 strain) such as TDV-3 is preferably at least about 10% of the total concentration in pfu/0.5 mL and more preferably the dengue serotype 4 (e.g. chimeric dengue serotype 2/4 strain) such as TDV-4 is at least about 70% of the total concentration in pfu/0.5 mL. In certain such embodiments the dengue serotype 4 (e.g. chimeric dengue serotype 2/4 strain) such as TDV-4 represents the highest concentration in the composition of all four serotypes, preferably with at least about 70% of the total concentration in pfu/0.5 mL, dengue serotype 3 (e.g. chimeric dengue serotype 2/3 strain) such as TDV-3 represents the second highest concentration in the composition of all four serotypes, preferably with at least about 10% of the total concentration in pfu/0.5 mL, and dengue serotype 1 (e.g. chimeric dengue serotype 2/1 strain) such as TDV-1 and dengue serotype 2 (e.g. dengue serotype 2 strain) such as TDV-2 each represent lower concentrations than the concentration of serotype 3 (e.g. chimeric dengue serotype 2/3 strain) such as TDV-3, and optionally together represent less than about 10% of the total concentration in pfu/0.5 mL.

Preferably, the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

In certain embodiments, the invention is directed to said methods, wherein the reconstituted unit dose of the invention as described herein is administered by subcutaneous injection. According to some of these embodiments, the subcutaneous injection is administered to the arm, preferably to the deltoid region of the arm.

In certain embodiments, the invention is directed to said methods, wherein the reconstituted unit dose is administered to a subject of unknown serostatus and/or wherein no test has been carried out to determine whether the subject is seropositive or seronegative (before) the unit dose as described herein is administered. In certain embodiments, the invention is directed to said methods which do not include a step of determination of a previous dengue infection in the subject or subjects. In certain embodiments, the invention is directed to said methods which do not include the analysis of the seroprevalence rate in the region or is conducted in a region with a seroprevalence of below 80%, below 70% or below 60%. In certain embodiments the invention is directed to a method wherein the serostatus of the subject is unknown. In such embodiments the serostatus is not determined at any time before and after administration in relation to this method. In certain embodiments of the invention the method is used in an outbreak situation. In certain embodiments, the invention is directed to said methods being conducted outside a clinical trial In certain embodiments, the invention is directed to said methods, wherein the subject, or subject population is seronegative to all dengue serotypes.

In certain embodiments, the invention is directed to said methods, wherein two unit doses of the invention as described herein are administered. In some embodiments the two unit doses are administered within 12 months or more, or within six months, or within three months, and optionally at least 4 weeks apart such as at day 0 and day 90 or at day 1 and day 90. According to some of these embodiments, a further third unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments, the method of the invention comprises or consists of a single unit dose of the invention being administered.

In certain embodiments, the invention is directed to said methods, wherein the reconstituted unit dose of the invention as described herein is administered subcutaneously to a subject or subject population that is seronegative with respect to all dengue serotypes. In other embodiments, the subject or subject population is seropositive with respect to at least one dengue serotype.

In certain embodiments, the invention is directed to said methods, wherein the unit dose of the invention as described herein is administered to a subject or subject population from a dengue endemic region. In some of these embodiments, the subject or subject population is from Singapore, Dominican Republic, Panama, Philippines, Colombia, Puerto Rico or Thailand, in particular from Singapore, Dominican Republic, Panama, or Philippines. In a preferred embodiment, the subject or subject population is from Asia Pacific or from Latin America. In some other of these embodiments, the subject or subject population is from Thailand, Sri Lanka, Philippines, Panama, Nicaragua, Dominican Republic, Colombia or Brazil. In other embodiments, the subject, or subject population is from a dengue non-endemic region. Such a subject population or such a subject may be vaccinated according to the present invention in the context of traveling to a dengue endemic region. In certain embodiments, the reconstituted unit dose of the invention as described herein is administered subcutaneously to a subject, or subject population that is from a dengue endemic region or a dengue non-endemic region.

In certain embodiments, the invention is directed to said methods, wherein the reconstituted unit dose of the invention as described herein is administered subcutaneously to a subject or subject population of 2 to 60 years of age. In some embodiments, the subjects or subject population are adults of more than 17 years, or more than 18 years, or 18 to 60 years. In further specific embodiments, the subjects or subject population are adults of more than 21 years, or 21 to 60 years, or 21 to 45 years of age.

In certain embodiments, the invention is directed to said methods, wherein the reconstituted unit dose of the invention as described herein is administered subcutaneously to children and adolescents of 2 to 17 years of age. In some embodiments, the subjects or subject population are less than 9 years of age, or less than 4 years of age. In some embodiments, the subjects or subject population are from 2 to 9 years of age, or from 2 to 5 years of age, or from 4 to 9 years of age or from 6 to 9 years of age. In other embodiment, the subject or subject population is 4 to 16 years of age. In some such embodiments, the subject or subject population is 4-5 years of age, 6-11 years of age or 12-16 years of age. Optionally, the subject or subject population is seronegative with respect to all dengue serotypes.

In certain embodiments, the invention is directed to said methods, wherein the unit dose of the invention as described herein is administered to a pediatric subject or pediatric subject population of less than 2 years of age, preferably of 2 months to 2 years or 2 months to 1.5 years or 2 months to 1 year. According to some of these embodiments, the pediatric subject or pediatric subject population is seronegative and from a dengue endemic region.

In certain embodiments, the invention is directed to said methods, wherein the reconstituted unit dose of the invention as described herein is administered to a pediatric subject or pediatric subject population of less than 2 years of age, preferably of 2 months to 2 years or 2 months to 1.5 years or 2 months to 1 year, preferably by subcutaneous injection. According to some of these embodiments, the pediatric subject or pediatric subject population is seronegative and from a dengue endemic region.

In a certain embodiments, the invention is directed to said methods, wherein the subject or subject population is 4-5 years of age and from Asia Pacific, 6-11 years of age and from Asia Pacific, or 12-16 years of age and from Asia Pacific. In other embodiments, the subject or subject population is 4-5 years of age and from Latin America, 6-11 years of age and from Latin America, or 12-16 years of age and from Latin America.

In a certain embodiments, the invention is directed to said methods, wherein the subject or subject population is 4-5 years of age and seropositive for at least 1 dengue serotype, 6-11 years of age and seropositive for at least 1 dengue serotype, or 12-16 years of age and seropositive for at least 1 dengue serotype. In other embodiments, the subject or subject population is 4-5 years of age and seronegative for all dengue serotypes, 6-11 years of age and seronegative for all dengue serotypes, or 12-16 years of age and seronegative for all dengue serotypes.

In a certain embodiments, the invention is directed to said methods, wherein the subject or subject population is from Asia Pacific or Latin America and seropositive for at least one dengue serotype at baseline. In other embodiments, the subject or subject population is from Asia Pacific or Latin America and seronegative for at all dengue serotype at baseline.

In certain embodiments, the invention is directed to said methods, wherein the subject or subject population is from Asia Pacific, seropositive for at least one dengue serotype at baseline and 4-5 years of age, 6-11 years of age, or 12-16 years of age. In other embodiments, the subject or subject population is from Asia Pacific, seronegative for all dengue serotypes at baseline and 4-5 years of age, 6-11 years of age, or 12-16 years of age. In yet other embodiments, the subject or subject population is from Latin America, seropositive for at least one dengue serotype at baseline and 4-5 years of age, 6-11 years of age, or 12-16 years of age. In other embodiments, the subject or subject population is from America, seronegative for all dengue serotypes at baseline and 4-5 years of age, 6-11 years of age, or 12-16 years of age.

In certain embodiments, the invention is directed to said methods, wherein the subject or subject population had prior vaccination against Yellow Fever. In other embodiments, the subject or subject population had prior vaccination against Japanese Encephalitis. In yet other embodiments, the subject or subject population had no prior vaccination against Yellow Fever. In other embodiments, the subject or subject population had no prior vaccination against Japanese Encephalitis. Prior vaccination indicates a vaccination prior to 30 days after a second administration, such as within 4 months after the first administration, with the reconstituted unit dose as described herein. For example for vaccine efficacy (VE) as determined in Example 6 from 30 days post-second vaccination, a prior vaccination of Yellow Fever is defined as a Yellow Fever vaccination occurring before 30 days post-second vaccination. In certain embodiments, the subject or subject population received Dengvaxia® within the administration regimen as described herein or within 4.5 years after administration of the first dose.

Particularly unbalanced titers of neutralizing antibodies against the four dengue serotypes are observed in seronegative populations or subjects after administration of the commercially available dengue vaccine. The present invention shows that in particular seronegative subjects show a more balanced immune response to the four dengue serotypes after administration of the reconstituted unit dose of the invention as described herein. It is therefore contemplated that the unit dose of the invention as described herein and methods of the present invention as described herein may provide a more robust immune response in a subject population including both seropositive and seronegative subjects. This balanced response and balanced efficacy and safety is required to allow inoculation without prior serostatus analysis which is a major advantage in vaccination programs and in particular in outbreak situations.

The present invention is directed in part to a method of preventing virologically confirmable dengue disease in a subject comprising administering to the subject a tetravalent dengue virus composition including four dengue virus strains representing serotype 1, serotype 2, serotype 3 and serotype 4, wherein the virus strains are optionally live, attenuated dengue virus strains.

The present invention is directed in part to a method of preventing virologically confirmable dengue disease in a subject consisting of administering to the subject a tetravalent dengue virus composition including four dengue virus strains representing serotype 1, serotype 2, serotype 3 and serotype 4, wherein the virus strains are optionally live, attenuated dengue virus strains.

In certain embodiments, the invention is directed to said methods, wherein there is no step of determining the serostatus of the subject at baseline, in other words, said methods do not comprise a determination of a previous dengue infection of the subject at baseline before the administration of the tetravalent dengue virus composition. In particular, such methods are safe and effective. Thus, in certain such embodiments, the subject has not been tested for the presence a previous dengue infection.

In certain embodiments, the invention is directed to said methods, wherein the vaccine administration is safe irrespective of whether there is a determination that the subject had a previous dengue infection before the administration of the tetravalent dengue virus composition. In particular, such methods are also effective.

In certain embodiments, the invention is directed to said methods, wherein the method is safe and/or effective.

In certain embodiments, the invention is directed to said methods, wherein the composition includes at least one chimeric dengue virus. In certain such embodiments, the invention is directed to said methods, wherein the composition includes at least one non-chimeric dengue virus and at least one chimeric dengue virus, in particular a chimeric dengue serotype 2/1 strain and a dengue serotype 2 strain and a chimeric dengue serotype 2/3 strain and a chimeric dengue serotype 2/4 strain. The details of the composition are described above.

Therefore, in certain embodiments, the invention is directed to said methods having a vaccine efficacy, preferably a combined vaccine efficacy against all four serotypes, in preventing virologically confirmable dengue disease with a 2-sided 95% confidence interval, wherein the lower bound is more than 25%, when measured against placebo in a subject population of at least 5,000 healthy subjects (or at least 10,000, or at least 15,000 healthy subjects) irrespective of serostatus at baseline and e.g. 14 to 16 years of age, wherein a reconstituted unit dose/tetravalent dengue virus composition as described herein or placebo is administered e.g. at least twice within less than 6 months, such as within 3 months, after first administration or 30 days after the second/last administration until at least 12 to 18 months (e.g. at 12 or at 18 months) after the second/last administration. In embodiments, the invention is directed to said methods having a vaccine efficacy, preferably a combined vaccine efficacy against all four serotypes, in preventing virologically confirmable dengue disease with a 2-sided 95% confidence interval, wherein the lower bound is more than 25%, when measured against placebo in a subject population of at least 5,000 healthy subjects (or at least 10,000, or at least 15,000 healthy subjects) irrespective of serostatus at baseline, wherein a reconstituted unit dose or tetravalent dengue virus composition as described herein or placebo is administered at least once, until 15 to 21 months (e.g. 15 or 21 months) after the first administration of the administration schedule. In certain such embodiments, the lower bound is more than 30%, more than 40%, more than 50%, more than 55%, more than 60%, more than 65%, more than 70% or more than 72%. Preferably said reconstituted unit dose or placebo is administered subcutaneously within about 3 months, such as on days 0 and 90.

Therefore, in certain embodiments, the invention is directed to said methods having a combined vaccine efficacy against all four serotypes, in preventing virologically confirmable dengue disease with a 2-sided 95% confidence interval, wherein the lower bound is more than 60%, when measured against placebo in a subject population of at least 5,000 healthy subjects (or at least 10,000, or at least 15,000 healthy subjects) irrespective of serostatus at baseline and 4 to 16 years of age, wherein a reconstituted unit dose/tetravalent dengue virus composition as described herein or placebo is administered e.g. at least twice within less than 6 months, such as within 3 months, after the first administration until 18 months after the last administration. In these embodiments, the lower bound is e.g. more than 62%, more than 64%, more than 66%, more than 68%, or more than 69%.

In certain embodiments, the invention is directed to said methods having a vaccine efficacy, preferably a combined vaccine efficacy against all four serotypes, in preventing virologically confirmable dengue disease of more than 30%, when measured against placebo in a subject population of at least 5,000 healthy subjects (or at least 10,000, or at least 15,000 healthy subjects) irrespective of serostatus at baseline and e.g. 14 to 16 years of age, wherein a reconstituted unit dose or tetravalent dengue virus composition as described herein or placebo is administered at least twice within less than 6 months, such as within 3 months, after first administration or 30 days after the second administration/last administration until at least 12 months or until 12 to 18 months (e.g. at 12 or at 18 months) after the second administration/last administration. In certain embodiments, the invention is directed to said methods having a vaccine efficacy, preferably a combined vaccine efficacy against all four serotypes, in preventing virologically confirmable dengue disease of more than 30%, when measured against placebo in a subject population of at least 5,000 healthy subjects (or at least 10,000, or at least 15,000 healthy subjects) irrespective of serostatus at baseline, wherein a reconstituted unit dose or tetravalent dengue virus composition as described herein or placebo is administered at least once, until 15 months after the first administration of the administration schedule. In certain such embodiments, the vaccine efficacy is more than 40%, more than 50%, more than 55%, more than 60%, more than 65%, more than 70%, more than 75%, more than 78%, more than 79% or about 80%. Preferably said reconstituted unit dose or placebo is administered subcutaneously within about 3 month, such as on days 0 and 90.

Therefore, in certain embodiments, the invention is directed to said methods having a combined vaccine efficacy against all four serotypes, in preventing virologically confirmable dengue disease of more than 66%, when measured against placebo in a subject population of at least 5,000 healthy subjects (or at least 10,000, or at least 15,000 healthy subjects) irrespective of serostatus at baseline and 14 to 16 years of age, wherein a reconstituted unit dose/tetravalent dengue virus composition as described herein or placebo is administered e.g. at least twice within less than 6 months, such as within 3 months, after the first administration until 18 months after the last administration. In these embodiments, the vaccine efficacy is e.g. more than 68%, more than 70%, more than 72%, or more than 74%.

In certain embodiments, the invention is directed to said methods having a vaccine efficacy, preferably a combined vaccine efficacy against all four serotypes, in preventing virologically confirmable dengue disease with hospitalization with a 2-sided 95% confidence interval, wherein the lower bound is more than 0%, when measured against placebo in a subject population of at least 5,000 healthy subjects (or at least 10,000, or at least 15,000 healthy subjects) irrespective of serostatus at baseline, wherein a reconstituted unit dose or tetravalent dengue virus composition as described herein or placebo is administered at least twice within less than 6 months, such as within 3 months, 30 days after the second administration until at least 18 months after the second administration. In certain such embodiments, the lower bound is more than 10%, is more than 20%, is more than 30%, is more than 40%, is more than 50%, is more than 55%, is more than 60%, is more than 65%, is more than 70% or is more than 80%, or more than 90%.

In certain embodiments, the invention is directed to said methods having a combined vaccine efficacy against all four dengue serotypes in seronegative subjects with a 2-sided 95% confidence interval, wherein the lower bound is more than 25%, when measured against placebo in a subject population of at least 1,500 or at least 2,000 healthy subjects being seronegative against all serotypes at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, is more than 50%, or is more than 55%.

In certain embodiments, the invention is directed to said methods having a combined vaccine efficacy against all four serotypes, in preventing virologically confirmable dengue disease with a 2-sided 95% confidence interval, wherein the lower bound is more than 25%, when measured against placebo in a subject population of at least 1,500 or at least 2,000 or at least 5,000 healthy subjects (or at least 10,000, or at least 15,000 healthy subjects) being seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the lower bound is more than 30%, is more than 35%, is more than 40%, or is more than 45%.

In certain embodiments, the invention is directed to said methods having a combined vaccine efficacy against all four serotypes, in preventing virologically confirmable dengue disease with a 2-sided 95% confidence interval, wherein the lower bound is more than 25%, when measured against placebo in a subject population of at least 5,000 healthy subjects (or at least 10,000, or at least 15,000 healthy subjects) being seropositive at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the lower bound is more than 40%, is more than 45%, is more than 50%, is more than 60%, or is more than 65%.

In certain embodiments, the invention is directed to said methods having a combined vaccine efficacy against all four serotypes, in preventing virologically confirmable dengue disease with a 2-sided 95% confidence interval, wherein the lower bound is more than 25%, when measured against placebo in a subject population of at least 5,000 healthy subjects (or at least 10,000, or at least 15,000 healthy subjects) being seropositive at baseline being or seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the difference between the lower bound provided by the seropositive subjects at baseline and the subjects seronegative against all serotypes at baseline is no more than 15%-points.

In certain embodiments, the invention is directed to said methods having a combined vaccine efficacy against all four dengue serotypes in seronegative subjects of more than 30%, when measured against placebo in a subject population of at least 1,500 or at least 2,000 healthy subjects being seronegative against all serotypes at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the combined vaccine efficacy against all four dengue serotypes in seronegative subjects is more than 40%, is more than 50%, is more than 60%, is more than 65%, or is more than 70%.

In certain embodiments, the invention is directed to said methods having a combined vaccine efficacy against all four serotypes, in preventing virologically confirmable dengue disease, when measured against placebo in a subject population of at least 1,500 or at least 2,000 or at least 5,000 healthy subjects (or at least 10,000, or at least 15,000 healthy subjects) being seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments the said vaccine efficacy is more than 30%, is more than 40%, is more than 50%, is more than 55%, is more than 60%, or is more than 65%.

In certain embodiments, the invention is directed to said methods having a combined vaccine efficacy against all four serotypes, in preventing virologically confirmable dengue disease, when measured against placebo in a subject population of at least 5,000 healthy subjects (or at least 10,000, or at least 15,000 healthy subjects) being seropositive at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments the said vaccine efficacy is more than 40%, is more than 50%, is more than 60%, is more than 65%, is more than 70%, or is more than 75%.

In certain embodiments, the invention is directed to said methods having a combined vaccine efficacy against all four serotypes, in preventing virologically confirmable dengue disease with a 2-sided 95% confidence interval, wherein the lower bound is more than 25%, when measured against placebo in a subject population of at least 5,000 healthy subjects (or at least 10,000, or at least 15,000 healthy subjects) being seropositive at baseline being or seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the difference between the lower bound provided by the seropositive subjects at baseline and the subjects seronegative against all serotypes at baseline is no more than 15%-points, or is no more than 10%-points.

In certain embodiments, the invention is directed to said methods having a combined vaccine efficacy against all four dengue serotypes with a 2-sided 95% confidence interval, wherein the lower bound is more than 25%, when measured against placebo in a subject population of at least 1,000 healthy subjects 4 to 5 years of age at the time of randomization and irrespective of serostatus at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, is more than 45%.

In certain embodiments, the invention is directed to said methods having a combined vaccine efficacy against all four dengue serotypes of more than 30%, when measured against placebo in a subject population of at least 1,000 healthy subjects 4 to 5 years of age at the time of randomization and irrespective of serostatus at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the combined vaccine efficacy against all four dengue serotypes is more than 40%, is more than 50%, is more than 60%, is more than 65%, or is more than 70%.

In certain embodiments, the invention is directed to said methods having a combined vaccine efficacy against all four dengue serotypes with a 2-sided 95% confidence interval, wherein the lower bound is more than 25%, when measured against placebo in a subject population of at least 1,000 healthy subjects 6 to 11 years of age at the time of randomization and irrespective of serostatus at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, is more than 50%, is more than 60%, or is more than 70%.

In certain embodiments, the invention is directed to said methods having a combined vaccine efficacy against all four dengue serotypes of more than 30%, when measured against placebo in a subject population of at least 1,000 healthy subjects 6 to 11 years of age at the time of randomization and irrespective of serostatus at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the combined vaccine efficacy against all four dengue serotypes is more than 40%, is more than 50%, is more than 60%, is more than 70%, is more than 75%, or is more than 80%.

In certain embodiments, the invention is directed to said methods having a combined vaccine efficacy against all four dengue serotypes with a 2-sided 95% confidence interval, wherein the lower bound is more than 25%, when measured against placebo in a subject population of at least 1,000 healthy subjects 12 to 16 years of age at the time of randomization and irrespective of serostatus at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, is more than 50%, is more than 60%, is more than 65%, or is more than 68%.

In certain embodiments, the invention is directed to said methods having a combined vaccine efficacy against all four dengue serotypes of more than 30%, when measured against placebo in a subject population of at least 1,000 healthy subjects 12 to 16 years of age at the time of randomization and irrespective of serostatus at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the combined vaccine efficacy against all four dengue serotypes is more than 40%, is more than 50%, is more than 60%, is more than 70%, is more than 75%, or is more than 80%.

In certain embodiments, the invention is directed to said methods having a vaccine efficacy against dengue serotype 1 with a 2-sided 95% confidence interval, wherein the lower bound is more than 25%, when measured against placebo in a subject population of at least 5,000 healthy subjects, or at least 10,000 healthy subjects, or at least 15,000 healthy subjects irrespective of serostatus at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, or is more than 50%.

In certain embodiments, the invention is directed to said methods having a vaccine efficacy against serotype 1, in preventing virologically confirmable dengue disease with a 2-sided 95% confidence interval, wherein the lower bound is more than 25%, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 or at 18 months) after the last administration. In certain such embodiments, the lower bound is more than 30%, is more than 35% is more than 40%, is more than 45%, is more than 50%, or is more than 54%. In certain such embodiments the subject population of at least 1,500 is seronegative against all serotypes at base line and the lower bound is more than 35%. In certain such embodiments the seronegative and seropositive population each provide a vaccine efficacy against serotype 1 with a 2-sided 95% confidence interval, wherein the lower bounds are within 10%-points.

In certain embodiments, the invention is directed to said methods having a vaccine efficacy against dengue serotype 1 of more than 30%, when measured against placebo in a subject population of at least 5,000 healthy subjects, or at least 10,000 healthy subjects, or at least 15,000 healthy subjects irrespective of serostatus at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the vaccine efficacy against dengue serotype 1 is more than 40%, is more than 50%, is more than 60%, is more than 65%, or is more than 70%.

In certain embodiments, the invention is directed to said methods having a vaccine efficacy against serotype 1, in preventing virologically confirmable dengue disease, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 or at 18 months) after the last administration. In certain such embodiments, the vaccine efficacy is more than 40%, is more than 50%, is more than 60%, or is more than 65%. In certain such embodiments the subject population of at least 1,500 is seronegative against all serotypes at base line. In certain such embodiments the seronegative and seropositive population each provide a vaccine efficacy against serotype 1 which are within 5%-points.

In certain embodiments, the invention is directed to said methods having a vaccine efficacy against dengue serotype 2 with a 2-sided 95% confidence interval, wherein the lower bound is more than 25%, when measured against placebo in a subject population of at least 5,000 healthy subjects, or at least 10,000 healthy subjects, or at least 15,000 healthy subjects irrespective of serostatus at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, is more than 50, is more than 60, is more than 70, is more than 80, or is more than 90%.

In certain embodiments, the invention is directed to said methods having a vaccine efficacy against serotype 2, in preventing virologically confirmable dengue disease with a 2-sided 95% confidence interval, wherein the lower bound is more than 25%, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 or at 18 months) after the last administration. In certain such embodiments, the lower bound is more than 50%, is more than 60%, is more than 70%, is more than 80%, or is more than 85%. In certain such embodiments the subject population of at least 1,500, is seronegative against all serotypes. In certain such embodiments the seronegative and seropositive population each provide a vaccine efficacy against serotype 2 with a 2-sided 95% confidence interval, wherein the lower bounds are within 5%-points.

In certain embodiments, the invention is directed to said methods having a vaccine efficacy against dengue serotype 2 of more than 30%, when measured against placebo in a subject population of at least 5,000 healthy subjects, or at least 10,000 healthy subjects, or at least 15,000 healthy subjects irrespective of serostatus at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the vaccine efficacy against dengue serotype 2 is more than 40%, is more than 50%, is more than 60%, is more than 70%, is more than 80, or is more than 90%.

In certain embodiments, the invention is directed to said methods having a vaccine efficacy against serotype 2, in preventing virologically confirmable dengue disease, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 or at 18 months) after the last administration. In certain such embodiments, the vaccine efficacy is more than 60%, is more than 70%, is more than 80%, or is more than 90%. In certain such embodiments the subject population of at least 1,500 is seronegative against all serotypes at base line. In certain such embodiments the seronegative and seropositive population each provide a vaccine efficacy against serotype 2 which are within 5%-points.

In certain embodiments, the invention is directed to said methods having a vaccine efficacy against dengue serotype 3 with a 2-sided 95% confidence interval, wherein the lower bound is more than 25%, when measured against placebo in a subject population of at least 5,000 healthy subjects, or at least 10,000 healthy subjects, or at least 15,000 healthy subjects irrespective of serostatus at baseline, wherein said unit dose/tetravalent dengue virus composition or said placebo is administered at least twice within less than 6 months, such as within 3 months, about 30 days after the second administration of the administration schedule until at least 12 months after the second administration of the administration schedule. In certain such embodiments, the lower bound is more than 30%, is more than 40%.

In certain embodiments, the invention is directed to said methods having a vaccine efficacy against dengue serotype 3 of more than 30%, when measured against placebo in a subject population of at least 5,000 healthy subjects, or at least 10,000 healthy subjects, or at least 15,000 healthy subjects irrespective of serostatus at baseline, wherein said unit dose/tetravalent dengue virus composition or said placebo is administered at least twice within less than 6 months, such as within 3 months, 30 days after the second administration until at least 12 months after the second administration. In certain such embodiments, the vaccine efficacy against dengue serotype 3 is more than 40%, is more than 50%, is more than 55%, or is more than 60%.

In certain embodiments, the invention is directed to said methods having a combined vaccine efficacy against all four serotypes, in preventing virologically confirmable dengue disease with hospitalization with a 2-sided 95% confidence interval, wherein the lower bound is more than 25%, when measured against placebo in a subject population of at least 5,000 healthy subjects (or at least 10,000, or at least 15,000 healthy subjects) irrespective of serostatus at baseline and 4 to 16 years of age, wherein a reconstituted unit dose/tetravalent dengue virus composition as described herein or placebo is e.g. administered at least twice within less than 6 months, such as within 3 months, from first administration until 12 to 18 months (e.g. at 12 months or at 18 months) after the last administration, or from 30 days post last administration until 12 to 18 months (e.g. at 12 or at 18 months) after the last administration. In certain such embodiments, the lower bound is more than 10%, is more than 20%, is more than 30%, is more than 40%, is more than 50%, is more than 55%, is more than 60%, is more than 65%, is more than 66%, is more than 67%, is more than 70%, is more than 75%, is more than 77%, or is more than 80%.

In certain embodiments, the invention is directed to said methods having a combined vaccine efficacy against all four serotypes, in preventing virologically confirmable dengue disease with hospitalization, when measured against placebo in a subject population of at least 5,000 healthy subjects (or at least 10,000, or at least 15,000 healthy subjects) irrespective of serostatus at baseline and 4 to 16 years of age, wherein a reconstituted unit dose/tetravalent dengue virus composition as described herein or placebo is e.g. administered at least twice within less than 6 months, such as within 3 months, from first administration until 12 to 18 months (e.g. at 12 months or at 18 months) after the last administration, or from 30 days post last administration until 12 to 18 months (e.g. at 12 or at 18 months) after the last administration. In certain such embodiments, the vaccine efficacy is more than is more than 70%, is more than 75%, is more than 80%, or is more than 82%, or is more than 85%, more than 88%.

In certain embodiments, the invention is directed to said methods having a combined vaccine efficacy against virologically-confirmed dengue with hospitalization against all four serotypes with a 2-sided 95% confidence interval, wherein the lower bound is more than 25%, when measured against placebo in a subject population of at least 1,500 or at least 2,000 healthy subjects being seronegative against all serotypes at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, is more than 50%, is more than 60%, is more than 70%, or is more than 75%.

In certain embodiments, the invention is directed to said methods having a combined vaccine efficacy against all four serotypes, in preventing virologically confirmable dengue disease with hospitalization with a 2-sided 95% confidence interval, wherein the lower bound is more than 25%, when measured against placebo in a subject population of at least 5,000 healthy subjects (or at least 10,000, or at least 15,000 healthy subjects) being seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration.

In certain such embodiments, the lower bound is more than 60%, is more than 65%, is more than 66%, is more than 67%, is more than 70%, is more than 75%, is more than 77% or is more than 80%.

In certain embodiments, the invention is directed to said methods having a combined vaccine efficacy against virologically-confirmed dengue with hospitalization against all four serotypes of more than 30%, when measured against placebo in a subject population of at least 1,500 or at least 2,000 healthy subjects, healthy subjects being seronegative against all serotypes at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the combined vaccine efficacy against virologically-confirmed dengue with hospitalization against all four serotypes is more than 40%, is more than 50%, is more than 60%, is more than 70%, is more than 80%, or is more than 90%.

In certain embodiments, the invention is directed to said methods having a combined vaccine efficacy against all four serotypes, in preventing virologically confirmable dengue disease with hospitalization, when measured against placebo in a subject population of at least 5,000 healthy subjects (or at least 10,000, or at least 15,000 healthy subjects) being seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the said vaccine efficacy is more than 60%, is more than 65%, is more than 66%, is more than 67%, is more than 70%, is more than 75%, is more than 77%, is more than 80, or is more than 85%.

In certain embodiments, the invention is directed to said methods having a combined vaccine efficacy against virologically-confirmed dengue with hospitalization against all four serotypes with a 2-sided 95% confidence interval, wherein the lower bound is more than 25%, when measured against placebo in a subject population of at least 1,500 or at least 2,000 healthy subjects being seropositive at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, is more than 50%, is more than 60%, is more than 70%, or is more than 80%.

In certain embodiments, the invention is directed to said methods having a combined vaccine efficacy against all four serotypes, in preventing virologically confirmable dengue disease with hospitalization with a 2-sided 95% confidence interval, wherein the lower bound is more than 25%, when measured against placebo in a subject population of at least 5,000 healthy subjects (or at least 10,000, or at least 15,000 healthy subjects) being seropositive at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the lower bound is more than 60%, is more than 65%, is more than 70%, is more than 75%, or is more than 80%.

In certain embodiments, the invention is directed to said methods having a combined vaccine efficacy against virologically-confirmed dengue with hospitalization against all four serotypes of more than 30%, when measured against placebo in a subject population at least 1,500 or of at least 2,000 healthy subjects, healthy subjects being seropositive at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the combined vaccine efficacy against virologically-confirmed dengue with hospitalization against all four serotypes is more than 40%, is more than 50%, is more than 60%, is more than 70%, is more than 80%, or is more than 90%.

In certain embodiments, the invention is directed to said methods having a combined vaccine efficacy against all four serotypes, in preventing virologically confirmable dengue disease with hospitalization, when measured against placebo in a subject population of at least 5,000 healthy subjects (or at least 10,000, or at least 15,000 healthy subjects) being seropositive at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the vaccine efficacy is more than 75%, is more than 70%, is more than 80%, is more than 85%, or is more than 90%.

In certain embodiments, the invention is directed to said methods having a combined vaccine efficacy against all four serotypes, in preventing virologically confirmable dengue disease with hospitalization with a 2-sided 95% confidence interval, wherein the lower bound is more than 25%, when measured against placebo in a subject population of at least 5,000 healthy subjects (or at least 10,000, or at least 15,000 healthy subjects) being seropositive at baseline being or seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the difference between the lower bound provided by the seropositive subjects at baseline and the subjects seronegative against all serotypes at baseline is no more than 15%-points.

In certain embodiments, the invention is directed to said methods having a combined vaccine efficacy against all four serotypes, in preventing virologically confirmable dengue disease with hospitalization, when measured against placebo in a subject population of at least 5,000 healthy subjects (or at least 10,000, or at least 15,000 healthy subjects) being seropositive at baseline being or seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the difference between the vaccine efficacy provided by the seropositive subjects at baseline and the subjects seronegative against all serotypes at baseline is no more than 10%-points or no more than 5%-points.

In certain embodiments, the invention is directed to said methods having a relative risk, preferably a combined relative risk against all four serotypes, with a 2-sided 95% confidence interval, wherein the upper bound is less than 0.75, when measured against placebo in a subject population of at least 5,000 healthy subjects (or at least 10,000, or at least 15,000 healthy subjects) irrespective of serostatus at baseline, wherein a reconstituted unit dose/tetravalent dengue virus composition as described herein or placebo is administered at least twice within less than 6 months, such as within 3 months, 30 days after the second administration until at least 12 months after the second administration. In certain such embodiments, the upper bound is less than 0.70, less than 0.65, less than 0.60, less than 0.55, less than 0.50, less than 0.45, less than 0.40, less than 0.35, less than 0.30 or less than 0.28. Preferably said reconstituted unit dose or placebo is administered subcutaneously within about 3 month, such as on days 0 and 90.

In certain embodiments, the invention is directed to said methods having a relative risk, preferably a combined relative risk against all four serotypes, of less than 0.70, when measured against placebo in a subject population of at least 5,000 healthy subjects (or at least 10,000, or at least 15,000 healthy subjects) irrespective of serostatus at baseline, wherein a reconstituted unit dose/tetravalent dengue virus composition as described herein or placebo is administered at least twice within less than 6 months, such as within 3 months, 30 days after the second administration until at least 12 months after the second administration. In certain such embodiments, the relative risk is less than 0.65, less than 0.60, less than 0.55, less than 0.50, less than 0.45, less than 0.40, less than 0.35, less than 0.30, less than 0.25 or less than 0.23. Preferably said reconstituted unit dose or placebo is administered subcutaneously within about 3 month, such as on days 0 and 90.

In certain embodiments, the invention is directed to said methods, wherein virologically confirmable dengue disease occurs in less than 2.5% of the subjects, when measured against placebo in a subject population of at least 5,000 healthy subjects (or at least 10,000, or at least 15,000 healthy subjects) irrespective of serostatus at baseline, wherein a reconstituted unit dose/tetravalent dengue virus composition as described herein or placebo is administered at least twice within less than 6 months, such as within 3 months, 30 days after the second administration until at least 12 months or at least 18 months after the second administration. In certain such embodiments, virologically confirmable dengue disease occurs in less than 2.0% of the subjects, less than 1.5% of the subjects, less than 1.0% of the subjects, less than 0.8% of the subjects, or less than 0.6% of the subjects. Preferably said reconstituted unit dose or placebo is administered subcutaneously within about 3 month, such as on days 0 and 90.

In certain embodiments, the invention is directed to said methods having a combined vaccine efficacy against all four serotypes with a 2-sided 95% confidence interval, wherein the lower bound is more than 61.0%, or more than 65.0 or more than 70.0% or more than 72.0% when measured against placebo in a subject population of at least 5,000 healthy subjects (or at least 10,000, or at least 15,000 healthy subjects) from endemic irrespective of serostatus at baseline and being selected from the group consisting of 4 to 16 year old subjects at the time of randomization, wherein said unit dose/tetravalent dengue virus composition or said placebo is administered at least twice within 6 months or less, about 30 days after the last administration of the administration schedule until at least 12 or 13 months after the last administration of the administration schedule.

In certain embodiments, the invention is directed to said methods having a combined vaccine efficacy against all four serotypes of more than 66%, or of more than 70%, or of more than 75%, or of more than 77%, or of more than 80.0%, when measured against placebo in a subject population of at least 5,000 healthy subjects (or at least 10,000, or at least 15,000 healthy subjects) from endemic areas irrespective of serostatus at baseline and being selected from the group consisting of 4 to 16 year old subjects at the time of randomization, wherein said unit dose/tetravalent dengue virus composition or said placebo is administered at least twice within 6 months or less, about 30 days after the last administration of the administration schedule until at least 12 months or 13 month after the last administration of the administration schedule.

In certain embodiments, the invention is directed to said methods, wherein the combined vaccine efficacy against all four serotypes is measured about 30 days after the last administration of the administration schedule until 12 or 13 months after the last administration of the administration schedule.

In certain embodiments, the invention is directed to said methods, wherein said unit dose or said placebo is administered at least twice within three months, in particular at about day 1 and about day 90, and wherein the combined vaccine efficacy against all four serotypes is measured 30 days after the second administration until 12 or 13 months after the second administration of the administration schedule.

In certain embodiments, the invention is directed to said methods, wherein said methods are effective and safe. In some of these embodiments, the subject or subject population is under 9 years of age, under 4 years of age, or under 2 years of age or from 2 to 9 years of age, or from 2 to 5 years of age, or from 4 to 9 years of age or from 6 to 9 years of age. Optionally the subject is seronegative with respect to all dengue serotypes.

In certain embodiments, the invention is directed to said methods, wherein said methods having a relative risk for virologically confirmed dengue with hospitalization of 1 or less, or 0.8 or less, or 0.6 or less, when measured against placebo in a subject population of at least 5,000 healthy subjects (or at least 10,000, or at least 15,000 healthy subjects). In some of these embodiments, the subject or subject population is under 9 years of age, under 4 years of age, or under 2 years of age or from 2 to 9 years of age, or from 2 to 5 years of age, or from 4 to 9 years of age or from 6 to 9 years of age. Optionally the subject is seronegative with respect to all dengue serotypes.

In certain embodiments, the invention is directed to said methods, wherein the healthy subjects of the subject population are 4 to 16 years of age. In some of such embodiments, the healthy subjects of the subject population are 4 to 5 years of age, 6 to 11 years of age, or 12 to 16 years of age.

In certain embodiments, the invention is directed to said methods, wherein the healthy subjects of the subject population are defined as being healthy in view of the exclusion criteria specified in Example 6.

In certain embodiments, the invention is directed to said methods, wherein the healthy subjects of the subject population are from Asia Pacific or Latin America.

In certain embodiments, the invention is directed to said methods, wherein the healthy subjects of the subject population are seropositive with respect to at least one serotype. In other embodiments, the healthy subjects of the subject population are seronegative with respect to all serotypes.

In certain embodiments, the invention is directed to said methods, wherein the healthy subjects of the subject population are 4-5 years of age and from Asia Pacific, 6-11 years of age and from Asia Pacific, or 12-16 years of age and from Asia Pacific. In other embodiments, the healthy subjects of the subject population are 4-5 years of age and from Latin America, 6-11 years of age and from Latin America, or 12-16 years of age and from Latin America.

In certain embodiments, the invention is directed to said methods, wherein the healthy subjects of the subject population are 4-5 years of age and seropositive for at least 1 dengue serotype, 6-11 years of age and seropositive for at least 1 dengue serotype, or 12-16 years of age and seropositive for at least 1 dengue serotype. In other embodiments, the healthy subjects of the subject population are 4-5 years of age and seronegative for all dengue serotypes, 6-11 years of age and seronegative for all dengue serotypes, or 12-16 years of age and seronegative for all dengue serotypes.

In certain embodiments, the invention is directed to said methods, wherein the healthy subjects of the subject population are from Asia Pacific or Latin America and seropositive for at least one dengue serotype at baseline. In other embodiments, the healthy subjects of the subject population are from Asia Pacific or Latin America and seronegative for at all dengue serotype at baseline.

In certain embodiments, the invention is directed to said methods, wherein the healthy subjects of the subject population are from Asia Pacific, seropositive for at least one dengue serotype at baseline and 4-5 years of age, 6-11 years of age, or 12-16 years of age. In other embodiments, the healthy subjects of the subject population are from Asia Pacific, seronegative for all dengue serotypes at baseline and 4-5 years of age, 6-11 years of age, or 12-16 years of age. In yet other embodiments, the healthy subjects of the subject population are from Latin America, seropositive for at least one dengue serotype at baseline and 4-5 years of age, 6-11 years of age, or 12-16 years of age. In other embodiments, the healthy subjects of the subject population are from America, seronegative for all dengue serotypes at baseline and 4-5 years of age, 6-11 years of age, or 12-16 years of age.

In certain embodiments, the invention is directed to said methods, wherein the healthy subjects of the subject population had prior vaccination against Yellow Fever. In other embodiments, the healthy subjects of the subject population had no prior vaccination against Yellow Fever. Prior vaccination indicates a vaccination prior to the first vaccination with the reconstituted unit dose as described herein. For example for vaccine efficacy (VE) as determined in Example 6 from 30 days post-second vaccination, a prior vaccination of Yellow Fever is defined as a Yellow Fever vaccination occurring before 30 days post-second vaccination.

In certain embodiments, the invention is directed to said methods, wherein the healthy subjects of the subject population had prior vaccination against Japanese Encephalitis. In other embodiments, the healthy subjects of the subject population had no prior vaccination against Japanese Encephalitis.

In certain embodiments, the invention is directed to said methods, wherein the healthy subjects of the subject population received Dengvaxia® within the administration regimen as described herein or within 4.5 years after administration of the first dose. In certain embodiments, the invention is directed to said methods, wherein the occurrence of vaccine related serious adverse events is less than 0.1%.

In certain embodiments, the invention is directed to said methods, wherein the occurrence of vaccine related unsolicited adverse events occurring within 4 weeks of administration is less than 2%.

In certain embodiments, the invention is directed to said methods, wherein the occurrence of vaccine related solicited adverse events occurring within 2 weeks of administration is less than 35%.

In certain embodiments, the invention is directed to said methods, wherein the occurrence of vaccine related solicited local reactions occurring within 1 weeks of administration is less than 40%.

In certain embodiments, the invention is directed to said methods, wherein the method does not increase the risk of virologically-confirmed dengue with hospitalization in the individual, such as in a seronegative individual.

In one embodiment, the unit dose is co-administered with a vaccine selected from the group of a DTaP/IPV/Hib vaccine, in particular a combined DTaP/IPV/Hib vaccine, an MMR vaccine, a yellow fever vaccine, in particular YF-17D, an HPV vaccine, in particular a 9vHPV vaccine, a tetanus, diphtheria, and pertussis (Tdap) vaccine, in particular a combined tetanus toxoid, reduced diphtheria toxoid and acellular pertussis (adsorbed) vaccine, and a hepatitis A vaccine as described in more detail below.

Unit Dose for Use in a Method of Preventing Dengue Disease

The present invention is directed in part to the composition or unit dose of the invention as described herein for use in a method of preventing dengue disease (in particular virologically-confirmable dengue, VCD) in a subject.

The present invention is directed in part to the composition or unit dose of the invention as described herein for use in a method of preventing dengue disease (in particular virologically-confirmable dengue, VCD) in a subject population.

Inoculating against dengue disease, vaccinating against dengue disease and preventing dengue disease have the same meaning. The present invention is directed in part to a method of preventing dengue hemorrhagic fever (DHF) and dengue shock syndrome (DSS).

Any method described herein above under the heading "Method of preventing, method of inoculating" is to be understood to be also disclosed as unit dose for use in such a method of preventing dengue disease in a subject or subject population irrespective of being expressly stated below.

According to a certain aspect the composition or unit dose of the invention is a tetravalent dengue virus composition including a chimeric dengue serotype 2/1 strain and a dengue serotype 2 strain and a chimeric dengue serotype 2/3 strain and a chimeric dengue serotype 2/4 strain. According to certain such aspects the dengue serotype 2 strain is derived from the wild type virus strain DEN-2 16681 (represented by SEQ ID NO 11) and differs in at least three nucleotides from the wild type as follows:

a) 5-noncoding region (NCR)-57 (nt-57 C-to-T)

b) NS1-53 Gly-to-Asp (nt-2579 G-to-A)

C) NS3-250 Glu-to-Val (nt-5270 A-to-T); and wherein the three chimeric dengue strains are derived from the serotype 2 strain by replacing the structural proteins prM and E from serotype 2 strain with the corresponding structural proteins from the other dengue serotypes, resulting in the following chimeric dengue strains:

a DENV-2/1 chimera, a DENV-2/3 chimera and a DENV-2/4 chimera.

Further information regarding the serotypes of the tetravalent composition can be derived from section "Dengue virus strains" above.

The tetravalent dengue virus composition for such use may be in the form of a unit dose comprising:

(i) a dengue serotype 1 in a concentration of at least 3.3 log 10 pfu/0.5 ml, (ii) a dengue serotype 2, in a concentration of at least 2.7 log 10 pfu/0.5 ml, (iii) a dengue serotype 3, in a concentration of at least 4.0 log 10 pfu/0.5 ml, and (iv) a dengue serotype 4, in a concentration of at least 4.5 log 10 pfu/0.5 ml.

The tetravalent dengue virus composition for such use may also be in the form of a lyophilized unit dose which upon reconstitution with 0.5 mL of a pharmaceutically acceptable diluent comprises:

(i) a dengue serotype 1 in a concentration of at least 3.3 log 10 pfu/0.5 ml, (ii) a dengue serotype 2, in a concentration of at least 2.7 log 10 pfu/0.5 ml, (iii) a dengue serotype 3, in a concentration of at least 4.0 log 10 pfu/0.5 ml, and (iv) a dengue serotype 4, in a concentration of at least 4.5 log 10 pfu/0.5 ml.

In the tetravalent dengue virus composition for such use according to one embodiment upon reconstitution with a pharmaceutically acceptable diluent (i), (ii), (iii), and (iv) provide a total concentration of pfu/0.5 mL and based on said total concentration the concentration of (ii) in pfu/0.5 mL is preferably less than 10%, and the concentration of (iv) in pfu/0.5 mL is preferably at least 50%, and the concentration of (i) in pfu/0.5 mL is preferably at least 1%, and the concentration of (iii) in pfu/0.5 mL is preferably at least 8%, or more preferred at least 10%, or at least 12%, or at least 14%, or at least 16%, or at least 18% and wherein the subject is preferably 2 to 17 years of age or 4 to 16 years of age.

In the tetravalent dengue virus composition for such use according to one embodiment upon reconstitution with a pharmaceutically acceptable diluent (i), (ii), (iii), and (iv) provide a total concentration of pfu/0.5 mL and based on said total concentration the concentration of (ii) in pfu/0.5 mL is preferably less than 2%, the concentration of (iv) in pfu/0.5 mL is preferably at least 50%, the concentration of (i) in pfu/0.5 mL is at preferably least 1%, and the concentration of (iii) in pfu/0.5 mL is preferably at least 6% and wherein the subject preferably is 18 to 60 years of age.

Further information regarding the tetravalent composition or the unit dose can be derived from section "Dengue vaccine composition" and "Unit dose" above.

According to one embodiment the unit dose for such use is directed to a method comprising a primary vaccination with only two administrations of the unit dose comprising the steps of:

(A) administering a first unit dose of the tetravalent dengue virus composition to the subject, and (B) administering a second unit does of the tetravalent dengue virus composition to the subject within 3 months of administration of the first unit dose.

According to this embodiment the administration of only two doses within 3 months is sufficient to provide effective protection against a subsequent dengue infection.

Such method preferably provides a combined vaccine efficacy against all four serotypes in preventing virologically confirmable dengue disease with a 2-sided 95% confidence interval, wherein the lower bound is more than 60%, when measured against placebo in a subject population of at least 5,000 healthy subjects irrespective of serostatus at baseline and 14 to 16 years of age, from the first administration of the administration schedule until 18 months after the second administration of the administration schedule.

Such method also preferably provides a combined vaccine efficacy against all four serotypes, in preventing virologically confirmable dengue disease with a 2-sided 95% confidence interval, wherein the lower bound is more than 45%, when measured against placebo in a subject population of at least 1,500 or at least 2,000 healthy subjects seronegative against all serotypes at baseline and 14 to 16 years of age, from 30 days after the second administration of the administration schedule until 18 months after the second administration of the administration schedule.

According to certain embodiments the use is for a method of inoculation against the virologically confirmable dengue disease is due to a dengue serotype 2, and/or due to a dengue serotype 1. The method has very high efficacy against dengue serotype 2 and dengue serotype 1 and the highest efficacy against dengue serotype 2.

In certain embodiments, the invention is directed to said methods having a vaccine efficacy against serotype 1, in preventing virologically confirmable dengue disease with a 2-sided 95% confidence interval, wherein the lower bound is more than 25%, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the lower bound is more than 30%, is more than 35% is more than 40%, is more than 45%, is more than 50%, or is more than 54%. In certain such embodiments the subject population of at least 1,500 is seronegative against all serotypes at base line and the lower bound is more than 35%. In certain such embodiments the seronegative and seropositive population each provide a vaccine efficacy against serotype 1 with a 2-sided 95% confidence interval, wherein the lower bounds are within 10%-points.

In certain embodiments, the invention is directed to said methods having a vaccine efficacy against serotype 1, in preventing virologically confirmable dengue disease, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the vaccine efficacy is more than 40%, is more than 50%, is more than 60%, or is more than 65%. In certain such embodiments the subject population of at least 1,500 is seronegative against all serotypes at base line. In certain such embodiments the seronegative and seropositive population each provide a vaccine efficacy against serotype 1 which are within 5%-points.

In certain embodiments, the invention is directed to said methods having a vaccine efficacy against serotype 2, in preventing virologically confirmable dengue disease with a 2-sided 95% confidence interval, wherein the lower bound is more than 25%, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the lower bound is more than 50%, is more than 60%, is more than 70%, is more than 80%, or is more than 85%. In certain such embodiments the subject population of at least 1,500, is seronegative against all serotypes. In certain such embodiments the seronegative and seropositive population each provide a vaccine efficacy against serotype 2 with a 2-sided 95% confidence interval, wherein the lower bounds are within 5%-points.

In certain embodiments, the invention is directed to said methods having a vaccine efficacy against serotype 2, in preventing virologically confirmable dengue disease, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the vaccine efficacy is more than 60%, is more than 70%, is more than 80%, or is more than 90%. In certain such embodiments the subject population of at least 1,500 is seronegative against all serotypes at base line. In certain such embodiments the seronegative and seropositive population each provide a vaccine efficacy against serotype 2 which are within 5%-points.

The efficacy of the method is further described in more detail in the section "method of preventing, method of inoculating".

In certain embodiments the unit dose is reconstituted and administered by subcutaneous injection. According to some of these embodiments, the subcutaneous injection is administered to the arm, preferably to the deltoid region of the arm.

According to one embodiment such a method does not include a step of determination of a previous dengue infection in the subjects preferably at any time before, during or after the steps of administration or wherein the serostatus of the subject is unknown preferably at any time before, during or after the steps of administration.

The method according to the invention does not require the testing of the serostatus before vaccination and thus allows immediate treatment and outbreak control. According to certain embodiments the use is for a method wherein the subject is exposed to a dengue outbreak. In certain such embodiments the outbreak is due to a dengue serotype 2, and/or due to a serotype 1.

According to one embodiment such a method the subject is from a region wherein the seroprevalence rate is unknown and/or wherein the seroprevalence rate is below 80%, or below 70%, or below 60%.

According to one embodiment of such a method the subject is seronegative at baseline and is from a region or travels to a region wherein the seroprevalence rate is high with respect to serotype 1 and/or serotype 2 i.e. 80%, or 90% or above.

According this embodiment the vaccine and corresponding method is safe for seronegative and seropositive subjects and thus does not require an analysis of the serostatus or a determination of a previous dengue infection or a high seroprevalence rate in the region. Such a method preferably provides a combined vaccine efficacy against virologically-confirmed dengue with hospitalization against all four serotypes with a 2-sided 95% confidence interval, wherein the lower bound is more than 65%, when measured against placebo in a subject population of at least 5,000 healthy 4 to 16 year old subjects irrespective of serostatus at baseline, preferably in at least 1,500 healthy 4 to 16 year old subjects seronegative at baseline, from first administration of the administration schedule until 12 to 18 months after the second administration of the administration schedule. Preferably, the 2-sided 95% confidence interval of the combined vaccine efficacy against virologically-confirmed dengue with hospitalization against all four serotypes when comparing seropositive and seronegative subjects provides for lower bounds of the 2-sided confidence interval which are within 10% points or within 15% points or within 20% points. The method is preferably safe with respect to serotype 1 and serotype 2 which may therefore be used in outbreak situations due to serotype 1 and/or serotype 2 or even for seronegative subjects (e.g. travelers) or subjects with unknown serostatus in regions with very high seroprevalence rates (>80%) due to serotype 1 and/or serotype 2.

The safety of the method is further described in more detail in the section "method of preventing, method of inoculating".

According to one embodiment such a method does not include the active surveillance with respect to febrile illness of the subject after the administration of the first- and second-unit dose. During active surveillance any subject with febrile illness (defined as fever 38° C. on any 2 of 3 consecutive days) will be asked to return to the site for dengue fever evaluation by the Investigator. Subjects/guardians will be contacted at least weekly to ensure robust identification of febrile illness by reminding subjects/guardians of their obligation to return to the site in case of febrile illness. This contact will be implemented through appropriate methods that may differ in each trial site (eg, phone calls, text messaging, home visits, school-based surveillance).

According to one embodiment such a method does not include vaccine immunogenicity analysis including GMTs for dengue neutralizing antibodies.

According to one embodiment such a method does not include a reactogenicity analysis. Such a reactogenicity analysis relates to solicited local AEs (injection site pain, injection site erythema, and injection site swelling) and solicited systemic AEs (child <6 years: fever, irritability/fussiness, drowsiness and loss of appetite; child 6 years: asthenia, fever, headache, malaise and myalgia) which will e.g. be assessed for 7 days and 14 days, respectively, following each vaccination (vaccination day included) via collection of diary cards.

According to one embodiment the method does not include an active surveillance, an immunogenicity analysis and a reactogenicity analysis.

According to such embodiments the vaccine and the corresponding method of inoculation are safe and therefore do not require further steps of surveillance or analysis.

In view of the above the method according to one embodiment comprises a primary vaccination consisting of the steps of:

(A) selecting a subject for administration of the unit doses of the tetravalent dengue virus composition in need for protection against dengue infection without determination of a previous dengue infection, and (B) administering a first unit dose of the tetravalent dengue virus composition to the subject, and (C) administering a second unit dose of the tetravalent dengue virus composition to the subject within 3 months of administration of the first unit dose.

Therefore the method of inoculating is finalized without determination of a previous dengue infection. The method however further optionally comprises at least 1 years after the administration of the second unit dose a booster dose of the unit dose.

Selecting the subject may include all types of considerations but preferably not the determination of a previous dengue infection. The selection may include consideration of the age, health conditions, and threat of infection. The threat of infection includes consideration of the seroprevalence rate in the region in which the subject normally lives or intends to travel, the serotype specific seroprevalence rate and an outbreak situation or serotype specific outbreak situations. The subject may be selected due to its exposure to serotype 1 and/or serotype 2 or due to the fact it requires protection against a specific dengue serotype, i.e. serotype 1 and/or serotype 2.

According to the invention the method is applicable to subjects of all kinds of ages. According to one embodiment the subject is under 9 years of age, or 4 to 5 years of age, or 6 to 11 years of age or 12 to 16 years, or 6 to 16 years of age or 4 to 16 years of age, or 2 to 17 years of age, or 9 years of age, or over 9 years of age, or 9 to 17 years of age, or 18 to 45 years of age, or 46 to 60 years of age, or over 60 years of age.

According to certain such embodiments the unit dose of the tetravalent dengue virus composition comprising (i), (ii), (iii), and (iv) upon reconstitution with a pharmaceutically acceptable diluent provides a total concentration of pfu/0.5 mL of (i), (ii), (iii), and (iv) and based on said total concentration the concentration of (ii) in pfu/0.5 mL is preferably less than 10%, and the concentration of (iv) in pfu/0.5 mL is preferably at least 50%, and the concentration of (i) in pfu/0.5 mL is preferably at least 1%, and the concentration of (iii) in pfu/0.5 mL is preferably at least 8%, or more preferred at least 10%, or at least 12%, or at least 14%, or at least 16%, or at least 18% and the subject is 2 to 17 years of age or 4 to 16 years of age.

According to certain such embodiments the unit dose of the tetravalent dengue virus composition comprising (i), (ii), (iii), and (iv) upon reconstitution with a pharmaceutically acceptable diluent provides a total concentration of pfu/0.5 mL of (i), (ii), (iii), and (iv) and based on said total concentration the concentration of (ii) in pfu/0.5 mL is preferably less than 2%, the concentration of (iv) in pfu/0.5 mL is preferably at least 50%, the concentration of (i) in pfu/0.5 mL is at preferably least 1%, and the concentration of (iii) in pfu/0.5 mL is preferably at least 6% and the subject is 18 to 60 years of age.

Further specific embodiments are described below.

The present invention is directed in part to a reconstituted unit dose of a dengue vaccine composition as described herein for use in a method of preventing virologically confirmable dengue disease in a subject comprising administering at least a first unit dose of the dengue vaccine composition to the subject, wherein the dengue vaccine composition is a tetravalent dengue virus composition including four dengue virus strains representing dengue serotype 1, dengue serotype 2, dengue serotype 3 and dengue serotype 4, optionally wherein the dengue virus strains are live, attenuated dengue virus strains and/or comprise chimeric dengue viruses and/or at least one non-chimeric dengue virus, and wherein upon reconstitution with 0.5 mL of a pharmaceutically acceptable diluent (i) dengue serotype 1 has a concentration of at least 3.3 log 10 pfu/0.5 mL and optionally to 5.0 log 10 pfu/0.5 mL, (ii) dengue serotype 2 has a concentration of at least 2.7 log 10 pfu/0.5 mL and optionally to 4.9 log 10 pfu/0.5 mL, (iii) dengue serotype 3 has a concentration of at least 4.0 log 10 pfu/0.5 mL and optionally to 5.7 log 10 pfu/0.5 mL, and (iv) dengue serotype 4 has a concentration of at least 4.5 log 10 pfu/0.5 mL and optionally to 6.2 log 10 pfu/0.5 mL.

The present invention is directed in part to a reconstituted unit dose of a dengue vaccine composition as described herein for use in a method of preventing virologically confirmable dengue disease in a subject comprising consecutively administering at least a first and a second unit dose of the dengue vaccine composition to the subject, wherein said first and second unit dose are administered subcutaneously within 3 months and at least 4 weeks apart, optionally at about day 1 and at about day 90, wherein the dengue vaccine composition is a tetravalent dengue virus composition including four dengue virus strains representing dengue serotype 1, dengue serotype 2, dengue serotype 3 and dengue serotype 4, optionally wherein the dengue virus strains are live, attenuated, and wherein upon reconstitution with 0.5 mL of a pharmaceutically acceptable diluent (v) dengue serotype 1 has a concentration of at least 3.3 log 10 pfu/0.5 mL and optionally to 5.0 log 10 pfu/0.5 mL, (vi) dengue serotype 2 has a concentration of at least 2.7 log 10 pfu/0.5 mL and optionally to 4.9 log 10 pfu/0.5 mL, (vii) dengue serotype 3 has a concentration of at least 4.0 log 10 pfu/0.5 mL and optionally to 5.7 log 10 pfu/0.5 mL, and (viii) dengue serotype 4 has a concentration of at least 4.5 log 10 pfu/0.5 mL and optionally to 6.2 log 10 pfu/0.5 mL.

In certain embodiments, the invention is directed to a reconstituted unit dose of a dengue vaccine composition for use in a method of preventing virologically confirmable dengue disease in a subject comprising consecutively administering at least a first and a second unit dose of the dengue vaccine composition to the subject, wherein said first and second unit dose are administered subcutaneously within 3 months and at least 4 weeks apart, optionally at about day 1 and at about day 90, wherein the dengue vaccine composition is a tetravalent dengue virus composition including four dengue virus strains representing dengue serotype 1, dengue serotype 2, dengue serotype 3 and dengue serotype 4, optionally wherein the dengue virus strains are live, attenuated, wherein the subject is under 9 years of age and/or when the serostatus of the subject is unknown or seronegative and wherein upon reconstitution with 0.5 mL of a pharmaceutically acceptable diluent (i) dengue serotype 1 has a concentration of at least 3.3 log 10 pfu/0.5 mL and optionally to 5.0 log 10 pfu/0.5 mL, (ii) dengue serotype 2 has a concentration of at least 2.7 log 10 pfu/0.5 mL and optionally to 4.9 log 10 pfu/0.5 mL, (iii) dengue serotype 3 has a concentration of at least 4.0 log 10 pfu/0.5 mL and optionally to 5.7 log 10 pfu/0.5 mL, and (iv) dengue serotype 4 has a concentration of at least 4.5 log 10 pfu/0.5 mL and optionally to 6.2 log 10 pfu/0.5 mL.

In certain embodiments, the reconstituted unit dose is administered to a subject of unknown serostatus and/or wherein no test has been carried out to determine whether the subject is seropositive or seronegative before the unit dose as described herein is administered.

In certain embodiments, the subject is under 9 years of age and/or the serostatus of the subject is unknown or seronegative. In certain such embodiments, the subject is under 9 years of age and the serostatus of the subject is unknown or seronegative, preferably seronegative.

In certain embodiments, the method is safe. In certain such embodiments, the subject is under 9 years of age or from 4 years of age and/or the serostatus of the subject is unknown or seronegative. In certain such embodiments, the subject is from 4 years of age and the serostatus of the subject is unknown or seronegative, preferably seronegative.

In certain embodiments, the method is effective. In certain such embodiments, the subject is under 9 years of age and/or the serostatus of the subject is unknown or seronegative. In certain such embodiments, the subject is under 9 years of age and the serostatus of the subject is unknown or seronegative, preferably seronegative.

In certain embodiments, the dengue serotype 1 and the dengue serotype 2 are present each in a concentration based on the total concentration in pfu/0.5 mL which is within 5%-points of each other and/or are together less than about 10% of the total concentration in pfu/0.5 mL. In certain such embodiments, the dengue serotype 3 is at least about 10% of the total concentration in pfu/0.5 mL and/or the dengue serotype 4 is at least about 70% of the total concentration in pfu/0.5 mL.

In certain embodiments, the dengue serotype 4 represents the highest concentration in the composition of all four serotypes, preferably with at least about 70% of the total concentration in pfu/0.5 mL, dengue serotype 3 represents the second highest concentration in the composition of all four serotypes, preferably with at least about 10% of the total concentration in pfu/0.5 mL, and dengue serotype 1 and dengue serotype 2 each represent lower concentrations than the concentration of serotype 3, and optionally together represent less than about 10% of the total concentration in pfu/0.5 mL.

In certain embodiments, the composition includes at least one chimeric dengue virus. In certain such embodiments, the composition includes at least one non-chimeric dengue virus and at least one chimeric dengue virus.

In certain embodiments, the subject is seronegative to all dengue serotypes at baseline and/or is from 4 years of age, optionally to 60 years of age. In certain such embodiments, the subject is 4 to 16 years of age, under 9 years of age, from 2 years of age to under 9 years of age, from 4 years of age to under 9 years of age, 4 to 5 years of age, 6 to 11 years of age, or 12 to 16 years of age. In other embodiments, the subject is seropositive to at least one dengue serotypes at baseline and/or is from 4 years of age, optionally to 60 years of age. In certain such embodiments, the subject is 4 to 16 years of age, under 9 years of age, from 2 years of age to under 9 years of age, from 4 years of age to under 9 years of age, 4 to 5 years of age, 6 to 11 years of age, or 12 to 16 years of age.

In certain embodiments, the method does not comprise a determination of a previous dengue infection in the subject before the administration of the first unit dose of the tetravalent dengue virus composition. Thus, in certain embodiments, the subject has not been tested for the presence a previous dengue infection.

In certain embodiments, the dengue serotype 1 is a chimeric dengue serotype 2/1 strain, the dengue serotype 2 is a non-chimeric dengue serotype 2 strain, the dengue serotype 3 is a chimeric dengue serotype 2/3 strain and the dengue serotype 4 is a chimeric dengue serotype 2/4 strain and the dengue serotype 1 has the amino acid sequence of SEQ ID NO. 2, the dengue serotype 2 has the amino acid sequence of SEQ ID NO. 4, the dengue serotype 3 has the amino acid sequence of SEQ ID NO. 6, and the dengue serotype 4 has the amino acid sequence of SEQ ID NO. 8.

In certain embodiments, the unit dose further comprises from about 10% w/v to about 20% w/v α,α-trehalose dihydrate or an equimolar amount of other forms of α,α-trehalose, from about 0.5% w/v to about 1.5% w/v poloxamer 407, from about 0.05% w/v to about 2% w/v human serum albumin, and from about 70 mM to 140 mM sodium chloride when measured in 0.5 mL. In certain such embodiments, the unit dose comprises about 15% (w/v) α,α-trehalose dihydrate, about 1% (w/v) poloxamer 407, about 0.1% (w/v) human serum albumin, and about 100 mM sodium chloride when measured in 0.5 mL.

In certain embodiments, the method is for preventing dengue hemorrhagic fever (DHF) or dengue shock syndrome (DSS).

In certain embodiments, the subject is from a dengue endemic region. In other embodiments, the subject is from a dengue non-endemic region.

In certain embodiments, the subject is from Asia Pacific or Latin America.

In certain embodiments, the reconstituted unit dose provides a seropositivity rate when it is administered to a subject population of at least 50 subjects in two unit doses subcutaneously at day 1 and at day 90, wherein the subjects of the subject population are seronegative to all dengue serotypes at baseline. In certain such embodiments, at least 80% of the subject population are seropositive for all four dengue serotypes at least one month after administration of the first unit dose, such as at day 30, and/or at least 80% of the subject population are seropositive for all four dengue serotypes before or at the time of the administration of the second unit dose, such as at day 90, and/or at least 80%, or at least 85% or at least 90%, or at least 95% of the subject population are seropositive for all four dengue serotypes after the administration of the second unit dose, such as at day 120, and/or at least 80%, or at least 85%, or at least 90% of the subject population are seropositive for all four dengue serotypes after the administration of the second unit dose, such as at day 270. In certain such embodiments, at least 80% of the subject population are seropositive for all four dengue serotypes at least one month after administration of the first unit dose, such as at day 30, and before or at the time of the administration of the second unit dose, such as at day 90, and after the administration of the second unit dose, such as at day 120 and at day 270.

In certain embodiments, the reconstituted unit dose provides a seropositivity rate, when it is administered to a subject population of at least 100 subjects in two unit doses subcutaneously at day 1 and at day 90, wherein the subjects of the subject population comprises from 20% to 40% subjects who are seronegative to all dengue serotypes and from 60% to 80% subjects who are seropositive to at least one dengue serotype at base line, wherein at day 120 and/or day 270 the seropositivity rate for all four dengue serotypes in the seronegative part of the subject population and the seropositivity rate for all four dengue serotypes in the seropositive part of the subject population do not deviate more than 10%-points and/or wherein at day 120 the seropositivity rate for all four dengue serotypes in the seronegative part of the subject population and the seropositivity rate for all four dengue serotypes in the seropositive part of the subject population do not deviate more than 5%-points.

In certain particular embodiments, the invention is directed to a dengue vaccine composition as described herein for use in a method of preventing virologically confirmable dengue disease in a subject comprising consecutively administering at least a first and a second unit dose of the dengue vaccine composition to the subject, wherein said first and second unit dose are administered subcutaneously within 3 months and at least 4 weeks apart, optionally at about day 1 and at about day 90, and wherein the dengue vaccine composition is a tetravalent dengue virus composition including four live, attenuated dengue virus strains representing dengue serotype 1, dengue serotype 2, dengue serotype 3 and dengue serotype 4, wherein the attenuated dengue virus strains comprise chimeric dengue viruses and at least one non-chimeric dengue virus, and wherein the dengue serotype 1 and the dengue serotype 2 are present each in a concentration based on the total concentration in pfu/0.5 mL which is within 5%-points of each other and/or are together less than about 10% of the total concentration in pfu/0.5 mL.

In certain embodiments, the method does not comprise a determination of a previous dengue infection of the subject before the administration of the first unit dose of the tetravalent dengue virus composition and wherein the method is safe and effective. Thus, in certain embodiments, the subject has not been tested for the presence a previous dengue infection.

In certain embodiments, the dengue serotype 3 is at least about 10% of the total concentration in pfu/0.5 mL and/or the dengue serotype 4 is at least about 70% of the total concentration in pfu/0.5 mL.

In certain embodiments, the dengue serotype 4 represents the highest concentration in the composition of all four serotypes, preferably with at least about 70% of the total concentration in pfu/0.5 mL, dengue serotype 3 represents the second highest concentration in the composition of all four serotypes, preferably with at least about 10% of the total concentration in pfu/0.5 mL, and dengue serotype 1 and dengue serotype 2 each represent lower concentrations than the concentration of serotype 3, and optionally together represent less than about 10% of the total concentration in pfu/0.5 mL.

In certain embodiments, the dengue serotype 1 is a chimeric dengue serotype 2/1 strain, the dengue serotype 2 is a non-chimeric dengue serotype 2 strain, the dengue serotype 3 is a chimeric dengue serotype 2/3 strain and the dengue serotype 4 is a chimeric dengue serotype 2/4 strain and the dengue serotype 1 has the amino acid sequence of SEQ ID NO. 2, the dengue serotype 2 has the amino acid sequence of SEQ ID NO. 4, the dengue serotype 3 has the amino acid sequence of SEQ ID NO. 6, and the dengue serotype 4 has the amino acid sequence of SEQ ID NO. 8.

In certain embodiments, in the unit dose upon reconstitution with 0.5 mL of a pharmaceutically acceptable diluent (i) dengue serotype 1 has a concentration of 3.3 log 10 pfu/0.5 mL to 5.0 log 10 pfu/0.5 mL, (ii) dengue serotype 2 has a concentration of 2.7 log 10 pfu/0.5 mL to 4.9 log 10 pfu/0.5 mL, (iii) dengue serotype 3 has a concentration of 4.0 log 10 pfu/0.5 mL to 5.7 log 10 pfu/0.5 mL, and (iv) dengue serotype 4 has a concentration of 4.5 log 10 pfu/0.5 mL to 6.2 log 10 pfu/0.5 mL, and optionally the composition further comprises about 15% (w/v) α,α-trehalose dihydrate, about 1% (w/v) poloxamer 407, about 0.1% (w/v) human serum albumin, and about 100 mM sodium chloride when measured in 0.5 mL.

In certain embodiments, the unit doses are administered to the deltoid region of the arm.

In certain embodiments, the composition is administered without determining the serostatus of the subject at baseline and wherein the administration is safe and effective regardless of the serostatus at base line.

In certain embodiments, the subject is seronegative to all dengue serotypes at baseline and/or is from 4 years of age, optionally to 60 years of age. In certain such embodiments, the subject is 4 to 16 years of age, under 9 years of age, from 2 years of age to under 9 years of age, from 4 years of age to under 9 years of age, 4 to 5 years of age, 6 to 11 years of age, or 12 to 16 years of age. In particular the subject may be under 9 years of age and seronegative to all four dengue serotypes at baseline. In other embodiments, the subject is seropositive to at least one dengue serotypes at baseline and/or is from 4 years of age, optionally to 60 years of age. In certain such embodiments, the subject is 4 to 16 years of age, under 9 years of age, from 2 years of age to under 9 years of age, from 4 years of age to under 9 years of age, 4 to 5 years of age, 6 to 11 years of age, or 12 to 16 years of age. In particular the subject may be under 9 years of age and seropositive to at least one dengue serotypes at baseline. In certain preferred embodiments, the subject is 4 to 5 years of age, 6 to 11 years of age or 12 to 16 years of age.

In certain embodiments, the method is for preventing dengue hemorrhagic fever (DHF) or dengue shock syndrome (DSS).

In certain embodiments, the subject is from a dengue endemic region or from a dengue non-endemic region.

In certain embodiments, the subject is from Asia Pacific or Latin America.

In certain embodiments, the composition provides a seropositivity rate when it is administered to a subject population of at least 50 subjects in two unit doses subcutaneously at day 1 and at day 90, wherein the subjects of the subject population are seronegative to all dengue serotypes at baseline, in particular wherein at least one month after administration of the first unit dose, such as at day 30, at least 80% of the subject population are seropositive for all four dengue serotypes, and/or at least 80% of the subject population are seropositive for all four dengue serotypes before or at the time of the administration of the second unit dose, such as at day 90, and/or at least 80%, or at least 85% or at least 90%, or at least 95% of the subject population are seropositive for all four dengue serotypes after the administration of the second unit dose, such as at day 120, and/or at least 80%, or at least 85%, or at least 90% of the subject population are seropositive for all four dengue serotypes after the administration of the second unit dose, such as at day 270.

In certain embodiments, the composition provides a seropositivity rate, when it is administered to a subject population of at least 100 subjects in two unit doses subcutaneously at day 1 and at day 90, wherein the subjects of the subject population comprises from 20% to 40% subjects who are seronegative to all dengue serotypes and from 60% to 80% subjects who are seropositive to at least one dengue serotype at base line, wherein at day 120 and/or day 270 the seropositivity rate for all four dengue serotypes in the seronegative part of the subject population and the seropositivity rate for all four dengue serotypes in the seropositive part of the subject population do not deviate more than 10%-points and/or wherein at day 120 the seropositivity rate for all four dengue serotypes in the seronegative part of the subject population and the seropositivity rate for all four dengue serotypes in the seropositive part of the subject population do not deviate more than 5%-points.

The present invention is in part directed to the unit dose of the invention as described herein for use in a method of preventing dengue disease (in particular virologically confirmable dengue, VCD) in a subject population comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the unit dose of the invention as described herein for use in a method of preventing dengue disease (in particular virologically confirmable dengue, VCD) in a subject comprising administering to the subject at least a first reconstituted unit dose of the invention as described herein, wherein certain ratios of neutralizing antibody titers at day 180 or 365 after administration of said first unit dose to the subject are achieved. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2: neutralizing antibody titer for GMT DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

The geometric mean neutralizing antibody titers (GMTs) of a subject population or the neutralizing antibody titers of a subject are determined in accordance with the microneutralization test disclosed herein, for example according to the method described in Example 2.

In certain embodiments the invention is directed to the reconstituted unit dose of the invention as described herein for said uses, wherein said unit dose is administered by subcutaneous injection. According to some of these embodiments the subcutaneous injection is administered to the arm, preferably to the deltoid region of the arm.

In certain embodiments the invention is directed to a reconstituted unit dose of the invention as described herein for said uses, wherein the subject or subject population is seronegative to all dengue serotypes.

In certain embodiments the invention is directed to a reconstituted unit dose of the invention as described herein for said uses, wherein a single unit dose of the invention as described herein is administered.

In certain embodiments the invention is directed to a reconstituted unit dose of the invention as described herein for said uses, wherein two reconstituted unit doses of the invention as described herein are administered. In some embodiments, the two reconstituted unit doses are administered within 12 months or more, or within six months, or within three months, such as at day 0 and day 90 or at day 1 and day 90. According to some of these embodiments, a third reconstituted unit dose of the invention as described herein may be administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to a reconstituted unit dose of the invention as described herein for said uses, wherein the reconstituted unit dose of the invention as described herein is administered at most in two doses or in one dose.

In certain embodiments of the invention the subject is seronegative with respect to all dengue serotypes. In certain embodiments of the invention the subject is seronegative with respect to all dengue serotypes and the reconstituted unit dose is administered to the seronegative subject by subcutaneous injection.

In certain other embodiments of the invention the subject is seropositive with respect to at least one dengue serotype.

In certain embodiments the invention is directed to the reconstituted unit dose of the invention as described herein for said uses, wherein the reconstituted unit dose of the invention as described herein is administered to a subject or subject population from a dengue endemic region. In some of these embodiments, the subject or subject population is from Singapore, Dominican Republic, Panama, Philippines, Colombia, Puerto Rico or Thailand, in particular from Singapore, Dominican Republic, Panama, or Philippines. In other embodiments, the subject or subject population is from a dengue non-endemic region. Such a subject population or such a subject may be vaccinated according to the invention in the context of traveling to a dengue-endemic region. In certain embodiments, the reconstituted unit dose of the invention as described herein is administered subcutaneously to a subject or subject population from a dengue endemic region or from a dengue non-endemic region.

In some embodiments the invention is directed to the unit dose of the invention as described herein for said uses, wherein the subject or subject population is of 2 to 60 years of age, or more than 17 years, or more than 18 years, or 18 to 60 years of age. In certain embodiments, the subject or subject population is of 1 to 17 years of age, or less than 9 years of age, or less than 4 years of age or less than 2 years of age. In further specific embodiments, the subjects or subject population are adults of more than 21 years, or 21 to 60 years, or 21 to 45 years of age. According to some of these embodiments the subject or subject population is seronegative and from a dengue-endemic region.

In certain embodiments, the invention is directed to the reconstituted unit dose of the invention as described herein for said uses, wherein the unit dose of the invention as described herein is administered to a pediatric subject or pediatric subject population of less than 2 years of age, preferably of 2 months to 2 years of age or 2 months to 1.5 years of age or 2 months to 1 year of age. According to some of these embodiments, the pediatric subject or pediatric subject population is seronegative and from a dengue endemic region.

In certain embodiments, the invention is directed to the reconstituted unit dose of the invention as described herein for said uses, wherein the reconstituted unit dose is administered subcutaneously to a pediatric subject or pediatric subject population of less than 2 years of age, preferably of 2 months to 2 years of age or 2 months to 1.5 years of age or 2 months to 1 year of age. According to some of these embodiments, the pediatric subject or pediatric subject population is seronegative and from a dengue endemic region.

The unit dose for use in the methods described above may be any unit dose of a dengue vaccine composition as described above under the headings “Unit dose” or “Dengue vaccine composition” and comprise any dengue virus strain as described above under the heading “Dengue virus strain”.

The present invention is directed in part to the unit dose of the invention as described herein for use in a method of preventing dengue hemorrhagic fever (DHF) and dengue shock syndrome (DSS) in an elderly subject.

In certain embodiments the invention is directed to a reconstituted unit dose of the invention as described herein for said uses, wherein the elderly subject is seronegative to all dengue serotypes.

In certain embodiments the invention is directed to a reconstituted unit dose of the invention as described herein for said uses, wherein the elderly subject is seronegative to all dengue serotypes.

In certain embodiments the invention is directed to a reconstituted unit dose of the invention as described herein for said uses, wherein two reconstituted unit doses of the invention as described herein are administered. In some embodiments, the two reconstituted unit doses are administered within 12 months or more, or within six months, or within three months, such as at day 0/1 and day 90. According to some of these embodiments, a third reconstituted unit dose of the invention as described herein may be administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments of the invention the elderly subject is seronegative with respect to all dengue serotypes. In certain embodiments of the invention the elderly subject is seronegative with respect to all dengue serotypes and the reconstituted unit dose is administered to the seronegative subject by subcutaneous injection.

In certain other embodiments of the invention the elderly subject is seropositive with respect to at least one dengue serotype.

In certain embodiments the invention is directed to the reconstituted unit dose of the invention as described herein for said uses, wherein the reconstituted unit dose of the invention as described herein is administered to an elderly subject from a dengue endemic region. In some of these embodiments, the elderly subject is from Singapore, Dominican Republic, Panama, Philippines, Colombia, Puerto Rico or Thailand, in particular from Singapore, Dominican Republic, Panama, or Philippines. In other embodiments, the elderly subject is from a dengue non-endemic region. Such an elderly subject may be vaccinated according to the invention in the context of traveling to a dengue-endemic region. In certain embodiments, the reconstituted unit dose of the invention as described herein is administered subcutaneously to an elderly subject from a dengue endemic region or from a dengue non-endemic region.

In certain embodiments, the invention is directed to the reconstituted unit dose of the invention as described herein for said uses, wherein the elderly subject has at least one chronic condition or disease. The at least one chronic condition or disease may be selected from diabetes, hypertension, allergies, previous strokes, ischemic heart disease, chronic renal impairment and chronic obstructive pulmonary disease.

In certain embodiments, the invention is directed to the reconstituted unit dose of the invention as described herein for said uses, wherein the elderly subject has an impaired immune system.

Use for the Manufacture of a Medicament for Preventing Dengue Disease

The present invention is directed in part to the use of a unit dose of the invention as described herein for the manufacture of a medicament for preventing dengue disease (in particular virologically confirmable dengue, VCD) in a subject.

The present invention is directed in part to the use of a unit dose of the invention as described herein for the manufacture of a medicament for preventing dengue disease (in particular virologically confirmable dengue, VCD) in a subject population.

The present invention is therefore directed to the use of a tetravalent dengue virus composition including four live attenuated dengue virus strains representing serotype 1, serotype 2, serotype 3 and serotype 4 in the manufacture of a medicament for the method of inoculating a subject against virologically confirmable dengue disease, wherein in particular the tetravalent dengue virus composition includes a chimeric dengue serotype 2/1 strain and a dengue serotype 2 strain and a chimeric dengue serotype 2/3 strain and a chimeric dengue serotype 2/4 strain, wherein in particular the dengue serotype 2 strain is derived from the wild type virus strain DEN-2 16681 (SEQ ID NO 11) and differs in at least three nucleotides from the wild type as follows:

d) 5-noncoding region (NCR)-57 (nt-57 C-to-T): major attenuation locus
e) NS1-53 Gly-to-Asp (nt-2579 G-to-A): major attenuation locus
f) NS3-250 Glu-to-Val (nt-5270 A-to-T): major attenuation locus; and wherein the three chimeric dengue strains are derived from the serotype 2 strain by replacing the structural proteins prM and E from serotype 2 strain with the corresponding structural proteins from the other dengue serotypes, resulting in the following chimeric dengue strains:

a DENV-2/1 chimera,
a DENV-2/3 chimera and
a DENV-2/4 chimera.

Further information regarding the serotypes of the tetravalent composition can be derived from section "Dengue virus strains" above.

The present invention is in particular directed to such use wherein the tetravalent dengue virus composition is in the form of a unit dose comprising:

(i) a dengue serotype 1 in a concentration of at least 3.3 log 10 pfu/0.5 ml,
(ii) a dengue serotype 2, in a concentration of at least 2.7 log 10 pfu/0.5 ml,
(iii) a dengue serotype 3, in a concentration of at least 4.0 log 10 pfu/0.5 ml, and
(iv) a dengue serotype 4, in a concentration of at least 4.5 log 10 pfu/0.5 ml.

The present invention is in particular directed to such use wherein the unit dose is lyophilized and upon reconstitution with 0.5 mL of a pharmaceutically acceptable diluent comprises:

(i) a dengue serotype 1 in a concentration of at least 3.3 log 10 pfu/0.5 ml,
(ii) a dengue serotype 2, in a concentration of at least 2.7 log 10 pfu/0.5 ml,
(iii) a dengue serotype 3, in a concentration of at least 4.0 log 10 pfu/0.5 ml, and
(iv) a dengue serotype 4, in a concentration of at least 4.5 log 10 pfu/0.5 ml.

The present invention is also in particular directed to such use wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 8%, or at least 10%, or at least 12%, or at least 14%, or at least 16%, or at least 18%, and wherein the subject is preferably 2 to 17 years of age or 4 to 16 years of age.

The present invention is also in particular directed to such use wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 2%, the concentration of (iv) in pfu/0.5 mL is at least 50%, the concentration of (i) in pfu/0.5 mL is at least 1%, and the concentration of (iii) in pfu/0.5 mL is at least 6% and wherein the subject preferably is 18 to 60 years of age.

Further information regarding the tetravalent composition or the unit dose can be derived from section "Dengue vaccine composition" and "Unit dose" above.

According to one embodiment the use is directed to a method comprising a primary vaccination with only two administrations of the unit dose comprising the steps of:

(A) administering a first unit dose of the tetravalent dengue virus composition to the subject, and
(B) administering a second unit does of the tetravalent dengue virus composition to the subject within 3 months of administration of the first unit dose.

According to this embodiment the administration of only two doses within 3 months is sufficient to provide effective protection against a subsequent dengue infection.

Such method preferably provides a combined vaccine efficacy against all four serotypes in preventing virologically confirmable dengue disease with a 2-sided 95% confidence interval, wherein the lower bound is more than 60%, when measured against placebo in a subject population of at least 5,000 healthy subjects irrespective of serostatus at baseline and 14 to 16 years of age, from the first administration of the administration schedule until 18 months after the second administration of the administration schedule.

Such method also preferably provides a combined vaccine efficacy against all four serotypes, in preventing virologically confirmable dengue disease with a 2-sided 95% confidence interval, wherein the lower bound is more than 45%, when measured against placebo in a subject population of at least 1,500 or at least 2,000 healthy subjects seronegative against all serotypes at baseline and 14 to 16 years of age, from 30 days after the second administration of the administration schedule until 18 months after the second administration of the administration schedule.

According to certain embodiments the use is for a method of inoculation against the virologically confirmable dengue disease is due to a dengue serotype 2, and/or due to a dengue serotype 1. The method has very high efficacy against dengue serotype 2 and dengue serotype 1 and the highest efficacy against dengue serotype 2.

In certain embodiments, the invention is directed to the use wherein said methods have a vaccine efficacy against serotype 1, in preventing virologically confirmable dengue disease with a 2-sided 95% confidence interval, wherein the lower bound is more than 25%, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the lower bound is more than 30%, is more than 35% is more than 40%, is more than 45%, is more than 50%, or is more than 54%. In certain such embodiments the subject population of at least 1,500 is seronegative against all serotypes at base line and the lower bound is more than 35%. In certain such embodiments the seronegative and seropositive population each provide a vaccine efficacy against serotype 1 with a 2-sided 95% confidence interval, wherein the lower bounds are within 10%-points.

In certain embodiments, the invention is directed to said use wherein said methods have a vaccine efficacy against serotype 1, in preventing virologically confirmable dengue disease, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the vaccine efficacy is more than 40%, is more than 50%, is more than 60%, or is more than 65%. In certain such embodiments the subject population of at least 1,500 is seronegative against all serotypes at base line. In certain such embodiments the seronegative and seropositive population each provide a vaccine efficacy against serotype 1 which are within 5%-points.

In certain embodiments, the invention is directed to said use wherein said methods have a vaccine efficacy against serotype 2, in preventing virologically confirmable dengue disease with a 2-sided 95% confidence interval, wherein the lower bound is more than 25%, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the lower bound is more than 50%, is more than 60%, is more than 70%, is more than 80%, or is more than 85%. In certain such embodiments the subject population of at least 1,500, is seronegative against all serotypes. In certain such embodiments the seronegative and seropositive population each provide a vaccine efficacy against serotype 2 with a 2-sided 95% confidence interval, wherein the lower bounds are within 5%-points.

In certain embodiments, the invention is directed to said use wherein said methods have a vaccine efficacy against serotype 2, in preventing virologically confirmable dengue disease, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the vaccine efficacy is more than 60%, is more than 70%, is more than 80%, or is more than 90%. In certain such embodiments the subject population of at least 1,500 is seronegative against all serotypes at base line. In certain such embodiments the seronegative and seropositive population each provide a vaccine efficacy against serotype 2 which are within 5%-points.

The efficacy of the method is further described in more detail in the section "method of preventing, method of inoculating".

In certain embodiments the unit dose is reconstituted and administered by subcutaneous injection. According to some of these embodiments, the subcutaneous injection is administered to the arm, preferably to the deltoid region of the arm.

According to one embodiment such use is directed to a method which does not include a step of determination of a previous dengue infection in the subjects preferably at any time before, during or after the steps of administration or wherein the serostatus of the subject is unknown preferably at any time before, during or after the steps of administration.

The method according to the invention does not require the testing of the serostatus before vaccination and thus allows immediate treatment and outbreak control. According to certain embodiments the use is for a method wherein the subject is exposed to a dengue outbreak. In certain such embodiments the outbreak is due to a dengue serotype 2, and/or due to a serotype 1.

According to one embodiment such a method the subject is from a region wherein the seroprevalence rate is unknown and/or wherein the seroprevalence rate is below 80%, or below 70%, or below 60%.

According to one embodiment of such a method the subject is seronegative at baseline and is from a region or travels to a region wherein the seroprevalence rate is high with respect to serotype 1 and/or serotype 2 i.e. 80%, or 90% or above.

According this embodiment the vaccine and corresponding method is safe for seronegative and seropositive subjects and thus does not require an analysis of the serostatus or a determination of a previous dengue infection or a high seroprevalence rate in the region. Such a method preferably provides a combined vaccine efficacy against virologically-confirmed dengue with hospitalization against all four serotypes with a 2-sided 95% confidence interval, wherein the lower bound is more than 65%, when measured against placebo in a subject population of at least 5,000 healthy 4 to 16 year old subjects irrespective of serostatus at baseline, preferably in at least 1,500 healthy 4 to 16 year old subjects seronegative at baseline, from first administration of the administration schedule until 12 to 18 months after the second administration of the administration schedule. Preferably, the 2-sided 95% confidence interval of the combined vaccine efficacy against virologically-confirmed dengue with hospitalization against all four serotypes when comparing seropositive and seronegative subjects provides for lower bounds of the 2-sided confidence interval which are within 10% points or within 15% points or within 20% points. The method is preferably safe with respect to serotype 1 and serotype 2 which may therefore be used in outbreak situations due to serotype 1 and/or serotype 2 or even for seronegative subjects (e.g. travelers) or subjects with unknown serostatus in regions with very high seroprevalence rates (>80%) due to serotype 1 and/or serotype 2.

The safety of the method is further described in more detail in the section "method of preventing, method of inoculating".

According to one embodiment such a method does not include the active surveillance with respect to febrile illness of the subject after the administration of the first- and second-unit dose. During active surveillance any subject with febrile illness (defined as fever ≥38° C. on any 2 of 3 consecutive days) will be asked to return to the site for dengue fever evaluation by the Investigator. Subjects/guardians will be contacted at least weekly to ensure robust identification of febrile illness by reminding subjects/guardians of their obligation to return to the site in case of febrile illness. This contact will be implemented through appropriate methods that may differ in each trial site (eg, phone calls, text messaging, home visits, school-based surveillance).

According to one embodiment such a method does not include vaccine immunogenicity analysis including GMTs for dengue neutralizing antibodies.

According to one embodiment such a method does not include a reactogenicity analysis. Such a reactogenicity analysis relates to solicited local AEs (injection site pain, injection site erythema, and injection site swelling) and solicited systemic AEs (child <6 years: fever, irritability/fussiness, drowsiness and loss of appetite; child ≥6 years: asthenia, fever, headache, malaise and myalgia) which will e.g. be assessed for 7 days and 14 days, respectively, following each vaccination (vaccination day included) via collection of diary cards.

According to one embodiment the method does not include an active surveillance, an immunogenicity analysis and a reactogenicity analysis.

According to such embodiments the vaccine and the corresponding method of inoculation are safe and therefore do not require further steps of surveillance or analysis.

In view of the above according to one embodiment the use is directed to a method comprises a primary vaccination consisting of the steps of:

(A) selecting a subject for administration of the unit doses of the tetravalent dengue virus composition in need for protection against dengue infection without determination of a previous dengue infection, and (B) administering a first unit dose of the tetravalent dengue virus composition to the subject, and (C) administering a second unit dose of the tetravalent dengue virus composition to the subject within 3 months of administration of the first unit dose.

Therefore the method of inoculating is finalized without determination of a previous dengue infection. The method however further optionally comprises at least 1 years after the administration of the second unit dose a booster dose of the unit dose.

Selecting the subject may include all types of considerations but preferably not the determination of a previous dengue infection. The selection may include consideration of the age, health conditions, and threat of infection. The threat of infection includes consideration of the seroprevalence rate in the region in which the subject normally lives or intends to travel, the serotype specific seroprevalence rate and an outbreak situation or serotype specific outbreak situations. The subject may be selected due to its exposure to serotype 1 and/or serotype 2 or due to the fact it requires protection against a specific dengue serotype, i.e. serotype 1 and/or serotype 2.

According to the invention the method is applicable to subjects of all kinds of ages. According to one embodiment the subject is under 9 years of age, or 4 to 5 years of age, or 6 to 11 years of age or 12 to 16 years, or 6 to 16 years of age or 4 to 16 years of age, or 2 to 17 years of age, or 9 years of age, or over 9 years of age, or 9 to 17 years of age, or 18 to 45 years of age, or 46 to 60 years of age, or over 60 years of age.

According to certain such embodiments the unit dose of the tetravalent dengue virus composition comprising (i), (ii), (iii), and (iv) upon reconstitution with a pharmaceutically acceptable diluent provides a total concentration of pfu/0.5 mL of (i), (ii), (iii), and (iv) and based on said total concentration the concentration of (ii) in pfu/0.5 mL is preferably less than 10%, and the concentration of (iv) in pfu/0.5 mL is preferably at least 50%, and the concentration of (i) in pfu/0.5 mL is preferably at least 1%, and the concentration of (iii) in pfu/0.5 mL is preferably at least 8%, or more preferred at least 10%, or at least 12%, or at least 14%, or at least 16%, or at least 18% and the subject is 2 to 17 years of age or 4 to 16 years of age.

According to certain such embodiments the unit dose of the tetravalent dengue virus composition comprising (i), (ii), (iii), and (iv) upon reconstitution with a pharmaceutically acceptable diluent provides a total concentration of pfu/0.5 mL of (i), (ii), (iii), and (iv) and based on said total concentration the concentration of (ii) in pfu/0.5 mL is preferably less than 2%, the concentration of (iv) in pfu/0.5 mL is preferably at least 50%, the concentration of (i) in pfu/0.5 mL is at preferably least 1%, and the concentration of (iii) in pfu/0.5 mL is preferably at least 6% and the subject is 18 to 60 years of age.

Any method described herein above under the heading "Method of preventing" is to be understood to be also disclosed as the use of a unit dose for the manufacture of a medicament for preventing dengue disease in a subject or subject population with such a method irrespective of whether it is expressly stated below.

Further specific embodiments are described below.

The present invention is in part directed to the use of a unit dose of the invention as described herein for the manufacture of a medicament for preventing dengue disease in a subject population, comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the use of a unit dose of the invention as described herein for the manufacture of a medicament for preventing dengue disease in a subject, comprising administering to the subject at least a first reconstituted unit dose of the invention as described herein, wherein certain ratios of neutralizing antibody titers at day 180 or 365 after administration of said first unit dose to the subject are achieved. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2:neutralizing antibody titer for GMT DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with the microneutralization test disclosed herein, for example according to the method described in Example 2.

In certain embodiments the invention is directed to said uses, wherein the reconstituted unit dose of the invention as described herein is administered by subcutaneous injection. According to some of these embodiments the subcutaneous injection is administered to the arm, preferably to the deltoid region of the arm.

In certain embodiments the invention is directed to said uses, wherein one reconstituted unit dose of the invention as described is administered by subcutaneous injection. According to some of these embodiments, the subcutaneous injection is administered to the arm, preferably to the deltoid region of the arm.

In certain embodiments the invention is directed to said uses, wherein two reconstituted unit doses of the invention as described herein are administered. In one embodiment, the two unit doses are administered within 12 months or more, or within six months, or within three months, such as at day 0 and day 90 or at day 1/0 and day 90. According to some of these embodiments a third unit dose of the invention as described herein may be administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments of the invention the subject is seronegative with respect to all dengue serotypes.

In certain other embodiments of the invention the subject is seropositive with respect to at least one dengue serotype.

In certain embodiments the invention is directed to said uses, wherein the reconstituted unit dose is administered to the seronegative subject by subcutaneous injection.

In certain embodiments the invention is directed to said uses, wherein the reconstituted unit dose is administered to a subject of unknown serostatus and/or wherein no test has been carried out to determine whether the subject is seropositive or seronegative before the unit dose is administered.

In certain embodiments the invention is directed to said uses, wherein the reconstituted unit dose of the invention as described herein is administered to a subject or subject population from a dengue endemic region. In some of these embodiments, the subject or subject population is from Singapore, Dominican Republic, Panama, Philippines, Colombia, Puerto Rico or Thailand, in particular from Singapore, Dominican Republic, Panama, or Philippines. In other embodiments, the subject or subject population is from a dengue non-endemic region. Such a subject population or subject may be vaccinated according to the invention in the context of traveling to a dengue endemic region. In certain embodiments, the reconstituted unit dose of the invention as described herein is administered subcutaneously to a subject or subject population from a dengue endemic region or from a dengue non-endemic region.

In certain embodiments the invention is directed to said uses, wherein the subject is of 2 to 60 years of age or more than 17 years, or more than 18 years, or 18 to 60 years of age. In certain embodiments the subject is 1 to 17 years of age, or less than 9 years of age, or less than 4 years of age or less than 2 years of age. In further embodiments, the subjects or subject population are adults of more than 21 years, or 21 to 60 years, or 21 to 45 years of age. According to some of these embodiments the subject is seronegative and from a dengue-endemic region.

In certain embodiments, the invention is directed to said uses, wherein the unit dose of the invention as described herein is administered to a pediatric subject or pediatric subject population of less than 2 years of age, preferably of 2 months to 2 years of age or 2 months to 1.5 years of age or 2 months to 1 year of age. According to some of these embodiments, the pediatric subject or pediatric subject population is seronegative and from a dengue endemic region.

In certain embodiments, the invention is directed to said uses, wherein the reconstituted unit dose of the invention as described herein is administered subcutaneously to a pediatric subject or pediatric subject population of less than 2 years of age, preferably of 2 months to 2 years of age or 2 months to 1.5 years of age or 2 months to 1 year of age. According to some of these embodiments, the pediatric subject or pediatric subject population is seronegative and from a dengue endemic region.

The present invention is directed in part to the use of a unit dose of the invention as described herein for the manufacture of a medicament for preventing dengue disease in an elderly subject.

The present invention is directed in part to the use of a unit dose of the invention as described herein for the manufacture of a medicament for preventing dengue hemorrhagic fever (DHF) and dengue shock syndrome (DSS) in an elderly subject.

In certain embodiments the invention is directed to said uses, wherein the reconstituted unit dose of the invention as described herein is administered by subcutaneous injection. According to some of these embodiments the subcutaneous injection is administered to the arm, preferably to the deltoid region of the arm.

In certain embodiments the invention is directed to said uses, wherein two reconstituted unit doses of the invention as described herein are administered. In one embodiment, the two unit doses are administered within 12 months or more, or within six months, or within three months, such as at day 0/1 and day 90. According to some of these embodiments a third unit dose of the invention as described herein may be administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments of the invention the elderly subject is seronegative with respect to all dengue serotypes.

In certain other embodiments of the invention the elderly subject is seropositive with respect to at least one dengue serotype.

In certain embodiments the invention is directed to said uses, wherein the reconstituted unit dose is administered to the seronegative elderly subject by subcutaneous injection.

In certain embodiments the invention is directed to said uses, wherein the reconstituted unit dose of the invention as described herein is administered to an elderly subject from a dengue endemic region.

In some of these embodiments, the elderly subject is from Singapore, Dominican Republic, Panama, Philippines, Colombia, Puerto Rico or Thailand, in particular from Singapore, Dominican Republic, Panama, or Philippines. In other embodiments, the elderly subject is from a dengue non-endemic region. Such an elderly subject may be vaccinated according to the invention in the context of traveling to a dengue endemic region. In certain embodiments, the reconstituted unit dose of the invention as described herein is administered subcutaneously to an elderly subject from a dengue endemic region or from a dengue non-endemic region.

In certain embodiments, the invention is directed to said uses, wherein the elderly subject has at least one chronic condition or disease. The at least one chronic condition or disease may be selected from diabetes, hypertension, allergies, previous strokes, ischemic heart disease, chronic renal impairment and chronic obstructive pulmonary disease.

In certain embodiments, the invention is directed to said uses, wherein the elderly subject has an impaired immune system.

Method of Preventing Dengue Disease and Yellow Fever and Uses

Method of Prevention

The present invention is directed in part to a method of preventing dengue disease as well as yellow fever in a subject. Thus, in certain embodiments the invention is directed to a method of preventing dengue disease in a subject, comprising administering to the subject a reconstituted unit dose of the invention as described herein, wherein the method further comprises preventing yellow fever in the subject by concomitant administration of a yellow fever vaccine, in particular YF-17D, to the subject.

The present invention is directed in part to a method of preventing dengue disease as well as yellow fever in a subject population. Thus, in certain embodiments the invention is directed to a method of preventing dengue disease in a subject population, comprising administering to the subject population a reconstituted unit dose of the invention as described herein, wherein the method further comprises preventing yellow fever in the subject population by concomitant administration of a yellow fever vaccine, in particular YF-17D, to the subject population.

The present invention is in part directed to said method for preventing dengue disease and yellow fever in a subject population comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a yellow fever vaccine, in particular YF-17D, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to said method for preventing dengue disease and yellow fever in a subject comprising administering to the subject at least a first reconstituted unit dose of the invention as described herein, wherein certain ratios of neutralizing antibody titers at day 180 or 365 after administration of said first unit dose to the subject are achieved, and concomitantly administering a yellow fever vaccine, in particular YF-17D, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2: neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to said methods, wherein the unit dose of the invention as described herein and the yellow fever vaccine, in particular YF-17D, are administered simultaneously. In some of these embodiments the simultaneous administration is on day 0 or day 90, preferably on day 0. In other embodiments the administration of the unit dose of the invention as described herein and the yellow fever vaccine, in particular YF-17D, are done sequentially.

In certain embodiments the invention is directed to said methods, wherein the reconstituted unit dose of the invention as described herein is administered and the yellow fever vaccine, in particular YF-17D, are administered by subcutaneous injection. According to some embodiments, the subcutaneous injections are administered to the arm, preferably to the deltoid region of the arm. According to some of these embodiments the subcutaneous injections of the unit dose of the invention as described herein and yellow fever vaccine, in particular YF-17D, are administered to different anatomical sites, such as to opposite arms, in particular when the vaccines are administered simultaneously.

In certain embodiments the invention is directed to said methods, wherein two unit doses of the invention as described herein are administered. In some embodiments the two unit doses of the invention as described herein are administered within 12 month or more, or within 6 month, or within three months, such as at day 0/1 and day 90. According to some of these embodiments a further third unit dose of the invention as described herein is administered after the second. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to said methods, wherein two reconstituted unit doses of the invention as described herein and one dose of a yellow fever vaccine, in particular YF-17D, are administered, in particular according to the following schedule an administration of said yellow fever vaccine on day 0, a first administration of the first reconstituted unit dose after said yellow fever vaccine administration, such as 3 months later and preferably on day 90, and a second administration of the second reconstituted unit dose after said first administration of the reconstituted unit dose, such as 3 months later and preferably on day 180.

In certain embodiments the invention is directed to said methods, wherein two reconstituted unit doses of the invention as described herein and one dose of a yellow fever vaccine, in particular YF-17D, are administered, in particular according to the following schedule a first administration of the first reconstituted unit dose on day 0, a second administration of the second reconstituted unit dose after said first administration of the reconstituted unit dose, such as 3 months later and preferably on day 90, and an administration of said yellow fever vaccine after said second administration of the reconstituted unit dose, such as 3 months later and preferably on day 180.

In certain embodiments the invention is directed to said methods, wherein two reconstituted unit doses of the invention as described herein and one dose of a yellow fever vaccine, in particular YF-17D, are administered, in particular according to the following schedule a simultaneous administration of the first reconstituted unit dose and said yellow fever vaccine on day 0, and a second administration of the second reconstituted unit dose after said simultaneous administration, such as 3 months later and preferably on day 90.

In a preferred embodiment, the yellow fever vaccine and unit dose of the invention as described herein are administered simultaneously on day 0 or simultaneously on day 90.

In certain embodiments, the invention is directed to said methods, wherein the subject or subject population is seronegative to all dengue serotypes. In certain embodiments, the invention is directed to said methods, wherein the reconstituted unit dose of the invention as described herein is administered subcutaneously to a subject or subject population and the yellow fever vaccine, in particular YF-17D vaccine, is administered subcutaneously to a subject or subject population, and wherein the subject or the subject population is seronegative with respect to all dengue serotypes. In other embodiments, the subject or subject population is seropositive with respect to at least one dengue serotype.

In certain embodiments, the invention is directed to said methods, wherein the unit dose of the invention as described herein and the yellow fever vaccine, in particular YF-17D, are administered to a subject or subject population from a dengue endemic region. In certain embodiments, the reconstituted unit dose of the invention as described herein and the yellow fever vaccine, in particular YF-17D, are administered subcutaneously to a subject or subject population from a dengue endemic region. In other embodiments, the subject or subject population is from a dengue non-endemic region. Such a subject population or such a subject may be vaccinated according to the present invention in the context of traveling to a dengue endemic region and yellow fever endemic region.

In certain embodiments the invention is directed to said methods, wherein the reconstituted unit dose of the invention as described herein and of the yellow fever vaccine, in particular YF-17D, are administered subcutaneously to a subject or subject population of more than 17 years, or more than 18 years, or 18 to 60 years of age. In further embodiments, the subjects or subject population are adults of more than 21 years, or 21 to 60 years, or 21 to 45 years of age. In some embodiments, the subject or subject population is from a dengue endemic region. In another embodiment, the subject or subject population is from a dengue non-endemic region, preferably from a dengue non-endemic and yellow fever non-endemic region. According to some of these embodiments, the subject or subject population are seronegative for all four dengue serotypes.

Unit Dose for Use in a Method of Prevention

The present invention is directed in part to the unit dose of the invention as described herein for use in a method of preventing dengue disease in a subject, wherein the method also comprises the prevention of yellow fever in the subject with a yellow fever vaccine, in particular YF-17D. In particular, the present invention is directed in part to a unit dose of a dengue vaccine composition as described herein and a yellow fever vaccine, in particular YF-17D, for use in a method of preventing dengue disease and yellow fever in a subject, respectively.

The present invention is directed in part to the unit dose of the invention as described herein for use in a method of preventing dengue disease in a subject population, wherein the method also comprises the prevention of yellow fever in the subject population with a yellow fever vaccine, in particular YF-17D. In particular, the present invention is directed in part to a unit dose of a dengue vaccine composition as described herein and a yellow fever vaccine, in particular YF-17D, for use in a method of preventing dengue disease and yellow fever in a subject population, respectively.

The present invention is in part directed to the unit dose of a dengue vaccine composition as described herein and the yellow fever vaccine, in particular YF-17D, for use in a method of preventing dengue disease and yellow fever in a subject population, comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a yellow fever vaccine, in particular YF-17D, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the unit dose of a dengue vaccine composition as described herein and the yellow fever vaccine, in particular YF-17D, for use in a method of preventing dengue disease and yellow fever in a subject comprising administering to the subject at least a first reconstituted unit dose of the invention as described herein, wherein certain ratios of neutralizing antibody titers at day 180 or 365 after administration of said first unit dose to the subject are achieved, and concomitantly administering a yellow fever vaccine, in particular YF-17D, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2: neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to the unit dose of the invention as described herein and the yellow fever vaccine, in particular YF-17D, for said uses, wherein said unit dose and said yellow fever vaccine are administered simultaneously. In some of these embodiments, the simultaneous administration is on day 0 or day 90, preferably on day 0. In other embodiments, the administration of said unit dose and said yellow fever vaccine, in particular YF-17D, are done sequentially.

In certain embodiments the invention is directed to the unit dose of the invention as described herein and the yellow fever vaccine, in particular YF-17D, for said uses, wherein said unit dose is administered by subcutaneous injection and wherein said yellow fever vaccine is administered by subcutaneous injection. According to some embodiments, the subcutaneous injections are administered to the arm, preferably to the deltoid region of the arm. According to some of these embodiments the subcutaneous injection of said unit dose and the subcutaneous injection of said yellow fever vaccine are administered to different anatomical sites, such as to opposite arms, in particular when the vaccines are administered simultaneously.

In certain embodiments the invention is directed to the unit dose of the invention as described herein and the yellow fever vaccine, in particular YF-17D, for said uses, wherein two reconstituted unit doses of the invention as described herein are administered. In some embodiments the two unit doses of the invention as described herein are administered within 12 months or more, or within six months, or within three months, such as at day 0/1 and day 90. According to some of these embodiments a further third reconstituted unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to the unit dose of the invention as described herein and the yellow fever vaccine, in particular YF-17D, for said uses, wherein two reconstituted unit doses of the invention as described herein and one dose of the yellow fever vaccine are administered, in particular according to the following schedule

- an administration of said yellow fever vaccine on day 0,
- a first administration of the first reconstituted unit dose after said yellow fever vaccine administration, such as 3 months later and preferably on day 90, and
- a second administration of the second reconstituted unit dose after said first administration of the reconstituted unit dose, such as 3 months later and preferably on day 180.

In another embodiment the invention is directed to the unit dose of the invention as described herein and the yellow fever vaccine, in particular YF-17D, for said uses, wherein two unit doses of the invention as described herein and one dose of the yellow fever vaccine are administered, in particular according to the following schedule

- a first administration of the first reconstituted unit on day 0,
- a second administration of the second reconstituted unit dose after said first administration of the reconstituted unit dose, such as 3 months later and preferably on day 90, and
- an administration of said yellow fever vaccine after said second administration of the reconstituted unit dose, such as 3 months later and preferably on day 180.

In another embodiment the invention is directed to the unit dose of the invention as described herein and the yellow fever vaccine, in particular YF-17D, for said uses, wherein two unit doses of the invention as described herein and one dose of the yellow fever vaccine are administered, in particular according to the following schedule

- a simultaneous administration of the first reconstituted unit dose and said yellow fever vaccine on day 0, and
- a second administration of the second reconstituted unit dose after said simultaneous administration, such as 3 months later and preferably on day 90.

In a preferred embodiment, the yellow fever vaccine and unit dose of the invention as described herein are administered simultaneously on day 0 or simultaneously on day 90.

In certain embodiments, the invention is directed to the unit dose of the invention as described herein and the yellow fever vaccine, in particular YF-17D, for said uses, wherein the subject or subject population is seronegative to all dengue serotypes. In certain embodiments, the invention is directed to the unit dose of the invention as described herein and the yellow fever vaccine, in particular YF-17D, for said uses, wherein said unit dose is reconstituted and administered subcutaneously to a subject or subject population and said yellow fever vaccine is administered subcutaneously to a subject or subject population, and wherein the subject or the subject population is seronegative with respect to all dengue serotypes. In other embodiments, the subject or subject population is seropositive with respect to at least one dengue serotype.

In certain embodiments, the invention is directed to the unit dose of the invention as described herein and the yellow fever vaccine, in particular YF-17D, for said uses, wherein said unit dose and said yellow fever vaccine are administered to a subject or subject population from a dengue endemic region. In certain embodiments, the reconstituted unit dose of the invention as described herein and the yellow fever vaccine, in particular YF-17D, are administered subcutaneously to a subject or subject population from a dengue endemic region. In other embodiments, the subject or subject population is from a dengue non-endemic region. Such a subject population or such a subject may be vaccinated according to the present invention in the context of traveling to a dengue endemic region and yellow fever endemic region.

In certain embodiments the invention is directed to the unit dose of the invention as described herein and the yellow fever vaccine, in particular YF-17D, for said uses, wherein the reconstituted unit dose of the invention as described herein and the yellow fever vaccine, in particular YF-17D, are administered subcutaneously to a subject or a subject population of more than 17 years, or more than 18 years, or 18 to 60 years of age. In some embodiments the subject or subject population is from a dengue endemic region. In another embodiment the subject or subject population is from a dengue non-endemic region, preferably from a dengue non-endemic and yellow fever non-endemic region. According to some of these embodiments, the subject or subject population is seronegative for all four dengue serotypes.

Use for the Manufacture of a Medicament in a Method of Prevention

The present invention is directed in part to the use of a unit dose of the invention as described herein for the manufacture of a medicament for preventing dengue disease in a subject, further comprising the use of a yellow fever vaccine, in particular YF-17D, for the manufacture of a medicament for preventing yellow fever in the subject. In particular, the present invention is directed in part to a use of a unit dose of a dengue vaccine composition as described herein and a yellow fever vaccine, in particular YF-17D, for the manufacture of a medicament for preventing dengue disease and yellow fever in a subject, respectively.

The present invention is directed in part to the use of a unit dose of the invention as described herein for the manufacture of a medicament for preventing dengue disease in a subject population, further comprising the use of a yellow fever vaccine, in particular YF-17D, for the manufacture of a medicament for preventing yellow fever in the subject population. In particular, the present invention is directed in part to a use of a unit dose of a dengue vaccine composition as described herein and a yellow fever vaccine, in particular YF-17D, for the manufacture of a medicament for preventing dengue disease and yellow fever in a subject population, respectively.

The present invention is in part directed to the use of a unit dose of the invention as described herein and a yellow fever vaccine, in particular YF-17D, for the manufacture of a medicament for preventing dengue disease and yellow fever in a subject population, comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a yellow fever vaccine, in particular YF-17D, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the use of a unit dose of the invention as described herein and a yellow fever vaccine, in particular YF-17D, for the manufacture of a medicament for preventing dengue disease and yellow fever in a subject, comprising administering to the subject at least a first reconstituted unit dose of the invention as described herein, wherein certain ratios of neutralizing antibody titers at day 180 or 365 after administration of said first unit dose to the subject are achieved, and concomitantly administering a yellow fever vaccine, in particular YF-17D, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2: neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to said uses, wherein the unit dose of the invention as described herein and the yellow fever vaccine, in particular YF-17D, are administered simultaneously. In some of these embodiments the simultaneous administration is on day 0 or day 90, preferably on day 0. In other embodiments the administration of the unit dose of the invention as described herein and the yellow fever vaccine, in particular YF-17D, are done sequentially.

In certain embodiments the invention is directed to said uses, wherein the unit dose of the invention as described herein is reconstituted and administered by subcutaneous injection and wherein the yellow fever vaccine, in particular YF-17D, is administered by subcutaneous injection. According to some embodiments the injections are administered to the arm, preferably to the deltoid region of the arm. According to some of these embodiments the subcutaneous injection of the unit dose of the invention as described herein and of the yellow fever vaccine, in particular YF-17D, are administered to different anatomical sites such as to opposite arms, in particular when the vaccines are administered simultaneously.

In certain embodiments the invention is directed to said uses, wherein two reconstituted unit doses of the invention as described herein are administered. In some embodiments the two unit doses of the invention as described herein are administered within 12 months or more, or within six months, or within three months, such as at day 0/1 and day 90. According to some of these embodiments a further third unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to said uses, wherein two unit doses of the invention as described herein and one dose of a yellow fever vaccine, in particular YF-17D, are administered, in particular according to the following schedule

- an administration of said yellow fever vaccine on day 0,
- a first administration of the first reconstituted unit dose after said yellow fever vaccine administration, such as 3 months later and preferably on day 90, and
- a second administration of the second reconstituted unit dose after said first administration of the reconstituted unit dose, such as 3 months later and preferably on day 180.

In certain embodiments the invention is directed to said uses, wherein two unit doses of the invention as described herein and one dose of a yellow fever vaccine, in particular YF-17D, are administered, in particular according to the following schedule

- a first administration of the first reconstituted unit dose on day 0,
- a second administration of the second reconstituted unit dose said first administration of the reconstituted unit dose, such as 3 months later and preferably on day 90, and
- an administration of said yellow fever vaccine after said second administration of the reconstituted unit dose, such as 3 months later and preferably on day 180.

In certain embodiments the invention is directed to said uses, wherein two unit doses of the invention as described herein and one dose of a yellow fever vaccine, in particular YF-17D, are administered, in particular according to the following schedule

- a simultaneous administration of the first reconstituted unit dose and said yellow fever vaccine on day 0, and
- a second administration of the second reconstituted unit dose after said simultaneous administration, such as 3 months later and preferably on day 90.

In certain embodiments, the invention is directed to said uses, wherein the subject or subject population is seronegative to all dengue serotypes. In certain embodiments, the invention is directed to said uses, wherein the unit dose of the invention as described herein is reconstituted and administered subcutaneously to a subject or subject population and the yellow fever vaccine, in particular YF-17D, is administered subcutaneously to a subject or subject population, and wherein the subject or the subject population is seronegative with respect to all dengue serotypes. In other embodiments, the subject or subject population is seropositive with respect to at least one dengue serotype.

In certain embodiments, the invention is directed to said uses, wherein the unit dose of the invention as described herein and the yellow fever vaccine, in particular YF-17D, are administered to a subject or subject population from a dengue endemic region. In certain embodiments, the reconstituted unit dose of the invention as described herein and the yellow fever vaccine, in particular YF-17D, are administered subcutaneously to a subject or subject population from a dengue endemic region. In other embodiments, the subject or subject population is from a dengue non-endemic region. Such a subject population or such a subject may be vaccinated according to the present invention in the context of traveling to a dengue endemic region and yellow fever endemic region.

In certain embodiments the invention is directed to said uses, wherein the reconstituted unit dose of the invention as described herein and the yellow fever vaccine, in particular YF-17D, are administered subcutaneously to a subject or subject population of more than 17 years, or more than 18 years, or 18 to 60 years of age. In further embodiments, the subjects or subject population are adults of more than 21 years, or 21 to 60 years, or 21 to 45 years of age. In some embodiments, the subject or subject population is from a dengue endemic region. In another embodiment, the subject or subject population is from a dengue non-endemic region, preferably from a dengue non-endemic and yellow fever non-endemic region. According to some of these embodiments, the subject or subject population is seronegative for all four dengue serotypes.

Method of Preventing Dengue Disease and Hepatitis A and Uses

Method of Prevention

The present invention is directed in part to a method of preventing dengue disease as well as hepatitis A in a subject. Thus, in certain embodiments the invention is directed to a method of preventing dengue disease in a subject, comprising administering to the subject a reconstituted unit dose of the invention as described herein, wherein the method further comprises preventing hepatitis A in the subject by concomitant administration of a hepatitis A vaccine, such as HAVRIX® or VAQTA®, to the subject.

The present invention is directed in part to a method of preventing dengue disease as well as hepatitis A in a subject population. Thus, in certain embodiments the invention is directed to a method of preventing dengue disease in a subject population, comprising administering to the subject population a reconstituted unit dose of the invention as described herein, wherein the method further comprises preventing hepatitis A in the subject population by concomitant administration of a hepatitis A vaccine, such as HAVRIX® or VAQTA®, to the subject population.

The present invention is in part directed to said method for preventing dengue disease and hepatitis A in a subject population comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a hepatitis A vaccine, such as HAVRIX® or VAQTA®, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or nor more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to said method for preventing dengue disease and hepatitis A in a subject comprising administering to the subject at least a first reconstituted unit dose of the invention as described herein, wherein certain ratios of neutralizing antibody titers at day 180 or 365 after administration of said first unit dose to the subject are achieved, and concomitantly administering a hepatitis A vaccine, such as HAVRIX® or VAQTA®, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2:neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to said methods, wherein the unit dose of the invention as described herein and the hepatitis A vaccine, such as HAVRIX® or VAQTA®, are administered simultaneously. In some of these embodiments, the simultaneous administration is on day 0 or day 90, preferably on day 0. In other embodiments, the administration of the unit dose of the invention as described herein and the hepatitis A vaccine, such as HAVRIX® or VAQTA®, are done sequentially.

In certain embodiments, the invention is directed to said methods, wherein the reconstituted unit dose of the invention as described herein is administered by subcutaneous injection and wherein the hepatitis A vaccine, such as HAVRIX® or VAQTA®, is administered by intramuscular injection. According to some embodiments, the injections are administered to the arm, preferably to the deltoid region of the arm. According to some of these embodiments, the subcutaneous injection of the reconstituted unit dose of the invention as described herein and the intramuscular injection of the hepatitis A vaccine, such as HAVRIX® or VAQTA®, are administered to different anatomical sites, such as to opposite arms, in particular when the vaccines are administered simultaneously.

In certain embodiments, the invention is directed to said methods, wherein two unit doses of the invention as described herein are administered. In some embodiments, the two unit doses of the invention as described herein are administered within 12 month or more, or within 6 month, or within three months, such as at day 0/1 and day 90. According to some of these embodiments, a further third unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments, the invention is directed to said methods, wherein two reconstituted unit doses of the invention as described herein and one dose of a hepatitis A vaccine, such as HAVRIX® or VAQTA®, are administered, in particular according to the following schedule

- a first simultaneous administration of the first reconstituted unit dose and said hepatitis A vaccine on day 0, and
- a second administration of the second reconstituted unit dose after said first simultaneous administration, such as 3 months later and preferably on day 90.

In certain embodiments, the invention is directed to said methods, wherein the subject or subject population is seronegative to all dengue serotypes. In certain embodiments, the invention is directed to said methods, wherein the reconstituted unit dose of the invention as described herein is administered subcutaneously to a subject or subject population and the hepatitis A vaccine, such as HAVRIX® or VAQTA®, is administered intramuscularly to a subject or subject population, and wherein the subject or the subject population is seronegative with respect to all dengue serotypes. In other embodiments, the subject or subject population is seropositive with respect to at least one dengue serotype.

In certain embodiments, the invention is directed to said methods, wherein the unit dose of the invention as described herein and the hepatitis A vaccine, such as HAVRIX® or VAQTA®, are administered to a subject or subject population from a dengue endemic region. In certain embodiments, the reconstituted unit dose of the invention as described herein is administered subcutaneously and the hepatitis A vaccine, such as HAVRIX® or VAQTA®, is administered intramuscularly to a subject or subject population from a dengue endemic region.

According to some embodiments, a second dose of a hepatitis A vaccine, such as HAVRIX® or VAQTA®, is administered. The second dose of the hepatitis A vaccine may be administered after the first administration of the hepatitis A vaccine. Such a second administration may act as a booster and may be administered 9 months after the first administration of the hepatitis A vaccine, such as on day 270.

In certain embodiments, the invention is directed to said methods, wherein the reconstituted unit dose of the invention as described herein is administered subcutaneously and wherein the hepatitis A vaccine, such as HAVRIX® or VAQTA®, is administered intramuscularly to a subject or subject population of more than 17 years, or more than 18 years, or 18 to 60 years of age. In further embodiments, the subjects or subject population are adults of more than 21 years, or 21 to 60 years, or 21 to 45 years of age. In some embodiments, the subject or subject population is from a dengue endemic region. In another embodiment, the subject or subject population is from a dengue non-endemic region, preferably from a dengue non-endemic and a hepatitis A non-endemic region. According to certain embodiments, the subject or subject population is seronegative for all four dengue serotypes.

Unit Dose for Use in a Method of Prevention

The present invention is directed in part to the unit dose of the invention as described herein for use in a method of preventing dengue disease in a subject, wherein the method also comprises the prevention of hepatitis A in the subject with a hepatitis A vaccine, such as HAVRIX® or VAQTA®. In particular, the present invention is directed in part to a unit dose of a dengue vaccine composition as described herein and a hepatitis A vaccine, such as HAVRIX® or VAQTA®, for use in a method of preventing dengue disease and hepatitis A in a subject, respectively.

The present invention is directed in part to the unit dose of the invention as described herein for use in a method of preventing dengue disease in a subject population, wherein the method also comprises the prevention of hepatitis A in the subject population with a hepatitis A vaccine, such as HAVRIX® or VAQTA®. In particular, the present invention is directed in part to a unit dose of a dengue vaccine composition as described herein and a hepatitis A vaccine, such as HAVRIX® or VAQTA®, for use in a method of preventing dengue disease and hepatitis A in a subject population, respectively.

The present invention is in part directed to the unit dose of a dengue vaccine composition as described herein and the hepatitis A vaccine, such as HAVRIX® or VAQTA®, for use in a method of preventing dengue disease and hepatitis A in a subject population, comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a hepatitis A vaccine, such as HAVRIX® or VAQTA®, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the unit dose of a dengue vaccine composition as described herein and the hepatitis A vaccine, such as HAVRIX® or VAQTA®, for use in a method of preventing dengue disease and hepatitis A in a subject comprising administering to the subject a hepatitis A vaccine, such as HAVRIX® or VAQTA®, and at least a first reconstituted unit dose of the invention as described herein, wherein certain ratios of neutralizing antibody titers at day 180 or 365 after administration of said first unit dose to the subject are achieved, and concomitantly administering a hepatitis A vaccine, such as HAVRIX® or VAQTA®, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2:neutralizing antibody titer for DENV-4 of not more than 50, or not more than 40, or not more than 30, or not more than 20, wherein the method further comprises preventing hepatitis A in the subject by concomitant administration of a hepatitis A vaccine, such as HAVRIX® or VAQTA®, to the subject. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to the unit dose of the invention as described herein and the hepatitis A vaccine, such as HAVRIX® or VAQTA®, for said uses, wherein said unit dose and said hepatitis A vaccine are administered simultaneously. In some of these embodiments, the simultaneous administration is on day 0 or day 90, preferably on day 0. In other embodiments, the administration of said unit dose and said hepatitis A vaccine are done sequentially.

In certain embodiments the invention is directed to the unit dose of the invention as described herein and the hepatitis A vaccine, such as HAVRIX® or VAQTA®, for said uses, wherein said unit dose is administered by subcutaneous injection and wherein said hepatitis A vaccine is administered by intramuscular injection. According to some embodiments, the injections are administered to the arm, preferably to the deltoid region of the arm. According to some of these embodiments, the subcutaneous injection of said unit dose and the intramuscular injection of said hepatitis A vaccine are administered to different anatomical sites, such as to opposite arms, in particular when the vaccines are administered simultaneously.

In certain embodiments, the invention is directed to the unit dose of the invention as described herein and the hepatitis A vaccine, such as HAVRIX® or VAQTA®, for said uses, wherein two reconstituted unit doses of the invention as described herein are administered. In some embodiments, the two unit doses of the invention as described herein are administered within 12 months or more, or within six months, or within three months, such as at day 0/1 and day 90. According to some of these embodiments a further third reconstituted unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments, the invention is directed to the unit dose of the invention as described herein and the hepatitis A vaccine, such as HAVRIX® or VAQTA®, for said uses, wherein two reconstituted unit doses of the invention as described herein and one dose of the hepatitis A vaccine are administered, in particular according to the following schedule

- a first simultaneous administration of the first reconstituted unit dose and a dose of said hepatitis A vaccine on day 0, and
- a second administration of the second reconstituted unit dose after said first simultaneous administration, such as 3 months later and preferably on day 90.

In certain embodiments, the invention is directed to the unit dose of the invention as described herein and the hepatitis A vaccine, such as HAVRIX® or VAQTA®, for said uses, wherein the subject or subject population is seronegative to all dengue serotypes. In certain embodiments, the invention is directed to the unit dose of the invention as described herein and the hepatitis A vaccine, such as HAVRIX® or VAQTA®, for said uses, wherein said unit dose is reconstituted and administered subcutaneously to a subject or subject population and said hepatitis A vaccine is administered intramuscularly to a subject or subject population, and wherein the subject or the subject population is seronegative with respect to all dengue serotypes. In other embodiments, the subject or subject population is seropositive with respect to at least one dengue serotype.

In certain embodiments, the invention is directed to the unit dose of the invention as described herein and the hepatitis A vaccine, such as HAVRIX® or VAQTA®, for said uses, wherein said unit dose and said hepatitis A vaccine are administered to a subject or subject population from a dengue endemic region. In certain embodiments, the reconstituted unit dose of the invention as described herein is administered subcutaneously and the hepatitis A vaccine, such as HAVRIX® or VAQTA®, is administered intramuscularly to a subject or subject population from a dengue endemic region.

In certain embodiments, the invention is directed to the unit dose of the invention as described herein and the hepatitis A vaccine, such as HAVRIX® or VAQTA®, for said uses, wherein a further second dose of a hepatitis A vaccine, such as HAVRIX® or VAQTA®, is administered. The second dose of the hepatitis A vaccine may be administered after the first administration of the hepatitis A vaccine. Such a second administration may act as a booster and may be administered 9 months after the first administration of the hepatitis A vaccine, such as on day 270.

In some embodiments, the invention is directed to the unit dose of the invention as described herein and the hepatitis A vaccine, such as HAVRIX® or VAQTA®, for said uses, wherein the reconstituted unit dose of the invention as described herein is administered subcutaneously and the hepatitis A vaccine, such as HAVRIX® or VAQTA®, is administered intramuscularly to a subject or subject population of more than 17 years, or more than 18 years, or 18 to 60 years of age. In further embodiments, the subjects or subject population are adults of more than 21 years, or 21 to 60 years, or 21 to 45 years of age. In some embodiments, the subject or subject population is from a dengue endemic region. In another embodiment, the subject or subject population is from a dengue non-endemic region, preferably from a dengue non-endemic and a hepatitis A non-endemic region. According to certain embodiments, the subject or subject population is seronegative for all four dengue serotypes.

Use for the Manufacture of a Medicament in a Method of Prevention

The present invention is directed in part to the use of a unit dose of the invention as described herein for the manufacture of a medicament for preventing dengue disease in a subject, further comprising the use of a hepatitis A vaccine, such as HAVRIX® or VAQTA®, for the manufacture of a medicament for preventing hepatitis A in the subject. In particular, the present invention is directed in part to a use of a unit dose of a dengue vaccine composition as described herein and a hepatitis A vaccine, such as HAVRIX® or VAQTA®, for the manufacture of a medicament for preventing dengue disease and hepatitis A in a subject, respectively.

The present invention is directed in part to the use of a unit dose of the invention as described herein for the manufacture of a medicament for preventing dengue disease in a subject population, further comprising the use of a hepatitis A vaccine, such as HAVRIX® or VAQTA®, for the manufacture of a medicament for preventing hepatitis A in the subject population. In particular, the present invention is directed in part to a use of a unit dose of a dengue vaccine composition as described herein and a hepatitis A vaccine, such as HAVRIX® or VAQTA®, for the manufacture of a medicament for preventing dengue disease and hepatitis A in a subject population, respectively.

The present invention is in part directed to the use of a unit dose of the invention as described herein and a hepatitis A vaccine, such as HAVRIX® or VAQTA®, for the manufacture of a medicament for preventing dengue disease and hepatitis A in a subject population, comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved and concomitantly administering a hepatitis A vaccine, such as HAVRIX® or VAQTA®, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the use of a unit dose of the invention as described herein and a hepatitis A vaccine, such as HAVRIX® or VAQTA®, for the manufacture of a medicament for preventing dengue disease and hepatitis A in a subject, comprising administering to the subject at least a first reconstituted unit dose of the invention as described herein, wherein certain ratios of neutralizing antibody titers at day 180 or 365 after administration of said first unit dose to the subject are achieved and concomitantly administering a hepatitis A vaccine, such as HAVRIX® or VAQTA®, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2:neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to said uses, wherein the unit dose of the invention as described herein and the hepatitis A vaccine, such as HAVRIX® or VAQTA®, are administered simultaneously. In some of these embodiments, the simultaneous administration is on day 0 or day 90, preferably on day 0. In other embodiments, the administration of the unit dose of the invention as described herein and the hepatitis A vaccine, such as HAVRIX® or VAQTA®, are done sequentially.

In certain embodiments the invention is directed to said uses, wherein the unit dose of the invention as described herein is reconstituted and administered by subcutaneous injection and wherein the hepatitis A vaccine, such as HAVRIX® or VAQTA®, is administered by intramuscular injection. According to some embodiments, the injections are administered to the arm, preferably to the deltoid region of the arm. According to some embodiments the subcutaneous injection of the unit dose of the invention as described herein and the intramuscular injection of the hepatitis A vaccine, such as HAVRIX® or VAQTA®, are administered to different anatomical sites, such as to opposite arms, in particular when the vaccines are administered simultaneously.

In certain embodiments, the invention is directed to said uses, wherein two reconstituted unit doses of the invention as described herein are administered. In some embodiments, the two unit doses of the invention as described herein are administered within 12 months or more, or within six months, or within three months, such as at day 0/1 and day 90. According to some of these embodiments a further third unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to said uses, wherein two unit doses of the invention as described herein and one dose of a hepatitis A vaccine, such as HAVRIX® or VAQTA®, are administered, in particular according to the following schedule a first simultaneous administration of the first reconstituted unit dose and said hepatitis A vaccine on day 0, and a second administration of the second reconstituted unit dose after said first simultaneous administration, such as 3 months later and preferably on day 90.

In certain embodiments, the invention is directed to said uses, wherein the subject or subject population is seronegative to all dengue serotypes. In certain embodiments, the invention is directed to said uses, wherein the unit dose of the invention as described herein is reconstituted and administered subcutaneously to a subject or subject population and the hepatitis A vaccine, such as HAVRIX® or VAQTA®, is administered intramuscularly to a subject or subject population, and wherein the subject or the subject population is seronegative with respect to all dengue serotypes. In other embodiments, the subject or subject population is seropositive with respect to at least one dengue serotype.

In certain embodiments, the invention is directed to said uses, wherein the unit dose of the invention as described herein and the hepatitis A vaccine, such as HAVRIX® or VAQTA®, are administered to a subject or subject population from a dengue endemic region. In certain embodiments, the reconstituted unit dose of the invention as described herein is administered subcutaneously and the hepatitis A vaccine, such as HAVRIX® or VAQTA®, is administered intramuscularly to a subject or subject population from a dengue endemic region.

In certain embodiments, the invention is directed to said uses, wherein a further second dose of a hepatitis A vaccine, such as HAVRIX® or VAQTA®, is administered. The second dose of the hepatitis A vaccine may be administered after the first administration of the hepatitis A vaccine. Such a second administration may act as a booster and may be administered 9 months after the first administration of the hepatitis A vaccine such as on day 270.

In certain embodiments, the invention is directed to said uses, wherein the reconstituted unit dose of the invention as described herein is administered subcutaneously and the hepatitis A vaccine, such as HAVRIX® or VAQTA®, is administered intramuscularly to a subject or subject population of more than 17 years, or more than 18 years, or 18 to 60 years of age. In further embodiments, the subjects or subject population are adults of more than 21 years, or 21 to 60 years, or 21 to 45 years of age. In some embodiments, the subject or subject population is from a dengue endemic region. In another embodiment, the subject or subject population is from a dengue non-endemic region, preferably from a dengue non-endemic and hepatitis A non-endemic region. According to some of these embodiments, the subject or subject population is seronegative for all four dengue serotypes.

Method of Preventing Dengue Disease and HPV Associated Diseases and Uses

Method of Prevention

The present invention is directed in part to a method of preventing dengue disease as well as HPV-associated cancers or genital warts in a subject. Thus, in certain embodiments the invention is directed to a method of preventing dengue disease in a subject, comprising administering to the subject a reconstituted unit dose of the invention as described herein, wherein the method further comprises preventing HPV-associated cancers or genital warts in the subject by concomitant administration of a HPV vaccine, in particular a 9vHPV vaccine, such as GARDASIL® 9, to the subject.

The present invention is directed in part to a method of preventing dengue disease as well as HPV-associated cancers or genital warts in a subject population. Thus, in certain embodiments the invention is directed to a method of preventing dengue disease in a subject population, comprising administering to the subject population a reconstituted unit dose of the invention as described herein, wherein the method further comprises preventing HPV-associated cancers or genital warts in the subject population by concomitant administration of a HPV vaccine, in particular a 9vHPV vaccine, such as GARDASIL® 9, to the subject population.

The present invention is in part directed to said method for preventing dengue disease and HPV-associated cancers or genital warts in a subject population comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a HPV vaccine, in particular a 9vHPV vaccine, such as GARDASIL® 9, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2: GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to said method for preventing dengue disease and HPV-associated cancers or genital warts in a subject comprising administering to the subject at least a first reconstituted unit dose of the invention as described herein, wherein certain ratios of neutralizing antibody titers at day 180 or 365 after administration of said first unit dose to the subject are achieved, and concomitantly administering a HPV vaccine, in particular a 9vHPV vaccine, such as GARDASIL® 9, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2:neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to said methods, wherein the unit dose of the invention as described herein and the HPV vaccine, in particular a 9vHPV vaccine, such as GARDASIL® 9, are administered simultaneously. In some of these embodiments the simultaneous administration is on day 0 or day 90, preferably on day 0. In other embodiments the administration of the unit dose of the invention as described herein and the HPV vaccine, in particular a 9vHPV vaccine, such as GARDASIL® 9, are done sequentially.

In certain embodiments the invention is directed to said methods, wherein the reconstituted unit dose of the invention as described herein is administered by subcutaneous injection and wherein the HPV vaccine, in particular a 9vHPV vaccine, such as GARDASIL® 9, is administered by intramuscular injection. According to some embodiments the injections are administered to the arm, preferably to the deltoid region of the arm. According to some of these embodiments the subcutaneous injection of the unit dose of the invention as described herein and the intramuscular injection of the HPV vaccine, in particular a 9vHPV vaccine, such as GARDASIL® 9, are administered to different anatomical sites, such as to opposite arms, in particular when the vaccines are administered simultaneously.

In certain embodiments the invention is directed to said methods, wherein two unit doses of the invention as described herein are administered. In some embodiments the two unit doses of the invention as described herein are administered within 12 month or more, or within 6 month, or within three months, such as at day 0/1 and day 90. According to some of these embodiments a further third unit dose of the invention as described herein is administered after the second. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to said methods, wherein two reconstituted unit doses of the invention as described herein and two doses of a HPV vaccine, in particular a 9vHPV vaccine, such as GARDASIL® 9, are administered, in particular according to the following schedule a first simultaneous administration of the first reconstituted unit dose and the first dose of said HPV vaccine on day 0, a second administration of the second reconstituted unit dose after said first simultaneous administration, such as 3 month later and preferably on day 90, and a third administration of the second dose of said HPV vaccine after said second administration of the reconstituted unit dose, such as 3 month later and preferably on day 180.

In certain embodiments, the invention is directed to said methods, wherein the subject or subject population is seronegative to all dengue serotypes. In certain embodiments, the invention is directed to said methods, wherein the reconstituted unit dose of the invention as described herein is administered subcutaneously to a subject or subject population and the HPV vaccine, in particular a 9vHPV vaccine, such as GARDASIL® 9, is administered intramuscularly to a subject or subject population, and wherein the subject or the subject population is seronegative with respect to all dengue serotypes. In other embodiments, the subject or subject population is seropositive with respect to at least one dengue serotype.

In certain embodiments, the invention is directed to said methods, wherein the unit dose of the invention as described herein and the HPV vaccine, in particular a 9vHPV vaccine, such as GARDASIL® 9, are administered to a subject or subject population from a dengue endemic region. In certain embodiments, the reconstituted unit dose of the invention as described herein is administered subcutaneously and the HPV vaccine, in particular a 9vHPV vaccine, such as GARDASIL® 9, is administered intramuscularly to a subject or subject population from a dengue endemic region.

In certain embodiments the invention is directed to said methods, wherein the reconstituted unit dose of the invention as described herein is administered subcutaneously and wherein the HPV vaccine, in particular a 9vHPV vaccine, such as GARDASIL® 9, is administered intramuscularly to a subject or subject population of 9 to 26 years of age, preferably 9 to 15 years of age. In some embodiments the subject or subject population is from a dengue endemic region. According to some of these embodiments, the subject or subject population is female. According to some of these embodiments, the subject or subject population is seronegative for all four dengue serotypes.

In a preferred embodiment the invention is directed to a method of preventing dengue disease and HPV-associated cancers or genital warts in a subject comprising administering to the subject a subcutaneous injection of the reconstituted unit dose of the invention as described herein and an intramuscular injection of the HPV vaccine, in particular a 9vHPV vaccine, such as GARDASIL® 9, according to the above described administration schedule, wherein the subject is a female subject of 9 to 15 years of age from a dengue endemic region.

Unit Dose for Use in a Method of Prevention

The present invention is directed in part to the unit dose of the invention as described herein for use in a method of preventing dengue disease in a subject, wherein the method also comprises the prevention of HPV-associated cancers or genital warts in the subject with a HPV vaccine, in particular a 9vHPV vaccine, such as GARDASIL® 9. In particular, the present invention is directed in part to a unit dose of a dengue vaccine composition as described herein and a HPV vaccine, in particular a 9vHPV vaccine, such as GARDASIL® 9, for use in a method of preventing dengue disease and HPV-associated cancers or genital warts in a subject, respectively.

The present invention is directed in part to the unit dose of the invention as described herein for use in a method of preventing dengue disease in a subject population, wherein the method also comprises the prevention of HPV-associated cancers or genital warts in the subject population with a HPV vaccine, in particular a 9vHPV vaccine, such as GARDASIL® 9. In particular, the present invention is directed in part to a unit dose of a dengue vaccine composition as described herein and a HPV vaccine, in particular a 9vHPV vaccine, such as GARDASIL® 9, for use in a method of preventing dengue disease and HPV-associated cancers or genital warts in a subject population, respectively.

The present invention is in part directed to the unit dose of a dengue vaccine composition as described herein and the HPV vaccine, in particular a 9vHPV vaccine, such as GARDASIL® 9, for use in a method of preventing dengue disease and HPV-associated cancers or genital warts in a subject population, comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a HPV vaccine, in particular a 9vHPV vaccine, such as GARDASIL® 9, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the unit dose of a dengue vaccine composition as described herein and the HPV vaccine, in particular a 9vHPV vaccine, such as GARDASIL® 9, for use in a method of preventing dengue disease and HPV-associated cancers or genital warts in a subject comprising administering to the subject at least a first reconstituted unit dose of the invention as described herein, wherein certain ratios of neutralizing antibody titers at day 180 or 365 after administration of said first unit dose to the subject are achieved, and concomitantly administering a HPV vaccine, in particular a 9vHPV vaccine, such as GARDASIL® 9, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2:neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to the unit dose of the invention as described herein and the HPV vaccine, in particular a 9vHPV vaccine, such as GARDASIL® 9, for said uses, wherein said unit dose and said HPV vaccine are administered simultaneously. In some of these embodiments the simultaneous administration is on day 0 or day 90, preferably on day 0. In other embodiments the administration of said unit dose and said HPV vaccine are done sequentially.

In certain embodiments the invention is directed to the unit dose of the invention as described herein and the HPV vaccine, in particular a 9vHPV vaccine, such as GARDASIL® 9, for said uses, wherein said unit dose is administered by subcutaneous injection and wherein said HPV vaccine is administered by intramuscular injection. According to some embodiments the injections are administered to the arm, preferably to the deltoid region of the arm. According to some of these embodiments the subcutaneous injection of said unit dose and the intramuscular injection of said HPV vaccine are administered to different anatomical sites, such as to opposite arms, in particular when the vaccines are administered simultaneously.

In certain embodiments the invention is directed to the unit dose of the invention as described herein and the HPV vaccine, in particular a 9vHPV vaccine, such as GARDASIL® 9, for said uses, wherein two reconstituted unit doses of the invention as described herein are administered. In some embodiments the two unit doses of the invention as described herein are administered within 12 months or more, or within six months, or within three months, such as at day 0/1 and day 90. According to some of these embodiments a further third reconstituted unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to the unit dose of the invention as described herein and the HPV vaccine, in particular a 9vHPV vaccine, such as GARDASIL® 9, for said uses, wherein two reconstituted unit doses of the invention as described herein and two doses of the HPV vaccine are administered, in particular according to the following schedule

- a first simultaneous administration of the first reconstituted unit dose and the first dose of said HPV vaccine on day 0,
- a second administration of the second reconstituted unit dose after said first simultaneous administration, such as 3 month later and preferably on day 90, and
- a third administration of the second dose of said HPV vaccine after said second administration of the reconstituted unit dose, such as 3 month later and preferably on day 180.

In certain embodiments, the invention is directed to the unit dose of the invention as described herein and the HPV vaccine, in particular a 9vHPV vaccine, such as GARDASIL® 9, for said uses, wherein the subject or subject population is seronegative to all dengue serotypes. In certain embodiments, the invention is directed to the unit dose of the invention as described herein and the HPV vaccine, in particular a 9vHPV vaccine, such as GARDASIL® 9, for said uses, wherein said unit dose is reconstituted and administered subcutaneously to a subject or subject population and said HPV vaccine is administered intramuscularly to a subject or subject population, and wherein the subject or the subject population is seronegative with respect to all dengue serotypes. In other embodiments, the subject or subject population is seropositive with respect to at least one dengue serotype.

In certain embodiments, the invention is directed to the unit dose of the invention as described herein and the HPV vaccine, in particular a 9vHPV vaccine, such as GARDASIL® 9, for said uses, wherein said unit dose and said HPV vaccine are administered to a subject or subject population from a dengue endemic region. In certain embodiments, the reconstituted unit dose of the invention as described herein is administered subcutaneously and the HPV vaccine, in particular a 9vHPV vaccine, such as GARDASIL® 9, is administered intramuscularly to a subject or subject population from a dengue endemic region.

In certain embodiments the invention is directed to the unit dose of the invention as described herein and the HPV vaccine, in particular a 9vHPV vaccine, such as GARDASIL® 9, for said uses, wherein the reconstituted unit dose of the invention as described herein is administered subcutaneously and wherein the HPV vaccine, in particular a 9vHPV vaccine, such as GARDASIL® 9, is administered intramuscular to a subject or subject population of 9 to 25 years of age, preferably of 9 to 15 years of age. In some embodiments the subject or subject population is from a dengue endemic region. According to some of these embodiments, the subject or subject population is female. According to some of these embodiments, the subject or subject population is seronegative for all four dengue serotypes.

In a preferred embodiment the invention is directed to the unit dose of the invention as described herein and the HPV vaccine, in particular a 9vHPV vaccine, such as GARDASIL® 9, for use in a method of preventing dengue disease and HPV-associated cancers or genital warts in a subject comprising administering to the subject a subcutaneous injection of the reconstituted unit dose of the invention as described herein and an intramuscular injection of the HPV vaccine, in particular a 9vHPV vaccine, such as GARDASIL® 9, according to the above described administration schedule, wherein the subject is a female subject of 9 to 15 years of age from a dengue endemic region.

Use for the Manufacture of a Medicament in a Method of Prevention

The present invention is directed in part to the use of a unit dose of the invention as described herein for the manufacture of a medicament for preventing dengue disease in a subject, further comprising the use of a HPV vaccine, in particular a 9vHPV vaccine, such as GARDASIL® 9, for the manufacture of a medicament for preventing HPV-associated cancers or genital warts in the subject. In particular, the present invention is directed in part to a use of a unit dose of a dengue vaccine composition as described herein and a HPV vaccine, in particular a 9vHPV vaccine, such as GARDASIL® 9, for the manufacture of a medicament for preventing dengue disease and HPV-associated cancers or genital warts in a subject, respectively.

The present invention is directed in part to the use of a unit dose of the invention as described herein for the manufacture of a medicament for preventing dengue disease in a subject population, further comprising the use of a HPV vaccine, in particular a 9vHPV vaccine, such as GARDASIL® 9, for the manufacture of a medicament for preventing HPV-associated cancers or genital warts in the subject population. In particular, the present invention is directed in part to a use of a unit dose of a dengue vaccine composition as described herein and a HPV vaccine, in particular a 9vHPV vaccine, such as GARDASIL® 9, for the manufacture of a medicament for preventing dengue disease and HPV-associated cancers or genital warts in a subject population, respectively.

The present invention is in part directed to the use of a unit dose of the invention as described herein and a HPV vaccine, in particular a 9vHPV vaccine, such as GARDASIL® 9, for the manufacture of a medicament for preventing dengue disease and HPV-associated cancers or genital warts in a subject population, comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a HPV vaccine, in particular a 9vHPV vaccine, such as GARDASIL® 9, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the use of a unit dose of the invention as described herein and a HPV vaccine, in particular a 9vHPV vaccine, such as GARDASIL® 9, for the manufacture of a medicament for preventing dengue disease and HPV-associated cancers or genital warts in a subject, comprising administering to the subject at least a first reconstituted unit dose of the invention as described herein, wherein certain ratios of neutralizing antibody titers at day 180 or 365 after administration of said first unit dose to the subject are achieved, and concomitantly administering a HPV vaccine, in particular a 9vHPV vaccine, such as GARDASIL® 9, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2 neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to said uses, wherein the unit dose of the invention as described herein and the HPV vaccine, in particular a 9vHPV vaccine, such as GARDASIL® 9, are administered simultaneously. In some of these embodiments the simultaneous administration is on day 0 or day 90, preferably on day 0. In other embodiments the administration of the unit dose of the invention as described herein and the HPV vaccine, in particular a 9vHPV vaccine, such as GARDASIL® 9, are done sequentially.

In certain embodiments the invention is directed to said uses, wherein the unit dose of the invention as described herein is reconstituted and administered by subcutaneous injection and wherein the HPV vaccine, in particular a 9vHPV vaccine, such as GARDASIL® 9, is administered by intramuscular injection. According to some embodiments the injections are administered to the arm, preferably to the deltoid region of the arm. According to some of these embodiments the subcutaneous injection of the unit dose of the invention as described herein and the intramuscular injection of the HPV vaccine, in particular a 9vHPV vaccine, such as GARDASIL® 9, are administered to different anatomical sites such as to opposite arms, in particular when the vaccines are administered simultaneously.

In certain embodiments the invention is directed to said uses, wherein two reconstituted unit doses of the invention as described herein are administered. In some embodiments the two unit doses of the invention as described herein are administered within 12 months or more, or within six months, or within three months, such as at day 0/1 and day 90. According to some of these embodiments a further third unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to said uses, wherein two unit doses of the invention as described herein and two doses of a HPV vaccine, in particular a 9vHPV vaccine, such as GARDASIL® 9, are administered, in particular according to the following schedule

- a first simultaneous administration of the first reconstituted unit dose and the first dose of said HPV vaccine on day 0,
- a second administration of the second reconstituted unit dose after said simultaneous administration, such as 3 month later and preferably on day 90, and a third administration of the second dose of said HPV vaccine after said second administration of the reconstituted unit dose, such as 3 month later and preferably on day 180.

In certain embodiments, the invention is directed to said uses, wherein the subject or subject population is seronegative to all dengue serotypes. In certain embodiments, the invention is directed to said uses, wherein the unit dose of the invention as described herein is reconstituted and administered subcutaneously to a subject or subject population and the HPV vaccine, in particular a 9vHPV vaccine, such as GARDASIL® 9, is administered intramuscularly to a subject or subject population, and wherein the subject or the subject population is seronegative with respect to all dengue serotypes. In other embodiments, the subject or subject population is seropositive with respect to at least one dengue serotype.

In certain embodiments, the invention is directed to said uses, wherein the unit dose of the invention as described herein and the HPV vaccine, in particular a 9vHPV vaccine, such as GARDASIL® 9, are administered to a subject or subject population from a dengue endemic region. In certain embodiments, the reconstituted unit dose of the invention as described herein is administered subcutaneously and the HPV vaccine, in particular a 9vHPV vaccine, such as GARDASIL® 9, is administered intramuscularly to a subject or subject population from a dengue endemic region.

In certain embodiments the invention is directed to said uses, wherein the reconstituted unit dose of the invention as described herein is administered subcutaneously and the HPV vaccine, in particular a 9vHPV vaccine, such as GARDASIL® 9, is administered intramuscularly to a subject or subject population of 9 years to 25 years of age, preferably of 9 to 15 years of age. In some embodiments the subject or subject population is from a dengue endemic region. According to some of these embodiments, the subject or subject population is female. According to some of these embodiments, the subject or subject population is seronegative for all four dengue serotypes.

In a preferred embodiment the invention is directed to the use of a unit dose of a dengue vaccine composition as described herein and a HPV vaccine, in particular a 9vHPV vaccine, such as GARDASIL® 9, for the manufacture of a medicament for preventing dengue disease and HPV-associated cancers or genital warts in a subject comprising administering to the subject a subcutaneous injection of the reconstituted unit dose of the invention as described herein and an intramuscular injection of the HPV vaccine, in particular a 9vHPV vaccine, such as GARDASIL® 9, according to the above described administration schedule, wherein the subject is a female subject of 9 to 15 years of age from a dengue endemic region.

Method of Preventing Dengue Disease and Measles, Mumps and Rubella and Uses

Method of Prevention

The present invention is directed in part to a method of preventing dengue disease as well as measles, mumps and rubella in a subject. Thus, in certain embodiments the invention is directed to a method of preventing dengue disease in a subject, comprising administering to the subject a reconstituted unit dose of the invention as described herein, wherein the method further comprises preventing measles, mumps and rubella in the subject by concomitant administration of a MMR vaccine, such as M-M-R® II, to the subject.

The present invention is directed in part to a method of preventing dengue disease as well as measles, mumps and rubella in a subject population. Thus, in certain embodiments the invention is directed to a method of preventing dengue disease in a subject population, comprising administering to the subject population a reconstituted unit dose of the invention as described herein, wherein the method further comprises preventing measles, mumps and rubella in the subject population by concomitant administration of a MMR vaccine, such as M-M-R® II, to the subject population.

The present invention is in part directed to said method for preventing dengue disease and measles, mumps and rubella in a subject population comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a MMR vaccine, such as M-M-R® II, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2: GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to said method for preventing dengue disease and measles, mumps and rubella in a subject comprising administering to the subject at least a first reconstituted unit dose of the invention as described herein, wherein certain ratios of neutralizing antibody titers at day 180 or 365 after administration of said first unit dose to the subject are achieved, and concomitantly administering a MMR vaccine, such as M-M-R® II, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2: neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV- 2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to said methods, wherein the unit dose of the invention as described herein and the MMR vaccine, such as M-M-R® II, are administered simultaneously.

In some of these embodiments the simultaneous administration is on day 0 or day 90, preferably on day 0. In other embodiments the administration of the unit dose of the invention as described herein and the MMR vaccine, such as M-M-R® II, are done sequentially.

In certain embodiments the invention is directed to said methods, wherein the reconstituted unit dose of the invention as described herein is administered by subcutaneous injection and wherein the MMR vaccine, such as M-M-R® II, is administered by subcutaneous injection. According to some embodiments the injections are administered to the arm, preferably to the deltoid region of the arm. According to some of these embodiments the subcutaneous injection of the unit dose of the invention as described herein and the subcutaneous injection of the MMR vaccine, such as M-M-R® II, are administered to different anatomical sites, such as to opposite arms, in particular when the vaccines are administered simultaneously.

In certain embodiments the invention is directed to said methods, wherein two unit doses of the invention as described herein are administered. In some embodiments the two unit doses of the invention as described herein are administered within 12 month or more, or within 6 month, or within three months, such as at day 0/1 and day 90. According to some of these embodiments a further third unit dose of the invention as described herein is administered after the second. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to said methods, wherein two reconstituted unit doses of the invention as described herein and two doses of a MMR vaccine, such as M-M-R® II, are administered, in particular according to the following schedule

- a first simultaneous administration of the first reconstituted unit dose and the first dose of said MMR vaccine on day 0,
- a second administration of the second reconstituted unit dose after said first simultaneous administration, such as 3 months later and preferably on day 90, and
- a third administration of the second dose of said MMR vaccine after said second administration of the second reconstituted unit dose, such as 3 to 6 years after said first simultaneous administration.

In certain embodiments, the invention is directed to said methods, wherein the subject or subject population is seronegative to all dengue serotypes. In certain embodiments, the invention is directed to said methods, wherein the reconstituted unit dose of the invention as described herein and the MMR vaccine, such as M-M-R® II, are administered subcutaneously to a subject or subject population, and wherein the subject or the subject population is seronegative with respect to all dengue serotypes. In other embodiments, the subject or subject population is seropositive with respect to at least one dengue serotype.

In certain embodiments, the invention is directed to said methods, wherein the unit dose of the invention as described herein and the MMR vaccine, such as M-M-R® II, are administered to a subject or subject population from a dengue endemic region. In certain embodiments, the reconstituted unit dose of the invention as described herein and the MMR vaccine, such as M-M-R® II, are administered subcutaneously to a subject or subject population from a dengue endemic region.

In certain embodiments the invention is directed to said methods, wherein the reconstituted unit dose of the invention as described herein and wherein the MMR vaccine, such as M-M-R® II, are administered subcutaneously to a subject or subject population of 1 to 10 years of age, preferably 2 months to 7 years of age. In some embodiments the subject or subject population is from a dengue endemic region. In another embodiment, the subject or subject population is from a dengue non-endemic region. According to some of these embodiments, the subject or subject population is seronegative for all four dengue serotypes.

Unit Dose for Use in a Method of Prevention

The present invention is directed in part to the unit dose of the invention as described herein for use in a method of preventing dengue disease in a subject, wherein the method also comprises the prevention of measles, mumps and rubella in the subject with a MMR vaccine, such as M-M-R® II. In particular, the present invention is directed in part to a unit dose of a dengue vaccine composition as described herein and a MMR vaccine, such as M-M-R® II, for use in a method of preventing dengue disease and measles, mumps and rubella in a subject, respectively.

The present invention is directed in part to the unit dose of the invention as described herein for use in a method of preventing dengue disease in a subject population, wherein the method also comprises the prevention of measles, mumps and rubella in the subject population with a MMR vaccine, such as M-M-R® II. In particular, the present invention is directed in part to a unit dose of a dengue vaccine composition as described herein and a MMR vaccine, such as M-M-R® II, for use in a method of preventing dengue disease and measles, mumps and rubella in a subject population, respectively.

The present invention is in part directed to the unit dose of a dengue vaccine composition as described herein and the MMR vaccine, such as M-M-R® II, for use in a method of preventing dengue disease and measles, mumps and rubella in a subject population, comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a MMR vaccine, such as M-M-R® II, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2: GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the unit dose of a dengue vaccine composition as described herein and the MMR vaccine, such as M-M-R® II, for use in a method of preventing dengue disease and measles, mumps and rubella in a subject comprising administering to the subject at least a first reconstituted unit dose of the invention as described herein, wherein certain ratios of neutralizing antibody titers at day 180 or 365 after administration of said first unit dose to the subject are achieved, and concomitantly administering a MMR vaccine, such as M-M-R® II, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2: neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to the unit dose of the invention as described herein and the MMR vaccine, such as M-M-R® II, for said uses, wherein said unit dose and said MMR vaccine are administered simultaneously. In some of these embodiments the simultaneous administration is on day 0 or day 90, preferably on day 0. In other embodiments the administration of said unit dose and said MMR vaccine are done sequentially.

In certain embodiments the invention is directed to the unit dose of the invention as described herein and the MMR vaccine, such as M-M-R® II, for said uses, wherein said unit dose is administered by subcutaneous injection and wherein said MMR vaccine is administered by subcutaneous injection. According to some embodiments the injections are administered to the arm, preferably to the deltoid region of the arm. According to some of these embodiments the subcutaneous injection of said unit dose and the subcutaneous injection of said MMR vaccine are administered to different anatomical sites, such as to opposite arms, in particular when the vaccines are administered simultaneously.

In certain embodiments the invention is directed to the unit dose of the invention as described herein and the MMR vaccine, such as M-M-R® II, for said uses, wherein two reconstituted unit doses of the invention as described herein are administered. In some embodiments the two unit doses of the invention as described herein are administered within 12 months or more, or within six months, or within three months, such as at day 0/1 and day 90. According to some of these embodiments a further third reconstituted unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to the unit dose of the invention as described herein and the MMR vaccine, such as M-M-R® II, for said uses, wherein two reconstituted unit doses of the invention as described herein and two doses of the MMR vaccine are administered, in particular according to the following schedule a first simultaneous administration of the first reconstituted unit dose and the first dose of said MMR vaccine on day 0, a second administration of the second reconstituted unit dose after said first simultaneous administration, such as 3 months later and preferably on day 90, and a third administration of the second dose of said MMR vaccine after said second administration of the second reconstituted unit dose, such as 3 to 6 years after said first simultaneous administration.

In certain embodiments, the invention is directed to the unit dose of the invention as described herein and the MMR vaccine, such as M-M-R® II, for said uses, wherein the subject or subject population is seronegative to all dengue serotypes. In certain embodiments, the invention is directed to the unit dose of the invention as described herein and the MMR vaccine, such as M-M-R® II, for said uses, wherein said unit dose is reconstituted and administered subcutaneously to a subject or subject population and said MMR vaccine is administered subcutaneously to a subject or subject population, and wherein the subject or the subject population is seronegative with respect to all dengue serotypes. In other embodiments, the subject or subject population is seropositive with respect to at least one dengue serotype.

In certain embodiments, the invention is directed to the unit dose of the invention as described herein and the MMR vaccine, such as M-M-R® II, for said uses, wherein said unit dose and said MMR vaccine are administered to a subject or subject population from a dengue endemic region. In certain embodiments, the reconstituted unit dose of the invention as described herein and the MMR vaccine, such as M-M-R® II, are administered subcutaneously to a subject or subject population from a dengue endemic region.

In certain embodiments the invention is directed to the unit dose of the invention as described herein and the MMR vaccine, such as M-M-R® II, for said uses, wherein the reconstituted unit dose of the invention as described herein and the MMR vaccine, such as M-M-R® II, are administered subcutaneously to a subject or subject population of 1 to 10 years of age, preferably of 2 months to 7 years of age. In some embodiments, the subject or subject population is from a dengue endemic region. In another embodiment, the subject or subject population is from a dengue non-endemic region. According to some of these embodiments, the subject or subject population is seronegative for all four dengue serotypes.

Use for the Manufacture of a Medicament in a Method of Prevention

The present invention is directed in part to the use of a unit dose of the invention as described herein for the manufacture of a medicament for preventing dengue disease in a subject, further comprising the use of a MMR vaccine, such as M-M-R® II, for the manufacture of a medicament for preventing measles, mumps and rubella in the subject. In particular, the present invention is directed in part to a use of a unit dose of a dengue vaccine composition as described herein and a MMR vaccine, such as M-M-R® II, for the manufacture of a medicament for preventing dengue disease and measles, mumps and rubella in a subject, respectively.

The present invention is directed in part to the use of a unit dose of the invention as described herein for the manufacture of a medicament for preventing dengue disease in a subject population, further comprising the use of a MMR vaccine, such as M-M-R® II, for the manufacture of a medicament for preventing measles, mumps and rubella in the subject population. In particular, the present invention is directed in part to a use of a unit dose of a dengue vaccine composition as described herein and a MMR vaccine, such as M-M-R® II, for the manufacture of a medicament for preventing dengue disease and measles, mumps and rubella in a subject population, respectively.

The present invention is in part directed to the use of a unit dose of the invention as described herein and a MMR vaccine, such as M-M-R® II, for the manufacture of a medicament for preventing dengue disease and measles, mumps and rubella in a subject population, comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a MMR vaccine, such as M-M-R® II, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the use of a unit dose of the invention as described herein and a MMR vaccine, such as M-M-R® II, for the manufacture of a medicament for preventing dengue disease and measles, mumps and rubella in a subject, comprising administering to the subject at least a first reconstituted unit dose of the invention as described herein, wherein certain ratios of neutralizing antibody titers at day 180 or 365 after administration of said first unit dose to the subject are achieved, and concomitantly administering a MMR vaccine, such as M-M-R® II, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2:neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to said uses, wherein the unit dose of the invention as described herein and the MMR vaccine, such as M-M-R® II, are administered simultaneously. In some of these embodiments the simultaneous administration is on day 0 or day 90, preferably on day 0. In other embodiments the administration of the unit dose of the invention as described herein and the MMR vaccine, such as M-M-R® II, are done sequentially.

In certain embodiments the invention is directed to said uses, wherein the unit dose of the invention as described herein is reconstituted and administered by subcutaneous injection and wherein the MMR vaccine, such as M-M-R® II, is administered by subcutaneous injection. According to some embodiments the injections are administered to the arm, preferably to the deltoid region of the arm. According to some of these embodiments the subcutaneous injection of the unit dose of the invention as described herein and the subcutaneous injection of the MMR vaccine, such as M-M-R® II, are administered to different anatomical sites such as to opposite arms, in particular when the vaccines are administered simultaneously.

In certain embodiments the invention is directed to said uses, wherein two reconstituted unit doses of the invention as described herein are administered. In some embodiments the two unit doses of the invention as described herein are administered within 12 months or more, or within six months, or within three months, such as at day 0/1 and day 90. According to some of these embodiments a further third unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to said uses, wherein two unit doses of the invention as described herein and two doses of a MMR vaccine, such as M-M-R® II, are administered, in particular according to the following schedule a first simultaneous administration of the first reconstituted unit dose and the first dose of said MMR vaccine on day 0, a second administration of the second reconstituted unit dose after said first simultaneous administration, such as 3 months later and preferably on day 90, and a third administration of the second dose of said MMR vaccine after said second administration of the second reconstituted unit dose, such as 3 to 6 years after said first simultaneous administration.

In certain embodiments, the invention is directed to said uses, wherein the subject or subject population is seronegative to all dengue serotypes. In certain embodiments, the invention is directed to said uses, wherein the unit dose of the invention as described herein is reconstituted and administered subcutaneously to a subject or subject population and the MMR vaccine, such as M-M-R® II, is administered subcutaneously to a subject or subject population, and wherein the subject or the subject population is seronegative with respect to all dengue serotypes. In other embodiments, the subject or subject population is seropositive with respect to at least one dengue serotype.

In certain embodiments, the invention is directed to said uses, wherein the unit dose of the invention as described herein and the MMR vaccine, such as M-M-R® II, are administered to a subject or subject population from a dengue endemic region. In certain embodiments, the reconstituted unit dose of the invention as described herein and the MMR vaccine, such as M-M-R® II, are administered subcutaneously to a subject or subject population from a dengue endemic region.

In certain embodiments the invention is directed to said uses, wherein the reconstituted unit dose of the invention as described herein and the MMR vaccine, such as M-M-R® II, are administered subcutaneously to a subject or subject population of 1 to 10 years of age, preferably of 2 months to 7 years of age. In some embodiments, the subject or subject population is from a dengue endemic region. In another embodiment, the subject or subject population is from a dengue non-endemic region. According to some of these embodiments, the subject or subject population is seronegative for all four dengue serotypes.

Method of Preventing Dengue Disease and Tetanus, Diphtheria, and Pertussis and Uses

Method of Prevention

The present invention is directed in part to a method of preventing dengue disease, as well as tetanus, diphtheria, and pertussis in a subject. Thus, in certain embodiments the invention is directed to a method of preventing dengue disease in a subject, comprising administering to the subject a reconstituted unit dose of the invention as described herein, wherein the method further comprises preventing tetanus, diphtheria, and pertussis in the subject by concomitant administration of a Tdap vaccine, in particular a combined tetanus toxoid, reduced diphtheria toxoid and acellular pertussis (adsorbed) vaccine, such as BOOSTRIX®, to the subject.

The present invention is directed in part to a method of preventing dengue disease, as well as tetanus, diphtheria, and pertussis in a subject population. Thus, in certain embodiments the invention is directed to a method of preventing dengue disease, in a subject population, comprising administering to the subject population a reconstituted unit dose of the invention as described herein, wherein the method further comprises preventing tetanus, diphtheria, and pertussis in the subject population by concomitant administration of a Tdap vaccine, in particular a combined tetanus toxoid, reduced diphtheria toxoid and acellular pertussis (adsorbed) vaccine, such as BOOSTRIX®, to the subject population.

The present invention is in part directed to said method for preventing dengue disease and tetanus, diphtheria, and pertussis in a subject population comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a Tdap vaccine, in particular a combined tetanus toxoid, reduced diphtheria toxoid and acellular pertussis (adsorbed) vaccine, such as BOOSTRIX®, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or nor more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to said method for preventing dengue disease and tetanus, diphtheria, and pertussis in a subject comprising administering to the subject at least a first reconstituted unit dose of the invention as described herein, wherein certain ratios of neutralizing antibody titers at day 180 or 365 after administration of said first unit dose to the subject are achieved, and concomitantly administering a Tdap vaccine, in particular a combined tetanus toxoid, reduced diphtheria toxoid and acellular pertussis (adsorbed) vaccine, such as BOOSTRIX®, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2:neutralizing antibody titer for GMT DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to said methods, wherein the unit dose of the invention as described herein and the Tdap vaccine, in particular a combined tetanus toxoid, reduced diphtheria toxoid and acellular pertussis (adsorbed) vaccine, such as BOOSTRIX®, are administered simultaneously. In some of these embodiments, the simultaneous administration is on day 0 or day 90, preferably on day 0. In other embodiments, the administration of the unit dose of the invention as described herein and the Tdap vaccine, in particular combined tetanus toxoid, reduced diphtheria toxoid and acellular pertussis (adsorbed) vaccine, such as BOOSTRIX®, are done sequentially.

In certain embodiments, the invention is directed to said methods, wherein the reconstituted unit dose of the invention as described herein is administered by subcutaneous injection and wherein the Tdap vaccine, in particular a combined tetanus toxoid, reduced diphtheria toxoid and acellular pertussis (adsorbed) vaccine, such as BOOSTRIX®, is administered by intramuscular injection. According to some embodiments, the injections are administered to the arm, preferably to the deltoid region of the arm. According to some of these embodiments, the subcutaneous injection of the unit dose of the invention as described herein and the intramuscular injection of the Tdap vaccine, in particular a combined tetanus toxoid, reduced diphtheria toxoid and acellular pertussis (adsorbed) vaccine, such as BOOSTRIX®, are administered to different anatomical sites, such as to opposite arms, in particular when the vaccines are administered simultaneously.

In certain embodiments, the invention is directed to said methods, wherein two unit doses of the invention as described herein are administered. In some embodiments, the two unit doses of the invention as described herein are administered within 12 months or more, or within 6 months, or within 3 months, such as at day 0/1 and day 90. According to some of these embodiments a further third unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments, the invention is directed to said methods, wherein two reconstituted unit doses of the invention as described herein and one dose of a Tdap vaccine, in particular a combined tetanus toxoid, reduced diphtheria toxoid and acellular pertussis (adsorbed) vaccine, such as BOOSTRIX®, are administered, in particular according to the following schedule:

a first simultaneous administration of the first reconstituted unit dose and said Tdap vaccine on day 0, and a second administration of the second reconstituted unit dose after said first simultaneous administration, such as 3 months later and preferably on day 90.

In certain embodiments, the invention is directed to said methods, wherein the subject or subject population is seronegative to all dengue serotypes. In certain embodiments, the invention is directed to said methods, wherein the reconstituted unit dose of the invention as described herein is administered subcutaneously to a subject or subject population and the Tdap vaccine, in particular a combined tetanus toxoid, reduced diphtheria toxoid and acellular pertussis (adsorbed) vaccine, such as BOOSTRIX®, is administered intramuscularly to a subject or subject population, and wherein the subject or the subject population is seronegative with respect to all dengue serotypes. In other embodiments, the subject or subject population is seropositive with respect to at least one dengue serotype.

In certain embodiments, the invention is directed to said methods, wherein the unit dose of the invention as described herein and the Tdap vaccine, in particular a combined tetanus toxoid, reduced diphtheria toxoid and acellular pertussis (adsorbed) vaccine, such as BOOSTRIX®, are administered to a subject or subject population from a dengue endemic region. In certain embodiments, the reconstituted unit dose of the invention as described herein is administered subcutaneously and the Tdap vaccine, in particular a combined tetanus toxoid, reduced diphtheria toxoid and acellular pertussis (adsorbed) vaccine, such as BOOSTRIX®, is administered intramuscularly to a subject or subject population from a dengue endemic region.

In certain embodiments, the invention is directed to said methods, wherein the reconstituted unit dose of the invention as described herein is administered subcutaneously and wherein the Tdap vaccine, in particular a combined tetanus toxoid, reduced diphtheria toxoid and acellular pertussis (adsorbed) vaccine, such as BOOSTRIX®, is administered intramuscularly to a subject or subject population of 10 to 18 years of age. In some embodiments, the subject or subject population is from a dengue endemic region. According to some of these embodiments, the subject or subject population is seronegative for all four dengue serotypes.

In a preferred embodiment, the invention is directed a method of preventing dengue disease, and tetanus, diphtheria and pertussis in a subject comprising administering to the subject a subcutaneous injection of the reconstituted unit dose of the invention as described herein and an intramuscular injection of the Tdap vaccine, in particular a combined tetanus toxoid, reduced diphtheria toxoid and acellular pertussis (adsorbed) vaccine, such as BOOSTRIX®, according to the above described administration schedule, wherein the subject is between 10 years and 18 years of age and from a dengue endemic region.

Unit Dose for Use in a Method of Prevention

The present invention is directed in part to the unit dose of the invention as described herein for use in a method of preventing dengue disease in a subject, wherein the method also comprises the prevention of tetanus, diphtheria, and pertussis in the subject with a Tdap vaccine, in particular a combined tetanus toxoid, reduced diphtheria toxoid and acellular pertussis (adsorbed) vaccine, such as BOOSTRIX®. In particular, the present invention is directed in part to a unit dose of a dengue vaccine composition as described herein and a Tdap vaccine, in particular a combined tetanus toxoid, reduced diphtheria toxoid and acellular pertussis (adsorbed) vaccine, such as BOOSTRIX®, for use in a method of preventing dengue disease, and tetanus, diphtheria, and pertussis in a subject, respectively.

The present invention is directed in part to the unit dose of the invention as described herein for use in a method of preventing dengue disease in a subject population, wherein the method also comprises the prevention of tetanus, diphtheria, and pertussis in a subject population with a Tdap vaccine, in particular a combined tetanus toxoid, reduced diphtheria toxoid and acellular pertussis (adsorbed) vaccine, such as BOOSTRIX®. In particular, the present invention is directed in part to a unit dose of a dengue vaccine composition as described herein and a Tdap vaccine, in particular a combined tetanus toxoid, reduced diphtheria toxoid and acellular pertussis (adsorbed) vaccine, such as BOOSTRIX®, for use in a method of preventing dengue disease, and tetanus, diphtheria, and pertussis in a subject population, respectively.

The present invention is in part directed to the unit dose of a dengue vaccine composition as described herein and the Tdap vaccine, in particular a combined tetanus toxoid, reduced diphtheria toxoid and acellular pertussis (adsorbed) vaccine, such as BOOSTRIX®, for use in a method of preventing dengue disease and tetanus, diphtheria, and pertussis in a subject population, comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a Tdap vaccine, in particular a combined tetanus toxoid, reduced diphtheria toxoid and acellular pertussis (adsorbed) vaccine, such as BOOSTRIX®, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the unit dose of a dengue vaccine composition as described herein and the Tdap vaccine, in particular a combined tetanus toxoid, reduced diphtheria toxoid and acellular pertussis (adsorbed) vaccine, such as BOOSTRIX®, for use in a method of preventing dengue disease and tetanus, diphtheria, and pertussis in a subject comprising administering to the subject at least a first reconstituted unit dose of the invention as described herein, wherein certain ratios of neutralizing antibody titers at day 180 or 365 after administration of said first unit dose to the subject are achieved, and concomitantly administering a Tdap vaccine, in particular a combined tetanus toxoid, reduced diphtheria toxoid and acellular pertussis (adsorbed) vaccine, such as BOOSTRIX®, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2:neutralizing antibody titer for GMT DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to the unit dose of the invention as described herein and the Tdap vaccine, in particular a combined tetanus toxoid, reduced diphtheria toxoid and acellular pertussis (adsorbed) vaccine, such as BOOSTRIX®, for said uses, wherein said unit dose and said Tdap vaccine are administered simultaneously. In some of these embodiments, the simultaneous administration is on day 0 or day 90, preferably on day 0. In other embodiments the administration of said unit dose and said Tdap vaccine are done sequentially.

In certain embodiments, the invention is directed to the unit dose of the invention as described herein and the Tdap vaccine, in particular a combined tetanus toxoid, reduced diphtheria toxoid and acellular pertussis (adsorbed) vaccine, such as BOOSTRIX®, for said uses, wherein said unit dose is administered by subcutaneous injection and wherein said Tdap vaccine is administered by intramuscular injection. According to some embodiments, the injections are administered to the arm, preferably to the deltoid region of the arm. According to some of these embodiments, the subcutaneous injection of said unit dose and the intramuscular injection of said Tdap vaccine are administered to different anatomical sites, such as to opposite arms, in particular when the vaccines are administered simultaneously.

In certain embodiments, the invention is directed to the unit dose of the invention as described herein and the Tdap vaccine, in particular a combined tetanus toxoid, reduced diphtheria toxoid and acellular pertussis (adsorbed) vaccine, such as BOOSTRIX®, for said uses, wherein two reconstituted unit doses of the invention as described herein are administered within 12 months or more, or within six months, or within three months, such as at day 0/1 and at day 90. According to some of these embodiments a further third reconstituted unit dose of the invention as described herein is administered after the second administration. Such a third administration may act as a booster and may be administered between 6 to 12 months after the first administration, such as 12 months after the first administration, or later than 12 months after the first administration, such as 12 months (1 year) after the second administration or even 5 years or longer after the first or second administration.

In certain embodiments the invention is directed to the unit dose of the invention as described herein and the Tdap vaccine, in particular a combined tetanus toxoid, reduced diphtheria toxoid and acellular pertussis (adsorbed) vaccine, such as BOOSTRIX®, for said uses, wherein two reconstituted unit doses of the invention as described herein and one dose of the Tdap vaccine are administered, in particular according to the following schedule

- a first simultaneous administration of the first reconstituted unit dose and said Tdap vaccine on day 0, and
- a second administration of the second reconstituted unit dose after said first simultaneous administration, such as 3 months later and preferably on day 90.

In certain embodiments, the invention is directed to the unit dose of the invention as described herein and the Tdap vaccine, in particular a combined tetanus toxoid, reduced diphtheria toxoid and acellular pertussis (adsorbed) vaccine, such as BOOSTRIX®, for said uses, wherein the subject or subject population is seronegative to all dengue serotypes. In certain embodiments, the invention is directed to the unit dose of the invention as described herein and the Tdap vaccine, in particular a combined tetanus toxoid, reduced diphtheria toxoid and acellular pertussis (adsorbed) vaccine, such as BOOSTRIX®, for said uses, wherein said unit dose is reconstituted and administered subcutaneously to a subject or subject population and said Tdap vaccine is administered intramuscularly to a subject or subject population, and wherein the subject or the subject population is seronegative with respect to all dengue serotypes. In other embodiments, the subject or subject population is seropositive with respect to at least one dengue serotype.

In certain embodiments, the invention is directed to the unit dose of the invention as described herein and the Tdap vaccine, in particular a combined tetanus toxoid, reduced diphtheria toxoid and acellular pertussis (adsorbed) vaccine, such as BOOSTRIX®, for said uses, wherein said unit dose and said Tdap vaccine are administered to a subject or subject population from a dengue endemic region. In certain embodiments, the reconstituted unit dose of the invention as described herein is administered subcutaneously and the Tdap vaccine, in particular a combined tetanus toxoid, reduced diphtheria toxoid and acellular pertussis (adsorbed) vaccine, such as BOOSTRIX®, is administered intramuscularly to a subject or subject population from a dengue endemic region.

In certain embodiments the invention is directed to the unit dose of the invention as described herein and the Tdap vaccine, in particular a combined tetanus toxoid, reduced diphtheria toxoid and acellular pertussis (adsorbed) vaccine, such as BOOSTRIX®, for said uses, wherein the reconstituted unit dose of the invention as described herein is administered subcutaneously and wherein the Tdap vaccine, in particular a combined tetanus toxoid, reduced diphtheria toxoid and acellular pertussis (adsorbed) vaccine, such as BOOSTRIX®, is administered intramuscularly to a subject or subject population of 10 to 18 years of age. In some embodiments, the subject or subject population is from a dengue endemic region. According to some of these embodiments, the subject or subject population is seronegative for all four dengue serotypes.

In a preferred embodiment, the invention is directed to the unit dose of the invention as described herein and the Tdap vaccine, in particular a combined tetanus toxoid, reduced diphtheria toxoid and acellular pertussis (adsorbed) vaccine, such as BOOSTRIX®, for use in a method of preventing dengue disease and tetanus, diphtheria and pertussis in a subject comprising administering to the subject a subcutaneous injection of the reconstituted unit dose of the invention as described herein and an intramuscular injection of the Tdap vaccine, in particular a combined tetanus toxoid, reduced diphtheria toxoid and acellular pertussis (adsorbed) vaccine, such as BOOSTRIX®, according to the above described administration schedule, wherein the subject is of 10 to 18 years of age and from a dengue endemic region.

Use for the Manufacture of a Medicament in a Method of Prevention

The present invention is directed in part to the use of a unit dose of the invention as described herein for the manufacture of a medicament for preventing dengue disease in a subject, further comprising the use of a Tdap vaccine, in particular a combined tetanus toxoid, reduced diphtheria toxoid and acellular pertussis (adsorbed) vaccine, such as BOOSTRIX®, for the manufacture of a medicament for preventing tetanus, diphtheria, and pertussis in the subject. In particular, the present invention is directed in part to a use of a unit dose of a dengue vaccine composition as described herein and a Tdap vaccine, in particular a combined tetanus toxoid, reduced diphtheria toxoid and acellular pertussis (adsorbed) vaccine, such as BOOSTRIX®, for the manufacture of a medicament for preventing dengue disease and tetanus, diphtheria, and pertussis in a subject, respectively.

The present invention is directed in part to the use of a unit dose of the invention as described herein for the manufacture of a medicament for preventing dengue disease, in a subject population, further comprising the use of a Tdap vaccine, in particular a combined tetanus toxoid, reduced diphtheria toxoid and acellular pertussis (adsorbed) vaccine, such as BOOSTRIX®, for the manufacture of a medicament for preventing tetanus, diphtheria, and pertussis in the subject population. In particular, the present invention is directed in part to a use of a unit dose of a dengue vaccination composition as described herein and a Tdap vaccine, in particular a combined tetanus toxoid, reduced diphtheria toxoid and acellular pertussis (adsorbed) vaccine, such as BOOSTRIX®, for the manufacture of a medicament for preventing dengue disease and tetanus, diphtheria, and pertussis in a subject population, respectively.

The present invention is in part directed to the use of a unit dose of the invention as described herein and a Tdap vaccine, in particular a combined tetanus toxoid, reduced diphtheria toxoid and acellular pertussis (adsorbed) vaccine, such as BOOSTRIX®, for the manufacture of a medicament for preventing dengue disease and tetanus, diphtheria, and pertussis, comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a Tdap vaccine, in particular a combined tetanus toxoid, reduced diphtheria toxoid and acellular pertussis (adsorbed) vaccine, such as BOOSTRIX®, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the use of a unit dose of the invention as described herein and a Tdap vaccine, in particular a combined tetanus toxoid, reduced diphtheria toxoid and acellular pertussis (adsorbed) vaccine, such as BOOSTRIX®, for the manufacture of a medicament for preventing dengue disease and tetanus, diphtheria, and pertussis in a subject, comprising administering to the subject at least a first reconstituted unit dose of the invention as described herein, wherein certain ratios of neutralizing antibody titers at day 180 or 365 after administration of said first unit dose to the subject are achieved, and concomitantly administering a Tdap vaccine, in particular a combined tetanus toxoid, reduced diphtheria toxoid and acellular pertussis (adsorbed) vaccine, such as BOOSTRIX®, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2:neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to said uses, wherein the unit dose of the invention as described herein and the Tdap vaccine, in particular a combined tetanus toxoid, reduced diphtheria toxoid and acellular pertussis (adsorbed) vaccine, such as BOOSTRIX®, are administered simultaneously. In some of these embodiments, the simultaneous administration is on day 0 or day 90, preferably on day 0. In other embodiments, the administration of the unit dose of the invention as described herein and the Tdap vaccine, in particular a combined tetanus toxoid, reduced diphtheria toxoid and acellular pertussis (adsorbed) vaccine, such as BOOSTRIX®, are done sequentially.

In certain embodiments, the invention is directed to said uses, wherein the unit dose of the invention as described herein is reconstituted and administered by subcutaneous injection and wherein the Tdap vaccine, in particular a combined tetanus toxoid, reduced diphtheria toxoid and acellular pertussis (adsorbed) vaccine, such as BOOSTRIX®, is administered by intramuscular injection. According to some embodiments, the injections are administered to the arm, preferably to the deltoid region of the arm. According to some of these embodiments the subcutaneous injection of the unit dose of the invention as described herein and the intramuscular injection of the Tdap vaccine, in particular a combined tetanus toxoid, reduced diphtheria toxoid and acellular pertussis (adsorbed) vaccine, such as BOOSTRIX®, are administered to different anatomical sites, such as to opposite arms, in particular when the vaccines are administered simultaneously.

In certain embodiments, the invention is directed to said uses, wherein two reconstituted unit doses of the invention as described herein are administered. In some embodiments, the two unit doses of the invention as described herein are administered within 12 months or more, or within six months, or within three months, such as at day 0/1 and day 90. According to some of these embodiments a further third unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments, the invention is directed to said uses, wherein two unit doses of the invention as described herein and one dose of a Tdap vaccine, in particular a combined tetanus toxoid, reduced diphtheria toxoid and acellular pertussis (adsorbed) vaccine, such as BOOSTRIX®, are administered, in particular according to the following schedule a first simultaneous administration of the first reconstituted unit dose and said Tdap vaccine on day 0, and a second administration of the second reconstituted unit dose after said first simultaneous administration, such as 3 months later and preferably on day 90.

In certain embodiments, the invention is directed to said uses, wherein the subject or subject population is seronegative to all dengue serotypes. In certain embodiments, the invention is directed to said uses, wherein the unit dose of the invention as described herein is reconstituted and administered subcutaneously to a subject or subject population and the Tdap vaccine, in particular a combined tetanus toxoid, reduced diphtheria toxoid and acellular pertussis (adsorbed) vaccine, such as BOOSTRIX®, is administered intramuscularly to a subject or subject population, and wherein the subject or the subject population is seronegative with respect to all dengue serotypes. In other embodiments, the subject or subject population is seropositive with respect to at least one dengue serotype.

In certain embodiments, the invention is directed to said uses, wherein the unit dose of the invention as described herein and the Tdap vaccine, in particular a combined tetanus toxoid, reduced diphtheria toxoid and acellular pertussis (adsorbed) vaccine, such as BOOSTRIX®, are administered to a subject or subject population from a dengue endemic region. In certain embodiments, the reconstituted unit dose of the invention as described herein is administered subcutaneously and the Tdap vaccine, in particular a combined tetanus toxoid, reduced diphtheria toxoid and acellular pertussis (adsorbed) vaccine, such as BOOSTRIX®, is administered intramuscularly to a subject or subject population from a dengue endemic region.

In certain embodiments, the invention is directed to said uses, wherein the reconstituted unit dose of the invention as described herein is administered subcutaneously and the Tdap vaccine, in particular a combined tetanus toxoid, reduced diphtheria toxoid and acellular pertussis (adsorbed) vaccine, such as BOOSTRIX®, is administered intramuscularly to a subject or subject population of 10 to 18 years of age. In some embodiments, the subject or subject population is from a dengue endemic region. According to some of these embodiments, the subject or subject population is seronegative for all four dengue serotypes.

In a preferred embodiment the invention is directed to the use of a unit dose of a dengue vaccine composition as described herein and the Tdap vaccine, in particular a combined tetanus toxoid, reduced diphtheria toxoid and acellular pertussis (adsorbed) vaccine, such as BOOSTRIX®, for the manufacture of a medicament for preventing dengue disease and tetanus, diphtheria and pertussis in a subject comprising administering to the subject a subcutaneous injection of the reconstituted unit dose of the invention as described herein and an intramuscular injection of the Tdap vaccine, in particular a combined tetanus toxoid, reduced diphtheria toxoid and acellular pertussis (adsorbed) vaccine, such as BOOSTRIX®, according to the above described administration schedule, wherein the subject is of 10 to 18 years of age and from a dengue endemic region.

Method of Preventing Dengue Disease and Diphtheria, Tetanus, Pertussis, Poliomyelitis and Diseases Caused by *Haemophilus influenzae* Type b and Uses

Method of Prevention

The present invention is directed in part to a method of preventing dengue disease as well as diphtheria, tetanus, pertussis, poliomyelitis and diseases caused by *Haemophilus influenzae* type b in a subject. Thus, in certain embodiments the invention is directed to a method of preventing dengue disease in a subject, comprising administering to the subject a reconstituted unit dose of the invention as described herein, wherein the method further comprises preventing diphtheria, tetanus, pertussis, poliomyelitis and diseases caused by *Haemophilus influenzae* type b in the subject by concomitant administration of a DTaP/IPV/Hib vaccine, in particular a combined DTaP/IPV/Hib vaccine, such as Pentacel®, to the subject.

The present invention is directed in part to a method of preventing dengue disease as well as diphtheria, tetanus, pertussis, poliomyelitis and diseases caused by *Haemophilus influenzae* type b in a subject population. Thus, in certain embodiments the invention is directed to a method of preventing dengue disease in a subject population, comprising administering to the subject population a reconstituted unit dose of the invention as described herein, wherein the method further comprises preventing diphtheria, tetanus, pertussis, poliomyelitis and diseases caused by *Haemophilus influenzae* type b in the subject population by concomitant administration of a DTaP/IPV/Hib vaccine, in particular a combined DTaP/IPV/Hib vaccine, such as Pentacel®, to the subject population.

The present invention is in part directed to said method for preventing dengue disease and diphtheria, tetanus, pertussis, poliomyelitis and diseases caused by *Haemophilus influenzae* type b in a subject population comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a DTaP/IPV/Hib vaccine, in particular a combined DTaP/IPV/Hib vaccine, such as Pentacel®, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to said method for preventing dengue disease and diphtheria, tetanus, pertussis, poliomyelitis and diseases caused by *Haemophilus influenzae* type b in a subject comprising administering to the subject at least a first reconstituted unit dose of the invention as described herein, wherein certain ratios of neutralizing antibody titers at day 180 or 365 after administration of said first unit dose to the subject are achieved, and concomitantly administering a DTaP/IPV/Hib vaccine, in particular a combined DTaP/IPV/Hib vaccine, such as Pentacel®, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2:neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to said methods, wherein the unit dose of the invention as described herein and the DTaP/IPV/Hib vaccine, in particular a combined DTaP/IPV/Hib vaccine, such as Pentacel®, are administered simultaneously. In some of these embodiments the simultaneous administration is on day 0 or day 90, preferably on day 0. In other embodiments the administration of the unit dose of the invention as described herein and the DTaP/IPV/Hib vaccine, in particular a combined DTaP/IPV/Hib vaccine, such as Pentacel®, are done sequentially.

In certain embodiments the invention is directed to said methods, wherein the reconstituted unit dose of the invention as described herein is administered by subcutaneous injection and wherein the DTaP/IPV/Hib vaccine, in particular a combined DTaP/IPV/Hib vaccine, such as Pentacel®, is administered by intramuscular injection. According to some embodiments, the unit dose of the invention as described herein is administered to the arm, preferably to the deltoid region of the arm. According to some embodiments, the subcutaneous injection of the unit dose of the invention as described herein and the intramuscular injection of the DTaP/IPV/Hib vaccine, in particular a combined DTaP/IPV/Hib vaccine, such as Pentacel®, are administered to different anatomical sites. According to some of these embodiments, said unit dose is administered subcutaneously to the arm, preferably to the deltoid region, and said DTaP/IPV/Hib vaccine is administered intramuscularly to the thigh, preferably to the anterolateral aspect of the thigh.

In certain embodiments the invention is directed to said methods, wherein two unit doses of the invention as described herein are administered. In some embodiments the two unit doses of the invention as described herein are administered within 12 month or more, or within 6 month, or within three months, such as at day 0/1 and day 90. According to some of these embodiments a further third unit dose of the invention as described herein is administered after the second. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to said methods, wherein two reconstituted unit doses of the invention as described herein and four doses of a DTaP/IPV/Hib vaccine, in particular a combined DTaP/IPV/Hib vaccine, such as Pentacel®, are administered, in particular according to the following schedule

- a first simultaneous administration of the first reconstituted unit dose and the first dose of said DTaP/IPV/Hib vaccine on day 0,
- a second administration of the second dose of said DTaP/IPV/Hib vaccine after said first simultaneous administration, such as 2 months later and preferably on day 60,
- a third administration of the second reconstituted unit dose after said second administration, such as 3 months after the first simultaneous administration and preferably on day 90,
- a fourth administration of the third dose of said DTaP/IPV/Hib vaccine after said third administration, such as 4 months after the first simultaneous administration and preferably on day 120, and
- a fifth administration of the fourth dose of said DTaP/IPV/Hib vaccine after said fourth administration, such as 9 to 12 months later and preferably on day 390.

In certain embodiments the invention is directed to said methods, wherein two reconstituted unit doses of the invention as described herein and four doses of a DTaP/IPV/Hib vaccine, in particular a combined DTaP/IPV/Hib vaccine, such as Pentacel®, are administered, in particular according to the following schedule

- a first administration of the first dose of said DTaP/IPV/Hib vaccine on day 0,
- a second administration of the second dose of said DTaP/IPV/Hib vaccine after said first administration, such as 2 months later and preferably on day 60,
- a third administration of the third dose of said DTaP/IPV/Hib vaccine after said second administration, such as 4 months after the first administration and preferably on day 120,
- a fourth simultaneous administration of the first reconstituted unit dose and the fourth dose of said DTaP/IPV/Hib vaccine after said third administration, such as 9 to 12 months later and preferably on day 390, and
- a fifth administration of the second reconstituted unit dose after said fourth simultaneous administration, such as 3 months later and preferably on day 480.

According to some embodiments, a fifth dose of a DTaP/IPV/Hib vaccine, in particular a combined DTaP/IPV/Hib vaccine, such as Pentacel®, is administered after the administration of the fourth dose of said DTaP/IPV/Hib vaccine. For this purpose a commercially available combined diphtheria, tetanus, pertussis, and poliomyelitis (DTaP-IPV) vaccine marketed under the tradename Quadracel® from Sanofi Pasteur may be used. Quadracel® is a diphtheria and tetanus toxoids and acellular pertussis adsorbed and inactivated poliovirus vaccine and is indicated for active immunization against diphtheria, tetanus, pertussis and poliomyelitis. A single dose of Quadracel® is for use in children 4 through 6 years of age as a fifth dose in the diphtheria, tetanus, pertussis vaccination (DTaP) series and as a fourth or fifth dose in the inactivated poliovirus vaccination (IPV) series in children who have received 4 doses of Pentacel®. Accordingly, in some embodiments, a further sixth administration of a fifth dose of a DTaP/IPV/Hib vaccine, in particular a combined DTaP/IPV/Hib vaccine, such as Quadracel®, may be conducted 30 to 57 months after the administration of the fourth dose of a DTaP/IPV/Hib vaccine, in particular a combined DTaP/IPV/Hib vaccine, such as Pentacel®.

In certain embodiments, the invention is directed to said methods, wherein the subject or subject population is seronegative to all dengue serotypes. In certain embodiments, the invention is directed to said methods, wherein the reconstituted unit dose of the invention as described herein is administered subcutaneously to a subject or subject population and the DTaP/IPV/Hib vaccine, in particular a combined DTaP/IPV/Hib vaccine, such as Pentacel®, is administered intramuscularly to a subject or subject population, and wherein the subject or the subject population is seronegative with respect to all dengue serotypes. In other embodiments, the subject or subject population is seropositive with respect to at least one dengue serotype.

In certain embodiments, the invention is directed to said methods, wherein the unit dose of the invention as described herein and the DTaP/IPV/Hib vaccine, in particular a combined DTaP/IPV/Hib vaccine, such as Pentacel®, are administered to a subject or subject population from a dengue endemic region. In certain embodiments, the reconstituted unit dose of the invention as described herein is administered subcutaneously and the DTaP/IPV/Hib vaccine, in particular a combined DTaP/IPV/Hib vaccine, such as Pentacel®, is administered intramuscularly to a subject or subject population from a dengue endemic region.

In certain embodiments the invention is directed to said methods, wherein the reconstituted unit dose of the invention as described herein is administered subcutaneously and wherein the DTaP/IPV/Hib vaccine, in particular a combined DTaP/IPV/Hib vaccine, such as Pentacel®, is administered intramuscularly to a subject or subject population of 2 months to 4 years of age. In some embodiments the subject or subject population is from a dengue endemic region. In other embodiments, the subject or subject population is from a dengue non-endemic region. According to some of these embodiments, the subject or subject population is seronegative for all four dengue serotypes.

In a preferred embodiment the invention is directed to a method of preventing dengue disease and diphtheria, tetanus, pertussis, poliomyelitis and diseases caused by *Haemophilus influenzae* type b in a subject comprising administering to the subject subcutaneous injections of the reconstituted unit dose of the invention as described herein and intramuscular injections of the DTaP/IPV/Hib vaccine, in particular a combined DTaP/IPV/Hib vaccine, such as Pentacel®, according to one of the above described administration schedule, wherein the subject is a subject of 2 months to 4 years of age from a dengue endemic region.

Unit Dose for Use in a Method of Prevention

The present invention is directed in part to the unit dose of the invention as described herein for use in a method of preventing dengue disease in a subject, wherein the method also comprises the prevention of diphtheria, tetanus, pertussis, poliomyelitis and diseases caused by *Haemophilus influenzae* type b in the subject with a DTaP/IPV/Hib vaccine, in particular a combined DTaP/IPV/Hib vaccine, such as Pentacel®. In particular, the present invention is directed in part to a unit dose of a dengue vaccine composition as described herein and a DTaP/IPV/Hib vaccine, in particular a combined DTaP/IPV/Hib vaccine, such as Pentacel®, for use in a method of preventing dengue disease and diphtheria, tetanus, pertussis, poliomyelitis and diseases caused by *Haemophilus influenzae* type b in a subject, respectively.

The present invention is directed in part to the unit dose of the invention as described herein for use in a method of preventing dengue disease in a subject population, wherein the method also comprises the prevention of diphtheria, tetanus, pertussis, poliomyelitis and diseases caused by *Haemophilus influenzae* type b in the subject population with a DTaP/IPV/Hib vaccine, in particular a combined DTaP/IPV/Hib vaccine, such as Pentacel®. In particular, the present invention is directed in part to a unit dose of a dengue vaccine composition as described herein and a DTaP/IPV/Hib vaccine, in particular a combined DTaP/IPV/Hib vaccine, such as Pentacel®, for use in a method of preventing dengue disease and diphtheria, tetanus, pertussis, poliomyelitis and diseases caused by *Haemophilus influenzae* type b in a subject population, respectively.

The present invention is in part directed to the unit dose of a dengue vaccine composition as described herein and the DTaP/IPV/Hib vaccine, in particular a combined DTaP/IPV/Hib vaccine, such as Pentacel®, for use in a method of preventing dengue disease and diphtheria, tetanus, pertussis, poliomyelitis and diseases caused by *Haemophilus influenzae* type b in a subject population, comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a DTaP/IPV/Hib vaccine, in particular a combined DTaP/IPV/Hib vaccine, such as Pentacel®, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the unit dose of a dengue vaccine composition as described herein and the DTaP/IPV/Hib vaccine, in particular a combined DTaP/IPV/Hib vaccine, such as Pentacel®, for use in a method of preventing dengue disease and diphtheria, tetanus, pertussis, poliomyelitis and diseases caused by *Haemophilus influenzae* type b in a subject comprising administering to the subject at least a first reconstituted unit dose of the invention as described herein, wherein certain ratios of neutralizing antibody titers at day 180 or 365 after administration of said first unit dose to the subject are achieved, and concomitantly administering a DTaP/IPV/Hib vaccine, in particular a combined DTaP/IPV/Hib vaccine, such as Pentacel®, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2:neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to the unit dose of the invention as described herein and the DTaP/IPV/Hib vaccine, in particular a combined DTaP/IPV/Hib vaccine, such as Pentacel®, for said uses, wherein said unit dose and said DTaP/IPV/Hib vaccine are administered simultaneously. In some of these embodiments the simultaneous administration is on day 0 or day 90, preferably on day 0.

In other embodiments the administration of said unit dose and said DTaP/IPV/Hib vaccine are done sequentially.

In certain embodiments the invention is directed to the unit dose of the invention as described herein and the DTaP/IPV/Hib vaccine, in particular a combined DTaP/IPV/Hib vaccine, such as Pentacel®, for said uses, wherein said unit dose is administered by subcutaneous injection and wherein said DTaP/IPV/Hib vaccine is administered by intramuscular injection. According to some embodiments, said unit dose is administered to the arm, preferably to the deltoid region of the arm. According to some embodiments, the subcutaneous injection of the unit dose of the invention as described herein and the intramuscular injection of the DTaP/IPV/Hib vaccine, in particular a combined DTaP/IPV/Hib vaccine, such as Pentacel®, are administered to different anatomical sites. According to some of these embodiments, said unit dose is administered subcutaneously to the arm, preferably to the deltoid region, and said DTaP/IPV/Hib vaccine is administered intramuscularly to the thigh, preferably to the anterolateral aspect of the thigh.

In certain embodiments the invention is directed to the unit dose of the invention as described herein and the DTaP/IPV/Hib vaccine, in particular a combined DTaP/IPV/Hib vaccine, such as Pentacel®, for said uses, wherein two reconstituted unit doses of the invention as described herein are administered. In some embodiments the two unit doses of the invention as described herein are administered within 12 months or more, or within six months, or within three months, such as at day 0/1 and day 90. According to some of these embodiments a further third reconstituted unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to the unit dose of the invention as described herein and the DTaP/IPV/Hib vaccine, in particular a combined DTaP/IPV/Hib vaccine, such as Pentacel®, for said uses, wherein two reconstituted unit doses of the invention as described herein and four doses of the DTaP/IPV/Hib vaccine are administered, in particular according to the following schedule

- a first simultaneous administration of the first reconstituted unit dose and the first dose of said DTaP/IPV/Hib vaccine on day 0,
- a second administration of the second dose of said DTaP/IPV/Hib vaccine after said first simultaneous administration, such as 2 months later and preferably on day 60,
- a third administration of the second reconstituted unit dose after said second administration, such as 3 months after the first simultaneous administration and preferably on day 90,
- a fourth administration of the third dose of said DTaP/IPV/Hib vaccine after said third administration, such as 4 months after the first simultaneous administration and preferably on day 120, and
- a fifth administration of the fourth dose of said DTaP/IPV/Hib vaccine after said fourth administration, such as 9 to 12 months later and preferably on day 390.

In certain embodiments the invention is directed to the unit dose of the invention as described herein and the DTaP/IPV/Hib vaccine, in particular a combined DTaP/IPV/Hib vaccine, such as Pentacel®, for said uses, wherein two reconstituted unit doses of the invention as described herein and four doses of the DTaP/IPV/Hib vaccine are administered, in particular according to the following schedule

- a first administration of the first dose of said DTaP/IPV/Hib vaccine on day 0,
- a second administration of the second dose of said DTaP/IPV/Hib vaccine after said first administration, such as 2 months later and preferably on day 60,
- a third administration of the third dose of said DTaP/IPV/Hib vaccine after said second administration, such as 4 months after the first administration and preferably on day 120,
- a fourth simultaneous administration of the first reconstituted unit dose and the fourth dose of said DTaP/IPV/Hib vaccine after said third administration, such as 9 to 12 months later and preferably on day 390, and
- a fifth administration of the second reconstituted unit dose after said fourth simultaneous administration, such as 3 months later and preferably on day 480.

According to some embodiments, a fifth dose of a DTaP/IPV/Hib vaccine, in particular a combined DTaP/IPV/Hib vaccine, such as Pentacel®, is administered after the administration of the fourth dose of said DTaP/IPV/Hib vaccine. For this purpose a commercially available combined diphtheria, tetanus, pertussis, and poliomyelitis (DTaP-IPV) vaccine marketed under the tradename Quadracel® from Sanofi Pasteur may be used. Quadracel® is a diphtheria and tetanus toxoids and acellular pertussis adsorbed and inactivated poliovirus vaccine and is indicated for active immunization against diphtheria, tetanus, pertussis and poliomyelitis. A single dose of Quadracel® is for use in children 4 through 6 years of age as a fifth dose in the diphtheria, tetanus, pertussis vaccination (DTaP) series and as a fourth or fifth dose in the inactivated poliovirus vaccination (IPV) series in children who have received 4 doses of Pentacel®. Accordingly, in some embodiments, a further sixth administration of a fifth dose of a DTaP/IPV/Hib vaccine, in particular a combined DTaP/IPV/Hib vaccine, such as Quadracel®, may be conducted 30 to 57 months after the administration of the fourth dose of a DTaP/IPV/Hib vaccine, in particular a combined DTaP/IPV/Hib vaccine, such as Pentacel®.

In certain embodiments, the invention is directed to the unit dose of the invention as described herein and the DTaP/IPV/Hib vaccine, in particular a combined DTaP/IPV/Hib vaccine, such as Pentacel®, for said uses, wherein the subject or subject population is seronegative to all dengue serotypes. In certain embodiments, the invention is directed to the unit dose of the invention as described herein and the DTaP/IPV/Hib vaccine, in particular a combined DTaP/IPV/Hib vaccine, such as Pentacel®, for said uses, wherein said unit dose is reconstituted and administered subcutaneously to a subject or subject population and said DTaP/IPV/Hib vaccine is administered intramuscularly to a subject or subject population, and wherein the subject or the subject population is seronegative with respect to all dengue serotypes. In other embodiments, the subject or subject population is seropositive with respect to at least one dengue serotype.

In certain embodiments, the invention is directed to the unit dose of the invention as described herein and the DTaP/IPV/Hib vaccine, in particular a combined DTaP/IPV/Hib vaccine, such as Pentacel®, for said uses, wherein said unit dose and said DTaP/IPV/Hib vaccine are administered to a subject or subject population from a dengue endemic region. In certain embodiments, the reconstituted unit dose of the invention as described herein is administered subcutaneously and the DTaP/IPV/Hib vaccine, in particular a combined DTaP/IPV/Hib vaccine, such as Pentacel®, is administered intramuscularly to a subject or subject population from a dengue endemic region.

In certain embodiments the invention is directed to the unit dose of the invention as described herein and the DTaP/IPV/Hib vaccine, in particular a combined DTaP/IPV/Hib vaccine, such as Pentacel®, for said uses, wherein the reconstituted unit dose of the invention as described herein is administered subcutaneously and wherein the DTaP/IPV/Hib vaccine, in particular a combined DTaP/IPV/Hib vaccine, such as Pentacel®, is administered intramuscular to a subject or subject population of 2 months to 4 years of age. In some embodiments the subject or subject population is from a dengue endemic region. In other embodiments, the subject or subject population is from a dengue non-endemic region. According to some of these embodiments, the subject or subject population is seronegative for all four dengue serotypes.

In a preferred embodiment the invention is directed to the unit dose of the invention as described herein and the DTaP/IPV/Hib vaccine, in particular a combined DTaP/IPV/Hib vaccine, such as Pentacel®, for use in a method of preventing dengue disease and diphtheria, tetanus, pertussis, poliomyelitis and diseases caused by *Haemophilus influenzae* type b in a subject comprising administering to the subject subcutaneous injections of the reconstituted unit dose of the invention as described herein and intramuscular injections of the DTaP/IPV/Hib vaccine, in particular a combined DTaP/IPV/Hib vaccine, such as Pentacel®, according to one of the above described administration schedule, wherein the subject is a subject of 2 months to 4 years of age from a dengue endemic region.

Use for the Manufacture of a Medicament in a Method of Prevention

The present invention is directed in part to the use of a unit dose of the invention as described herein for the manufacture of a medicament for preventing dengue disease in a subject, further comprising the use of a DTaP/IPV/Hib vaccine, in particular a combined DTaP/IPV/Hib vaccine, such as Pentacel®, for the manufacture of a medicament for preventing diphtheria, tetanus, pertussis, poliomyelitis and diseases caused by *Haemophilus influenzae* type b in the subject. In particular, the present invention is directed in part to a use of a unit dose of a dengue vaccine composition as described herein and a DTaP/IPV/Hib vaccine, in particular a combined DTaP/IPV/Hib vaccine, such as Pentacel®, for the manufacture of a medicament for preventing dengue disease and diphtheria, tetanus, pertussis, poliomyelitis and diseases caused by *Haemophilus influenzae* type b in a subject, respectively.

The present invention is directed in part to the use of a unit dose of the invention as described herein for the manufacture of a medicament for preventing dengue disease in a subject population, further comprising the use of a DTaP/IPV/Hib vaccine, in particular a combined DTaP/IPV/Hib vaccine, such as Pentacel®, for the manufacture of a medicament for preventing diphtheria, tetanus, pertussis, poliomyelitis and diseases caused by *Haemophilus influenzae* type b in the subject population. In particular, the present invention is directed in part to a use of a unit dose of a dengue vaccine composition as described herein and a DTaP/IPV/Hib vaccine, in particular a combined DTaP/IPV/Hib vaccine, such as Pentacel®, for the manufacture of a medicament for preventing dengue disease and diphtheria, tetanus, pertussis, poliomyelitis and diseases caused by *Haemophilus influenzae* type b in a subject population, respectively.

The present invention is in part directed to the use of a unit dose of the invention as described herein and a DTaP/IPV/Hib vaccine, in particular a combined DTaP/IPV/Hib vaccine, such as Pentacel®, for the manufacture of a medicament for preventing dengue disease and diphtheria, tetanus, pertussis, poliomyelitis and diseases caused by *Haemophilus influenzae* type b in a subject population, comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a DTaP/IPV/Hib vaccine, in particular a combined DTaP/IPV/Hib vaccine, such as Pentacel®, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the use of a unit dose of the invention as described herein and a DTaP/IPV/Hib vaccine, in particular a combined DTaP/IPV/Hib vaccine, such as Pentacel®, for the manufacture of a medicament for preventing dengue disease and diphtheria, tetanus, pertussis, poliomyelitis and diseases caused by *Haemophilus influenzae* type b in a subject, comprising administering to the subject at least a first reconstituted unit dose of the invention as described herein, wherein certain ratios of neutralizing antibody titers at day 180 or 365 after administration of said first unit dose to the subject are achieved, and concomitantly administering a DTaP/IPV/Hib vaccine, in particular a combined DTaP/IPV/Hib vaccine, such as Pentacel®, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2:neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to said uses, wherein the unit dose of the invention as described herein and the DTaP/IPV/Hib vaccine, in particular a combined DTaP/IPV/Hib vaccine, such as Pentacel®, are administered simultaneously. In some of these embodiments the simultaneous administration is on day 0 or day 90, preferably on day 0. In other embodiments the administration of the unit dose of the invention as described herein and the DTaP/IPV/Hib vaccine, in particular a combined DTaP/IPV/Hib vaccine, such as Pentacel®, are done sequentially.

In certain embodiments the invention is directed to said uses, wherein the unit dose of the invention as described herein is reconstituted and administered by subcutaneous injection and wherein the DTaP/IPV/Hib vaccine, in particular a combined DTaP/IPV/Hib vaccine, such as Pentacel®, is administered by intramuscular injection. According to some embodiments, the unit dose of the invention as described herein is administered to the arm, preferably to the deltoid region of the arm. According to some embodiments, the subcutaneous injection of the unit dose of the invention as described herein and the intramuscular injection of the DTaP/IPV/Hib vaccine, in particular a combined DTaP/IPV/Hib vaccine, such as Pentacel®, are administered to different anatomical sites. According to some of these embodiments, said unit dose is administered subcutaneously to the arm, preferably to the deltoid region, and said DTaP/IPV/Hib vaccine is administered intramuscularly to the thigh, preferably to the anterolateral aspect of the thigh.

In certain embodiments the invention is directed to said uses, wherein two reconstituted unit doses of the invention as described herein are administered. In some embodiments the two unit doses of the invention as described herein are administered within 12 months or more, or within six months, or within three months, such as at day 0/1 and day 90. According to some of these embodiments a further third unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to said uses, wherein two unit doses of the invention as described herein and four doses of a DTaP/IPV/Hib vaccine, in particular a combined DTaP/IPV/Hib vaccine, such as Pentacel®, are administered, in particular according to the following schedule

- a first simultaneous administration of the first reconstituted unit dose and the first dose of said DTaP/IPV/Hib vaccine on day 0,
- a second administration of the second dose of said DTaP/IPV/Hib vaccine after said first simultaneous administration, such as 2 months later and preferably on day 60,
- a third administration of the second reconstituted unit dose after said second administration, such as 3 months after the first simultaneous administration and preferably on day 90,
- a fourth administration of the third dose of said DTaP/IPV/Hib vaccine after said third administration, such as 4 months after the first simultaneous administration and preferably on day 120, and
- a fifth administration of the fourth dose of said DTaP/IPV/Hib vaccine after said fourth administration, such as 9 to 12 months later and preferably on day 390.

In certain embodiments the invention is directed to said uses, wherein two unit doses of the invention as described herein and four doses of a DTaP/IPV/Hib vaccine, in particular a combined DTaP/IPV/Hib vaccine, such as Pentacel®, are administered, in particular according to the following schedule

- a first administration of the first dose of said DTaP/IPV/Hib vaccine on day 0,
- a second administration of the second dose of said DTaP/IPV/Hib vaccine after said first administration, such as 2 months later and preferably on day 60,
- a third administration of the third dose of said DTaP/IPV/Hib vaccine after said second administration, such as 4 months after the first administration and preferably on day 120,
- a fourth simultaneous administration of the first reconstituted unit dose and the fourth dose of said DTaP/IPV/Hib vaccine after said third administration, such as 9 to 12 months later and preferably on day 390, and
- a fifth administration of the second reconstituted unit dose after said fourth simultaneous administration, such as 3 months later and preferably on day 480.

According to some embodiments, a fifth dose of a DTaP/IPV/Hib vaccine, in particular a combined DTaP/IPV/Hib vaccine, such as Pentacel®, is administered after the administration of the fourth dose of said DTaP/IPV/Hib vaccine. For this purpose a commercially available combined diphtheria, tetanus, pertussis, and poliomyelitis (DTaP-IPV) vaccine marketed under the tradename Quadracel® from Sanofi Pasteur may be used. Quadracel® is a diphtheria and tetanus toxoids and acellular pertussis adsorbed and inactivated poliovirus vaccine and is indicated for active immunization against diphtheria, tetanus, pertussis and poliomyelitis. A single dose of Quadracel® is for use in children 4 through 6 years of age as a fifth dose in the diphtheria, tetanus, pertussis vaccination (DTaP) series and as a fourth or fifth dose in the inactivated poliovirus vaccination (IPV) series in children who have received 4 doses of Pentacel®. Accordingly, in some embodiments, a further sixth administration of a fifth dose of a DTaP/IPV/Hib vaccine, in particular a combined DTaP/IPV/Hib vaccine, such as Quadracel®, may be conducted 30 to 57 months after the administration of the fourth dose of a DTaP/IPV/Hib vaccine, in particular a combined DTaP/IPV/Hib vaccine, such as Pentacel®.

In certain embodiments, the invention is directed to said uses, wherein the subject or subject population is seronegative to all dengue serotypes. In certain embodiments, the invention is directed to said uses, wherein the unit dose of the invention as described herein is reconstituted and administered subcutaneously to a subject or subject population and the DTaP/IPV/Hib vaccine, in particular a combined DTaP/IPV/Hib vaccine, such as Pentacel®, is administered intramuscularly to a subject or subject population, and wherein the subject or the subject population is seronegative with respect to all dengue serotypes. In other embodiments, the subject or subject population is seropositive with respect to at least one dengue serotype.

In certain embodiments, the invention is directed to said uses, wherein the unit dose of the invention as described herein and the DTaP/IPV/Hib vaccine, in particular a combined DTaP/IPV/Hib vaccine, such as Pentacel®, are administered to a subject or subject population from a dengue endemic region. In certain embodiments, the reconstituted unit dose of the invention as described herein is administered subcutaneously and the DTaP/IPV/Hib vaccine, in particular a combined DTaP/IPV/Hib vaccine, such as Pentacel®, is administered intramuscularly to a subject or subject population from a dengue endemic region.

In certain embodiments the invention is directed to said uses, wherein the reconstituted unit dose of the invention as described herein is administered subcutaneously and the DTaP/IPV/Hib vaccine, in particular a combined DTaP/IPV/Hib vaccine, such as Pentacel®, is administered intramuscularly to a subject or subject population of 2 months to 4 years of age. In some embodiments the subject or subject population is from a dengue endemic region. In other embodiments, the subject or subject population is from a dengue non-endemic region. According to some of these embodiments, the subject or subject population is seronegative for all four dengue serotypes.

In a preferred embodiment the invention is directed to the use of a unit dose of a dengue vaccine composition as described herein and a DTaP/IPV/Hib vaccine, in particular a combined DTaP/IPV/Hib vaccine, such as Pentacel®, for the manufacture of a medicament for preventing dengue disease and diphtheria, tetanus, pertussis, poliomyelitis and diseases caused by *Haemophilus influenzae* type b in a subject comprising administering to the subject subcutaneous injections of the reconstituted unit dose of the invention as described herein and intramuscular injections of the DTaP/IPV/Hib vaccine, in particular a combined DTaP/IPV/Hib vaccine, such as Pentacel®, according to one of the above described administration schedule, wherein the subject is a subject of 2 months to 4 years of age from a dengue endemic region.

Method of Prevention Using Multiple Co-Vaccinations

In case multiple disease should be prevented the unit dose according to the invention (TDV) can be co-administered in at least any of the following combinations.

Double Vaccine Combinations:

TDV+YF, TDV+Hepatitis A, TDV+MMR, TDV+Tdap, TDV+DTap, or TDV+HPV

Triple Vaccine Combinations:

TDV+YF+Hepatitis A, TDV+YF+MMR, TDV+YF+Tdap, TDV+YF+Dtap, TDV+YF+HPV, TDV+Hepatitis A+MMR, TDV+Hepatitis A+Tdap, TDV+Hepatitis A+DTap, TDV+Hepatitis A+HPV, TDV+MMR+Tdap, TDV+MMR+DTap, TDV+MMR+HPV, TDV+Tdap+DTap, TDV+Tdap+HPV, or TDV+DTap+HPV.

Quadruple Vaccine Combinations

TDV+YF+Hepatitis A+MMR, TDV+YF+Hepatitis A+Tdap, TDV+YF+Hepatitis A+DTap, TDV+YF+Hepatitis A+HPV, TDV+YF+MMR+Tdap, TDV+YF+MMR+DTap, TDV+YF+MMR+HPV, TDV+YF+Tdap+DTap, TDV+YF+Tdap+HPV, TDV+YF+DTap+HPV, TDV+Hepatitis A+MMR+Tdap, TDV+Hepatitis A+MMR+DTap, TDV+Hepatitis A+MMR+HPV, TDV+Hepatitis A+Tdap+DTap, TDV+Hepatitis A+Tdap+HPV, TDV+Hepatitis A+DTap+HPV, TDV+MMR+Tdap+DTap, TDV+MMR+Tdap+HPV, TDV+MMR+DTap+HPV, or TDV+Tdap+DTap+HPV.

Quintuple Vaccine Combinations

TDV+YF+Hepatitis A+MMR+Tdap, TDV+YF+Hepatitis A+MMR+Dtap, TDV+YF+Hepatitis A+MMR+HPV, TDV+YF+Hepatitis A+Tdap+DTap, TDV+YF+Hepatitis A+Tdap+HPV, TDV+YF+Hepatitis A+DTap+HPV, TDV+YF+MMR+Tdap+DTap, TDV+YF+MMR+Tdap+HPV, TDV+YF+MMR+DTap+HPV, TDV+YF+Tdap+DTap+HPV, TDV+Hepatitis A+MMR+Tdap+DTap, TDV+Hepatitis A+MMR+Tdap+HPV, TDV+Hepatitis A+MMR+DTap+HPV, TDV+Hepatitis A+Tdap+Dtap+HPV, or TDV+MMR+Tdap+DTap+HPV.

Sextuple Vaccine Combinations

TDV+YF+Hepatitis A+MMR+Tdap+DTap, TDV+YF+Hepatitis A+MMR+Tdap+HPV, TDV+YF+Hepatitis A+MMR+DTap+HPV, TDV+YF+Hepatitis A+Tdap+DTap+HPV, TDV+YF+MMR+Tdap+DTap+HPV, or TDV+Hepatitis A+MMR+Tdap+DTap+HPV.

Septuple Vaccine Combinations

TDV+YF+Hepatitis A+MMR+Tdap+DTap+HPV.

A preferred combination is e.g. TDV, YF and MMR.

Method of Co-Vaccinations with Other Dengue Vaccines

In certain embodiments of the invention the method is directed to a co-administration with other dengue vaccines such as Dengvaxia®. Dengvaxia® is a tetravalent dengue vaccine based on a yellow fever backbone, CYD-TDV (Dengvaxia®, Sanofi Pasteur, Lyon, France), and has been licensed in several countries based on the clinical demonstration of an overall vaccine efficacy (VE) against virologically-confirmed dengue (VCD) of 56-61% in children in Asia and Latin America (Capeding M R et al. Clinical efficacy and safety of a novel tetravalent dengue vaccine in healthy children in Asia: a phase 3, randomised, observer-masked, placebo-controlled trial. Lancet 2014, 384:1358-65; Villar L A et al. Safety and immunogenicity of a recombinant tetravalent dengue vaccine in 9-16 year olds: a randomized, controlled, phase II trial in Latin America. Pediatr Infect Dis J 2013, 32:1102-9). The preparation of these particular strains CYD1, CYD2, CYD3 and CYD4 has been described in detail in international patent applications WO 98/37911, WO 03/101397, WO07/021672, WO 08/007021, WO 08/047023 and WO 08/065315, to which reference may be made for a precise description of the processes for their preparation. The corresponding nucleotide sequences of the prM-E regions of CYD1, CYD2, CYD3 and CYD4 are provided in WO2016034629 and SEQ ID NOs are set out in Table 16.

Method of Co-Vaccinations with Other Travel Vaccines

In certain embodiments of the invention the method is directed to a co-administration with other travel vaccines such as Cholera, Hepatitis A, Hepatitis E, Japanese encephalitis, Meningococcal disease, Rabies, Tick-borne encephalitis, Typhoid fever, and Yellow fever.

According to one embodiment the dengue vaccine according to the invention is co-administered with all of the above vaccines.

According to one embodiment the dengue vaccine according to the invention is co-administered with one ore more of the above vaccines.

Method of Stimulating an Immune Response and Uses

Method of Stimulating an Immune Response

In certain embodiments the invention is directed to a method for stimulating an immune response, preferably a balanced immune response, to all four dengue serotypes in a subject, comprising administering to the subject a reconstituted unit dose of the invention as described herein.

In certain embodiments, the method includes a reconstituted unit dose/tetravalent dengue virus composition of a dengue vaccine composition administered for stimulating an immune response, preferably a balanced immune response, to all four dengue serotypes in a subject or subject population, the reconstituted unit dose comprising: a tetravalent virus composition including four live attenuated dengue virus strains, wherein the unit dose, described herein, is lyophilized and upon reconstitution with 0.5 mL of a pharmaceutically acceptable diluent the reconstituted unit dose is obtained, wherein the reconstituted unit dose comprises:

(i) a dengue serotype 1, such as a chimeric dengue serotype 2/1 strain, in a concentration of at least 3.3 log 10 pfu/0.5 ml, (ii) a dengue serotype 2, such as a dengue serotype 2 strain, in a concentration of at least 2.7 log 10 pfu/0.5 ml, (iii) a dengue serotype 3, such as a chimeric dengue serotype 2/3 strain, in a concentration of at least 4.0 log 10 pfu/0.5 ml, and (vi) a dengue serotype 4, such as a chimeric dengue serotype 2/4 strain, in a concentration of at least 4.5 log 10 pfu/0.5 ml.

It is preferred that the reconstituted unit dose/tetravalent dengue virus composition is used in the method of stimulating an immune response of the present invention, wherein upon reconstitution of the unit dose with a pharmaceutically acceptable diluent dengue serotypes (i), (ii), (iii), and (iv) provide a total concentration of pfu/0.5 mL and based on said total concentration the concentration of (ii) in pfu/0.5 mL is less than 2%, the concentration of (iv) in pfu/0.5 mL is at least 50%, the concentration of (i) in pfu/0.5 mL is at least 1%, and the concentration of (iii) in pfu/0.5 mL is at least 6% and wherein the subject or subject population is of 18 to 60 years of age.

In another preferred embodiment, the reconstituted unit dose/tetravalent dengue virus composition is used in the method of stimulating an immune response of the present invention, wherein upon reconstitution with a pharmaceutically acceptable diluent dengue serotypes (i), (ii), (iii), and (iv) provide a total concentration of pfu/0.5 mL and based on said total concentration the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 8% and wherein the subject or subject population is of 2 to 17 years of age.

The present invention is in part directed to a method for stimulating an immune response to all four serotypes of dengue virus in a subject, comprising administering to the subject a reconstituted unit dose of the invention as described herein by subcutaneous injection.

In certain embodiments, the invention is directed to said method, wherein the immune response to all four serotypes of dengue virus is balanced.

In certain embodiments, the invention is directed to said method, wherein the reconstituted unit dose is administered by subcutaneous injection to the arm, preferably to the deltoid region of the arm.

In certain embodiments, the invention is directed to said method, wherein the subject is seronegative to all dengue serotypes.

In certain embodiments, the invention is directed to said method, wherein two reconstituted unit doses of the invention as described herein are administered. In some embodiments, the two reconstituted doses are administered within 12 months or more, or within six months, or within three months, such as at day 0 and day 90 or at day 1 and day 90. According to some of these embodiments, a third unit dose of the invention as described herein is administered between 6 and 12 months after the administration of said first unit dose, such as 12 months after the first administration, or later than 12 month after the first administration, such as 12 months after the second administration.

In certain embodiments, the invention is directed to said method, wherein the unit dose of the invention as described herein is administered to a subject from a dengue endemic region. In some of these embodiments, the subject is from Singapore, Dominican Republic, Panama, Philippines, Colombia, Puerto Rico or Thailand, in particular from Singapore, Dominican Republic, Panama, or Philippines. In other embodiments, the subject is from a dengue non-endemic region. Such a subject may be subject to a vaccination according to the invention in the context of traveling to a dengue endemic region. In certain embodiments, the reconstituted unit dose of the invention as described herein is administered subcutaneously to a subject that is from a dengue endemic region or a dengue non-endemic region.

In certain embodiments, the invention is directed to said method, wherein the reconstituted unit dose of the invention as described herein is administered subcutaneously to a subject that is seronegative with respect to all dengue serotypes. In other embodiments, the subject is seropositive with respect to at least one dengue serotype.

In certain embodiments, the invention is directed to said method, wherein the neutralizing antibody titers of the subject when tested at day 180 or day 365 after at least a first administration of said unit dose, and optionally a second administration of said unit dose 90 days after said first administration, provide a ratio of not more than 50, or not more than 40, or nor more than 30, or not more than 20 for the neutralizing antibody titer of dengue serotype 2 to the neutralizing antibody titer of dengue serotype 4. In certain embodiments, said neutralizing antibody titers of the subject further provide a ratio of not more than 20 for the neutralizing antibody titer of dengue serotype 2 to the neutralizing antibody titer of dengue serotype 1, and/or a ratio of not more than 20 for the neutralizing antibody titer of dengue serotype 2 to the neutralizing antibody titer of dengue serotype 3.

In certain embodiments, the invention is directed to said method, wherein the unit dose of the invention as described herein is administered to a subject of 2 to 60 years of age, or more than 17 years, or more than 18 years, or 18 to 60 years of age. In certain embodiments the subject is 1 to 17 years of age, or less than 9 years of age, or less than 4 years of age or less than 2 years of age. In further embodiments, the subjects or subject population are adults of more than 21 years, or 21 to 60 years, or 21 to 45 years of age. According to some of these embodiments the subject is seronegative and from a dengue-endemic region.

In certain embodiments, the invention is directed to said method, wherein the unit dose of the invention as described herein is administered to a pediatric subject of less than 2 years of age, preferably of 2 months to 2 years of age or 2 months to 1.5 years of age or 2 months to 1 year of age. According to some of these embodiments, the pediatric subject is seronegative and from a dengue endemic region.

In certain embodiments, the invention is directed to said method, wherein the reconstituted unit dose of the invention as described herein is administered subcutaneously to a pediatric subject of less than 2 years of age, preferably of 2 months to 2 years of age or 2 months to 1.5 years of age or 2 months to 1 year of age. According to some of these embodiments, the pediatric subject is seronegative and from a dengue endemic region.

In certain embodiments, the invention is directed to said method, wherein the reconstituted unit dose of the invention as described herein is administered concomitantly with another vaccine. In one embodiments, the reconstituted unit dose of the invention as described herein is administered concomitantly with a yellow fever vaccine, in particular YF-17D. It is particularly preferred that the reconstituted unit dose of the invention as described herein is administered concomitantly with a yellow fever vaccine, in particular YF-17D, as described in the previous section.

In certain embodiments, the invention is directed to said method, wherein the reconstituted unit dose of the invention as described herein is administered concomitantly with another vaccine. In one embodiments, the reconstituted unit dose of the invention as described herein is administered concomitantly with a HPV vaccine, in particular a 9vHPV vaccine, such as GARDASIL® 9. It is particularly preferred that the reconstituted unit dose of the invention as described herein is administered concomitantly with a HPV vaccine, in particular a 9vHPV vaccine, such as GARDASIL® 9, as described in the previous section.

In certain embodiments, the invention is directed to said method, wherein the reconstituted unit dose of the invention as described herein is administered concomitantly with another vaccine. In one embodiments, the reconstituted unit dose of the invention as described herein is administered concomitantly with a MMR vaccine, such as M-M-R® II. It is particularly preferred that the reconstituted unit dose of the invention as described herein is administered concomitantly with a MMR vaccine, such as M-M-R® II, as described in the previous section.

In certain embodiments, the invention is directed to said method, wherein the reconstituted unit dose of the invention as described herein is administered concomitantly with another vaccine. In one embodiments, the reconstituted unit dose of the invention as described herein is administered concomitantly with a DTaP/IPV/Hib vaccine, in particular a combined DTaP/IPV/Hib vaccine, such as Pentacel®. It is particularly preferred that the reconstituted unit dose of the invention as described herein is administered concomitantly with a DTaP/IPV/Hib vaccine, in particular a combined DTaP/IPV/Hib vaccine, such as Pentacel®, as described in the previous section.

In certain embodiments the invention is directed to a method for stimulating an immune response, preferably a balanced immune response, to all four dengue serotypes in an elderly subject, comprising administering to the elderly subject a reconstituted unit dose of the invention as described herein.

The present invention is in part directed to a method for stimulating an immune response to all four serotypes of dengue virus in an elderly subject, comprising administering to the elderly subject a reconstituted unit dose of the invention as described herein by subcutaneous injection.

In certain embodiments, the invention is directed to said method, wherein the immune response to all four serotypes of dengue virus is balanced.

In certain embodiments, the invention is directed to said method, wherein the reconstituted unit dose is administered by subcutaneous injection to the arm, preferably to the deltoid region of the arm.

In certain embodiments, the invention is directed to said method, wherein the elderly subject is seronegative to all dengue serotypes.

In certain embodiments, the invention is directed to said method, wherein two reconstituted unit doses of the invention as described herein are administered. In some embodiments, the two reconstituted doses are administered within 12 months or more, or within six months, or within three months, such as at day 0 and day 90. According to some of these embodiments, a third unit dose of the invention as described herein is administered between 6 and 12 months after the administration of said first unit dose, such as 12 months after the first administration, or later than 12 month after the first administration, such as 12 months after the second administration.

In certain embodiments, the invention is directed to said method, wherein the unit dose of the invention as described herein is administered to an elderly subject from a dengue endemic region. In some of these embodiments, the elderly subject is from Singapore, Dominican Republic, Panama, Philippines, Colombia, Puerto Rico or Thailand, in particular from Singapore, Dominican Republic, Panama, or Philippines. In other embodiments, the elderly subject is from a dengue non-endemic region. Such an elderly subject may be subject to a vaccination according to the invention in the context of traveling to a dengue endemic region. In certain embodiments, the reconstituted unit dose of the invention as described herein is administered subcutaneously to an elderly subject that is from a dengue endemic region or a dengue non-endemic region.

In certain embodiments, the invention is directed to said method, wherein the reconstituted unit dose of the invention as described herein is administered subcutaneously to an elderly subject that is seronegative with respect to all dengue serotypes. In other embodiments, the elderly subject is seropositive with respect to at least one dengue serotype.

In certain embodiments, the invention is directed to said method, wherein the elderly subject has at least one chronic condition or disease. The at least one chronic condition or disease may be selected from diabetes, hypertension, allergies, previous strokes, ischemic heart disease, chronic renal impairment and chronic obstructive pulmonary disease.

In certain embodiments, the invention is directed to said method, wherein the elderly subject has an impaired immune system.

Use for the Manufacture of a Medicament for Stimulating an Immune Response

The present invention is in part directed to the use of the reconstituted unit dose of the invention as described herein for the manufacture of a medicament for stimulating an immune response to all four serotypes of dengue virus in a subject. In one embodiment a reconstituted unit dose of the invention as described herein is administered by subcutaneous injection.

In certain embodiments, the present invention is directed to a use of the reconstituted unit dose/tetravalent dengue virus composition of a dengue vaccine composition for the manufacture of a medicament for stimulating an immune response to all four serotypes of dengue virus in a subject or in a subject population, wherein the reconstituted unit dose comprises a tetravalent virus composition including four live attenuated dengue virus strains, wherein a unit dose, as described herein, is lyophilized and upon reconstitution with 0.5 mL of a pharmaceutically acceptable diluent the reconstituted unit dose is obtained, wherein the reconstituted unit dose comprises:

(i) a dengue serotype 1, such as a chimeric dengue serotype 2/1 strain, in a concentration of at least 3.3 log 10 pfu/0.5 ml, (ii) a dengue serotype 2, such as a dengue serotype 2 strain, in a concentration of at least 2.7 log 10 pfu/0.5 ml, (iii) a dengue serotype 3, such as a chimeric dengue serotype 2/3 strain, in a concentration of at least 4.0 log 10 pfu/0.5 ml, and (vi) a dengue serotype 4, such as a chimeric dengue serotype 2/4 strain, in a concentration of at least 4.5 log 10 pfu/0.5 ml.

It is preferred that the use of the reconstituted unit dose/tetravalent dengue virus composition for the manufacture of a medicament in a method for stimulating an immune response to all four serotypes of dengue virus in a subject or in a subject population is obtained upon reconstitution of the unit dose with a pharmaceutically acceptable diluent and the dengue serotypes (i), (ii), (iii), and (iv) provide a total concentration of pfu/0.5 mL and based on said total concentration the concentration of (ii) in pfu/0.5 mL is less than 2%, the concentration of (iv) in pfu/0.5 mL is at least 50%, the concentration of (i) in pfu/0.5 mL is at least 1%, and the concentration of (iii) in pfu/0.5 mL is at least 6% and wherein the subject or subject population is of 18 to 60 years of age.

In another preferred embodiment, the use of reconstituted unit dose/tetravalent dengue virus composition for the manufacture of a medicament for a method for stimulating an immune response to all four serotypes of dengue virus in a subject or in a subject population is obtained upon reconstitution of the unit dose described herein with a pharmaceutically acceptable diluent and the dengue serotypes (i), (ii), (iii), and (iv) provide a total concentration of pfu/0.5 mL and based on said total concentration the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 8% and wherein the subject or subject population is of 2 to 17 years of age.

In certain embodiments, the invention is directed to said use, wherein the immune response to all four serotypes of dengue virus is balanced.

In certain embodiments, the invention is directed to said use, wherein the reconstituted unit dose is administered by subcutaneous injection to the arm, preferably to the deltoid region of the arm.

In certain embodiments, the invention is directed the reconstituted unit dose of the invention as described herein for said use, wherein the subject is seronegative to all dengue serotypes.

In certain embodiments, the invention is directed to said use, wherein two reconstituted unit doses of the invention as described herein are administered. In some embodiments, the two reconstituted unit doses are administered within 12 months or more, or within six months, or within three months, such as at day 0 and day 90 or at day 1 and day 90. According to some of these embodiments, a third reconstituted unit dose is administered 6 to 12 months after the administration of the first reconstituted unit dose, such as 12 months after the first administration, or later than 12 month after the first administration, such as 12 months (1 year) after the second administration or even 5 years or longer after the first or second administration.

In certain embodiments, the invention is directed to said use, wherein the subject is from a dengue endemic region. In other embodiments, the subject is from a dengue non-endemic region. Such a subject may be subject to a vaccination according to the invention in the context of traveling to a dengue endemic region. In certain embodiments, the reconstituted unit dose of the invention as described herein is administered subcutaneously to a subject that is from a dengue endemic region or a dengue non-endemic region.

In certain embodiments, the invention is directed to said use, wherein the reconstituted unit dose of the invention as described herein is administered subcutaneously to a subject that is seronegative with respect to all dengue serotypes. In other embodiments, the subject is seropositive with respect to at least one dengue serotype.

In certain embodiments, the invention is directed to said use, wherein the neutralizing antibody titers of the subject when tested at day 180 or day 365 after at least a first administration of said unit dose, and optionally a second administration of said unit dose 90 days after said first administration, provide a ratio of not more than 50, or not more than 40, or nor more than 30, or not more than 20 for the neutralizing antibody titer of dengue serotype 2 to the neutralizing antibody titer of dengue serotype 4. In certain embodiments, said neutralizing antibody titers of the subject further provide a ratio of not more than 20 for the neutralizing antibody titer of dengue serotype 2 to the neutralizing antibody titer of dengue serotype 1, and/or a ratio of not more than 20 for the neutralizing antibody titer of dengue serotype 2 to the neutralizing antibody titer of dengue serotype 3.

In certain embodiments, the invention is directed to said use, wherein the reconstituted unit dose of the invention as described herein is administered to a subject of 2 to 60 years of age or more than 17 years, or more than 18 years, or 18 to 60 years of age. In certain embodiments the subject is 1 to 17 years of age, or less than 9 years of age, or less than 4 years of age or less than 2 years of age. In further embodiments, the subjects or subject population are adults of more than 21 years, or 21 to 60 years, or 21 to 45 years of age. According to some of these embodiments the subject is seronegative and from a dengue-endemic region.

In certain embodiments, the invention is directed to said use, wherein the unit dose of the invention as described herein is administered to a pediatric subject of less than 2 years of age, preferably of 2 months to 2 years of age or 2 months to 1.5 years of age or 2 months to 1 year of age. According to some of these embodiments, the pediatric subject is seronegative and from a dengue endemic region.

In certain embodiments, the invention is directed to said use, wherein the reconstituted unit dose of the invention as described herein is administered subcutaneously to a pediatric subject of less than 2 years of age, preferably of 2 months to 2 years of age or 2 months to 1.5 years of age or 2 months to 1 year of age. According to some of these embodiments, the pediatric subject is seronegative and from a dengue endemic region.

In certain embodiments, the invention is directed said use, wherein the reconstituted unit dose of the invention as described herein is administered concomitantly with another vaccine. In one embodiments, the reconstituted unit dose of the invention as described herein is administered concomitantly with a yellow fever vaccine, in particular YF-17D. It is particularly preferred that the reconstituted unit dose of the invention as described herein is administered concomitantly with a yellow fever vaccine, in particular YF-17D, as described in the previous section.

In certain embodiments, the invention is directed said use, wherein the reconstituted unit dose of the invention as described herein is administered concomitantly with another vaccine. In one embodiments, the reconstituted unit dose of the invention as described herein is administered concomitantly with a HPV vaccine, in particular a 9vHPV vaccine, such as GARDASIL® 9. It is particularly preferred that the reconstituted unit dose of the invention as described herein is administered concomitantly with a HPV vaccine, in particular a 9vHPV vaccine, such as GARDASIL® 9, as described in the previous section.

In certain embodiments, the invention is directed said use, wherein the reconstituted unit dose of the invention as described herein is administered concomitantly with another vaccine. In one embodiments, the reconstituted unit dose of the invention as described herein is administered concomitantly with a MMR vaccine, such as M-M-R® II. It is particularly preferred that the reconstituted unit dose of the invention as described herein is administered concomitantly with a MMR vaccine, such as M-M-R® II, as described in the previous section.

In certain embodiments, the invention is directed said use, wherein the reconstituted unit dose of the invention as described herein is administered concomitantly with another vaccine. In one embodiments, the reconstituted unit dose of the invention as described herein is administered concomitantly with a DTaP/IPV/Hib vaccine, in particular a combined DTaP/IPV/Hib vaccine, such as Pentacel®. It is particularly preferred that the reconstituted unit dose of the invention as described herein is administered concomitantly with a DTaP/IPV/Hib vaccine, in particular a combined DTaP/IPV/Hib vaccine, such as Pentacel®, as described in the previous section.

The present invention is in part directed to the use of the reconstituted unit dose of the invention as described herein for the manufacture of a medicament for stimulating an immune response to all four serotypes of dengue virus in an elderly subject. In one embodiment a reconstituted unit dose of the invention as described herein is administered by subcutaneous injection.

In certain embodiments, the invention is directed to said use, wherein the immune response to all four serotypes of dengue virus is balanced.

In certain embodiments, the invention is directed to said use, wherein the reconstituted unit dose is administered by subcutaneous injection to the arm, preferably to the deltoid region of the arm.

In certain embodiments, the invention is directed the reconstituted unit dose of the invention as described herein for said use, wherein the elderly subject is seronegative to all dengue serotypes.

In certain embodiments, the invention is directed to said use, wherein two reconstituted unit doses of the invention as described herein are administered. In some embodiments, the two reconstituted unit doses are administered within 12 months or more, or within six months, or within three months, such as at day 0 and day 90. According to some of these embodiments, a third reconstituted unit dose is administered 6 to 12 months after the administration of the first reconstituted unit dose, such as 12 months after the first administration, or later than 12 month after the first administration, such as 12 months (1 year) after the second administration or even 5 years or longer after the first or second administration.

In certain embodiments, the invention is directed to said use, wherein the elderly subject is from a dengue endemic region. In other embodiments, the elderly subject is from a dengue non-endemic region. Such an elderly subject may be subject to a vaccination according to the invention in the context of traveling to a dengue endemic region. In certain embodiments, the reconstituted unit dose of the invention as described herein is administered subcutaneously to an elderly subject that is from a dengue endemic region or a dengue non-endemic region.

In certain embodiments, the invention is directed to said use, wherein the reconstituted unit dose of the invention as described herein is administered subcutaneously to an elderly subject that is seronegative with respect to all dengue serotypes. In other embodiments, the elderly subject is seropositive with respect to at least one dengue serotype.

In certain embodiments, the invention is directed to said use, wherein the elderly subject has at least one chronic condition or disease. The at least one chronic condition or disease may be selected from diabetes, hypertension, allergies, previous strokes, ischemic heart disease, chronic renal impairment and chronic obstructive pulmonary disease.

In certain embodiments, the invention is directed to said use, wherein the elderly subject has an impaired immune system.

Method for Determining the Titer of Neutralizing Antibodies

The present disclosure provides a method for determining the titer of neutralizing antibodies against each of dengue serotypes 1, 2, 3 and 4 in a blood serum sample, the method comprising the steps of:

(a) seeding cells from a dengue-susceptible cell line on 96-well assay plates and culturing the cells for a culture period;
(b) preparing serial dilutions of the blood serum sample;
(c) separately mixing the serially diluted blood serum samples prepared in step (b) with dengue serotype 1, dengue serotype 2, dengue serotype 3 and dengue serotype 4 to obtain separate mixtures for each dengue serotype and incubating the separate mixtures;
(d) adding the separate mixtures prepared in (c) to the cells seeded and cultured in step (a) and incubating the cells with the separate mixtures;
(e) providing an overlay for the inoculated cells and incubating the cells for an incubation period of 40 to 75 hours;
(f) determining the number of plaques in each well and comparing the number of plaques in each well to a control to determine the level of neutralizing antibodies against each of dengue serotypes 1, 2, 3 and 4.

Different incubation periods may be used in step (e) for the mixtures of different dengue serotypes. The incubation period for mixtures of dengue serotype 4 may be shorter than the incubation period for mixtures of dengue serotypes 1, 2 and 3, for example the incubation period for mixtures of dengue serotype 4 may be less than 50 hours, preferably 46±2 hours. In some embodiments, the incubation period for mixtures of dengue serotype 2 may be longer than the incubation period for mixtures of dengue serotypes 1, 3 and 4, for example the incubation period for mixtures of dengue serotype 2 may be between 60 and 70 hours, preferably 70±2 hours.

The dengue-susceptible cell line used in step (a) may be selected from Vero cells, LLC-MK2 cells and BHK-21 cells. The culture period of the cells may be 12 to 36 hours.

In step (c) the dengue serotype 1 may be DENV-1 strain 16007, dengue serotype 2 may be DENV-2 strain 16681, dengue serotype 3 may be DENV-3 strain 16562 and dengue serotype 4 may be DENV-4 strain 1036.

The separate mixtures in step (c) may be incubated overnight at a temperature of 2 to 8° C.

The overlay in step (e) may be selected from the group consisting of methylcellulose, carboxymethylcellulose and agarose. The cells with the overlay may be incubated at a temperature of 33° C. to 35° C.

The number of plaques in each well may be determined using serotype-specific anti-dengue monoclonal antibodies.

The disclosure also provides a method for determining the titer of neutralizing antibodies against each of dengue serotypes 1, 2, 3 and 4 in a blood serum sample, the method comprising the steps of:

(a) seeding Vero cells on 96-well assay plates and culturing the Vero cells for a period of 20 to 30 hours;
(b) preparing serial dilutions of the serum sample;
(c) separately mixing the serially diluted serum samples with dengue serotype 1, dengue serotype 2, dengue serotype 3 and dengue serotype 4 to prepare separate mixtures and incubating the separate mixtures overnight at a temperature of 2 to 8° C.;
(d) incubating the cells seeded and cultured in step (a) with the separate mixtures prepared in step (c) in separate wells for 90 to 120 minutes;
(e) providing a methylcellulose overlay for the inoculated cells and incubating the cells for an incubation period of 40 to 75 hours at 34° C.;
(f) determining the number of plaques in each well using serotype-specific anti-dengue monoclonal antibodies and comparing the number of plaques in each well to a control to determine the level of neutralizing antibodies against each of dengue serotypes 1, 2, 3 and 4.

The disclosure also provides the use of said method for determining the dengue serostatus of a subject before vaccination with a dengue virus vaccine or for analyzing a subject's immune response after vaccination with a dengue virus vaccine.

EXAMPLES

The following Examples are included to demonstrate certain aspects and embodiments of the invention as described in the claims. It should be appreciated by those of skill in the art, however, that the following description is illustrative only and should not be taken in any way as a restriction of the invention.

Example 1: Preparation of the Dengue Virus Strains

The methods used to generate the chimeric dengue strains TDV-1, -3 and -4 were standard molecular cloning and DNA engineering methods and are described in Huang et al. (2003) J. Virology 77(21): 11436-11447. The following well-known methods were used to construct and introduce the prM-E genes of dengue serotypes 1, 3 and 4 into the TDV-2 backbone: Reverse-transcriptase PCR (RT-PCR), PCR, restriction enzyme digestion, DNA fragment ligation, bacterial transformations by electroporation, plasmid DNA preparations, in vitro transcription by T7 RNA polymerase, and transfection of Vero cells by electroporation.

After growing and purifying the different dengue serotypes separately as described in Huang et al. (2013) PLOS Neglected Dis, 7(5):e2243, they are mixed in the concentrations provided in Table 5. The mixture of dengue serotypes is present in a dengue vaccine composition and combined with a composition of pharmaceutically acceptable excipients resulting in a dengue vaccine composition comprising 15% w/v α,α trehalose dihydrate, 1% w/v poloxamer 407, 0.1% w/v human serum albumin and 100 mM sodium chloride. The dengue vaccine composition is lyophilized and represents a lyophilized unit dose of TDV. The lyophilized unit dose is reconstituted with 37 mM aqueous sodium chloride solution and the reconstituted unit dose comprises 15% w/v α,α trehalose dihydrate, 1% w/v poloxamer 407, 0.1% w/v human serum albumin and 137 mM sodium chloride.

Example 2: Microneutralization Test

Immunogenicity was measured by a microneutralization assay to each one of the four dengue serotypes with titers defined as the dilution resulting in a 50% reduction in plaque values (MNT50). Briefly, on day 1 Vero cells were seeded on 96-well assay plates in DMEM and 10% FBS at a density of $2.5\times10^5$ cells/ml and incubated at 37° C. for 24 hours. On day 2 serial dilutions of the heat-inactivated antibody-containing test and control sera samples (dilutions range 1:10 to 1:20480) were prepared and mixed with a constant concentration of dengue viruses, in particular DENV-1 strain 16007, DENV-2 strain 16681, DENV-3 strain 16562 and DENV-4 strain 1036, (target 60-80 pfu/well) in a 96 well microtiter plate and incubated overnight at 2-8° C. to enable the neutralization of the virus by the antibodies present in the sera. After the incubation the mixture of virus and antibodies was transferred onto the 96 well plates with Vero cells and the plates were incubated at 37° C. for 90-120 minutes to infect the Vero cells. A 1% methylcellulose overlay in DMEM was applied to the plate to restrict spread of progeny virus and the plate was incubated for 46-70 hours at 34° C. depending on the Dengue serotype:

DENV1—66±2 hours
DENV2—70±2 hours
DENV3—66±2 hours
DENV4—46±2 hours

After the incubation the cells were washed twice with PBS and fixed by adding cold methanol and incubating for 60 minutes at a temperature of ≤−20° C. After fixing the plates were dried and washed three times with washing buffer (1×PBS, pH 7.4 with 0.5% Tween), before 50 μl of serotype-specific anti-dengue monoclonal antibodies in blocking solution (2.5% nonfat dry milk in PBST) per well were added and incubated with the cells for 18±4 hours at 2-8° C.

The monoclonal antibodies were made as described in Gentry et al. (1982) Am. J. Trop. Med. Hyg. 31, 548-555; Henchal et al. (1985) Am. J. Trop. Med. Hyg. 34, 162-169; and Henchal et al. (1982) Am. J. Trop. Med. Hyg. 31(4): 830-6). Briefly, the anti-DENV-1 HBD was made against dengue 1 strain Hawaii, Envelope, the anti-DENV-2 was made against dengue 2 strain New Guinea C, Envelope, isotype 1, the anti-DENV-3 HBD was made against dengue 3 strain H87, Envelope, isotype 2A, and the anti-DENV-4 HBD was made against dengue 4 strain H241, Envelope, isotype 2A.

After incubation, the plates were washed three times with washing buffer and 50 μl of a secondary peroxidase labelled goat anti-mouse IgG (H+L) (KPL Cat #074-1806) in blocking solution was added and incubated for 90 to 120 minutes at 37° C. Then the plates were washed three times with washing buffer and 50 μl of precipitant substrate (2-amino-9-ethyl carbazole (AEC) tablet in 2.5 ml DMSO, 47.5 ml 50 mM acetate buffer and 250 μl hydrogen peroxide) were added and the mixture was incubated for 20 minutes at room temperature. Finally, the substrate was removed, the plates were rinsed with $dH_2O$ and dried.

Sample titers are calculated using the linear regression method and reported as MNT50 titers for each sample. Clinical data are reported as a geometric mean titer for all the individual MNT50 titers in each treatment group. Briefly, the number of infectious foci in each well was counted and the titer of neutralizing antibodies was determined by comparing the percent reduction of infectious foci centers in wells containing antibody (test samples) in comparison to wells containing virus alone. The MNT50 was calculated using the following linear regression equation:

$$\text{MNT50}=10\hat{\ }[(50-c)/m]) \text{ where } c=y \text{ intercept of regression line and } m=\text{slope of regression line}$$

Figure 2:
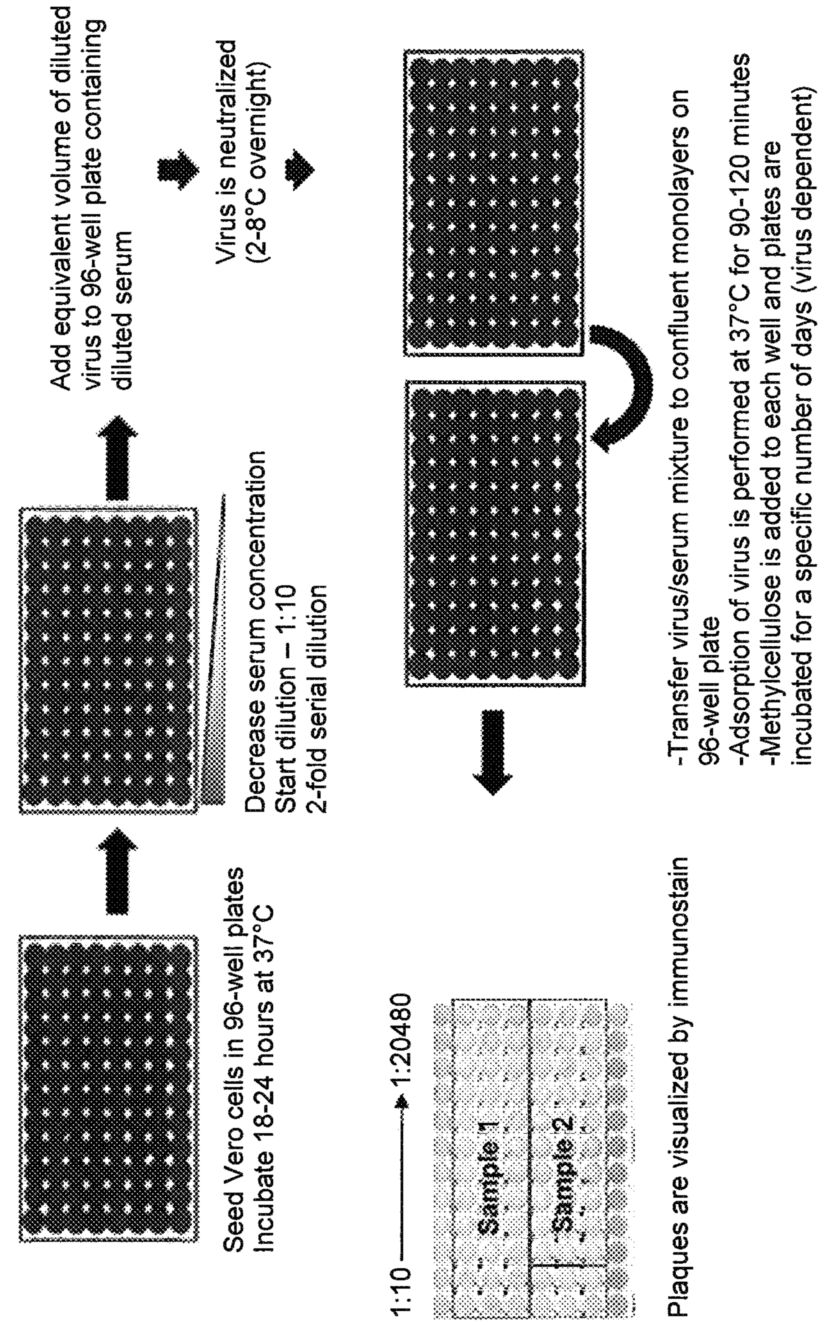
FIG. 2: Schematic drawing illustrating the microneutralization test (MNT) used to determine the titer of neutralizing antibodies.

Each test sample was tested in triplicates and the titer was calculated from the average of the triplicates. A schematic drawing of the steps performed in this test is provided in FIG. 2.

Example 3: Clinical Trial Comparing Two Different Unit Doses

A descriptive Phase II, double-blind, randomized, and controlled trial in 351 subjects aged 21 to 45 years living in Singapore was performed comparing two different formulations of a tetravalent dengue vaccine. Subjects were randomized (1:1), stratified by baseline dengue serostatus, into two treatment groups: groups 1 received one subcutaneous (SC) dose of HD-TDV and group 2 received one subcutaneous dose of TDV. The dengue vaccine formulations were prepared as described in Example 1. The concentration of the four dengue serotypes in the HD-TDV vaccine (high dose tetravalent dengue vaccine) and in the TDV vaccine (corresponding to the unit dose of the invention as described herein) is outlined in Table 5.

TABLE 5

| Unit doses used in the trial. | |
|---|---|
| Comparative unit dose (HD-TDV) | 0.5 mL comprising TDV-1, TDV-2, TDV-3 and TDV-4 containing 3.2 x $10^4$ PFU, 1.3 x $10^5$ PFU, 2.5 x $10^5$ PFU, and 4 x $10^5$ PFU, respectively. Administered by subcutaneous injection on day 1. |
| Example 1 unit dose (TDV) | 0.5 mL comprising TDV-1, TDV-2, TDV-3 and TDV-4 containing 2.5 x $10^4$ PFU, 6.3 x $10^3$ PFU, 3.2 x $10^4$ PFU, and 4 x $10^5$ PFU, respectively. Administered by subcutaneous injection on day 1. |

Immunogenicity was evaluated at Days 15, 30, 90, 180, and 365 post-vaccination as geometric mean titers (GMTs) and seropositivity rates. Immunogenicity of the vaccines against each of the four dengue serotypes was assessed using a microneutralization assay, with titers corresponding to the dilution resulting in a 50% reduction in plaque reduction (MNT50) as described in Example 2. Primary immunogenicity endpoints were reported in terms of geometric mean titers (GMTs) of neutralizing antibodies, and seropositivity rates (which were defined as percentages of subjects with reciprocal neutralizing titers ≥10 for each of the DENV serotypes) in the overall trial population. As a secondary endpoint, GMTs and seropositivity rates were analyzed by dengue baseline seropositivity status. Seropositive at baseline was defined as being seropositive for at least one DENV serotype, whereas seronegative at baseline was defined as being seronegative for all four DENV serotypes.

Solicited and unsolicited adverse events (AEs) were assessed by severity and causality.

a) Seropositivity

Dengue seropositivity is based on the result of the microneutralization test (MNT) described in Example 2 and is defined as a reciprocal neutralizing antibody titer ≥10 for one or more dengue serotype at baseline. The baseline seropositivity rate for each dengue serotype is defined as the percentage of seropositive subjects for the given dengue serotype and was derived from the neutralizing antibodies titers of the dengue serotypes as measured in the subjects before administration of the first unit dose. The seropositivity rate at day 180 or day 365 is defined as the percentage of seropositive subjects and was derived from the neutralizing antibodies titers of the dengue serotypes as measured in the subjects 180 and 365 days after administration of the first unit dose, respectively.

In total, 187 subjects (53.6%) were seropositive, based on MNT50, for at least one dengue serotype at baseline: 48.7% were seropositive for DENV-1, 49.0% for DENV-2, 45.2% for DENV-3, and 41.2% for DENV-4. The seropositive status and rate at baseline of the two different vaccination groups is shown in Table 6.

TABLE 6

| Serostatus and seropositivity rate at baseline | Comparative unit dose | Example 1 unit dose |
|---|---|---|
| Baseline seropositivity status (count of participants) | | |
| Seropositive for at least one dengue serotype | 92 | 95 |
| Seronegative for all dengue serotypes | 83 | 80 |
| Baseline seropositivity rate for each serotype (percentage of participants) | | |
| TDV-1 | 48.6 | 48.6 |
| TDV-2 | 47.4 | 50.3 |
| TDV-3 | 44.0 | 46.3 |
| TDV-4 | 41.7 | 40.6 |

Figure 3A:
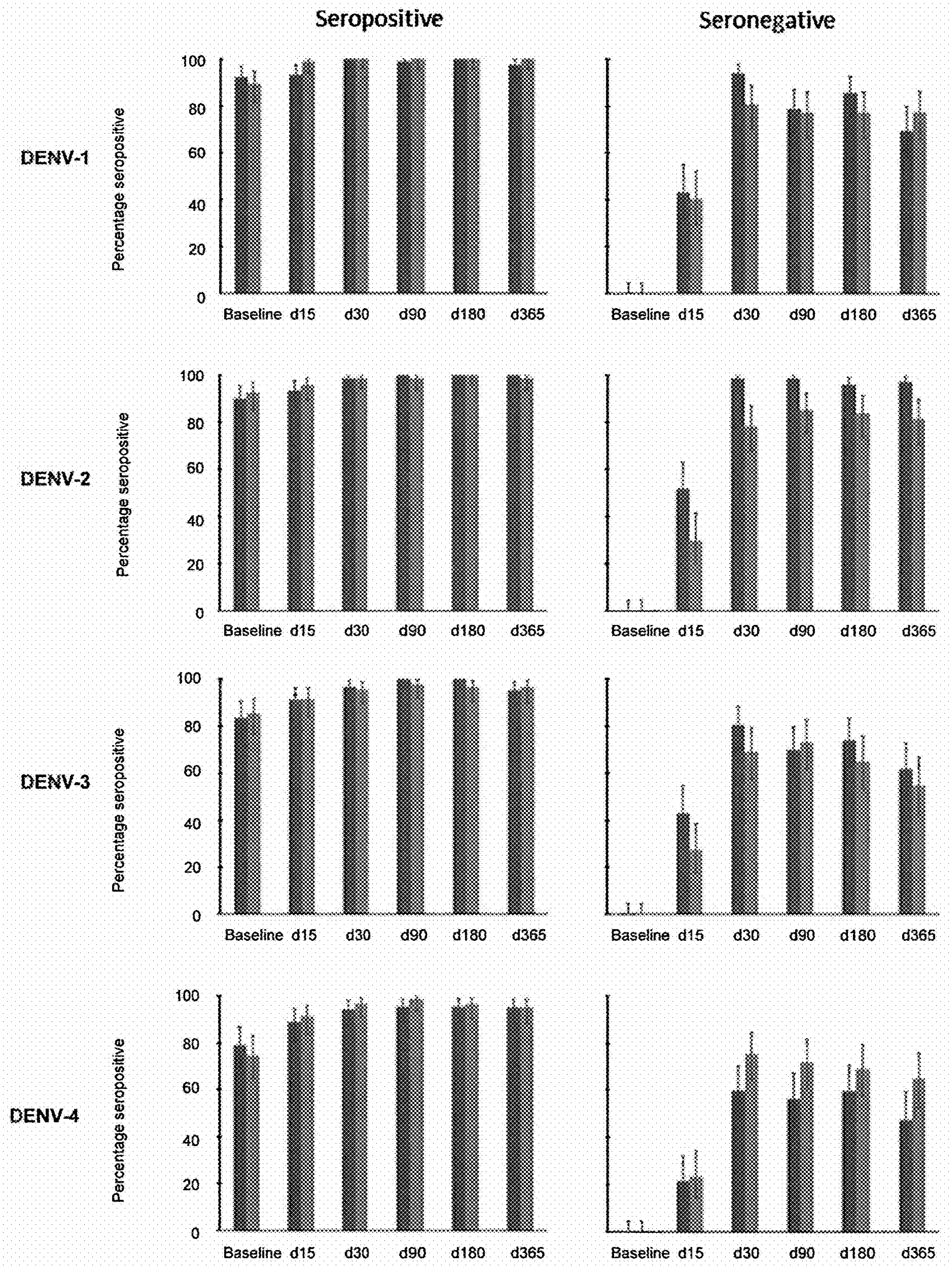
FIGS. 3A-3B: Percentage of subjects (t 95% confidence intervals) who were seropositive (reciprocal neutralizing titer ≥10) for each of the dengue serotypes at different time points of the trial in the HD-TDV group (dark colored, left bar) and TDV group (light colored, right bar) throughout the trial. Time points shown are baseline, day 15 (d15), day 30 (d30), day 90 (d90), day 180 (d180) and day 365 (d365). Part A shows the results for participants seropositive (set of graphs on the left) and seronegative (set of graphs on the right) at baseline, per-protocol set. Part B shows the results for the entire trial population (all) per-protocol set.
Figure 3B:
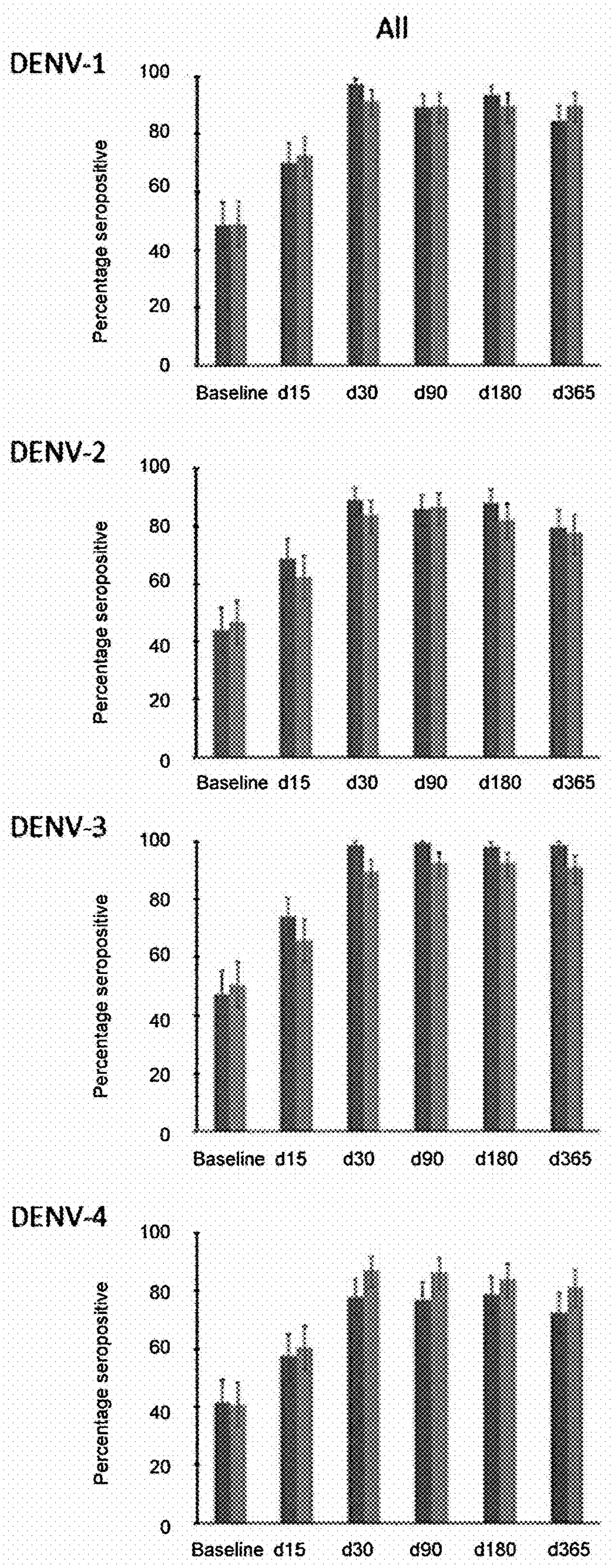

Seropositivity rates increased to Day 30 after administration of the unit doses, and remained high through to Day 365 for each of the four serotypes (FIG. 3). For the overall trial population, the percentages of subjects who were seropositive for DENV-1 and DENV-3 were similar in the HD-TDV and TDV groups, whereas higher post-baseline seropositivity rates were seen for the HD-TDV group against DENV-2, and for the TDV group against DENV-4 (FIG. 3B). In general, higher seropositivity rates were seen in subjects already seropositive at baseline than in seronegative subjects. Seropositivity rates rose to nearly 100% against all four dengue serotypes in the seropositive vaccine groups by Day 30, and remained at this level through to Day 365; no difference was seen between HD-TDV and TDV (FIG. 3A). In the seronegative group, the seropositivity rates increased more gradually to a peak at Day 30, with limited decline until Day 365. The rates were consistently higher for HD-TDV than TDV against DENV-2, but were higher for TDV than HD-TDV against DENV-4, through to Day 365 (FIG. 3A).

TABLE 7

| Seropositivity rate at day 180 | Comparative unit dose | Example 1 unit dose |
|---|---|---|
| Overall number of participants analyzed | 166 | 163 |
| Seropositivity rate at day 180 (95% Confidence Interval) | | |
| Day 180, TDV-1 | 93.4 (88.5 to 96.6) | 89.6 (83.8 to 93.8) |
| Day 180, TDV-2 | 98.2 (94.8 to 99.6) | 92.6 (87.5 to 96.1) |
| Day 180, TDV-3 | 88.0 (82.0 to 92.5) | 82.2 (75.5 to 87.7) |
| Day 180, TDV-4 | 78.9 (71.9 to 84.9) | 84.0 (77.5 to 89.3) |

TABLE 8

| Seropositivity rate at day 365 | Comparative unit dose | Example 1 unit dose |
|---|---|---|
| Overall number of participants analyzed | 160 | 156 |
| Seropositivity rate at day 365 (95% Confidence Interval) | | |
| Day 365, TDV-1 | 84.4 (77.8 to 89.6) | 89.7 (83.9 to 94.0) |
| Day 365, TDV-2 | 98.8 (95.6 to 99.8) | 91.0 (85.4 to 95.0) |
| Day 365, TDV-3 | 79.4 (72.3 to 85.4) | 77.6 (70.2 to 83.8) |
| Day 365, TDV-4 | 72.5 (64.9 to 79.3) | 81.4 (74.4 to 87.2) |

b) Geometric Mean Neutralizing Antibody Titers (GMTs)

Neutralizing antibody titers (GMTs) for each dengue serotype were determined in a serum sample of a subject taken before administration of the first unit dose of the dengue vaccine composition and 180 or 365 days after administration of the first unit dose of the dengue vaccine composition using the microneutralization (MNT) assay as described in Example 2.

Figure 4A:
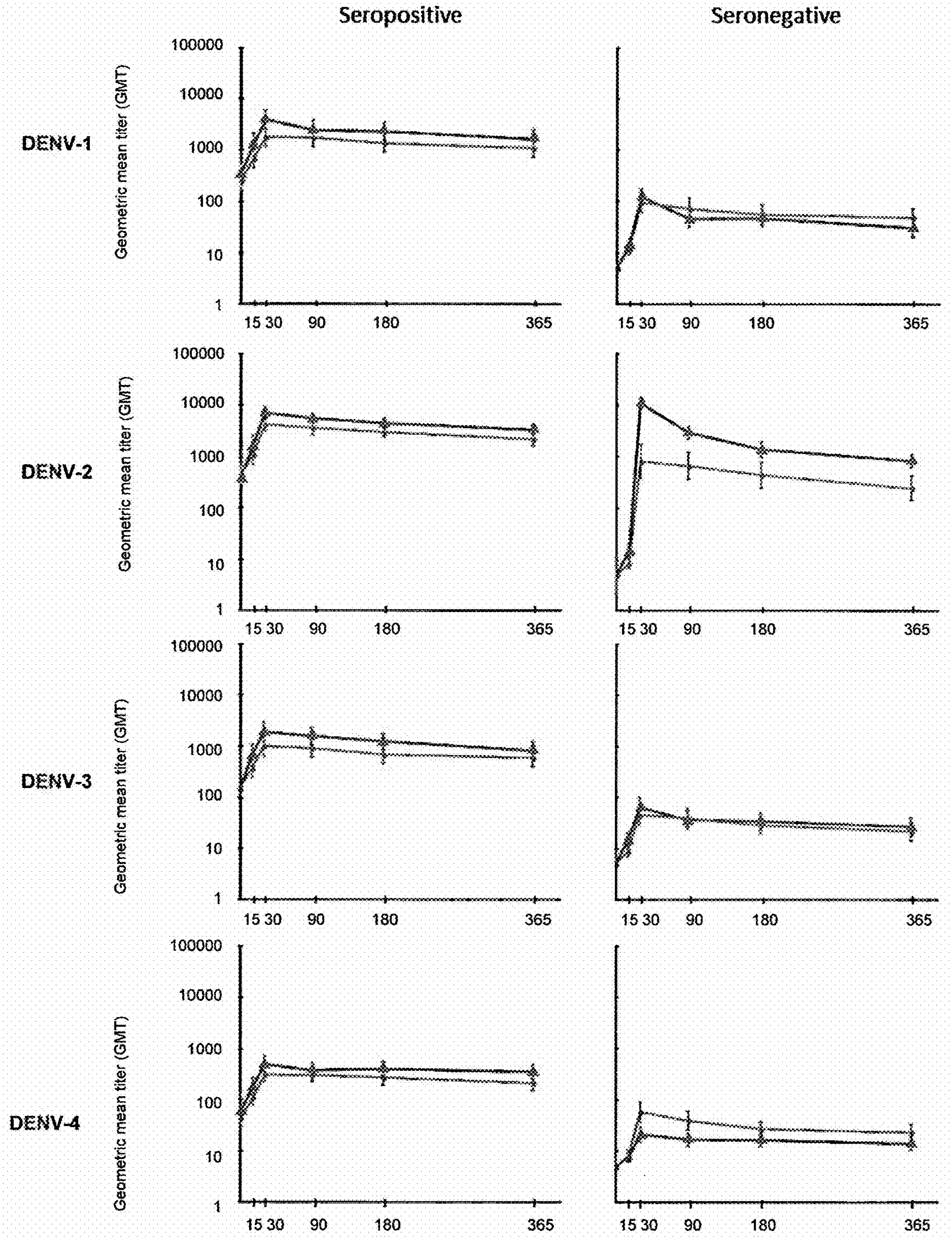
FIGS. 4A-4B: Geometric mean titers (GMTs) (±95% confidence intervals) of neutralizing antibodies against each of the four dengue serotypes during the course of the trial for HD-TDV (dark line with triangles) and TDV (light line with circles) recipients, for the entire trial population (part B) and for participants seropositive and seronegative at baseline (part A), per-protocol set.
Figure 4B:
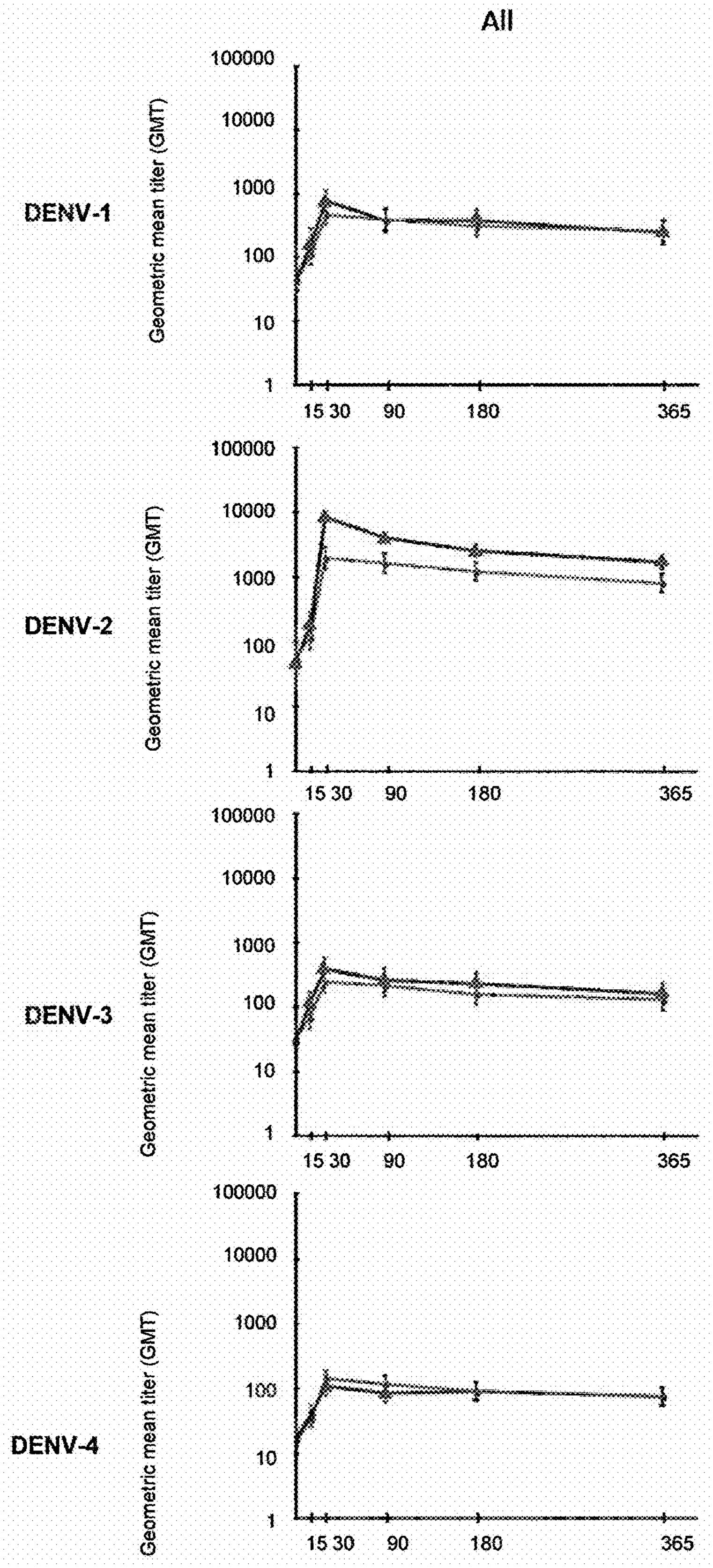

For both HD-TDV and TDV, an increase in GMTs was observed by Day 15, reaching a maximum by Day 30 (FIG. 4). Antibody titers remained above baseline levels throughout the trial for both unit doses. In the overall trial population, no substantial differences were seen in GMT titers between the two unit dose groups, except against DENV-2, where the response was higher for the HD-TDV group compared with the TDV group (8640.3 versus 1992.7 at Day 30). When assessed by baseline seropositivity status, the GMT profiles were similar as for the entire population, with a rise by Day 15, peak at Day 30, and gradual decline thereafter (FIG. 4B3). In the group who were seropositive at baseline, the difference between the unit dose groups in response to DENV-2 was reduced, with GMTs of 6970.3 and 4193.3 at Day 30 for the HD-TDV and TDV groups, respectively. Responses were higher against DENV-1, DENV-3, and DENV-4 in the baseline seropositive group, compared with the baseline seronegative group, across both unit doses. Against DENV-2, a lower response was seen in baseline seronegative subjects receiving TDV, compared with HD-TDV; Day 30 GMTs were 812.9 in the TDV group, compared with 10965.9 in the HD-TDV group. The response in these subjects also differed against DENV-4, with a higher response being observed in the

TABLE 9

Geometric mean neutralizing antibody titers (GMTs) at day 180

| | Comparative unit dose | Example 1 unit dose |
|---|---|---|
| Overall number of participants analyzed GMTs (95% Confidence Interval) [units: Titer] | 166 | 163 |
| Day 180, TDV-1 | 379.4 (252.3 to 570.3) | 312.2 (212.2 to 459.2) |
| Day 180, TDV-2 | 2585.5 (2088.8 to 3200.3) | 1235.0 (890.7 to 1712.5) |
| Day 180, TDV-3 | 236.2 (162.2 to 344.0) | 161.0 (110.5 to 234.6) |
| Day 180, TDV-4 | 91.0 (65.7 to 125.9) | 92.9 (68.9 to 125.4) |

TABLE 10

Ratio of geometric mean neutralizing antibody titers (GMTs) at day 180

| | Comparative unit dose | Example 1 unit dose |
|---|---|---|
| TDV-2:TDV-1 | 7 | 4 |
| TDV-2:TDV-3 | 11 | 8 |
| TDV-2:TDV-4 | 28 | 13 |

TABLE 11

Geometric mean neutralizing antibody titers (GMTs) at day 365

| | Comparative unit dose | Example 1 unit dose |
|---|---|---|
| Overall number of participants analyzed GMTs (95% Confidence Interval) [units: Titer] | 160 | 156 |
| Day 365, TDV-1 | 247.3 (160.9 to 380.2) | 264.1 (181.1 to 385.1 |
| Day 365, TDV-2 | 1726.0 (1392.6 to 2139.3) | 809.5 (576.6 to 1136.4) |
| Day 365, TDV-3 | 163.2 (110.0 to 242.3) | 132.6 (89.9 to 195.5) |
| Day 365, TDV-4 | 75.3 (53.8 to 105.4) | 77.0 (56.9 to 104.2) |

TABLE 12

Ratio of geometric mean neutralizing antibody titers (GMTs) at day 365

| | Comparative unit dose | Example 1 unit dose |
|---|---|---|
| TDV-2:TDV-1 | 7 | 3 |
| TDV-2:TDV-3 | 11 | 6 |
| TDV-2:TDV-4 | 23 | 11 |

TABLE 13

Geometric mean neutralizing antibody titers (GMTs) of all four dengue serotypes assessed by dengue baseline seropositivity status at day 180

| | Comparative unit dose | Example 1 unit dose |
|---|---|---|
| Seropositive | 89 Participants | 88 Participants |
| Day 180, TDV-1 (Seropositive) | 2327.2 (1550.4 to 3493.3) | 1356.2 (905.5 to 2031.2) |
| Day 180, TDV-2 (Seropositive) | 4412.0 (3586.6 to 5427.4) | 2952.0 (2358.2 to 3695.4) |
| Day 180, TDV-3 (Seropositive) | 1248.3 (879.7 to 1771.3) | 693.6 (459.6 to 1046.6) |
| Day 180, TDV-4 (Seropositive) | 399.5 (291.3 to 547.9) | 268.3 (190.2 to 378.6) |
| Seronegative | 77 Participants | 75 Participants |
| Day 180, TDV-1 (Seronegative) | 46.6 (32.0 to 67.9) | 55.7 (35.6 to 87.1) |
| Day 180, TDV-2 (Seronegative) | 1394.1 (983.2 to 1976.6) | 444.3 (247.2 to 798.5) |
| Day 180, TDV-3 (Seronegative) | 34.5 (23.4 to 50.7) | 29.0 (19.4 to 43.3) |
| Day 180, TDV-4 (Seronegative) | 16.4 (12.3 to 22.0) | 26.8 (19.0 to 37.7) |

TABLE 14

Ratio of geometric mean neutralizing antibody titers (GMTs) assessed by dengue baseline seropositivity status at day 180 and 365

| | Comparative unit dose | Example 1 unit dose |
|---|---|---|
| Seropositive 180 Days | | |
| TDV-2:TDV-1 | 1.9 | 2.2 |
| TDV-2:TDV-3 | 3.5 | 4.3 |
| TDV-2:TDV-4 | 11.0 | 11.0 |
| Seronegative 180 Days | | |
| TDV-2:TDV-1 | 29.9 | 8.0 |
| TDV-2:TDV-3 | 40.4 | 15.3 |
| TDV-2:TDV-4 | 85.0 | 16.6 |

TABLE 15

Geometric mean neutralizing antibody titers (GMTs) of all four dengue serotypes assessed by dengue baseline seropositivity status at day 365

| | Comparative unit dose | Example 1 unit dose |
|---|---|---|
| Seropositive | 84 Participants | 85 Participants |
| Day 365, TDV-1 (Seropositive) | 1633.3 (1055.8 to 2526.7) | 1081.5 (724.0 to 1615.6) |
| Day 365, TDV-2 (Seropositive) | 3316.0 (2623.8 to 4190.9) | 2177.3 (1613.5 to 2938.1) |
| Day 365, TDV-3 (Seropositive) | 830.6 (551.2 to 1251.5) | 600.2 (402.3 to 895.3) |
| Day 365, TDV-4 (Seropositive) | 346.3 (249.2 to 481.1) | 212.6 (152.2 to 296.9) |
| Seronegative | 76 Participants | 71 Participants |
| Day 365, TDV-1 (Seronegative) | 30.7 (20.4 to 46.2) | 48.8 (32.1 to 74.2) |
| Day 365, TDV-2 (Seronegative) | 838.7 (621.9 to 1131.1) | 247.6 (143.9 to 426.1) |
| Day 365, TDV-3 (Seronegative) | 27.0 (17.8 to 41.1) | 21.7 (14.3 to 33.1) |
| Day 365, TDV-4 | 13.9 (10.3 to 19.0) | 22.9 (15.8 to 33.1) |

TABLE 16

Ratio of geometric mean neutralizing antibody titers (GMTs) assessed by dengue baseline seropositivity status at day 365

| | Comparative unit dose | Example 1 unit dose |
|---|---|---|
| Seropositive 365 Days | | |
| TDV-2:TDV-1 | 2.0 | 2.0 |
| TDV-2:TDV-3 | 4.0 | 3.6 |
| TDV-2:TDV-4 | 9.6 | 10.2 |
| Seronegative 365 Days | | |
| TDV-2:TDV-1 | 27.3 | 5.1 |
| TDV-2:TDV-3 | 31.1 | 11.4 |
| TDV-2:TDV-4 | 60.3 | 10.8 |

c) Safety

Overall, rates of solicited local and systemic adverse events (AEs), unsolicited AEs, and serious adverse events (SAEs) were similar across the two unit dose groups. No deaths or AEs leading to discontinuation were recorded in the trial. Three subjects in each unit dose group experienced SAEs, one of these events in the HD-TDV group was considered by the sponsor to be vaccine-related based on temporal association. The SAE was polyarthritis which began six days following receipt of the vaccine. Rates of solicited reactions were similar across unit dose groups, and seropositivity status at baseline. Overall, 47.4% and 53.7% of subjects reported local reactions, and 52.0% and 50.9% reported solicited systemic AEs, in the HD-TDV and TDV groups, respectively. Most reactions were mild or moderate. The most commonly reported local adverse reaction was injection site pain (46.3% in the HD-TDV group, 52.0% in the TDV group) and the most common systemic AE was headache (28.6% in the HD-TDV group, 34.9% in the TDV group).

d) Conclusion

Both unit doses showed an acceptable safety profile. The results show a more balanced immune response with the new TDV unit dose compared to the early HD-TDV unit dose, particularly in the subjects who were seronegative prior to vaccination: (i) in baseline seronegative subjects, response to DENV-2 was less dominant with TDV and (ii) DENV-4 seropositivity rates and GMTs were also higher with TDV in these subjects.

Example 4: Cell-Mediated Immunity Stimulated by the Dengue Vaccine

A gamma interferon (IFNγ) enzyme-linked immunosorbent spot (ELISPOT) assay was performed using peripheral blood mononuclear cells (PBMCs) from the subjects taking part in the clinical trial of Example 3 and the commercial ELISpot assay kit available from Mabtech according to the manufacturer's instructions. Briefly, cryopreserved PBMCs were thawed and left to rest overnight, then incubated with various peptide pools for 18-22 hours in plates coated with anti-IFNγ antibodies. PBMCs were then removed and spots were developed and then counted. Results were reported as mean spot forming cells (SFC) per $10^6$ PBMCs. Peptide pools matched selected DENV-derived proteins, covering the entire DENV-2 proteome with NS1, NS3, and NS5 proteins from New Guinea C (NGC) and Thailand/16681/84 strains; and C, prM+E, NS2 and NS4 proteins from Thailand/16681/84 only plus TDV-1, TDV-3 and TDV-4 prM+E inserts from DENV-1, -3 and -4 strains Thailand/16007/1964, Philippines/16562/1964 and Indonesia/1036/1976, respectively.

Figure 5:
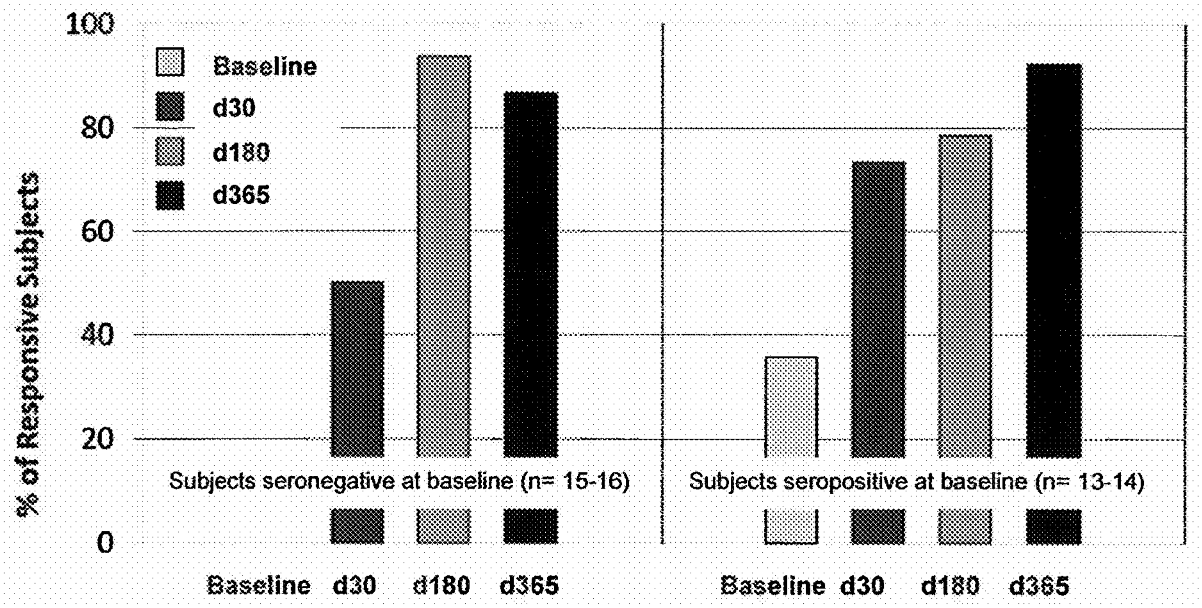
FIG. 5: IFNγ ELISpot analysis of peripheral blood mononuclear cells before vaccination (baseline) and at different time points after administration of TDV. Shown are the response frequencies to the entire DENV-2 proteome. A subject was considered responsive if response to more than one peptide pool from DENV-2 was positive (i.e. ≥4× mean of negative control and ≥50 SFC/$10^6$ PBMCs).

Response rates to DENV-2 proteome at 6 and 12 months post-single dose of TDV were ≥90%, and were comparable between subjects seronegative and seropositive at baseline (FIG. 5).

Figure 6:
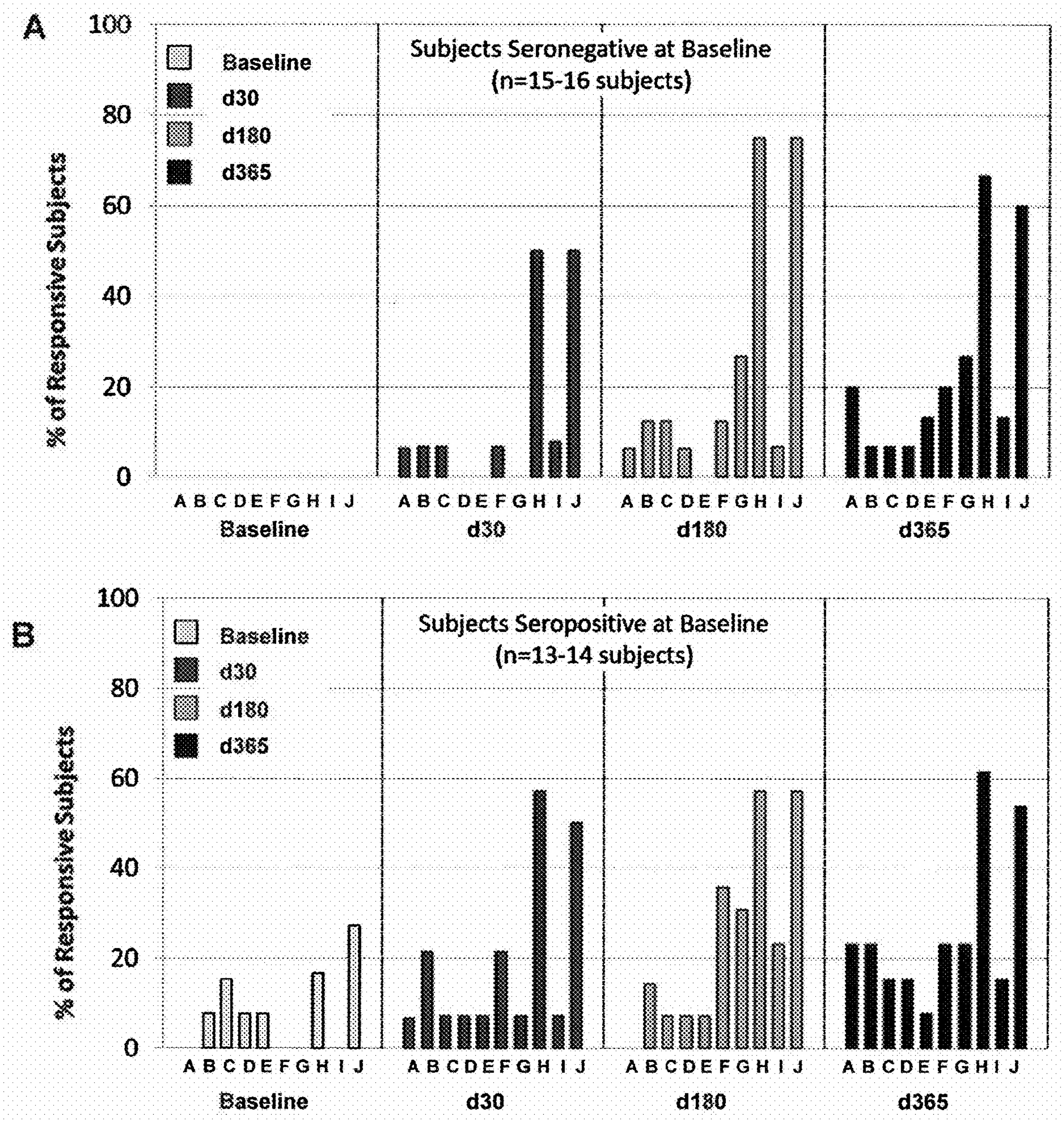
FIG. 6: IFNγ ELISpot analysis of peripheral blood mononuclear cells before vaccination (baseline) and at different time points after administration of TDV. Shown are the response frequencies to peptide pools matching selected DENV-derived proteins as indicated. A subject was considered responsive if response to more than one peptide pool from DENV-2 was positive (i.e. >4× mean of negative control and >50 SFC/$10^6$ PBMCs). A=DENV-2 C; B=DENV-1 prM+E; C=DENV-2 prM+E; D=DENV-3 prM+E; E=DENV-4 prM+E; F=DENV-2 NS1; G=DENV-2 NS2; H=DENV-2 NS3; I=DENV-2 NS4; J=DENV-2 NS5.

The response was primarily directed to the NS proteins, particularly in subjects seronegative at baseline (FIG. 6).

The NS3 and NS5 proteins were the most recognized antigens (by 50-75% of subjects). Immunodominance of NS3 and NS5 was independent of baseline serostatus. Durability of the response was maintained equally between NS3 and NS5 throughout the 12-month post-single vaccination follow-up.

Example 5: Antibody Responses to Non-Structural Proteins

The non-structural protein NS-1 from all four dengue serotypes can induce endothelial hyperpermeability of human pulmonary microvascular endothelial cells (HP-MEC) as measured by transendothelial electrical resistance (TEER) (Puerta-Guardo et al. (2016) PloS Pathog. 12(7): e1005738). It also interacts with endothelial cells to induce degradation of the glycocalyx via activation of sialidases and the cathepsin L/heparanase pathway (Glasner et al. (2017) PloS Pathog. 13(11): e1006673). In view of these effects, it was investigated whether the comparative unit dose induces antibodies against NS1 and inhibits NS1-mediated physiological effects.

a) Anti-NS1 Antibodies

Serum samples were collected at day 0 before vaccination and day 120 after administration of the first unit dose. Serum was collected from 6 dengue seronegative and 6 dengue seropositive subjects at both day 0 and day 120, and Ab concentrations were determined by ELISA.

The anti-NS1 antibody concentration in seronegative and seropositive subjects at day 0 and day 120 is shown in Tables 17 and 18:

TABLE 17

Anti-NS1 antibody concentration in seronegative subjects at day 0 and day 120
Dengue seronegative subjects
Anti-NS1 antibody concentration (RU/ml)

| | DENV1 | | DENV2 | | DENV3 | | DENV4 | |
|---|---|---|---|---|---|---|---|---|
| Subj. | d0 | d120 | d0 | d120 | d0 | d120 | d0 | d120 |
| 1023014 | 13.49 | 602.56 | 16.22 | 2570.40 | 10.00 | 489.78 | 28.18 | 302.00 |
| 1025011 | 66.07 | 173.78 | 35.48 | 794.33 | 67.61 | 117.49 | 42.66 | 85.11 |
| 1025013 | 5.62 | 380.19 | 24.55 | 2454.71 | 16.98 | 316.23 | 10.00 | 186.21 |
| 1035002 | 34.67 | 177.83 | 31.62 | 977.24 | 17.78 | 114.82 | 19.05 | 44.67 |
| 1035005 | 50.12 | 467.74 | 20.42 | 1659.59 | 104.71 | 309.03 | 66.07 | 288.40 |
| 1035001 | 40.74 | 186.21 | 52.48 | 489.78 | 44.67 | 169.82 | 51.29 | 177.83 |

TABLE 18

Anti-NS1 antibody concentration in seropositive subjects at day 0 and day 120
Dengue seropositive subjects
Anti-NS1 antibody concentration (RU/ml)

| | DENV1 | | DENV2 | | DENV3 | | DENV4 | |
|---|---|---|---|---|---|---|---|---|
| Subj. | d0 | d120 | d0 | d120 | d0 | d120 | d0 | d120 |
| 1052010 | 691.83 | 11481.54 | 309.03 | 12022.64 | 436.52 | 7585.78 | 245.47 | 4677.35 |
| 1052014 | 758.58 | 1445.44 | 407.38 | 891.25 | 758.58 | 1122.02 | 724.44 | 707.95 |
| 1052015 | 3890.45 | 3467.37 | 2570.40 | 2344.23 | 3235.94 | 2818.38 | 660.69 | 707.95 |
| 1071007 | 478.63 | 851.14 | 239.88 | 478.63 | 660.69 | 1202.26 | 870.96 | 1258.93 |
| 1071012 | 691.83 | 776.25 | 724.44 | 676.08 | 776.25 | 812.83 | 346.74 | 446.68 |
| 1082009 | 5888.44 | 5370.32 | 7413.10 | 6309.57 | 5248.07 | 4897.79 | 891.25 | 794.33 |

These data show that the vaccine induces antibodies against NS1 from all dengue serotypes in both seropositive and seronegative subjects.

b) Transendothelial Electrical Resistance (TEER)

The effect of recombinant NS1 proteins from dengue serotypes 1, 2, 3 and 4 and sera from vaccinated seronegative and seropositive subjects on endothelial permeability was evaluated by measuring TEER of HPMEC grown on a 24-well Transwell polycarbonate membrane system (Transwell® permeable support, 0.4 μM, 6.5 mm insert; Corning Inc.) as previously described (Beatty et al. (2015) Sci. Transl. Med. 7(304): 304ra141; Puerta-Guardo et al. (2016) PloS Pathog. 12(7):e1005738). Briefly, TEER was measured in Ohms (Ω) at sequential 2-hour time-points following the addition of test proteins using an Epithelial Volt Ohm Meter (EVOM) with “chopstick” electrodes (World Precision Instruments). Untreated endothelial cells grown on Transwell inserts were used as negative untreated controls, and inserts with medium alone were used for blank resistance measurements. Relative TEER represents a ratio of resistance values (Ω) as follows: (Ω experimental condition−Ω medium alone)/(Ω non-treated endothelial cells−Ω medium alone). After 24 hours of treatment, 50% of upper and lower chamber media was replaced by fresh endothelial cell medium. For experiments using sera, 30 μl of culture supernatant was removed from the apical chamber and replaced with 30 μl of serum samples immediately before the addition of 5 μg/ml DENV-2 NS1.

Figure 7A:
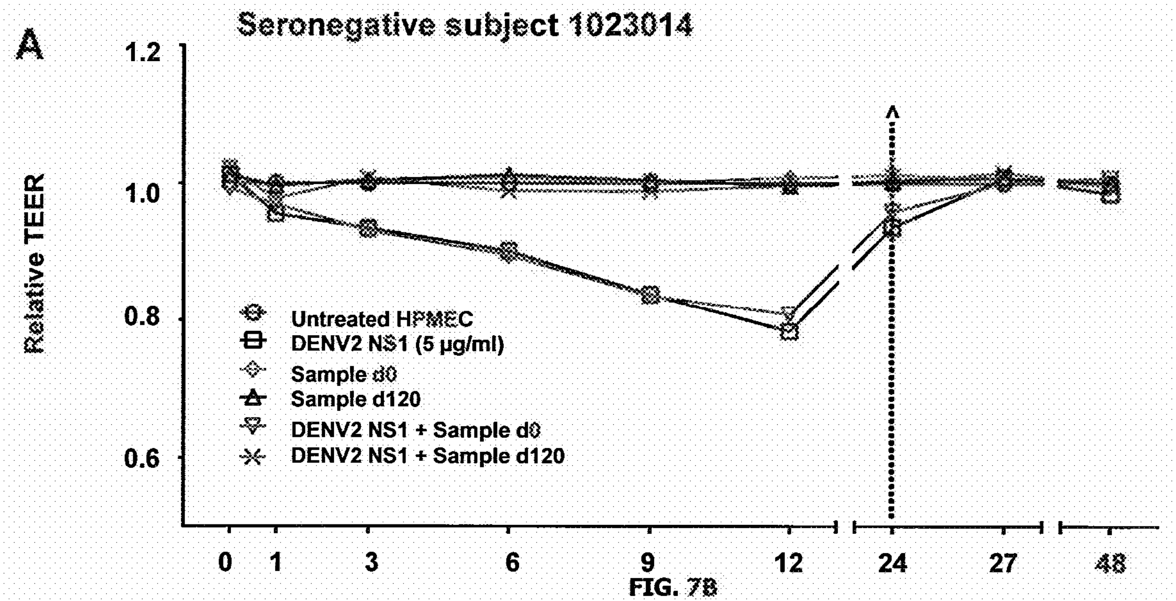
FIGS. 7A-7B: Effect of sera from a seronegative subject (A) and a seropositive subject (A) to whom TDV was administered on DENV-2 NS1-induced hyperpermeability as determined by TEER. HPMEC were grown on Transwell semi-permeable membranes (0.4 μm pore size), and serum samples (30 μl) were added to the apical chamber in the presence or absence of DENV2 NS1 (5 μg/ml). DENV2 NS1 is depicted as squares; day 0 serum alone is depicted as diamonds; day 120 serum alone is depicted as triangles; day 0 serum+DENV2 NS1, is depicted as upside-down triangles; day 120 serum+DENV2 NS1 is depicted as X's. (^) represents media change. Endothelial permeability was measured at indicated time-points over 48 hours. Relative TEER values from one independent experiment performed in duplicate are plotted. Error bars indicate standard error of the mean (SEM).
Figure 7B:
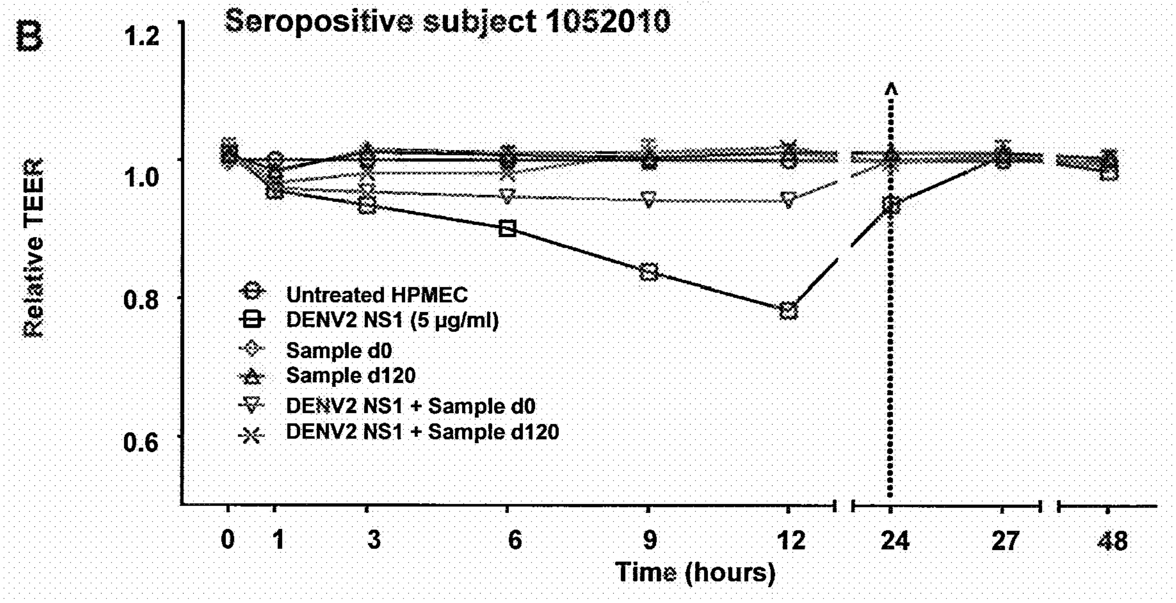

Day 0 serum samples from seronegative subjects did not protect against NS1-mediated barrier dysfunction, but day 120 samples from all seronegative subjects blocked decreases in TEER values induced by NS1 (see FIG. 7A). Day 0 samples from seropositive subjects produced varying levels of protection, and all day 120 samples from seropositive subjects completely abrogated NS1-induced hyperpermeability (see FIG. 7B).

c) Degradation of Glycocalyx-Like Layer (EGL)

Microscopy was performed as previously described (Puerta-Guardo et al. (2016) PloS Pathog. 12(7):e1005738). For imaging experiments, HPMEC were grown on coverslips coated with 0.2% gelatin (Sigma) and imaged on a Zeiss LSM 710 Axio Observer inverted fluorescence microscope equipped with a 34-channel spectral detector. Images acquired using the Zen 2010 software (Zeiss) were processed and analyzed with ImageJ software. All RGB images were converted to grayscale, then mean grayscale values and integrated density from selected areas were taken, along with adjacent background readings, and plotted as mean fluorescence intensity (MFI). To assess the effect of sera from vaccinated subjects on DENV2 NS1-induced EGL disruption, the distribution of sialic acid and heparan sulfate was examined on confluent HPMEC monolayers treated with DENV2 NS1 (5 μg/ml)+negative control serum (30 μl), NS1+positive control serum (30 μl), or NS1+serum from vaccinated subjects (30 μl) and fixed with 4% paraformaldehyde (PFA) at 6 hours post-treatment. Primary antibodies (Wheat germ agglutinin (WGA) lectin conjugated to Alexa Fluor 647 (WGA-A647, Molecular Probes) to stain N-acetyl neuraminic acid (sialic acid); Ab Heparan Sulfate, purified (clone F58-10E4, Amsbio) were incubated overnight at 4° C., and detection was performed using secondary species-specific anti-IgG or anti-IgM antibodies conjugated to Alexa fluorophores (488 and 647).

Figure 8A:
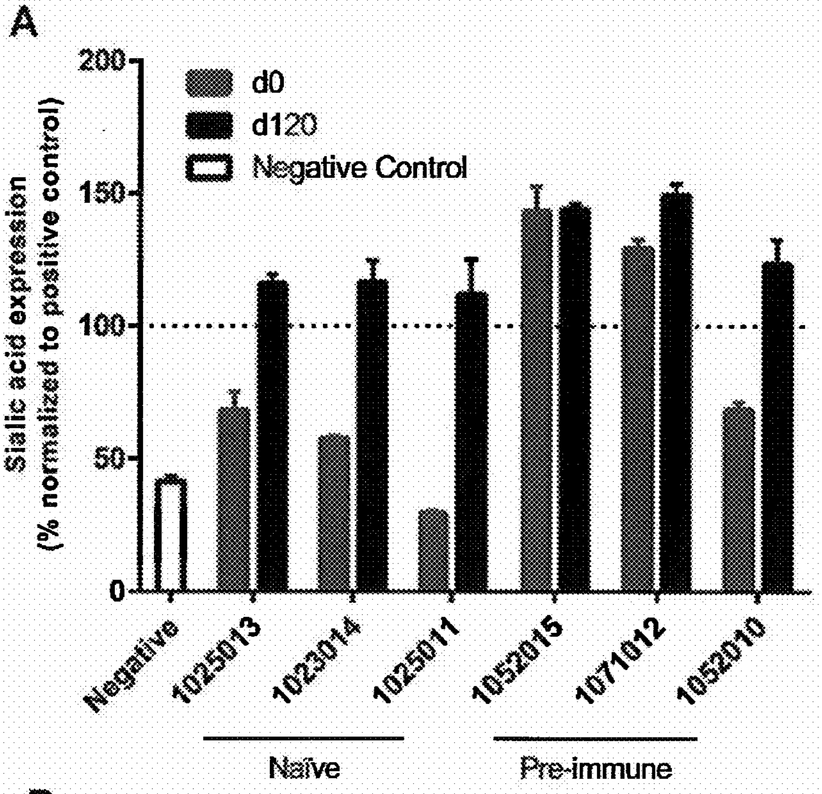
FIGS. 8A-8B: Effect of sera from seronegative and seropositive subjects to which TDV was administered on NS1-induced sialic acid and heparan sulfate degradation. Shown is the quantification of mean fluorescence intensity (MFI) of (A) sialic acid and (B) heparan sulfate expression after staining with sialic acid- and heparan sulfate-specific fluorescent antibodies as visualized by confocal microscopy. Values are normalized to MFI from the NS1+positive control serum group (represented by dotted line at 100%) and expressed as percentage of control. Error bars indicate SEM. The left bar for each subject shows the results at day 0 (d0), the right car for each subject shows the results at day 120 (d120).
Figure 8B:
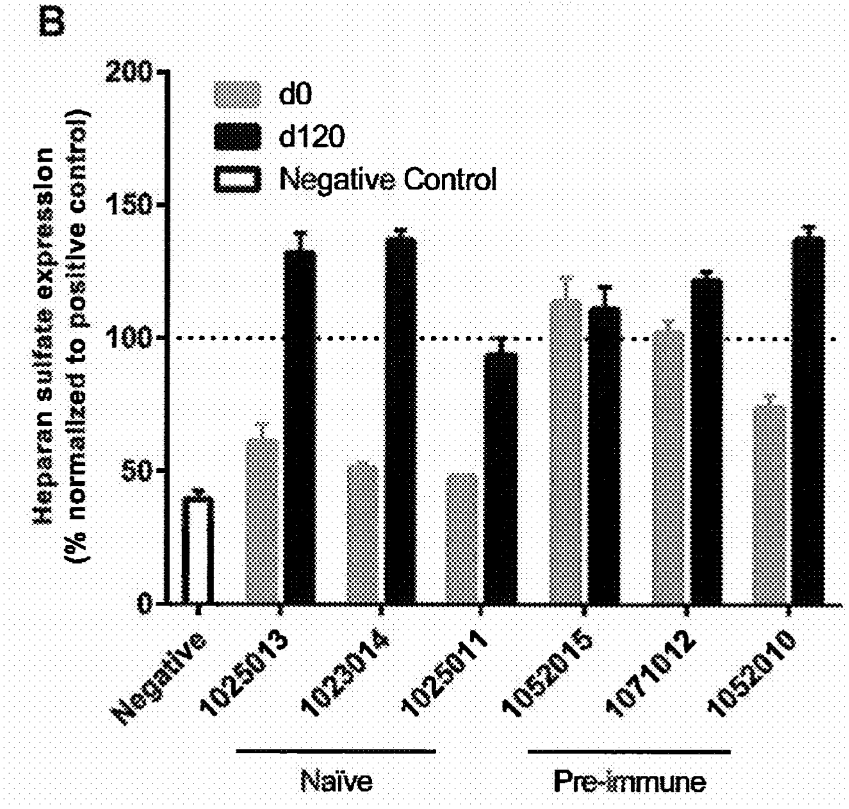

Day 0 sera from seronegative subjects had no substantial protective effect, while day 120 sera from seronegative subjects completely blocked degradation of both sialic acid and heparan sulfate. Similarly, day 0 samples from seropositive subjects exhibited varying levels of protection, and sera from seropositive subjects at day 120 were completely protective (see FIG. 8). Positive control serum was used as a baseline for protection, and negative control serum represented maximum NS1-mediated disruption. These results show that the anti-NS1 antibody response stimulated by the dengue vaccine can protect against NS1-induced hyperpermeability by preventing the degradation of key EGL components.

Taken together, these results suggest that the dengue vaccine stimulates robust and protective anti-DENV2 NS1 Ab responses following vaccination.

Example 6: Phase III Clinical Trial in Children

A Phase III, double-blind, randomized, and placebo-controlled trial in 20100 subjects aged 4 to 16 years living in Thailand, Sri Lanka, Philippines, Panama, Nicaragua, Dominican Republic, Colombia or Brazil was performed evaluating the efficacy, safety and immunogenicity of a tetravalent dengue vaccine referred to hereinafter as TDV. The trial includes 3 parts. Part 1 evaluates vaccine efficacy (VE) and lasts until both of the following 2 criteria are fulfilled: (i) 120 cases of dengue fever are confirmed and (ii) minimum duration of subject follow-up of 12 months post-second vaccination. Part 2 is for an additional 6 months to evaluate VE and for secondary efficacy analyses. Part 3 will evaluate long-term safety by following participants for side effects and will last an additional 3 years.

Part 1: Active surveillance for the primary assessment of efficacy in all subjects. During this time subjects were contacted at least weekly to ensure identification of febrile illness that could potentially be due to dengue. This part commenced on the day of vaccination and finished once both of the following 2 criteria were fulfilled: (i) 120 cases of dengue fever are confirmed and (ii) minimum duration of subject follow-up of 12 months post-second vaccination. The end of Part 1 was defined for each subject so that the duration of follow up after the second vaccination was approximately the same for all subjects. Virologically-confirmed cases in Part 1 count towards the primary efficacy objective if occurring at least 30 days post-second vaccination. Part 1 was finished 12 months post-second vaccination Part 2: Active surveillance for an additional 6 months for each subject following the completion of Part 1, I, i.e. 18 month post second vaccination. During this time subjects were contacted at least weekly to ensure identification of febrile illness that could potentially be due to dengue. Virologically-confirmed cases in Parts 1 and 2 contribute towards the secondary efficacy objectives.

Part 3: Modified active surveillance for the assessment of safety in all subjects following the completion of Part 2 and lasting 3 years for each subject. The modified surveillance during Part 3 will maintain at least weekly contacts through Part 3 of the trial, but the intensity of investigation will be modified based on the need for hospitalization. Surveillance will identify febrile illness of any severity that could potentially be due to dengue.

Criteria for Inclusion include:

The subject was aged 4 to 16 years inclusive, at the time of randomization.

Individuals who were in good health at the time of entry into the trial as determined by medical history, physical examination (including vital signs) and clinical judgment of the Investigator.

The subject and/or the subject's parent/guardian signed and dated an assent/written informed consent form where applicable, and any required privacy authorization prior to the initiation of any trial procedures, after the nature of the trial has been explained according to local regulatory requirements.

Individuals who can comply with trial procedures and are available for the duration of follow-up.

Exclusion criteria include:

1. Febrile illness (temperature 38° C.) or moderate or severe acute illness or infection at the time of randomization.
2. History or any illness that, in the opinion of the Investigator, might interfere with the results of the trial or pose an additional risk to the subject due to participation in the trial, including but not limited to:
   a. Known hypersensitivity or allergy to any of the vaccine components.
   b. Female subjects (post-menarche) who are pregnant or breastfeeding.
   c. Individuals with any serious chronic or progressive disease according to judgment of the Investigator (e.g., neoplasm, insulin-dependent diabetes, cardiac, renal or hepatic disease, neurologic or seizure disorder or Guillain-Barre syndrome).
   d. Known or suspected impairment/alteration of immune function, including:
      i. Chronic use of oral steroids (equivalent to 20 mg/day prednisone ≥12 weeks/2 mg/kg body weight/day prednisone ≥2 weeks) within 60 days prior to Day 1 (Month 0) (use of inhaled, intranasal, or topical corticosteroids is allowed).
      ii. Receipt of parenteral steroids (equivalent to 20 mg/day prednisone ≥12 weeks/≥2 mg/kg body weight/day prednisone ≥2 weeks) within 60 days prior to Day 1 (Month 0).
      iii. Administration of immunoglobulins and/or any blood products within the 3 months prior to Day 1 (Month 0) or planned administration during the trial.
      iv. Receipt of immunostimulants within 60 days prior to Day 1 (Month 0).
      v. Immunosuppressive therapy such as anti-cancer chemotherapy or radiation therapy within 6 months prior to Day 1 (Month 0).
      vi. Human Immunodeficiency Virus (HIV) infection or HIV-related disease.
      vii. Genetic immunodeficiency.
3. Receipt of any other vaccine within 14 days (for inactivated vaccines) or 28 days (for live vaccines) prior to Day 1 (Month 0) or planning to receive any vaccine within 28 days after Day 1 (Month 0).
4. Participation in any clinical trial with another investigational product 30 days prior to Day 1 (Month 0) or intent to participate in another clinical trial at any time during the conduct of this trial.
5. Previous participation in any clinical trial of a dengue candidate vaccine, or previous receipt of a dengue vaccine.
6. First degree relatives of individuals involved in trial conduct.
7. Females of childbearing potential who are sexually active, and who have not used any of the acceptable contraceptive method for at least 2 months prior to Day 1 (Month 0).

8. Females of childbearing potential who are sexually active, and who refuse to use an acceptable contraceptive method up to 6 weeks post-second vaccination.
9. Deprived of freedom by administrative or court order, or in an emergency setting, or hospitalized involuntarily.
10. Current alcohol abuse or drug addiction that may interfere with the subject's ability to comply with trial procedures.
11. Identified as an employee of the Investigator or trial center, with direct involvement in the proposed trial or other trials under the direction of that Investigator or trial center.

Eligible subjects were randomized (2:1) into two treatment groups: groups 1 received one subcutaneous (SC) dose of TDV in the upper arm on Day 1 and on Day 90, and group 2 received one subcutaneous dose of placebo in the upper arm on Day 1 and on Day 90. Randomization was stratified by region (Asia Pacific and Latin America) and age range (children aged 4-5 years, 6-11 years, and 12-16 years) to ensure each age range has the appropriate ratio of TDV to placebo in each region. After randomization dropouts were not replaced. Study Day 1 is defined to be the date of the first dose administration of TDV or placebo. The TDV was prepared as described in Example 1. Each subcutaneous dose of TDV was 0.5 mL and the concentration of the four dengue serotypes in the TDV vaccine in each dose was 3.6 $\log_{10}$ PFU/dose, 4.0 $\log_{10}$ PFU/dose, 4.6 $\log_{10}$ PFU/dose and 5.1 $\log_{10}$ PFU/dose of TDV-1, TDV-2, TDV-3 and TDV-4, respectively.

The "total concentration in pfu/0.5 ml" which serves as a base value for the calculation of the percentage concentration for each individual component of a tetravalent dengue vaccine is shown for one exemplary tetravalent vaccine composition comprising dengue serotype 1 in a concentration of 3.60 $\log_{10}$ pfu/0.5 ml, a dengue serotype 2 concentration of 4.00 $\log_{10}$ pfu/0.5 ml, a dengue serotype 3 concentration of 4.60 log 10 pfu/0.5 ml and a dengue serotype 4 concentration of 5.11 $\log_{10}$ pfu/0.5 ml. Primarily, the logarithmic values of the concentrations are converted into numerical values. The results of this conversion are $4\times10^3$ pfu/0.5 ml for serotype 1, $1\times10^4$ pfu/0.5 ml for serotype 2, $4\times10^4$ pfu/0.5 ml for serotype 3 and $1.3\times10^5$ pfu/0.5 ml for serotype 4. The total concentration in pfu/0.5 ml is the sum of the preceding numerical values resulting in $1.84\times10^5$ pfu/0.5 ml.

The "percentage concentration" for each of the serotypes 1, 2, 3 and 4 is obtained by dividing the numerical concentration value (expressed as pfu/0.5 ml) of an individual serotype by the total concentration (expressed in pfu/0.5 ml) and multiplying the result by 100 i.e.: Percentage concentration of serotype 1=($4\times10^3$ pfu/0.5 ml÷$1.84\times10^5$ pfu/0.5 ml)×100=2% Percentage concentration of serotype 2=($1\times10^4$ pfu/0.5 ml÷$1.84\times10^5$ pfu/0.5 ml)×100=5% Percentage concentration of serotype 3=($4\times10^4$ pfu/0.5 ml÷$1.84\times10^5$ pfu/0.5 ml)×100=22% Percentage concentration of serotype 4=($1.3\times10^5$ pfu/0.5 ml÷$1.84\times10^5$ pfu/0.5 ml)×100=71%. The percentage concentrations are rounded to whole numbers.

Primary Outcome Measures included the vaccine efficacy (VE) of two doses of TDV in preventing virologically-confirmed dengue (VCD) fever induced by any dengue serotype [time frame: 30 days post-second vaccination (Day 120) until the end of Part 1]. VE is defined as $1-(\lambda v/\lambda c)$, wherein $\lambda v$ and $\lambda c$ denote the hazard rates for the TDV and placebo groups, respectively. A virologically-confirmed dengue case is defined as febrile illness (defined as temperature ≥38° C. on any 2 of 3 consecutive days) or illness clinically suspected to be dengue by the Investigator with a positive serotype-specific reverse transcriptase polymerase chain reaction (RT-PCR). A febrile illness will require an interval of at least 14 days from a previous febrile illness to avoid overlap of acute and convalescent visits from one episode with those from a second episode.

Secondary Outcome Measures include:

1) VE of two doses of TDV in preventing virologically-confirmed dengue fever induced by each dengue serotype [time frame: from 30 days post-second vaccination (Day 120) until the end of Part 2].
2) VE of two doses of TDV in preventing virologically-confirmed dengue fever induced by any dengue serotype in participants dengue seronegative at baseline [time frame: from 30 days post-second vaccination (Day 120) until the end of Part 2 (up to 21 months)].
3) VE of two doses of TDV in preventing virologically-confirmed dengue fever induced by any dengue serotype in participants dengue seropositive at baseline [time frame: from 30 days post-second vaccination (Day 120) until the end of Part 2].
4) VE of two doses of TDV in preventing hospitalization due to virologically-confirmed dengue fever induced by any dengue serotype [time frame: from 30 days post-second vaccination (Day 120) until the end of Part 2].
5) VE of two doses of TDV in preventing virologically-confirmed severe dengue fever induced by any dengue serotype [time frame: from 30 days post-second vaccination (Day 120) until the end of Part 2].
6) Percentage of participants with solicited local injection site adverse events (AEs) in the safety subset [time frame: Days 1 through 7 after each vaccination] and severity of solicited local injection AEs. Solicited local AEs at injection site are defined as pain, erythema and swelling that occurred within 7 days after each vaccination.
7) Percentage of participants with solicited systemic adverse events (AEs) in the safety subset [time frame: Days 1 through 14 after each vaccination] and severity of solicited systemic AEs. Solicited systemic AEs in children (<6 years) are defined as fever, irritability/fussiness, drowsiness and loss of appetite that occurred within 14 days after each vaccination. Solicited systemic AEs in children (≥6 years) are defined as fever, headache, asthenia, malaise and myalgia that occurred within 14 days after each vaccination.
8) Percentage of participants with any unsolicited adverse events (AEs) in the safety subset [time frame: Days 1 through 28 after each vaccination]. Unsolicited AEs are any AEs that are not solicited local or systemic AEs, as defined above.
9) Percentage of participants with serious adverse events (SAEs) during Parts 1 and 2 [time frame: from Day 1 until the end of Parts 1 and 2]. A serious adverse event (SAE) is any untoward medical occurrence or effect that at any dose results in death, is life-threatening, requires inpatient hospitalization or prolongation of existing hospitalization, results in persistent or significant disability/incapacity, is a congenital anomaly/birth defect or is medically important due to other reasons than the above mentioned criteria.
10) Percentage of participants with fatal SAEs and SAEs related to study drug during the first and second half of Part 3 [time frame: for 3 years (18 month halves)

beginning at the end of Part 2 (approximately 21 months after the first vaccination)].

11) Percentage of participants with a seropositive response for each of the four dengue serotypes in the immunogenicity subset [time frame: Day 1 and months 1, 3, 4, 9, 15 and then annually (up to 3 years)]. Seropositive response is defined as a reciprocal neutralizing titer 10. The four DENV serotypes are DEN-1, DEN-2, DEN-3 and DEN-4.

12) Percentage of participants with a seropositive response for multiple dengue serotypes in the immunogenicity subset [time frame: Day 1 and months 1, 3, 4, 9, 15 and then annually (up to 3 years)].

13) Geometric Mean Titers (GMTs) of neutralizing antibodies for each of the four dengue serotypes in the immunogenicity subset [time frame: Day 1 and months 1, 3, 4, 9, 15 and then annually (up to 3 years)]. GMTs of neutralizing antibodies will be measured via microneutralization test (MNT) as described in Example 2.

a) Study Population

Figure 9:
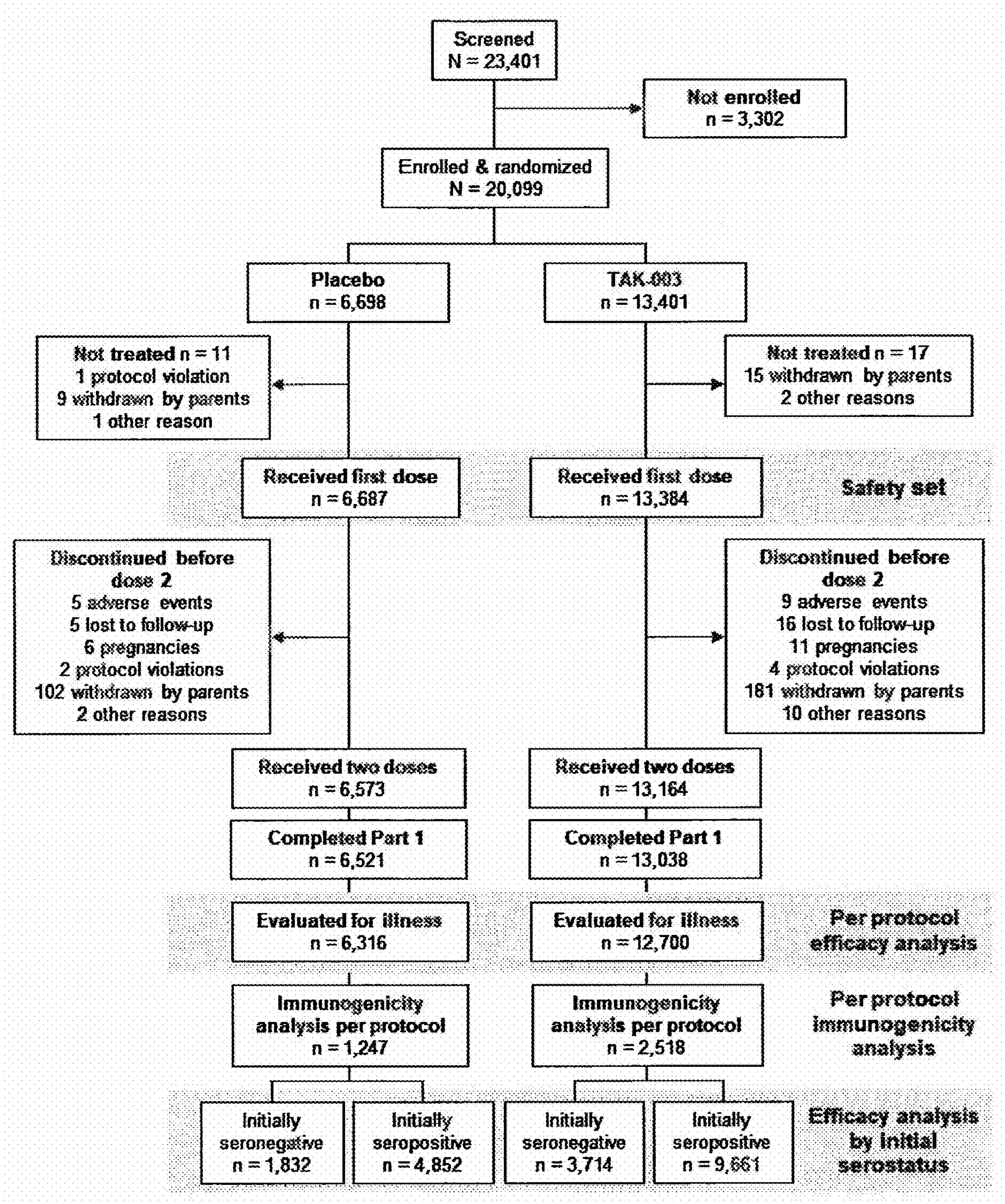
FIG. 9: Flow diagram of the clinical trial of Example 6.

After screening, 20,099 participants were randomized, and 20,071 received at least one injection. In total, 97.4% of placebo participants (n/N: 6,521/6,698) and 97.3% of vaccinees (n/N: 13,038/13,401) completed Part 1 of the study (FIG. 9). Reasons for study withdrawals included AEs, participants lost to follow-up, pregnancy, protocol violations, and withdrawal by participants (or parents/guardians). Baseline characteristics were similar across both treatment groups (Table 19). Mean age of study participants was 9.6 years, with baseline seronegativity of 27.7%, and enrollment was broadly balanced across regions (46.5% in Asia, 53.5% in Latin America). The highest seronegative rate was in Panama (62.2%), followed by Sri Lanka (38.5%), Thailand (34.4%), Brazil (28.8%), Nicaragua (22.3%), Colombia (15.4%), the Philippines (12.4%), and the Dominican Republic (2.8%).

TABLE 19

Baseline characteristics of study population (number, %)

| | TDV | Placebo | Total |
|---|---|---|---|
| **Per Protocol Set** | | | |
| Number of Participants | 12,704 | 6,317 | 19,021 |
| Mean Age (Years, SD) | 9.6 (3.35) | 9.6 (3.34) | 9.6 (3.35) |
| Baseline Seronegative[a] | 3,533 (27.8) | 1,726 (27.3) | 5,259 (27.7) |
| Female | 6,314 (49.7) | 3,098 (49.0) | 9,412 (49.5) |
| Male | 6,390 (50.3) | 3,219 (51.0) | 9,609 (50.5) |
| Asia Pacific | 5,896 (46.4) | 2,942 (46.6) | 8,838 (46.5) |
| Baseline Seronegative[a] | 1,503 (25.5) | 773 (26.3) | 2,276 (25.8) |
| Latin America | 6,808 (53.6) | 3,375 (53.4) | 10,183 (53.5) |
| Baseline Seronegative[a] | 2,030 (29.8) | 953 (28.2) | 2,983 (29.3) |
| **Safety Set[b]** | | | |
| Number of Participants | 13,380 | 6,687 | 20,071 |
| Mean Age (Years, SD) | 9.6 (3.36) | 9.6 (3.34) | 9.6 (3.35) |
| Baseline Seronegative[a] | 3,714 (27.8) | 1,832 (27.4) | 5,547 (27.6) |
| Female | 6,651 (49.7) | 3,276 (49.0) | 9,929 (49.5) |
| Male | 6,729 (50.3) | 3,411 (51.0) | 10,142 (50.5) |
| **Safety Set of Subset[b]** | | | |
| Number of Participants | 2,663 | 1,329 | 3,993 |
| Baseline Seronegative[a] | 740 (27.8) | 369 (27.8) | 1,109 (27.8) |

[a]Seronegative for all serotypes; seropositive defined as reciprocal neutralizing antibody titer ≥10; SD, standard deviation.
[b]numbers of participants in TVD plus placebo groups are not equal to total numbers shown because misallocated participants (i.e. those who received both TVD and placebo due to an administrative error) are not included in the TDV and placebo group data.

b) Febrile Illnesses and VCD

During Part 1, 5,754 and 4,663 episodes of febrile illness were reported in Asian and Latin American sites, respectively. Acute samples were obtained in 99.5% and 96.6% of these cases, with 98.3% and 85.1% of samples taken within five days, in Asia and Latin America, respectively. There were 278 VCD cases (76 hospitalized) in the safety set during the entire Part 1 period, of which 210 (58 hospitalized) were 30 days post-second vaccination in the PPS (Table 20; Table 22) and were included in primary endpoint analysis.

c) Distribution of VCD Included in Primary Endpoint Analysis

DENV-1 was reported in all countries with VCD and included all the 21 cases in Panama. In Sri Lanka, 54 of 60 VCD were DENV-2, and 87 of 109 VCD in the Philippines were DENV-3. All seven DENV-4 VCD were reported in the Philippines. No VCD were reported in Nicaragua or the Dominican Republic. Of the associated 58 hospitalized VCD, 43 were reported in Sri Lanka. A total of two severe dengue (both DENV-3) and five dengue hemorrhagic fever (DHF; three DENV-2; two DENV-3) cases were reported (Table 21). These seven were also the only such cases in the entire part 1 safety set.

d) Vaccine Efficacy

Figure 10A:
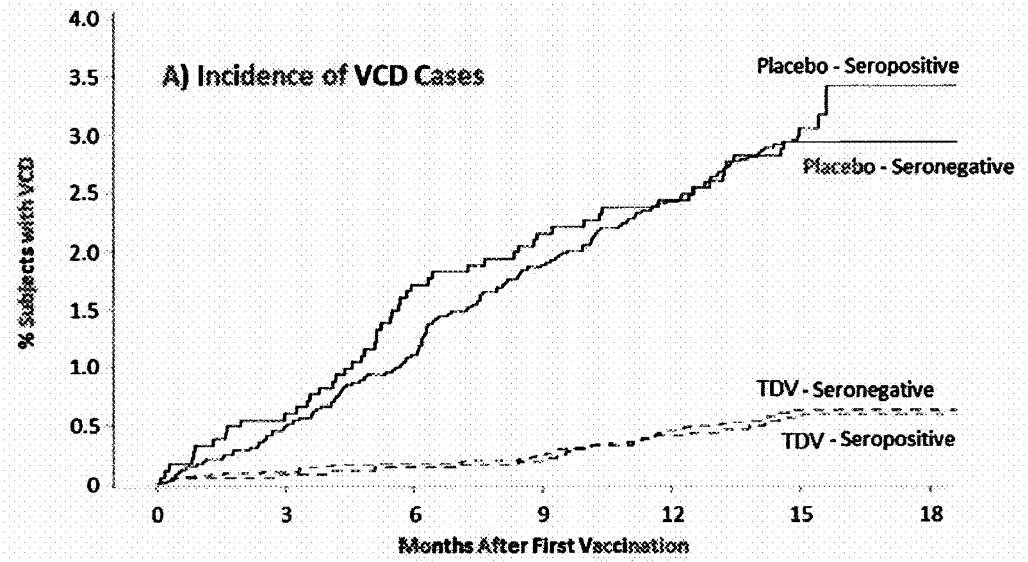
FIGS. 10A-10B: Cumulative incidence of A) virologically-confirmed dengue cases and B) hospitalized virologically-confirmed dengue cases over time during Part 1 study period by baseline serostatus (safety set data; data presented truncated at Month 18). Tables show numbers of participants under follow-up at various time points to end of Part 1 study period.
Figure 10B:
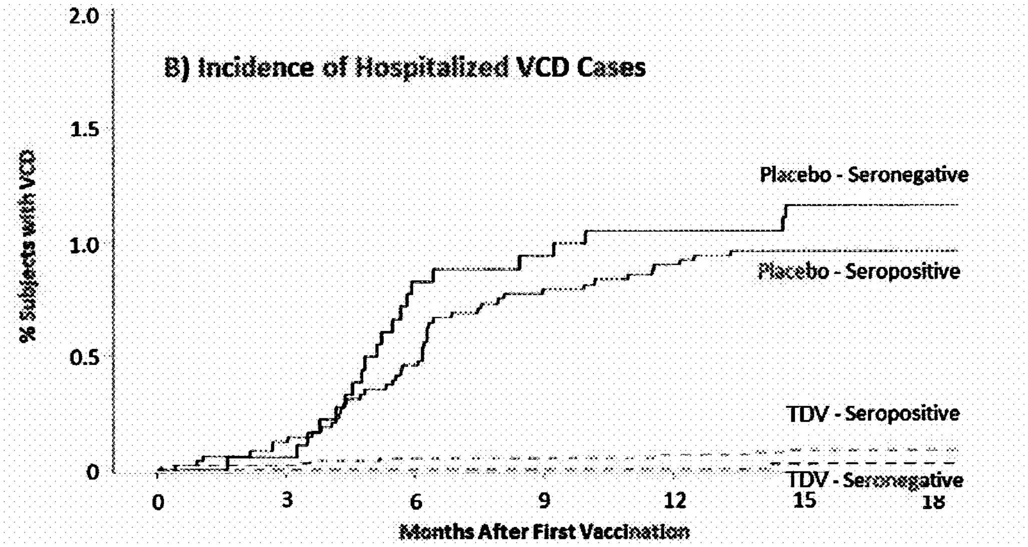
Figure 11:
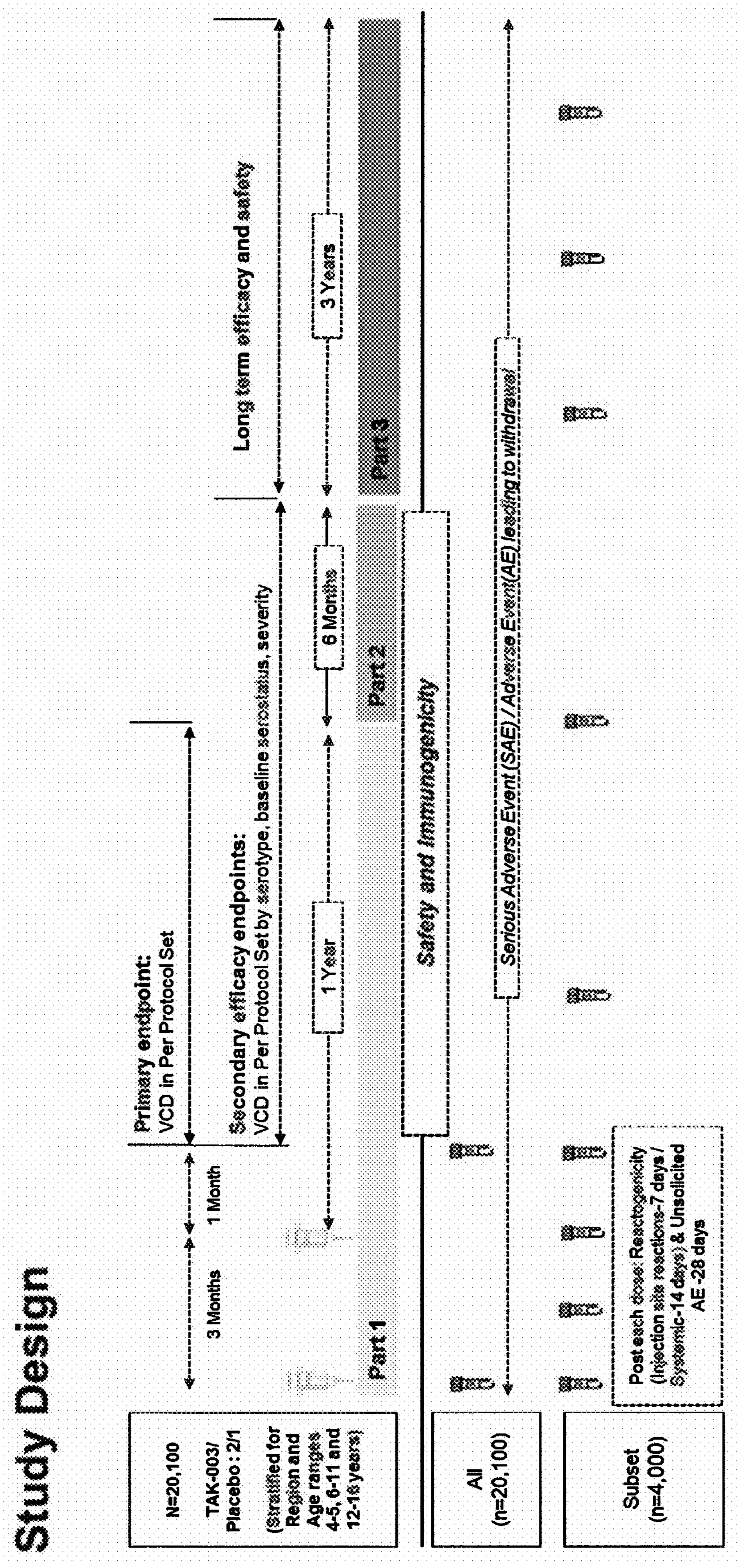
FIG. 11: Study design of phase III study described in example 6

VE against VCD of any serotype was 80.2% (95% CI: 73.3-85.3; P<0.001). A similar efficacy of 81% (95% CI: 64.1-90.0) between the doses and from first dose onwards in the safety set (Table 20) suggests that the vaccine was efficacious after the first dose. Exploratory analysis of the secondary efficacy endpoints showed a trend of differential efficacy by serotype, with the highest efficacy against DENV-2 (97.7%), followed by DENV-1 (73.7%), DENV-4 (63.2% with CI containing zero), and DENV-3 (62.6%; Table 3). Overall, efficacy was similar in baseline seronegatives (74.9%) and seropositives (82.2%; FIG. 10A); however, this varied by serotype. Efficacy against DENV-2 was not impacted by serostatus; efficacy against DENV-1 was slightly higher in baseline seropositives (79.8%; 95% CI: 51.3-91.6) than baseline seronegatives (67.2%; 95% CI: 23.2-86.0). No efficacy was observed against DENV-3 in baseline seronegatives (−38.7%; 95% CI: −335.7-55.8) compared to baseline seropositives (71.3%; 95% CI: 54.2-82.0). Efficacy by serostatus could not be calculated for DENV-4 because no cases were observed in baseline seronegatives. In the primary endpoint timeframe of the PPS, only five VCD requiring hospitalization were reported in the vaccine group compared with 53 cases in the placebo group, with a VE of 95.4% (95% CI: 88.4-98.2; 97.2% for baseline seronegatives and 94.4% for baseline seropositives; Table 21; FIG. 10B), consistent with a VE of 93.3% (95% CI: 86.7-96.7) in the safety set from first dose onwards.

The primary vaccine efficacy (VE) of two doses of TDV in preventing virologically-confirmed dengue (VCD) fever induced by any dengue serotype is shown in Table 20.

TABLE 20

Vaccine efficacy of TDV in preventing virologically-confirmed dengue (VCD) fever against any serotype from 30 days post-second vaccination until end of part 1 Per Protocol Set (PPS), i.e. 12 months post-second vaccination. Safety set analysis from first dose to end of Part 1 study period, i.e. 12 months post-second vaccination

| | Placebo n = 6317 | TDV (PPS) n = 12,704 |
|---|---|---|
| number of subject evaluated | 6,316 | 12,700 |
| number of subjects with febrile illness | 1,712 | 3,195 |
| number of febrile illness cases | 2,591 | 4,692 |
| virologically confirmed dengue fever (n [%]) | 149 [2.4] | 61 [0.5] |
| Person-years at risk | 5,670.1 | 11,578.7 |
| incident density | 2.6 | 0.5 |
| relative risk | 0.20 | |
| 95% CI of relative risk | (0.15, 0.27) | |
| vaccine efficacy (%) | 80.2 | |
| 95% CI of vaccine efficacy | (73.3, 85.3) | |
| p-value for vaccine efficacy | <0.001 | |
| | **Placebo** | **TDV (Safety Set)*** |
| number of subject evaluated | 6,687 | 13,380 |
| virologically confirmed dengue fever (n [%]) | 199 [3.0] | 78 [0.6] |
| Person-years at risk | 8,072.0 | 16,351.5 |
| incident density | 2.5 | 0.5 |
| vaccine efficacy (%) | 80.9 | |
| 95% CI of vaccine efficacy | (75.2, 85.3) | |

Note 1: Percentage of virologically confirmed dengue (VCD) fever are based on number of subjects evaluated.

Note 2: Person-years at risks is defined as cumulative time in years until start of VCD fever or until end of Part 1 study period or discontinuation date, whichever comes first. Incident density is defined as the number of cases per 100 person-years at risk. Percentages are based on total number (denominator) of analysis set participants evaluated and may not be equal to the total number of participants in the per protocol analysis set.

*One participant had two instances of VCD during Part 1, only the first VCD was included in efficacy calculation Note 3: Vaccine efficacy (VE) and 2-sided 95% CIs are estimated from a Cox proportional hazard model with TDV as a factor, adjusted for age and stratified by region.

Note 4: Statistical significance will be concluded if the lower bound of the 95% CI for VE is above 25%. Since the hypotheses will be tested in a confirmatory manner at a 2-sided significance level of 5%, the calculated p-value should be compared with 0.025.

Note 5: Relative risk is calculated as the number of events divided by the number of subjects evaluated in the TDV group, over the number of events divided by the number of subjects evaluated in the placebo group.

For the efficacy evaluation shown in Table 20, a case of VCD was defined as febrile illness (defined as fever ≥38° C. on any 2 of 3 consecutive days) with a positive serotype-specific RT-PCR (i.e., positive dengue detection RT-PCR) and occurring at any time starting from 30 days post-second vaccination (Day 120 [Month 4]) through the end of Part 1. The analysis was performed on the Per-Protocol Set (PPS) and Safety Set.

As used herein, the "Per-Protocol Set (PPS)" consist of all subjects in the Full Analysis Set (FAS) consisting of all randomized subjects who received at least one dose of TDV or placebo who had no major protocol violations. Major protocol violations are not receiving both doses of TDV or placebo administration, not receiving both doses in the correct interval, not having the correct administration of TDV or placebo, use of prohibited medications/vaccines by the subject, the subject meets any of the exclusion criteria of 2 d, 3, 4 or 5 defined above or product preparation error.

The p-value is obtained by solving the critical value Z in the following equation: Upper bound of 1-sided (1−p %) CI of HR=0.75, wherein HR is the hazard ratio and defined as $HR=\lambda V/\lambda C$.

$e^{[\hat{\beta}+Z*\hat{SE}]}=0.75$, wherein $\hat{\beta}$ defines the treatment and $\hat{SE}$ the related standard error.

The 1-sided p-value is 1−(area to the left of the critical value Z from a standard normal distribution). Since the hypotheses will be tested in a confirmatory manner 2-sided at a significance level of 5%, the calculated 1-sided p-value should be compared with 0.025.

In summary in Part 1 of this study, a high vaccine efficacy of 80.2% against virologically-confirmed dengue of any serotype in children 4-16 years of age was found. It included an efficacy of 74.9% in baseline seronegatives and a robust 95.4% reduction in hospitalizations. Onset of protection could be seen after the first dose with 81% efficacy between doses. Overall, these results suggest a potential benefit for each vaccine recipient regardless of prior dengue exposure or age. This finding is significant because vaccine development against dengue has been challenging, especially for dengue naïve individuals, and dengue remains one of the WHO's top ten threats to global health in 2019.19 Furthermore, the onset of protection after the first dose has potential utility in the context of outbreak control or travel vaccination, offering a reduction in the risk of dengue after only one dose.

Severe forms of dengue were assessed as follows: Dengue Hemorrhagic Fever (DHF) as defined by the 1997 WHO definition. Severe Dengue through the Dengue Case Adjudication Committee. The Dengue Case Adjudication Committee (DCAC) consisted of four members: a voting chairperson, two voting members, and an independent non-voting statistician. The three DCAC voting members are all physicians and clinical dengue experts. DCAC members are not study investigators and do not have any conflict of interest that would bias their review of the trial data. All non-hospitalized cases were considered non-severe. The DCAC severe dengue case criteria applied in a blinded manner to virologically-confirmed hospitalized dengue cases are as follows: 1) bleeding abnormality, for a case to be considered severe there needs to be a significant intervention required in response to the bleeding episode such as blood transfusion, nasal packing, hormonal therapy, or, bleeding occurred into critical organs such as the brain; 2) plasma leakage, for a case to be considered severe there needs to be evidence of both plasma leakage and functional impairment (plasma leakage includes clinical evidence, radiological evidence, or hematocrit elevated ≥20% above normal levels or baseline; functional impairment defined as shock or respiratory distress); 3) liver, for a case to be considered severe there needs to be evidence of both hepatitis and functional impairment (hepatitis defined as an aspartate aminotransferase [AST] or alanine aminotransferase [ALT]>10 upper limit of normal range [ULN]; functional impairment defined as prothrombin [PT]>1.5 ULN or hypoalbuminemia); 4) renal, serum creatinine >2.5 times ULN or requiring dialysis; 5) cardiac, abnormalities intrinsic to the heart (i.e. not resulting from intravascular volume depletion) and with evidence of functional impairment (examples of intrinsic abnormality: myocarditis, pericarditis, and myopericarditis; example of functional impairment: new conduction abnormality resulting in irregular heart rhythm [i.e. not transient first-degree heart block]); 6) central nervous system, any abnormality with the exception of a simple febrile convulsion or a brief delirium; 7) shock, all shock cases considered severe. At least 1 functional impairment (of criterion 3, 4, 5, 6), needs to be present but the totality of data were considered by the members in their assessment.

Further results of part 1 and part 2 are presented in Tables 21a to c.

TABLE 21a

Distribution of cases contributing to primary endpoint by per protocol set subgroup (30 days after second vaccination until end of Part 1, i.e. 12 months after second vaccination)

| | TDV Dengue Cases | TDV Incidence Density | Placebo Dengue Cases | Placebo Incidence Density | Vaccine Efficacy (95% CI) |
|---|---|---|---|---|---|
| | | | VCD cases | | |
| Baseline Seropositive[a] | 41/9,165 (0.4%) | 0.5 | 110/4,587 (2.4%) | 2.7 | 82.2% (74.5%-87.6%) |
| Baseline Seronegative[a] | 20/3,531 (0.6%) | 0.6 | 39/1,726 (2.3%) | 2.5 | 74.9% (57.0%-85.4%) |
| DENV-1 | 16/12,700 (0.1%) | 0.1 | 30/6,316 (0.5%) | 0.5 | 73.7% (51.7%-85.7%) |
| DENV-2 | 3/12,700 (<0.1%) | <0.1 | 64/6,316 (1.0%) | 1.1 | 97.7% (92.7%-99.3%) |
| DENV-3 | 39/12,700 (0.3%) | 0.3 | 51/6,316 (0.8%) | 0.9 | 62.6% (43.3%-75.4%) |
| DENV-4[d] | 3/12,700 (<0.1%) | <0.1 | 4/6,316 (<0.1%) | <0.1 | 63.2% (−64.6%-91.8%) |
| 4-5 Years Old | 13/1,619 (0.8%) | 0.9 | 23/801 (2.9%) | 3.2 | 72.8% (46.2%-86.2%) |
| 6-11 Years Old | 34/7,009 (0.5%) | 0.5 | 85/3,491 (2.4%) | 2.7 | 80.7% (71.3%-87.0%) |
| 12-16 Years Old | 14/4,072 (0.3%) | 0.4 | 41/2,024 (2.0%) | 2.2 | 83.3% (69.3%-90.9%) |
| Asia | 54/5,894 (0.9%) | 1.0 | 127/2,942 (4.3%) | 4.9 | 79.5% (71.8%-85.1%) |
| Latin America | 7/6,806 (0.1%) | 0.1 | 22/3,374 (0.7%) | 0.7 | 84.3% (63.1%-93.3%) |
| | | | Hospitalized VCD cases | | |
| Baseline Seropositive[a] | 4/9,165 (<0.1%) | <0.1 | 35/4,587 (0.8%) | 0.8 | 94.4% (84.3%-98.0%) |
| Baseline Seronegative[a] | 1/3,531 (<0.1%) | <0.1 | 18/1,726 (1.0%) | 1.2 | 97.2% (79.1%-99.6%) |
| | | | Cases of DHF[b] | | |
| All participants | 1/12,700 (<0.1%) | <0.1 | 4/6,316 (<0.1%) | <0.1 | 87.3% (−13.5%-98.6%) |
| | | | Severe VCD Cases[c] | | |
| All participants | 1/12,700 (<0.1%) | <0.1 | 1/6,316 (<0.1%) | <0.1 | 50.8% (−686.9%-96.9%) |

VCD, virologically-confirmed dengue; DHF, dengue hemorrhagic fever

[a]Seronegative for all serotypes; baseline seropositive defined as reciprocal neutralizing antibody titer ≥10 to one or more serotypes.

[b]VCD cases meeting WHO 1997 DHF criteria; incidence density defined as the number of cases per 100 person-years at risk; percentages are based on total number (denominator) of per protocol set participants evaluated.

[c]two severe VCD were not classified as DHF.

[d]The number of cases identified was sufficient to provide reasonably precise estimates of vaccine efficacy against all individual serotypes, except DENV-4.

TABLE 21b

Distribution of cases contributing to secondary endpoint by per protocol set subgroup (30 days after second vaccination until end of Part 2, i.e. 18 months after second vaccination)

| | TDV Dengue Cases | TDV Incidence Density | Placebo Dengue Cases | Placebo Incidence Density | Vaccine Efficacy (95% CI) |
|---|---|---|---|---|---|
| | | | VCD cases | | |
| Overall | | | | | 73.3% (66.5%-78.8%) |
| Baseline Seropositive[a] | 75 | 0.6 | 150 | 2.4 | 76.1% (68.5%-81.9%) |
| Baseline Seronegative[a] | 39 | 0.8 | 56 | 2.4 | 66.2% (49.1%-77.5%) |
| DENV-1 | 38 | 0.2 | 62 | 0.7 | 69.8% (54.8%-79.9%) |
| Baseline Seropositive[a] | 21 | 0.2 | 37 | 0.6 | 72.0 (52.2%-83.6%) |
| Baseline Seronegative[a] | 17 | 0.3 | 25 | 1 | 67.8 (40.3%-82.6%) |
| DENV-2 | 8 | <0.1 | 80 | 0.9 | 95.1% (89.9%-97.6%) |
| Baseline Seropositive[a] | 7 | <0.1 | 54 | 0.9 | 93.7 (86.1%-97.1%) |
| Baseline Seronegative[a] | 1 | <0.1 | 26 | 1.1 | 98.1 (85.8%-99.7%) |

TABLE 21b-continued

Distribution of cases contributing to secondary endpoint by per protocol set subgroup (30 days after second vaccination until end of Part 2, i.e. 18 months after second vaccination)

| | TDV Dengue Cases | TDV Incidence Density | Placebo Dengue Cases | Placebo Incidence Density | Vaccine Efficacy (95% CI) |
|---|---|---|---|---|---|
| Hospitalized VCD cases | | | | | |
| Overall | 13 | <0.1 | 66 | 0.8 | 90.4% (82.6%-94.7%) |
| Baseline Seropositive[a] | 8 | <0.1 | 45 | 0.7 | 91.4% (81.7%-95.9%) |
| Baseline Seronegative[a] | 5 | 0.1 | 21 | 0.9 | 88.1% (68.5%-95.5%) |

VCD, virologically-confirmed dengue;
[a]Seronegative for all serotypes; baseline seropositive defined as reciprocal neutralizing antibody titer ≥10 to one or more serotypes.

TABLE 21c

Distribution of cases contributing to secondary endpoint by safety set (first vaccination until end of Part 2, i.e. 21 months after first vaccination)

| | TDV Dengue Cases | TDV Incidence Density | Placebo Dengue Cases | Placebo Incidence Density | Vaccine Efficacy (95% CI) |
|---|---|---|---|---|---|
| VCD cases | | | | | |
| Overall | | | | | 75.3% (69.5%-80.0%) |
| Overall in between[a] | | | | | 81.0% (64.1%-90.0%) |
| Baseline Seropositive[b] | 89 | 0.5 | 187 | 2.3 | 77.2% (70.6%-82.3%) |
| Baseline Seronegative[b] | 42 | 0.7 | 70 | 2.3 | 70.6% (56.9%-79.9%) |
| DENV-1 | 41 | 0.2 | 78 | 0.7 | 73.9% (61.9%-82.1%) |
| DENV-2 | 14 | <0.1 | 109 | 1.0 | 93.7% (89.0%-96.4%) |
| Hospitalized VCD cases | | | | | |
| Overall | 17 | <0.1 | 81 | 0.7 | 89.7% (82.6%-93.9%) |

VCD, virologically-confirmed dengue;
[a]In between: VCD after first vaccination and before second vaccination.
[b]Seronegative for all serotypes; baseline seropositive defined as reciprocal neutralizing antibody titer ≥10 to one or more serotypes.

TABLE 21d

Dengvaxia ® VCD (first vaccination until 25 months after first vaccination (i.e. 13 month after third vaccination), ITT from CYD15, 9 to 16 years of age)[a]

| | Vaccine Efficacy (95% CI) |
|---|---|
| Overall VCD | 64.7% (58.7%-69.8%) |
| Baseline Seropositive[b] | 83.7% (62.2%-93.7%) |
| Baseline Seronegative[b] | 43.2% (−61.5%-80.0%) |
| DENV-1 | 58.8% (40.2%-65.9%) |
| DENV-2 | 50.2% (31.8%-63.6%) |

TABLE 21d-continued

Dengvaxia ® VCD (first vaccination until 25 months after first vaccination (i.e. 13 month after third vaccination), ITT from CYD15, 9 to 16 years of age)[a]

| | Vaccine Efficacy (95% CI) |
|---|---|
| Overall Hospitalized VCD | 80.3% (64.7%-89.5%) |

[a]Luis Villar et al. Efficacy of a tetravalent dengue vaccine in Children in Latin America: N Engl J of Med 2015 Vol. 372 No2, 113-123

Clinical signs and symptoms of virologically-confirmed dengue cases during Part 1 study period in safety set data are shown in Table 22.

TABLE 22

Clinical signs and symptoms of virologically-confirmed dengue cases during Part 1 study period (safety set data)

| | TDV (N = 13,380) | Placebo (N = 6,687) | Relative Risk |
|---|---|---|---|
| Number of VCD Cases | 78 | 200 | — |
| Median Duration of Febrile Illness (days; 95% CI)[a] | 6.0 (5.7-7.4) | 6.0 (5.9-6.8) | — |
| Median Duration of Fever (days; 95% CI) | 4.0 (3.9-4.6) | 5.0 (4.5-5.0) | — |
| Number of Hospitalized VCD Cases | 9 | 67 | — |

TABLE 22-continued

Clinical signs and symptoms of virologically-confirmed dengue cases during Part 1 study period (safety set data)

| | TDV (N = 13,380) | Placebo (N = 6,687) | Relative Risk |
|---|---|---|---|
| Median Duration of Hospitalization (days; 95% CI) | 5.0 (2.8-5.4) | 5.0 (4.6-5.4) | — |
| Evidence of Bleeding (%, n/N) | 3.8% (3/78) | 3.5% (7/200) | 1.10 |
| Plasma Leakage (%, n/N) | 2.6% (2/78) | 6.5% (13/200) | 0.39 |
| Plasma Leakage - Pleural Effusion (%, n/N) | 1.3% (1/78) | 1.5% (3/200) | — |
| Plasma Leakage - Ascites (%, n/N) | 1.3% (1/78) | 3.0% (6/200) | — |
| Plasma Leakage - Radiological Signs (%, n/N) | 40.0% (2/5) | 19.6% (10/51) | — |
| Plasma Leakage - Hematocrit Increase ≥20% (%, n/N)[b] | 3.8% (2/53) | 9.5% (13/137) | — |
| Platelet Count ≤100 × $10^9$ (%, n/N)[c] | 6.4% (5/78) | 22.0% (44/200) | 0.29 |
| Platelet Count ≤50 × $10^9$ (%, n/N)[c] | 3.8% (3/78) | 11.0% (22/200) | 0.35 |
| ALT or AST ≥1000 U/L (%, n/N)[c] | 0% (0/78) | 0% (0/200) | — |

VCD, virologically-confirmed dengue; ALT, alanine aminotransferase; AST, aspartate aminotransferase

[a]Duration of febrile illness defined as start date of earliest symptom to end date of latest symptom plus one day (symptoms considered include fever and any general symptoms).

[b]Hematocrit increase defined as maximum hematocrit between Day 3 and Day 7 inclusive, from onset of fever ≥20% increase over minimum hematocrit before Day 3 or after Day 7 from onset of fever.

[c]For platelet, ALT, and AST data, assessments within 14 days of onset of febrile illness have been considered.

N refers to number of VCD cases with available data for the specific parameter e) Immunogenicity The highest geometric mean titers (GMTs) were observed against DENV-2 regardless of baseline serostatus (Table 24). A very high tetravalent seropositivity rate (99.5%) in baseline seronegatives one month after the second dose (Tables 23 and 24) was observed.

Seropositivity rate (% of seropositive subjects) for each of the four dengue serotypes is determined at prevaccination on Day 1 (Month 0), post-first vaccination on Day 30 (Month 1), prevaccination on Day 90 (Month 3), post-second vaccination on Day 120 (Month 4), Day 270 (Month 9), Day 450 (Month 15), and then annually. Seropositivity rates (% participants, 95% CI) by dengue serotype per protocol set for immunogenicity data for Day 0, Day 30, Day 90, Day 120, and Day 270 are shown in Table 23.

Seropositivity rates (% participants, 95% CI) by dengue serotype against three or more serotypes (trivalent) and against all four serotypes (tetravalent) per protocol set for immunogenicity data for Day 0, Day 30, Day 90, Day 120, and Day 270 are shown in Table 23. The tetravalent seropositivity rates were high (>91%) in baseline seronegatives six months after second dose.

TABLE 23

Seropositivity rates (% participants, 95% CI) by dengue serotype (per protocol set for immunogenicity data)

| BASELINE SEROPOSITIVE | | BASELINE SERONEGATIVE | |
|---|---|---|---|
| TDV N = 1,816 | Placebo N = 902 | TDV N = 702 | Placebo N = 345 |
| DENV-1 | | | |
| 89.1 (87.6-90.5) | 90.6 (88.5-92.4) | 0 (0-0.5) | 0 (0-1.1) |
| 99.5 (99.1-99.8) | 88.6 (86.3-90.7) | 94.1 (92.0-95.8) | 4.9 (2.8-7.8) |
| 99.3 (98.8-99.6) | 90.2 (88.1-92.1) | 91.6 (89.3-93.5) | 6.1 (3.8-9.2) |
| >99.9 (99.7-100) | 90.3 (88.1-92.3) | 99.5 (98.6-99.9) | 8.3 (5.5-11.9) |
| 99.6 (99.1-99.8) | 89.8 (87.5-91.8) | 95.1 (93.0-96.6) | 9.0 (6.0-12.8) |
| DENV-2 | | | |
| 96.5 (95.6-97.3) | 97.2 (95.9-98.2) | 0 (0-0.5) | 0 (0-1.1) |
| 99.9 (99.6-100) | 93.3 (91.4-94.9) | 98.6 (97.4-99.4) | 10.7 (7.5-14.5) |
| >99.9 (99.7-100) | 94.0 (92.2-95.5) | 99.0 (98.0-99.6) | 12.2 (8.9-16.1) |
| 99.9 (99.6-100) | 93.6 (91.7-95.2) | 100 (99.4-100) | 14.7 (11.0-19.1) |
| 100 (99.8-100) | 94.6 (92.8-96.1) | 100 (99.4-100) | 18.3 (14.1-23.2) |
| DENV-3 | | | |
| 88.1 (86.5-89.6) | 88.0 (85.7-90.1) | 0 (0-0.5) | 0 (0-1.1) |
| 99.8 (99.4-99.9) | 87.6 (85.1-89.7) | 96.1 (94.3-97.4) | 4.0 (2.1-6.7) |
| 99.5 (99.1-99.8) | 87.3 (84.9-89.4) | 94.4 (92.5-96.0) | 2.0 (0.8-4.1) |
| 99.8 (99.5-100) | 87.9 (85.5-90.1) | 100 (99.4-100) | 5.1 (2.9-8.2) |
| 99.7 (99.4-99.9) | 87.1 (84.6-89.4) | 96.4 (94.6-97.7) | 7.7 (4.9-11.3) |
| DENV-4 | | | |
| 88.1 (86.5-89.6) | 87.4 (85.0-89.5) | 0 (0-0.5) | 0 (0-1.1) |
| 99.6 (99.2-99.9) | 86.6 (84.1-88.8) | 90.5 (88.0-92.6) | 1.8 (0.7-3.9) |
| 99.3 (98.8-99.7) | 86.9 (84.5-89.0) | 92.0 (89.8-93.9) | 2.9 (1.4-5.3) |
| >99.9 (99.7-100) | 88.3 (85.9-90.4) | 99.8 (99.1-100) | 4.8 (2.7-7.8) |
| 99.7 (99.3-99.9) | 87.6 (85.1-89.9) | 97.0 (95.4-98.2) | 6.3 (3.9-9.7) |

TABLE 23-continued

Seropositivity rates (% participants, 95% CI) by dengue serotype (per protocol set for immunogenicity data)

| BASELINE SEROPOSITIVE | | BASELINE SERONEGATIVE | |
|---|---|---|---|
| TDV N = 1,816 | Placebo N = 902 | TDV N = 702 | Placebo N = 345 |
| Three or More Serotypes | | | |
| 87.5 (85.9-89.0) | 87.3 (84.9-89.4) | 0 (0-0.5) | 0 (0-1.1) |
| 99.8 (99.5-100) | 87.2 (84.7-89.4) | 96.5 (94.8-97.8) | 1.2 (0.3-3.1) |
| 99.7 (99.3-99.9) | 87.7 (85.3-89.7) | 94.9 (93.0-96.4) | 1.7 (0.6-3.7) |
| 99.9 (99.6-100) | 88.4 (86.0-90.5) | 99.8 (99.1-100) | 4.2 (2.2-7.0) |
| 99.7 (99.4-99.9) | 87.3 (84.7-89.5) | 97.5 (96.0-98.6) | 5.7 (3.3-8.9) |
| All Four Serotypes | | | |
| 83.5 (81.7-85.2) | 83.5 (80.9-85.8) | 0 (0-0.5) | 0 (0-1.1) |
| 99.1 (98.5-99.5) | 82.9 (80.2-85.4) | 85.3 (82.4-87.9) | 0.9 (0.2-2.6) |
| 98.6 (97.9-99.1) | 83.6 (81.0-86.0) | 84.3 (81.4-86.9) | 1.4 (0.5-3.3) |
| 99.8 (99.5-100) | 85.2 (82.6-87.6) | 99.5 (98.6-99.9) | 3.5 (1.8-6.2) |
| 99.2 (98.7-99.6) | 84.6 (81.9-87.0) | 91.3 (88.7-93.4) | 5.3 (3.1-8.5) |

Seropositivity rates (% participants, 95% CI) by dengue serotype (per protocol set for immunogenicity data; seropositive defined as a reciprocal neutralizing antibody titer ≥10; baseline seronegative defined as seronegative to all serotype; baseline seropositive defined as seropositive to one or more serotypes; N refers to number of participants in the analysis set; number of participants evaluated at each time-point may vary)

Geometric mean titers (GMTs) of neutralizing antibodies (microneutralization test [MNT]) for each dengue serotype are determined at pre-vaccination on Day 1 (Month 0), post-first vaccination on Day 30 (Month 1), pre-vaccination on Day 90 (Month 3), post-second vaccination on Day 120 (Month 4), Day 270 (Month 9), Day 450 (Month 15), and then annually. Geometric mean titers (95% CI) by dengue serotype per protocol set for immunogenicity data for Day 0, Day 30, Day 90, Day 120, and Day 270 are shown in Table 24.

TABLE 24

Geometric mean titers (95% CI) by dengue serotype (per protocol set for immunogenicity data)

| | BASELINE SEROPOSITIVE | | BASELINE SERONEGATIVE | |
|---|---|---|---|---|
| | TDV N = 1,816 | Placebo N-902 | TDV N = 702 | Placebo N = 345 |
| DENV-1 | | | | |
| Day 1 | 410 (365-461) | 445 (377-524) | 5.0 (5.0-5.0) | 5.0 (5.0-5.0) |
| Day 30 | 2,404 (2,204-2,622) | 430 (361-512) | 118 (106-131) | 5.8 (5.3-6.3) |
| Day 90 | 1,945 (1,791-2,112) | 410 (349-481) | 91 (82-102) | 5.9 (5.4-6.3) |
| Day 120 | 2,115 (1,957-2,286) | 451 (381-534) | 184 (169-201) | 6.3 (5.7-7.0) |
| Day 270 | 1,447 (1,329-1,574) | 415 (350-492) | 87 (79-97) | 6.3 (5.7-6.9) |
| DENV-2 | | | | |
| Day 1 | 745 (674-825) | 802 (697-924) | 5.0 (5.0-5.0) | 5.0 (5.0-5.0) |
| Day 30 | 6,697 (6,301-7,117) | 744 (635-870) | 6,277 (5,648-6,977) | 6.6 (6.0-7.3) |
| Day 90 | 4,826 (4,571-5,096) | 729 (629-845) | 1,682 (1,544-1,834) | 7.0 (6.3-7.9) |
| Day 120 | 4,897 (4,646-5,163) | 766 (655-896) | 1,730 (1,614-1,855) | 7.7 (6.7-8.8) |
| Day 270 | 3,692 (3,496-3,898) | 776 (665-906) | 929 (856-1,010) | 8.7 (7.4-10.2) |
| DENV-3 | | | | |
| Day 1 | 357 (321-398) | 356 (305-415) | 5.0 (5.0-5.0) | 5.0 (5.0-5.0) |
| Day 30 | 2,255 (2,094-2,428) | 349 (298-409) | 194 (173-218) | 5.5 (5.2-5.9) |
| Day 90 | 1,563 (1,453-1,682) | 321 (277-374) | 94 (85-104) | 5.5 (5.1-5.9) |
| Day 120 | 1,761 (1,646-1,885) | 353 (301-414) | 228 (212-246) | 6.0 (5.4-6.6) |
| Day 270 | 1,089 (1,009-1,175) | 307 (261-360) | 72 (66-78) | 6.3 (5.7-7.0) |
| DENV-4 | | | | |
| Day 1 | 218 (198-241) | 234 (203-270) | 5.0 (5.0-5.0) | 5.0 (5.0-5.0) |
| Day 30 | 1,303 (1,221-1,391) | 222 (191-258) | 111 (98-125) | 5.4 (5.0-5.7) |
| Day 90 | 1,002 (940-1,069) | 215 (187-248) | 63 (57-70) | 5.5 (5.1-5.9) |
| Day 120 | 1,129 (1,066-1,196) | 241 (208-280) | 144 (134-155) | 5.8 (5.3-6.4) |
| Day 270 | 778 (730-830) | 229 (197-266) | 64 (59-70) | 6.2 (5.6-6.9) |

Vaccine viremia is assessed by three PCRs: dengue detection RT-PCR, vaccine screening PCR and TDV sequencing in subjects with febrile illness within 30 days after each vaccination.

f) Safety

Rates of serious adverse events (SAEs) were similar in the vaccine and placebo groups (3.1% and 3.8% of participants, respectively; Table 25). One vaccinee and four placebo recipients experienced SAEs considered to be related to receiving blinded investigational product by the investigator (two experienced hypersensitivity, two were diagnosed with dengue, and one with DHF). There were five deaths during Part 1, and all were considered unrelated to the investigational product or study procedures. Total rates of unsolicited AEs were similar between the vaccine and placebo groups. The most commonly (≥1% of vaccine-recipients) reported unsolicited AEs within four weeks of any dose by preferred term were pyrexia (vaccine group 1.5%; placebo 1.4%), nasopharyngitis (vaccine 2.7%; placebo 3.0%), upper respiratory tract infection (vaccine 2.6%; placebo 2.9%), and viral infection (vaccine 1.1%; placebo 0.9%). Solicited local reactions were reported more frequently in the vaccine group.

TABLE 25a

Overview of safety data. Subjects with at least one adverse event after any vaccine dose. Data presented as number of events (percentage of subjects; number [n] of subjects/total [N] subjects) unless otherwise stated (safety set data)

| | TDV | Placebo |
|---|---|---|
| Safety Set | N = 13,380 | N = 6,687 |
| SAEs | 3.1% (409/13,380) | 3.8% (255/6,687) |
| Non-IP-Related[a] SAEs | 3.0% (408/13,380) | 3.8% (251/6,687) |
| IP-Related[a] SAEs | <0.1% (1/13,380) | <0.1% (4/6,687) |
| SAEs Leading to IP Withdrawal and/or Trial Discontinuation | 0.1% (18/13,380) | 0.1% (8/6,687) |
| Deaths | <0.1% (4/13,380) | <0.1% (1/6,687) |
| IP-Related Deaths | 0% (0/13,380) | 0% (0/6,687) |
| Safety Subset | N = 2,663 | N = 1,329 |
| Unsolicited AEs Occurring Within 4 Weeks of Any Dose | 18.4% (490/2,663) | 18.8% (250/1,329) |
| IP-Related[a] Unsolicited AEs Occurring Within 4 Weeks of Any Dose | 1.0% (27/2,663) | 1.6% (21/1,329) |
| Solicited Systemic AEs Occurring Within 2 Weeks of Any Dose[b] | 42.0% (1,107/2,635) | 38.0% (501/1,317) |
| IP-Related[a] Solicited Systemic AEs Occurring Within 2 Weeks of Any Dose | 31.2% (821/2,635) | 28.2% (371/1,317) |
| Solicited Local Reactions Occurring Within 1 Week of Any Dose[c] | 36.7% (967/2,633) | 25.7% (338/1,317) |

AE, adverse event; SAE, serious adverse event; IP, investigational product/TDV
[a]IP-related, defined as related to the investigational product as assessed by investigator
[b]only participants with diary data available were evaluated
[c]all injection site (solicited local) reactions considered to be IP-related TABLE 25b Number of participants (%) with serious adverse events after any vaccination during Part 1 by MedDRA (Medical Dictionary for Regulatory Activities) System Organ Class in the order of decreasing frequency (safety set data presented by TDV and placebo group for events that occurred in >3 participants due to risk of unblinding).

| MedDRA System Organ Class | TDV N = 13,380 | Placebo N = 6,687 | Total* N = 20,071 |
|---|---|---|---|
| Any Serious Adverse Events | 409 (3.1) | 255 (3.8) | 664 (3.3) |
| Infections and infestations | 235 (1.8) | 179 (2.7) | 414 (2.1) |
| Injury, poisoning and procedural complications | 87 (0.7) | 37 (0.6) | 124 (0.6) |
| Gastrointestinal disorders | 23 (0.2) | 9 (0.1) | 32 (0.2) |
| Nervous system disorders | 14 (0.1) | 6 (<0.1) | 20 (<0.1) |
| Respiratory, thoracic and mediastinal disorders | 14 (0.1) | 6 (<0.1) | 20 (<0.1) |
| Renal and urinary disorders | 15 (0.1) | 3 (<0.1) | 18 (<0.1) |
| Blood and lymphatic system disorders | 8 (<0.1) | 2 (<0.1) | 10 (<0.1) |
| Pregnancy, puerperium and perinatal conditions | 8 (<0.1) | 2 (<0.1) | 10 (<0.1) |
| Skin and subcutaneous tissue disorders | 7 (<0.1) | 3 (<0.1) | 10 (<0.1) |
| Psychiatric disorders | 7 (<0.1) | 2 (<0.1) | 9 (<0.1) |
| General disorders and administration site conditions | 5 (<0.1) | 3 (<0.1) | 8 (<0.1) |
| Immune system disorders | 3 (<0.1) | 4 (<0.1) | 7 (<0.1) |
| Metabolism and nutrition disorders | 6 (<0.1) | 1 (<0.1) | 7 (<0.1) |
| Musculoskeletal and connective tissue | 1 (<0.1) | 5 (<0.1) | 6 (<0.1) |
| Social circumstances | 2 (<0.1) | 4 (<0.1) | 6 (<0.1) |

TABLE 25b-continued

Number of participants (%) with serious adverse events after any vaccination during Part 1 by MedDRA (Medical Dictionary for Regulatory Activities) System Organ Class in the order of decreasing frequency (safety set data presented by TDV and placebo group for events that occurred in >3 participants due to risk of unblinding).

| MedDRA System Organ Class | TDV N = 13,380 | Placebo N = 6,687 | Total* N = 20,071 |
|---|---|---|---|
| Congenital, familial and genetic disorders | 3 (<0.1) | 2 (<0.1) | 5 (<0.1) |
| Neoplasms benign, malignant and unspecified (including cysts and polyps) | 3 (<0.1) | 1 (<0.1) | 4 (<0.1) |
| Endocrine disorders | — | — | 3 (<0.1) |
| Hepatobiliary disorders | — | — | 3 (<0.1) |
| Reproductive system and breast disorders | — | — | 3 (<0.1) |
| Vascular disorders | — | — | 3 (<0.1) |
| Cardiac disorders | — | — | 2 (<0.1) |
| Eye disorders | — | — | 2 (<0.1) |
| Investigations | — | — | 1 (<0.1) |
| Product issues | — | — | 1 (<0.1) |
| Surgical and medical procedures | — | — | 1 (<0.1) |

*Total column includes participants who received both TAK-003 and placebo due to administration error and are excluded from the TAK-003 and placebo groups. N in column header refers to number of participants in the safety set TABLE 25c Number of participants (%) with unsolicited adverse events of any severity up to 28-days after any vaccination by MedDRA System Organ Class in the order of decreasing frequency (Subset of safety set data presented by TDV and placebo group for events that occurred in >6 participants due to risk of unblinding).

| MedDRA System Organ Class | TDV N = 2,663 | Placebo N = 1,329 | Total N = 3,993 |
|---|---|---|---|
| Any Unsolicited Adverse Events | 487 (18.3) | 249 (18.7) | 736 (18.4) |
| Infections and infestations | 368 (13.8) | 190 (14.3) | 558 (14.0) |
| Injury, poisoning and procedural complications | 21 (0.8) | 22 (1.7) | 43 (1.1) |
| Gastrointestinal disorders | 33 (1.2) | 9 (0.7) | 42 (1.1) |
| General disorders and administration site conditions | 30 (1.1) | 11 (0.8) | 41 (1.0) |
| Skin and subcutaneous tissue disorders | 27 (1.0) | 7 (0.5) | 34 (0.9) |
| Nervous system disorders | 18 (0.7) | 13 (1.0) | 31 (0.8) |
| Respiratory, thoracic and mediastinal disorders | 18 (0.7) | 10 (0.8) | 28 (0.7) |
| Blood and lymphatic system disorders | 6 (0.2) | 5 (0.4) | 11 (0.3) |
| Musculoskeletal and connective tissue disorders | 6 (0.2) | 5 (0.4) | 11 (0.3) |
| Immune system disorders | — | — | 6 (0.2) |
| Psychiatric disorders | — | — | 3 (<0.1) |
| Reproductive system and breast disorders | — | — | 3 (<0.1) |
| Ear and labyrinth disorders | — | — | 2 (<0.1) |
| Cardiac disorders | — | — | 1 (<0.1) |
| Congenital, familial and genetic disorders | — | — | 1 (<0.1) |
| Eye disorders | — | — | 1 (<0.1) |
| Renal and urinary disorders | — | — | 1 (<0.1) |
| Social circumstances | — | — | 1 (<0.1) |

*Total column includes participants who received both TAK-003 and placebo due to administration error and are excluded from the TAK-003 and placebo groups. N in column header refers to number of participants in the subset of safety set.

TABLE 25d

Summary of diary reported injection site reactions up to 7 days and systemic adverse events up to 14 days after any vaccination (Subset of safety set data). Data presented as number of participants with events/number of evaluated participants in the analysis set (% of evaluated participants with events).

| Solicited Events | TDV | Placebo |
|---|---|---|
| Injection site reactions (Age <6 years) | | |
| Any | 106/331 (32.0) | 43/169 (25.4) |
| Pain | 104/331 (31.4) | 43/169 (25.4) |
| Erythema | 5/331 (1.5) | 1/169 (0.6) |
| Swelling | 11/331 (3.3) | 2/169 (1.2) |
| Injection site reactions (Age ≥6 years) | | |
| Any | 861/2302 (37.4) | 295/1148 (25.7) |
| Pain | 853/2302 (37.1) | 293/1148 (25.5) |
| Erythema | 33/2301 (1.4) | 1/1147 (<0.1) |
| Swelling | 33/2300 (1.4) | 6/1147 (0.5) |
| Systemic adverse events (Age <6 years) | | |
| Any | 88/331 (26.6) | 35/169 (20.7) |
| Irritability/Fussiness | 41/331 (12.4) | 16/169 (9.5) |
| Drowsiness | 45/331 (13.6) | 21/169 (12.4) |
| Loss of Appetite | 57/331 (17.2) | 22/169 (13.0) |
| Fever (Body temperature >=38° C. or 100.4° F.) | 45/327 (13.8) | 23/169 (13.6) |
| Systemic adverse events (Age ≥6 years) | | |
| Any | 941/2302 (40.9) | 422/1147 (36.8) |
| Headache | 715/2302 (31.1) | 326/1147 (28.4) |
| Asthenia | 404/2302 (17.5) | 187/1147 (16.3) |
| Malaise | 510/2301 (22.2) | 226/1147 (19.7) |
| Myalgia | 554/2302 (24.1) | 216/1147 (18.8) |
| Fever (Body temperature >=38° C. or 100.4° F.) | 221/2279 (9.7) | 124/1134 (10.9) |

Example 7: Concomitant Administration of a Yellow Fever Vaccine and a Dengue Vaccine A phase 3, observer-blind, randomized, multi-center trial will be conducted in about 900 healthy adults aged 18 to 60 years in non-endemic areas for dengue disease and yellow fever to investigate the immunogenicity and safety of the concomitant and sequential administration of the unit dose as described herein (TDV) and YF-17D vaccine. Subjects will be randomized equally (1:1:1 ratio) to one of the following 3 trial groups (300 subjects per trial group):

Group 1: YF-17D vaccine and placebo concomitantly administered on day 0 (month 0), first dose of TDV administered on day 90 (month 3), and second dose of TDV administered on day 180 (month 6).

Group 2: first dose of TDV and placebo concomitantly administered on day 0 (month 0), second dose of TDV administered on day 90 (month 3), and YF-17D vaccine administered on day 180 (month 6).

Group 3: first dose of TDV and YF-17D vaccine concomitantly administered on day 0 (month 0), second dose of TDV administered on day 90 (month 3), and placebo administered on day 180 (month 6).

Concomitantly administered vaccines will be injected to opposite arms. All subjects will be followed-up for 6 months after the third vaccination (administered approximately 6 months after the first vaccination), so the trial duration will be approximately 360 days (12 months) for each subject.

For evaluation of the immune response to TDV and YF-17D blood samples will be collected and analyzed. Blood samples for the measurement of dengue neutralizing antibodies (microneutralization test 50% (MNT50)) will be collected at pre-first vaccination (Day 0 (month 0)), 1 month post first vaccination (Day 30 (month 1)), pre-second vaccination (Day 90 (month 3)), 1 month post second vaccination (Day 120 (month 4)), pre-third vaccination (Day 180 (month 6)), and 1 month post third vaccination (Day 210 (month 7)). Blood samples for the measurement of YF neutralizing antibodies (plaque reduction neutralization test (PRNT)) will be collected at pre-first vaccination (Day 0 (month 0)), 1 month post first vaccination (Day 30 (month 1)), pre-third vaccination (Day 180 (month 6)), and 1 month post third vaccination (Day 210 (month 7)).

Example 8: Concomitant Administration of a Hepatitis a Vaccine and a Dengue Vaccine A randomized, observer blind, phase 3 trial will be conducted in about 900 healthy adult subjects aged 18 to 60 years (distributed across the entire age range) in non-endemic countries for dengue and hepatitis A virus (HAV) to investigate the immunogenicity and safety of 2 doses of tetravalent dengue vaccine TDV (subcutaneous (SC) injection), and of the co-administration of a single dose of HAV vaccine (intramuscular (IM) injection) and TDV (SC injection). Subjects will be randomized equally (1:1:1 ratio) to one of the following 3 trial groups (300 subjects per group):

- Group 1: HAV vaccine (IM) and placebo (SC), co-administered at day 0 (month 0); placebo (SC) administered at day 90 (month 3).
- Group 2: TDV (SC) and placebo (IM), co-administered at day 0 (month 0); TDV (SC) administered at day 90 (month 3).
- Group 3: TDV (SC) and HAV vaccine (IM), co-administered at day 0 (month 0); TDV (SC) administered at day 90 (month 3).

Co-administered trial vaccines will be injected to opposite arms. Normal saline solution for injection (0.9% NaCl) will be used as placebo. A blood sample for an anti-HAV antibody test will be collected at screening from all subjects to exclude subjects who are positive for anti-HAV antibodies. All subjects will be followed-up for 6 months after the second vaccination at day 90 (month 3), so the trial duration will be 270 days or 9 months for each subject (not including the screening period). Outside the context of this trial, subjects in Groups 1 and 3 will be offered a HAV vaccine booster dose after the completion of trial procedures at day 270 (month 9).

Dengue neutralizing antibodies (microneutralization test (MNT50)) will be measured using blood samples collected at pre-first trial vaccination (day 0 (month 0)), 1 month post first trial vaccination (day 30 (month 1)), and 1 month post second trial vaccination (day 120 (month 4)). Blood samples for the measurement of anti-HAV antibodies (enzyme-linked immunosorbent assay (ELISA)) will be collected at pre-first trial vaccination (day 0 (month 0)) and 1 month post first trial vaccination (day 30 (month 1)).

The primary endpoint includes the proportion of HAV/DENV-naive subjects at baseline who are seroprotected against HAV at day 30 (month 1) as measured by enzyme-linked immunosorbent assay (ELISA) (seroprotection rate) in a subset of 120 subjects in each group (immunogenicity subset) will be determined. Seroprotection is defined as serum anti-HAV antibody levels ≥10 mIU/mL. Immunological naivety to HAV/DENV is defined as anti-HAV antibody levels <10 mIU/mL and reciprocal neutralizing titers for all 4 dengue serotypes <10.

The secondary endpoints include the geometric mean titers of neutralizing antibodies (GMTs) (microneutralization test (MNT50)) for each of the 4 dengue serotypes at day 30 (month 1) and day 120 (month 4) will be determined in HAV/DENV-naive subjects at baseline, the proportion of HAV/DENV-naive subjects at baseline who are seropositive for each of the 4 dengue serotypes at day 30 (month 1) and day 120 (month 4) (seropositivity rate), and Geometric mean concentrations (GMC) of anti-HAV antibodies at day 30 (month 1) in subjects HAV/DENV-naive at baseline.

Seropositivity for dengue virus is defined as a reciprocal neutralizing titer 10 for any of the four dengue serotypes.

Example 9: Concomitant Administration of a HPV Vaccine and a Dengue Vaccine

A phase 3, open-label, randomized, multicenter trial will be conducted in about 430 healthy females aged ≥9 to <15 years in dengue endemic regions to investigate the immunogenicity and safety of the co-administration of TDV and 9vHPV vaccine vs 9vHPV vaccine alone. Subjects will be randomized equally to 1 of 2 groups (about 215 subjects per trial group):

- Group 1: first doses of 9vHPV vaccine+TDV co-administered on day 0 (month 0), second dose of TDV administered on Day 90 (month 3), second dose of 9vHPV vaccine administered on Day 180 (month 6).
- Group 2: first dose of 9vHPV vaccine administered on day 0 (month 0), second dose of 9vHPV vaccine administered on Day 180 (month 6).

Concomitantly administered vaccines will be injected to opposite arms. All subjects will be followed-up for 6 months after the last trial vaccination, so the trial duration will be approximately 360 days (or 12 months) for each subject.

Blood samples for the measurement of HPV neutralizing antibodies (Merck assay) for both Groups 1 and 2 will be collected at pre-first vaccination (day 0 (Month 0)) and at 1 month post-second 9vHPV vaccination (day 210 (month 7)). Blood samples for the measurement of dengue neutralizing antibodies (by microneutralization test 50% (MNT50)) will be collected for Group 1 only at pre-first vaccination (day 0 (month 0)) and at 1 month post-second TDV vaccination (day 120 (month 4)).

The primary endpoints includes the geometric mean titers (GMTs) for HPV Types 6, 11, 16, 18, 31, 33, 45, 52, 58 on day 210 (month 7).

The secondary endpoints includes seropositivity rates (% of subjects seropositive) for HPV Types 6, 11, 16, 18, 31, 33, 45, 52 and 58 on day 210 (month 7) as measured by competitive Luminex immunoassay (cLIA) or equivalent assay, GMTs of neutralizing antibodies (by MNT50) for each of the 4 dengue serotypes on day 120 (month 4), and seropositivity rates (% of subjects seropositive) for each of the 4 dengue serotypes and for multiple (2, 3 or 4) dengue serotypes on day 120 (month 4).

Seropositivity for dengue virus is defined as a reciprocal neutralizing antibody titer ≥10 for any of the 4 dengue serotypes.

Seropositivity for HPV is defined as an anti-HPV titer greater than or equal to the pre-specified serostatus cut-off for a given HPV type. Seronegativity is defined as an anti-HPV titer less than the pre-specified serostatus cut-off for a given HPV type. The serostatus cut-off is the antibody titer level above the assay's lower limit of quantification that reliably distinguishes sera samples classified by clinical likelihood of HPV infection and positive or negative status by previous versions of cLIA or equivalent assay. The lower limits of quantification and serostatus cut-offs for each of the 9 vaccine HPV types are shown below.

TABLE 26

Competitive Luminex Immunoassay Limits of Quantification and Serostatus Cutoffs for 9vHPV types

| HPV type | cLIA Lower Limit of Quantification (mMU[a]/mL) | cLIA Serostatus Cutoff (mMU[a]/mL) |
|---|---|---|
| HPV 6 | 16 | 30 |
| HPV 11 | 6 | 16 |
| HPV 16 | 12 | 20 |
| HPV 18 | 8 | 24 |
| HPV 31 | 4 | 10 |
| HPV 33 | 4 | 8 |
| HPV 45 | 3 | 8 |
| HPV 52 | 3 | 8 |
| HPV 58 | 4 | 8 |

[a]mMU = milli-Merck Units

Serum antibodies to HPV types 6, 11, 16, 18, 31, 33, 45, 52, and 58 will be measured with a competitive Luminex immunoassay or equivalent assay. Titers will be reported in milli Merck Units/mL with the use of the Luminex immunoassay.

Example 10: Concomitant Administration of a Tdap Vaccine and a Dengue Vaccine A phase 3, open-label, randomized trial will be conducted in about 840 healthy subjects aged of ≥10 to <18 years in dengue endemic areas, where the Tdap vaccine is licensed for children and adolescents from 10 up to 18 years of age to investigate the immunogenicity and safety of the co-administration of TDV and the Tdap vaccine BOOSTRIX® vs BOOSTRIX® alone.

TDV will be administered subcutaneously and BOOSTRIX® will be administered intramuscularly. Subjects will be randomized equally (1:1 ratio) to each one of the following 2 trial groups (about 420 subjects per trial group):

Group 1: first dose of TDV+Tdap vaccine co-administered on day 0 (month 0); and second dose of TDV administered on day 90 (month 3).

Group 2: Tdap vaccine administered on day 0 (month 0).

Concomitantly administered vaccines will be injected to opposite arms. All subjects will be followed up for 9 months (270 days) after the first vaccination, so the trial duration will be approximately 270 days for each subject.

For each subject there will be 5 scheduled clinic visits: day 0 (month 0), day 30 (month 1), day 90 (month 3), day 120 (month 4), and day 270 (month 9). Blood samples for the measurement of antibody response to the Tdap vaccine will be collected on day 0 (month 0) and on day 30 (month 1) from all subjects in Group 1 and 2. Antibodies against the following antigens will be measured:

pertussis antigens (inactivated pertussis toxin (iPT), formaldehyde-treated filamentous hemagglutinin (FHA)), and pertactin (PRN)), tetanus toxoid antigen, and diphtheria toxoid antigen.

Blood samples for the measurement of dengue neutralizing antibodies (by microneutralization test 50% (MNT50)) will be collected from Group 1 on day 0 (month 0), day 30 (month 1), and day 120 (month 4). Blood samples will also be collected prior to vaccination.

The primary endpoints include:

(i) the proportion of subjects seroprotected for diphtheria as measured by Neutralizing Toxin Assay (NTA) or equivalent assay on day 30 (month 1), wherein seroprotection is defined as anti-diphtheria antibody levels (NTA or equivalent assay) ≥0.1 IU/mL in serum (ii) The proportion of subjects seroprotected for tetanus as measured by Enzyme Linked Immunosorbent Assay (ELISA) or equivalent assay on day 30 (month 1), wherein seroprotection is defined as anti-tetanus antibody levels (ELISA or equivalent assay) ≥0.1 IU/mL in the serum.

(iii) Geometric mean concentration (GMC) of acellular pertussis antibodies (anti-iPT antibodies, anti-FHA antibodies, anti-PRN antibodies,) as measured by ELISA or equivalent assay on day 30 (month 1).

The secondary endpoints include evaluations include geometric mean neutralizing antibody titers (GMTs) of antibodies (by MNT50) for each of the four dengue serotypes on day 30 (month 1) following a first dose with TDV and on day 120 (month 4) following a second dose of TDV, seropositivity rates (% of subjects seropositive) for each of the four dengue serotypes and for multiple (2, 3 or 4) dengue serotypes on day 30 (month 1) following a first dose with TDV and on day 120 (month 4) following a second dose of TDV, wherein seropositive for each dengue serotype is defined as the percentage of subjects with a reciprocal neutralizing antibody titer of 10.

The invention claimed is:

1. A method for vaccinating against dengue disease and yellow fever in a subject or a population of subjects, the method comprising:

administering one unit dose of a dengue virus composition and administering a live attenuated yellow fever vaccine on the same day;

wherein the method provides efficacy against yellow fever and dengue within three months after administration of both the one unit dose of the dengue virus composition and the live attenuated yellow fever vaccine;

wherein the dengue virus composition is TAK-003.

2. The method according to claim 1, wherein the method further comprises administering a second unit dose of the dengue virus composition to the subject or the subject population, wherein the second unit dose is administered at least 4 weeks after the administration of the first unit dose.

3. The method according to claim 1, wherein the subject or subject population is between the ages of 2 months to 2 years or wherein the subject or the subject population is less than 4 years of age, between 2-40 years of age, 2-60 years of age, 18-60 years of age, or 61-100 years of age.

4. The method according to claim 1, wherein the vaccinating is performed during a dengue outbreak.

5. The method of claim 4, wherein the outbreak is due to a dengue serotype 2 or dengue serotype 1.

6. The method according to claim 1, further comprising co-vaccination with another dengue vaccine composition.

7. The method of claim 6, wherein the co-vaccination with the another dengue vaccine composition occurs within 4.5 years from the administration of the one unit dose.

8. The method of claim 1, wherein the vaccinating is performed due to travel to a dengue-endemic region.

9. The method of claim 1, wherein the vaccinating is performed due to travel to a region wherein the seroprevalence rate is at least 80% with respect to dengue serotype 1 and/or dengue serotype 2.

10. The method of claim 1, wherein the method is for vaccinating against dengue disease caused by dengue-1 serotype or dengue-2 serotype.

11. The method according to claim 1, wherein the method further comprises administering a booster dose of the dengue virus composition to the subject or the subject population, wherein the booster dose is administered at least 4 weeks after the administration of the first unit dose.

12. The method of claim 2, wherein the second unit dose is administered 3 months after the administration of the first unit dose.

13. The method of claim 1, wherein the subject or the subject population is from a dengue and yellow fever non-endemic region.

14. The method of claim 1, wherein the vaccinating is performed due to travel to a dengue and yellow fever endemic region.

15. The method of claim 1, wherein the subject or the subject population is seronegative with respect to all dengue serotypes at baseline.

16. The method of claim 1, wherein the subject or the subject population is seropositive with respect to at least one dengue serotype at baseline.

17. A vaccine combination comprising (i) a unit dose of a dengue virus composition and (ii) a yellow fever vaccine, wherein the dengue virus composition is TAK-003.

18. The method of claim 1, wherein the subject or population of subjects lives in a dengue endemic region.

19. The method of claim 1, wherein the subject or population of subjects lives in a region wherein the seroprevalence rate is more than 80% with respect to dengue.

20. The method of claim 1, wherein the dengue virus composition and the yellow fever vaccine are administered to different anatomical sites.

21. The method of claim 20, wherein the dengue virus composition and the yellow fever vaccine are administered to opposite arms.

* * * * *

SEQUENCE LISTING

```
Sequence total quantity: 16
SEQ ID NO: 1            moltype = DNA  length = 10723
FEATURE                 Location/Qualifiers
source                  1..10723
                        mol_type = other DNA
                        note = chimeric dengue serotype 2/1
                        organism = synthetic construct
SEQUENCE: 1
agttgttagt ctacgtggac cgacaaagac agattctttg agggagctaa gctcaatgta   60
gttctaacag ttttttaatt agagagcaga tctctgatga ataaccaacg gaaaaaggcg  120
aaaaacacgc ctttcaatat gctgaaacgc gagagaaacc gcgtgtcgac tgtgcaacag  180
ctgacaaaga gattctcact tggaatgctg cagggacgag gaccattaaa actgttcatg  240
gccctggtgg cgttccttcg tttcctaaca atcccaccaa cagcagggat attgaagaga  300
tggggaacaa ttaaaaaatc aaaagctatt aatgttttga gagggttcag gaaagagatt  360
ggaaggatgc tgaacatctt gaataggaga cgcagatctg caggcatgat cattatgctg  420
attccaacag tgatggcgtt ccatttaacc acgcgtgggg gagagccgca tatgatagtt  480
agcaagcagg aaagaggaaa gtcacttttg ttcaagacct ctgcaggtgt caacatgtgc  540
accctcattg cgatggattt gggagagttg tgtgaggaca cgatgaccta caaatgcccc  600
```

```
cggatcactg aggcggaacc agatgacgtt gactgttggt gcaatgccac ggacacatgg  660
gtgacctatg gaacgtgctc tcaaactggc gaacaccgac gagacaaacg ttccgtcgca  720
ttggccccac acgtggggct tggcctagaa acaagagccg aaacgtggat gtcctctgaa  780
ggtgcttgga aacagataca aaaagtagag acttgggctc tgagacatcc aggattcacg  840
gtgatagccc tttttctagc acatgccata ggaacatcca tcacccagaa agggatcatt  900
ttcattttgc tgatgctggt aacaccatct atggccatgc gatgcgtggg aataggcaac  960
agagacttcg tggaaggact gtcaggagca acatgggtgg atgtggtact ggagcatgga  1020
agttgcgtca ccaccatggc aaaaaacaaa ccaacactgg acattgaact cttgaagacg  1080
gaggtcacaa accctgcagt tctgcgtaaa ttgtgcattg aagctaaaat atcaaacacc  1140
accaccgatt cgagatgtcc aacacaagga gaagccacac tggtggaaga acaagacgcg  1200
aactttgtgt gccgacgaac gttcgtggac agaggctggg gcaatggctg tgggctattc  1260
ggaaaaggta gtctaataac gtgtgccaag tttaagtgtg tgacaaaact agaaggaaag  1320
atagttcaat atgaaaacct aaaatattca gtgatagtca ccgtccacac tggagatcag  1380
caccaggtgg gaaatgagac tacagaacat ggaacaactg caaccataac acctcaagct  1440
cctacgtcgg aaatacagct gaccgactac ggaaccctta cattagattg ttcacctagg  1500
acagggctag attttaacga gatggtgttg ctgacaatga aagaaagatc atggcttgtc  1560
cacaaacaat ggttcctaga cttaccactg ccttggacct ctggggcttc aacatcccaa  1620
gagacttgga acagacaaga tttactggtc acatttaaga cagctcatgc aaagaagcag  1680
gaagtagtcg tactaggatc acaagaagga gcaatgcaca ctgcgctgac tggagcgaca  1740
gaaatccaaa cgtcaggaac gacaacaatt ttcgcaggac acctaaaatg cagactaaaa  1800
atggacaaac taactttaaa agggatgtca tatgtgatgt gcacaggctc attcaagtta  1860
gagaaagaag tggctgagac ccagcatgga actgttctgg tgcaggttaa atatgaagga  1920
acagacgcac catgcaagat tcccttttcg acccaagatg agaaaggagc aacccagaat  1980
gggagattaa taacagccaa ccccatagtc actgacaaag aaaaaccagt caatattgag  2040
gcagaaccac cctttggtga gagctacatc gtggtaggag caggtgaaaa agctttgaaa  2100
ctaagctggt tcaagaaagg aagcagcata gggaaaatgt ttgaagcaac tgcccgagga  2160
gcacgaagga tggccattct gggagacacc gcatgggact tcggttctat aggaggagtg  2220
ttcacgtcta tgggaaaact ggtacaccag gtttttggaa ctgcatatgg agttttgttt  2280
agcggagttt cttggaccat gaaaatagga atagggattc tgctgacatg gctaggatta  2340
aattcaagga acacgtccct ttcgatgatg tgcatcgcag ccggcattgt gacactgtat  2400
ttgggagtca tggtgcaggc cgatagtggt tgcgttgtga gctggaaaaa caaagaactg  2460
aaatgtggca gtgggatttt catcacagac aacgtgcaca catggacaga acaatacaag  2520
ttccaaccag aatccccttc aaaactagct tcagctatcc agaaagccca tgaagaggac  2580
atttgtggaa tccgctcagt aacaagactg gagaatctga tgtggaaaca aataacacca  2640
gaattgaatc acattctatc agaaaatgag gtgaagttaa ctattatgac aggagacatc  2700
aaaggaatca tgcaggcagg aaaacgatct ctgcggcctc agcccactga gctgaagtat  2760
tcatggaaaa catggggcaa agcaaaaatg ctctctacag agtctcataa ccagaccttt  2820
ctcattgatg gccccgaaac agcagaatgc cccaacacaa atagagcttg gaattcgttg  2880
gaagttgaag actatggctt tggagtattc accaccaata tatggctaaa attgaaagaa  2940
aaacaggatg tattctgcga ctcaaaactc atgtcagcgg ccataaaaga caacagagcc  3000
gtccatgccg atatgggtta ttggatagaa agtgcactca atgacacatg gaagatagag  3060
aaagcctctt tcattgaagt taaaaactgc cactggccaa aatcacacac cctctggagc  3120
aatggagtgc tagaaagtga gatgataatt ccaaagaatc tcgctggacc agtgtctcaa  3180
cacaactata gaccaggcta ccatacacaa ataacaggac catggcatct aggtaagctt  3240
gagatggact ttgatttctg tgatggaaca acagtggtag tgactgagga ctgcggaaat  3300
agaggaccct ctttgagaac aaccactgcc tctggaaaac tcataacaga atggtgctgc  3360
cgatcttgca cattaccacc gctaagatac agaggtgagg atgggtgctg gtacgggatg  3420
gaaatcagac cattgaagga gaaagaagag aatttggtca actccttggt cacagctgga  3480
catgggcagg tcgacaactt ttcactagga gtcttgggaa tggcattgtt cctggaggaa  3540
atgcttagga cccgagtagg aacgaaacat gcaatactac tagttgcagt ttcttttgtg  3600
acattgatca cagggaacat gtcctttaga gacctgggaa gagtgatggt tatggtaggc  3660
gccactatga cggatgacat aggtatgggc gtgacttatc ttgccctact agcagccttc  3720
aaagtcagac caacttttgc agctggacta ctcttgagaa agctgacctc caaggaattg  3780
atgatgacta ctataggaat tgtactcctc tcccagagca ccctaccaga gaccattctt  3840
gagttgactg atgcgttagc cttaggcatg atggtcctca aaatggtgag aaatatggaa  3900
aagtatcaat tggcagtgac tatcatggct atcttgtgcg tcccaaacgc agtgatatta  3960
caaaacgcat ggaaagtgag ttgcacaata ttggcagtgg tgtccgtttc cccactgttc  4020
ttaacatcct cacagcaaaa aacagattgg ataccattag cattgacgat caaaggtctc  4080
aatccaacag ctatttttct aacaaccctc tcaagaacca gcaagaaaag gagctggcca  4140
ttaaatgagg ctatcatggc agtcgggatg gtgagcattt tagccagttc tctcctaaaa  4200
aatgatattc ccatgacagg accattagtg gctggagggc tcctcactgt gtgctacgtg  4260
ctcactggac gatcggccga tttggaactg gagagagcag ccgatgtcaa atgggaagac  4320
caggcagaga tatcaggaag cagtccaatc ctgtcaataa caatatcaga agatggtagc  4380
atgtcgataa aaaatgaaga ggaagatcaa acactgacca tactcattag aacaggattg  4440
ctggtgatct caggactttt tcctgtatca ataccaatca cggcagcagc atggtacctg  4500
tgggaagtga agaaacaacg ggccggagta ttgtgggatg ttccttcacc cccacccatg  4560
ggaaaggctg aactggaaga tggagcctat agaattaagc aaaaagggat tcttggatat  4620
tcccagatcg gagccggagt ttacaaagaa ggaacattcc atacaatgtg gcatgtcaca  4680
cgtggcgctg ttctaatgca taaaggaaag aggattgaac catcatgggc ggacgtcaag  4740
aaagacctaa tatcatatgg aggaggctgg aagttagaag gagaatggaa ggaaggagaa  4800
gaagtccagg tattggcact ggagcctgga aaaaatccaa gagccgtcca aacgaaacct  4860
ggtcttttca aaaccaacgc cggaacaata ggtgctgtat ctctggactt ttctcctgga  4920
acgtcaggat ctccaattat cgacaaaaaa ggaaaagttg tgggtcttta tggtaatggt  4980
gttgttacaa ggagtggagc atatgtgagt gctatagccc agactgaaaa aagcattgaa  5040
gacaacccag agatcgaaga tgacattttc cgaaagagaa gactgaccat catggacctc  5100
cacccaggag cgggaaagac gaagagatac cttccggcca tagtcagaga agctataaaa  5160
cggggtttga gaacattaat cttggccccc actagagttg tggcagctga aatggaggaa  5220
gcccttagag gacttccaat aagataccag accccagcca tcagagctgt gcacaccggg  5280
cgggagattg tggacctaat gtgtcatgcc acatttacca tgaggctgct atcaccagtt  5340
```

```
agagtgccaa actacaacct gattatcatg gacgaagccc atttcacaga cccagcaagt  5400
atagcagcta gaggatacat ctcaactcga gtggagatgg gtgaggcagc tgggattttt  5460
atgacagcca ctcccccggg aagcagagac ccatttcctc agagcaatgc accaatcata  5520
gatgaagaaa gagaaatccc tgaacgctcg tggaattccg gacatgaatg ggtcacggat  5580
tttaaaggga agactgtttg gttcgttcca agtataaaag caggaaatga tatagcagct  5640
tgcctgagga aaaatggaaa gaaagtgata caactcagta ggaagacctt tgattctgag  5700
tatgtcaaga ctagaaccaa tgattgggac ttcgtggtta caactgacat ttcagaaatg  5760
ggtgccaatt tcaaggctga gagggttata gaccccagac gctgcatgaa accagtcata  5820
ctaacagatg gtgaagagcg ggtgattctg gcaggaccta tgccagtgac ccactctagt  5880
gcagcacaaa gaagagggag aataggaaga aatccaaaaa atgagaatga ccagtacata  5940
tacatggggg aacctctgga aaatgatgaa gactgtgcac actggaaaga agctaaaatg  6000
ctcctagata acatcaacac gccagaagga atcattccta gcatgttcga accagagcgt  6060
gaaaaggtgg atgccattga tggcgaatac cgcttgagag gagaagcaag gaaaaccttt  6120
gtagacttaa tgagaagagg agacctacca gtctggttgg cctacagagt ggcagctgaa  6180
ggcatcaact acgcagacag aaggtggtgt tttgatggag tcaagaacaa ccaaatccta  6240
gaagaaaacg tggaagttga aatctggaca aaagaagggg aaaggaagaa attgaaaccc  6300
agatggttgg atgctaggat ctattctgac ccactggcgc taaaagaatt taaggaattt  6360
gcagccggaa gaaagtctct gaccctgaac ctaatcacag aaatgggtag gctcccaacc  6420
ttcatgactc agaaggcaag agacgcactg gacaacttag cagtgctgca cacggctgag  6480
gcaggtggaa gggcgtacaa ccatgctctc agtgaactgc cggagaccct ggagacattg  6540
cttttactga cacttctggc tacagtcacg ggagggatct ttttattctt gatgagcgca  6600
aggggcatag ggaagatgac cctgggaatg tgctgcataa tcacggctag catcctccta  6660
tggtacgcac aaatacagcc acactggata gcagcttcaa taatactgga gtttttctc  6720
atagttttgc ttattccaga acctgaaaaa cagagaacac cccaagacaa ccaactgacc  6780
tacgttgtca tagccatcct cacagtggtg gccgcaacca tggcaaacga gatgggtttc  6840
ctagaaaaaa cgaagaaaga tctcggattg ggaagcattg caacccagca acccgagagc  6900
aacatcctgg acatagatct acgtcctgca tcagcatgga cgctgtatgc cgtggccaca  6960
acatttgtta caccaatgtt gagacatagc attgaaaatt cctcagtgaa tgtgtcccta  7020
acagctatag ccaaccaagc cacagtgtta atgggtctcg ggaaaggatg gccattgtca  7080
aagatggaca tcggagttcc ccttctcgcc attggatgct actcacaagt caaccccata  7140
actctcacag cagctctttt cttattggta gcacattatg ccatcatagg gccaggactc  7200
caagcaaaag caaccagaga agctcagaaa agagcagcgg cgggcatcat gaaaaaccca  7260
actgtcgatg gaataacagt gattgaccta gatccaatac cttatgatcc gaagtttgaa  7320
aagcagttgg gacaagtaat gctcctagtc ctctgcgtga ctcaagtatt gatgatgagg  7380
actacatggg ctctgtgtga ggctttaacc ttagctaccg ggcccatctc cacattgtgg  7440
gaaggaaatc cagggaggtt ttggaacact accattgcgg tgtcaatggc taacattttt  7500
agagggagtt acttggccgg agctggactt ctcttttcta ttatgaagaa cacaaccaac  7560
acaagaaggg gaactggcaa cataggagag acgcttggag agaaatggaa aagccgattg  7620
aacgcattgg gaaaaagtga attccagatc tacaagaaaa gtggaatcca ggaagtggat  7680
agaaccttag caaaagaagg cattaaaaga ggagaaacgg accatcacgc tgtgtcgcga  7740
ggctcagcaa aactgagatg gttcgttgag agaaacatgg tcacaccaga agggaaagta  7800
gtggacctcg gttgtggcag aggaggctgg tcatactatt gtggaggact aaagaatgta  7860
agagaagtca aaggcctaac aaaaggagga ccaggacacg aagaacccat ccccatgtca  7920
acatatgggt ggaatctagt gcgtcttcaa agtggagttg acgttttctt catcccgcca  7980
gaaaagtgtg acacattatt gtgtgacata ggggagtcat caccaaatcc cacagtggaa  8040
gcaggacgaa cactcagagt ccttaactta gtagaaaatt ggttgaacaa caacactcaa  8100
ttttgcataa aggttctcaa cccatatatg ccctcagtca tagaaaaaat ggaagcacta  8160
caaaggaaat atggaggagc cttagtgagg aatccactct cacgaaactc cacacatgag  8220
atgtactggg tatccaatgc ttccgggaac atagtgtcat cagtgaacat gatttcaagg  8280
atgttgatca acagatttac aatgagatac aagaaagcca cttacgagcc ggatgttgac  8340
ctcggaagcg gaacccgtaa catcgggatt gaaagtgaga taccaaacct agatataatt  8400
gggaaaagaa tagaaaaaat aaagcaagag catgaaacat catggcacta tgaccaagac  8460
cacccataca aaacgtgggc ataccatggt agctatgaaa caaaacagac tggatcagca  8520
tcatccatgg tcaacggagt ggtcaggctg ctgacaaaac cttgggacgt cgtccccatg  8580
gtgacacaga tggcaatgac agacacgact ccatttggac aacagcgcgt ttttaaagag  8640
aaagtggaca cgagaaccca agaaccgaaa gaaggcacga agaaactaat gaaaataaca  8700
gcagagtggc tttggaaaga attagggaag aaaaagacac ccaggatgtg caccagagaa  8760
gaattcacaa gaaaggtgag aagcaatgca gccttggggg ccatattcac tgatgagaac  8820
aagtggaagt cggcacgtga ggctgttgaa gatagtaggt tttgggagct ggttgacaag  8880
gaaaggaatc tccatcttga aggaaagtgt gaaacatgtg tgtacaacat gatgggaaaa  8940
agagagaaga agctagggga attcggcaag gcaaaaggca gcagagccat atggtacatg  9000
tggcttggag cacgcttctt agagtttgaa gccctaggat tcttaaatga agatcactgg  9060
ttctccagag agaactccct gagtggagtg gaaggagaag ggctgcacaa gctaggttac  9120
attctaagag acgtgagcaa gaaagaggga ggagcaatgt atgccgatga caccgcagga  9180
tgggatacaa gaatcacact agaagaccta aaaaatgaag aaatggtaac aaaccacatg  9240
gaaggagaac acaagaaact agccgaggcc attttcaaac taacgtacca aaacaaggtg  9300
gtgcgtgtgc aaagaccaac accaagaggc acagtaatgg acatcatatc gagaagagac  9360
caaagaggta gtggacaagt tggcacctat ggactcaata ctttcaccaa tatggaagcc  9420
caactaatca gacagatgga gggagaagga gtctttaaaa gcattcagca cctaacaatc  9480
acagaagaaa tcgctgtgca aaactggtta gcaagagtgg ggcgcgaaag gttatcaaga  9540
atggccatca gtggagatga ttgtgttgtg aaacctttag atgacaggtt cgcaagcgct  9600
ttaacagctc taaatgacat gggaaagatt aggaaagaca tacaacaatg ggaaccttca  9660
agaggatgga atgattggac acaagtgccc ttctgttcac accatttcca tgagttaatc  9720
atgaaagacg gtcgcgtact cgttgttcca tgtagaaacc aagatgaact gattggcaga  9780
gcccgaatct cccaaggagc agggtggtct ttgcgggaga cggcctgttt ggggaagtct  9840
tacgcccaaa tgtggagctt gatgtacttc cacagacgcg acctcaggct ggcggcaaat  9900
gctatttgct cggcagtacc atcacattgg gttccaacaa gtcgaacaac ctggtccata  9960
catgctaaac atgaatggat gacaacggaa gacatgctga cagtctggaa cagggtgtgg  10020
attcaagaaa acccatggat ggaagacaaa actccagtgg aatcatggga ggaaatccca  10080
```

```
tacttgggga aaagagaaga ccaatggtgc ggctcattga ttgggttaac aagcagggcc  10140
acctgggcaa agaacatcca agcagcaata aatcaagtta gatcccttat aggcaatgaa  10200
gaatacacag attacatgcc atccatgaaa agattcagaa gagaagagga agaagcagga  10260
gttctgtggt agaaagcaaa actaacatga aacaaggcta gaagtcaggt cggattaagc  10320
catagtacgg aaaaaactat gctacctgtg agccccgtcc aaggacgtta aaagaagtca  10380
ggccatcata aatgccatag cttgagtaaa ctatgcagcc tgtagctcca cctgagaagg  10440
tgtaaaaaat ccgggaggcc acaaaccatg gaagctgtac gcatggcgta gtggactagc  10500
ggttagagga gacccctccc ttacaaatcg cagcaacaat gggggcccaa ggcgagatga  10560
agctgtagtc tcgctggaag gactagaggt tagaggagac ccccccgaaa caaaaaacag  10620
catattgacg ctgggaaaga ccagagatcc tgctgtctcc tcagcatcat tccaggcaca  10680
gaacgccaga aaatggaatg gtgctgttga atcaacaggt tct                    10723

SEQ ID NO: 2            moltype = AA  length = 3391
FEATURE                 Location/Qualifiers
source                  1..3391
                        mol_type = protein
                        note = chimeric dengue serotype 2/1
                        organism = synthetic construct
SEQUENCE: 2
MNNQRKKAKN TPFNMLKRER NRVSTVQQLT KRFSLGMLQG RGPLKLFMAL VAFLRFLTIP  60
PTAGILKRWG TIKKSKAINV LRGFRKEIGR MLNILNRRRR SAGMIIMLIP TVMAFHLTTR  120
GGEPHMIVSK QERGKSLLFK TSAGVNMCTL IAMDLGELCE DTMTYKCPRI TEAEPDDVDC  180
WCNATDTWVT YGTCSQTGEH RRDKRSVALA PHVGLGLETR AETWMSSEGA WKQIQKVETW  240
ALRHPGFTVI ALFLAHAIGT SITQKGIIFI LLMLVTPSMA MRCVGIGNRD FVEGLSGATW  300
VDVVLEHGSC VTTMAKNKPT LDIELLKTEV TNPAVLRKLC IEAKISNTTT DSRCPTQGEA  360
TLVEEQDANF VCRRTFVDRG WGNGCGLFGK GSLITCAKFK CVTKLEGKIV QYENLKYSVI  420
VTVHTGDQHQ VGNETTEHGT TATITPQAPT SEIQLTDYGT LTLDCSPRTG LDFNEMVLLT  480
MKERSWLVHK QWFLDLPLPW TSGASTSQET WNRQDLLVTF KTAHAKKQEV VVLGSQEGAM  540
HTALTGATEI QTSGTTTIFA GHLKCRLKMD KLTLKGMSYV MCTGSFKLEK EVAETQHGTV  600
LVQVKYEGTD APCKIPFSTQ DEKGATQNGR LITANPIVTD KEKPVNIEAE PPFGESYIVV  660
GAGEKALKLS WFKKGSSIGK MFEATARGAR RMAILGDTAW DFGSIGGVFT SMGKLVHQVF  720
GTAYGVLFSG VSWTMKIGIG ILLTWLGLNS RNTSLSMMCI AAGIVTLYLG VMVQADSGCV  780
VSWKNKELKC GSGIFITDNV HTWTEQYKFQ PESPSKLASA IQKAHEEDIC GIRSVTRLEN  840
LMWKQITPEL NHILSENEVK LTIMTGDIKG IMQAGKRSLR PQPTELKYSW KTWGKAKMLS  900
TESHNQTFLI DGPETAECPN TNRAWNSLEV EDYGFGVFTT NIWLKLKEKQ DVFCDSKLMS  960
AAIKDNRAVH ADMGYWIESA LNDTWKIEKA SFIEVKNCHW PKSHTLWSNG VLESEMIIPK  1020
NLAGPVSQHN YRPGYHTQIT GPWHLGKLEM DFDFCDGTTV VVTEDCGNRG PSLRTTTASG  1080
KLITEWCCRS CTLPPLRYRG EDGCWYGMEI RPLKEKEENL VNSLVTAGHG QVDNFSLGVL  1140
GMALFLEEML RTRVGTKHAI LLVAVSFVTL ITGNMSFRDL GRVMVMVGAT MTDDIGMGVT  1200
YLALLAAFKV RPTFAAGLLL RKLTSKELMM TTIGIVLLSQ STLPETILEL TDALALGMMV  1260
LKMVRNMEKY QLAVTIMAIL CVPNAVILQN AWKVSCTILA VVSVSPLFLT SSQQKTDWIP  1320
LALTIKGLNP TAIFLTTLSR TSKKRSWPLN EAIMAVGMVS ILASSLLKND IPMTGPLVAG  1380
GLLTVCYVLT GRSADLELER AADVKWEDQA EISGSSPILS ITISEDGSMS IKNEEEDQTL  1440
TILIRTGLLV ISGLFPVSIP ITAAAWYLWE VKKQRAGVLW DVPSPPPMGK AELEDGAYRI  1500
KQKGILGYSQ IGAGVYKEGT FHTMWHVTRG AVLMHKGKRI EPSWADVKKD LISYGGGWKL  1560
EGEWKEGEEV QVLALEPGKN PRAVQTKPGL FKTNAGTIGA VSLDFSPGTS GSPIIDKKGK  1620
VVGLYGNGVV TRSGAYVSAI AQTEKSIEDN PEIEDDIFRK RRLTIMDLHP GAGKTKRYLP  1680
AIVREAIKRG LRTLILAPTR VVAAEMEEAL RGLPIRYQTP AIRAVHTGRE IVDLMCHATF  1740
TMRLLSPVRV PNYNLIIMDE AHFTDPASIA ARGYISTRVE MGEAAGIFMT ATPPGSRDPF  1800
PQSNAPIIDE EREIPERSWN SGHEWVTDFK GKTVWFVPSI KAGNDIAACL RKNGKKVIQL  1860
SRKTFDSEYV KTRTNDWDFV VTTDISEMGA NFKAERVIDP RRCMKPVILT DGEERVILAG  1920
PMPVTHSSAA QRRGRIGRNP KNENDQYIYM GEPLENDEDC AHWKEAKMLL DNINTPEGII  1980
PSMFEPEREK VDAIDGEYRL RGEARKTFVD LMRRGDLPVW LAYRVAAEGI NYADRRWCFD  2040
GVKNNQILEE NVEVEIWTKE GERKKLKPRW LDARIYSDPL ALKEFKEFAA GRKSLTLNLI  2100
TEMGRLPTFM TQKARDALDN LAVLHTAEAG GRAYNHALSE LPETLETLLL LTLLATVTGG  2160
IFLFLMSARG IGKMTLGMCC IITASILLWY AQIQPHWIAA SIILEFFLIV LLIPEPEKQR  2220
TPQDNQLTYV VIAILTVVAA TMANEMGFLE KTKKDLGLGS IATQQPESNI LDIDLRPASA  2280
WTLYAVATTF VTPMLRHSIE NSSVNVSLTA IANQATVLMG LGKGWPLSKM DIGVPLLAIG  2340
CYSQVNPITL TAALFLLVAH YAIIGPGLQA KATREAQKRA AAGIMKNPTV DGITVIDLDP  2400
IPYDPKFEKQ LGQVMLLVLC VTQVLMMRTT WALCEALTLA TGPISTLWEG NPGRFWNTTI  2460
AVSMANIFRG SYLAGAGLLF SIMKNTTNTR RGTGNIGETL GEKWKSRLNA LGKSEFQIYK  2520
KSGIQEVDRT LAKEGIKRGE TDHHAVSRGS AKLRWFVERN MVTPEGKVVD LGCGRGGWSY  2580
YCGGLKNVRE VKGLTKGGPG HEEPIPMSTY GWNLVRLQSG VDVFFIPPEK CDTLLCDIGE  2640
SSPNPTVEAG RTLRVLNLVE NWLNNNTQFC IKVLNPYMPS VIEKMEALQR KYGGALVRNP  2700
LSRNSTHEMY WVSNASGNIV SSVNMISRML INRFTMRYKK ATYEPDVDLG SGTRNIGIES  2760
EIPNLDIIGK RIEKIKQEHE TSWHYDQDHP YKTWAYHGSY ETKQTGSASS MVNGVVRLLT  2820
KPWDVVPMVT QMAMTDTTPF GQQRVFKEKV DTRTQEPKEG TKKLMKITAE WLWKELGKKK  2880
TPRMCTREEF TRKVRSNAAL GAIFTDENKW KSAREAVEDS RFWELVDKER NLHLEGKCET  2940
CVYNMMGKRE KKLGEFGKAK GSRAIWYMWL GARFLEFEAL GFLNEDHWFS RENSLSGVEG  3000
EGLHKLGYIL RDVSKKEGGA MYADDTAGWD TRITLEDLKN EEMVTNHMEG EHKKLAEAIF  3060
KLTYQNKVVR VQRPTPRGTV MDIISRRDQR GSGQVGTYGL NTFTNMEAQL IRQMEGEGVF  3120
KSIQHLTITE EIAVQNWLAR VGRERLSRMA ISGDDCVVKP LDDRFASALT ALNDMGKIRK  3180
DIQQWEPSRG WNDWTQVPFC SHHFHELIMK DGRVLVVPCR NQDELIGRAR ISQGAGWSLR  3240
ETACLGKSYA QMWSLMYFHR RDLRLAANAI CSAVPSHWVP TSRTTWSIHA KHEWMTTEDM  3300
LTVWNRVWIQ ENPWMEDKTP VESWEEIPYL GKREDQWCGS LIGLTSRATW AKNIQAAINQ  3360
VRSLIGNEEY TDYMPSMKRF RREEEEAGVL W                                 3391

SEQ ID NO: 3            moltype = DNA  length = 10723
FEATURE                 Location/Qualifiers
```

```
source                  1..10723
                        mol_type = other DNA
                        note = dengue serotype 2
                        organism = synthetic construct
SEQUENCE: 3
agttgttagt ctacgtggac cgacaaagac agattctttg agggagctaa gctcaatgta  60
gttctaacag tttttaatt agagagcaga tctctgatga ataaccaacg gaaaaaggcg  120
aaaaacacgc ctttcaatat gctgaaacgc gagagaaacc gcgtgtcgac tgtgcaacag  180
ctgacaaaga gattctcact tggaatgctg cagggacgag gaccattaaa actgttcatg  240
gccctggtgg cgttccttcg tttcctaaca atcccaccaa cagcagggat attgaagaga  300
tggggaacaa ttaaaaaatc aaaagctatt aatgttttga gagggttcag gaaagagatt  360
ggaaggatgc tgaacatctt gaataggaga cgcagatctg caggcatgat cattatgctg  420
attccaacag tgatggcgtt ccatttaacc acacgtaacg gagaaccaca catgatcgtc  480
agcagacaag agaaagggaa aagtcttctg tttaaaacag aggttggcgt gaacatgtgt  540
accctcatgg ccatggacct tggtgaattg tgtgaagaca caatcacgta cgagtgtccc  600
cttctcaggc agaatgagcc agaagacata gactgttggt gcaactctac gtccacgtgg  660
gtaacttatg ggacgtgtac caccatggga gaacatagaa gagaaaaaag atcagtggca  720
ctcgttccac atgtgggaat gggactggag acacgaactg aaacatggat gtcatcagaa  780
ggggcctgga aacatgtcca gagaattgaa acttggatct tgagacatcc aggcttcacc  840
atgatggcag caatcctggc atacaccata ggaacgacac atttccaaag agccctgatc  900
ttcatcttac tgacagctgt cactccttca atgacaatgc gttgcatagg aatgtcaaat  960
agagactttg tggaaggggt ttcaggagga agctgggttg acatagtctt agaacatgga  1020
agctgtgtga cgacgatggc aaaaaacaaa ccaacattgg attttgaact gataaaaaca  1080
gaagccaaac agcctgccac cctaaggaag tactgtatag aggcaaagct aaccaacaca  1140
acaacagaat ctcgctgccc aacacaaggg gaacccagcc taaatgaaga gcaggacaaa  1200
aggttcgtct gcaaacactc catggtagac agaggatggg gaaatggatg tggactattt  1260
ggaaagggag gcattgtgac ctgtgctatg ttcagatgca aaaagaacat ggaaggaaaa  1320
gttgtgcaac cagaaaactt ggaatacacc attgtgataa cacctcactc aggggaagag  1380
catgcagtcg gaaatgacac aggaaaacat ggcaaggaaa tcaaaataac accacagagt  1440
tccatcacag aagcagaatt gacaggttat ggcactgtca caatggagtg ctctccaaga  1500
acgggcctcg acttcaatga gatggtgttg ctgcagatgg aaaataaagc ttggctggtg  1560
cacaggcaat ggttcctaga cctgccgtta ccatggttgc ccggagcgga cacacaaggg  1620
tcaaattgga tacagaaaga gacattggtc actttcaaaa atccccatgc gaagaaacag  1680
gatgttgttg ttttaggatc ccaagaaggg gccatgcaca cagcacttac aggggccaca  1740
gaaatccaaa tgtcatcagg aaacttactc ttcacaggac atctcaagtg caggctgaga  1800
atggacaagc tacagctcaa aggaatgtca tactctatgt gcacaggaaa gtttaaagtt  1860
gtgaaggaaa tagcagaaac acaacatgga acaatagtta tcagagtgca atatgaaggg  1920
gacggctctc catgcaagat ccctttttgag ataatggatt tggaaaaaag acatgtctta  1980
ggtcgcctga ttacagtcaa cccaattgtg acagaaaaag atagcccagt caacatagaa  2040
gcagaacctc catttggaga cagctacatc atcataggag tagagccggg acaactgaag  2100
ctcaactggt ttaagaaagg aagttctatc ggccaaatgt ttgagacaac aatgaggggg  2160
gcgaagagaa tggccatttt aggtgacaca gcctgggatt ttggatcctt gggaggagtg  2220
tttacatcta taggaaaggc tctccaccaa gtctttggag caatctatgg agctgccttc  2280
agtggggttt catggactat gaaaatcctc ataggagtca ttatcacatg gataggaatg  2340
aattcacgca gcacctcact gtctgtgaca ctagtattgg tgggaattgt gacactgtat  2400
ttgggagtca tggtgcaggc cgatagtggt tgcgttgtga gctggaaaaa caaagaactg  2460
aaatgtggca gtgggatttt catcacagac aacgtgcaca catggacaga acaatacaag  2520
ttccaaccag aatccccttc aaaactagct tcagctatcc agaaagccca tgaagaggac  2580
atttgtggaa tccgctcagt aacaagactg gagaatctga tgtggaaaca aataacacca  2640
gaattgaatc acattctatc agaaaatgag gtgaagttaa ctattatgac aggagacatc  2700
aaaggaatca tgcaggcagg aaaacgatct ctgcggcctc agcccactga gctgaagtat  2760
tcatggaaaa catggggcaa agcaaaaatg ctctctacag agtctcataa ccagaccttt  2820
ctcattgatg gccccgaaac agcagaatgc cccaacacaa atagagcttg gaattcgttg  2880
gaagttgaag actatggctt tggagtattc accaccaata tatggctaaa attgaaagaa  2940
aaacaggatg tattctgcga ctcaaaactc atgtcagcgg ccataaaaga caacagagcc  3000
gtccatgccg atatgggtta ttggatagaa agtgcactca atgacacatg gaagatagag  3060
aaagcctctt tcattgaagt taaaaactgc cactggccaa aatcacacac cctctggagc  3120
aatggagtgc tagaaagtga gatgataatt ccaaagaatc tcgctggacc agtgtctcaa  3180
cacaactata gaccaggcta ccatacacaa ataacaggac catggcatct aggtaagctt  3240
gagatggact ttgatttctg tgatggaaca acagtggtag tgactgagga ctgcggaaat  3300
agaggaccct ctttgagaac aaccactgcc tctggaaaac tcataacaga atggtgctgc  3360
cgatcttgca cattaccacc gctaagatac agaggtgagg atgggtgctg gtacgggatg  3420
gaaatcagac cattgaagga gaaagaagag aatttggtca actccttggt cacagctgga  3480
catgggcagg tcgacaactt ttcactagga gtcttgggaa tggcattgtt cctggaggaa  3540
atgcttagga cccgagtagg aacgaaacat gcaatactac tagttgcagt ttcttttgtg  3600
acattgatca cagggaacat gtcctttaga gacctgggaa gagtgatggt tatggtaggc  3660
gccactatga cggatgacat aggtatgggc gtgacttatc ttgccctact agcagccttc  3720
aaagtcagac caacttttgc agctggacta ctcttgagaa agctgacctc caaggaattg  3780
atgatgacta ctataggaat tgtactcctc tcccagagca ccataccaga gaccattctt  3840
gagttgactg atgcgttagc cttaggcatg atggtcctca aaatggtgag aaatatggaa  3900
aagtatcaat tggcagtgac tatcatggct atcttgtgcg tcccaaacgc agtgatatta  3960
caaaacgcat ggaaagtgag ttgcacaata ttggcagtgg tgtccgtttc cccactgttc  4020
ttaacatcct cacagcaaaa aacagattgg ataccattag cattgacgat caaaggtctc  4080
aatccaacag ctattttttct aacaaccctc tcaagaacca gcaagaaaag gagctggcca  4140
ttaaatgagg ctatcatggc agtcgggatg gtgagcattt tagccagttc tctcctaaaa  4200
aatgatattc ccatgacagg accattagtg gctggagggc tcctcactgt gtgctacgtg  4260
ctcactggac gatcggccga tttggaactg gagagagcag ccgatgtcaa atgggaagac  4320
caggcagaga tatcaggaag cagtccaatc ctgtcaataa caatatcaga agatggtagc  4380
atgtcgataa aaaatgaaga ggaagaacaa acactgacca tactcattag aacaggattg  4440
```

```
ctggtgatct caggactttt tcctgtatca ataccaatca cggcagcagc atggtacctg  4500
tgggaagtga agaaacaacg ggccggagta ttgtgggatg ttccttcacc cccacccatg  4560
ggaaaggctg aactggaaga tggagcctat agaattaagc aaaaagggat tcttggatat  4620
tcccagatcg gagccggagt ttacaaagaa ggaacattcc atacaatgtg gcatgtcaca  4680
cgtggcgctg ttctaatgca taaaggaaag aggattgaac catcatgggc ggacgtcaag  4740
aaagacctaa tatcatatgg aggaggctgg aagttagaag gagaatggaa ggaaggagaa  4800
gaagtccagg tattggcact ggagcctgga aaaaatccaa gagccgtcca aacgaaacct  4860
ggtcttttca aaaccaacgc cggaacaata ggtgctgtat ctctggactt ttctcctgga  4920
acgtcaggat ctccaattat cgacaaaaaa ggaaaagttg tgggtcttta tggtaatggt  4980
gttgttacaa ggagtggagc atatgtgagt gctatagccc agactgaaaa aagcattgaa  5040
gacaacccag agatcgaaga tgacattttc cgaaagagaa gactgaccat catggacctc  5100
cacccaggag cgggaaagac gaagagatac cttccggcca tagtcagaga agctataaaa  5160
cggggtttga gaacattaat cttggccccc actagagttg tggcagctga aatggaggaa  5220
gcccttagag gacttccaat aagataccag accccagcca tcagagctgt gcacaccggg  5280
cgggagattg tggacctaat gtgtcatgcc acatttacca tgaggctgct atcaccagtt  5340
agagtgccaa actacaacct gattatcatg gacgaagccc atttcacaga cccagcaagt  5400
atagcagcta gaggatacat ctcaactcga gtggagatgg gtgaggcagc tgggattttt  5460
atgacagcca ctcccccggg aagcagagac ccatttcctc agagcaatgc accaatcata  5520
gatgaagaaa gagaaatccc tgaacgctcg tggaattccg gacatgaatg ggtcacggat  5580
tttaaaggga agactgtttg gttcgttcca agtataaaag caggaaatga tatagcagct  5640
tgcctgagga aaaatggaaa gaaagtgata caactcagta ggaagacctt tgattctgag  5700
tatgtcaaga ctagaaccaa tgattgggac ttcgtggtta caactgacat ttcagaaatg  5760
ggtgccaatt tcaaggctga gagggttata gaccccagac gctgcatgaa accagtcata  5820
ctaacagatg gtgaagagcg ggtgattctg gcaggaccta tgccagtgac ccactctagt  5880
gcagcacaaa gaagagggag aataggaaga aatccaaaaa atgagaatga ccagtacata  5940
tacatggggg aacctctgga aaatgatgaa gactgtgcac actggaaaga agctaaaatg  6000
ctcctagata acatcaacac gccagaagga atcattccta gcatgttcga accagagcgt  6060
gaaaaggtgg atgccattga tggcgaatac cgcttgagag gagaagcaag gaaaaccttt  6120
gtagacttaa tgagaagagg agacctacca gtctggttgg cctacagagt ggcagctgaa  6180
ggcatcaact acgcagacag aaggtggtgt tttgatggag tcaagaacaa ccaaatccta  6240
gaagaaaacg tggaagttga aatctggaca aaagaagggg aaaggaagaa attgaaaccc  6300
agatggttgg atgctaggat ctattctgac ccactggcgc taaaagaatt taaggaattt  6360
gcagccggaa gaaagtctct gaccctgaac ctaatcacag aaatgggtag gctcccaacc  6420
ttcatgactc agaaggcaag agacgcactg gacaacttag cagtgctgca cacggctgag  6480
gcaggtggaa gggcgtacaa ccatgctctc agtgaactgc cggagaccct ggagacattg  6540
cttttactga cacttctggc tacagtcacg ggagggatct tttattctt gatgagcgca  6600
aggggcatag ggaagatgac cctgggaatg tgctgcataa tcacggctag catcctccta  6660
tggtacgcac aaatacagcc acactggata gcagcttcaa taatactgga gtttttctc  6720
atagttttgc ttattccaga acctgaaaaa cagagaacac cccaagacaa ccaactgacc  6780
tacgttgtca tagccatcct cacagtggtg gccgcaacca tggcaaacga gatgggtttc  6840
ctagaaaaaa cgaagaaaga tctcggattg ggaagcattg caacccagca acccgagagc  6900
aacatcctgg acatagatct acgtcctgca tcagcatgga cgctgtatgc cgtggccaca  6960
acatttgtta caccaatgtt gagacatagc attgaaaatt cctcagtgaa tgtgtcccta  7020
acagctatag ccaaccaagc cacagtgtta atgggtctcg ggaaaggatg gccattgtca  7080
aagatggaca tcggagttcc ccttctcgcc attggatgct actcacaagt caaccccata  7140
actctcacag cagctctttt cttattggta gcacattatg ccatcatagg gccaggactc  7200
caagcaaaag caaccagaga agctcagaaa agagcagcgg cgggcatcat gaaaaaccca  7260
actgtcgatg gaataacagt gattgaccta gatccaatac cttatgatcc aaagtttgaa  7320
aagcagttgg gacaagtaat gctcctagtc ctctgcgtga ctcaagtatt gatgatgagg  7380
actacatggg ctctgtgtga ggctttaacc ttagctaccg ggcccatctc cacattgtgg  7440
gaaggaaatc cagggaggtt ttggaacact accattgcgg tgtcaatggc taacattttt  7500
agagggagtt acttggccgg agctggactt ctcttttcta ttatgaagaa cacaaccaac  7560
acaagaaggg gaactggcaa cataggagag acgcttggag agaaatggaa aagccgattg  7620
aacgcattgg gaaaaagtga attccagatc tacaagaaaa gtggaatcca ggaagtggat  7680
agaaccttag caaaagaagg cattaaaaga ggagaaacgg accatcacgc tgtgtcgcga  7740
ggctcagcaa aactgagatg gttcgttgag agaaacatgg tcacaccaga agggaaagta  7800
gtggacctcg gttgtggcag aggaggctgg tcatactatt gtggaggact aaagaatgta  7860
agagaagtca aaggcctaac aaaaggagga ccaggacacg aagaacccat ccccatgtca  7920
acatatgggt ggaatctagt gcgtcttcaa agtggagttg acgttttctt catcccgcca  7980
gaaaagtgtg acacattatt gtgtgacata ggggagtcat caccaaatcc cacagtggaa  8040
gcaggacgaa cactcagagt ccttaactta gtagaaaatt ggttgaacaa caacactcaa  8100
ttttgcataa aggttctcaa cccatatatg ccctcagtca tagaaaaaat ggaagcacta  8160
caaaggaaat atggaggagc cttagtgagg aatccactct cacgaaactc cacacatgag  8220
atgtactggg tatccaatgc ttccgggaac atagtgtcat cagtgaacat gatttcaagg  8280
atgttgatca acagatttac aatgagatac aagaaagcca cttacgagcc ggatgttgac  8340
ctcggaagcg gaacccgtaa catcgggatt gaaagtgaga taccaaacct agatataatt  8400
gggaaaagaa tagaaaaaat aaagcaagag catgaaacat catggcacta tgaccaagac  8460
cacccataca aaacgtgggc ataccatggt agctatgaaa caaaacagac tggatcagca  8520
tcatccatgg tcaacggagt ggtcaggctg ctgacaaaac cttgggacgt cgtccccatg  8580
gtgacacaga tggcaatgac agacacgact ccatttggac aacagcgcgt ttttaaagag  8640
aaagtggaca cgagaaccca agaaccgaaa gaaggcacga agaaactaat gaaaataaca  8700
gcagagtggc tttggaaaga attagggaag aaaaagacac ccaggatgtg caccagagaa  8760
gaattcacaa gaaaggtgag aagcaatgca gccttggggg ccgtattcac tgatgagaac  8820
aagtggaagt cggcacgtga ggctgttgaa gatagtaggt tttgggagct ggttgacaag  8880
gaaaggaatc tccatcttga aggaaagtgt gaaacatgtg tgtacaacat gatgggaaaa  8940
agagagaaga agctagggga attcggcaag gcaaaaggca gcagagccat atggtacatg  9000
tggcttggag cacgcttctt agagtttgaa gccctaggat tcttaaatga agatcactgg  9060
ttctccagag agaactccct gagtggagtg gaaggagaag ggctgcacaa gctaggttac  9120
attctaagag acgtgagcaa gaaagaggga ggagcaatgt atgccgatga caccgcagga  9180
```

```
tgggatacaa gaatcacact agaagaccta aaaaatgaag aaatggtaac aaaccacatg  9240
gaaggagaac acaagaaact agccgaggcc attttcaaac taacgtacca aaacaaggtg  9300
gtgcgtgtgc aaagaccaac accaagaggc acagtaatgg acatcatatc gagaagagac  9360
caaagaggta gtggacaagt tggcacctat ggactcaata ctttcaccaa tatggaagcc  9420
caactaatca gacagatgga gggagaagga gtctttaaaa gcattcagca cctaacaatc  9480
acagaagaaa tcgctgtgca aaactggtta gcaagagtgg ggcgcgaaag gttatcaaga  9540
atggccatca gtggagatga ttgtgttgtg aaacctttag atgacaggtt cgcaagcgct  9600
ttaacagctc taaatgacat gggaaagatt aggaaagaca tacaacaatg ggaaccttca  9660
agaggatgga atgattggac acaagtgccc ttctgttcac accatttcca tgagttaatc  9720
atgaaagacg gtcgcgtact cgttgttcca tgtagaaacc aagatgaact gattggcaga  9780
gcccgaatct cccaaggagc agggtggtct ttgcgggaga cggcctgttt ggggaagtct  9840
tacgccccaaa tgtggagctt gatgtacttc cacagacgcg acctcaggct ggcggcaaat  9900
gctatttgct cggcagtacc atcacattgg gttccaacaa gtcgaacaac ctggtccata  9960
catgctaaac atgaatggat gacaacggaa gacatgctga cagtctggaa cagggtgtgg  10020
attcaagaaa acccatggat ggaagacaaa actccagtgg aatcatggga ggaaatccca  10080
tacttgggga aaagagaaga ccaatggtgc ggctcattga ttgggttaac aagcagggcc  10140
acctgggcaa agaacatcca agcagcaata aatcaagtta gatcccttat aggcaatgaa  10200
gaatacacag attacatgcc atccatgaaa agattcagaa gagaagagga agaagcagga  10260
gttctgtggt agaaagcaaa actaacatga aacaaggcta gaagtcaggt cggattaagc  10320
catagtacgg aaaaaactat gctacctgtg agccccgtcc aaggacgtta aaagaagtca  10380
ggccatcata aatgccatag cttgagtaaa ctatgcagcc tgtagctcca cctgagaagg  10440
tgtaaaaaat ccgggaggcc acaaaccatg gaagctgtac gcatggcgta gtggactagc  10500
ggttagagga gacccctccc ttacaaatcg cagcaacaat gggggcccaa ggcgagatga  10560
agctgtagtc tcgctggaag gactagaggt tagaggagac ccccccgaaa caaaaaacag  10620
catattgacg ctgggaaaga ccagagatcc tgctgtctcc tcagcatcat tccaggcaca  10680
gaacgccaga aaatggaatg gtgctgttga atcaacaggt tct                   10723

SEQ ID NO: 4            moltype = AA  length = 3391
FEATURE                 Location/Qualifiers
source                  1..3391
                        mol_type = protein
                        note = dengue serotype 2
                        organism = synthetic construct
SEQUENCE: 4
MNNQRKKAKN TPFNMLKRER NRVSTVQQLT KRFSLGMLQG RGPLKLFMAL VAFLRFLTIP  60
PTAGILKRWG TIKKSKAINV LRGFRKEIGR MLNILNRRRR SAGMIIMLIP TVMAFHLTTR  120
NGEPHMIVSR QEKGKSLLFK TEVGVNMCTL MAMDLGELCE DTITYECPLL RQNEPEDIDC  180
WCNSTSTWVT YGTCTTMGEH RREKRSVALV PHVGMGLETR TETWMSSEGA WKHVQRIETW  240
ILRHPGFTMM AAILAYTIGT THFQRALIFI LLTAVTPSMT MRCIGMSNRD FVEGVSGGSW  300
VDIVLEHGSC VTTMAKNKPT LDFELIKTEA KQPATLRKYC IEAKLTNTTT ESRCPTQGEP  360
SLNEEQDKRF VCKHSMVDRG WGNGCGLFGK GGIVTCAMFR CKKNMEGKVV QPENLEYTIV  420
ITPHSGEEHA VGNDTGKHGK EIKITPQSSI TEAELTGYGT VTMECSPRTG LDFNEMVLLQ  480
MENKAWLVHR QWFLDLPLPW LPGADTQGSN WIQKETLVTF KNPHAKKQDV VVLGSQEGAM  540
HTALTGATEI QMSSGNLLFT GHLKCRLRMD KLQLKGMSYS MCTGKFKVVK EIAETQHGTI  600
VIRVQYEGDG SPCKIPFEIM DLEKRHVLGR LITVNPIVTE KDSPVNIEAE PPFGDSYIII  660
GVEPGQLKLN WFKKGSSIGQ MFETTMRGAK RMAILGDTAW DFGSLGGVFT SIGKALHQVF  720
GAIYGAAFSG VSWTMKILIG VIITWIGMNS RSTSLSVTLV LVGIVTLYLG VMVQADSGCV  780
VSWKNKELKC GSGIFITDNV HTWTEQYKFQ PESPSKLASA IQKAHEEDIC GIRSVTRLEN  840
LMWKQITPEL NHILSENEVK LTIMTGDIKG IMQAGKRSLR PQPTELKYSW KTWGKAKMLS  900
TESHNQTFLI DGPETAECPN TNRAWNSLEV EDYGFGVFTT NIWLKLKEKQ DVFCDSKLMS  960
AAIKDNRAVH ADMGYWIESA LNDTWKIEKA SFIEVKNCHW PKSHTLWSNG VLESEMIIPK  1020
NLAGPVSQHN YRPGYHTQIT GPWHLGKLEM DFDFCDGTTV VVTEDCGNRG PSLRTTTASG  1080
KLITEWCCRS CTLPPLRYRG EDGCWYGMEI RPLKEKEENL VNSLVTAGHG QVDNFSLGVL  1140
GMALFLEEML RTRVGTKHAI LLVAVSFVTL ITGNMSFRDL GRVMVMVGAT MTDDIGMGVT  1200
YLALLAAFKV RPTFAAGLLL RKLTSKELMM TTIGIVLLSQ STIPETILEL TDALALGMMV  1260
LKMVRNMEKY QLAVTIMAIL CVPNAVILQN AWKVSCTILA VVSVSPLFLT SSQQKTDWIP  1320
LALTIKGLNP TAIFLTTLSR TSKKRSWPLN EAIMAVGMVS ILASSLLKND IPMTGPLVAG  1380
GLLTVCYVLT GRSADLELER AADVKWEDQA EISGSSPILS ITISEDGSMS IKNEEEEQTL  1440
TILIRTGLLV ISGLFPVSIP ITAAAWYLWE VKKQRAGVLW DVPSPPPMGK AELEDGAYRI  1500
KQKGILGYSQ IGAGVYKEGT FHTMWHVTRG AVLMHKGKRI EPSWADVKKD LISYGGGWKL  1560
EGEWKEGEEV QVLALEPGKN PRAVQTKPGL FKTNAGTIGA VSLDFSPGTS GSPIIDKKGK  1620
VVGLYGNGVV TRSGAYVSAI AQTEKSIEDN PEIEDDIFRK RRLTIMDLHP GAGKTKRYLP  1680
AIVREAIKRG LRTLILAPTR VVAAEMEEAL RGLPIRYQTP AIRAVHTGRE IVDLMCHATF  1740
TMRLLSPVRV PNYNLIIMDE AHFTDPASIA ARGYISTRVE MGEAAGIFMT ATPPGSRDPF  1800
PQSNAPIIDE EREIPERSWN SGHEWVTDFK GKTVWFVPSI KAGNDIAACL RKNGKKVIQL  1860
SRKTFDSEYV KTRTNDWDFV VTTDISEMGA NFKAERVIDP RRCMKPVILT DGEERVILAG  1920
PMPVTHSSAA QRRGRIGRNP KNENDQYIYM GEPLENDEDC AHWKEAKMLL DNINTPEGII  1980
PSMFEPEREK VDAIDGEYRL RGEARKTFVD LMRRGDLPVW LAYRVAAEGI NYADRRWCFD  2040
GVKNNQILEE NVEVEIWTKE GERKKLKPRW LDARIYSDPL ALKEFKEFAA GRKSLTLNLI  2100
TEMGRLPTFM TQKARDALDN LAVLHTAEAG GRAYNHALSE LPETLETLLL LTLLATVTGG  2160
IFLFLMSARG IGKMTLGMCC IITASILLWY AQIQPHWIAA SIILEFFLIV LLIPEPEKQR  2220
TPQDNQLTYV VIAILTVVAA TMANEMGFLE KTKKDLGLGS IATQQPESNI LDIDLRPASA  2280
WTLYAVATTF VTPMLRHSIE NSSVNVSLTA IANQATVLMG LGKGWPLSKM DIGVPLLAIG  2340
CYSQVNPITL TAALFLLVAH YAIIGPGLQA KATREAQKRA AAGIMKNPTV DGITVIDLDP  2400
IPYDPKFEKQ LGQVMLLVLC VTQVLMMRTT WALCEALTLA TGPISTLWEG NPGRFWNTTI  2460
AVSMANIFRG SYLAGAGLLF SIMKNTTNTR RGTGNIGETL GEKWKSRLNA LGKSEFQIYK  2520
KSGIQEVDRT LAKEGIKRGE TDHHAVSRGS AKLRWFVERN MVTPEGKVVD LGCGRGGWSY  2580
YCGGLKNVRE VKGLTKGGPG HEEPIPMSTY GWNLVRLQSG VDVFFIPPEK CDTLLCDIGE  2640
SSPNPTVEAG RTLRVLNLVE NWLNNNTQFC IKVLNPYMPS VIEKMEALQR KYGGALVRNP  2700
```

-continued

```
LSRNSTHEMY WVSNASGNIV SSVNMISRML INRFTMRYKK ATYEPDVDLG SGTRNIGIES  2760
EIPNLDIIGK RIEKIKQEHE TSWHYDQDHP YKTWAYHGSY ETKQTGSASS MVNGVVRLLT  2820
KPWDVVPMVT QMAMTDTTPF GQQRVFKEKV DTRTQEPKEG TKKLMKITAE WLWKELGKKK  2880
TPRMCTREEF TRKVRSNAAL GAVFTDENKW KSAREAVEDS RFWELVDKER NLHLEGKCET  2940
CVYNMMGKRE KKLGEFGKAK GSRAIWYMWL GARFLEFEAL GFLNEDHWFS RENSLSGVEG  3000
EGLHKLGYIL RDVSKKEGGA MYADDTAGWD TRITLEDLKN EEMVTNHMEG EHKKLAEAIF  3060
KLTYQNKVVR VQRPTPRGTV MDIISRRDQR GSGQVGTYGL NTFTNMEAQL IRQMEGEGVF  3120
KSIQHLTITE EIAVQNWLAR VGRERLSRMA ISGDDCVVKP LDDRFASALT ALNDMGKIRK  3180
DIQQWEPSRG WNDWTQVPFC SHHFHELIMK DGRVLVVPCR NQDELIGRAR ISQGAGWSLR  3240
ETACLGKSYA QMWSLMYFHR RDLRLAANAI CSAVPSHWVP TSRTTWSIHA KHEWMTTEDM  3300
LTVWNRVWIQ ENPWMEDKTP VESWEEIPYL GKREDQWCGS LIGLTSRATW AKNIQAAINQ  3360
VRSLIGNEEY TDYMPSMKRF RREEEEAGVL W                                3391

SEQ ID NO: 5            moltype = DNA  length = 10717
FEATURE                 Location/Qualifiers
source                  1..10717
                        mol_type = other DNA
                        note = chimeric dengue serotype 2/3
                        organism = synthetic construct
SEQUENCE: 5
agttgttagt ctacgtggac cgacaaagac agattctttg agggagctaa gctcaatgta  60
gttctaacag ttttttaatt agagagcaga tctctgatga ataaccaacg gaaaaaggcg  120
aaaaacacgc ctttcaatat gctgaaacgc gagagaaacc gcgtgtcgac tgtgcaacag  180
ctgacaaaga gattctcact tggaatgctg cagggacgag gaccattaaa actgttcatg  240
gccctggtgg cgttccttcg tttcctaaca atcccaccaa cagcagggat attgaagaga  300
tggggaacaa ttaaaaaatc aaaagctatt aatgttttga gagggttcag gaaagagatt  360
ggaaggatgc tgaacatctt gaataggaga cgcagatctg caggcatgat cattatgctg  420
attccaacag tgatggcgtt ccatttaacc acgcgtgatg gagagccgcg catgattgtg  480
gggaagaatg aaagaggaaa atccctactt ttcaagacag cctctggaat caacatgtgc  540
acactcatag ctatggatct gggagagatg tgtgatgaca cggtcactta caaatgcccc  600
cacattaccg aagtggagcc tgaagacatt gactgctggt gcaaccttac atcgacatgg  660
gtgacttatg gaacatgcaa tcaagctgga gagcatagac gcgataagag atcagtggcg  720
ttagctcccc atgttggcat gggactggac acacgcactc aaacctggat gtcggctgaa  780
ggagcttgga gacaagtcga gaaggtagag acatgggccc ttaggcaccc agggtttacc  840
atactagccc tatttcttgc ccattacata ggcacttcct tgacccagaa agtggttatt  900
tttatactat taatgctggt taccccatcc atgacaatga gatgtgtagg agtaggaaac  960
agagattttg tggaaggcct atcgggagct acgtgggttg acgtggtgct cgagcacggt  1020
gggtgtgtga ctaccatggc taagaacaag cccacgctgg acatagagct tcagaagacc  1080
gaggccaccc aactggcgac cctaaggaag ctatgcattg agggaaaaat taccaacata  1140
acaaccgact caagatgtcc cacccaaggg gaagcgattt tacctgagga gcaggaccag  1200
aactacgtgt gtaagcatac atacgtggac agaggctggg gaaacggttg tggtttgttt  1260
ggcaagggaa gcttggtgac atgcgcgaaa tttcaatgtt tagaatcaat agagggaaaa  1320
gtggtgcaac atgagaacct caaatacacc gtcatcatca cagtgcacac aggagaccaa  1380
caccaggtgg gaaatgaaac gcagggagtc acggctgaga taacacccca ggcatcaacc  1440
gctgaagcca ttttacctga atatggaacc ctcgggctag aatgctcacc acggacaggt  1500
ttggatttca atgaaatgat ctcattgaca atgaagaaca aagcatggat ggtacataga  1560
caatggttct ttgacttacc cctaccatgg acatcaggag cttcagcaga aacaccaact  1620
tggaacagga aagagcttct tgtgacattt aaaaatgcac atgcaaaaaa gcaagaagta  1680
gttgttcttg gatcacaaga gggagcaatg catacagcac tgacaggagc tacagagatc  1740
caaacctcag gaggcacaag tatctttgcg gggcacttaa aatgtagact caagatggac  1800
aaattggaac tcaaggggat gagctatgca atgtgcttga gtagctttgt gttgaagaaa  1860
gaagtctccg aaacgcagca tgggacaata ctcattaagg ttgagtacaa aggggaagat  1920
gcaccctgca agattccttt ctccacggag gatggacaag gaaaagctct caatggcaga  1980
ctgatcacag ccaatccagt ggtgaccaag aaggaggagc ctgtcaacat tgaggctgaa  2040
cctccttttg gagaaagtaa catagtaatt ggaattggag acaaagccct gaaaatcaac  2100
tggtacaaga agggaagctc gattgggaag atgttcgagg ccactgccag aggtgcaagg  2160
cgcatggcca tcttgggaga cacagcctgg gactttggat cagtgggtgg tgttttgaat  2220
tcattaggga aaatggtcca ccaaatattt gggagtgctt acacagccct atttggtgga  2280
gtctcctgga tgatgaaaat tggaataggt gtcctcttaa cctggatagg gttgaactca  2340
aaaaatactt ctatgtcatt ttcatgcatc gcggccggca ttgtgacact gtatttggga  2400
gtcatggtgc aggccgatag tggttgcgtt gtgagctgga aaaacaaaga actgaaatgt  2460
ggcagtggga ttttcatcac agacaacgtg cacacatgga cagaacaata caagttccaa  2520
ccagaatccc cttcaaaact agcttcagct atccagaaag cccatgaaga ggacatttgt  2580
ggaatccgct cagtaacaag actggagaat ctgatgtgga aacaaataac accagaattg  2640
aatcacattc tatcagaaaa tgaggtgaag ttaactatta tgacaggaga catcaaagga  2700
atcatgcagg caggaaaacg atctctgcgg cctcagccca ctgagctgaa gtattcatgg  2760
aaaacatggg gcaaagcaaa aatgctctct acagagtctc ataaccagac ctttctcatt  2820
gatggccccg aaacagcaga atgccccaac acaaatagag cttggaattc gttggaagtt  2880
gaagactatg gctttggagt attcaccacc aatatatggc taaaattgaa agaaaaacag  2940
gatgtattct gcgactcaaa actcatgtca gcggccataa aagacaacag agccgtccat  3000
gccgatatgg gttattggat agaaagtgca ctcaatgaca catggaagat agagaaagcc  3060
tctttcattg aagttaaaaa ctgccactgg ccaaaatcac acaccctctg gagcaatgga  3120
gtgctagaaa gtgagatgat aattccaaag aatctcgctg gaccagtgtc tcaacacaac  3180
tatagaccag gctaccatac acaaataaca ggaccatggc atctaggtaa gcttgagatg  3240
gactttgatt tctgtgatgg aacaacagtg gtagtgactg aggactgcgg aaatagagga  3300
ccctctttga gaacaaccac tgcctctgga aaactcataa cagaatggtg ctgccgatct  3360
tgcacattac caccgctaag atacagaggt gaggatgggt gctggtacgg gatggaaatc  3420
agaccattga aggagaaaga agagaatttg gtcaactcct tggtcacagc tggacatggg  3480
caggtcgaca acttttcact aggagtcttg ggaatggcat tgttcctgga ggaaatgctt  3540
```

```
aggacccgag taggaacgaa acatgcaata ctactagttg cagtttcttt tgtgacattg  3600
atcacaggga acatgtcctt tagagacctg ggaagagtga tggttatggt aggcgccact  3660
atgacggatg acataggtat gggcgtgact tatcttgccc tactagcagc cttcaaagtc  3720
agaccaactt ttgcagctgg actactcttg agaaagctga cctccaagga attgatgatg  3780
actactatag gaattgtact cctctcccag agcaccatac cagagaccat tcttgagttg  3840
actgatgcgt tagccttagg catgatggtc ctcaaaatgg tgagaaatat ggaaaagtat  3900
caattggcag tgactatcat ggctatcttg tgcgtcccaa acgcagtgat attacaaaac  3960
gcatggaaag tgagttgcac aatattggca gtggtgtccg tttccccact gttcttaaca  4020
tcctcacagc aaaaaacaga ttggatacca ttagcattga cgatcaaagg tctcaatcca  4080
acagctattt ttctaacaac cctctcaaga accagcaaga aaaggagctg gccattaaat  4140
gaggctatca tggcagtcgg gatggtgagc attttagcca gttctctcct aaaaaatgat  4200
attcccatga caggaccatt agtggctgga gggctcctca ctgtgtgcta cgtgctcact  4260
ggacgatcgg ccgatttgga actggagaga gcagccgatg tcaaatggga agaccaggca  4320
gagatatcag gaagcagtcc aatcctgtca ataacaatat cagaagatgg tagcatgtcg  4380
ataaaaaatg aagaggaaga acaaacactg accatactca ttagaacagg attgctggtg  4440
atctcaggac tttttcctgt atcaatacca atcacggcag cagcatggta cctgtgggaa  4500
gtgaagaaac aacgggccgg agtattgtgg gatgttcctt cacccccacc catgggaaag  4560
gctgaactgg aagatggagc ctatagaatt aagcaaaaag ggattcttgg atattcccag  4620
atcggagccg gagtttacaa agaaggaaca ttccatacaa tgtggcatgt cacacgtggc  4680
gctgttctaa tgcataaagg aaagaggatt gaaccatcat gggcggacgt caagaaagac  4740
ctaatatcat atggaggagg ctggaagtta gaaggagaat ggaaggaagg agaagaagtc  4800
caggtattgg cactggagcc tggaaaaaat ccaagagccg tccaaacgaa acctggtctt  4860
ttcaaaacca acgccggaac aataggtgct gtatctctgg acttttctcc tggaacgtca  4920
ggatctccaa ttatcgacaa aaaaggaaaa gttgtgggtc tttatggtaa tggtgttgtt  4980
acaaggagtg gagcatatgt gagtgctata gcccagactg aaaaaagcat tgaagacaac  5040
ccagagatcg aagatgacat tttccgaaag agaagactga ccatcatgga cctccaccca  5100
ggagcgggaa agacgaagag ataccttccg gccatagtca gagaagctat aaaacggggt  5160
ttgagaacat taatcttggc cccccactaga gttgtggcag ctgaaatgga ggaagccctt  5220
agaggacttc caataagata ccagacccca gccatcagag ctgtgcacac cgggcgggag  5280
attgtggacc taatgtgtca tgccacattt accatgaggc tgctatcacc agttagagtg  5340
ccaaactaca acctgattat catggacgaa gcccatttca cagacccagc aagtatagca  5400
gctagaggat acatctcaac tcgagtggag atgggtgagg cagctgggat ttttatgaca  5460
gccactcccc cgggaagcag agacccattt cctcagagca atgcaccaat catagatgaa  5520
gaaagagaaa tccctgaacg ctcgtggaat tccggacatg aatgggtcac ggattttaaa  5580
gggaagactg tttggttcgt tccaagtata aaagcaggaa atgatatagc agcttgcctg  5640
aggaaaaatg gaaagaaagt gatacaactc agtaggaaga cctttgattc tgagtatgtc  5700
aagactagaa ccaatgattg ggacttcgtg gttacaactg acatttcaga aatgggtgcc  5760
aatttcaagg ctgagagggt tatagacccc agacgctgca tgaaaccagt catactaaca  5820
gatggtgaag agcgggtgat tctggcagga cctatgccag tgacccactc tagtgcagca  5880
caaagaagag ggagaatagg aagaaatcca aaaaatgaga atgaccagta catatacatg  5940
ggggaacctc tggaaaatga tgaagactgt gcacactgga aagaagctaa aatgctccta  6000
gataacatca acacgccaga aggaatcatt cctagcatgt tcgaaccaga gcgtgaaaag  6060
gtggatgcca ttgatggcga ataccgcttg agaggagaag caaggaaaac ctttgtagac  6120
ttaatgagaa gaggagacct accagtctgg ttggcctaca gagtggcagc tgaaggcatc  6180
aactacgcag acagaaggtg gtgttttgat ggagtcaaga acaaccaaat cctagaagaa  6240
aacgtggaag ttgaaatctg gacaaaagaa ggggaaagga agaaattgaa acccagatgg  6300
ttggatgcta ggatctattc tgacccactg gcgctaaaag aatttaagga atttgcagcc  6360
ggaagaaagt ctctgaccct gaacctaatc acagaaatgg gtaggctccc aaccttcatg  6420
actcagaagg caagagacgc actggacaac ttagcagtgc tgcacacggc tgaggcaggt  6480
ggaagggcgt acaaccatgc tctcagtgaa ctgccggaga ccctggagac attgctttta  6540
ctgacacttc tggctacagt cacgggaggg atctttttat tcttgatgag cgcaaggggc  6600
atagggaaga tgaccctggg aatgtgctgc ataatcacgg ctagcatcct cctatggtac  6660
gcacaaatac agccacactg gatagcagct tcaataatac tggagttttt tctcatagtt  6720
ttgcttattc cagaacctga aaaacagaga acaccccaag acaaccaact gacctacgtt  6780
gtcatagcca tcctcacagt ggtggccgca accatggcaa acgagatggg tttcctagaa  6840
aaaacgaaga aagatctcgg attgggaagc attgcaaccc agcaacccga gagcaacatc  6900
ctggacatag atctacgtcc tgcatcagca tggacgctgt atgccgtggc cacaacattt  6960
gttacaccaa tgttgagaca tagcattgaa aattcctcag tgaatgtgtc cctaacagct  7020
atagccaacc aagccacagt gttaatgggt ctcgggaaag gatggccatt gtcaaagatg  7080
gacatcggag ttccccttct cgccattgga tgctactcac aagtcaaccc cataactctc  7140
acagcagctc ttttcttatt ggtagcacat tatgccatca tagggccagg actccaagca  7200
aaagcaacca gagaagctca gaaaagagca gcggcgggca tcatgaaaaa cccaactgtc  7260
gatggaataa cagtgattga cctagatcca ataccttatg atccaaagtt tgaaaagcag  7320
ttgggacaag taatgctcct agtcctctgc gtgactcaag tattgatgat gaggactaca  7380
tgggctctgt gtgaggcttt aaccttagct accgggccca tctccacatt gtgggaagga  7440
aatccaggga ggttttggaa cactaccatt gcggtgtcaa tggctaacat ttttagaggg  7500
agttacttgg ccggagctgg acttctcttt tctattatga agaacacaac caacacaaga  7560
aggggaactg gcaacatagg agagacgctt ggagagaaat ggaaaagccg attgaacgcg  7620
ttgggaaaaa gtgaattcca gatctacaag aaaagtggaa tccaggaagt ggatagaacc  7680
ttagcaaaag aaggcattaa aagaggagaa acggaccatc acgctgtgtc gcgaggctca  7740
gcaaaactga gatggttcgt tgagagaaac atggtcacac cagaagggaa agtagtggac  7800
ctcggttgtg gcagaggagg ctggtcatac tattgtggag gactaaagaa tgtaagagaa  7860
gtcaaaggcc taacaaaagg aggaccagga cacgaagaac ccatccccat gtcaacatat  7920
gggtggaatc tagtgcgtct tcaaagtgga gttgacgttt tcttcatccc gccagaaaag  7980
tgtgacacat tattgtgtga catagggggag tcatcaccaa atcccacagt ggaagcagga  8040
cgaacactca gagtccttaa cttagtagaa aattggttga acaacaacac tcaattttgc  8100
ataaaggttc tcaacccata tatgccctca gtcatagaaa aaatggaagc actacaaagg  8160
aaatatggag gagccttagt gaggaatcca ctctcacgaa actccacaca tgagatgtac  8220
tgggtatcca atgcttccgg gaacatagtg tcatcagtga acatgatttc aaggatgttg  8280
```

```
atcaacagat ttacaatgag atacaagaaa gccacttacg agccggatgt tgacctcgga  8340
agcggaaccc gtaacatcgg gattgaaagt gagataccaa acctagatat aattgggaaa  8400
agaatagaaa aaataaagca agagcatgaa acatcatggc actatgacca agaccaccca  8460
tacaaaacgt gggcatacca tggtagctat gaaacaaaac agactggatc agcatcatcc  8520
atggtcaacg gagtggtcag gctgctgaca aaaccttggg acgtcgtccc catggtgaca  8580
cagatggcaa tgacagacac gactccattt ggacaacagc gcgtttttaa agagaaagtg  8640
gacacgagaa cccaagaacc gaaagaaggc acgaagaaac taatgaaaat aacagcagag  8700
tggctttgga aagaattagg gaagaaaaag acacccagga tgtgcaccag agaagaattc  8760
acaagaaagg tgagaagcaa tgcagccttg ggggccatat tcactgatga gaacaagtgg  8820
aagtcggcac gtgaggctgt tgaagatagt aggttttggg agctggttga caaggaaagg  8880
aatctccatc ttgaaggaaa gtgtgaaaca tgtgtgtaca acatgatggg aaaaagagag  8940
aagaagctag gggaattcgg caaggcaaaa ggcagcagag ccatatggta catgtggctt  9000
ggagcacgct tcttagagtt tgaagcccta ggattcttaa atgaagatca ctggttctcc  9060
agagagaact ccctgagtgg agtggaagga gaagggctgc acaagctagg ttacattcta  9120
agagacgtga gcaagaaaga gggaggagca atgtatgccg atgacaccgc aggatgggat  9180
acaagaatca cactagaaga cctaaaaaat gaagaaatgg taacaaacca catggaagga  9240
gaacacaaga aactagccga ggccatttc aaactaacgt accaaaacaa ggtggtgcgt  9300
gtgcaaagac caacaccaag aggcacagta atggacatca tatcgagaag agaccaaaga  9360
ggtagtggac aagttggcac ctatggactc aatactttca ccaatatgga agcccaacta  9420
atcagacaga tggagggaga aggagtcttt aaaagcattc agcacctaac aatcacagaa  9480
gaaatcgctg tgcaaaactg gttagcaaga gtggggcgcg aaaggttatc aagaatggcc  9540
atcagtggag atgattgtgt tgtgaaacct ttagatgaca ggttcgcaag cgctttaaca  9600
gctctaaatg acatgggaaa gattaggaaa gacatacaac aatgggaacc ttcaagagga  9660
tggaatgatt ggacacaagt gcccttctgt tcacaccatt tccatgagtt aatcatgaaa  9720
gacggtcgcg tactcgttgt tccatgtaga aaccaagatg aactgattgg cagagcccga  9780
atctcccaag gagcagggtg gtctttgcgg gagacggcct gtttggggaa gtcttacgcc  9840
caaatgtgga gcttgatgta cttccacaga cgcgacctca ggctggcggc aaatgctatt  9900
tgctcggcag taccatcaca ttgggttcca acaagtcgaa caacctggtc catacatgct  9960
aaacatgaat ggatgacaac ggaagacatg ctgacagtct ggaacagggt gtggattcaa  10020
gaaaacccat ggatggaaga caaaactcca gtggaatcat gggaggaaat cccatacttg  10080
gggaaaagag aagaccaatg gtgcggctca ttgattgggt taacaagcag ggccacctgg  10140
gcaaagaaca tccaagcagc aataaatcaa gttagatccc ttataggcaa tgaagaatac  10200
acagattaca tgccatccat gaaaagattc agaagagaag aggaagaagc aggagttctg  10260
tggtagaaag caaaactaac atgaaacaag gctagaagtc aggtcggatt aagccatagt  10320
acggaaaaaa ctatgctacc tgtgagcccc gtccaaggac gttaaaagaa gtcaggccat  10380
cataaatgcc atagcttgag taaactatgc agcctgtagc tccacctgag aaggtgtaaa  10440
aaatccggga ggccacaaac catggaagct gtacgcatgg cgtagtggac tagcggttag  10500
aggagacccc tcccttacaa atcgcagcaa caatgggggc ccaaggcgag atgaagctgt  10560
agtctcgctg gaaggactag aggttagagg agaccccccc gaaacaaaaa acagcatatt  10620
gacgctggga aagaccagag atcctgctgt ctcctcagca tcattccagg cacagaacgc  10680
cagaaaatgg aatggtgctg ttgaatcaac aggttct                           10717

SEQ ID NO: 6            moltype = AA  length = 3389
FEATURE                 Location/Qualifiers
source                  1..3389
                        mol_type = protein
                        note = chimeric dengue serotype 2/3
                        organism = synthetic construct
SEQUENCE: 6
MNNQRKKAKN TPFNMLKRER NRVSTVQQLT KRFSLGMLQG RGPLKLFMAL VAFLRFLTIP  60
PTAGILKRWG TIKKSKAINV LRGFRKEIGR MLNILNRRRR SAGMIIMLIP TVMAFHLTTR  120
DGEPRMIVGK NERGKSLLFK TASGINMCTL IAMDLGEMCD DTVTYKCPHI TEVEPEDIDC  180
WCNLTSTWVT YGTCNQAGEH RRDKRSVALA PHVGMGLDTR TQTWMSAEGA WRQVEKVETW  240
ALRHPGFTIL ALFLAHYIGT SLTQKVVIFI LLMLVTPSMT MRCVGVGNRD FVEGLSGATW  300
VDVVLEHGGC VTTMAKNKPT LDIELQKTEA TQLATLRKLC IEGKITNITT DSRCPTQGEA  360
ILPEEQDQNY VCKHTYVDRG WGNGCGLFGK GSLVTCAKFQ CLESIEGKVV QHENLKYTVI  420
ITVHTGDQHQ VGNETQGVTA EITPQASTAE AILPEYGTLG LECSPRTGLD FNEMISLTMK  480
NKAWMVHRQW FFDLPLPWTS GASAETPTWN RKELLVTFKN AHAKKQEVVV LGSQEGAMHT  540
ALTGATEIQT SGGTSIFAGH LKCRLKMDKL ELKGMSYAMC LSSFVLKKEV SETQHGTILI  600
KVEYKGEDAP CKIPFSTEDG QGKALNGRLI TANPVVTKKE EPVNIEAEPP FGESNIVIGI  660
GDKALKINWY KKGSSIGKMF EATARGARRM AILGDTAWDF GSVGGVLNSL GKMVHQIFGS  720
AYTALFGGVS WMMKIGIGVL LTWIGLNSKN TSMSFSCIAA GIVTLYLGVM VQADSGCVVS  780
WKNKELKCGS GIFITDNVHT WTEQYKFQPE SPSKLASAIQ KAHEEDICGI RSVTRLENLM  840
WKQITPELNH ILSENEVKLT IMTGDIKGIM QAGKRSLRPQ PTELKYSWKT WGKAKMLSTE  900
SHNQTFLIDG PETAECPNTN RAWNSLEVED YGFGVFTTNI WLKLKEKQDV FCDSKLMSAA  960
IKDNRAVHAD MGYWIESALN DTWKIEKASF IEVKNCHWPK SHTLWSNGVL ESEMIIPKNL  1020
AGPVSQHNYR PGYHTQITGP WHLGKLEMDF DFCDGTTVVV TEDCGNRGPS LRTTTASGKL  1080
ITEWCCRSCT LPPLRYRGED GCWYGMEIRP LKEKEENLVN SLVTAGHGQV DNFSLGVLGM  1140
ALFLEEMLRT RVGTKHAILL VAVSFVTLIT GNMSFRDLGR VMVMVGATMT DDIGMGVTYL  1200
ALLAAFKVRP TFAAGLLLRK LTSKELMMTT IGIVLLSQST IPETILELTD ALALGMMVLK  1260
MVRNMEKYQL AVTIMAILCV PNAVILQNAW KVSCTILAVV SVSPLFLTSS QQKTDWIPLA  1320
LTIKGLNPTA IFLTTLSRTS KKRSWPLNEA IMAVGMVSIL ASSLLKNDIP MTGPLVAGGL  1380
LTVCYVLTGR SADLELERAA DVKWEDQAEI SGSSPILSIT ISEDGSMSIK NEEEEQTLTI  1440
LIRTGLLVIS GLFPVSIPIT AAAWYLWEVK KQRAGVLWDV PSPPPMGKAE LEDGAYRIKQ  1500
KGILGYSQIG AGVYKEGTFH TMWHVTRGAV LMHKGKRIEP SWADVKKDLI SYGGGWKLEG  1560
EWKEGEEVQV LALEPGKNPR AVQTKPGLFK TNAGTIGAVS LDFSPGTSGS PIIDKKGKVV  1620
GLYGNGVVTR SGAYVSAIAQ TEKSIEDNPE IEDDIFRKRR LTIMDLHPGA GKTKRYLPAI  1680
VREAIKRGLR TLILAPTRVV AAEMEEALRG LPIRYQTPAI RAVHTGREIV DLMCHATFTM  1740
RLLSPVRVPN YNLIIMDEAH FTDPASIAAR GYISTRVEMG EAAGIFMTAT PPGSRDPFPQ  1800
```

-continued

```
SNAPIIDEER EIPERSWNSG HEWVTDFKGK TVWFVPSIKA GNDIAACLRK NGKKVIQLSR  1860
KTFDSEYVKT RTNDWDFVVT TDISEMGANF KAERVIDPRR CMKPVILTDG EERVILAGPM  1920
PVTHSSAAQR RGRIGRNPKN ENDQYIYMGE PLENDEDCAH WKEAKMLLDN INTPEGIIPS  1980
MFEPEREKVD AIDGEYRLRG EARKTFVDLM RRGDLPVWLA YRVAAEGINY ADRRWCFDGV  2040
KNNQILEENV EVEIWTKEGE RKKLKPRWLD ARIYSDPLAL KEFKEFAAGR KSLTLNLITE  2100
MGRLPTFMTQ KARDALDNLA VLHTAEAGGR AYNHALSELP ETLETLLLLT LLATVTGGIF  2160
LFLMSARGIG KMTLGMCCII TASILLWYAQ IQPHWIAASI ILEFFLIVLL IPEPEKQRTP  2220
QDNQLTYVVI AILTVVAATM ANEMGFLEKT KKDLGLGSIA TQQPESNILD IDLRPASAWT  2280
LYAVATTFVT PMLRHSIENS SVNVSLTAIA NQATVLMGLG KGWPLSKMDI GVPLLAIGCY  2340
SQVNPITLTA ALFLLVAHYA IIGPGLQAKA TREAQKRAAA GIMKNPTVDG ITVIDLDPIP  2400
YDPKFEKQLG QVMLLVLCVT QVLMMRTTWA LCEALTLATG PISTLWEGNP GRFWNTTIAV  2460
SMANIFRGSY LAGAGLLFSI MKNTTNTRRG TGNIGETLGE KWKSRLNALG KSEFQIYKKS  2520
GIQEVDRTLA KEGIKRGETD HHAVSRGSAK LRWFVERNMV TPEGKVVDLG CGRGGWSYYC  2580
GGLKNVREVK GLTKGGPGHE EPIPMSTYGW NLVRLQSGVD VFFIPPEKCD TLLCDIGESS  2640
PNPTVEAGRT LRVLNLVENW LNNNTQFCIK VLNPYMPSVI EKMEALQRKY GGALVRNPLS  2700
RNSTHEMYWV SNASGNIVSS VNMISRMLIN RFTMRYKKAT YEPDVDLGSG TRNIGIESEI  2760
PNLDIIGKRI EKIKQEHETS WHYDQDHPYK TWAYHGSYET KQTGSASSMV NGVVRLLTKP  2820
WDVVPMVTQM AMTDTTPFGQ QRVFKEKVDT RTQEPKEGTK KLMKITAEWL WKELGKKKTP  2880
RMCTREEFTR KVRSNAALGA IFTDENKWKS AREAVEDSRF WELVDKERNL HLEGKCETCV  2940
YNMMGKREKK LGEFGKAKGS RAIWYMWLGA RFLEFEALGF LNEDHWFSRE NSLSGVEGEG  3000
LHKLGYILRD VSKKEGGAMY ADDTAGWDTR ITLEDLKNEE MVTNHMEGEH KKLAEAIFKL  3060
TYQNKVVRVQ RPTPRGTVMD IISRRDQRGS GQVGTYGLNT FTNMEAQLIR QMEGEGVFKS  3120
IQHLTITEEI AVQNWLARVG RERLSRMAIS GDDCVVKPLD DRFASALTAL NDMGKIRKDI  3180
QQWEPSRGWN DWTQVPFCSH HFHELIMKDG RVLVVPCRNQ DELIGRARIS QGAGWSLRET  3240
ACLGKSYAQM WSLMYFHRRD LRLAANAICS AVPSHWVPTS RTTWSIHAKH EWMTTEDMLT  3300
VWNRVWIQEN PWMEDKTPVE SWEEIPYLGK REDQWCGSLI GLTSRATWAK NIQAAINQVR  3360
SLIGNEEYTD YMPSMKRFRR EEEEAGVLW                                    3389

SEQ ID NO: 7           moltype = DNA  length = 10723
FEATURE                Location/Qualifiers
source                 1..10723
                       mol_type = other DNA
                       note = chimeric dengue seroytpe 2/4
                       organism = synthetic construct
SEQUENCE: 7
agttgttagt ctacgtggac cgacaaagac agattctttg agggagctaa gctcaatgta  60
gttctaacag ttttttaatt agagagcaga tctctgatga ataaccaacg gaaaaaggcg  120
aaaaacacgc ctttcaatat gctgaaacgc gagagaaacc gcgtgtcgac tgtgcaacag  180
ctgacaaaga gattctcact tggaatgctg cagggacgag gacctttaaa actgttcatg  240
gccctggtgg cgttccttcg tttcctaaca atcccaccaa cagcagggat attgaagaga  300
tggggaacaa ttaaaaaatc aaaagctatt aatgttttga gagggttcag gaaagagatt  360
ggaaggatgc tgaacatctt gaataggaga cgcagctctg caggcatgat cattatgctg  420
attccaacag tgatggcgtt ccatttaacc acgcgtgatg gcgaacccct catgatagtg  480
gcaaaacatg aaagggggag acctctcttg tttaagacaa cagaggggat caacaaatgc  540
actctcattg ccatggactt gggtgaaatg tgtgaggaca ctgtcacgta taaatgcccc  600
ttactggtca ataccgaacc tgaagacatt gattgctggt gcaatctcac gtctacctgg  660
gtcatgtatg ggacatgcac ccagagcgga gaacggagac gagagaagcg ctcagtagct  720
ttaacaccac attcaggaat gggattggaa acaagagctg agacatggat gtcatcggaa  780
ggggcttgga agcatgctca gagagtagag agctggatac tcagaaaccc aggattcgcg  840
ctcttggcag gatttatggc ttatatgatt gggcaaacag gaatccagcg aactgtcttc  900
tttgtcctaa tgatgctggt cgccccatcc tacggaatgc gatgcgtagg agtaggaaac  960
agagactttg tggaaggagt ctcaggtgga gcatgggtcg atctggtgct agaacatgga  1020
ggatgcgtca caaccatggc ccagggaaaa ccaaccttgg attttgaact gactaagaca  1080
acagccaagg aagtggctct gttaagaacc tattgcattg aagcctcaat atcaaacata  1140
accacggcaa caagatgtcc aacgcaagga gagccttatc taaaagagga acaagaccaa  1200
cagtacattt gccggagaga tgtggtagac agagggtggg gcaatggctg tggcttgttt  1260
ggaaaaggag gagttgtgac atgtgcgaag ttttcatgtt cggggaagat aacaggcaat  1320
ttggtccaaa ttgagaacct tgaatacaca gtggttgtaa cagtccacaa tggagacacc  1380
catgcagtag gaaatgacac gtccaatcat ggagttacag ccacgataac tcccaggtca  1440
ccatcggtgg aagtcaaatt gccggactat ggagaactaa cactcgattg tgaacccagg  1500
tctggaattg actttaatga gatgattctg atgaaaatga aaaagaaaac atggcttgtg  1560
cataagcaat ggtttttgga tctacctcta ccatggacag caggagcaga cacatcagag  1620
gttcactgga attacaaaga gagaatggtg acatttaagg ttcctcatgc caagagacag  1680
gatgtgacag tgctgggatc tcaggaagga gccatgcatt ctgccctcgc tggagccaca  1740
gaagtggact ccggtgatgg aaatcacatg tttgcaggac atctcaagtg caaagtccgt  1800
atggagaaat tgagaatcaa gggaatgtca tacacgatgt gttcaggaaa gttctcaatt  1860
gacaaagaga tggcagaaac acagcatggg acaacagtgg tgaaagtcaa gtatgaaggt  1920
gctggagctc cgtgtaaagt ccccatagag ataagagatg tgaacaagga aaaagtggtt  1980
gggcgtatca tctcatccac ccctttggct gagaatacca acagtgtaac caacatagag  2040
ttagaacccc cctttgggga cagctacata gtgataggtg ttggaaacag tgcattaaca  2100
ctccattggt tcaggaaagg gagttccatt ggcaagatgt ttgagtccac atacagaggt  2160
gcaaaacgaa tggccattct aggtgaaaca gcttgggatt ttggttccgt tggtggactg  2220
ttcacatcat tgggaaaggc tgtgcaccag gtttttggaa gtgtgtatac aaccctgttt  2280
ggaggagtct catggatgat tagaatccta attgggttcc tagtgttgtg gattggcacg  2340
aactcaagga acacttcaat ggctatgacg tgcatagctg ccggcattgt gacactgtat  2400
ttgggagtca tggtgcaggc cgatagtggt tgcgttgtga gctggaaaaa caaagaactg  2460
aaatgtggca gtgggatttt catcacagac aacgtgcaca catggacaga acaatacaag  2520
ttccaaccag aatccccttc aaaactagct tcagctatcc agaaagccca tgaagaggac  2580
atttgtggaa tccgctcagt aacaagactg gagaatctga tgtggaaaca aataacacca  2640
```

```
gaattgaatc acattctatc agaaaatgag gtgaagttaa ctattatgac aggagacatc  2700
aaaggaatca tgcaggcagg aaaacgatct ctgcggcctc agcccactga gctgaagtat  2760
tcatggaaaa catggggcaa agcaaaaatg ctctctacag agtctcataa ccagaccttt  2820
ctcattgatg gccccgaaac agcagaatgc cccaacacaa atagagcttg gaattcgttg  2880
gaagttgaag actatggctt tggagtattc accaccaata tatggctaaa attgaaagaa  2940
aaacaggatg tattctgcga ctcaaaactc atgtcagcgg ccataaaaga caacagagcc  3000
gtccatgccg atatgggtta ttggatagaa agtgcactca atgacacatg gaagatagag  3060
aaagcctctt tcattgaagt taaaaactgc cactggccaa aatcacacac cctctggagc  3120
aatggagtgc tagaaagtga gatgataatt ccaaagaatc tcgctggacc agtgtctcaa  3180
cacaactata gaccaggcta ccatacacaa ataacaggac catggcatct aggtaagctt  3240
gagatggact ttgatttctg tgatggaaca acagtggtag tgactgagga ctgcggaaat  3300
agaggaccct ctttgagaac aaccactgcc tctggaaaac tcataacaga atggtgctgc  3360
cgatcttgca cattaccacc gctaagatac agaggtgagg atgggtgctg gtacgggatg  3420
gaaatcagac cattgaagga gaaagaagag aatttggtca actccttggt cacagctgga  3480
catgggcagg tcgacaactt ttcactagga gtcttgggaa tggcattgtt cctggaggaa  3540
atgcttagga cccgagtagg aacgaaacat gcaatactac tagttgcagt ttcttttgtg  3600
acattgatca cagggaacat gtcctttaga gacctgggaa gagtgatggt tatggtaggc  3660
gccactatga cgggtgacat aggtatgggc gtgacttatc ttgccctact agcagccttc  3720
aaagtcagac caacttttgc agctggacta ctcttgagaa agctgacctc carggaattg  3780
atgatgacta ctataggaat tgtactcctc tcccagagca ccataccaga gaccattctt  3840
gagttgactg atgcgttagc cttaggcatg atggtcctca aaatggtgag aaatatggaa  3900
aagtatcaat tggcagtgac tatcatggct atcttgtgcg tcccaaacgc agtgatatta  3960
caaaacgcat ggaaagtgag ttgcacaata ttggcagtgg tgtccgtttc cccactgttc  4020
ttaacatcct cacagcaaaa aacagattgg ataccattag cattgacgat caaaggtctc  4080
aatccaacag ctatttttct aacaaccctc tcaagaacca gcaagaaaag gagctggcca  4140
ttaaatgagg ctatcatggc agtcgggatg gtgagcattt tagccagttc tctcctaaaa  4200
aatgatattc ccatgacagg accattagtg gctggagggc tcctcactgt gtgctacgtg  4260
ctcactggac gatcggccga tttggaactg gagagagcag ccgatgtcaa atgggaagac  4320
caggcagaga tatcaggaag cagtccaatc ctgtcaataa caatatcaga agatggtagc  4380
atgtcgataa aaaatgaaga ggaagaacaa acactgacca tactcattag aacaggattg  4440
ctggtgatct caggactttt tcctgtatca ataccaatca cggcagcagc atggtacctg  4500
tgggaagtga agaaacaacg ggccggagta ttgtgggatg ttccttcacc cccacccatg  4560
ggaaaggctg aactggaaga tggagcctat agaattaagc aaaaagggat tcttggatat  4620
tcccagatcg gagccggagt ttacaaagaa ggaacattcc atacaatgtg gcatgtcaca  4680
cgtggcgctg ttctaatgca taaaggaaag aggattgaac catcatgggc ggacgtcaag  4740
aaagacctaa tatcatatgg aggaggctgg aagttagaag gagaatggaa ggaaggagaa  4800
gaagtccagg tattggcact ggagcctgga aaaaatccaa gagccgtcca aacgaaacct  4860
ggtcttttca aaaccaacgc cggaacaata ggtgctgtat ctctggactt ttctcctgga  4920
acgtcaggat ctccaattat cgacaaaaaa ggaaaagttg tgggtcttta tggtaatggt  4980
gttgttacaa ggagtggagc atatgtgagt gctatagccc agactgaaaa aagcattgaa  5040
gacaacccag agatcgaaga tgacattttc cgaaagagaa gactgaccat catggacctc  5100
cacccaggag cgggaaagac gaagagatac cttccggcca tagtcagaga agctataaaa  5160
cggggtttga gaacattaat cttggccccc actagagttg tggcagctga aatggaggaa  5220
gcccttagag gacttccaat aagataccag accccagcca tcagagctgt gcacaccggg  5280
cgggagattg tggacctaat gtgtcatgcc acatttacca tgaggctgct atcaccagtt  5340
agagtgccaa actacaacct gattatcatg gacgaagccc atttcacaga tccagcaagt  5400
atagcagcta gaggatacat ctcaactcga gtggagatgg gtgaggcagc tgggattttt  5460
atgacagcca ctcccccggg aagcagagac ccatttcctc agagcaatgc accaatcata  5520
gatgaagaaa gagaaatccc tgaacgctcg tggaattccg gacatgaatg ggtcacggat  5580
tttaaaggga agactgtttg gttcgttcca agtataaaag caggaaatga tatagcagct  5640
tgcctgagga aaaatggaaa gaaagtgata caactcagta ggaagacctt tgattctgag  5700
tatgtcaaga ctagaaccaa tgattgggac ttcgtggtta caactgacat ttcagaaatg  5760
ggtgccaatt tcaaggctga gagggttata gaccccagac gctgcatgaa accagtcata  5820
ctaacagatg gtgaagagcg ggtgattctg gcaggaccta tgccagtgac ccactctagt  5880
gcagcacaaa gaagagggag aataggaaga aatccaaaaa atgagaatga ccagtacata  5940
tacatggggg aacctctgga aaatgatgaa gactgtgcac actggaaaga agctaaaatg  6000
ctcctagata acatcaacac gccagaagga atcattccta gcatgttcga accagagcgt  6060
gaaaaggtgg atgccattga tggcgaatac cgcttgagag gagaagcaag gaaaaccttt  6120
gtagacttaa tgagaagagg agacctacca gtctggttgg cctacagagt ggcagctgaa  6180
ggcatcaact acgcagacag aaggtggtgt tttgatggag tcaagaacaa ccaaatccta  6240
gaagaaaacg tggaagttga aatctggaca aaagaagggg aaaggaagaa attgaaaccc  6300
agatggttgg atgctaggat ctattctgac ccactggcgc taaaagaatt taaggaattt  6360
gcagccggaa gaaagtctct gaccctgaac ctaatcacag aaatgggtag gctcccaacc  6420
ttcatgactc agaaggtaag agacgcactg gacaacttag cagtgctgca cacggctgag  6480
gcaggtggaa gggcgtacaa ccatgctctc agtgaactgc cggagaccct ggagacattg  6540
cttttactga cacttctggc tacagtcacg ggagggatct tttattcttt gatgagcgca  6600
aggggcatag ggaagatgac cctgggaatg tgctgcataa tcacggctag catcctccta  6660
tggtacgcac aaatacagcc acactggata gcagcttcaa taatactgga gtttttttctc  6720
atagttttgc ttattccaga acctgaaaaa cagagaacac cccaagacaa ccaactgacc  6780
tacgttgtca tagccatcct cacagtggtg gccgcaacca tggcaaacga gatgggtttc  6840
ctagaaaaaa cgaagaaaga tctcggattg ggaagcattg caacccagca acccgagagc  6900
aacatcctgg acatagatct acgtcctgca tcagcatgga cgctgtatgc cgtggccaca  6960
acatttgtta caccaatgtt gagacatagc attgaaaatt cctcagtgaa tgtgtcccta  7020
acagccatag ccaaccaagc cacagtgtta atgggtctcg ggaaaggatg gccattgtca  7080
aagatggaca tcggagttcc ccttctcgcc attggatgct actcacaagt caaccccata  7140
actctcacag cagctctttt cttattggta gcacattatg ccatcatagg gccaggactc  7200
caagcaaaag caaccagaga agctcagaaa agagcagcgg cgggcatcat gaaaaaccca  7260
actgtcgatg gaataacagt gattgaccta gatccaatac cttatgatcc aaagtttgaa  7320
aagcagttgg gacaagtaat gctcctagtc ctctgcgtga ctcaagtatt gatgatgagg  7380
```

```
actacatggg ctctgtgtga ggctttaacc ttagctaccg ggcccatctc cacattgtgg  7440
gaaggaaatc cagggaggtt ttggaacact accattgcgg tgtcaatggc taacattttt  7500
agagggagtt acttggccgg agctggactt ctcttttcta ttatgaagaa cacaaccaac  7560
acaagaaggg gaactggcaa cataggagag acgcttggag agaaatggaa aagccgattg  7620
aacgcattgg gaaaaagtga attccagatc tacaagaaaa gtggaatcca ggaagtggat  7680
agaaccttag caaaagaagg cattaaaaga ggagaaacgg accatcacgc tgtgtcgcga  7740
ggctcagcaa aactgagatg gttcgttgag agaaacatgg tcacaccaga agggaaagta  7800
gtggacctcg gttgtggcag aggaggctgg tcatactatt gtggaggact aaagaatgta  7860
agagaagtca aaggcctaac aaaaggagga ccaggacacg aagaacccat ccccatgtca  7920
acatatgggt ggaatctagt gcgtcttcaa agtggagttg acgttttctt catcccgcca  7980
gaaaagtgtg acacattatt gtgtgacata ggggagtcat caccaaatcc cacagtggaa  8040
gcaggacgaa cactcagagt ccttaactta gtagaaaatt ggttgaacaa caacactcaa  8100
ttttgcataa aggttctcaa cccatatatg ccctcagtca tagaaaaaat ggaagcacta  8160
caaaggaaat atggaggagc cttagtgagg aatccactct cacgaaactc cacacatgag  8220
atgtactggg tatccaatgc ttccgggaac atagtgtcat cagtgaacat gatttcaagg  8280
atgttgatca acagatttac aatgagatac aagaaagcca cttacgagcc ggatgttgac  8340
ctcggaagcg gaacccgtaa catcgggatt gaaagtgaga taccaaacct agatataatt  8400
gggaaaagaa tagaaaaaat aaagcaagag catgaaacat catggcacta tgaccaagac  8460
cacccataca aaacgtgggc ataccatggt agctatgaaa caaaacagac tggatcagca  8520
tcatccatgg tcaacggagt ggtcaggctg ctgacaaaac cttgggacgt cgtccccatg  8580
gtgacacaga tggcaatgac agacacgact ccatttggac aacagcgcgt ttttaaagag  8640
aaagtggaca cgagaaccca agaaccgaaa gaaggcacga agaaactaat gaaaataaca  8700
gcagagtggc tttggaaaga attagggaag aaaaagacac ccaggatgtg caccagagaa  8760
gaattcacaa gaaaggtgag aagcaatgca gccttggggg ccatattcac tgatgagaac  8820
aagtggaagt cggcacgtga ggctgttgaa gatagtaggt tttgggagct ggttgacaag  8880
gaaaggaatc tccatcttga aggaaagtgt gaaacatgtg tgtacaacat gatgggaaaa  8940
agagagaaga agctagggga attcggcaag gcaaaaggca gcagagccat atggtacatg  9000
tggcttggag cacgcttctt agagtttgaa gccctaggat tcttaaatga agatcactgg  9060
ttctccagag agaactccct gagtggagtg gaaggagaag ggctgcacaa gctaggttac  9120
attctaagag acgtgagcaa gaaagaggga ggagcaatgt atgccgatga caccgcagga  9180
tgggatacaa gaatcacact agaagaccta aaaaatgaag aaatggtaac aaaccacatg  9240
gaaggagaac acaagaaact agccgaggcc attttcaaac taacgtacca aaacaaggtg  9300
gtgcgtgtgc aaagaccaac accaagaggc acagtaatgg acatcatatc gagaagagac  9360
caaagaggta gtggacaagt tggcacctat ggactcaata ctttcaccaa tatggaagcc  9420
caactaatca gacagatgga gggagaagga gtctttaaaa gcattcagca cctaacaatc  9480
acagaagaaa tcgctgtgca aaactggtta gcaagagtgg ggcgcgaaag gttatcaaga  9540
atggccatca gtggagatga ttgtgttgtg aaacctttag atgacaggtt cgcaagcgct  9600
ttaacagctc taaatgacat gggaaagatt aggaaagaca tacaacaatg ggaaccttca  9660
agaggatgga atgattggac acaagtgccc ttctgttcac accatttcca tgagttaatc  9720
atgaaagacg gtcgcgtact cgttgttccc tgtagaaacc aagatgaact gattggcaga  9780
gcccgaatct cccaaggagc agggtggtct ttgcgggaga cggcctgttt ggggaagtct  9840
tacgcccaaa tgtggagctt gatgtacttc cacagacgcg acctcaggct ggcggcaaat  9900
gctatttgct cggcagtacc atcacattgg gttccaacaa gtcgaacaac ctggtccata  9960
catgctaaac atgaatggat gacaacggaa gacatgctga cagtctggaa cagggtgtgg  10020
attcaagaaa acccatggat ggaagacaaa actccagtgg aatcatggga ggaaatccca  10080
tacttgggga aaagagaaga ccaatggtgc ggctcattga ttgggttaac aagcagggcc  10140
acctgggcaa agaacatcca agcagcaata aatcaagtta gatcccttat aggcaatgaa  10200
gaatacacag attacatgcc atccatgaaa agattcagaa gagaagagga agaagcagga  10260
gttctgtggt agaaagcaaa actaacatga aacaaggcta gaagtcaggt cggattaagc  10320
catagtacgg aaaaaactat gctacctgtg agccccgtcc aaggacgtta aaagaagtca  10380
ggccatcata aatgccatag cttgagtaaa ctatgcagcc tgtagctcca cctgagaagg  10440
tgtaaaaaat ccgggaggcc acaaaccatg gaagctgtac gcatggcgta gtggactagc  10500
ggttagagga gacccctccc ttacaaatcg cagcaacaat gggggcccaa ggcgagatga  10560
agctgtagtc tcgctggaag gactagaggt tagaggagac ccccccgaaa caaaaaacag  10620
catattgacg ctgggaaaga ccagagatcc tgctgtctcc tcagcatcat tccaggcaca  10680
gaacgccaga aaatggaatg gtgctgttga atcaacaggt tct                   10723
```

```
SEQ ID NO: 8           moltype = AA  length = 3391
FEATURE                Location/Qualifiers
VARIANT                1226
                       note = X - R or K
source                 1..3391
                       mol_type = protein
                       note = chimeric dengue seroytpe 2/4
                       organism = synthetic construct
SEQUENCE: 8
MNNQRKKAKN TPFNMLKRER NRVSTVQQLT KRFSLGMLQG RGPLKLFMAL VAFLRFLTIP  60
PTAGILKRWG TIKKSKAINV LRGFRKEIGR MLNILNRRRS SAGMIIMLIP TVMAFHLTTR  120
DGEPLMIVAK HERGRPLLFK TTEGINKCTL IAMDLGEMCE DTVTYKCPLL VNTEPEDIDC  180
WCNLTSTWVM YGTCTQSGER RREKRSVALT PHSGMGLETR AETWMSSEGA WKHAQRVESW  240
ILRNPGFALL AGFMAYMIGQ TGIQRTVFFV LMMLVAPSYG MRCVGVGNRD FVEGVSGGAW  300
VDLVLEHGGC VTTMAQGKPT LDFELTKTTA KEVALLRTYC IEASISNITT ATRCPTQGEP  360
YLKEEQDQQY ICRRDVVDRG WGNGCGLFGK GGVVTCAKFS CSGKITGNLV QIENLEYTVV  420
VTVHNGDTHA VGNDTSNHGV TATITPRSPS VEVKLPDYGE LTLDCEPRSG IDFNEMILMK  480
MKKKTWLVHK QWFLDLPLPW TAGADTSEVH WNYKERMVTF KVPHAKRQDV TVLGSQEGAM  540
HSALAGATEV DSGDGNHMFA GHLKCKVRME KLRIKGMSYT MCSGKFSIDK EMAETQHGTT  600
VVKVKYEGAG APCKVPIEIR DVNKEKVVGR IISSTPLAEN TNSVTNIELE PPFGDSYIVI  660
GVGNSALTLH WFRKGSSIGK MFESTYRGAK RMAILGETAW DFGSVGGLFT SLGKAVHQVF  720
GSVYTTLFGG VSWMIRILIG FLVLWIGTNS RNTSMAMTCI AAGIVTLYLG VMVQADSGCV  780
```

```
VSWKNKELKC GSGIFITDNV HTWTEQYKFQ PESPSKLASA IQKAHEEDIC GIRSVTRLEN  840
LMWKQITPEL NHILSENEVK LTIMTGDIKG IMQAGKRSLR PQPTELKYSW KTWGKAKMLS  900
TESHNQTFLI DGPETAECPN TNRAWNSLEV EDYGFGVFTT NIWLKLKEKQ DVFCDSKLMS  960
AAIKDNRAVH ADMGYWIESA LNDTWKIEKA SFIEVKNCHW PKSHTLWSNG VLESEMIIPK  1020
NLAGPVSQHN YRPGYHTQIT GPWHLGKLEM DFDFCDGTTV VVTEDCGNRG PSLRTTTASG  1080
KLITEWCCRS CTLPPLRYRG EDGCWYGMEI RPLKEKEENL VNSLVTAGHG QVDNFSLGVL  1140
GMALFLEEML RTRVGTKHAI LLVAVSFVTL ITGNMSFRDL GRVMVMVGAT MTGDIGMGVT  1200
YLALLAAFKV RPTFAAGLLL RKLTSXELMM TTIGIVLLSQ STIPETILEL TDALALGMMV  1260
LKMVRNMEKY QLAVTIMAIL CVPNAVILQN AWKVSCTILA VVSVSPLFLT SSQQKTDWIP  1320
LALTIKGLNP TAIFLTTLSR TSKKRSWPLN EAIMAVGMVS ILASSLLKND IPMTGPLVAG  1380
GLLTVCYVLT GRSADLELER AADVKWEDQA EISGSSPILS ITISEDGSMS IKNEEEEQTL  1440
TILIRTGLLV ISGLFPVSIP ITAAAWYLWE VKKQRAGVLW DVPSPPPMGK AELEDGAYRI  1500
KQKGILGYSQ IGAGVYKEGT FHTMWHVTRG AVLMHKGKRI EPSWADVKKD LISYGGGWKL  1560
EGEWKEGEEV QVLALEPGKN PRAVQTKPGL FKTNAGTIGA VSLDFSPGTS GSPIIDKKGK  1620
VVGLYGNGVV TRSGAYVSAI AQTEKSIEDN PEIEDDIFRK RRLTIMDLHP GAGKTKRYLP  1680
AIVREAIKRG LRTLILAPTR VVAAEMEEAL RGLPIRYQTP AIRAVHTGRE IVDLMCHATF  1740
TMRLLSPVRV PNYNLIIMDE AHFTDPASIA ARGYISTRVE MGEAAGIFMT ATPPGSRDPF  1800
PQSNAPIIDE EREIPERSWN SGHEWVTDFK GKTVWFVPSI KAGNDIAACL RKNGKKVIQL  1860
SRKTFDSEYV KTRTNDWDFV VTTDISEMGA NFKAERVIDP RRCMKPVILT DGEERVILAG  1920
PMPVTHSSAA QRRGRIGRNP KNENDQYIYM GEPLENDEDC AHWKEAKMLL DNINTPEGII  1980
PSMFEPEREK VDAIDGEYRL RGEARKTFVD LMRRGDLPVW LAYRVAAEGI NYADRRWCFD  2040
GVKNNQILEE NVEVEIWTKE GERKKLKPRW LDARIYSDPL ALKEFKEFAA GRKSLTLNLI  2100
TEMGRLPTFM TQKVRDALDN LAVLHTAEAG GRAYNHALSE LPETLETLLL LTLLATVTGG  2160
IFLFLMSARG IGKMTLGMCC IITASILLWY AQIQPHWIAA SIILEFFLIV LLIPEPEKQR  2220
TPQDNQLTYV VIAILTVVAA TMANEMGFLE KTKKDLGLGS IATQQPESNI LDIDLRPASA  2280
WTLYAVATTF VTPMLRHSIE NSSVNVSLTA IANQATVLMG LGKGWPLSKM DIGVPLLAIG  2340
CYSQVNPITL TAALFLLVAH YAIIGPGLQA KATREAQKRA AAGIMKNPTV DGITVIDLDP  2400
IPYDPKFEKQ LGQVMLLVLC VTQVLMMRTT WALCEALTLA TGPISTLWEG NPGRFWNTTI  2460
AVSMANIFRG SYLAGAGLLF SIMKNTTNTR RGTGNIGETL GEKWKSRLNA LGKSEFQIYK  2520
KSGIQEVDRT LAKEGIKRGE TDHHAVSRGS AKLRWFVERN MVTPEGKVVD LGCGRGGWSY  2580
YCGGLKNVRE VKGLTKGGPG HEEPIPMSTY GWNLVRLQSG VDVFFIPPEK CDTLLCDIGE  2640
SSPNPTVEAG RTLRVLNLVE NWLNNNTQFC IKVLNPYMPS VIEKMEALQR KYGGALVRNP  2700
LSRNSTHEMY WVSNASGNIV SSVNMISRML INRFTMRYKK ATYEPDVDLG SGTRNIGIES  2760
EIPNLDIIGK RIEKIKQEHE TSWHYDQDHP YKTWAYHGSY ETKQTGSASS MVNGVVRLLT  2820
KPWDVVPMVT QMAMTDTTPF GQQRVFKEKV DTRTQEPKEG TKKLMKITAE WLWKELGKKK  2880
TPRMCTREEF TRKVRSNAAL GAIFTDENKW KSAREAVEDS RFWELVDKER NLHLEGKCET  2940
CVYNMMGKRE KKLGEFGKAK GSRAIWYMWL GARFLEFEAL GFLNEDHWFS RENSLSGVEG  3000
EGLHKLGYIL RDVSKKEGGA MYADDTAGWD TRITLEDLKN EEMVTNHMEG EHKKLAEAIF  3060
KLTYQNKVVR VQRPTPRGTV MDIISRRDQR GSGQVGTYGL NTFTNMEAQL IRQMEGEGVF  3120
KSIQHLTITE EIAVQNWLAR VGRERLSRMA ISGDDCVVKP LDDRFASALT ALNDMGKIRK  3180
DIQQWEPSRG WNDWTQVPFC SHHFHELIMK DGRVLVVPCR NQDELIGRAR ISQGAGWSLR  3240
ETACLGKSYA QMWSLMYFHR RDLRLAANAI CSAVPSHWVP TSRTTWSIHA KHEWMTTEDM  3300
LTVWNRVWIQ ENPWMEDKTP VESWEEIPYL GKREDQWCGS LIGLTSRATW AKNIQAAINQ  3360
VRSLIGNEEY TDYMPSMKRF RREEEEAGVL W                                3391

SEQ ID NO: 9            moltype = DNA  length = 10735
FEATURE                 Location/Qualifiers
source                  1..10735
                        mol_type = other DNA
                        note = dengue virus
                        organism = synthetic construct
SEQUENCE: 9
agttgttagt ctacgtggac cgacaagaac agtttcgaat cggaagcttg cttaacgtag  60
ttctaacagt tttttattag agagcagatc tctgatgatc aaccaacgaa aaaagacggg  120
tcgaccgtct ttcaatatgc tgaaacgcgc gagaaaccgc gtgtcaactg tttcacagtt  180
ggcgaagaga ttctcaaaag gattgctctc aggccaagga cccatgaaat tggtgatggc  240
tttcatagca ttcttaagat ttctagccat acccccaaca gcaggaattt tggctagatg  300
gggctcattc aagaagaatg gagcgattaa agtgttacgg ggtttcaaga gagaaatctc  360
aaacatgcta aacataatga acaggaggaa aagatccgtg accatgctcc ttatgctgct  420
gcccacagcc ctggcgttcc atctgacgac acgaggggga gagccgcata tgatagttag  480
caagcaggaa agaggaaagt cacttttgtt caagacctct gcaggtgtca acatgtgcac  540
cctcattgcg atggatttgg gagagttgtg tgaggacacg atgacctaca aatgcccccg  600
gatcactgag gcggaaccag atgacgttga ctgttggtgc aatgccacgg acacatgggt  660
gacctatgga acgtgctctc aaactggcga acaccgacga gacaaacgtt ccgtcgcatt  720
ggccccacac gtggggcttg gcctagaaac aagagccgaa acgtggatgt cctctgaagg  780
tgcttggaaa cagatacaaa aagtagagac ttgggctctg agacatccag gattcacggt  840
gatagccctt tttctagcac atgccatagg aacatccatc acccagaaag ggatcatttt  900
cattttgctg atgctggtaa caccatctat ggccatgcga tgcgtgggaa taggcaacag  960
agacttcgtg gaaggactgt caggagcaac atgggtggat gtggtactgg agcatggaag  1020
ttgcgtcacc accatggcaa aaaacaaacc aacactggac attgaactct tgaagacgga  1080
ggtcacaaac cctgcagttc tgcgtaaatt gtgcattgaa gctaaaatat caaacaccac  1140
caccgattcg agatgtccaa cacaaggaga agccacactg gtggaagaac aagacgcgaa  1200
ctttgtgtgc cgacgaacgt tcgtggacag aggctggggc aatggctgtg ggctattcgg  1260
aaaaggtagt ctaataacgt gtgccaagtt taagtgtgtg acaaaactag aaggaaagat  1320
agttcaatat gaaaacctaa aatattcagt gatagtcacc gtccacactg gagatcagca  1380
ccaggtggga aatgagacta cagaacatgg aacaactgca accataacac ctcaagctcc  1440
tacgtcggaa atacagctga ccgactacgg aacccttaca ttagattgtt cacctaggac  1500
agggctagat tttaacgaga tggtgttgct gacaatgaaa gaaagatcat ggcttgtcca  1560
caaacaatgg tttctagact taccactgcc ttggacctct ggggcttcaa catcccaaga  1620
```

```
gacttggaac agacaagatt tactggtcac atttaagaca gctcatgcaa agaagcagga  1680
agtagtcgta ctaggatcac aagaaggagc aatgcacact gcgctgactg gagcgacaga  1740
aatccaaacg tcaggaacga caacaatttt cgcaggacac ctaaaatgca gactaaaaat  1800
ggacaaacta actttaaaag ggatgtcata tgtgatgtgc acaggctcat tcaagttaga  1860
gaaagaagtg gctgagaccc agcatggaac tgttctggtg caggttaaat atgaaggaac  1920
agacgcacca tgcaagattc ccttttcgac ccaagatgag aaaggagcaa cccagaatgg  1980
gagattaata acagccaacc ccatagtcac tgacaaagaa aaaccagtca atattgaggc  2040
agaaccaccc tttggtgaga gctacatcgt ggtaggagca ggtgaaaaag ctttgaaact  2100
aagctggttc aagaaaggaa gcagcatagg gaaaatgttt gaagcaactg cccgaggagc  2160
acgaaggatg gccattctgg gagacaccgc atgggacttc ggttctatag gaggagtgtt  2220
cacgtctatg ggaaaactgg tacaccaggt ttttggaact gcatatggag ttttgtttag  2280
cggagtttct tggaccatga aaataggaat agggattctg ctgacatggc taggattaaa  2340
ttcaaggaac acgtcccttt cgatgatgtg catcgcagtt ggcatggtca cactgtacct  2400
aggagtcatg gttcaggcag attcgggatg tgtaatcaac tggaaaggca gagaacttaa  2460
atgtggaagc ggcatttttg tcactaatga agttcacact tggacagagc aatacaaatt  2520
ccaggctgac tcccccaaga gactatcagc agccattggg aaggcatggg aggagggtgt  2580
gtgtggaatc cgatcagcca ctcgtctcga gaacatcatg tggaaacaaa tatcaaatga  2640
attgaaccac atcctacttg aaaatgacat gaaatttaca gtggtcgtgg gagatgttag  2700
tggaatcttg gcccaaggga aaaaaatgat taggccacaa cccatggaac acaaatactc  2760
gtggaaaagc tggggaaaag ccaaaatcat aggagcggat gtacagaaca ccaccttcat  2820
catcgacggc ccaaacaccc cagaatgccc tgacaatcaa agagcatgga atatttggga  2880
agtagaggac tatggatttg ggattttcac gacaaacata tggttgaaat tgcgtgactc  2940
ctacacccaa gtatgtgacc accggctgat gtcagctgcc attaaggaca gcaaggcagt  3000
ccatgctgac atggggtact ggatagaaag tgaaaagaac gagacatgga agttggcgag  3060
agcctccttt atagaagtta agacatgcat ctggccaaaa tcccacactc tatggagcaa  3120
tggagttctg gaaagtgaaa tgataattcc aaagatatat ggaggaccaa tatctcagca  3180
caactacaga ccaggatatt tcacacaaac agcagggccg tggcacctag gcaagttgga  3240
actagatttc gatttttgtg aaggtaccac agttgttgtg gatgaacatt gtggaaatcg  3300
aggaccatct ctcagaacca caacagtcac aggaaagata atccatgaat ggtgctgcag  3360
atcttgtacg ctacccccc tacgtttcaa aggggaagac gggtgttggt acggcatgga  3420
aatcagacca gtgaaggaca aggaagagaa cctggtcaag tcaatggtct ctgcagggtc  3480
aggagaagtg gacagctttt cactaggact gctatgcata tcaataatga ttgaagaagt  3540
gatgagatcc agatggagca aaaaaatgct gatgactgga acactggctg tgttcctcct  3600
tcttataatg ggacaattga catggagtga tctgatcagg ttatgtatta tggttggagc  3660
caacgcttca gacaagatgg ggatgggaac aacgtaccta gctttaatgg ccactttcaa  3720
aatgagacca atgttcgccg tcgggctatt atttcgcaga ctaacatcta gagaagttct  3780
tcttcttaca attggcttga gcctggtggc atccgtggag ctaccaagtt ccctagagga  3840
gctgggggat ggacttgcaa taggcatcat gatgttgaaa ttattgactg attttcagtc  3900
acaccagcta tgggctactc tgctatcctt gacatttatt aaaacaactt tttcattgca  3960
ctatgcatgg aagacaatgg ctatggtact gtcaattgta tctctcttcc ctttatgcct  4020
gtccacgacc tctcaaaaaa caacatggct tccggtgctg ttgggatctc ttggatgcaa  4080
accactaccc atgtttctta taacagaaaa caaaatctgg ggaaggaaga gttggcccct  4140
caatgaagga attatggctg ttggaatagt tagtattcta ctaagttcac ttttaaaaaa  4200
tgatgtgccg ctagccggcc cattaatagc tggaggcatg ctaatagcat gttatgtcat  4260
atccggaagc tcagctgatt tatcactgga gaaagcggct gaggtctcct gggaggaaga  4320
agcagaacac tcaggcgcct cacacaacat actagtagag gttcaagatg atggaaccat  4380
gaagataaaa gatgaagaga gagatgacac gctcaccatt ctccttaaag caactctgct  4440
ggcagtctca ggggtgtacc caatgtcaat accagcgacc ctttttgtgt ggtatttttg  4500
gcagaaaaag aaacagagat caggagtgct atgggacaca cccagccccc cagaagtgga  4560
aagagcagtt cttgatgatg gcatctatag aattttgcaa agaggactgt tgggcaggtc  4620
ccaagtagga gtaggagttt tccaagaagg cgtgttccac acaatgtggc acgtcactag  4680
gggagctgtc ctcatgtatc aaggaaaaag gctggaacca agctgggcca gtgtcaaaaa  4740
agacttgatc tcatatggag gaggttggag gtttcaagga tcctggaaca cgggagaaga  4800
agtacaggtg attgctgttg aaccgggaaa aaaccccaaa aatgtacaaa caacgccggg  4860
taccttcaag acccctgaag gcgaagttgg agccatagcc ttagacttta aacctggcac  4920
atctggatct cccatcgtaa acagagaggg aaaaatagta ggtctttatg gaaatggagt  4980
ggtgacaaca agcggaactt acgttagtgc catagctcaa gctaaggcat cacaagaagg  5040
gcctctacca gagattgagg acgaggtgtt taggaaaaga aacttaacaa taatggacct  5100
acatccagga tcgggaaaaa caagaagata ccttccagcc atagtccgtg aggccataaa  5160
aaggaagctg cgcacgctaa tcctagctcc cacaagagtt gtcgcttctg aaatggcaga  5220
ggcactcaag ggagtgccaa taaggtatca gacaacagca gtgaagagtg aacacacagg  5280
aaaggagata gttgacctta tgtgccacgc cactttcacc atgcgcctcc tgtctcccgt  5340
gagagttccc aattataaca tgattatcat ggatgaagca cacttcaccg atccagccag  5400
catagcagcc agagggtaca tctcaacccg agtgggtatg ggtgaagcag ctgcgatctt  5460
tatgacagcc actcccccag gatcggtgga ggcctttcca cagagcaatg caattatcca  5520
agatgaggaa agagacattc ctgagagatc atggaactca ggctatgact ggatcactga  5580
ttttccaggt aaaacagtct ggtttgttcc aagcatcaaa tcaggaaatg acattgccaa  5640
ctgtttaaga aaaaacggga aacgggtgat ccaattgagc agaaaaacct ttgacactga  5700
gtaccagaaa acaaaaaaca acgactggga ctatgtcgtc acaacagaca tttccgaaat  5760
gggagcaaat ttccgggccg acagggtaat agacccaagg cggtgtctga aaccggtaat  5820
actaaaagat ggtccagagc gcgtcattct agccggaccg atgccagtga ctgtggccag  5880
tgccgcccag aggagaggaa gaattggaag gaaccaaaac aaggaaggtg atcagtatat  5940
ttacatggga cagcctttaa acaatgatga ggaccacgct cattggacag aagcaaagat  6000
gctccttgac aatataaaca caccagaagg gattatccca gccctctatg agccggagag  6060
agaaaagagt gcagctatag acggggaata cagactgcgg ggtgaagcaa ggaaaacgtt  6120
cgtggagctc atgagaagag gggatctacc agtctggcta tcctacaaag ttgcctcaga  6180
aggcttccag tactccgaca gaaggtggtg cttcgatggg gaaaggaaca accaggtgtt  6240
ggaggagaac atggacgtgg agatctggac aaaagaagga gaaagaaaga aactacgacc  6300
tcgctggttg gacgccagaa catactctga cccactggct ctgcgcgagt ttaaagagtt  6360
```

```
tgcagcagga agaagaagcg tctcaggtga cctaatatta gaaataggga aacttccaca  6420
acatttgacg caaagggccc agaatgcttt ggacaacttg gtcatgttgc acaattccga  6480
acaaggagga aaagcctata gacatgctat ggaagaactg ccagacacaa tagaaacgtt  6540
gatgctccta gccttgatag ctgtgttgac tggtggagtg acgctgttct tcctatcagg  6600
aagaggtcta ggaaaaacat ctatcggctt actctgcgtg atggcctcaa gcgcactgtt  6660
atggatggcc agtgtggagc cccattggat agcggcctcc atcatactgg agttctttct  6720
gatggtactg cttattccag agccagacag acagcgcact ccacaggaca accagctagc  6780
atatgtggtg ataggtctgt tattcatgat attgacagtg gcagccaatg agatgggatt  6840
attggaaacc acaaagaaag acctggggat tggccatgta gctgctgaaa accaccacca  6900
tgctacaatg ctggacgtag acctacatcc agcttcagcc tggaccctct atgcagtggc  6960
cacaacaatc atcactccta tgatgagaca cacaattgaa aacacaacgg caaatatttc  7020
cctgacagcc atcgcaaacc aagcagctat attgatggga cttgacaagg gatggccaat  7080
atcgaagatg gacataggag ttccacttct cgccttgggg tgctattccc aagtgaatcc  7140
gctgacactg atagcggcag tattgatgct agtagctcat tacgccataa ttggacctgg  7200
actgcaagca aaagctacta gagaagctca aaaaagaaca gcggctggaa taatgaaaaa  7260
tccaactgtc gacgggattg ttgcaataga cttagatccc gtggtttacg atgcaaaatt  7320
tgaaaaacaa ctaggccaaa taatgttgtt gatactttgc acatcacaga ttcttttgat  7380
gcggactaca tgggccttgt gtgaatccat cacattggct actggacctc tgaccactct  7440
ttgggaggga tctccaggaa aattctggaa caccacaata gcggtatcca tggcaaacat  7500
tttcaggggg agttatctag caggagcagg tctggccttc tcattaatga aatctctagg  7560
aggaggtagg agaggcacgg gagcccaagg ggaaacactg ggagaaaaat ggaaaagaca  7620
actaaaccaa ctgagcaagt cagaattcaa tacttacaag aggagtggga ttatggaggt  7680
ggatagatcc gaagccaaag agggactgaa aagaggagaa acaaccaaac acgcagtatc  7740
gagaggaacg gccaaactga ggtggttcgt ggagaggaac cttgtgaaac cagaagggaa  7800
agtcatagac ctcggttgtg gaagaggtgg ctggtcatat tattgcgctg ggctgaagaa  7860
agtcacagaa gtgaaaggat acacaaaagg aggacctgga catgaggaac caatcccaat  7920
ggcgacctat ggatggaacc tagtaaagct gcactccgga aaagatgtat tttttatacc  7980
acctgagaaa tgtgacaccc ttttgtgtga tattggtgag tcctctccga acccaactat  8040
agaggaagga agaacgttac gtgttctgaa aatggtggaa ccatggctca gaggaaacca  8100
attttgcata aaaattctaa atccctatat gccgagcgtg gtagaaactc tggaacaaat  8160
gcaaagaaaa catggaggaa tgctagtgcg aaacccactc tcaagaaatt ccacccatga  8220
aatgtactgg gtttcatgtg gaacaggaaa cattgtgtca gcagtaaaca tgacatctag  8280
aatgttgcta aatcggttca caatggctca caggaagcca acatatgaaa gagacgtgga  8340
cttaggcgct ggaacaagac atgtggcagt agaaccagag gtagccaacc tagatatcat  8400
tggccagagg atagagaata taaaaaatga acataagtca acatggcatt atgatgagga  8460
caatccatac aaaacatggg cctatcatgg atcatatgag gttaagccat caggatcggc  8520
ctcatccatg gtcaatggcg tggtgagatt gctcaccaaa ccatgggatg ttatccccat  8580
ggtcacacaa atagccatga ctgataccac accctttgga caacagaggg tgtttaaaga  8640
gaaagttgac acgcgcacac caaaagcaaa acgtggcaca gcacaaatta tggaagtgac  8700
agccaggtgg ttatggggtt tcctttctag aaacaaaaaa cccagaattt gcacaagaga  8760
ggagtttaca agaaaagtta ggtcaaacgc agctattgga gcagtgttcg ttgatgaaaa  8820
tcaatggaac tcggcaaaag aagcagtgga agacgaacgg ttctgggaac ttgtccacag  8880
agagagggag cttcataaac aggggaaatg tgccacgtgt gtctacaata tgatggggaa  8940
gagagagaaa aaattaggag agttcggaaa ggcaaaagga agtcgtgcaa tatggtacat  9000
gtggttggga gcacgcttcc tagagtttga agcccttggt ttcatgaatg aagatcactg  9060
gttcagtaga gagaattcac tcagtggagt ggaaggagaa ggactccaca aacttggata  9120
catactcaga gacatatcaa ggattccagg ggggaacatg tatgcagatg acacagccgg  9180
atgggacaca agaataacag aggatgatct ccagaatgag gctaaaatca ctgacatcat  9240
ggagcccgaa catgccctgc tggctacgtc aatctttaag ctgacctacc aaaataaggt  9300
ggtaagggtg cagagaccag caaaaaatgg aaccgtgatg gatgttatat ccagacgtga  9360
ccagagaggc agtggacagg ttggaactta tggcttaaac actttcacca acatggaggc  9420
ccaactgata agacaaatgg agtccgaggg aatcttttta cccagcgaat tggaaacccc  9480
aaatctagcc ggaagagttc tcgactggtt ggaaaaatat ggtgtcgaaa ggctgaaaag  9540
aatggcaatc agcggagatg actgtgtggt gaaaccaatt gatgacaggt tcgcaacagc  9600
cttaacagct ttgaatgaca tgggaaaagt aagaaaagac ataccacaat gggaaccttc  9660
aaaaggatgg aatgattggc aacaagtgcc tttctgttca caccacttcc accagctaat  9720
tatgaaggat gggagggaga tagtggtgcc atgccgcaac caagatgaac ttgtggggag  9780
ggccagagta tcacaaggcg ccggatggag cctgagagaa accgcatgcc taggcaagtc  9840
atatgcacaa atgtggcagc tgatgtattt ccacaggaga gacctgagac tggcggctaa  9900
cgctatttgt tcagccgttc cagttgattg ggtcccaacc agccgcacca cctggtcgat  9960
ccatgcccat caccaatgga tgacaacaga agacatgtta tcagtatgga atagggtctg  10020
gatagaggaa aacccatgga tggaggataa gactcatgtg tccagttggg aagaagttcc  10080
atacctagga aagagggaag atcagtggtg tggatccctg ataggcttaa cagcaagggc  10140
cacctgggcc actaatatac aagtggccat aaaccaagtg agaaggctca ttgggaatga  10200
gaattatcta gattacatga catcaatgaa gagattcaag aatgagagtg atcccgaagg  10260
ggcactctgg taagtcaaca cattcacaaa ataaaggaaa ataaaaaatc aaatgaggca  10320
agaagtcagg ccagattaag ccatagtacg gtaagagcta tgctgcctgt gagccccgtc  10380
caaggacgta aaatgaagtc aggccgaaag ccacggtttg agcaagccgt gctgcctgtg  10440
gctccatcgt ggggatgtaa aaacccggga ggctgcaacc catggaagct gtacgcatgg  10500
ggtagcagac tagtggttag aggagacccc tcccaagaca caacgcagca gcggggccca  10560
acaccagggg aagctgtacc ctggtggtaa ggactagagg ttagaggaga ccccccgcgt  10620
aacaataaac agcatattga cgctgggaga gaccagagat cctgctgtct ctacagcatc  10680
attccaggca cagaacgcca gaaaatggaa tggtgctgtt gaatcaacag gttct       10735
```

```
SEQ ID NO: 10           moltype = AA  length = 3392
FEATURE                 Location/Qualifiers
source                  1..3392
                        mol_type = protein
                        organism = Dengue virus
```

```
SEQUENCE: 10
MINQRKKTGR PSFNMLKRAR NRVSTVSQLA KRFSKGLLSG QGPMKLVMAF IAFLRFLAIP  60
PTAGILARWG SFKKNGAIKV LRGFKREISN MLNIMNRRKR SVTMLLMLLP TALAFHLTTR  120
GGEPHMIVSK QERGKSLLFK TSAGVNMCTL IAMDLGELCE DTMTYKCPRI TEAEPDDVDC  180
WCNATDTWVT YGTCSQTGEH RRDKRSVALA PHVGLGLETR AETWMSSEGA WKQIQKVETW  240
ALRHPGFTVI ALFLAHAIGT SITQKGIIFI LLMLVTPSMA MRCVGIGNRD FVEGLSGATW  300
VDVVLEHGSC VTTMAKNKPT LDIELLKTEV TNPAVLRKLC IEAKISNTTT DSRCPTQGEA  360
TLVEEQDANF VCRRTFVDRG WGNGCGLFGK GSLITCAKFK CVTKLEGKIV QYENLKYSVI  420
VTVHTGDQHQ VGNETTEHGT TATITPQAPT SEIQLTDYGT LTLDCSPRTG LDFNEMVLLT  480
MKERSWLVHK QWFLDLPLPW TSGASTSQET WNRQDLLVTF KTAHAKKQEV VVLGSQEGAM  540
HTALTGATEI QTSGTTTIFA GHLKCRLKMD KLTLKGMSYV MCTGSFKLEK EVAETQHGTV  600
LVQVKYEGTD APCKIPFSTQ DEKGATQNGR LITANPIVTD KEKPVNIEAE PPFGESYIVV  660
GAGEKALKLS WFKKGSSIGK MFEATARGAR RMAILGDTAW DFGSIGGVFT SMGKLVHQVF  720
GTAYGVLFSG VSWTMKIGIG ILLTWLGLNS RNTSLSMMCI AVGMVTLYLG VMVQADSGCV  780
INWKGRELKC GSGIFVTNEV HTWTEQYKFQ ADSPKRLSAA IGKAWEEGVC GIRSATRLEN  840
IMWKQISNEL NHILLENDMK FTVVVGDVSG ILAQGKKMIR PQPMEHKYSW KSWGKAKIIG  900
ADVQNTTFII DGPNTPECPD NQRAWNIWEV EDYGFGIFTT NIWLKLRDSY TQVCDHRLMS  960
AAIKDSKAVH ADMGYWIESE KNETWKLARA SFIEVKTCIW PKSHTLWSNG VLESEMIIPK  1020
IYGGPISQHN YRPGYFTQTA GPWHLGKLEL DFDFCEGTTV VVDEHCGNRG PSLRTTTVTG  1080
KIIHEWCCRS CTLPPLRFKG EDGCWYGMEI RPVKDKEENL VKSMVSAGSG EVDSFSLGLL  1140
CISIMIEEVM RSRWSKKMLM TGTLAVFLLL IMGQLTWSDL IRLCIMVGAN ASDKMGMGTT  1200
YLALMATFKM RPMFAVGLLF RRLTSREVLL LTIGLSLVAS VELPSSLEEL GDGLAIGIMM  1260
LKLLTDFQSH QLWATLLSLT FIKTTFSLHY AWKTMAMVLS IVSLFPLCLS TTSQKTTWLP  1320
VLLGSLGCKP LPMFLITENK IWGRKSWPLN EGIMAVGIVS ILLSSLLKND VPLAGPLIAG  1380
GMLIACYVIS GSSADLSLEK AAEVSWEEEA EHSGASHNIL VEVQDDGTMK IKDEERDDTL  1440
TILLKATLLA VSGVYPMSIP ATLFVWYFWQ KKKQRSGVLW DTPSPPEVER AVLDDGIYRI  1500
LQRGLLGRSQ VGVGVFQEGV FHTMWHVTRG AVLMYQGKRL EPSWASVKKD LISYGGGWRF  1560
QGSWNTGEEV QVIAVEPGKN PKNVQTTPGT FKTPEGEVGA IALDFKPGTS GSPIVNREGK  1620
IVGLYGNGVV TTSGTYVSAI AQAKASQEGP LPEIEDEVFR KRNLTIMDLH PGSGKTRRYL  1680
PAIVREAIKR KLRTLILAPT RVVASEMAEA LKGVPIRYQT TAVKSEHTGK EIVDLMCHAT  1740
FTMRLLSPVR VPNYNMIIMD EAHFTDPASI AARGYISTRV GMGEAAAIFM TATPPGSVEA  1800
FPQSNAIIQD EERDIPERSW NSGYDWITDF PGKTVWFVPS IKSGNDIANC LRKNGKRVIQ  1860
LSRKTFDTEY QKTKNNDWDY VVTTDISEMG ANFRADRVID PRRCLKPVIL KDGPERVILA  1920
GPMPVTVASA AQRRGRIGRN QNKEGDQYIY MGQPLNNDED HAHWTEAKML LDNINTPEGI  1980
IPALYEPERE KSAAIDGEYR LRGEARKTFV ELMRRGDLPV WLSYKVASEG FQYSDRRWCF  2040
DGERNNQVLE ENMDVEIWTK EGERKKLRPR WLDARTYSDP LALREFKEFA AGRRSVSGDL  2100
ILEIGKLPQH LTQRAQNALD NLVMLHNSEQ GGKAYRHAME ELPDTIETLM LLALIAVLTG  2160
GVTLFFLSGR GLGKTSIGLL CVMASSALLW MASVEPHWIA ASIILEFFLM VLLIPEPDRQ  2220
RTPQDNQLAY VVIGLLFMIL TVAANEMGLL ETTKKDLGIG HVAAENHHHA TMLDVDLHPA  2280
SAWTLYAVAT TIITPMMRHT IENTTANISL TAIANQAAIL MGLDKGWPIS KMDIGVPLLA  2340
LGCYSQVNPL TLIAAVLMLV AHYAIIGPGL QAKATREAQK RTAAGIMKNP TVDGIVAIDL  2400
DPVVYDAKFE KQLGQIMLLI LCTSQILLMR TTWALCESIT LATGPLTTLW EGSPGKFWNT  2460
TIAVSMANIF RGSYLAGAGL AFSLMKSLGG GRRGTGAQGE TLGEKWKRQL NQLSKSEFNT  2520
YKRSGIMEVD RSEAKEGLKR GETTKHAVSR GTAKLRWFVE RNLVKPEGKV IDLGCGRGGW  2580
SYYCAGLKKV TEVKGYTKGG PGHEEPIPMA TYGWNLVKLH SGKDVFFIPP EKCDTLLCDI  2640
GESSPNPTIE EGRTLRVLKM VEPWLRGNQF CIKILNPYMP SVVETLEQMQ RKHGGMLVRN  2700
PLSRNSTHEM YWVSCGTGNI VSAVNMTSRM LLNRFTMAHR KPTYERDVDL GAGTRHVAVE  2760
PEVANLDIIG QRIENIKNEH KSTWHYDEDN PYKTWAYHGS YEVKPSGSAS SMVNGVVRLL  2820
TKPWDVIPMV TQIAMTDTTP FGQQRVFKEK VDTRTPKAKR GTAQIMEVTA RWLWGFLSRN  2880
KKPRICTREE FTRKVRSNAA IGAVFVDENQ WNSAKEAVED ERFWELVHRE RELHKQGKCA  2940
TCVYNMMGKR EKKLGEFGKA KGSRAIWYMW LGARFLEFEA LGFMNEDHWF SRENSLSGVE  3000
GEGLHKLGYI LRDISRIPGG NMYADDTAGW DTRITEDDLQ NEAKITDIME PEHALLATSI  3060
FKLTYQNKVV RVQRPAKNGT VMDVISRRDQ RGSGQVGTYG LNTFTNMEAQ LIRQMESEGI  3120
FLPSELETPN LAGRVLDWLE KYGVERLKRM AISGDDCVVK PIDDRFATAL TALNDMGKVR  3180
KDIPQWEPSK GWNDWQQVPF CSHHFHQLIM KDGREIVVPC RNQDELVGRA RVSQGAGWSL  3240
RETACLGKSY AQMWQLMYFH RRDLRLAANA ICSAVPVDWV PTSRTTWSIH AHHQWMTTED  3300
MLSVWNRVWI EENPWMEDKT HVSSWEEVPY LGKREDQWCG SLIGLTARAT WATNIQVAIN  3360
QVRRLIGNEN YLDYMTSMKR FKNESDPEGA LW                               3392

SEQ ID NO: 11          moltype = DNA  length = 10723
FEATURE                Location/Qualifiers
source                 1..10723
                       mol_type = other DNA
                       note = dengue virus
                       organism = synthetic construct
SEQUENCE: 11
agttgttagt ctacgtggac cgacaaagac agattctttg agggagctaa gctcaacgta  60
gttctaacag ttttttaatt agagagcaga tctctgatga ataaccaacg gaaaaaggcg  120
aaaaacacgc ctttcaatat gctgaaacgc gagagaaacc gcgtgtcgac tgtgcaacag  180
ctgacaaaga gattctcact tggaatgctg cagggacgag gaccattaaa actgttcatg  240
gccctggtgg cgttccttcg tttcctaaca atcccaccaa cagcagggat attgaagaga  300
tggggaacaa ttaaaaaatc aaaagctatt aatgttttga gagggttcag gaaagagatt  360
ggaaggatgc tgaacatctt gaataggaga cgcagatctg caggcatgat cattatgctg  420
attccaacag tgatggcgtt ccatttaacc acacgtaacg gagaaccaca catgatcgtc  480
agcagacaag agaaagggaa aagtcttctg tttaaaacag aggatggcgt gaacatgtgt  540
accctcatgg ccatggacct tggtgaattg tgtgaagaca caatcacgta caagtgtccc  600
cttctcaggc agaatgagcc agaagacata gactgttggt gcaactctac gtccacgtgg  660
gtaacttatg ggacgtgtac caccatggga gaacatagaa gagaaaaaag atcagtggca  720
ctcgttccac atgtgggaat gggactggag acacgaactg aaacatggat gtcatcagaa  780
```

```
ggggcctgga aacatgtcca gagaattgaa acttggatct tgagacatcc aggcttcacc  840
atgatggcag caatcctggc atacaccata ggaacgacac atttccaaag agccctgatt  900
ttcatcttac tgacagctgt cactccttca atgacaatgc gttgcatagg aatgtcaaat  960
agagactttg tggaaggggt ttcaggagga agctgggttg acatagtctt agaacatgga  1020
agctgtgtga cgacgatggc aaaaaacaaa ccaacattgg attttgaact gataaaaaca  1080
gaagccaaac agcctgccac cctaaggaag tactgtatag aggcaaagct aaccaacaca  1140
acaacagaat ctcgctgccc aacacaaggg gaacccagcc taaatgaaga gcaggacaaa  1200
aggttcgtct gcaaacactc catggtagac agaggatggg gaaatggatg tggactattt  1260
ggaaagggag gcattgtgac ctgtgctatg ttcagatgca aaaagaacat ggaaggaaaa  1320
gttgtgcaac cagaaaactt ggaatacacc attgtgataa cacctcactc aggggaagag  1380
catgcagtcg gaaatgacac aggaaaacat ggcaaggaaa tcaaaataac accacagagt  1440
tccatcacag aagcagaatt gacaggttat ggcactgtca caatggagtg ctctccaaga  1500
acgggcctcg acttcaatga gatggtgttg ctgcagatgg aaaataaagc ttggctggtg  1560
cacaggcaat ggttcctaga cctgccgtta ccatggttgc ccggagcgga cacacaaggg  1620
tcaaattgga tacagaaaga gacattggtc actttcaaaa atccccatgc gaagaaacag  1680
gatgttgttg ttttaggatc ccaagaaggg gccatgcaca cagcacttac aggggccaca  1740
gaaatccaaa tgtcatcagg aaacttactc ttcacaggac atctcaagtg caggctgaga  1800
atggacaagc tacagctcaa aggaatgtca tactctatgt gcacaggaaa gtttaaagtt  1860
gtgaaggaaa tagcagaaac acaacatgga acaatagtta tcagagtgca atatgaaggg  1920
gacggctctc catgcaagat cccttttgag ataatggatt tggaaaaaag acatgtctta  1980
ggtcgcctga ttacagtcaa cccaattgtg acagaaaaag atagcccagt caacatagaa  2040
gcagaacctc cattcggaga cagctacatc atcataggag tagagccggg acaactgaag  2100
ctcaactggt ttaagaaagg aagttctatc ggccaaatgt ttgagacaac aatgaggggg  2160
gcgaagagaa tggccatttt aggtgacaca gcctgggatt ttggatcctt gggaggagtg  2220
tttacatcta taggaaaggc tctccaccaa gtctttggag caatctatgg agctgccttc  2280
agtggggttt catggactat gaaaatcctc ataggagtca ttatcacatg gataggaatg  2340
aattcacgca gcacctcact gtctgtgaca ctagtattgg tgggaattgt gacactgtat  2400
ttgggagtca tggtgcaggc cgatagtggt tgcgttgtga gctggaaaaa caaagaactg  2460
aaatgtggca gtgggatttt catcacagac aacgtgcaca catggacaga acaatacaag  2520
ttccaaccag aatccccttc aaaactagct tcagctatcc agaaagccca tgaagagggc  2580
atttgtggaa tccgctcagt aacaagactg gagaatctga tgtggaaaca aataacacca  2640
gaattgaatc acattctatc agaaaatgag gtgaagttaa ctattatgac aggagacatc  2700
aaaggaatca tgcaggcagg aaaacgatct ctgcggcctc agcccactga gctgaagtat  2760
tcatggaaaa catggggcaa agcaaaaatg ctctctacag agtctcataa ccagaccttt  2820
ctcattgatg gccccgaaac agcagaatgc cccaacacaa atagagcttg gaattcgttg  2880
gaagttgaag actatggctt tggagtattc accaccaata tatggctaaa attgaaagaa  2940
aaacaggatg tattctgcga ctcaaaactc atgtcagcgg ccataaaaga caacagagcc  3000
gtccatgccg atatgggtta ttggatagaa agtgcactca atgacacatg gaagatagag  3060
aaagcctctt tcattgaagt taaaaactgc cactggccaa aatcacacac cctctggagc  3120
aatggagtgc tagaaagtga gatgataatt ccaaagaatc tcgctggacc agtgtctcaa  3180
cacaactata gaccaggcta ccatacacaa ataacaggac catggcatct aggtaagctt  3240
gagatggact ttgatttctg tgatggaaca acagtggtag tgactgagga ctgcggaaat  3300
agaggaccct ctttgagaac aaccactgcc tctggaaaac tcataacaga atggtgctgc  3360
cgatcttgca cattaccacc gctaagatac agaggtgagg atgggtgctg gtacgggatg  3420
gaaatcagac cattgaagga gaaagaagag aatttggtca actccttggt cacagctgga  3480
catgggcagg tcgacaactt ttcactagga gtcttgggaa tggcattgtt cctggaggaa  3540
atgcttagga cccgagtagg aacgaaacat gcaatactac tagttgcagt ttcttttgtg  3600
acattgatca cagggaacat gtcctttaga gacctgggaa gagtgatggt tatggtaggc  3660
gccactatga cggatgacat aggtatgggc gtgacttatc ttgccctact agcagccttc  3720
aaagtcagac caacttttgc agctggacta ctcttgagaa agctgacctc caaggaattg  3780
atgatgacta ctataggaat tgtactcctc tcccagagca ccataccaga gaccattctt  3840
gagttgactg atgcgttagc cttaggcatg atggtcctca aaatggtgag aaatatggaa  3900
aagtatcaat tggcagtgac tatcatggct atcttgtgcg tcccaaacgc agtgatatta  3960
caaaacgcat ggaaagtgag ttgcacaata ttggcagtgg tgtccgtttc ccccactgctc  4020
ttaacatcct cacagcaaaa aacagattgg ataccattag cattgacgat caaaggtctc  4080
aatccaacag ctatttttct aacaaccctc tcaagaacca gcaagaaaag gagctggcca  4140
ttaaatgagg ctatcatggc agtcgggatg gtgagcattt tagccagttc tctcctaaaa  4200
aatgatattc ccatgacagg accattagtg gctggagggc tcctcactgt gtgctacgtg  4260
ctcactggac gatcggccga tttggaactg gagagagcag ccgatgtcaa atgggaagac  4320
caggcagaga tatcaggaag cagtccaatc ctgtcaataa caatatcaga agatggtagc  4380
atgtcgataa aaaatgaaga ggaagaacaa acactgacca tactcattag aacaggattg  4440
ctggtgatct caggactttt tcctgtatca ataccaatca cggcagcagc atggtacctg  4500
tgggaagtga agaaacaacg ggccggagta ttgtgggatg ttccttcacc cccacccatg  4560
ggaaaggctg aactggaaga tggagcctat agaattaagc aaaaagggat tcttggatat  4620
tcccagatcg gagccggagt ttacaaagaa ggaacattcc atacaatgtg gcatgtcaca  4680
cgtggcgctg ttctaatgca taaaggaaag aggattgaac catcatgggc ggacgtcaag  4740
aaagacctaa tatcatatgg aggaggctgg aagttagaag gagaatggaa ggaaggagaa  4800
gaagtccagg tattggcact ggagcctgga aaaaatccaa gagccgtcca aacgaaacct  4860
ggtcttttca aaaccaacgc cggaacaata ggtgctgtat ctctggactt ttctcctgga  4920
acgtcaggat ctccaattat cgacaaaaaa ggaaaagttg tgggtcttta tggtaatggt  4980
gttgttacaa ggagtggagc atatgtgagt gctatagccc agactgaaaa aagcattgaa  5040
gacaacccag agatcgaaga tgacattttc cgaaagagaa gactgaccat catggacctc  5100
cacccaggag cgggaaagac gaagagatac cttccggcca tagtcagaga agctataaaa  5160
cggggtttga gaacattaat cttggccccc actagagttg tggcagctga aatggaggaa  5220
gcccttagag gacttccaat aagataccag accccagcca tcagagctga gcacaccggg  5280
cgggagattg tggacctaat gtgtcatgcc acatttacca tgaggctgct atcaccagtt  5340
agagtgccaa actacaacct gattatcatg gacgaagccc atttcacaga cccagcaagt  5400
atagcagcta gaggatacat ctcaactcga gtggagatgg gtgaggcagc tgggattttt  5460
atgacagcca ctcccccggg aagcagagac ccatttcctc agagcaatgc accaatcata  5520
```

```
gatgaagaaa gagaaatccc tgaacgttcg tggaattccg gacatgaatg ggtcacggat  5580
tttaaaggga agactgtttg gttcgttcca agtataaaag caggaaatga tatagcagct  5640
tgcctgagga aaaatggaaa gaaagtgata caactcagta ggaagacctt tgattctgag  5700
tatgtcaaga ctagaaccaa tgattgggac ttcgtggtta caactgacat ttcagaaatg  5760
ggtgccaatt tcaaggctga gagggttata gaccccagac gctgcatgaa accagtcata  5820
ctaacagatg gtgaagagcg ggtgattctg gcaggaccta tgccagtgac ccactctagt  5880
gcagcacaaa gaagagggag aataggaaga aatccaaaaa atgagaatga ccagtacata  5940
tacatggggg aacctctgga aaatgatgaa gactgtgcac actggaaaga agctaaaatg  6000
ctcctagata acatcaacac gccagaagga atcattccta gcatgttcga accagagcgt  6060
gaaaaggtgg atgccattga tggcgaatac cgcttgagag gagaagcaag gaaaaccttt  6120
gtagacttaa tgagaagagg agacctacca gtctggttgg cctacagagt ggcagctgaa  6180
ggcatcaact acgcagacag aaggtggtgt tttgatggag tcaagaacaa ccaaatccta  6240
gaagaaaacg tggaagttga aatctggaca aaagaagggg aaaggaagaa attgaaaccc  6300
agatggttgg atgctaggat ctattctgac ccactggcgc taaaagaatt taaggaattt  6360
gcagccggaa gaaagtctct gaccctgaac ctaatcacag aaatgggtag gctcccaacc  6420
ttcatgactc agaaggcaag agacgcactg gacaacttag cagtgctgca cacggctgag  6480
gcaggtggaa gggcgtacaa ccatgctctc agtgaactgc cggagaccct ggagacattg  6540
cttttactga cacttctggc tacagtcacg ggagggatct tttttattct tgatgagcgga  6600
aggggcatag ggaagatgac cctgggaatg tgctgcataa tcacggctag catcctccta  6660
tggtacgcac aaatacagcc acactggata gcagcttcaa taatactgga gttttttctc  6720
atagttttgc ttattccaga acctgaaaaa cagagaacac cccaagacaa ccaactgacc  6780
tacgttgtca tagccatcct cacagtggtg gccgcaacca tggcaaacga gatgggtttc  6840
ctagaaaaaa cgaagaaaga tctcggattg ggaagcattg caacccagca acccgagagc  6900
aacatcctgg acatagatct acgtcctgca tcagcatgga cgctgtatgc cgtggccaca  6960
acatttgtta caccaatgtt gagacatagc attgaaaatt cctcagtgaa tgtgtcccta  7020
acagctatag ccaaccaagc cacagtgtta atgggtctcg ggaaaggatg gccattgtca  7080
aagatggaca tcggagttcc ccttctcgcc attggatgct actcacaagt caaccccata  7140
actctcacag cagctctttt cttattggta gcacattatg ccatcatagg gccaggactc  7200
caagcaaaag caaccagaga agctcagaaa agagcagcgg cgggcatcat gaaaaaccca  7260
actgtcgatg gaataacagt gattgaccta gatccaatac cttatgatcc aaagtttgaa  7320
aagcagttgg gacaagtaat gctcctagtc ctctgcgtga ctcaagtatt gatgatgagg  7380
actacatggg ctctgtgtga ggctttaacc ttagctaccg ggcccatctc cacattgtgg  7440
gaaggaaatc cagggaggtt ttggaacact accattgcgg tgtcaatggc taacattttt  7500
agagggagtt acttggccgg agctggactt ctcttttcta ttatgaagaa cacaaccaac  7560
acaagaaggg gaactggcaa cataggagag acgcttggag agaaatggaa aagccgattg  7620
aacgcattgg gaaaaagtga attccagatc tacaagaaaa gtggaatcca ggaagtggat  7680
agaaccttag caaaagaagg cattaaaaga ggagaaacgg accatcacgc tgtgtcgcga  7740
ggctcagcaa aactgagatg gttcgttgag agaaacatgg tcacaccaga agggaaagta  7800
gtggacctcg gttgtggcag aggaggctgg tcatactatt gtggaggact aaagaatgta  7860
agagaagtca aaggcctaac aaaaggagga ccaggacacg aagaacccat ccccatgtca  7920
acatatgggt ggaatctagt gcgtcttcaa agtggagttg acgttttctt catcccgcca  7980
gaaaagtgtg acacattatt gtgtgacata ggggagtcat caccaaatcc cacagtggaa  8040
gcaggacgaa cactcagagt ccttaactta gtagaaaatt ggttgaacaa caacactcaa  8100
ttttgcataa aggttctcaa cccatatatg ccctcagtca tagaaaaaat ggaagcacta  8160
caaaggaaat atggaggagc cttagtgagg aatccactct cacgaaactc cacacatgag  8220
atgtactggg tatccaatgc ttccgggaac atagtgtcat cagtgaacat gatttcaagg  8280
atgttgatca acagatttac aatgagatac aagaaagcca cttacgagcc ggatgttgac  8340
ctcggaagcg gaacccgtaa catcgggatt gaaagtgaga taccaaacct agatataatt  8400
gggaaaagaa tagaaaaaat aaagcaagag catgaaacat catggcacta tgaccaagac  8460
cacccataca aaacgtgggc ataccatggt agctatgaaa caaaacagac tggatcagca  8520
tcatccatgg tcaacggagt ggtcaggctg ctgacaaaac cttgggacgt cgtccccatg  8580
gtgacacaga tggcaatgac agacacgact ccatttggac aacagcgcgt tttaaagag  8640
aaagtggaca cgagaaccca agaaccgaaa gaaggcacga agaaactaat gaaaataaca  8700
gcagagtggc tttggaaaga attagggaag aaaaagacac ccaggatgtg caccagagaa  8760
gaattcacaa gaaaggtgag aagcaatgca gccttggggg ccatattcac tgatgagaac  8820
aagtggaagt cggcacgtga ggctgttgaa gatagtaggt tttgggagct ggttgacaag  8880
gaaaggaatc tccatcttga aggaaagtgt gaaacatgtg tgtacaacat gatgggaaaa  8940
agagagaaga agctagggga attcggcaag gcaaaaggca gcagagccat atggtacatg  9000
tggcttggag cacgcttctt agagtttgaa gccctaggat tcttaaatga agatcactgg  9060
ttctccagag agaactccct gagtggagtg gaaggagaag ggctgcacaa gctaggttac  9120
attctaagag acgtgagcaa gaaagaggga ggagcaatgt atgccgatga caccgcagga  9180
tgggatacaa gaatcacact agaagaccta aaaaatgaag aaatggtaac aaaccacatg  9240
gaaggagaac acaagaaact agccgaggcc attttcaaac taacgtacca aaacaaggtg  9300
gtgcgtgtgc aaagaccaac accaagaggc acagtaatgg acatcatatc gagaagagac  9360
caaagaggta gtggacaagt tggcacctat ggactcaata ctttcaccaa tatggaagcc  9420
caactaatca gacagatgga gggagaagga gtctttaaaa gcattcagca cctaacaatc  9480
acagaagaaa tcgctgtgca aaactggtta gcaagagtgg ggcgcgaaag gttatcaaga  9540
atggccatca gtggagatga ttgtgttgtg aaacctttag atgacaggtt cgcaagcgct  9600
ttaacagctc taaatgacat gggaaagatt aggaaagaca tacaacaatg ggaaccttca  9660
agaggatgga atgattggac acaagtgccc ttctgttcac accatttcca tgagttaatc  9720
atgaaagacg gtcgcgtact cgttgttcca tgtagaaacc aagatgaact gattggcaga  9780
gcccgaatct cccaaggagc agggtggtct ttgcgggaga cggcctgttt ggggaagtct  9840
tacgcccaaa tgtggagctt gatgtacttc cacagacgcg acctcaggct ggcggcaaat  9900
gctatttgct cggcagtacc atcacattgg gttccaacaa gtcgaacaac ctggtccata  9960
catgctaaac atgaatggat gacaacggaa gacatgctga cagtctggaa cagggtgtgg  10020
attcaagaaa acccatggat ggaagacaaa actccagtgg aatcatggga ggaaatccca  10080
tacttgggga aaagagaaga ccaatggtgc ggctcattga ttgggttaac aagcagggcc  10140
acctgggcaa agaacatcca agcagcaata aatcaagtta gatcccttat aggcaatgaa  10200
gaatacacag attacatgcc atccatgaaa agattcagaa gagaagagga agaagcagga  10260
```

```
gttctgtggt agaaagcaaa actaacatga aacaaggcta gaagtcaggt cggattaagc  10320
catagtacgg aaaaaactat gctacctgtg agccccgtcc aaggacgtta aaagaagtca  10380
ggccatcata aatgccatag ctggagtaaa ctatgcagcc tgtagctcca cctgagaagg  10440
tgtaaaaaat ccgggaggcc acaaaccatg gaagctgtac gcatggcgta gtggactagc  10500
ggttagagga gacccctccc ttacaaatcg cagcaacaat gggggcccaa ggcgagatga  10560
agctgtagtc tcgctggaag gactagaggt tagaggagac ccccccgaaa caaaaaacag  10620
catattgacg ctgggaaaga ccagagatcc tgctgtctcc tcagcatcat tccaggcaca  10680
gaacgccaga aaatggaatg gtgctgttga atcaacaggt tct                    10723

SEQ ID NO: 12          moltype = AA  length = 3391
FEATURE                Location/Qualifiers
source                 1..3391
                       mol_type = protein
                       organism = Dengue virus
SEQUENCE: 12
MNNQRKKAKN TPFNMLKRER NRVSTVQQLT KRFSLGMLQG RGPLKLFMAL VAFLRFLTIP  60
PTAGILKRWG TIKKSKAINV LRGFRKEIGR MLNILNRRRR SAGMIIMLIP TVMAFHLTTR  120
NGEPHMIVSR QEKGKSLLFK TEDGVNMCTL MAMDLGELCE DTITYKCPLL RQNEPEDIDC  180
WCNSTSTWVT YGTCTTMGEH RREKRSVALV PHVGMGLETR TETWMSSEGA WKHVQRIETW  240
ILRHPGFTMM AAILAYTIGT THFQRALIFI LLTAVTPSMT MRCIGMSNRD FVEGVSGGSW  300
VDIVLEHGSC VTTMAKNKPT LDFELIKTEA KQPATLRKYC IEAKLTNTTT ESRCPTQGEP  360
SLNEEQDKRF VCKHSMVDRG WGNGCGLFGK GGIVTCAMFR CKKNMEGKVV QPENLEYTIV  420
ITPHSGEEHA VGNDTGKHGK EIKITPQSSI TEAELTGYGT VTMECSPRTG LDFNEMVLLQ  480
MENKAWLVHR QWFLDLPLPW LPGADTQGSN WIQKETLVTF KNPHAKKQDV VVLGSQEGAM  540
HTALTGATEI QMSSGNLLFT GHLKCRLRMD KLQLKGMSYS MCTGKFKVVK EIAETQHGTI  600
VIRVQYEGDG SPCKIPFEIM DLEKRHVLGR LITVNPIVTE KDSPVNIEAE PPFGDSYIII  660
GVEPGQLKLN WFKKGSSIGQ MFETTMRGAK RMAILGDTAW DFGSLGGVFT SIGKALHQVF  720
GAIYGAAFSG VSWTMKILIG VIITWIGMNS RSTSLSVTLV LVGIVTLYLG VMVQADSGCV  780
VSWKNKELKC GSGIFITDNV HTWTEQYKFQ PESPSKLASA IQKAHEEGIC GIRSVTRLEN  840
LMWKQITPEL NHILSENEVK LTIMTGDIKG IMQAGKRSLR PQPTELKYSW KTWGKAKMLS  900
TESHNQTFLI DGPETAECPN TNRAWNSLEV EDYGFGVFTT NIWLKLKEKQ DVFCDSKLMS  960
AAIKDNRAVH ADMGYWIESA LNDTWKIEKA SFIEVKNCHW PKSHTLWSNG VLESEMIIPK  1020
NLAGPVSQHN YRPGYHTQIT GPWHLGKLEM DFDFCDGTTV VVTEDCGNRG PSLRTTTASG  1080
KLITEWCCRS CTLPPLRYRG EDGCWYGMEI RPLKEKEENL VNSLVTAGHG QVDNFSLGVL  1140
GMALFLEEML RTRVGTKHAI LLVAVSFVTL ITGNMSFRDL GRVMVMVGAT MTDDIGMGVT  1200
YLALLAAFKV RPTFAAGLLL RKLTSKELMM TTIGIVLLSQ STIPETILEL TDALALGMMV  1260
LKMVRNMEKY QLAVTIMAIL CVPNAVILQN AWKVSCTILA VVSVSPLLLT SSQQKTDWIP  1320
LALTIKGLNP TAIFLTTLSR TSKKRSWPLN EAIMAVGMVS ILASSLLKND IPMTGPLVAG  1380
GLLTVCYVLT GRSADLELER AADVKWEDQA EISGSSPILS ITISEDGSMS IKNEEEEQTL  1440
TILIRTGLLV ISGLFPVSIP ITAAAWYLWE VKKQRAGVLW DVPSPPPMGK AELEDGAYRI  1500
KQKGILGYSQ IGAGVYKEGT FHTMWHVTRG AVLMHKGKRI EPSWADVKKD LISYGGGWKL  1560
EGEWKEGEEV QVLALEPGKN PRAVQTKPGL FKTNAGTIGA VSLDFSPGTS GSPIIDKKGK  1620
VVGLYGNGVV TRSGAYVSAI AQTEKSIEDN PEIEDDIFRK RRLTIMDLHP GAGKTKRYLP  1680
AIVREAIKRG LRTLILAPTR VVAAEMEEAL RGLPIRYQTP AIRAEHTGRE IVDLMCHATF  1740
TMRLLSPVRV PNYNLIIMDE AHFTDPASIA ARGYISTRVE MGEAAGIFMT ATPPGSRDPF  1800
PQSNAPIIDE EREIPERSWN SGHEWVTDFK GKTVWFVPSI KAGNDIAACL RKNGKKVIQL  1860
SRKTFDSEYV KTRTNDWDFV VTTDISEMGA NFKAERVIDP RRCMKPVILT DGEERVILAG  1920
PMPVTHSSAA QRRGRIGRNP KNENDQYIYM GEPLENDEDC AHWKEAKMLL DNINTPEGII  1980
PSMFEPEREK VDAIDGEYRL RGEARKTFVD LMRRGDLPVW LAYRVAAEGI NYADRRWCFD  2040
GVKNNQILEE NVEVEIWTKE GERKKLKPRW LDARIYSDPL ALKEFKEFAA GRKSLTLNLI  2100
TEMGRLPTFM TQKARDALDN LAVLHTAEAG GRAYNHALSE LPETLETLLL LTLLATVTGG  2160
IFLFLMSGRG IGKMTLGMCC IITASILLWY AQIQPHWIAA SIILEFFLIV LLIPEPEKQR  2220
TPQDNQLTYV VIAILTVVAA TMANEMGFLE KTKKDLGLGS IATQQPESNI LDIDLRPASA  2280
WTLYAVATTF VTPMLRHSIE NSSVNVSLTA IANQATVLMG LGKGWPLSKM DIGVPLLAIG  2340
CYSQVNPITL TAALFLLVAH YAIIGPGLQA KATREAQKRA AAGIMKNPTV DGITVIDLDP  2400
IPYDPKFEKQ LGQVMLLVLC VTQVLMMRTT WALCEALTLA TGPISTLWEG NPGRFWNTTI  2460
AVSMANIFRG SYLAGAGLLF SIMKNTTNTR RGTGNIGETL GEKWKSRLNA LGKSEFQIYK  2520
KSGIQEVDRT LAKEGIKRGE TDHHAVSRGS AKLRWFVERN MVTPEGKVVD LGCGRGGWSY  2580
YCGGLKNVRE VKGLTKGGPG HEEPIPMSTY GWNLVRLQSG VDVFFIPPEK CDTLLCDIGE  2640
SSPNPTVEAG RTLRVLNLVE NWLNNNTQFC IKVLNPYMPS VIEKMEALQR KYGGALVRNP  2700
LSRNSTHEMY WVSNASGNIV SSVNMISRML INRFTMRYKK ATYEPDVDLG SGTRNIGIES  2760
EIPNLDIIGK RIEKIKQEHE TSWHYDQDHP YKTWAYHGSY ETKQTGSASS MVNGVVRLLT  2820
KPWDVVPMVT QMAMTDTTPF GQQRVFKEKV DTRTQEPKEG TKKLMKITAE WLWKELGKKK  2880
TPRMCTREEF TRKVRSNAAL GAIFTDENKW KSAREAVEDS RFWELVDKER NLHLEGKCET  2940
CVYNMMGKRE KKLGEFGKAK GSRAIWYMWL GARFLEFEAL GFLNEDHWFS RENSLSGVEG  3000
EGLHKLGYIL RDVSKKEGGA MYADDTAGWD TRITLEDLKN EEMVTNHMEG EHKKLAEAIF  3060
KLTYQNKVVR VQRPTPRGTV MDIISRRDQR GSGQVGTYGL NTFTNMEAQL IRQMEGEGVF  3120
KSIQHLTITE EIAVQNWLAR VGRERLSRMA ISGDDCVVKP LDDRFASALT ALNDMGKIRK  3180
DIQQWEPSRG WNDWTQVPFC SHHFHELIMK DGRVLVVPCR NQDELIGRAR ISQGAGWSLR  3240
ETACLGKSYA QMWSLMYFHR RDLRLAANAI CSAVPSHWVP TSRTTWSIHA KHEWMTTEDM  3300
LTVWNRVWIQ ENPWMEDKTP VESWEEIPYL GKREDQWCGS LIGLTSRATW AKNIQAAINQ  3360
VRSLIGNEEY TDYMPSMKRF RREEEEAGVL W                                 3391

SEQ ID NO: 13          moltype = DNA  length = 10696
FEATURE                Location/Qualifiers
source                 1..10696
                       mol_type = other DNA
                       note = dengue virus
                       organism = synthetic construct
```

SEQUENCE: 13
agttgttagt ctacgtggac cgacaagaac agtttcgact cggaagcttg cttaacgtag 60
tgctgacagt tttttattag agagcagatc tctgatgaac aaccaacgga aaaagacggg 120
aaaaccgtct atcaatatgc tgaaacgcgt gagaaaccgt gtgtcaactg gatcacagtt 180
ggcgaagaga ttctcaagag gattgctgaa cggccaagga ccaatgaaat tggttatggc 240
atttatagct ttcctcagat ttctagccat tccaccgaca gcaggagtct tggctagatg 300
gggtaccttt aagaagtcgg gggctattaa ggtcttaaaa ggcttcaaga aggagatctc 360
aaacatgctg agcattatca acaaacggaa aaagacatcg ctctgtctca tgatgatgtt 420
accagcaaca cttgctttcc acttaacttc acgagatgga gagccgcgca tgattgtggg 480
gaagaatgaa agaggaaaat ccctactttt caagacagcc tctggaatca acatgtgcac 540
actcatagcc atggatctgg gagagatgtg tgatgacacg gtcacttaca aatgccccca 600
cattaccgaa gtggagcctg aagacattga ctgctggtgc aaccttacat cgacatgggt 660
gacttatgga acatgcaatc aagctggaga gcatagacgc gataagagat cagtggcgtt 720
agctccccat gttggcatgg gactggacac acgcactcaa acctggatgt cggctgaagg 780
agcttggaga caagtcgaga aggtagagac atgggccctt aggcacccag ggtttaccat 840
actagcccta tttcttgccc attacatagg cacttccttg acccagaaag tggttatttt 900
tatactatta atgctggtta ccccatccat gacaatgaga tgtgtaggag taggaaacag 960
agattttgtg gaaggcctat cgggagctac gtgggttgac gtggtgctcg agcacggtgg 1020
gtgtgtgact accatggcta agaacaagcc cacgctggac atagagcttc agaagaccga 1080
ggccacccaa ctggcgaccc taaggaagct atgcattgag ggaaaaatta ccaacataac 1140
aaccgactca agatgtccca cccaagggga agcgatttta cctgaggagc aggaccagaa 1200
ctacgtgtgt aagcatacat acgtggacag aggctgggga aacggttgtg gtttgtttgg 1260
caagggaagc ttggtgacat gcgcgaaatt tcaatgttta gaatcaatag agggaaaagt 1320
ggtgcaacat gagaacctca aatacaccgt catcatcaca gtgcacacag gagaccaaca 1380
ccaggtggga aatgaaacgc agggagtcac ggctgagata acaccccagg catcaaccgc 1440
tgaagtcatt ttacctgaat atggaaccct cgggctagaa tgctcaccac ggacaggttt 1500
ggatttcaat gaaatgatct cattgacaat gaagaacaaa gcatggatgg tacatagaca 1560
atggttcttt gacttacccc taccatggac atcaggagct acagcagaaa caccaacttg 1620
gaacaggaaa gagcttcttg tgacatttaa aaatgcacat gcaaaaaagc aagaagtagt 1680
tgttcttgga tcacaagagg gagcaatgca tacagcactg acaggagcta cagagatcca 1740
aacctcagga ggcacaagta tctttgcggg gcacttaaaa tgtagactca agatggacaa 1800
attggaactc aaggggatga gctatgcaat gtgcttgagt agctttgtgt tgaagaaaga 1860
agtctccgaa acgcagcatg ggacaatact cattaaggtt gagtacaaag gggaagatgc 1920
accctgcaag attcctttct ccacggagga tggacaagga aaagctcaca atggcagact 1980
gatcacagcc aatccagtgg tgaccaagaa ggaggagcct gtcaacattg aggctgaacc 2040
tccttttgga gaaagtaaca tagtaattgg aattggagac aaagccctga aaatcaactg 2100
gtacaagaag ggaagctcga ttgggaagat gttcgaggcc actgccagag gtgcaaggcg 2160
catggccatc ttgggagaca cagcctggga ctttggatca gtgggtggtg ttttgaattc 2220
attagggaaa atggtccacc aaatatttgg gagtgcttac acagccctat ttggtggagt 2280
ctcctggatg atgaaaattg gaataggtgt cctcttaacc tggataggt tgaactcaaa 2340
aaatacttct atgtcatttt catgcatcgc gataggaatc attacactct atctgggagc 2400
cgtggtgcaa gctgacatgg ggtgtgtcat aaactggaaa ggcaaagaac tcaaatgtgg 2460
aagtggaatt ttcgtcacta atgaggtcca cacctggaca gagcaataca aatttcaagc 2520
agactccccc aagagactgg caacagccat tgcaggcgct tgggaaaatg gagtgtgcgg 2580
aattaggtca acaaccagaa tggagaacct cttgtggaag caaatagcca atgaactgaa 2640
ttacatatta tgggaaaaca acattaaatt aacggtagtt gtaggcgaca taactggggt 2700
cttagagcaa gggaaaagaa cactaacacc acaacccatg gagctaaaat attcttggaa 2760
aacatgggga aaggcaaaaa tagtgacagc tgaaacacaa aattcctctt tcataataga 2820
tgggccaagc acaccggagt gtccaagtgc ctcaagagca tggaatgtgt gggaggtgga 2880
ggattacggg ttcggagttt tcacaaccaa catatggctg aaactccgag aggtgtacac 2940
ccaactatgt gaccataggc taatgtcggc agccgtcaag gatgagaggg ctgtacatgc 3000
cgacatgggc tattggatag aaagccaaaa gaatgggagt tggaagctag aaaaagcatc 3060
cttcatagag gtgaaaacct gcacatggcc aaaatcacac actctctgga gcaatggtgt 3120
gctagagagt gacatgatta tcccaaagag tctagctggt cccatttcgc aacacaacca 3180
caggcccggg taccacaccc aaacggcagg accctggcac ttaggaaaat tggagctgga 3240
cttcaactat tgtgaaggaa caacagttgt catctcagaa aactgtggga caagaggccc 3300
atcattgaga acaacaacgg tgtcagggaa gttgatacac gaatggtgct gccgctcgtg 3360
cacacttcct cccctacgat acatgggaga agacggctgc tggtatggca tggaaatcag 3420
acccattaat gagaaagaag agaatatggt aaagtctcta gcctcagcag ggagtggaaa 3480
ggtggacaac ttcacaatgg gtgtcttgtg tttggcaatc ctctttgaag aggtgatgag 3540
aggaaaattt gggaaaaaac acatgattgc aggggttctc ttcacgtttg tgctcctcct 3600
ctcagggcaa ataacatgga gagacatggc gcacacactc ataatgattg ggtccaacgc 3660
ctctgacaga atggggatgg gcgtcactta cctagctcta attgcaacat ttaaaattca 3720
gccattcctg gctttgggat tcttcctgag gaaactgaca tctagagaaa atttattgct 3780
gggagttggg ttggccatgg cagcaacgtt acgactgcca gaggacattg aacagatggc 3840
gaatggaatt gctttggggc tcatggctct taaactgata acacaatttg aaacatacca 3900
actatggacg gcattagttt ccctaacgtg ttcaaataca attttcacgt tgactgttgc 3960
ctggagaaca gccactctga ttttagccgg aatttcgctt ttgccagtgt gccagtcttc 4020
gagcatgagg aaaacagatt ggctcccaat gactgtggca gctatgggag ctcaacccct 4080
accacttttt attttcagtc tgaaagatac actcaaaagg agaagctggc cactgaatga 4140
gggggtgatg gcagttggac ttgtgagcat tctagctagt tctctcctta ggaatgatgt 4200
gcctatggct ggaccattag tggctggggg cttgctgata gcgtgctacg tcataactgg 4260
cacgtcagca gacctcactg tagaaaaagc agcagatgta acatgggagg aagaggccga 4320
gcaaacagga gtgtcccaca atttaatggt cacagttgat gatgatggaa caatgagaat 4380
aaaagatgac gagactgaga acatcttaac agtgctttta aaaacagcac tactaatagt 4440
atcaggcatc tttccatact ccatacccgc aacactgttg gtctggcata cttggcaaaa 4500
gcaaacccaa agatccggcg tcctatggga cgtacccagc cccccagaga cacagaaagc 4560
ggaactggaa gaaggggtct ataggatcaa acagcaagga atttttggga aaacccaagt 4620
gggggttgga gtacagaaag aaggagtttt ccacaccatg tggcatgtca caagaggggc 4680

-continued

```
agtgttgaca cacaatggga aaagactgga accaaactgg gctagcgtga aaaaagatct  4740
gatttcatac ggaggaggat ggagattgag tgcacaatgg caaaaggggg aggaggtgca  4800
ggttattgcc gtagagcctg ggaagaaccc aaagaacttt caaaccatgc caggcatttt  4860
tcagacaaca acaggggaaa taggagcaat tgcactggat ttcaagcctg gaacttcagg  4920
atctcccatc ataaacagag agggaaaggt agtgggactg tatggcaatg gagtggttac  4980
aaagaatgga ggctatgtca gtggaatagc gcaaacaaat gcagaaccag atggaccgac  5040
accagagttg gaagaagaga tgttcaaaaa gcgaaatcta accataatgg atctccatcc  5100
tgggtcagga aagacgcgga aatatcttcc agctattgtt agagaggcaa tcaagagacg  5160
cttaaggact ctaattttgg caccaacaag ggtagttgca gctgagatgg aagaagcatt  5220
gaaagggctc ccaataaggt atcaaacaac tgcaacaaaa tctgaacaca caggaagaga  5280
gattgttgat ctaatgtgtc acgcaacgtt cacaatgcgc ttgctgtcac cagtcagggt  5340
tccaaactac aacttgataa taatggatga ggcccatttc acagacccag ccagtatagc  5400
ggctagaggg tacatatcaa ctcgtgtagg aatgggagag gcagccgcaa ttttcatgac  5460
agcaacaccc cctggaacag ctgatgcctt tcctcagagc aacgctccaa ttcaagatga  5520
agagagagac ataccggaac gctcatggaa ttcaggcaat gaatggatta ctgactttgt  5580
tgggaagaca gtgtggtttg tccctagcat caaagccgga aatgacatag caaactgctt  5640
gcggaaaaat ggaaaaaagg ttattcaact cagcaggaag acctttgaca cagaatatca  5700
aaagaccaaa ctgaatgatt gggactttgt ggtgacaaca gacatttcag aaatgggagc  5760
caatttcaaa gcagatagag tgatcgaccc aagaagatgt ctcaagccgg tgattttgac  5820
agatggaccc gagcgggtga tcctggctgg accaatgcca gtcaccgtag cgagcgctgc  5880
gcaaaggaga gggagagttg gcaggaaccc acaaaaagaa aatgaccagt acatattcat  5940
gggccagcct ctcaacaatg atgaagacca tgctcactgg acagaagcaa aaatgctgct  6000
ggacaacatc aacacaccag aagggattat accagctctc tttgaaccag aaagggagaa  6060
gtcagccgcc atagacggcg aataccgcct gaagggtgag tccaggaaga ctttcgtgga  6120
actcatgagg aggggtgacc tcccagtttg gctagcccat aaagtagcat cagaagggat  6180
caaatataca gatagaaaat ggtgctttga tggagaacgt aataatcaaa ttttagagga  6240
gaatatggat gtggaaatct ggacaaagga aggagaaaag aaaaaactga gacctaggtg  6300
gcttgatgcc cgcacttatt cagatccttt agcactcaaa gaattcaagg attttgcagc  6360
tggcagaaag tcaatcgccc ttgatcttgt gacagaaata ggaagagtgc cttcacactt  6420
agcccacaga acgagaaacg ccctggataa tttggtgatg ctgcacacgt cagaacatgg  6480
cggtagggcc tacaggcatg cagtggagga actaccagaa acgatggaaa cactcttact  6540
cctgggactg atgatcttgt taacaggtgg agcaatgctc ttcttgatat caggtaaagg  6600
gattggaaag acttcaatag gactcatttg tgtaattgct tccagcggca tgttatggat  6660
ggctgatgtc ccactccaat ggatcgcatc ggctatagtc ctggagtttt ttatgatggt  6720
gttgctcata ccagaaccag aaaagcagag aactccccaa gacaaccaac tcgcatatgt  6780
cgtgataggc atacttacat tggctgcaat agtagcggcc aatgaaatgg gactgttgga  6840
aactacaaag agagatttag gaatgtctaa agaaccaggt gttgtttctc caaccagcta  6900
tttggatgtg gacttgcacc cagcatcagc ctggacattg tacgccgtgg ccacaacagt  6960
aataacacca atgttgagac acaccataga gaattccaca gcaaatgtgt ctctggcagc  7020
catagctaac caggcagtgg tcctgatggg tttagacaaa ggatggccga tatcgaaaat  7080
ggacttgggc gtaccactat tggcactggg ttgctattca caagtgaacc cactaactct  7140
tgcagcggca gtacttttgc tagtcacaca ttatgcaatt ataggtccag gattgcaggc  7200
aaaagccacc cgtgaagctc agaaaaggac agctgctgga ataatgaaga atccaacggt  7260
ggatggaata atgacaatag acctagatcc tgtaatatat gattcaaaat ttgaaaagca  7320
actaggacag gtcatgctcc tggttctgtg tgcagtccaa cttttattga tgagaacatc  7380
atgggccttg tgtgaagttc taaccctagc cacaggacca ataacaacac tctgggaagg  7440
atcacctggg aagttctgga acaccacgat agctgtttcc atggcgaaca tctttagagg  7500
gagctattta gcaggagctg ggcttgcttt ttctatcatg aaatcagttg gaacaggaaa  7560
gagaggaaca gggtcacaag gtgaaacctt aggagaaaag tggaaaaaga aattaaatca  7620
gttatcccgg aaagagtttg acctttacaa gaaatccgga atcaccgaag tggatagaac  7680
agaagccaaa gaagggttaa aaagaggaga aataacacac catgccgtgt ccagaggcag  7740
cgcaaaactt caatggttcg tggagagaaa catggtcatt cctgaaggaa gagtcataga  7800
cctaggctgt ggaagaggag gctggtcata ttactgtgca ggactgaaaa aagttacaga  7860
agtgcgagga tacacaaaag gcggcccagg acacgaagaa ccagtaccta tgtctacata  7920
cggatggaac atagtcaagt taatgagtgg aaaggatgtt ttttatctgc cacctgaaaa  7980
gtgtgatacc ctattgtgtg acattggaga atcttcacca agcccaacag tggaagaaag  8040
cagaaccata agagttttga agatggttga accatggcta aagaacaacc agttttgcat  8100
taaagtattg aacccataca tgccaactgt gattgagcac ttagaaagac tacaaaggaa  8160
acatggagga atgcttgtga gaaatccact ctcacgaaac tccacgcacg aaatgtattg  8220
gatatccaat ggtacaggca atatcgtctc ttcagtcaac atggtatcca gattgctact  8280
gaacagattc acaatgacac acaggagacc caccatagag aaagatgtgg atctaggagc  8340
aggaacccga catgtcaatg cggaaccaga aacacccaac atggatgtca ttggggaaag  8400
aataaaaagg atcaaagagg agcatagttc aacatggcac tatgatgatg aaaatcctta  8460
caaaacgtgg gcttaccatg gatcctatga agtaaaagcc acaggctcag cctcctccat  8520
gataaatgga gtcgtgaaac tcctcacaaa accatgggat gtggtgccca tggtgacaca  8580
gatggcaatg acagatacaa ctccattcgg ccagcaaaga gtttttaaag agaaagtgga  8640
caccaggaca cctaggccca tgccaggaac aagaaaggtt atggagatca cagcggagtg  8700
gctttggagg accctgggaa ggaacaaaag acccagatta tgcacaaggg aggaattcac  8760
aaagaaggtc agaaccaacg cagctatggg cgctgtcttc acagaagaga accaatggga  8820
cagtgcgaga gctgctgttg aggacgaaga attttggaaa cttgtggaca gagaacgtga  8880
actccacaaa ctgggcaagt gtggaagctg cgtttacaac atgatgggca agagagagaa  8940
aaaacttgga gagtttggta aagcaaaagg cagtagggct atatggtaca tgtggttggg  9000
agccaggtac cttgagttcg aggcgctcgg attcctcaat gaagaccact ggttctcgcg  9060
tgaaaactct tacagtggag tagaaggaga aggactgcac aagctgggat acatcttgag  9120
agatatttcc aagataccog gaggagccat gtatgctgat gacacagccg gttgggacac  9180
aagaataaca gaagatgacc tgcacaatga ggaaaaaatc acacagcaga tggaccctga  9240
acacaggcag ctagcgaacg ctatattcaa gctcacatac caaaacaaag tggtcaaagt  9300
ccaacgacca actccaaagg gcacggtaat ggacatcata tctaggaaag accaaagagg  9360
cagtggacag gtgggaactt atggtctgaa cacattcacc aacatggaag cccagctaat  9420
```

-continued

```
cagacaaatg gaaggagaag gcgtgttgtc aaaggcagac ctcgagaacc cccatccgct  9480
agagaagaaa attacacaat ggttggaaac taaaggagtg gaaaggttaa aaagaatggc  9540
catcagcggg gatgattgcg ttgtgaaacc aatcgacgac agattcgcca atgccctgct  9600
tgccctgaac gatatgggaa aggttagaaa ggacatacct caatggcagc catcaaaggg  9660
atggcatgat tggcaacagg tccccttctg ctcccaccac tttcatgaat tgatcatgaa  9720
agatggaaga aagttggtag ttccctgcag accccaggac gaactaatag gaagagcgag  9780
aatctcccaa ggagcaggat ggagccttag agaaactgca tgtctaggga aagcctacgc  9840
tcaaatgtgg gctctcatgt attttcacag aagagatctt agactagcat ccaacgccat  9900
atgttcagca gtaccagtcc actgggtccc cacgagcaga acgacatggt ctattcatgc  9960
tcaccatcag tggatgacta cagaagacat gcttactgtc tggaacaggg tgtggataga  10020
ggacaatcca tggatggaag acaaaactcc agtcacaacg tgggaagatg ttccatatct  10080
agggaagaga gaagaccaat ggtgcggatc actcataggt ctcacttcca gagcaacctg  10140
ggcccagaac atactcacag caatccaaca ggtgagaagc ctcataggca atgaagagtt  10200
tctggactac atgccttcga tgaagagatt caggaaggag gaggagtcag agggagccat  10260
ttggtaaaag caggaggtaa actgtcaggc cacattaagc cacagtacgg aagaagctgt  10320
gcagcctgtg agccccgtcc aaggacgtta aaagaagaag tcaggcccaa aagccacggt  10380
ttgagcaaac cgtgctgcct gtagctccgt cgtggggacg taaagcctgg gaggctgcaa  10440
accgtggaag ctgtacgcac ggtgtagcag actagtggtt agaggagacc cctcccatga  10500
cacaacgcag cagcggggcc cgagcactga gggaagctgt acctccttgc aaaggactag  10560
aggttagagg agaccccccg caaacaaaaa cagcatattg acgctgggag agaccagaga  10620
tcctgctgtc tcctcagcat cattccaggc acagaacgcc agaaaatgga atggtgctgt  10680
tgaatcaaca ggttct                                                  10696

SEQ ID NO: 14          moltype = AA  length = 3390
FEATURE                Location/Qualifiers
source                 1..3390
                       mol_type = protein
                       organism = Dengue virus
SEQUENCE: 14
MNNQRKKTGK PSINMLKRVR NRVSTGSQLA KRFSRGLLNG QGPMKLVMAF IAFLRFLAIP  60
PTAGVLARWG TFKKSGAIKV LKGFKKEISN MLSIINKRKK TSLCLMMMLP ATLAFHLTSR  120
DGEPRMIVGK NERGKSLLFK TASGINMCTL IAMDLGEMCD DTVTYKCPHI TEVEPEDIDC  180
WCNLTSTWVT YGTCNQAGEH RRDKRSVALA PHVGMGLDTR TQTWMSAEGA WRQVEKVETW  240
ALRHPGFTIL ALFLAHYIGT SLTQKVVIFI LLMLVTPSMT MRCVGVGNRD FVEGLSGATW  300
VDVVLEHGGC VTTMAKNKPT LDIELQKTEA TQLATLRKLC IEGKITNITT DSRCPTQGEA  360
ILPEEQDQNY VCKHTYVDRG WGNGCGLFGK GSLVTCAKFQ CLESIEGKVV QHENLKYTVI  420
ITVHTGDQHQ VGNETQGVTA EITPQASTAE VILPEYGTLG LECSPRTGLD FNEMISLTMK  480
NKAWMVHRQW FFDLPLPWTS GATAETPTWN RKELLVTFKN AHAKKQEVVV LGSQEGAMHT  540
ALTGATEIQT SGGTSIFAGH LKCRLKMDKL ELKGMSYAMC LSSFVLKKEV SETQHGTILI  600
KVEYKGEDAP CKIPFSTEDG QGKAHNGRLI TANPVVTKKE EPVNIEAEPP FGESNIVIGI  660
GDKALKINWY KKGSSIGKMF EATARGARRM AILGDTAWDF GSVGGVLNSL GKMVHQIFGS  720
AYTALFGGVS WMMKIGIGVL LTWIGLNSKN TSMSFSCIAI GIITLYLGAV VQADMGCVIN  780
WKGKELKCGS GIFVTNEVHT WTEQYKFQAD SPKRLATAIA GAWENGVCGI RSTTRMENLL  840
WKQIANELNY ILWENNIKLT VVVGDITGVL EQGKRTLTPQ PMELKYSWKT WGKAKIVTAE  900
TQNSSFIIDG PSTPECPSAS RAWNVWEVED YGFGVFTTNI WLKLREVYTQ LCDHRLMSAA  960
VKDERAVHAD MGYWIESQKN GSWKLEKASF IEVKTCTWPK SHTLWSNGVL ESDMIIPKSL  1020
AGPISQHNHR PGYHTQTAGP WHLGKLELDF NYCEGTTVVI SENCGTRGPS LRTTTVSGKL  1080
IHEWCCRSCT LPPLRYMGED GCWYGMEIRP INEKEENMVK SLASAGSGKV DNFTMGVLCL  1140
AILFEEVMRG KFGKKHMIAG VLFTFVLLLS GQITWRDMAH TLIMIGSNAS DRMGMGVTYL  1200
ALIATFKIQP FLALGFFLRK LTSRENLLLG VGLAMAATLR LPEDIEQMAN GIALGLMALK  1260
LITQFETYQL WTALVSLTCS NTIFTLTVAW RTATLILAGI SLLPVCQSSS MRKTDWLPMT  1320
VAAMGAQPLP LFIFSLKDTL KRRSWPLNEG VMAVGLVSIL ASSLLRNDVP MAGPLVAGGL  1380
LIACYVITGT SADLTVEKAA DVTWEEEAEQ TGVSHNLMVT VDDDGTMRIK DDETENILTV  1440
LLKTALLIVS GIFPYSIPAT LLVWHTWQKQ TQRSGVLWDV PSPPETQKAE LEEGVYRIKQ  1500
QGIFGKTQVG VGVQKEGVFH TMWHVTRGAV LTHNGKRLEP NWASVKKDLI SYGGGWRLSA  1560
QWQKGEEVQV IAVEPGKNPK NFQTMPGIFQ TTTGEIGAIA LDFKPGTSGS PIINREGKVV  1620
GLYGNGVVTK NGGYVSGIAQ TNAEPDGPTP ELEEEMFKKR NLTIMDLHPG SGKTRKYLPA  1680
IVREAIKRRL RTLILAPTRV VAAEMEEALK GLPIRYQTTA TKSEHTGREI VDLMCHATFT  1740
MRLLSPVRVP NYNLIIMDEA HFTDPASIAA RGYISTRVGM GEAAAIFMTA TPPGTADAFP  1800
QSNAPIQDEE RDIPERSWNS GNEWITDFVG KTVWFVPSIK AGNDIANCLR KNGKKVIQLS  1860
RKTFDTEYQK TKLNDWDFVV TTDISEMGAN FKADRVIDPR RCLKPVILTD GPERVILAGP  1920
MPVTVASAAQ RRGRVGRNPQ KENDQYIFMG QPLNNDEDHA HWTEAKMLLD NINTPEGIIP  1980
ALFEPEREKS AAIDGEYRLK GESRKTFVEL MRRGDLPVWL AHKVASEGIK YTDRKWCFDG  2040
ERNNQILEEN MDVEIWTKEG EKKKLRPRWL DARTYSDPLA LKEFKDFAAG RKSIALDLVT  2100
EIGRVPSHLA HRTRNALDNL VMLHTSEHGG RAYRHAVEEL PETMETLLLL GLMILLTGGA  2160
MLFLISGKGI GKTSIGLICV IASSGMLWMA DVPLQWIASA IVLEFFMMVL LIPEPEKQRT  2220
PQDNQLAYVV IGILTLAAIV AANEMGLLET TKRDLGMSKE PGVVSPTSYL DVDLHPASAW  2280
TLYAVATTVI TPMLRHTIEN STANVSLAAI ANQAVVLMGL DKGWPISKMD LGVPLLALGC  2340
YSQVNPLTLA AAVLLLVTHY AIIGPGLQAK ATREAQKRTA AGIMKNPTVD GIMTIDLDPV  2400
IYDSKFEKQL GQVMLLVLCA VQLLLMRTSW ALCEVLTLAT GPITTLWEGS PGKFWNTTIA  2460
VSMANIFRGS YLAGAGLAFS IMKSVGTGKR GTGSQGETLG EKWKKKLNQL SRKEFDLYKK  2520
SGITEVDRTE AKEGLKRGEI THHAVSRGSA KLQWFVERNM VIPEGRVIDL GCGRGGWSYY  2580
CAGLKKVTEV RGYTKGGPGH EEPVPMSTYG WNIVKLMSGK DVFYLPPEKC DTLLCDIGES  2640
SPSPTVEESR TIRVLKMVEP WLKNNQFCIK VLNPYMPTVI EHLERLQRKH GGMLVRNPLS  2700
RNSTHEMYWI SNGTGNIVSS VNMVSRLLLN RFTMTHRRPT IEKDVDLGAG TRHVNAEPET  2760
PNMDVIGERI KRIKEEHSST WHYDDENPYK TWAYHGSYEV KATGSASSMI NGVVKLLTKP  2820
WDVVPMVTQM AMTDTTPFGQ QRVFKEKVDT RTPRPMPGTR KVMEITAEWL WRTLGRNKRP  2880
RLCTREEFTK KVRTNAAMGA VFTEENQWDS ARAAVEDEEF WKLVDREREL HKLGKCGSCV  2940
YNMMGKREKK LGEFGKAKGS RAIWYMWLGA RYLEFEALGF LNEDHWFSRE NSYSGVEGEG  3000
```

```
LHKLGYILRD ISKIPGGAMY ADDTAGWDTR ITEDDLHNEE KITQQMDPEH RQLANAIFKL  3060
TYQNKVVKVQ RPTPKGTVMD IISRKDQRGS GQVGTYGLNT FTNMEAQLIR QMEGEGVLSK  3120
ADLENPHPLE KKITQWLETK GVERLKRMAI SGDDCVVKPI DDRFANALLA LNDMGKVRKD  3180
IPQWQPSKGW HDWQQVPFCS HHFHELIMKD GRKLVVPCRP QDELIGRARI SQGAGWSLRE  3240
TACLGKAYAQ MWALMYFHRR DLRLASNAIC SAVPVHWVPT SRTTWSIHAH HQWMTTEDML  3300
TVWNRVWIED NPWMEDKTPV TTWEDVPYLG KREDQWCGSL IGLTSRATWA QNILTAIQQV  3360
RSLIGNEEFL DYMPSMKRFR KEEESEGAIW                                   3390

SEQ ID NO: 15          moltype = DNA  length = 10648
FEATURE                Location/Qualifiers
source                 1..10648
                       mol_type = other DNA
                       note = dengue virus
                       organism = synthetic construct
SEQUENCE: 15
agttgttagt ctgtgtggac cgacaaggac agttccaaat cggaagcttg cttaacacag  60
ttctaacagt ttgtttgaat agagagcaga tctctggaaa aatgaaccaa cgaaaaaagg  120
tggttagacc acctttcaat atgctgaaac gcgagagaaa ccgcgtatca acccctcaag  180
ggttggtgaa gagattctca accggacttt tttctgggaa aggaccctta cggatggtgc  240
tagcattcat cacgtttttg cgagtccttt ccatcccacc aacagcaggg attctgaaaa  300
gatgggggaca gttgaagaaa aataaggcca tcaggatact gattggattc aggaaggaga  360
taggccgcat gctgaacatc ttgaacggga gaaaaaggtc aacgataaca ttgctgtgct  420
tgattcccac cgtaatggcg tttcacttgt caacaagaga tggcgaaccc ctcatgatag  480
tggcaaaaca tgaaaggggg agacctctct tgtttaagac aacagagggg atcaacaaat  540
gcactctcat tgccatggac ttgggtgaaa tgtgtgagga cactgtcacg tataaatgcc  600
ccttactggt caataccgaa cctgaagaca ttgattgctg gtgcaatctc acgtctacct  660
gggtcatgta tgggacatgc acccagagcg gagaacggag acgagagaag cgctcagtag  720
ctttaacacc acattcagga atgggattgg aaacaagagc tgagacatgg atgtcatcgg  780
aaggggcttg gaagcatgct cagagagtag agagctggat actcagaaac ccaggattcg  840
cgctcttggc aggatttatg gcttatatga ttgggcaaac aggaatccag cgaactgtct  900
tctttgtcct aatgatgctg gtcgccccat cctacggaat gcgatgcgta ggagtaggaa  960
acagagactt tgtggaagga gtctcaggtg gagcatgggt cgatctggtg ctagaacatg  1020
gaggatgcgt cacaaccatg gcccagggaa aaccaacctt ggattttgaa ctgactaaga  1080
caacagccaa ggaagtggct ctgttaagaa cctattgcat tgaagcctca atatcaaaca  1140
taaccacggc aacaagatgt ccaacgcaag gagagcctta tctaaaagag gaacaagacc  1200
aacagtacat ttgccggaga gatgtggtag acagagggtg gggcaatggc tgtggcttgt  1260
ttggaaaagg aggagttgtg acatgtgcga agttttcatg ttcggggaag ataacaggca  1320
atttggtcca aattgagaac cttgaataca cagtggttgt aacagtccac aatggagaca  1380
cccatgcagt aggaaatgac acatccaatc atggagttac agccacgata actcccaggt  1440
caccatcggt ggaagtcaaa ttgccggact atggagaact aacactcgat tgtgaaccca  1500
ggtctggaat tgactttaat gagatgattc tgatgaaaat gaaaaagaaa acatggcttg  1560
tgcataagca atggtttttg gatctacctc taccatggac agcaggagca gacacatcag  1620
aggttcactg gaattacaaa gagagaatgg tgacatttaa ggttcctcat gccaagagac  1680
aggatgtgac agtgctggga tctcaggaag gagccatgca ttctgccctc gctggagcca  1740
cagaagtgga ctccggtgat ggaaatcaca tgtttgcagg acatctcaag tgcaaagtcc  1800
gtatggagaa attgagaatc aagggaatgt catacacgat gtgttcagga aagttctcaa  1860
ttgacaaaga gatggcagaa acacagcatg ggacaacagt ggtgaaagtc aagtatgaag  1920
gtgctggagc tccgtgtaaa gtccccatag agataagaga tgtgaacaag gaaaaagtgg  1980
ttgggcgtat catctcatcc accccttggg ctgagaatac caacagtgca accaacatag  2040
agttagaacc cccctttggg gacagctaca tagtgatagg tgttggaaac agtgcattaa  2100
cactccattg gttcaggaaa gggagttcca ttggcaagat gtttgagtcc acatacagag  2160
gtgcaaaacg aatggccatt ctaggtgaaa cagcttggga ttttggttcc gttggtggac  2220
tgttcacatc attgggaaag gctgtgcacc aggtttttgg aagtgtgtat acaaccatgt  2280
ttggaggagt ctcatggatg attagaatcc taattgggtt cctagtgttg tggattggca  2340
cgaactcaag gaacacttca atggctatga cgtgcatagc tgttggagga atcactctgt  2400
ttctgggctt cacagttcaa gcagacatgg gttgtgtggt gtcatggagt gggaaagaat  2460
tgaagtgtgg aagcggaatt tttgtggttg acaacgtgca cacttggaca gaacagtaca  2520
aatttcaacc ggagtcccca gcgagactag cgtctgcaat attgaatgcc cacaaagatg  2580
gggtctgtgg aattagatca accacgaggc tggaaaatgt catgtggaag caaataacca  2640
acgagctaaa ttatgttctc tgggaaggag gacatgacct cactgtagtg gctggggatg  2700
tgaagggggt gttgaccaaa ggcaagagag cactcacacc cccagtgaat gatctgaaat  2760
attcatggaa gacatgggga aaagcaaaaa tcttcacccc agaagcaaga aatagcacat  2820
ttttaataga cggaccagac acctccgaat gccccaatga acgaagagca tggaactttc  2880
ttgaggtgga agactatgga tttggcatgt tcacgaccaa catatggatg aaattccgag  2940
aaggaagttc agaagtgtgt gaccacaggt taatgtcagc ggcaattaaa gatcagaaag  3000
ctgtgcatgc tgacatgggt tattggatag agagctcaaa aaaccagacc tggcagatag  3060
agaaagcatc tcttattgaa gtgaaaacat gtctgtggcc caagacccac acattgtgga  3120
gcaatggagt gctggaaagc cagatgctca ttccaaaatc atatgcgggc cctttttcac  3180
agcacaatta ccgccagggc tatgccacgc aaaccgtggg cccatggcac ttaggcaaat  3240
tagagataga ctttggagaa tgccccggaa caacagtcgc aattcaggag gattgtgacc  3300
atagaggccc atctttgagg accaccactg catctggaaa actagtcacg caatggtgct  3360
gccgctcctg cacgatgcct ccccttaggt tcttgggaga agatgggtgc tggtatggga  3420
tggagattag gcccttgagt gaaaaagaag agaacatggt caaatcacag gtaacggccg  3480
gacagggcac atcagaaact ttttctatgg gtctgttgtg cctgaccttg tttgtggaag  3540
aatgcttgag gagaagagtc actaggaaac acatgatatt ggttgtggtg atcactcttt  3600
gtgccatcat cctaggaggc ctcacatgga tggacttact acgagccctc atcatgttgg  3660
gggacactat gtctggtaga ataggaggac agatccacct agccatcatg gcagtgttca  3720
agatgtcacc aggatacgtg ctgggtgtgt ttttaaggaa actcacttca agagagacag  3780
cactaatggt aataggaatg gccatgacaa cggtgctttc aattccacat gaccttatgg  3840
```

```
aactcattga tggaatatca ctggggctaa ttttgctaaa aatagtgaca cattttgaca  3900
acacccaagt gggaacctta gccctttcct tgaccttcat aagatcaaca atgccattgg  3960
tcatggcttg gaggaccatt atggctgtgt tgtttgtggt cacactcatt cctttgtgca  4020
ggacaagctg tcttcaaaaa cagtctcatt gggtagaaat aacagcactc atcctaggag  4080
cccaagctct gccagtgtac ctaatgactc ttatgaaagg agcctcaaga agatcttggc  4140
ctcttaacga gggcataatg gctgtgggtt tggttagtct cttaggaagc gctcttttaa  4200
agaatgatgt ccctttagct ggcccaatgg tggcaggagg cttacttctg gcggcttacg  4260
tgatgagtgg tagctcagca gatctgtcac tagagaaggc cgccaatgtg cagtgggatg  4320
aaatggcaga cataacaggc tcaagcccaa tcatagaagt gaagcaggat gaagatggct  4380
ctttctccat acgggacgtc gaggaaacca atatgataac ccttttggtg aaactggcac  4440
tgataacagt gtcaggtctc taccccttgg caattccagt cacaatgacc ttatggtaca  4500
tgtggcaagt gaaaacacaa agatcaggag ccctgtggga cgtcccctca cccgctgcca  4560
ctcaaaaagc cgcactgtct gaaggagtgt acaggatcat gcaaagaggg ttatttggga  4620
aaactcaggt tggagtaggg atacacatgg aaggtgtatt tcacacaatg tggcatgtaa  4680
caagaggatc agtgatctgc catgagactg ggagattgga gccatcttgg gctgacgtca  4740
ggaatgacat gatatcatac ggtgggggat ggagacttgg agacaaatgg gacaaagaag  4800
aagatgttca ggtcctcgcc atagaaccag gaaaaaatcc taaacatgtc caaacgaaac  4860
ccggcctttt caagacccta actggagaaa ttggagcagt aacattagat ttcaaacccg  4920
gaacgtctgg ttctcccatc atcaacagga aaggaaaagt catcggactc tatggaaatg  4980
gagtagttac caaatcaggt gattacgtca gtgccataac gcaagccgaa agaattggag  5040
agccagatta tgaagtggat gaggacattt ttcgaaagaa aagattaact ataatggact  5100
tacaccccgg agctggaaag acaaaaagaa ttcttccatc aatagtgaga gaagccttaa  5160
aaaggaggct gcgaaccttg attttggctc ccacgagagt ggtggcggcc gagatggaag  5220
aggccctacg tggactgcca atccgttatc agaccccagc tgtgaaatca gaacacacag  5280
gaagagagat tgtagacctc atgtgtcatg caaccttcac aacaagactt ttgtcatcaa  5340
ccagagttcc aaattacaac ctcatagtga tggatgaagc acatttcacc gatccttcta  5400
gtgtcgcggc tagaggatac atctcgacca gggtggaaat gggagaggca gcagccatct  5460
tcatgaccgc aacccctccc ggagcgacag atccctttcc ccagagcaac agcccaatag  5520
aagacatcga gagggaaatt ccggaaaggt catggaacac agggttcgac tggataacag  5580
actaccaagg gaaaactgtg tggtttgttc ccagcataaa agctggaaat gacattgcaa  5640
attgtttgag aaagtcggga aagaaagtta tccagttgag taggaaaacc tttgatacag  5700
agtatccaaa aacgaaactc acggactggg attttgtggt cactacagac atatctgaaa  5760
tgggggccaa ttttagagct gggagagtga tagaccctag gagatgcctc aagccagtta  5820
tcctaacaga tgggccagag agagtcattt tagcaggtcc tattccagtg actccagcaa  5880
gcgctgctca gagaagaggg cgaataggaa ggaacccagc acaagaagac gaccaatacg  5940
ttttctccgg agacccacta aaaaatgatg aagatcatgc ccactggaca gaagcaaaga  6000
tgctgcttga caatatctac accccagaag ggatcattcc aacattgttt ggtccggaaa  6060
gggaaaaaac ccaagccatt gatggagagt ttcgcctcag aggggaacaa aggaagactt  6120
ttgtggaatt aatgaggaga ggagaccttc cggtgtggct gagctataag gtagcttctg  6180
ctggcatttc ttacaaagat cgggaatggt gcttcacagg ggaaaggaat aaccaaattt  6240
tagaagaaaa catggaggtt gaaatttgga ctagagaggg agaaaagaaa aagctaaggc  6300
caagatggtt agatgcacgt gtatacgctg accccatggc tttgaaggat tttaaggagt  6360
ttgctagtgg aaggaagagc ataactctcg acatcctaac agagattgcc agtttgccaa  6420
cttacctttc ctctagggcc aagctcgccc ttgataacat agtcatgctc cacacaacag  6480
aaagaggagg gagggcctac caacacgccc tgaacgaact cccggagtca ctggaaacac  6540
ttatgcttgt agctttacta ggtgctatga cagcaggtat cttcctgttt ttcatgcaag  6600
ggaaaggaat agggaaattg tcaatgggtt tgataaccat tgcggtggct agtggcttgc  6660
tctgggtagc agaaattcaa ccccagtgga tagcggcctc aatcatacta gagttttttc  6720
tcatggtact gttgataccg gaaccagaaa aacaaaggac cccacaagac aatcaattga  6780
tctacgtcat attgaccatt ctcaccatta ttggtctcat agcagccaac gagatggggc  6840
tgattgaaaa aacaaaaacg gattttgggt tttaccaggt aaaaacagaa accaccatcc  6900
tcgatgtgga cttgagacca gcttcagcat ggacgctcta tgcagtagcc accacaattc  6960
tgactcccat gctgagacac accatagaaa acacgtcggc caacctatct ctagcagcca  7020
ttgccaacca ggcggccgtc ctaatggggc ttggaaaagg atggccgctc cacagaatgg  7080
acctcggtgt gccgctgtta gcaatgggat gctattctca agtgaaccca acaactttga  7140
cagcatcctt agtcatgctt ttagtccatt atgcaataat aggtccagga ttgcaggcaa  7200
aagccacaag agaggcccag aaaaggacag ctgctgggat catgaaaaac cccacggtgg  7260
acgggataac agtaatagat ctagaaccaa tatcctatga cccaaaattt gaaaagcaat  7320
tagggcaggt catgctactc gtcttgtgtg ctggacaact actcttgatg agaacaacat  7380
gggctttctg tgaagtcttg actttggcca caggaccaat cttgaccttg tgggagggca  7440
acccgggaag gttttggaac acgaccatag ccgtatccac cgccaacatt ttcaggggaa  7500
gttacctggc gggagctgga ctggcttttt cactcataaa gaatgtacaa accccctagga  7560
ggggaactgg gaccacagga gagacactgg gagagaagtg gaagagacag ctaaactcat  7620
tagacagaaa agagtttgaa gagtataaaa gaagtggaat actagaagtg gacaggactg  7680
aagccaagtc tgccctgaaa gatgggtcta aaatcaagca tgcagtatct agagggtcca  7740
gtaagattag atggattgtt gagagaggga tggtaaagcc aaaagggaaa gttgtagatc  7800
ttggctgtgg gagaggagga tggtcttatt acatggcgac gctcaagaac gtgactgaag  7860
tgaaagggta tacaaaagga ggtccaggac atgaagaacc gattcccatg gctacttatg  7920
gctggaattt ggtcaaactc cattcagggg ttgacgtgtt ctacaaaccc acagagcaag  7980
tggacaccct gctctgtgat attggggagt catcttctaa tccaacaata gaggaaggaa  8040
gaacattaag agttttgaag atggtggagc catggctctc ttcaaaacct gaattctgca  8100
tcaaagtcct taacccctac atgccaacag tcatagaaga gctggagaaa ctgcagagaa  8160
aacatggtgg gaaccttgtc agatgcccgc tgtccaggaa ctccacccat gagatgtatt  8220
gggtgtcagg agcgtcggga aacattgtga gctctgtgaa cacaacatca aagatgttgt  8280
tgaacaggtt cacaacaagg cataggaaac ccacttatga gaaggacgta gatcttgggg  8340
caggaacgag aagtgtctcc actgaaacag aaaaaccaga catgacaatt attgggagaa  8400
ggcttcagcg attgcaagag gagcacaaag aaacctggca ttatgatcag gaaaacccat  8460
acagaacctg ggcgtatcat ggaagctatg aagctccttc gacaggctct gcatcctcca  8520
tggtgaacgg ggtagtaaaa ctgctaacaa aaccttggga tgtggttcca atggtgaccc  8580
```

```
agttagccat gacagacaca accccttttg ggcaacaaag agtgttcaaa gagaaggtgg  8640
ataccagaac accacaacca aaacccggta cacgaatggt tatgaccacg acagccaatt  8700
ggctgtgggc cctccttggg aagaagaaaa atcccagact gtgcacaagg gaagagttca  8760
tctcaaaagt tagatcaaac gcagccatag gcgcagtctt tcaggaagaa cagggatgga  8820
catcagccag tgaagctgtg aatgacagcc ggttttggga actggttgac aaagaaaggg  8880
ccctacacca ggaagggaaa tgtgaatcgt gtgtctacaa catgatggga aaacgtgaga  8940
aaaagttagg agagtttggc agagccaagg gaagccgagc aatctggtac atgtggctgg  9000
gagcgcggtt tctggaattt gaagccctgg gtttttgaa tgaagatcac tggtttggca  9060
gagaaaattc atggagtgga gtggaagggg aaggtctgca cagattggga tatatcctgg  9120
aggagataga caagaaggat ggagacctaa tgtatgctga tgacacagca ggctgggaca  9180
caagaatcac tgaggatgac cttcaaaatg aagaactgat cacggaacag atggcccccc  9240
accacaagat cctagccaaa gccattttca aactaaccta tcaaaacaaa gtggtgaaag  9300
tcctcagacc cacaccgaga ggagcggtga tggatatcat atccaggaaa gaccaaagag  9360
gtagtggaca agttggaaca tatggtttga acacattcac caacatggaa gttcaactca  9420
tccgccaaat ggaagctgaa ggagtcatca cacaagatga catgcagaac ccaaaagggt  9480
tgaaagaaag agttgagaaa tggctgaaag agtgtggtgt cgacaggtta aagaggatgg  9540
caatcagtgg agacgattgc gtggtgaagc ccctggatga gaggtttggc acttccctcc  9600
tcttcttgaa cgacatggga aaggtgagga aagacattcc gcagtgggaa ccatctaagg  9660
gatggaaaaa ctggcaagag gttccttttt gctcccacca ctttcacaag atcttcatga  9720
aggatggccg ctcactagtt gttccatgta gaaaccagga tgaactgata gggagagcca  9780
gaatctcgca gggggctgga tggagcttaa gagaaacagc ctgcctgggc aaagcttacg  9840
cccagatgtg gtcgctcatg tacttccaca gaagggatct gcgtttagcc tccatggcca  9900
tatgctcagc agttccaacg gaatggtttc caacaagcag aacaacatgg tcaatccacg  9960
ctcatcatca gtggatgacc actgaagata tgctcaaagt gtggaacaga gtgtggatag  10020
aagacaaccc taatatgact gacaagactc cagtccattc gtgggaagat ataccttacc  10080
tagggaaaag agaggatttg tggtgtggat ccctgattgg actttcttcc agagccacct  10140
gggcgaagaa cattcacacg gccataaccc aggtcagaaa cctgatcgga aaagaggaat  10200
acgtggatta catgccagta atgaaaagat acagcgctcc ttcagagagt gaaggagttc  10260
tgtaattacc aacaacaaac accaaaggct attgaagtca ggccacttgt gccacggctt  10320
gagcaaaccg tgctgcctgt agctccgcca ataatgggag gcgtgaaatc cctagggagg  10380
ccatgcgcca cggaagctgt acgcgtggca tattggacta gcggttagag gagacccctc  10440
ccatcactga caaaacgcag caaaaggggg cccgaagcca ggaggaagct gtactcctgg  10500
tggaaggact agaggttaga ggagaccccc ccaacacaaa aacagcatat tgacgctggg  10560
aaagaccaga gatcctgctg tctctgcaac atcaatccag gcacagagcg ccgcaagatg  10620
gattggtgtt gttgatccaa caggttct                                    10648
```

```
SEQ ID NO: 16          moltype = AA  length = 3387
FEATURE                Location/Qualifiers
source                 1..3387
                       mol_type = protein
                       organism = Dengue virus
SEQUENCE: 16
MNQRKKVVRP PFNMLKRERN RVSTPQGLVK RFSTGLFSGK GPLRMVLAFI TFLRVLSIPP  60
TAGILKRWGQ LKKNKAIRIL IGFRKEIGRM LNILNGRKRS TITLLCLIPT VMAFHLSTRD  120
GEPLMIVAKH ERGRPLLFKT TEGINKCTLI AMDLGEMCED TVTYKCPLLV NTEPEDIDCW  180
CNLTSTWVMY GTCTQSGERR REKRSVALTP HSGMGLETRA ETWMSSEGAW KHAQRVESWI  240
LRNPGFALLA GFMAYMIGQT GIQRTVFFVL MMLVAPSYGM RCVGVGNRDF VEGVSGGAWV  300
DLVLEHGGCV TTMAQGKPTL DFELTKTTAK EVALLRTYCI EASISNITTA TRCPTQGEPY  360
LKEEQDQQYI CRRDVVDRGW GNGCGLFGKG GVVTCAKFSC SGKITGNLVQ IENLEYTVVV  420
TVHNGDTHAV GNDTSNHGVT ATITPRSPSV EVKLPDYGEL TLDCEPRSGI DFNEMILMKM  480
KKKTWLVHKQ WFLDLPLPWT AGADTSEVHW NYKERMVTFK VPHAKRQDVT VLGSQEGAMH  540
SALAGATEVD SGDGNHMFAG HLKCKVRMEK LRIKGMSYTM CSGKFSIDKE MAETQHGTTV  600
VKVKYEGAGA PCKVPIEIRD VNKEKVVGRI ISSTPLAENT NSATNIELEP PFGDSYIVIG  660
VGNSALTLHW FRKGSSIGKM FESTYRGAKR MAILGETAWD FGSVGGLFTS LGKAVHQVFG  720
SVYTTMFGGV SWMIRILIGF LVLWIGTNSR NTSMAMTCIA VGGITLFLGF TVQADMGCVV  780
SWSGKELKCG SGIFVVDNVH TWTEQYKFQP ESPARLASAI LNAHKDGVCG IRSTTRLENV  840
MWKQITNELN YVLWEGGHDL TVVAGDVKGV LTKGKRALTP PVNDLKYSWK TWGKAKIFTP  900
EARNSTFLID GPDTSECPNE RRAWNFLEVE DYGFGMFTTN IWMKFREGSS EVCDHRLMSA  960
AIKDQKAVHA DMGYWIESSK NQTWQIEKAS LIEVKTCLWP KTHTLWSNGV LESQMLIPKS  1020
YAGPFSQHNY RQGYATQTVG PWHLGKLEID FGECPGTTVA IQEDCDHRGP SLRTTTASGK  1080
LVTQWCCRSC TMPPLRFLGE DGCWYGMEIR PLSEKEENMV KSQVTAGQGT SETFSMGLLC  1140
LTLFVEECLR RRVTRKHMIL VVVITLCAII LGGLTWMDLL RALIMLGDTM SGRIGGQIHL  1200
AIMAVFKMSP GYVLGVFLRK LTSRETALMV IGMAMTTVLS IPHDLMELID GISLGLILLK  1260
IVTHFDNTQV GTLALSLTFI RSTMPLVMAW RTIMAVLFVV TLIPLCRTSC LQKQSHWVEI  1320
TALILGAQAL PVYLMTLMKG ASRRSWPLNE GIMAVGLVSL LGSALLKNDV PLAGPMVAGG  1380
LLLAAYVMSG SSADLSLEKA ANVQWDEMAD ITGSSPIIEV KQDEDGSFSI RDVEETNMIT  1440
LLVKLALITV SGLYPLAIPV TMTLWYMWQV KTQRSGALWD VPSPAATQKA ALSEGVYRIM  1500
QRGLFGKTQV GVGIHMEGVF HTMWHVTRGS VICHETGRLE PSWADVRNDM ISYGGGWRLG  1560
DKWDKEEDVQ VLAIEPGKNP KHVQTKPGLF KTLTGEIGAV TLDFKPGTSG SPIINRKGKV  1620
IGLYGNGVVT KSGDYVSAIT QAERIGEPDY EVDEDIFRKK RLTIMDLHPG AGKTKRILPS  1680
IVREALKRRL RTLILAPTRV VAAEMEEALR GLPIRYQTPA VKSEHTGREI VDLMCHATFT  1740
TRLLSSTRVP NYNLIVMDEA HFTDPSSVAA RGYISTRVEM GEAAAIFMTA TPPGATDPFP  1800
QSNSPIEDIE REIPERSWNT GFDWITDYQG KTVWFVPSIK AGNDIANCLR KSGKKVIQLS  1860
RKTFDTEYPK TKLTDWDFVV TTDISEMGAN FRAGRVIDPR RCLKPVILTD GPERVILAGP  1920
IPVTPASAAQ RRGRIGRNPA QEDDQYVFSG DPLKNDEDHA HWTEAKMLLD NIYTPEGIIP  1980
TLFGPEREKT QAIDGEFRLR GEQRKTFVEL MRRGDLPVWL SYKVASAGIS YKDREWCFTG  2040
ERNNQILEEN MEVEIWTREG EKKKLRPRWL DARVYADPMA LKDFKEFASG RKSITLDILT  2100
EIASLPTYLS SRAKLALDNI VMLHTTERGG RAYQHALNEL PESLETLMLV ALLGAMTAGI  2160
FLFFMQGKGI GKLSMGLITI AVASGLLWVA EIQPQWIAAS IILEFFLMVL LIPEPEKQRT  2220
```

-continued

```
PQDNQLIYVI LTILTIIGLI AANEMGLIEK TKTDFGFYQV KTETTILDVD LRPASAWTLY  2280
AVATTILTPM LRHTIENTSA NLSLAAIANQ AAVLMGLGKG WPLHRMDLGV PLLAMGCYSQ  2340
VNPTTLTASL VMLLVHYAII GPGLQAKATR EAQKRTAAGI MKNPTVDGIT VIDLEPISYD  2400
PKFEKQLGQV MLLVLCAGQL LLMRTTWAFC EVLTLATGPI LTLWEGNPGR FWNTTIAVST  2460
ANIFRGSYLA GAGLAFSLIK NVQTPRRGTG TTGETLGEKW KRQLNSLDRK EFEEYKRSGI  2520
LEVDRTEAKS ALKDGSKIKH AVSRGSSKIR WIVERGMVKP KGKVVDLGCG RGGWSYYMAT  2580
LKNVTEVKGY TKGGPGHEEP IPMATYGWNL VKLHSGVDVF YKPTEQVDTL LCDIGESSSN  2640
PTIEEGRTLR VLKMVEPWLS SKPEFCIKVL NPYMPTVIEE LEKLQRKHGG NLVRCPLSRN  2700
STHEMYWVSG ASGNIVSSVN TTSKMLLNRF TTRHRKPTYE KDVDLGAGTR SVSTETEKPD  2760
MTIIGRRLQR LQEEHKETWH YDQENPYRTW AYHGSYEAPS TGSASSMVNG VVKLLTKPWD  2820
VVPMVTQLAM TDTTPFGQQR VFKEKVDTRT PQPKPGTRMV MTTTANWLWA LLGKKKNPRL  2880
CTREEFISKV RSNAAIGAVF QEEQGWTSAS EAVNDSRFWE LVDKERALHQ EGKCESCVYN  2940
MMGKREKKLG EFGRAKGSRA IWYMWLGARF LEFEALGFLN EDHWFGRENS WSGVEGEGLH  3000
RLGYILEEID KKDGDLMYAD DTAGWDTRIT EDDLQNEELI TEQMAPHHKI LAKAIFKLTY  3060
QNKVVKVLRP TPRGAVMDII SRKDQRGSGQ VGTYGLNTFT NMEVQLIRQM EAEGVITQDD  3120
MQNPKGLKER VEKWLKECGV DRLKRMAISG DDCVVKPLDE RFGTSLLFLN DMGKVRKDIP  3180
QWEPSKGWKN WQEVPFCSHH FHKIFMKDGR SLVVPCRNQD ELIGRARISQ GAGWSLRETA  3240
CLGKAYAQMW SLMYFHRRDL RLASMAICSA VPTEWFPTSR TTWSIHAHHQ WMTTEDMLKV  3300
WNRVWIEDNP NMTDKTPVHS WEDIPYLGKR EDLWCGSLIG LSSRATWAKN IHTAITQVRN  3360
LIGKEEYVDY MPVMKRYSAP SESEGVL                                      3387
```